US011168090B2

(12) United States Patent
Andrews et al.

(10) Patent No.: US 11,168,090 B2
(45) Date of Patent: Nov. 9, 2021

(54) SUBSTITUTED PYRAZOLO[1,5-A]PYRAZINES AS RET KINASE INHIBITORS

(71) Applicant: Array BioPharma Inc., Indianapolis, IN (US)

(72) Inventors: Steven W Andrews, Boulder, CO (US); James F Blake, Boulder, CO (US); Julia Haas, Boulder, CO (US); Yutong Jiang, Boulder, CO (US); Gabrielle R Kolakowski, Boulder, CO (US); David A Moreno, Boulder, CO (US); Li Ren, Boulder, CO (US); Shane M Walls, Boulder, CO (US)

(73) Assignee: Array BioPharma Inc., Indianapolis, IN (US)

( * ) Notice: Subject to any disclaimer, the term of this patent is extended or adjusted under 35 U.S.C. 154(b) by 0 days.

(21) Appl. No.: 16/478,071

(22) PCT Filed: Jan. 18, 2018

(86) PCT No.: PCT/US2018/014279
§ 371 (c)(1),
(2) Date: Jul. 15, 2019

(87) PCT Pub. No.: WO2018/136661
PCT Pub. Date: Jul. 26, 2018

(65) Prior Publication Data
US 2020/0055860 A1 Feb. 20, 2020

Related U.S. Application Data

(60) Provisional application No. 62/447,862, filed on Jan. 18, 2017.

(51) Int. Cl.
*A61K 31/4985* (2006.01)
*C07D 487/04* (2006.01)

(52) U.S. Cl.
CPC .................................. *C07D 487/04* (2013.01)

(58) Field of Classification Search
CPC .......................... A61K 31/4985; C07D 487/04
USPC .......................................... 514/249; 544/350
See application file for complete search history.

(56) References Cited

U.S. PATENT DOCUMENTS

| | | | |
|---|---|---|---|
| 5,430,021 | A | 7/1995 | Rudnic et al. |
| 5,844,092 | A | 12/1998 | Presta et al. |
| 5,877,016 | A | 3/1999 | Presta et al. |
| 5,910,574 | A | 6/1999 | Presta et al. |
| 6,025,166 | A | 2/2000 | Presta et al. |
| 6,027,927 | A | 2/2000 | Presta et al. |
| 6,153,189 | A | 11/2000 | Presta et al. |
| 6,531,152 | B1 | 3/2003 | Lerner et al. |
| 6,534,085 | B1 | 3/2003 | Zeligs |
| 6,861,509 | B1 | 3/2005 | Sanicola-Nadel et al. |
| 7,384,632 | B2 | 6/2008 | Devaux et al. |
| 7,465,726 | B2 | 12/2008 | Ahmed et al. |
| 7,504,509 | B2 | 3/2009 | Ibrahim et al. |
| 7,514,446 | B2 | 4/2009 | Davis-Ward et al. |
| 7,615,383 | B2 | 11/2009 | Devaux et al. |
| 7,795,273 | B2 | 9/2010 | Imbach et al. |
| 7,863,288 | B2 | 1/2011 | Ibrahim et al. |
| 7,863,289 | B2 | 1/2011 | Spevak et al. |
| 8,026,247 | B2 | 9/2011 | Bold et al. |
| 8,067,434 | B2 | 11/2011 | Ibrahim et al. |
| 8,106,069 | B2 | 1/2012 | Salom et al. |
| 8,114,989 | B2 | 2/2012 | Wang et al. |
| 8,129,374 | B2 | 3/2012 | Bhagwat et al. |
| 8,198,298 | B2 | 6/2012 | Salom et al. |
| 8,299,057 | B2 | 10/2012 | Lombardi Borgia et al. |
| 8,338,417 | B2 | 12/2012 | Li et al. |
| 8,354,526 | B2 | 1/2013 | Ding et al. |

(Continued)

FOREIGN PATENT DOCUMENTS

| | | |
|---|---|---|
| CN | 101052629 | 10/2007 |
| CN | 105255927 | 1/2016 |

(Continued)

OTHER PUBLICATIONS

Jordan, V. C. Nature Reviews: Drug Discovery, 2, 2003, 205.*
Hackam, et al. JAMA, 296(14), 2006, 1731-1732.*
International Search Report for PCT/US2018/014279.
Written Opinion for PCT/US2018/014279.
Ahmed et al., "Nine novel germline gene variants in the RET proto-oncogene identified in twelve unrelated cases.", The Journal of Molecular Diagnostics, 7(2), 283-288, 2005.
Anunobi et al., "Extracellular DNA promotes colorectal tumor cell survival after cytotoxic chemotherapy", J Surg. Res. Mar. 28, 2018.
Arriola et al., "Comparison of plasma ctDNA and tissue/cytology-based techniques for the detection of EGFR mutation status in advanced NSCLC: Spanish data subset from Assess", Clin. Transl. Oneal., 20: 1261-1267, Apr. 5, 2018.

(Continued)

*Primary Examiner* — Douglas M Willis
(74) *Attorney, Agent, or Firm* — Meunier Carlin & Curfman LLC

(57) ABSTRACT

Provided herein are compounds of the Formula I:

I

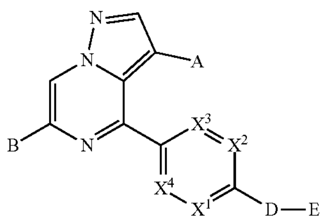

and stereoisomers and pharmaceutically acceptable salts or solvates thereof, in which A, B, D, E, $X^1$, $X^2$, $X^3$ and $X^4$ have the meanings given in the specification, which are inhibitors of RET kinase and are useful in the treatment and prevention of diseases which can be treated with a RET kinase inhibitor, including diseases or disorders mediated by a RET kinase.

12 Claims, No Drawings

Specification includes a Sequence Listing.

(56) References Cited

U.S. PATENT DOCUMENTS 8,399,442 B2 3/2013 Berdini et al.
8,450,322 B2 5/2013 Andrews et al.
8,461,161 B2 6/2013 Burns et al.
8,501,756 B2 8/2013 Artman, III et al.
8,513,263 B2 8/2013 Haas et al.
8,524,709 B2 9/2013 Liang et al.
8,552,002 B2 10/2013 Ding et al.
8,568,998 B2 10/2013 Mani et al.
8,629,135 B2 1/2014 Gujral et al.
8,637,256 B2 1/2014 Ernst
8,637,516 B2 1/2014 Fan et al.
8,642,035 B2 2/2014 Luehrsen
8,673,347 B2 3/2014 Traversa et al.
8,686,005 B2 4/2014 Gregor
8,691,221 B2 4/2014 Pavone et al.
8,741,849 B2 6/2014 Panitch et al.
8,754,209 B2 6/2014 Sim et al.
8,791,123 B2 7/2014 Allen et al.
8,815,901 B2 7/2014 Furet et al.
8,815,906 B2 8/2014 Gregor et al.
8,895,744 B2 11/2014 Gambacorti Passerinni et al.
8,912,194 B2 12/2014 Ciomei et al.
8,912,204 B2 12/2014 Ibrahim et al.
8,933,084 B2 1/2015 Andrews et al.
8,933,230 B2 1/2015 Yun et al.
8,937,071 B2 1/2015 Eidam et al.
8,946,226 B2 2/2015 Ciomei et al.
9,006,256 B2 4/2015 Matsui
9,035,063 B2 5/2015 Eidam et al.
9,102,671 B2 8/2015 Molteni et al.
9,149,464 B2 10/2015 Bakale et al.
9,150,517 B2 10/2015 Bakale et al.
9,186,318 B2 11/2015 Yun et al.
9,216,172 B2 12/2015 Kohno et al.
9,242,977 B2 1/2016 Takeuchi et al.
9,260,437 B2 2/2016 Ibrahim et al.
9,273,051 B2 3/2016 Chen et al.
9,297,011 B2 3/2016 Chen et al.
9,321,772 B2 4/2016 Dar et al.
9,487,491 B2 11/2016 Shimada et al.
9,493,455 B2 11/2016 Cheve et al.
9,505,784 B2 11/2016 Choi et al.
9,522,910 B2 12/2016 Chilov et al.
9,550,772 B2 1/2017 Cheve et al.
9,604,980 B2 3/2017 Menichincheri et al.
9,669,028 B2 6/2017 Vankayalapati et al.
9,682,083 B2 6/2017 Angiolini et al.
9,738,660 B2 8/2017 Yang et al.
9,758,508 B2 9/2017 Hong et al.
9,789,100 B2 10/2017 Eidam
9,801,880 B2 10/2017 Micklem
10,023,570 B2 7/2018 Andrews et al.
10,138,243 B2 11/2018 Andrews et al.
10,174,027 B2 1/2019 Andrews et al.
10,174,028 B2 1/2019 Andrews et al.
2004/0185547 A1 9/2004 Mohammai et al.
2005/0209195 A1 9/2005 Menta et al.
2005/0222171 A1 10/2005 Bold et al.
2006/0183900 A1 8/2006 Huang et al.
2007/0117800 A1 5/2007 Arnold et al.
2007/0149523 A1 6/2007 Ehlert et al.
2007/0184117 A1 8/2007 Gregory et al.
2007/0265274 A1 11/2007 Fagin et al.
2008/0199426 A1 8/2008 Sukhatme et al.
2008/0234267 A1 9/2008 Lackey
2008/0234276 A1 9/2008 Boyle et al.
2008/0234284 A1 9/2008 Imbach et al.
2008/0262021 A1 10/2008 Capraro et al.
2008/0275054 A1 11/2008 Holzer et al.
2008/0287427 A1 11/2008 Bold et al.
2008/0312192 A1 12/2008 Bold et al.
2008/0319005 A1 12/2008 Bold et al.
2009/0012045 A1 1/2009 Hitoshi et al.
2009/0027556 A1 1/2009 Bleau et al.
2009/0048249 A1 2/2009 Chiu et al.
2009/0069360 A1 3/2009 Batt et al.
2009/0099167 A1 4/2009 Bold et al.
2009/0130229 A1 5/2009 Lanzi
2009/0143399 A1 6/2009 Hurley et al.
2009/0152083 A1 6/2009 Cheng et al.
2009/0209496 A1 8/2009 Chaplin et al.
2009/0215761 A1 8/2009 Whitten et al.
2009/0227556 A1 9/2009 Obaishi
2009/0312321 A1 12/2009 Ren et al.
2010/0004239 A1 1/2010 Tang et al.
2010/0048540 A1 2/2010 Boyle et al.
2010/0069395 A1 3/2010 Imbach et al.
2010/0075916 A1 3/2010 Gant et al.
2010/0081675 A1 4/2010 Hsieh et al.
2010/0152219 A1 6/2010 Block et al.
2010/0173954 A1 7/2010 Wilhelm et al.
2010/0209488 A1 8/2010 Wrasidlo et al.
2010/0280012 A1 11/2010 Lee
2010/0297115 A1 11/2010 Blaustein
2010/0324065 A1 12/2010 Ibrahim et al.
2011/0046370 A1 2/2011 Sim et al.
2011/0053934 A1 3/2011 Angell et al.
2011/0118245 A1 5/2011 Abraham et al.
2011/0133637 A1 6/2011 Ota
2011/0189167 A1 8/2011 Flynn et al.
2011/0195072 A1 8/2011 Boulay et al.
2011/0212053 A1 9/2011 Qian et al.
2011/0269739 A1 11/2011 Kim et al.
2011/0281841 A1 11/2011 Lee et al.
2011/0301157 A1 12/2011 Bold et al.
2012/0065233 A1 3/2012 Gregor
2012/0070410 A1 3/2012 Apuy et al.
2012/0157451 A1 6/2012 Gradl et al.
2012/0157452 A1 6/2012 Gradl et al.
2012/0225057 A1 9/2012 Flynn et al.
2012/0271048 A1 10/2012 Sim et al.
2012/0277247 A1 11/2012 Menet et al.
2012/0277274 A1 11/2012 Kocherlakota et al.
2012/0277424 A1 11/2012 Sim et al.
2012/0283261 A1 11/2012 Bearss et al.
2012/0302567 A1 11/2012 Jung et al.
2013/0012703 A1 1/2013 Sim et al.
2013/0029925 A1 1/2013 Vandier et al.
2013/0053370 A1 2/2013 Son et al.
2013/0079343 A1 3/2013 Sim et al.
2013/0303518 A1 11/2013 Tang et al.
2014/0121239 A1 5/2014 Aftab
2014/0137274 A1 5/2014 Ishikawa
2014/0213580 A1 7/2014 Cao et al.
2014/0272951 A1 9/2014 Chakravarti et al.
2014/0371219 A1 12/2014 Bae et al.
2015/0018336 A1 1/2015 Chen et al.
2015/0051222 A1 2/2015 Barbugian et al.
2015/0057335 A1 2/2015 Kohno et al.
2015/0065468 A1 3/2015 Holladay et al.
2015/0099721 A1 4/2015 Acquaviva et al.
2015/0099762 A1 4/2015 Eidam et al.
2015/0166564 A1 6/2015 Allen et al.
2015/0177246 A1 6/2015 Shibata et al.
2015/0238477 A1 8/2015 Aftab
2015/0272958 A1 10/2015 Kodama et al.
2015/0283132 A1 10/2015 Lim et al.
2015/0306086 A1 10/2015 Wilcoxen
2016/0000783 A1 1/2016 Takeuchi et al.
2016/0009709 A1 1/2016 Cheve et al.
2016/0046636 A1 2/2016 Gray et al.
2016/0137654 A1 5/2016 Arrigo et al.
2016/0176865 A1 6/2016 Ibrahim et al.
2016/0318929 A1 11/2016 Hudkins et al.
2017/0014413 A1 1/2017 Downing et al.
2017/0044106 A1 2/2017 Aftab et al.
2017/0096425 A1 4/2017 Andrews et al.
2017/0114032 A1 4/2017 Cheng et al.
2017/0121312 A1 5/2017 Brubaker et al.
2017/0226100 A1 8/2017 Jiaang et al.
2017/0281632 A1 10/2017 Cox et al.
2017/0283404 A1 10/2017 Cheung et al.
2017/0298074 A1 10/2017 Cheung et al.
2017/0349953 A1 12/2017 Lovejoy et al.

(56) References Cited

U.S. PATENT DOCUMENTS

| | | | |
|---|---|---|---|
| 2018/0009817 | A1 | 1/2018 | Miyazaki et al. |
| 2018/0009818 | A1 | 1/2018 | Miyazaki et al. |
| 2018/0022732 | A1 | 1/2018 | Brubaker et al. |
| 2018/0133200 | A1 | 5/2018 | Andrews et al. |
| 2018/0133207 | A1 | 5/2018 | Andrews et al. |
| 2018/0133213 | A1 | 5/2018 | Andrews et al. |
| 2018/0134702 | A1 | 5/2018 | Andrews et al. |
| 2018/0134703 | A1 | 5/2018 | Andrews et al. |
| 2018/0148445 | A1 | 5/2018 | Andrews et al. |
| 2018/0179203 | A1 | 6/2018 | Andrews et al. |
| 2018/0186790 | A1 | 7/2018 | Andrews et al. |
| 2018/0186791 | A1 | 7/2018 | Andrews et al. |
| 2019/0127373 | A1 | 5/2019 | Andrews et al. |
| 2019/0127374 | A1 | 5/2019 | Andrews et al. |
| 2019/0127375 | A1 | 5/2019 | Andrews et al. |
| 2019/0352403 | A1 | 11/2019 | Schwab et al. |
| 2020/0055838 | A1 | 2/2020 | Youhong et al. |
| 2020/0339579 | A1 | 10/2020 | Walls et al. |
| 2020/0339589 | A1 | 10/2020 | Blake et al. |
| 2020/0399279 | A1 | 12/2020 | Blake et al. |

FOREIGN PATENT DOCUMENTS

| | | |
|---|---|---|
| JP | 2015109806 | 6/2015 |
| WO | 87/05297 | 9/1987 |
| WO | 97/044356 | 11/1997 |
| WO | 2001016169 | 3/2001 |
| WO | 2001062273 | 8/2001 |
| WO | 2003020698 | 3/2003 |
| WO | 2005044835 | 5/2005 |
| WO | 2005051366 | 6/2005 |
| WO | 2005062795 | 7/2005 |
| WO | 2005070431 | 8/2005 |
| WO | 2006089298 | 8/2006 |
| WO | 2006123113 | 11/2006 |
| WO | 2006130613 | 12/2006 |
| WO | 2006131952 | 12/2006 |
| WO | 2007002325 | 1/2007 |
| WO | 2007002433 | 1/2007 |
| WO | 2007022999 | 3/2007 |
| WO | 2007054357 | 5/2007 |
| WO | 2007057397 | 5/2007 |
| WO | 2007057399 | 5/2007 |
| WO | 2007087245 | 8/2007 |
| WO | 2007109045 | 9/2007 |
| WO | 2007110344 | 10/2007 |
| WO | 2007136103 | 11/2007 |
| WO | 2008031551 | 3/2008 |
| WO | 2008079903 | 7/2008 |
| WO | 2008079906 | 7/2008 |
| WO | 2008079909 | 7/2008 |
| WO | 2008080001 | 7/2008 |
| WO | 2008080015 | 7/2008 |
| WO | 2009007748 | 1/2009 |
| WO | 2009012283 | 1/2009 |
| WO | 2009013126 | 1/2009 |
| WO | 2009014637 | 1/2009 |
| WO | 2009017838 | 2/2009 |
| WO | 2009023978 | 2/2009 |
| WO | 2009042646 | 4/2009 |
| WO | 2009053442 | 4/2009 |
| WO | 2009071480 | 6/2009 |
| WO | 2009092049 | 7/2009 |
| WO | 2009118411 | 10/2009 |
| WO | 2009143018 | 11/2009 |
| WO | 2009143024 | 11/2009 |
| WO | 2009152083 | 12/2009 |
| WO | 2010031816 | 3/2010 |
| WO | 2010033941 | 3/2010 |
| WO | 2010048314 | 4/2010 |
| WO | 2010058006 | 5/2010 |
| WO | 2010111527 | 9/2010 |
| WO | 2010145998 | 12/2010 |
| WO | 2011006074 | 1/2011 |
| WO | 2011022439 | 2/2011 |
| WO | 2011045344 | 4/2011 |
| WO | 2011092120 | 8/2011 |
| WO | 2011133637 | 10/2011 |
| WO | 2011143459 | 11/2011 |
| WO | 2011146336 | 11/2011 |
| WO | 2012034091 | 3/2012 |
| WO | 2012034095 | 3/2012 |
| WO | 2012047017 | 4/2012 |
| WO | 2012053606 | 4/2012 |
| WO | 2012101029 | 8/2012 |
| WO | 2012101032 | 8/2012 |
| WO | 2012109075 | 8/2012 |
| WO | 2012113774 | 8/2012 |
| WO | 2012116217 | 8/2012 |
| WO | 2012139930 | 10/2012 |
| WO | 2012143248 | 10/2012 |
| WO | 2012152763 | 11/2012 |
| WO | 2012158413 | 11/2012 |
| WO | 2012171337 | 12/2012 |
| WO | 2013014039 | 1/2013 |
| WO | 2013016720 | 1/2013 |
| WO | 2013036232 | 3/2013 |
| WO | 2013042137 | 3/2013 |
| WO | 2013050446 | 4/2013 |
| WO | 2013050448 | 4/2013 |
| WO | 2013074518 | 5/2013 |
| WO | 2013102059 | 7/2013 |
| WO | 2013174876 | 11/2013 |
| WO | 2013183578 | 12/2013 |
| WO | 2014011900 | 1/2014 |
| WO | 2014019908 | 2/2014 |
| WO | 2014075035 | 5/2014 |
| WO | 2014078322 | 5/2014 |
| WO | 2014078323 | 5/2014 |
| WO | 2014078325 | 5/2014 |
| WO | 2014078328 | 5/2014 |
| WO | 2014078331 | 5/2014 |
| WO | 2014078372 | 5/2014 |
| WO | 2014078378 | 5/2014 |
| WO | 2014078408 | 5/2014 |
| WO | 2014078417 | 5/2014 |
| WO | 2014078454 | 5/2014 |
| WO | 2014083567 | 6/2014 |
| WO | 2014086284 | 6/2014 |
| WO | 2014141187 | 9/2014 |
| WO | 2014160521 | 10/2014 |
| WO | 2014160524 | 10/2014 |
| WO | 2014184069 | 11/2014 |
| WO | 2014194127 | 12/2014 |
| WO | 2015017528 | 2/2015 |
| WO | 2015017533 | 2/2015 |
| WO | 2015057873 | 4/2015 |
| WO | 2015058129 | 4/2015 |
| WO | 2015061572 | 4/2015 |
| WO | 2015079251 | 6/2015 |
| WO | 2015108992 | 7/2015 |
| WO | 2015112806 | 7/2015 |
| WO | 2015124697 | 8/2015 |
| WO | 2015161274 | 10/2015 |
| WO | 2015161277 | 10/2015 |
| WO | 2015175788 | 11/2015 |
| WO | 2015191666 | 12/2015 |
| WO | 2015191667 | 12/2015 |
| WO | 2016011141 | 1/2016 |
| WO | 2016011144 | 1/2016 |
| WO | 2016011147 | 1/2016 |
| WO | 2016022569 | 2/2016 |
| WO | 2016027754 | 2/2016 |
| WO | 2016037578 | 3/2016 |
| WO | 2016038519 | 3/2016 |
| WO | 2016038552 | 3/2016 |
| WO | 2016075224 | 5/2016 |
| WO | 2016077841 | 5/2016 |
| WO | 2016081450 | 5/2016 |
| WO | 2016/090285 | 6/2016 |
| WO | 2016090285 | 6/2016 |
| WO | 2016096709 | 6/2016 |
| WO | 2016127074 | 8/2016 |
| WO | 2016137060 | 9/2016 |

(56) References Cited

FOREIGN PATENT DOCUMENTS

| | | |
|---|---|---|
| WO | 2016140974 | 9/2016 |
| WO | 2016141169 | 9/2016 |
| WO | 2016149261 | 9/2016 |
| WO | 2016168992 | 10/2016 |
| WO | 2017009644 | 1/2017 |
| WO | 2017011776 | 1/2017 |
| WO | 2017013160 | 1/2017 |
| WO | 2017026718 | 2/2017 |
| WO | 2017027883 | 2/2017 |
| WO | 2017043550 | 3/2017 |
| WO | 2017049462 | 3/2017 |
| WO | 2017079140 | 5/2017 |
| WO | 2017097697 | 6/2017 |
| WO | 2017122815 | 7/2017 |
| WO | 2017145050 | 8/2017 |
| WO | 2017146116 | 8/2017 |
| WO | 2017178844 | 10/2017 |
| WO | 2017178845 | 10/2017 |
| WO | 2017197051 | 11/2017 |
| WO | 2018071447 | 4/2018 |
| WO | WO 18/136661 * | 7/2018 |
| WO | 2019143977 | 7/2019 |
| WO | 2019143991 | 7/2019 |
| WO | 2019143994 | 7/2019 |
| WO | 2020055672 | 3/2020 |

OTHER PUBLICATIONS

Aslibekyan et al., "Association of Methylation Signals With Incident Coronary Heart Disease in an Epigenome-Wide Assessment of Circulating Tumor Necrosis Factor α", JAMA Cardiol., 463-472, Apr. 4, 2018.
Attie et al., "Diversity of RET proto-oncogene mutations in familial and sporadic Hirschsprung disease", Human Molecular Genetics 4(8): 1381-1386, 1995.
Bartsch et al., "A RET double mutation in the germline of a kindred with FMTC.", Exp Clin Endocrinol Diabetes 108(2): 128-132, 2000.
Boeckx et al. "Effect of primary tumor location on second-or later-line treatment outcomes in patients with RAS wild-type metastatic colorectal cancer and all treatment lines in patients with RAS mutations in four randomized panitumumab studies." Clinical colorectal cancer 17.3 (2018): 170-178.
Bosic et al., "Targeted molecular profiling reveals genetic heterogeneity of poromas and porocarcinomas", Pathology. 50(3): 327-332, 2018.
Caira et al, "Crystalline Polymorphism of Organic compounds," Topics in Current Chemistry, Jan. 1998, 198: 163-208.
Cao et al., "The utilization of next-generation sequencing to detect somatic mutations and predict clinical prognosis of Chinese non-small cell lung cancer patients.", Onco. Targets. Ther., (11): 2637-2646, 2018.
Chai et al., "An integrated analysis of cancer genes in thyroid cancer", Oncology Reports, 35(2): 962-970. doi: 10.3892/or.2015.4466, 2015.
Chaudhuri et al., "Early Detection of Molecular Residual Disease in Localized Lung Cancer by Circulating Tumor DNA Profiling.", Cancer Discov; 7(12); 1394-403, 2017.
Chen et al., "Studies on a pedigree of multiple endocrine neoplasia type 2A caused by RET proto-oncogeneC634R mutation with G691S, R982C polymorphisms with review of literature", Medical Journal of Chinese People's Liberation Army, 2013, vol. 38, No. 4, 308-31. English Abstract Only.
Ciampi et al., European Thyroid Journal, vol. 7, Supp. 1, pp. 63. Abstract No. OP-09-66. Meeting Info: 41st Annual Meeting of the European Thyroid Association, ETA 2018. Sep. 15, 2018-Sep. 18, 2018. doi: 10.1159/000491542.
Cohen, Joshua D., et al. "Detection and localization of surgically resectable cancers with a multi-analyte blood test." Science 359.6378 (2018): 926-930.
Comino-Mendez et al., "Predicting Relapse with Circulating Tumor DNA Analysis in Lung Cancer.", Cancer Discov; 7(12); 1368-70, 2017.
Dabir et al., "RAS mutation and expression in small-cell lung cancer.", Journal of Thoracic Oncology, 9(9), 1316-1323, 2014.
Drilon et al. "A phase I/Ib study of RXDX-105, an oral RET and BRAF inhibitor, in patients with advanced solid tumors." S143, 2016.
Dvorakova et al., "New multiple somatic mutations in the RET proto-oncogene associated with a sporadic medullary thyroid carcinoma.", Thyroid, 16(3), 311-316, 2006.
Elisei et al., "Ret Oncogene and Thyroid Carcinoma", Journal of Genetic Syndromes & Gene Therapy, 5(1), 1, 2014.
Fitze et al., "Association between c135G/A genotype and RET proto-oncogene germline mutations and phenotype of Hirschsprung's disease.", Lancet, 393(9313): 1200-1205, 2002.
Gao et al., "Driver Fusions and Their Implications in the Development and Treatment of Human Cancers.", Cell Reports, 23(1), 227-238, 2018.
Gautschi et al., "Targeting RET in Patients With RET-Rearranged Lung Cancers: Results From the Global, Multicenter RET Registry.", Journal of Clinical Oncology, 35(13) 1403-1410, 2017.
Gudernova et al., "One reporter for in-cell activity profiling of majority of protein kinase oncogenes", eLife, 6:e21536. doi: 10.7554/eLife.21536, 2017.
Guerin et al., "Looking beyond the thyroid: advances in the understanding of pheochromocytoma and hyperparathyroidism phenotypes in MEN2 and of non-MEN2 familial forms.", Endocr Relat Cancer, 25(2):TI5-T28. doi: 10.1530/ERC-17-0266, 2017.
Guilmette et al., "Novel gene fusions in secretory carcinoma of the salivary glands: enlarging theETV6 family", Hum Pathol., 83, 50-58, 2019.
Huang, Kuan-lin, et al. "Pathogenic germline variants in 10,389 adult cancers." Cell 173.2 (2018): 355-370.
International Search Report and Written Opinion in International Application No. PCT/US2018/055255, dated Dec. 17, 2018, 8 pages.
International Search Report and Written Opinion in International Application No. PCT/US2018/055279, dated Apr. 1, 2019, 20 pages.
International Search Report and Written Opinion in International Application No. PCT/US2019/049859, dated Jan. 28, 2020, 9 pages.
Isbell et al., "Circulating tumor DNA: A promising biomarker to guide postoperative treatment and surveillance of non-small cell lung cancer.", J Thorac. Cardiovasc. Surg., 155(6), 2628-2631, 2018.
Jhiang et al., "RET mutation screening in MEN2 patients and discovery of a novel mutation in a sporadic medullary thyroid carcinoma." Thyroid, 6(2): 115-21, 1996.
Kaczmarek-Ryś et al., "Modifying impact of RET gene haplotypes on medullary thyroid carcinoma clinical course." Endocrine-related cancer., 25(4): 421-36, 2018.
Kim et al., "Fibroblast growth factor receptor 3 (FGFR3) aberrations in muscle-invasive urothelial carcinoma.", BMC Urol 18(1): 68, 2018.
Lee et al., "A practical guide to pharmaceutical polymorph screening & selection," Asian J of Pharma Sci, Mar. 2014, 9(4): 163-175.
Lee, S-H., et al. "Vandetanib in pretreated patients with advanced non-small cell lung cancer-harboring RET rearrangement: a phase II clinical trial." Annals of Oncology 28.2 (2017): 292-297.
Lu et al., "Circulating free DNA in the era of precision oncology: Pre- and post-analytical concerns.", Chronic Dis. Transl. Med 2(4): 223-230, 2016.
Luo, Wenxin, et al. "Characteristics of genomic alterations of lung adenocarcinoma in young never-smokers." International journal of cancer 143.7 (2018): 1696-1705.
Makki et al., "Serum biomarkers of papillary thyroid cancer.", J Otolaryngol Head Neck Surg., 42(1): 16, 2013.
Moati et al., "Role of circulating tumor DNA in the management of patients with colorectal cancer", Clin. Res. Hepatol. Gastroenterol., 42, 396-402, Apr. 4, 2018.
Moon et al., "Clinical indications for, and the future of, circulating tumor cell", Adv. Drug Deliv. Rev. Apr. 4, 2018.

(56) References Cited

OTHER PUBLICATIONS

Morano et al., "Abstract B049: Characterizing andtargeting RET fusions-positive metastaticcolorectal cancer (mCRC)", Molecular Cancer Therapeutics, vol. 17, No. 1, Molecular Targets and Cancer Therapeutics, 2017.
Nakao et al., "Novel tandem germline RET proto-oncogene mutations in a patient with multiple endocrine neoplasia type 2B: Report of a case and a literature review of tandem RET mutations with in silico analysis", Head and Neck, 35: E363-E368, 2013.
Nakaoku, Takashi, et al. "A secondary RET mutation in the activation loop conferring resistance to vandetanib." Nature communications 9.1 (2018): 1-9.
Nunes, Adriana B., et al. "A Novel Val 648 Ile Substitution in RET Protooncogene Observed in a Cys 634 Arg Multiple Endocrine Neoplasia Type 2A Kindred Presenting with an Adrenocorticotropin-Producing Pheochromocytoma." The Journal of Clinical Endocrinology & Metabolism 87.12 (2002): 5658-5661.
Oliveira, Duarte Mendes, et al. "Next-generation sequencing analysis of receptor-type tyrosine kinase genes in surgically resected colon cancer: identification of gain-of-function mutations in the RET proto-oncogene." Journal of Experimental & Clinical Cancer Research 37.1 (2018): 1-12.
Oussalah et al., "Plasma mSEPT9: A Novel Circulating Cell-free DNA-Based Epigenetic Biomarker to Diagnose Hepatocellular Carcinoma", EBioMedicine, 138-147, 2018.
Plaza-Menacho, Iván. "Structure and function of RET in multiple endocrine neoplasia type 2." Endocrine-related cancer 25.2 (2018): T79-T90.
Qi et al., "RET germline mutations identified by exome sequencing in a Chinese multiple endocrine neoplasia type 2A/familial medullary thyroid carcinoma family.", PLoS One 6(5):e20353, doi: 10.1371/journal.pone.0020353, 2011.
Quintela-Fandino, Miguel, et al. "Selective activity over a constitutively active RET-variant of the oral multikinase inhibitor dovitinib: Results of the CNIO-BR002 phase I-trial." Molecular oncology 8.8 (2014): 1719-1728.
Raue et al., "Long-Term Survivorship in Multiple Endocrine Neoplasia Type 2B Diagnosed Before and in the New Millennium.", J Clin Endocrinol Metab, 103(1): 235-243. doi: 10.1210/jc.2017-01884, 2018.
Reithdorf et al., "The current status and clinical value of circulating tumor cells and circulating cell-free tumor DNA in bladder cancer.", Transl. Andro., Urol. 6(6): 1090-1110, 2017.
Romei et al., "Next generation sequencing revealed RET or RAS mutations in medullary thyroid cancer that were negative at sanger sequencing", European Thyroid Journal, vol. 7, Supp. 1, pp. 63. Abstract No. PI-07-69, 2018.
Romei et al., "RET mutation heterogeneity in primary advanced medullary thyroid cancers and their metastases.", Oncotarget, 9(11): 9875-9884. doi: 10.18632/oncotarget.23986, 2018.
Roskoski et al., "Role of RET protein-tyrosine kinase inhibitors in the treatment RET-driven thyroid and lung cancers.", Pharmacol. Res., 128, 1-17, 2018.
Roy, Madhuchhanda, Herbert Chen, and Rebecca S. Sippel. "Current understanding and management of medullary thyroid cancer." The Oncologist 18.10 (2013): 1093.
Santoro et al., "Minireview: RET: normal and abnormal functions.", Endocrinology, 145(12), 5448-5451, doi: 10.1210/en.2004-0922, 2004.
Severskaya et al., "Germline Polymorphisms of RET and GFRA1 Genes in Patients with Medullary Thyroid Carcinoma", Genomics Transcriptomics Proteomics, 40(3) 375-384, 2006.
Soca-Chafre et al., "Targeted next generation sequencing identified a high frequency genetic mutated profile in wood smoke exposure-related lung adenocarcinoma patients.", Oncotarget 9(55):30499-30512, doi: 10.18632/oncotarget.25369, 2018.
Solassaol et al., "Comparison of five cell-free DNA isolation methods to detect the EGFR T790M mutation in plasma samples of patients with lung cancer", Clin. Chem. Lab Med., vol. 56, issue 9,e243-e246, 2018.
Song et al., "Case report: Whole exome sequencing of circulating cell-free tumor DNA in a follicular thyroid carcinoma patient with lung and bone metastases", J Circ. Biomark., vol. 7, 1-6, Mar. 25, 2018.
Tan et al., "The prognostic value of circulating cell-free DNA in breast cancer: A meta-analysis.", Medicine 97(13):e0197, 2018.
Uchino et al., "Somatic mutations in RET exons 12 and 15 in sporadic medullary thyroid carcinomas: different spectrum of mutations in sporadic type from hereditary type.", Cancer Science, 90(11), 1231-1237, doi: 10.1111/j.1349-7006.1999.tb00701.x, 1999.
Urbini et al., "Whole Exome Sequencing Uncovers Germline Variants of Cancer-Related Genes in Sporadic Pheochromocytoma.", Int J Genomics, 6582014. doi: 10.I 155/2018/6582014, 2018.
VandenBoom et al., "Genomic Fusions in Pigmented Spindle Cell Nevus of Reed.", Am. J Surg. Pathol. 42(8): 1042-1051, 2018.
Volckmar et al., "A field guide for cancer diagnostics using cell-free DNA: From principles to practice and clinical applications.", Genes Chromosomes Cancer 57(3): 123-139, 2018.
Wang et al., "Genomic Profiling of Driver Gene Mutations in 498 Chinese NSCLC Patients", Journal of Thoracic Oncology, (Nov. 2017) vol. 12, No. 11, Supp. Supplement 2, pp. S2105. Abstract No. P2.02-018.
Weng et al., "A comparison of clinical characteristics between 2 pedigrees of multiple endocrine neoplasia type 2A with different RET mutations.", Zhonghua Nei Ke Za Zhi, 57(2): 134-137, 2018. English Abstract Only.
Yao et al., "DelD631: a novel mutation of the RET proto-oncogene in multiple endocrine neoplasia type 2A (MEN2A)", Natl Med J China, 87(28): 1962-1965, 2007. English Abstract Only.
Yeganeh et al., "RET proto oncogene mutation detection and medullary thyroid carcinoma prevention.", Asian Pac J Cancer Prev, 16(6), 2107-17, 2015.
Yi et al., "A Novel RET D898Y Germline Mutation in a Patient with Pheochromocytoma", Case Rep. Endocrinol. 2018:8657314, 2018. doi: 10.I 155/2018/8657914, 6 pages, 2018.
Yu et al. "Multiple Biomarker Testing Tissue Consumption and Completion Rates With Single-gene Tests and Investigational Use of Oncomine Dx Target Test for Advanced NoneSmall-cell Lung Cancer: A Single-center Analysis", Clin Lung Cancer, 20-29, 2019.
Zamay et al., "Current and Prospective Protein Biomarkers of Lung Cancer.", Cancers (Basel). 9(11): 155, 2017.
Zhang et al., "Identification of a novel KIF13A-RET fusion in lung adenocarcinoma by next-generation sequencing", Lung Cancer, 118, 27-29. doi: 10.1016/j.lungcan.2017.08.019, 2018.
Zhao et al., "Mutation profiling and treatment choosing of Chinese RET positive advanced lung cancer patients", Journal of Clinical Oncology vol. 36, No. 15, Supp. [S], MA e21139, 2018.
Albaugh et al., "Discovery of GNF-5837, a Selective TRK Inhibitor with Efficacy in Rodent Cancer Tumor Models," ACS Med Chem. Lett., Jan. 1, 2012;3(2):140-145.
Amit Met al., "Upregulation of cRET induces perineurial invasion of pancreatic adenocarcinoma." Oncogene Jun. 8, 2017; 36:3232-3239.
Andreucci et al., "Targeting the receptor tyrosine kinase RET in combination with aromatase inhibitors in ER positive breast cancer xenografts," Oncotarget, Dec. 6, 2016, 7(49):80543-80553.
Antonescu et al., "Molecular characterization of inflammatory myofibroblastic tumors with frequent ALK and ROS1 gene fusions and rare novel RET rearrangement," Am J Surg Pathol, Jul. 2015;39(7):957-967.
Arighi et al., "RET tyrosine kinase signaling in development and cancer," Cytokine Growth Factor Rev, Aug.-Oct. 2005;16(4-5):441-467.
Ballerini et al., "RET fusion genes are associated with chronic myelomonocytic leukemia and enhance monocytic differentiation," Leukemia, Nov. 2012;26(11):2384-2389.
Bastien et al., "Detection and characterization of a novel RET translocation in lung adenocarcinoma." Journal of Molecular Diagnostics, 18(6):1027, Abstract No. SI20, 2016 Annual Meeting of the Association for Molecular Pathology, Charlotte, NC, 2016.
Behrens et al., "Go 6976 is a potent inhibitor of neurotrophin-receptor intrinsic tyrosine kinase," J Neurochem. Mar. 1999;72(3):919-924.

(56) References Cited

OTHER PUBLICATIONS

Bhinge et al., "EGFR mediates activation ofRET in lung adenocarcinoma with neuroendocrine differentiation characterized by ASCLI expression," Oncotarget, Apr. 18, 2017, 8(16):27155-27165.
Borecka et al., "Identification of pancreatic cancer susceptibility genes in the Czech Republic." European Journal of Cancer, (Jul. 2016) vol. 61, No. 1, pp. S26, Abstract No. 162, Meeting Info: 24th Biennial Congress of the European Association for Cancer Research, EACR 2016. Manchester, United Kingdom.
Borre, P. Vanden et al., "Pediatric, adolescent and young adult (PAYA) thyroid carcinoma harbors frequent and diverse targetable genomic alterations including kinase fusions." Annals of Oncology, 2016, vol. 27, Supp. Supplement 6. Abstract No. 427PD; European Society for Medical Oncology Congress, ESMP 2016. Copenhagen, Denmark. Oct. 7, 2016-Oct. 11, 2016.
Borrello et al., "RET inhibition: implications in cancer therapy," Expert Opin. Ther. Targets, Apr. 2013, 17(4):403-419.
Boulay et al., "The Ret receptor tyrosine kinase pathway functionally interacts with the ERalpha pathway in breast cancer," Cancer Res., May 15, 2008;68(10):3743-3751.
Brodeur, "Neuroblastoma: biological insights into a clinical enigma," Nat Rev Cancer., Mar. 2003, 3(3):203-216.
Calero et al., "Sunitinib suppress neuroblastoma growth through degradation of MYCN and inhibition of angiogenesis," PLoS One. Apr. 23, 2014;9(4):e95628.
Camilleri, "Peripheral mechanisms in irritable bowel syndrome," N Engl J Med, Oct. 25, 2012, 367(17):1626-1635.
Camoratto et al., "CEP-751 inhibits TRK receptor tyrosine kinase activity in vitro exhibits anti-tumor activity," Int J Cancer. Aug. 7, 1997;72(4):673-679.
Camos et al., "Gene expression profiling of acute myeloid leukemia with translocation t(8;16)(pll;pl3) and MYST3-CREBBP rearrangement reveals a distinctive signature with a specific pattern of HOX gene expression," Cancer Res., Jul. 15, 2006;66(14):6947-6954.
Cancer Genome Atlas Network, "Comprehensive molecular characterization of human colon and rectal cancer," Nature, Jul. 18, 2012;487(7407):330-337.
Carlomagno et al., "Identification of tyrosine 806 as a molecular determinant of RET kinase sensitivity to ZD6474," Endocr. Rel. Cancer, Mar. 2009;I6(1):233-241.
Carpinelli et al., "PHA-739358, a potent inhibitor of Aurora kinases with a selective target inhibition profile relevant to cancer," Mol Cancer Ther., Dec. 2007;6(12 Pt 1):3158-68.
Cecchirini et al., "Somatic in frame deletions not involving juxtamembranous cysteine residues strongly activate the RET proto-oncogene," Oncogene, May 29, 1997;14(21):2609-2612.
Ceolin et al., "Effect of 3'UTR RET Variants on RET mRNA Secondary Structure and Disease Presentation in Medullary Thyroid Carcinoma," PLoS One, Feb. 1, 2016;11(2):e0147840. doi: 10.137Ii'joumal.pone.0147840. eCollection 2016.
Chang et al., "EGF Induced RET Inhibitor Resistance in CCDC6-RET Lung Cancer Cells," Yonsei Med J, Jan. 2017, 58(1):9-18.
Choi et al., "(R)-2-Phenylpyrrolidine Substituted Imidazopyridazines: A New Class of Potent and Selective Pan-TRK Inhibitors," ACS Med Chem Lett., Mar. 16, 2015;6(5):562-567.
Corsello et al., "A case of MEN2A associated to Leu56Met RET mutation." Endocrine Reviews, (Jun. 2014) vol. 35, No. 3, Suppl. 5, pp. SUN-0322, Meeting Info.: 96th Annual Meeting and Expo of the Endocrine-Society, Chicago, IL, USA, Jun. 21-24, 2014.
Cranston et al., "RET is constitutively activated by novel tandem mutations that alter the active site resulting in multiple endocrine neoplasia type 2B," Cancer Res., Oct. 15, 2006;66(20): 10179-10187.
Croucher et al., "TrkB inhibition by GNF-4256 slows growth and enhances chemotherapeutic efficacy in neuroblastoma xenografts," Cancer Chemother Pharmcol., Jan. 2015;75(1):131-141.
Das, Shubhajit, Pralok K. Samanta, and Swapan K. Pati. "Watson-Crick base pairing, electronic and photophysical properties of triazole modified adenine analogues: a computational study." New Journal of Chemistry 39.12 (2015): 9249-9256.
Davila et al., "Comprehensive genomic profiling of a rare thyroid follicular dendritic cell sarcoma," Rare Tumors, 2017, 9(2):6834.
Dawson et al., "Altered expression of RET proto-oncogene product in prostatic intraepithelial neoplasia and prostate cancer," J Natl Cancer Inst, Apr. 1, 1998;90(7):519-523.
De Almeida et al., "Expanded analysis of variants of unknown significance of RET gene." Endocrine Reviews, 2016, vol. 37, No. 2, Supp. Supplement 1. Abstract No. SUN-068; 93th Annual Meeting and Expo of the Endocrine Society, ENDO 2016. Boston, MA, US. Apr. 1, 2016-Apr. 4, 2016.
De Groot et al., "RET as a diagnostic and therapeutic target in sporadic and hereditary endocrine tumors," Endocrine Rev, Aug. 2006 27(5):535-560.
Demeure et al., "Whole-genome Sequencing of an Aggressive BRAF Wild-type Papillary Thyroid Cancer Identified EML4-ALK Translocation as a Therapeutic Target," World J. Surg., Jun. 2014, 38(6):1296-305.
Diner er al., "Preparation of 3-substituted-1-isopropyl-1H-pyrazolo[3,4-d]pyrimidin-4-amines as RET kinase inhibitors," J. Med. Chem., May 24, 2012, 55(10):4872-4876.
Ding et al., "Artemin, a member of the glial cell line-derived neurotrophic factor family of ligands, is HER2-regulated and mediates acquired trastuzumab resistance by promoting cancer stem cell-like behavior in mammary carcinoma cells," J Biol Chem, Jun. 6, 2014, 289(23):16057-71.
Dogan et al., "Genomic profiling of the two closely related "cousins" acinic cell carcinoma and mammary analog secretory carcinoma of salivary glands reveals novel NCOA-4-RET fusion in mammary analog secretory carcinomas." Laboratory Investigation, (Feb. 2017) vol. 97, Supp. 1, pp. 323A. Abstract No. 1298, Meeting Info: 106th Annual Meeting of the United States and Canadian Academy of Pathology, USCAP 2017. San Antonio, TX, United States.
Drilon et al., "Phase II study of cabozantinib for patients with advanced RET-rearranged lung cancers," Journal of Clinical Oncology, May 20, 2015, 51st Annual Meeting, 33(15S):8007-8007 [Abstract Only], 6 pages.
Esseghir et al., "A role for glial cell derived neurotrophic factor induced expression by inflammatory cytokines and RET/GFR alpha 1 receptor up-regulation in breast cancer," Cancer Res, Dec. 15, 2007;67(24):11732-11741.
Fang et al., "Detection of a novel RET gene fusion in a non-small cell lung cancer patient using AMP chemistry." Journal of Thoracic Oncology, Feb. 1, 2016,11(2):S21-S22.
Flavin et al., "RET protein expression in papillary renal cell carcinoma," Urol. Oncol., Nov.-Dec. 2012 30(6):900-905.
Fugazzola et al., "Molecular and biochemical analysis of RET/PTC4, a novel oncogenic rearrangement between RET and ELE1 genes, in a post-Chemobyl papillary thyroid cancer," Oncogene, Sep. 1996, 13(5): 1093-7.
Futami et al., "A novel somatic point mutation of the RET Proto-oncogene in tumor tissues of small cell lung cancer patients," Jpn. J. Cancer Res., Dec. 1995, 86(12):1127-1130.
Gao et al., "Neurotrophic Factor Artemin Promotes Invasiveness and Neurotrophic Function of Pancreatic Adenocarcinoma In Vivo and In Vitro," Pancreas, Jan. 2015, 44(1):134-143.
Gattei et al., "Expression of the RET receptor tyrosine kinase and GDNFR-alpha in normal and leukemic human hematopoietic cells and stromal cells of the bone marrow microenvironment," Blood, Apr. 15, 1997;89(8):2925-2937.
Gattei, et al., "Differential expression of the RET gene in human acute myeloid leukemia," Ann. Hematol, Nov. 1998, 77(5):207-210.
Gattelli et al., "Ret inhibition decreases growth and metastatic potential of estrogen receptor positive breast cancer cells," EMBO Mol. Med., Sep. 2013;5(9):1335-1350.
Gazizova et al., "Mutation analysis of the RET proto-oncogene in 35 Russian families with Men 2A, Men 2B and Fmtc: Four novel mutations for Men 2A." Endocrine Reviews, (Jun. 2014) vol. 35, No. 3, Suppl. S, pp. SAT-0304, Meeting Info.: 96th Annual Meeting and Expo of the Endocrine-Society, Chicago, IL, USA, Jun. 21-24, 2014.

(56) References Cited

OTHER PUBLICATIONS

Gil et al., "Paracrine regulation of pancreatic cancer cell invasion by peripheral nerves," J. Natl. Cancer Inst., Jan. 20, 2010;102(2):107-118.
Gozgit et al., "RET fusions identified in colorectal cancer PDX models are sensitive to the potent RET inhibitor ponatinib," AACR Annnal Meeting, Apr. 7, 2014, Presentation Abstract, [Abstract Only], 1 page.
Greco et al., "Molecular pathology of differentiated thyroid cancer," J. Nucl. Med. Mol. Imaging, Oct. 2009, 53:440-454.
Greene & Wuts, eds., "Protecting Groups in Organic Synthesis", 2nd ed. New York; John Wiley & Sons, Inc., 1991, Chapter One, 20 pages.
Grey et al., "The RET E616Q Variant is a Gain of Function Mutation Present in a Family with Features of Multiple Endocrine Neoplasia 2A," Endocrine Pathology, Mar. 2017, 28(1):41-48.
Grieco et al., "PTC is a novel rearranged form of the ret proto-oncogene and is frequently detected in vivo in human thyroid papillary carcinomas," Cell, Feb. 23, 1990, 60(4):557-563.
Grubbs et al., "RET fusion as a novel driver of medullary thyroid carcinoma," J. Clin. Endocrinol. Metab., Mar. 2015;I00(3):788-793.
Gura et al., Systems for identifying new drugs are often faulty, Science, 278:1041-1042, 1997.
Hackam, Daniel G., and Donald A. Redelmeier. "Translation of research evidence from animals to humans." Jama 296.14 (2006): 1731-1732.
Halkova et al., "A novel RET/PTC variant detected in a pediatric patient with papillary thyroid cancer without ionization history," Human Pathology, Dec. 2015, 46(12):1962-1969.
Hezam et al., "Artemin promotes oncogenicity, metastasis and drug resistance in cancer cells," Rev Neurosci, Jan. 26, 2018, 29(1):93-98.
Hirshfield et al., "Abstract P3-07-02: are we missing actionable targets in breast cancer? Novel insights into recurrent Ret alterations." Cancer Research, (Feb. 2017) vol. 77, No. 4, Supp. 1. Abstract No. P3-07-02. Meeting Info: 39th Annual CTRC-AACR San Antonio Breast Cancer Symposium. San Antonio, TX, United States. Dec. 6, 2016-Dec. 10, 2016.
Hoffman et al., "Activation of colonic mucosal 5-HT(4) receptors accelerates propulsive motility and inhibits visceral hypersensitivity," Gastroenterology, Apr. 2012;I42(4):844-854.
Hofstra et al., "No mutations found by RET mutation scanning in sporadic and hereditary neuroblastoma," Hum Genet., Mar. 1996, 97(3):362-364.
Huang et al., "Preclinical Modeling of KIF5B-RET Fusion Lung Adenocarcinoma," Mol. Cancer Ther., Oct. 2016, 15(10):2521-2529.
Ibrahimpasic et al., "Genomic Alterations in Fatal Forms of Non-Anaplastic Thyroid Cancer: Identification of MED12 and RBMIO as Novel Thyroid Cancer Genes Associated with Tumor Virulence," Clin. Cancer Res., Oct. 2017, 23(19):5970-5980.
International Preliminary Report on Patentability in International Application No. PCT/US2016/042576, dated Jan. 25, 2018, 7 pages.
International Preliminary Report on Patentability in International Application No. PCT/US2018/014279, dated Jul. 23, 2019, 7 pages.
International Preliminary Report on Patentability in International Application No. PCT/US2019/014272, dated Jul. 21, 2020, 13 pages.
International Preliminary Report on Patentability in International Application No. PCT/US2019/014277, dated Jul. 21, 2020, 11 pages.
International Preliminary Report on Patentability in International Application No. PCT/US2019/014248, dated Jul. 21, 2020, 11 pages.
International Search Report and Written Opinion in International Application No. PCT/US2016/042576, dated Sep. 27, 2016, 12 pages.
International Search Report and Written Opinion in International Application No. PCT/US2018/014279, dated May 3, 2018, 10 pages.
International Search Report and Written Opinion in International Application No. PCT/US2019/014272, dated May 24, 2019, 19 pages.
International Search Report and Written Opinion in International Application No. PCT/US2019/014277, dated May 24, 2019, 17 pages.
International Search Report and Written Opinion in International Application No. PCT/US2019/014248, dated May 24, 2019, 21 pages.
Ito et al., "Expression of glial cell line-derived neurotrophic factor family members and their receptors in pancreatic cancers," Surgery, Oct. 2005, 138(4):788-794.
Iwahashi et al., "Expression of glial cell line-derived neurotrophic factor correlates with perineural invasion of bile duct carcinoma," Cancer, Jan. 1, 2002, 94(1):167-174.
Iyama et al., "Identification of Three Novel Fusion Oncogenes, SQSTMI/NTRK.3, AFAP1L2/RET, and PPFIBP2/RET, in Thyroid Cancers of Young Patients in Fukushima ," Thyroid, Jun. 2017, 27(6):811-818.
Iyer et al, "AZ64 inhibits TrkB and enhances the efficacy of chemotherapy and local radiation in neuroblastoma xenografts," Cancer Chemother Pharmacol., Sep. 2012;70(3):477-486.
Johnson et al., Relationships between drug activity in NCI preclinical in vitro and in vivo models and early clinical trials, British Journal of Cancer, 84(10):1424-1431,2001.
Jordan, V. Craig. "Tamoxifen: a most unlikely pioneering medicine." Nature reviews Drug discovery 2.3 (2003): 205-213.
Joung et al., "Diffuse sclerosing variant of papillary thyroid carcinoma: major genetic alterations and prognostic implications," Histopathology, Jul. 2016, 69(1):45-53.
Jovanovic et al., "Novel RET mutations in macedonian patients with medullary thyroid carcinoma: genotype-phenotype correlations," Pril (Makedon Akad Nauk Umet Odd Med Nauki), 2015;36(1):93-107.
Ju et al., "A transforming KIF5B and RET gene fusion in lung adenocarcinoma revealed from whole-genome and transcriptome sequencing," Genome Res., Mar. 2012;22(3):436-445.
Kaneta et al., Abstract B173: Preclinical characterization and antitumor efficacy ofDS-5010, a highly potent and selective RET inhibitor, Mol Cancer Ther Jan. 1, 2018 (17) (1 Supplement) BI 73; DOI:10.1158/1535-7163.TARG-I7-BI73.
Karachialiou et al., "Real-time liquid biopsies become a reality in cancer treatment," Ann. Transl. Med, Mar. 2015, 3(3):36.
Karrasch et al., "How to Assess the Clinical Relevance of Novel RET Missense Variants in the Absence of Functional Studies?" Eur. Thyroid J., Mar. 2016;5(1):73-77.
Kato et al., "Repair by Src kinase of function-impaired RET with multiple endocrine neoplasia type 2A mutation with substitutions of tyrosines in the COOR-terminal kinase domain for phenylalanine," Cancer Res., Apr. 15, 2002, 62(8):2414-2422.
Kato et al., "RET Aberrations in Diverse Cancers: Next-Generation Sequencing of 4,871 Patients," Clin. Cancer Res., Apr. 15, 2017, 23(8):1988-1997.
Keszthelyi et al., "Revisiting concepts of visceral nociception in irritable bowel syndrome," Eur. J. Pain, Nov. 2012 16(10):1444-1454.
Kheiroddin et al., "RET Gene Analysis in Patients with Medullary Thyroid Carcinoma," Clin. Lab., Jan. 2016, 62(5):871-876.
Kim et al., "A new germline ALA641Thr variant in the transmembrane domain of the RET gene associated with medullary thyroid cancer," Acta Endocrinologica-Bucharest, Apr. 2015, 11(2):189-194.
Kim et al., "Mammaglobin-A is a target for breast cancer vaccination," Oncoimmunology. Feb. 26, 2016;5(2):el069940. eCollection Feb. 2016.
Kloosterman et al., "A systematic analysis of oncogenic gene fusions in primary colon cancer," Cancer Res., Jul. 15, 2017, 77(14):3814-3822.
Klugbauer et al., "A novel type of RET rearrangement (PTC8) in childhood papillary thyroid carcinomas and characterization of the involved gene (RFG8)," Cancer Res., Dec. 15, 2000;60(24):7028-32.
Kohlmann et al., "Next-Generation Sequencing Technology Reveals a Characteristic Pattern of Molecular Mutations in 72.8% of Chronic

(56) References Cited

OTHER PUBLICATIONS

Myelomonocytic Leukemia by Detecting Frequent Alterations in TET2, CBL, RAS, and RUNXI," J. Clin. Oncol. Aug. 20, 2010, 28(24):3858-3865.
Kohno et al., "KIF5B-RET fusions in lung adenocarcinoma," Nature Med., Feb. 12, 2012;18(3):375-377.
Kooistra et al., "KLIFS: A structural kinase ligand interaction database," Nucleic Acids Res., Jan. 2016, 44(DI)D365-D371.
Kraft et al, "Abstract 4882: genomic mechanisms of disease progression in pediatric medullary thyroid cancer (MTC)." Cancer Research, 2017, vol. 77, No. 13, Supp. Supplement 1. American Association for Cancer Research Annual Meeting 2017. Washington, DC, United States. Apr. 1, 2017-Apr. 5, 2017.
Krampitz et al., "RET gene mutations (genotype and phenotype) of multiple endocrine neoplasia type 2 and familial medullary thyroid carcinoma," Cancer, Jul. 2014 I; 120(13):1920-1931.
Kubler et al. "Self-adjuvanted mRNA vaccination in advanced prostate cancer patients: a first-in-man phase I/IIa study," J Immunother Cancer. Jun. 16, 2015, 3:26, 14 pages.
Latteyer et al., "A 6-Base Pair in Frame Germline Deletion in Exon 7 OfRET Leads to Increased RET Phosphorylation, ERK Activation, and MEN2A," J. Clin Endocrinol. Metab., Mar. 2016;101(3):1016-1022.
Le Rolle et al., "Identification and characterization of RET fusions in advanced colorectal cancer," Oncotarget, Oct. 6, 2015;6(30):28929-28937.
Lecht et al., "Angiostatic effects of K252a, a Trk inhibitor, in murine brain capillary endothelial cells," Mol Cell Biochem. Jun. 2010;339(1-2):201-213.
Lee et al., "Identification of a novel partner gene, KIAA1217, fused to RET: Functional characterization and inhibitor sensitivity of two isoforms in lung adenocarcinoma," Oncotarget, May 2, 2016, 7(24):36101-36114.
Lee et al., "Whole-exome sequencing identified mutational profiles of high-grade colon adenomas," Oncotarget, Jan. 2017, 8(4): 6579-6588.
Li et al., "Trk inhibitor attenuates the BDNF/frkB-induced protection of neuroblastoma cells from etoposide in vitro and in vivo," Cancer Biol Ther., 2015;16(3):477-483.
Lipson et al., "Identification of new ALK and RET gene fusions from colorectal and lung cancer biopsies," Nature Med., Feb. 12, 2012;18(3):382-384.
Liu et al., "Oncogenic RET receptors display different autophosphorylation sites and substrate binding specificities," J Biol. Chem., J Biol Chem. Mar. 8, 1996;271(10):5309-5312.
Lopez-Delisle, Lucille, et al. "Activated ALK signals through the ERK-ETV5-RET pathway to drive neuroblastoma oncogenesis." Oncogene 37.11 (2018): 1417-1429.
Louis et al., "The 2016 World Health Organization Classification of Tumors of the Central Nervous System: a summary," Acta Neuropathol, Jun. 2016, 131(6):803-820.
Lu et al., "Targeted next generation sequencing identifies somatic mutations and gene fusions in papillary thyroid carcinoma," Oncotarget, Jul. 2017, 8(28):45784-45792.
Luo et al., "RET is a potential tumor suppressor gene in colorectal cancer," Oncogene, Apr. 18, 2013;32(16):2037-2047.
Mamedova et al., "Abstract #6: Construction of Baculovirial Vectors for RET Kinase Domain Mutants," Summer Undergraduate Research Programs (SURF) Student Abstracts, University of Oklahoma Health Sciences Center, 2016, p. 28 [Abstract Only].
Matsubara et al., "Identification of CCDC6-RET fusion in the human lung adenocarcinoma cell line, LC-2/ad," Journal of Thoracic Oncology, Dec. 2012;7(12):1872-1876.
McCarthy et al., "Tropomyosin receptor kinase inhibitors: a patent update 2009-2013," Expert. Opin. Ther. Pat., Jul. 2014;24(7):731-744.
Mendiola et al., "Preparation, Use, and Safety of O-Mesitylenesulfonylhydroxylamine," Org. Process Res. Dev., Jan. 2009, 13(2):263-267.
Montagnoli et al., "Anti-proliferative effects of GW441756, a novel inhibitor of NGF receptor tyrosine kinase a (TRKA), in human sarcoma," Italian Journal of Anatomy and Embryology, Nov. 11, 2010, 115(1/2):117.
Morandi et al., "GDNF-RET signaling in ER-positive breast cancers is a key determinant of response and resistance to aromatase inhibitors," Cancer Res., Jun. 15, 2013;73(12):3783-3795.
Morgensztem et al., "Circulating cell-free tumor DNA (cfDNA) testing in small cell lung cancer." Journal of Thoracic Oncology, (Jan. 2017) vol. 12, No. 1, Supp. 1, pp. S717-S718, Abstract No. PI.07-035, Meeting Info: 17th World Conference of the International Association for the Study of Lung Cancer, IASLC 2016. Vienna, Austria. Dec. 4, 2016.
Mulligan et al., "Investigation of the genes for RET and its ligand complex, GDNF/GFR alpha-I, in small cell lung carcinoma," Genes Chromosomes Cancer, Apr. 1998, 21(4):326-332.
Mulligan, "RET revisited: expanding the oncogenic portfolio," Nature Reviews Cancer, Mar. 2014, 14(3):173-186.
Narayanan et al., "Discovery and preclinical characterization of novel small molecule TRK and ROS1 tyrosine kinase inhibitors for the treatment of cancer and inflammation," PLoS One. Dec. 26, 2013;8(12):e83380.
Narita et al., "Functional RET G691S polymorphism in cutaneous malignant melanoma," Oncogene, Aug. 27, 2009;28(34):3058-3068.
Nelson-Taylor et al., "Resistance to RET-Inhibition in RET-Rearranged NSCLC Is Mediated by Reactivation of RAS/MAPK Signaling," Mol. Cancer Ther., Aug. 2017, 16(8):1623-1633.
Ott et al., "An immunogenic personal neoantigen vaccine for patients with melanoma," Nature. Jul. 13, 2017, 547(7662):217-221.
Pearce et al., Failure modes in anticancer drug discovery and development, Cancer Drug Design and Discovery Edited by Stephen Neidle, Chapter 18, pp. 424-435 (2008).
Petersen et al. "The RET and TRKA pathways collaborate to regulate neuroblastoma differentiation," Oncogene, Jan. 8, 2004;23(1):213-225.
Pirker et al., "Alectinib in RET-rearranged non-small cell lung cancer—Another progress in precision medicine?" Transl. Lung Cancer Res., Dec. 2015;4(6):797-800.
Plaza-Menacho et al., "Targeting the receptor tyrosine kinase RET sensitizes breast cancer cells to tamoxifen treatment and reveals a role for RET in endocrine resistance," Oncogene, Aug. 19, 2010;29(33):4648-4657.
Plenker et al., "Drugging the catalytically inactive state of RET kinase in RET-rearranged tumors," Sci Transl Med, Jun. 14, 2017, 9(394). 11 pages.
Plosker, "Sipuleucel-T: in metastatic castration-resistant prostate cancer," Drugs. Jan. 1, 2011;71(1):101-108.
Postow et al., "Immune Checkpoint Blockade in Cancer Therapy," Journal of Clinical Oncology, Jun. 10, 2015;33(17):1974-1982.
Qi, et al., "RET mutation p.S891A in a Chinese family with familial medullary thyroid carcinoma and associated cutaneous amyloidosis binding OSMR variant p.G513D," Oncotarget, Oct. 20, 2015;6(32):33993-4003.
Rausch et al., "mRNA vaccine CV9103 and CV9104 for the treatment of prostate cancer," Human Vaccin immunother, 2014;10(11):3146-3152.
Reeser et al., "Validation of a Targeted RNA Sequencing Assay for Kinase Fusion Detection in Solid Tumors," J Mol. Diagn., Sep. 2017, 19(5):682-696.
Reungwetwattana et al., "Targeted therapies in development for non-small cell lung cancer," J Carcinog., Dec. 31, 2013;12:22.
Roblin et al., "Topical TrkA Kinase Inhibitor CT327 is an Effective, Novel Therapy for the Treatment of Pruritus due to Psoriasis: Results from Experimental Studies, and Efficacy and Safety of CT327 in a Phase 2b Clinical Trial in Patients with Psoriasis," Acta Denn Venereal, May 2015;95(5):542-548.
Romei and Elisei, "RET/PTC Translocations and Clinico-Pathological Features in Human Papillary Thyroid Carcinoma," Front Endocrinol (Lausanne), Apr. 11, 2012, 3:54.
Romei et al., The mutation profile of medullary thyroi carcinoma can be different in primary and metastatic tissues. European Thyroid

(56) References Cited

OTHER PUBLICATIONS

Journal (Aug. 2016) vol. 5, Supp. Supplement 1, pp. 75; 39th Annual Meeting of the European Thyroid Association, ETA 2016. Copenhagen, Denmark. Sep. 3, 2016-Sep. 6, 2016.
Rosenzweig et al., "A case of advanced infantile myofibromatosis harboring a novel MYHIO-RET fusion," Pediatr Blood Cancer, Jul. 2017;64(7). doi: 10.1002/pbc.26377. Epub Dec. 28, 2016.
Sabari et al., "Targeting RET-rearranged lung cancers with multikinase inhibitors," Oncoscience, Mar. 2017, 4(3-4):23-24.
Sahin et al., "Personalized RNA mutanome vaccines mobilize poly-specific therapeutic immunity against cancer," Nature, Jul. 13, 2017, 547(7662):222-226.
Saito et al., "Gene aberrations for precision medicine against lung adenocarcinoma," Cancer Science, Jun. 2016;107(6):713-720.
Santoro et al., "Development of thyroid papillary carcinomas secondary to tissue-specific expression of the RET/PTCI oncogene in transgenic mice," Oncogene, Apr. 18, 1996, 12(8):1821-1826.
Scollo et al., "A novel RET gene mutation in a patient with apparently sporadic pheochromocytoma," Endocr. J., 2016;63(1):87-91.
Silva et al., "Identification and characterization of two novel germline RET variants associated with medullary thyroid carcinoma," Endrocrine, Jun. 2015, 49(2):366-372.
Simone, Oncology: Introduction, Cecil Textbook of Medicine, 20th Edition, vol. 1, pp. 1004-1010, 1995.
Sjoblom et al., "The consensus coding sequences of human breast and colorectal cancers," Science, Oct. 13, 2006;314(5797):268-274.
Skalova et al., "Molecular Profiling of Mammary Analog Secretory Carcinoma Revealed a Subset of Tumors Harboring a Novel ETV6-RET Translocation: Report of 10 Cases," Am. J Surg. Pathol., Feb. 2018, 42(2):234-246.
Song et al., "Potent antitumor activity of cabozantinib, a c-MET and VEGFR2 inhibitor, in a colorectal cancer patient-derived tumor explant model," "International Journal of Cancer, Apr. 15, 2015;136(8):1967-1975".
Sromek et al., "Analysis of Newly Identified and Rare Synonymous Genetic Variants in the RET Gene in Patients with Medullary Thyroid Carcinoma in Polish Population," Endocr Pathol., Sep. 2017, 28(3):198-206.
Su et al., "RET/PTC Rearrangements Are Associated with Elevated Postoperative TSH Levels and Multifocal Lesions in Papillary Thyroid Cancer without Concomitant Thyroid Benign Disease," PLoS One, Nov. 1, 2016, II(II):e0165596.
Takeuchi et al., "RET, ROSI and ALK fusions in lung cancer," Nature Med., Feb. 12, 2012;18(3):378-381.
Tang, Zhenya, et al. "Coexistent genetic alterations involving ALK, RET, ROS1 or MET in 15 cases of lung adenocarcinoma." Modern Pathology 31.2 (2018): 307-312.
Taraviras et al., "Signalling by the RET receptor tyrosine kinase and its role in the development of the mammalian enteric nervous system," Development, Jun. 1999;I26(12):2785-2797.
Thress et al., "Identification and preclinical characterization of AZ-23, a novel, selective, and orally bioavailable inhibitor of the Trk kinase pathway," Mol. Cancer Ther., Jul. 2009;8(7):1818-1827.
Tjaden et al., "The developmental etiology and pathogenesis of Hirschsprung disease," Transl. Res., Jul. 2013 162(1):1-15.
Van Linden et al., "KLIFS: A knowledge based structural database to navigate kinase-ligand interaction space," J Med Chem., Jan. 23, 2014, 57(2):249-277.
Velcheti et al., "FRMD4A/RET: A Novel RET Oncogenic Fusion Variant in Non-Small Cell Lung Carcinoma," J Thorac Oncol., Feb. 2017, 12(2):e15-e16.
Wang et al., "Identification of 4-aminopyrazolylpyrimidines as potent inhibitors of Trk kinases," J Med Chem. Aug. 14, 2008;51(15):4672-4684.
Wang, Chengyan, et al. "Synthesis and structure-activity relationship study of pyrazolo [3, 4-d] pyrimidines as tyrosine kinase RET inhibitors." Bioorganic & medicinal chemistry letters 27.11 (2017): 2544-2548.
Wang et al., "Trk kinase inhibitors as new treatments for cancer and pain," Expert Opin. Ther. Pat., Mar. 19, 2009; (3):305-319.
Wells et al. "Targeting the RET pathway in thyroid cancer," Clin Cancer Res., Dec. 1, 2009;15(23):7119-7123.
Wells et al., "Revised American Thyroid Association guidelines for the management of medullary thyroid carcinoma," Thyroid, Jun. 2015;25(6):567-610.
Wood et al, "The genomic landscapes of human breast and colorectal cancers," Science, Nov. 16, 2007, 318(5853):1108-1113.
Yoon et al., "A Pyrazolo[3,4-d]pyrimidin-4-amine Derivative Containing an Isoxazole Moiety Is a Selective and Potent Inhibitor of RET Gatekeeper Mutants," J. Med. Chem., Jan. 14, 2016, 59(1):358-373.
Zage et al.,"The selective Trk inhibitor AZ623 inhibits brain-derived neurotrophic factor-mediated neuroblastoma cell proliferation and signaling and is synergistic with topotecan," Cancer, Mar. 15, 2011;117(6):1321-1391. doi: 10.1002/cncr.25674. Epub Oct. 19, 2010.
Zeng et al. "The relationship between overexpression of glial cell-derived neurotrophic factor and its RET receptor with progression and prognosis of human pancreatic cancer," J. Int. Med. Res., Jul.-Aug. 2008;36(4):656-664.
Zhang et al., "Morphological and molecular features of gastric glomus tumors." Laboratory Investigation, (Feb. 2017) vol. 97, Supp. 1, pp. 209A. Abstract No. 840, Meeting Info: 106th Annual Meeting of the United States and Canadian Academy of Pathology, USCAP 2017. San Antonio, TX, United States.

* cited by examiner

SUBSTITUTED PYRAZOLO[1,5-A]PYRAZINES AS RET KINASE INHIBITORS

CROSS-REFERENCE TO RELATED APPLICATIONS

This application claims priority to U.S. Provisional Application Ser. No. 62/447,862, filed on Jan. 18, 2017, which is hereby incorporated by reference in its entirety.

BACKGROUND

The present disclosure relates to novel compounds which exhibit Rearranged during Transfection (RET) kinase inhibition, pharmaceutical compositions comprising the compounds, processes for making the compounds, and the use of the compounds in therapy. More particularly, it relates to substituted pyrazolo[1,5-a]pyrazine compounds useful in the treatment and prevention of diseases which can be treated with a RET kinase inhibitor, including RET-associated diseases and disorders.

RET is a single-pass transmembrane receptor belonging to the tyrosine kinase superfamily that is required for normal development, maturation and maintenance of several tissues and cell types (Mulligan, L. M., *Nature Reviews Cancer,* 2014, 14, 173-186). The extracellular portion of the RET kinase contains four calcium-dependent cadherin-like repeats involved in ligand binding and a juxtamembrane cysteine-rich region necessary for the correct folding of the RET extracellular domain, while the cytoplasmic portion of the receptor includes two tyrosine kinase subdomains.

RET signaling is mediated by the binding of a group of soluble proteins of the glial cell line-derived neurotrophic factor (GDNF) family ligands (GFLs), which also includes neurturin (NTRN), artemin (ARTN) and persephin (PSPN) (Arighi et al., *Cytokine Growth Factor Rev.,* 2005, 16, 441-67). Unlike other receptor tyrosine kinases, RET does not directly bind to GFLs and requires an additional co-receptor: that is, one of four GDNF family receptor-α (GFRα) family members, which are tethered to the cell surface by a glycosylphosphatidylinositol linkage. GFLs and GFRα family members form binary complexes that in turn bind to RET and recruit it into cholesterol-rich membrane subdomains, which are known as lipid rafts, where RET signaling occurs.

Upon binding of the ligand-co-receptor complex, RET dimerization and autophosphorylation on intracellular tyrosine residues recruits adaptor and signaling proteins to stimulate multiple downstream pathways. Adaptor protein binding to these docking sites leads to activation of Ras-MAPK and PI3K-Akt/mTOR signaling pathways or to recruitment of the CBL family of ubiquitin ligases that functions in RET downregulation of the RET-mediated functions.

Aberrant RET expression and/or activity have been demonstrated in different cancers and in gastrointestinal disorders such as irritable bowel syndrome (IBS).

SUMMARY OF THE INVENTION

It has now been found that substituted pyrazolo[1,5-a]pyrazine compounds are inhibitors of RET kinase, which are useful for treating diseases such as proliferative diseases such as cancers.

Accordingly, provided herein is a compound of the Formula I:

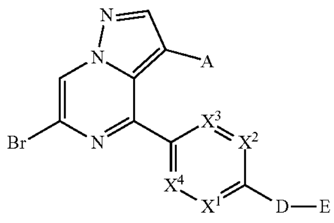

I or pharmaceutically acceptable salt or solvate thereof, wherein A, B, D, E, $X^1$, $X^2$, $X^3$ and $X^4$ are as defined herein.

Also provided herein is a pharmaceutical composition comprising a compound of Formula I or a pharmaceutically acceptable salt or solvate thereof, in admixture with a pharmaceutically acceptable diluent or carrier.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

Also provided herein is a method of treating a RET-associated disease or disorder in a patient in need of such treatment, the method comprising administering to the patient a therapeutically effective amount of a compound of Formula I or a pharmaceutically acceptable salt or solvate thereof, or a pharmaceutical composition thereof as defined herein.

Also provided herein is a method of treating cancer and/or inhibiting metastasis associated with a particular cancer in a patient in need of such treatment, the method comprising administering to the patient a therapeutically effective amount of a compound of Formula I or a pharmaceutically acceptable salt or solvate thereof or a pharmaceutical composition thereof as defined herein.

Also provided herein is a method of treating irritable bowel syndrome (IBS) and/or pain associated with IBS in a patient in need of such treatment, the method comprising administering to the patient a therapeutically effective amount of a compound of Formula I or a pharmaceutically acceptable salt or solvate thereof or a pharmaceutical composition thereof as defined herein.

Also provided is a method of providing supportive care to a cancer patient, including preventing or minimizing gastrointestinal disorders, such as diarrhea, associated with treatment, including chemotherapeutic treatment, the method comprising administering to the patient a therapeutically effective amount of a compound of Formula I or a pharmaceutically acceptable salt or solvate thereof or a pharmaceutical composition thereof as defined herein.

Also provided herein is a compound of Formula I or a pharmaceutically acceptable salt or solvate thereof, or a pharmaceutical composition thereof as defined herein for use in therapy.

Also provided herein is a compound of Formula I or a pharmaceutically acceptable salt or solvate thereof or a pharmaceutical composition thereof as defined herein for use in the treatment of cancer and/or inhibiting metastasis associated with a particular cancer.

Also provided herein is a compound of Formula I or a pharmaceutically acceptable salt or solvate thereof or a pharmaceutical composition thereof as defined herein for use in the treatment of irritable bowel syndrome (IBS) or pain associated with IBS.

Also provided is a compound of Formula I or a pharmaceutically acceptable salt or solvate thereof or a pharmaceutical composition thereof as defined herein for use providing supportive care to a cancer patient, including preventing or minimizing gastrointestinal disorders, such as diarrhea, associated with treatment, including chemotherapeutic treatment.

Also provided herein is a compound of Formula I or a pharmaceutically acceptable salt or solvate thereof for use in the inhibition of RET kinase activity.

Also provided herein is a compound of Formula I or a pharmaceutically acceptable salt or solvate thereof or a pharmaceutical composition thereof as defined herein, for use in the treatment of a RET-associated disease or disorder.

Also provided herein is the use of a compound of Formula I or a pharmaceutically acceptable salt or solvate thereof, as defined herein in the manufacture of a medicament for the treatment of cancer and/or inhibiting metastasis associated with a particular cancer.

Also provided herein is the use of a compound of Formula I or a pharmaceutically acceptable salt or solvate thereof, as defined herein in the manufacture of a medicament for the treatment of irritable bowel syndrome (IBS) or pain associated with IBS.

Also provided herein is the use of a compound of Formula I or a pharmaceutically acceptable salt or solvate thereof, as defined herein in the manufacture of a medicament for providing supportive care to a cancer patient, including preventing or minimizing gastrointestinal disorders, such as diarrhea, associated with treatment, including chemotherapeutic treatment.

Also provided herein is a use of a compound of Formula I or a pharmaceutically acceptable salt or solvate thereof, as defined herein in the manufacture of a medicament for the inhibition of RET kinase activity.

Also provided herein is the use of a compound of Formula I or a pharmaceutically acceptable salt or solvate thereof, as defined herein, in the manufacture of a medicament for the treatment of a RET-associated disease or disorder.

Also provided herein is a method for treating cancer in a patient in need thereof, the method comprising (a) determining if the cancer is associated with a dysregulation of a RET gene, a RET kinase, or expression or activity or level of any of the same (e.g., a RET-associated cancer); and (b) if the cancer is determined to be associated with a dysregulation of a RET gene, a RET kinase, or expression or activity or level of any of the same (e.g., a RET-associated cancer), administering to the patient a therapeutically effective amount of a compound of Formula I or a pharmaceutically acceptable salt or solvate thereof, or a pharmaceutical composition thereof.

Also provided herein is a pharmaceutical combination for treating cancer (e.g., a RET-associated cancer, such as a RET-associated cancer having one or more RET inhibitor resistance mutations) in a patient in need thereof, which comprises (a) a compound of Formula I or a pharmaceutically acceptable salt or solvate thereof, (b) an additional therapeutic agent, and (c) optionally at least one pharmaceutically acceptable carrier, wherein the compound of Formula I or the pharmaceutically acceptable salt or solvate thereof and the additional therapeutic are formulated as separate compositions or dosages for simultaneous, separate or sequential use for the treatment of cancer, wherein the amounts of the compound of Formula I or a pharmaceutically acceptable salt or solvate thereof and of the additional therapeutic agent are together effective in treating the cancer. Also provided herein is a pharmaceutical composition comprising such a combination. Also provided herein is the use of such a combination for the preparation of a medicament for the treatment of cancer. Also provided herein is a commercial package or product comprising such a combination as a combined preparation for simultaneous, separate or sequential use; and to a method of treatment of cancer a patient in need thereof.

Also provided herein is a method for reversing or preventing acquired resistance to an anticancer drug, comprising administering a therapeutically effective amount of a compound of Formula I or a pharmaceutically acceptable salt or solvate thereof, to a patient at risk for developing or having acquired resistance to an anticancer drug. In some embodiments, the patient is administered a dose of the anticancer drug (e.g., at substantially the same time as a dose of a compound of Formula I or a pharmaceutically acceptable salt or solvate thereof is administered to the patient).

Also provided herein is a method of delaying and/or preventing development of cancer resistant to an anticancer drug in an individual, comprising administering to the individual an effective amount of a compound of Formula I or a pharmaceutically acceptable salt or solvate thereof, before, during, or after administration of an effective amount of the anticancer drug.

Also provided herein is a method of treating an individual with cancer who has an increased likelihood of developing resistance to an anticancer drug, comprising administering to the individual (a) an effective amount of a compound of Formula I before, during, or after administration of (b) an effective amount of the anticancer drug.

Also provided are methods of treating an individual with a RET-associated cancer that has one or more RET inhibitor resistance mutations that increase resistance of the cancer to a first RET inhibitor (e.g., one or more amino acid substitutions in the kinase domain (e.g., amino acid positions 723 to 1012 in a wildtype RET protein), a gatekeeper amino acid (e.g., amino acid position 804 in a wildtype RET protein), the P-loop (e.g., amino acid positions 730-737 in a wildtype RET protein), the DFG motif (e.g., amino acid positions 892-894 in a wildtype RET protein), ATP cleft solvent front amino acids (e.g., amino acid positions 758, 811, and 892 in a wildtype RET protein), the activation loop (e.g., amino acid positions 891-916 in a wildtype RET protein), the C-helix and loop preceeding the C-helix (e.g., amino acid positions 768-788 in a wildtype RET protein), and/or the ATP binding site (e.g., amino acid positions 730-733, 738, 756, 758, 804, 805, 807, 811, 881, and 892 in a wildtype RET protein) (e.g., a substitution at amino acid position 804, e.g., V804M, V804L, or V804E, and/or one or more RET inhibitor resistance mutations listed in Tables 3 and 4), that include administering a compound of Formula I or a pharmaceutically acceptable salt or solvate thereof, before, during, or after administration of another anticancer drug (e.g., a second RET kinase inhibitor). See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res., vol.* 44, no. DI, pp. D365-D371, 2016; and O. P. J. Van Linden, A. J. Kooistra, R. Leurs, I. J. P. De Esch, and C. De Graaf, "KLIFS: A knowledge-based structural database to navigate kinase-ligand interaction space," *J. Med. Chem., vol.* 57, no. 2, pp. 249-277, 2014, both of which are incorporated by reference in their entirey herein. In some embodiments, a wildtype RET protein is the exemplary wildtype RET protein described herein.

Also provided are methods of treating an individual with a RET-associated cancer that include administering a compound of Formula I or a pharmaceutically acceptable salt or solvate thereof, before, during, or after administration of another anticancer drug (e.g., a first RET kinase inhibitor).

Also provided herein is a method for treating irritable bowel syndrome (IBS) in a patient in need thereof, the method comprising (a) determining if the IBS is associated with a dysregulation of a RET gene, a RET kinase, or expression or activity or level of any of the same; and (b) if the IBS is determined to be associated with a dysregulation of a RET gene, a RET kinase, or expression or activity or level of any of the same, administering to the patient a therapeutically effective amount of a compound of Formula I or a pharmaceutically acceptable salt or solvate thereof, or a pharmaceutical composition thereof.

Also provided herein is a pharmaceutical combination for treating irritable bowel syndrome (IBS) in a patient in need thereof, which comprises administering (a) a compound of Formula I or a pharmaceutically acceptable salt or solvate thereof, (b) an additional therapeutic agent, and (c) optionally at least one pharmaceutically acceptable carrier, for simultaneous, separate or sequential use for the treatment of IBS, wherein the amounts of the compound of Formula I or a pharmaceutically acceptable salt or solvate thereof and of the additional therapeutic agent are together effective in treating the IBS. Also provided herein is a pharmaceutical composition comprising such a combination. Also provided herein is the use of such a combination for the preparation of a medicament for the treatment of the IBS. Also provided herein is a commercial package or product comprising such a combination as a combined preparation for simultaneous, separate or sequential use; and to a method of treatment of the IBS a patient in need thereof.

Also provided herein is a process for preparing a compound of Formula I or a pharmaceutically acceptable salt or solvate thereof.

Also provided herein is a compound of Formula I or a pharmaceutically acceptable salt or solvate thereof obtained by a process of preparing the compound as defined herein.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DETAILED DESCRIPTION OF THE INVENTION

Provided herein is a compound of the Formula I:

I

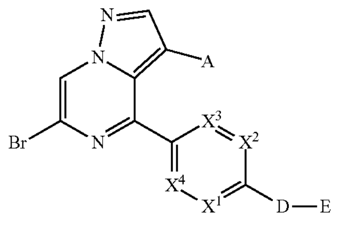

or a pharmaceutically acceptable salt or solvate thereof, wherein:

$X^1$ is CH, $CCH_3$, CF, CCl or N;

$X^2$ is CH, CF or N;

$X^3$ is CH, CF or N;

$X^4$ is CH, CF or N;

wherein zero, one or two of $X^1$, $X^2$, $X^3$ and $X^4$ is N;

A is H, Cl, CN, Br, $CH_3$, $CH_2CH_3$ or cyclopropyl;

B is $hetAr^1$;

$hetAr^1$ is a 5-membered heteroaryl ring having 1-3 ring heteroatoms independently selected from N, S and O, wherein the heteroaryl ring is optionally substituted with one or more substituents independently selected from the group consisting of halogen, C1-C6 alkyl (optionally substituted with one to three fluoros), hydroxyC1-C6 alkyl-, cyanoC1-C6 alkyl-(C1-C6 alkoxy)C1-C6 alkyl-, (C1-C4 alkoxy) $CH_2C(=O)$—, (C1-C4 alkoxy)C(=O)C1-C3 alkyl-, C3-C6 cycloalkyl, ($R^aR^b$N)C1-C6 alkyl-, ($R^aR^b$N)C(=O)C1-C6 alkyl-, (C1-C6 alkyl$SO_2$)C1-C6 alkyl-, $hetCyc^a$, $hetCyc^a$C1-C6 alkyl-, and 4-methoxybenzyl;

$R^a$ and $R^b$ are independently H or C1-C6 alkyl;

$hetCyc^a$ is a 4-6 membered heterocyclic ring having a ring heteroatom selected from N and O, wherein the heterocyclic ring is optionally substituted with halogen, C1-C6 alkyl (optionally substituted with one to three fluoros), (C1-C6 alkoxy)C1-C6 alkyl-, di(C1-C3 alkyl)$NCH_2C(=O)$—, (C1-C6 alkoxy)C(=O)— or (C1-C6 alkoxy)$CH_2C(=O)$—;

D is $hetCyc^1$, $hetCyc^2$, $hetCyc^3$ or $hetCyc^9$;

$hetCyc^1$ is a 4-6 membered heterocyclic ring having 1-2 ring atoms independently selected from N and O, wherein the heterocyclic ring is optionally substituted with one or more substituents independently selected from the group consisting of C1-C3 alkyl (optionally substituted with one to three fluoros), and OH, or said heterocyclic ring is substituted with a C3-C6 cycloalkylidene ring, or said heterocyclic ring is substituted with an oxo group;

$hetCyc^2$ is a 7-8 membered bridged heterocyclic ring having 1-3 ring heteroatoms independently selected from N and O, wherein the heterocyclic ring is optionally substituted with one or more substituents independently selected from the group consisting of C1-C3 alkyl;

$hetCyc^3$ is a 7-11 membered heterospirocyclic ring having 1-2 ring heteroatoms independently selected from N and O, wherein the ring is optionally substituted with C1-C3 alkyl;

$hetCyc^9$ is a fused 9-10 membered heterocyclic ring having 1-3 ring nitrogen atoms, wherein the heterocyclic ring is optionally substituted with oxo;

E is (a) hydrogen, (b) OH, (c) R'R"$N(CH_2)_n$— wherein R' is H or C1-C6 alkyl, R" is H, C1-C6 alkyl or phenyl, and n is 0 or 1;

(d) C1-C6 alkyl optionally substituted with one to three fluoros, (e) hydroxyC1-C6 alkyl- optionally substituted with one to three fluoros, (f) C1-C6 alkoxy optionally substituted with one to three fluoros, (g) hydroxyC1-C6 alkoxy- optionally substituted with one to three fluoros, (h) (C1-C6 alkoxy)hydroxy C1-C6 alkyl- optionally substituted with one to three fluoros, (i) (C1-C6 alkyl)C(=O)—, wherein said alkyl portion is optionally substituted with one to three fluoros, or said alkyl portion is substituted with R'R"N— or R'R"$NCH_2$— wherein R' and R" are independently H or C1-C6 alkyl, (j) (hydroxy C1-C6 alkyl)C(=O)— optionally substituted with one to three fluoros, (k) (C1-C6 alkoxy)C(=O)—, (l) (C1-C6 alkoxy)(C1-C6 alkyl)C(=O)—, (m) HC(=O)—, (n) $Cyc^1$, (o) $Cyc^1C(=O)$—, (p) $Cyc^1$(C1-C6 alkyl)C(=O)— wherein the alkyl portion is optionally substituted with one or more groups independently selected from the group consisting of OH, fluoro, C1-C3 alkoxy and $R^cR^dN$—, where $R^c$ and $R^d$ are independently H or C1-C6 alkyl, (q) $hetCyc^4$, (r) $hetCyc^4C(=O)$—, (s) $hetCyc^4$(C1-C6 alkyl)C(=O)—, (t) $hetCyc^4C(=O)$C1-C6 alkyl-, (u) $hetCyc^4C(=O)NR^g$—, where $R^g$ is H or C1-C6 alkyl, (v) $Ar^2$, (w) $Ar^2C(=O)$—, (x) ($Ar^2$)C1-C6 alkyl-, (y) ($Ar^2$)hydroxy C2-C6 alkyl-, (z) $Ar^2$(C1-C6 alkyl)C(=O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^fN$— and ($R^eR^fN$)C1-C3 alkyl-wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (aa) $hetAr^2C(=O)$—, (bb) ($hetAr^2$)hydroxyC2-C6 alkyl-, (cc) $hetAr^2$(C1-C6 alkyl)C(=O)— wherein the alkyl portion is optionally substituted with one or two groups independently selected from the group consisting of OH, C1-C6 alkyl, hydroxyC1-C6 alkyl, C1-C6 alkoxy, $R^eR^fN$— and ($R^eR^fN$)C1-C3 alkyl-, wherein $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl, (dd) $R^1R^2NC(=O)$—, (ee) $R^1R^2N$(C1-C6 alkyl)C(=O)— wherein the alkyl portion is optionally substituted with phenyl, (ff) $R^1R^2NC(=O)$C1-C6 alkyl-, (gg) $R^1R^2NC(=O)NH$—, (hh) $CH_3SO_2$(C1-C6 alkyl)C(=O)—, (ii) (C1-C6 alkyl)$SO_2$—, (jj) (C3-C6 cycloalkyl)$CH_2SO_2$—, (kk) $hetCyc^5$-$SO_2$—, (ll) $R^4R^5NSO_2$—, (mm) $R^6C(=O)NH$—, (nn) $hetCyc^6$;

(oo) $hetAr^2$C1-C6 alkyl-, (pp) ($hetCyc^4$)C1-C6 alkyl-, (qq) (C1-C6 alkoxy)C1-C6 alkyl- wherein said alkoxy portion is optionally substituted with 1-3 fluoros, (rr) (C3-C6 cycloalkoxy)C1-C6 alkyl-, (ss) (C3-C6 cycloalkyl)C1-C6 alkyl- wherein said cycloalkyl is optionally substituted with 1-2 fluoros, (tt) ($R^gR^hN$)C1-C6 alkyl- wherein $R^g$ and $R^h$ are independently H or C1-C6 alkyl, (uu) $Ar^2$—O—, (vv) (C1-C6 alkyl$SO_2$)C1-C6 alkyl-, (ww) (C1-C6 alkoxy)C(=O)NHC1-C6 alkyl-, (xx) (C3-C6 cycloalkoxy)C(=O)—, (yy) (C3-C6 cycloalkyl)$SO_2$— wherein said cycloalkyl is optionally substituted with C1-C6 alkyl, (zz) $Ar^4CH_2OC(=O)$—, (aaa) (N—(C1-C3 alkyl)pyridinonyl)C1-C6 alkyl-, (bbb) ($Ar^4SO_2$)C1-C6 alkyl-, and (ccc) ($hetAr^2$)—O—;

$Cyc^1$ is a C3-C6 cycloalkyl, wherein (a) the cycloalkyl is optionally substituted with one or more substituents independently selected from the group consisting of OH, halogen, C1-C6 alkoxy, CN, hydroxyC1-C6 alkyl-, (C1-C6 alkoxy)C1-C6 alkyl-, and C1-C6 alkyl optionally substituted with 1-3 fluoros, or (b) the cycloalkyl is substituted with phenyl, wherein the phenyl is optionally substituted with one or more substituents independently selected from the group consisting of halogen, C1-C3 alkyl, C1-C3 alkoxy and $CF_3$, or (c) the cycloalkyl is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and $CF_3$;

$Ar^2$ is phenyl optionally substituted with one or more substituents independently selected from the group consisting of halogen, C1-C6 alkyl (optionally substituted with one to three fluoros), C1-C6 alkoxy (optionally substituted with 1-3 fluoros), CN, a 5-6 membered heterocyclic ring having 1-2 ring heteroatoms independently selected from N and O, and $R^iR^jN$— where $R^i$ and $R^j$ are independently selected from H and C1-C6 alkyl;

$hetAr^2$ is a 5-6 membered monocyclic heteroaryl ring having 1-3 ring heteroatoms independently selected from N, O and S or a 9-10 membered bicyclic heteroaryl ring having 1-2 ring nitrogen atoms, wherein $hetAr^2$ is optionally substituted with one or more substituents independently selected from the group consisting of halogen, C1-C6 alkyl (optionally substituted with one to three fluoros), C1-C6 alkoxy (optionally substituted with 1-3 fluoros), hydroxyC1-C6 alkyl, (C3-C6)cycloalkyl, (C1-C6 alkoxy)C1-C6 alkyl-, CN and R'R"N— where R' and R" are independently H or C1-C3 alkyl;

$hetCyc^4$ is (a) a 4-6 membered heterocyclic ring having 1-2 ring heteroatoms independently selected from N, O and S wherein said S is optionally oxidized to $SO_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O, wherein the heterocyclic ring is optionally independently substituted with one to two C1-C6 alkyl substituents, or (d) a 7-10 membered spirocyclic heterocyclic ring having 1-2 ring heteroatoms independently selected from N and O, wherein each of the heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl-, (C3-C6)cycloalkyl, (C1-C6 alkyl)C(=O)—, a 5-6 membered heterocyclic ring having 1-2 ring heteroatoms independently selected from N and O, and phenyl wherein said phenyl is optionally substituted with one or more substituents independently selected from halogen, C1-C6 alkyl and C1-C6 alkoxy;

$hetCyc^5$ is a 5-6 membered heterocyclic ring having a ring heteroatom selected from O and N;

$hetCyc^6$ is a 5 membered heterocyclic ring having one or two ring heteroatoms independently selected from N and O, wherein the ring substituted with oxo and wherein the ring is further optionally substituted with one or more substituents independently selected from the group consisting of OH and C1-C6 alkyl;

$R^1$ is H, C1-C6 alkyl or (C1-C6 alkoxy)C1-C6 alkyl-;

$R^2$ is H, C1-C6 alkyl (optionally substituted with 1-3 fluoros), (C1-C6 alkoxy)C1-C6 alkyl- (optionally substituted with 1-3 fluoros), $Cyc^3$, hydroxyC1-C6 alkyl (optionally substituted with 1-3 fluoros), C1-C6 alkoxy (optionally substituted with 1-3 fluoros), (C1-C6 alkoxy)C(═O), $hetCyc^7$, $Ar^3$, $Ar^3$C1-C3 alkyl-, hydroxyC1-C6 alkoxy or (C3-C6 cycloalkyl)$CH_2O$—;

$Cyc^3$ is a 3-6 membered carbocyclic ring optionally substituted with 1-2 groups independently selected from the group consisting of C1-C6 alkoxy, OH and halogen;

$hetCyc^7$ is a 5-6 membered heterocyclic ring having a ring heteroatom selected from O and N wherein the ring is optionally substituted with C1-C6 alkyl;

$Ar^3$ is phenyl optionally substituted with one or more substituents independently selected from halogen, C1-C3 alkyl (optionally substituted with one to three fluoros), and C1-C3 alkoxy;

$R^4$ and $R^5$ are independently H or C1-C6 alkyl;

$R^6$ is C1-C6 alkyl, hydroxyC1-C6 alkyl, C1-C6 alkoxy, (C1-C6 alkoxy)C1-C6 alkyl-, phenyl or $hetCyc^8$;

$hetCyc^8$ is a 5-6 membered heterocyclic ring having a ring heteroatom selected from O and N, wherein the heterocyclic ring is optionally substituted with C1-C6 alkyl; and $Ar^4$ is phenyl optionally substituted with one or more halogens.

As used herein, the word "a" before a noun represents one or more of the particular noun. For example, the phrase "a cell" represents "one or more cells."

For complex chemical names employed herein, a substituent group is typically named before the group to which it attaches. For example, methoxyethyl group comprises an ethyl backbone with a methoxy substituent.

The term "halogen" means —F (sometimes referred to herein as "fluoro" or "fluoros"), —Cl, —Br and —I.

The term "azacyclic ring" as used herein refers to a saturated heterocyclic ring having one ring nitrogen atom.

The terms "C1-C3 alkyl" and "C1-C6 alkyl" as used herein refer to saturated linear or branched-chain monovalent hydrocarbon radicals of one to three or one to six carbon atoms, respectively. Examples include, but are not limited to, methyl, ethyl, 1-propyl, isopropyl, 1-butyl, isobutyl, sec-butyl, tert-butyl, 2-methyl-2-propyl, pentyl, and hexyl. A C1-C3 alkyl or C1-C6 alkyl optionally substituted with 1-3 fluoros includes, but is not limited to, fluoromethyl, 3-fluoromethyl, 2-fluoroethyl, difluoromethyl, 2,2,fluoromethyl, 1,3-difluoroprop-2-yl, trifluoromethyl, 2,2,2-trifluoroethyll and 3,3,3-trifluoropropyl.

The terms "C1-C3 alkoxy", "C1-C4 alkoxy" and "C1-C6 alkoxy", as used herein refer to saturated linear or branched-chain monovalent alkoxy radicals of one to three, one to four or one to six carbon atoms, respectively, wherein the radical is on the oxygen atom. Examples include methoxy, ethoxy, propoxy, isopropoxy, and butoxy.

The term "(C1-C6 alkoxy)C1-C6 alkyl-" as used herein refers to saturated linear or branched-chain monovalent radicals of one to six carbon atoms, wherein one of the carbon atoms is substituted with a (C1-C6 alkoxy) group as defined herein. Examples include methoxymethyl ($CH_3OCH_2$—) and methoxyethyl ($CH_3OCH_2CH_2$—).

The term "hydroxyC1-C6 alkyl" as used herein refers to saturated linear or branched-chain monovalent alkyl radicals of one to six carbon atoms, wherein one of the carbon atoms is substituted with a hydroxy group.

The term "hydroxyC1-C6 alkoxy" as used herein refers to saturated linear or branched-chain monovalent alkoxy radicals of one to six carbon atoms, wherein one of the carbon atoms is substituted with a hydroxy group.

The term "(C1-C6 alkoxy)hydroxyC1-C6 alkyl" as used herein refers to a hydroxy (C1-C6 alkyl) radical as defined herein, wherein one of the carbon atoms is substituted with a C1-C6 alkoxy group as defined herein.

The term "$Cyc^1$(C1-C6 alkyl)" as used herein refers to saturated linear or branched-chain monovalent alkyl radicals of one to six carbon atoms, wherein one of the carbon atoms is substituted with a 3-6 membered cycloalkyl ring.

The term "$Cyc^1$(C1-C6 alkyl)C(═O)—" as used herein refers to a (C1-C6 alkyl)C(═O)— group, wherein the C1-C6 alkyl is a saturated linear or branched-chain monovalent radical of one to six carbon atoms and wherein one of the carbon atoms of the C1-C6 alkyl portion is substituted with a C3-C6 cycloalkyl group.

The term "$Ar^2$C1-C6 alkyl" as used herein refers to C1-C6 alkyl radical as defined herein one of the carbon atoms of the alkyl portion is substituted with $Ar^2$.

The term "($Ar^2$)hydroxy C2-C6 alkyl" as used herein refers to a hydroxyC1-C6 alkyl radical as defined herein wherein one of the carbon atoms of the alkyl portion is substituted with $Ar^2$.

The term "$Ar^2$(C1-C6 alkyl)C(═O)—" as used herein refers to a C1-C6 alkyl(C═O)— radical wherein the C1-C6 alkyl portion is a saturated linear or branched-chain monovalent alkyl radicals of one to three carbon atoms, wherein one of the carbon atoms is substituted with $Ar^2$.

The term "($hetAr^2$)hydroxy C2-C6 alkyl" as used herein refers to a hydroxyC2-C6 alkyl radical as defined herein wherein one of the carbon atoms is substituted with $hetAr^2$.

The term "$hetAr^2$(C1-C6 alkyl)C(═O)—" as used herein refers to a C1-C6 alkyl(C═O)— radical wherein the C1-C6 alkyl portion is a saturated linear or branched-chain monovalent alkyl radical of one to three carbon atoms, wherein one of the carbon atoms is substituted with $hetAr^2$.

The term "$R^1R^2$NC(═O)C1-C6 alkyl" as used herein refers to a C1-C6 alkyl radical wherein one of the carbon atoms is substituted with a $R^1R^2$NC(═O)— group.

The term "$R^1R^2$N(C1-C6 alkyl)C(═O)—" as used herein refers to a C1-C3 alkyl(C═O)— radical wherein the C1-C6 alkyl portion is a saturated linear or branched-chain monovalent alkyl radicals of one to three carbon atoms, wherein one of the carbon atoms is substituted with a $R^1R^2$N— group, wherein $R^1$ and $R^2$ are as defined for Formula I.

The term "(C1-C6 alkyl$SO_2$)C1-C6 alkyl" as used herein as used herein refers to saturated linear or branched-chain monovalent radicals of one to six carbon atoms, wherein one of the carbon atoms is substituted with a (C1-C6 alkyl) $SO_2$— group (e.g., a $(CH_3)_2CH_2SO_2$— group).

The term "($Ar^4SO_2$)C1-C6 alkyl" as used herein as used herein refers to saturated linear or branched-chain monovalent radicals of one to six carbon atoms, wherein one of the carbon atoms is substituted with a $(Ar^4)SO_2$— group.

The term "bridged heterocyclic ring" as used herein refers to a bicyclic heterocycle, wherein two common nonadjacent carbon atoms of the ring are linked by an alkylene bridge of 1, 2, 3, or 4 carbon atoms. Examples of bridged heterocyclic ring systems include 3,6-diazabicyclo[3.1.1]heptane, 2,5-diazabicyclo[2.2.1]heptane, 3,8-diazabicyclo[3.2.1]octane, 3,8-diazabicyclo[3.2.1]octane, 8-azabicyclo[3.2.1]octane and 7-azabicyclo[2.2.1]heptane.

The term "spirocyclic ring" as used herein refers to a group having two rings joined by a spirocyclic linkage through a common single carbon atom, wherein each ring is a 4-7-membered ring (including the common carbon atom).

The term "heterospirocyclic" as used herein refers to a group having two rings joined by a spirocyclic linkage through a carbon atom, wherein each ring has 4 to 6 ring atoms (with one ring atom being common to both rings), and wherein 1 or 2 of the ring atoms is a heteroatom selected from the group consisting of N and O, provided that the heteroatoms are not adjacent. Examples include 2,6-diazaspiro[3.3]heptane, 2,5-diazaspiro[3.4]octane, 2,6-diazaspiro[3.4]octane, 6-oxa-2-azaspiro[3.4]octane, 2-oxa-7-azaspiro[4.4]nonane, 7-oxa-2-azaspiro[4.5]decane, 7-oxa-2-azaspiro[3.5]nonane, 2,7-diazaspiro[3.5]nonane, 2,6-diazaspiro[3.5]nonane, 2,5-diazaspiro[3.5]nonane, 1,6-diazaspiro[3.4]octane, 1,7-diazaspiro[4.4]nonane, 2,7-diazaspiro[4.4]nonane, 2,8-diazaspiro[4.5]decane, 2,7-diazaspiro[4.5]decane, 2,6-diazaspiro[4.5]decane, 1,7-diazaspiro[3.5]nonane, 2,7-diazaspiro[3.5]nonane, 1,6-diazaspiro[3.5]nonane, 1,8-diazaspiro[4.5]decane, 2,8-diazaspiro[4.5]decane, 2,7-diazaspiro[4.5]decane, 1,7-diazaspiro[4.5]decane, 2,9-diazaspiro[5.5]undecane, and 7-azaspiro[3.5]nonane.

As used herein, the term "cycloalkylidine ring" refers to a divalent carbocyclic ring. The suffix "ylidine" refers to bivalent radical derived from a saturated hydrocarbon by removal of two hydrogen atoms from the same carbon atom.

The term "compound," as used herein is meant to include all stereoisomers, geometric isomers, tautomers, and isotopes of the structures depicted. Compounds herein identified by name or structure as one particular tautomeric form are intended to include other tautomeric forms unless otherwise specified.

The term "tautomer" as used herein refers to compounds whose structures differ markedly in arrangement of atoms, but which exist in easy and rapid equilibrium, and it is to be understood that compounds provided herein may be depicted as different tautomers, and when compounds have tautomeric forms, all tautomeric forms are intended to be within the scope of the invention, and the naming of the compounds does not exclude any tautomer.

The term "oxo" as used herein means an oxygen that is double bonded to a carbon atom. For example, a non-limiting example of a heterocyclic ring that is substituted with an oxo group is the structure:

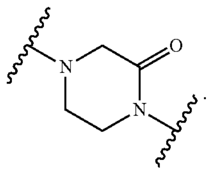 [SMILES: *N1CCN(*)C(=O)C1]

The term "(N—(C1-C3 alkyl)pyridinonyl)C1-C6 alkyl" as used herein refers to a C1-C6 alkyl radical as defined herein where one of the carbon atoms of the alkyl portion is substituted with a 2-oxo-1,2-dihydropyridine that is substituted on the pyridone nitrogen with 1-3 carbons. Examples include 1-methyl-1,2-dihydropyridin-2-one.

In one embodiment of Formula I, $X^1$ is CH, $CCH_3$, CF, or CCl, $X^2$ is CH or CF, $X^3$ is CH or CF, and $X^4$ is CH or CF. In one embodiment, $X^1$ is CH or $CH_3$, $X^2$ is CH, $X^3$ is CH, and $X^3$ is CH. In one embodiment, each of $X^1$, $X^2$, $X^3$ and $X^4$ is CH.

In one embodiment of Formula I, $X^1$ is CH, $CCH_3$, CF, CCl or N, $X^2$ is CH, CF or N, $X^3$ is CH, CF or N, and $X^4$ is CH, CF or N, wherein one of $X^1$, $X^2$, $X^3$ and $X^4$ is N.

In one embodiment, $X^1$ is N, CH or $CH_3$, $X^2$ is CH or N, $X^3$ is CH or N, and $X^3$ is CH or N, wherein one of $X^1$, $X^2$, $X^3$ and $X^4$ is N.

In certain embodiments of Formula I, $X^1$ is N, $X^2$ is CH or CF, $X^3$ is CH or CF, and $X^4$ is CH or CF. In one embodiment, $X^1$ is N, and $X^2$, $X^3$ and $X^4$ are CH.

In one embodiment of Formula I, $X^1$ is $CCH_3$, $X^2$ is CH, CF or N; $X^3$ is CH, CF or N, and $X^4$ is CH, CF or N; wherein one of $X^2$, $X^3$ and $X^4$ is N. In one embodiment, $X^1$ is $CCH_3$, $X^2$ is N; $X^3$ is CH or CF, and $X^4$ is CH or CF. In one embodiment, $X^1$ is $CCH_3$, $X^2$ is N, and $X^3$ and $X^4$ are CH.

In one embodiment of Formula I, $X^1$ is CH, $CCH_3$, CF, CCl or N; $X^2$ is CH, CF or N; $X^3$ is CH, CF or N; and $X^4$ is CH, CF or N, wherein two of $X^1$, $X^2$, $X^3$ and $X^4$ are N.

In one embodiment of Formula I, $X^1$ and $X^2$ are N, and $X^3$ and $X^4$ are CH or CF. In one embodiment, $X^1$ and $X^2$ are N, and $X^3$ and $X^4$ are CH.

In one embodiment, $X^1$ and $X^3$ are N, and $X^2$ and $X^4$ are CH or CF. In one embodiment, $X^1$ and $X^3$ are N, and $X^2$ and $X^4$ are CH.

In one embodiment, A is H.

In one embodiment, A is Cl.

In one embodiment, A is CN.

In one embodiment, A is Br.

In one embodiment, A is $CH_3$.

In one embodiment, A is $CH_3CH_2$—.

In one embodiment, A is cyclopropyl.

In one embodiment, A is H, Cl or CN.

In one embodiment, $hetAr^1$ is pyrazolyl, imidazolyl, oxazolyl, isoxazolyl thiazolyl, thiadiazolyl, triazolyl or oxadiazolyl optionally substituted with one or more substituents independently selected from the group consisting of halogen, C1-C6 alkyl (optionally substituted with one to three fluoros), hydroxyC1-C6 alkyl-, cyanoC1-C6 alkyl-(C1-C6 alkoxy)C1-C6 alkyl-, (C1-C4 alkoxy)$CH_2C$(═O)—, (C1-C4 alkoxy)C(═O)C1-C3 alkyl-, C3-C6 cycloalkyl, $(R^aR^bN)$C1-C6 alkyl-, $(R^aR^bN)C$(═O)C1-C6 alkyl-, (C1-C6 $alkylSO_2$)C1-C6 alkyl-, $hetCyc^a$, $hetCyc^a$C1-C6 alkyl-, and 4-methoxybenzyl.

In one embodiment, B is $hetAr^1$, where $hetAr^1$ is a 5 membered heteroaryl having 1-2 ring heteroatoms independently selected from N, O and S and optionally substituted with one or more substituents independently selected from the group consisting of C1-C6 alkyl (optionally substituted with one to three fluoros), (C1-C6 alkoxy)C1-C6 alkyl-, (C1-C6 $alkylSO_2$)C1-C6 alkyl-, $hetCyc^a$, and $hetCyc^a$C1-C6 alkyl. In one embodiment, $hetAr^1$ is pyrazolyl optionally substituted with one or more substituents independently selected from the group consisting of C1-C6 alkyl (optionally substituted with one to three fluoros), (C1-C6 alkoxy) C1-C6 alkyl-, (C1-C6 $alkylSO_2$)C1-C6 alkyl-, $hetCyc^a$, and $hetCyc^a$C1-C6 alkyl.

In one embodiment, B is $hetAr^1$, wherein $hetAr^1$ is a pyrazolyl ring optionally substituted with one or more substituents independently selected from the group consisting of C1-C6 alkyl (optionally substituted with one to three fluoros).

In one embodiment, B is pyrazolyl optionally substituted with one or more substituents independently selected from the group consisting of C1-C6 alkyl (optionally substituted with one to three fluoros) and hydroxyC1-C6 alkyl-.

In one embodiment, B is pyrazolyl optionally substituted with one or more independently selected C1-C6 alkyl substituents.

Non-limiting examples of $hetAr^1$ include the structures:

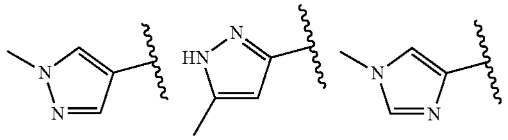

-continued

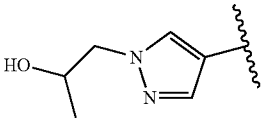
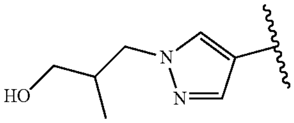
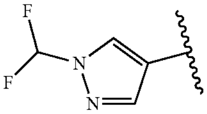
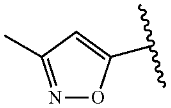
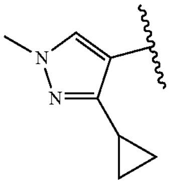
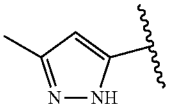
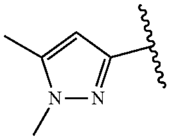
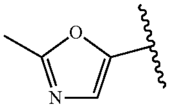
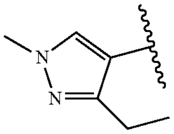
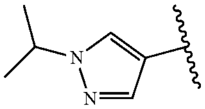
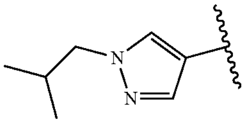
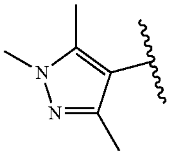
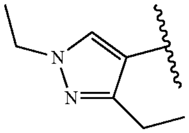
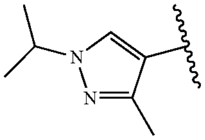
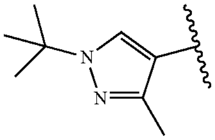
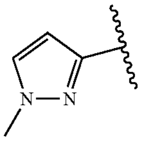
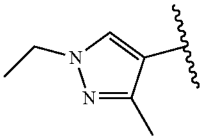
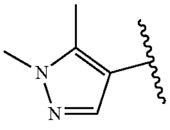
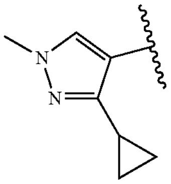
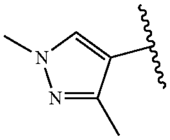
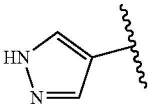
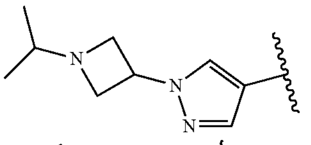
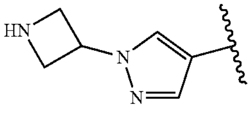
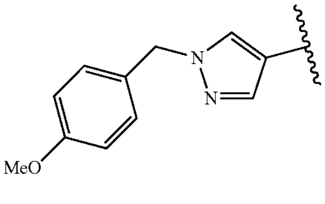

-continued

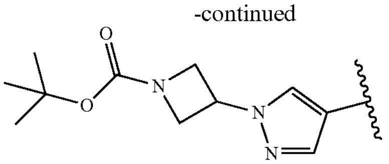
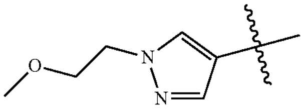
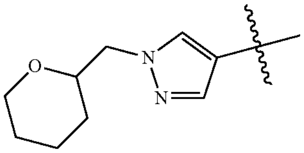
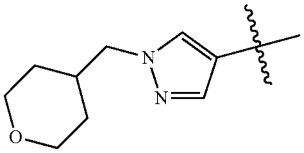
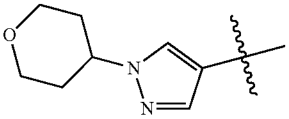
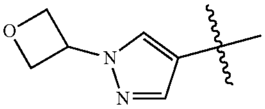
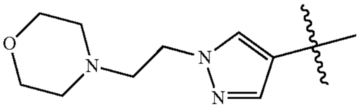
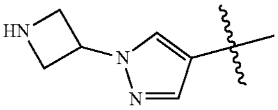
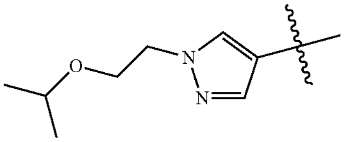
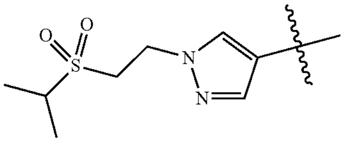
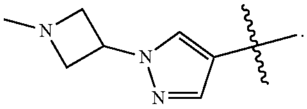

In one embodiment, D is hetCyc[1] where hetCyc[1] is a 4-6 membered heterocyclic ring having 1-2 ring atoms independently selected from N and O, wherein the heterocyclic ring is optionally substituted with one or more substituents independently selected from the group consisting of C1-C3 alkyl (optionally substituted with one to three fluoros) and OH, or the heterocyclic ring is substituted with a C3-C6 cycloalkylidene ring, or the heterocyclic ring is substituted with an oxo group.

In one embodiment, hetCyc[1] is a pyrrolidinyl, piperidinyl, piperazinyl, morpholinyl or azetidinyl ring optionally substituted with one or more substituents independently selected from the group consisting of C1-C3 alkyl (optionally substituted with one to three fluoros) and OH, or hetCyc[1] is a piperazinyl ring substituted with a C3-C6 cycloalkylidene ring, or said heterocyclic ring is a piperazinyl ring substituted with an oxo group.

In one embodiment, hetCyc[1] is a 4-6 membered heterocyclic ring having one ring nitrogen atom, wherein said ring is optionally substituted with C1-C3 alkyl (optionally substituted with one to three fluoros) or OH. Non-limiting examples include the structures:

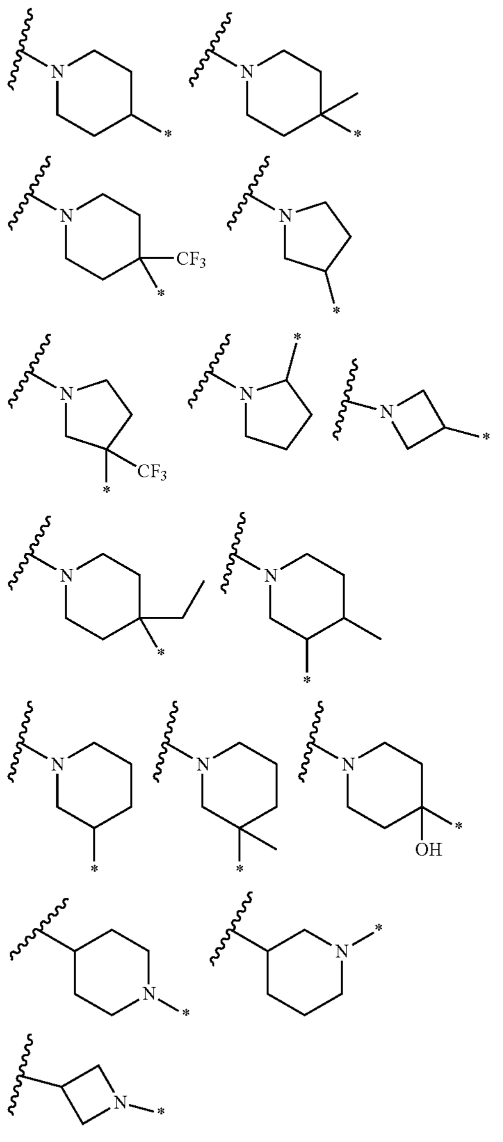

where the asterisk indicates the point of attachment to the E group and the wavy line indicates the point of attachment to the ring comprising $X^1$, $X^2$, $X^3$ and $X^4$, wherein $X^1$, $X^2$, $X^3$, $X^4$ and E are as defined for Formula I.

In one embodiment, hetCyc[1] is a 4-6 membered heterocyclic ring having one ring nitrogen atom, wherein said ring is optionally substituted with C1-C3 alkyl (optionally substituted with one to three fluoros) or OH. In one embodiment, hetCyc[1] is represented by the structures:

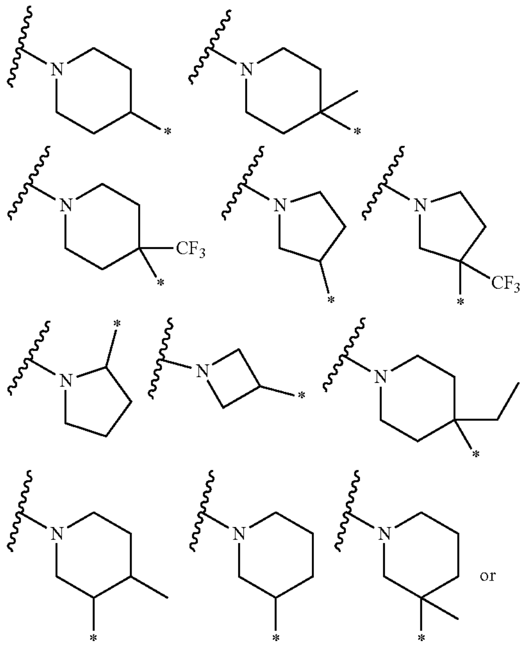

or

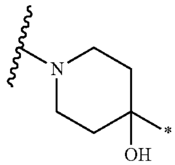

where the asterisk indicates the point of attachment to the E group and the wavy line indicates the point of attachment to the ring comprising $X^1$, $X^2$, $X^3$ and $X^4$, wherein $X^1$, $X^2$, $X^3$, $X^4$ and E are as defined for Formula I. In one embodiment, E is (a) hydrogen, (b) OH, (c) $R'R''N(CH_2)_n$— wherein R' is H or C1-C6 alkyl, R" is H, C1-C6 alkyl or phenyl, and n is 0 or 1, (f) C1-C6 alkoxy optionally substituted with one to three fluoros, (g) hydroxyC1-C6 alkoxy-optionally substituted with one to three fluoros, (k) (C1-C6 alkoxy)C(═O)—, (m) HC(═O)—, (r) $hetCyc^4C$(═O)—, (u) $hetCyc^4C({=}O)NR^g$—, where $R^g$ is H or C1-C6 alkyl, (v) $Ar^2$, (x) $(Ar^2)$C1-C6 alkyl-, (dd) $R^1R^2NC$(═O)—, (ff) $R^1R^2NC$(═O)C1-C6 alkyl-, (gg) $R^1R^2NC$(═O)NH—, (ll) $R^4R^5NSO_2$—, (mm) $R^6C$(═O)NH—, (nn) $hetCyc^6$, (oo) $(hetAr^2)$C1-C6 alkyl-, (tt) $(R^gR^hN)$C1-C6 alkyl- wherein $R^g$ and $R^h$ are independently H or C1-C6 alkyl, (uu) $Ar^2$—O—, or (ccc) $hetAr^2$—O—, where $hetCyc^4$, $Ar^2$, $R^1$, $R^2$, $R^4$, $R^5$, $R^6$, $hetCyc^6$, and $hetAr^2$ are as defined for Formula I.

In one embodiment, hetCyc[1] is a 4-6 membered heterocyclic ring having two ring nitrogen atoms, wherein said ring is optionally substituted with a C3-C6 cycloalkylidene ring or oxo. In one embodiment, hetCyc[1] is represented by the structures:

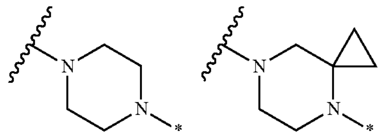

-continued

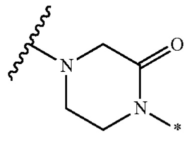

where the asterisk indicates the point of attachment to the E group and the wavy line indicates the point of attachment to the ring comprising $X^1$, $X^2$, $X^3$ and $X^4$, where E is as defined for Formula I. In one embodiment, E is (a) hydrogen, (d) C1-C6 alkyl optionally substituted with one to three fluoros, (e) hydroxyC1-C6 alkyl- optionally substituted with one to three fluoros, (h) (C1-C6 alkoxy)hydroxy C1-C6 alkyl-, (i) (C1-C6 alkyl)C(═O)— wherein said alkyl portion is optionally substituted with one to three fluoros, or said alkyl portion is substituted with R'R"N— or R'R"$NCH_2$— wherein R' and R" are independently H or C1-C6 alkyl, (j) (hydroxy C1-C6 alkyl)C(═O)— optionally substituted with one to three fluoros, (k) (C1-C6 alkoxy)C(═O)—, (l) (C1-C6 alkoxy)(C1-C6 alkyl)C(═O)—, (n) $Cyc^1$, (o) $Cyc^1$C(═O)—, (p) $Cyc^1$(C1-C6 alkyl)C(═O)— wherein the alkyl portion is optionally substituted with one or more groups independently selected from the group consisting of OH, fluoro, C1-C3 alkoxy and $R^cR^dN$—, where $R^c$ and $R^d$ are independently H or C1-C6 alkyl, (q) $hetCyc^4$, (r) $hetCyc^4$C(═O)—, (s) $hetCyc^4$(C1-C6 alkyl)C(═O)—, (t) $hetCyc^4$C(═O)C1-C6 alkyl-, (w) $Ar^2$C(═O)—, (x) ($Ar^2$)C1-C6 alkyl-, (y) ($Ar^2$)hydroxy C2-C6 alkyl-, (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^fN$— and ($R^eR^fN$) C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (aa) $hetAr^2$C(═O)—, (bb) ($hetAr^2$)hydroxy C2-C6 alkyl-, (cc) $hetAr^2$(C1-C6 alkyl)C(═O)— wherein the alkyl portion is optionally substituted with one or two groups independently selected from the group consisting of OH, C1-C6 alkyl, hydroxyC1-C6 alkyl, C1-C6 alkoxy, $R^eR^fN$— and ($R^eR^fN$)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (dd) $R^1R^2$NC(═O)—, (ee) $R^1R^2$N(C1-C6 alkyl)C(═O)— wherein the alkyl portion is optionally substituted with phenyl, (ff) $R^1R^2$NC(═O)C1-C6 alkyl-, (hh) $CH_3SO_2$(C1-C6 alkyl)C(═O)—, (ii) (C1-C6 alkyl)$SO_2$—, (jj) (C3-C6 cycloalkyl)$CH_2SO_2$—, (kk) $hetCyc^5$-$SO_2$—, (ll) $R^4R^5NSO_2$—, (oo) ($hetAr^2$)C1-C6 alkyl-, (pp) ($hetCyc^4$) C1-C6 alkyl-, (qq) (C1-C6 alkoxy)C1-C6 alkyl- wherein said alkoxy portion is optionally substituted with 1-3 fluoros, (rr) (C3-C6 cycloalkoxy)C1-C6 alkyl-, (ss) (C3-C6 cycloalkyl)C1-C6 alkyl-, (tt) ($R^gR^hN$)C1-C6 alkyl- wherein $R^g$ and $R^h$ are independently H or C1-C6 alkyl, (vv) (C1-C6 alkyl)$SO_2$C1-C6 alkyl-, (ww) (C1-C6 alkoxy)C(═O) NHC1-C6 alkyl-, (yy) (C3-C6 cycloalkyl)$SO_2$— wherein said cycloalkyl is optionally substituted with C1-C6 alkyl, (aaa) (N—(C1-C3 alkyl)pyridinonyl)C1-C6 alkyl-, or (bbb) ($Ar^4SO_2$)C1-C6 alkyl-, where $Cyc^1$, $hetCyc^4$, $Ar^2$, $hetAr^2$, $R^1$, $R^2$, $R^4$, $R^5$ and $Ar^4$ are as defined for Formula I.

In one embodiment of the D-E group, D is $hetCyc^1$ and E is hydrogen. In one embodiment, $hetCyc^1$ is a 4-6 membered heterocyclic ring having one to two ring nitrogen atoms, wherein the ring is optionally substituted with a C3-C6 cycloalkylidene ring. Non-limiting examples include the structures:

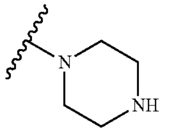

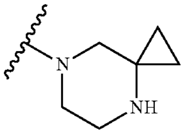

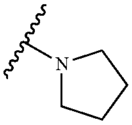

In one embodiment, D is $hetCyc^1$ and E is OH. In one embodiment, $hetCyc^1$ is a 5-6 membered heterocyclic ring having one ring nitrogen atom, wherein the ring is optionally substituted with trifluoroC1-C3 alkyl. Non-limiting examples include the structures:

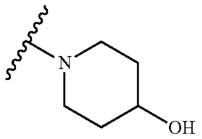

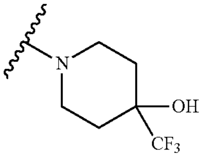

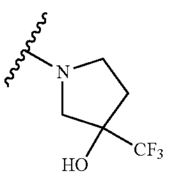

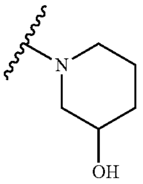

In one embodiment, D is $hetCyc^1$ and E is R'R"N($CH_2$)$_n$—, wherein R' is H or C1-C6 alkyl, R" is H, C1-C6 alkyl or phenyl, and n is 0 or 1. In one embodiment, $hetCyc^1$ is a 6 membered heterocyclic ring having one ring nitrogen atom, wherein the ring is optionally substituted with C1-C3 alkyl. Non-limiting examples include the structures:

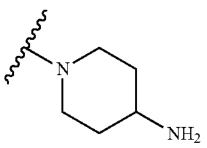

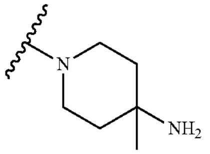

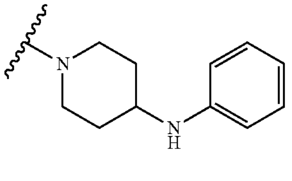

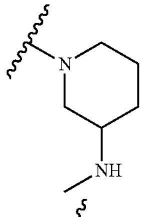

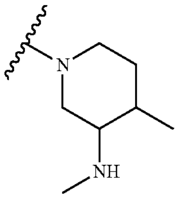

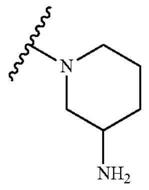

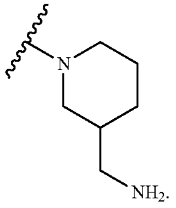

In one embodiment of the D-E group, D is $hetCyc^1$ and E is C1-C6 alkyl optionally substituted with one to three fluoros. In one embodiment, hetCyc[1] is a 6-membered heterocyclic ring having two ring nitrogen atoms. Non-limiting examples include the structures:

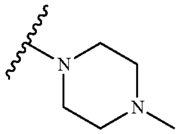
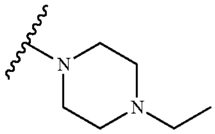
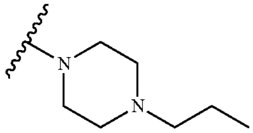
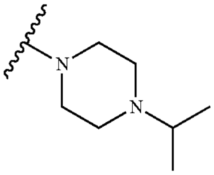
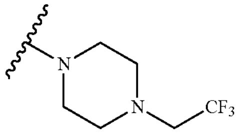
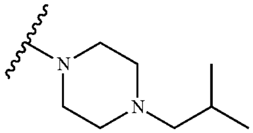
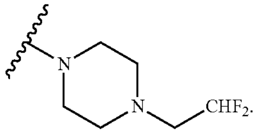

In one embodiment, D is hetCyc[1] and E is hydroxyC1-C6 alkyl- optionally substituted with one to three fluoros. In one embodiment, hetCyc[1] is a 6-membered heterocyclic ring having two ring nitrogen atoms. Non-limiting examples include the structures:

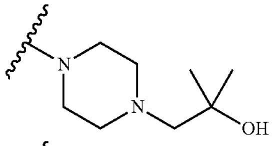
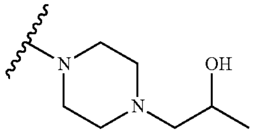
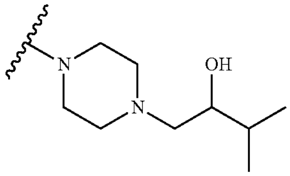
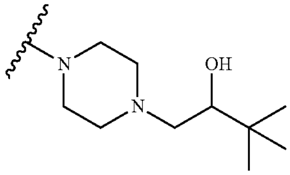
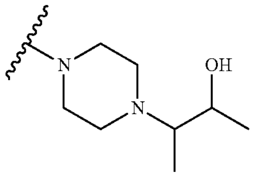

-continued

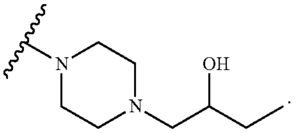

In one embodiment, D is hetCyc[1] and E is C1-C6 alkoxy optionally substituted with one to three fluoros. In one embodiment, hetCyc[1] is a 6-membered heterocyclic ring having one ring nitrogen atom. Non-limiting examples include the structures:

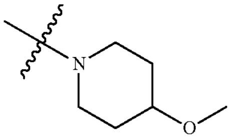
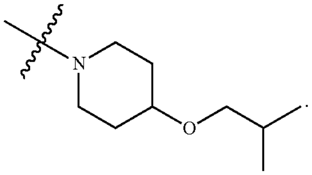

In one embodiment, D is hetCyc[1] and E is hydroxyC1-C6 alkoxy- optionally substituted with one to three fluoros. In one embodiment, hetCyc[1] is a 6-membered heterocyclic ring having one ring nitrogen atom. A non-limiting examples include the structure:

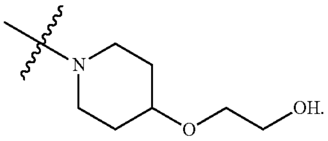 [SMILES: *N1CCC(OCCO)CC1]

In one embodiment, D is hetCyc[1] and E is (C1-C6 alkoxy)hydroxy C1-C6 alkyl-optionally substituted with one to three fluoros. In one embodiment, hetCyc[1] is a 6-membered heterocyclic ring having two ring nitrogen atoms. A non-limiting example includes the structure:

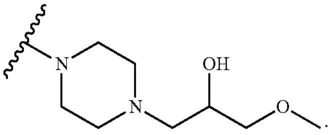 [SMILES: *N1CCN(CC(O)COC)CC1]

In one embodiment, D is hetCyc[1] and E is (C1-C6 alkyl)C(═O)—, wherein said alkyl portion is optionally substituted with one to three fluoros, or said alkyl portion is substituted with R'R"N— or R'R"$NCH_2$— wherein R' and R" are independently H or C1-C6 alkyl. In one embodiment, hetCyc[1] is a 6-membered heterocyclic ring having 1-2 ring nitrogen atoms, wherein the heterocyclic ring is optionally substituted with cyclopropyl. Non-limiting examples include the structures:

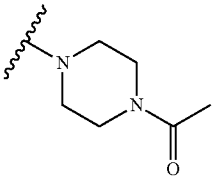
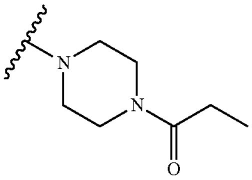
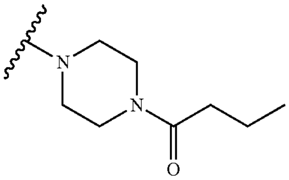
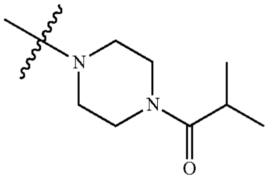
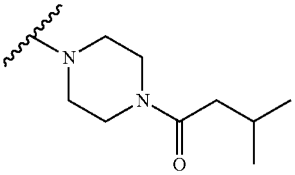
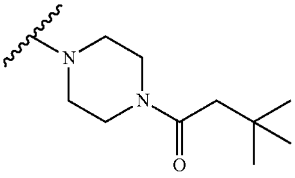
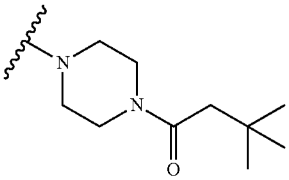
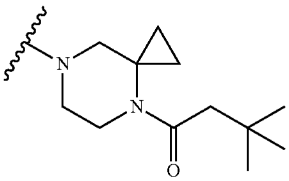
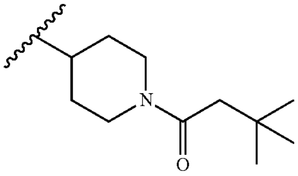
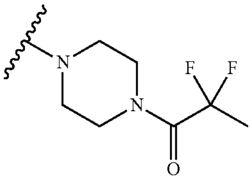
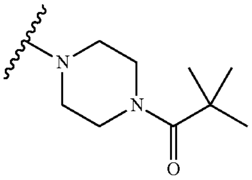
-continued
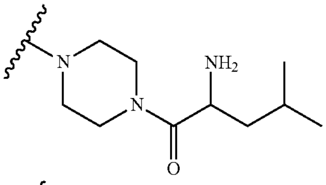
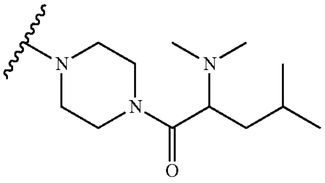
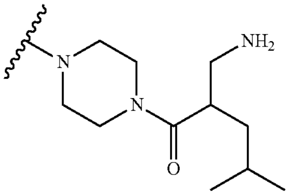
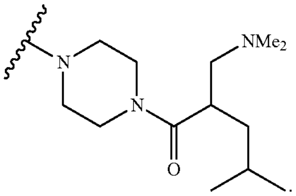
In one embodiment, D is hetCyc[1] and E is (hydroxy C1-C6 alkyl)C(=O)— optionally substituted with one to three fluoros. In one embodiment, hetCyc[1] is a 6-membered heterocyclic ring having two ring nitrogen atoms, wherein the heterocyclic ring is optionally substituted with cyclopropyl. Non-limiting examples include the structures:
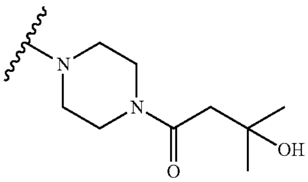
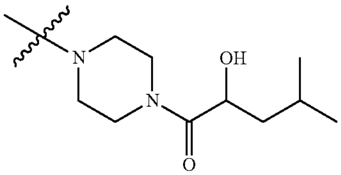
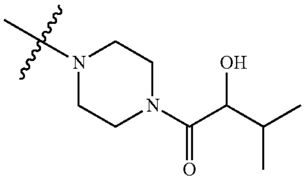
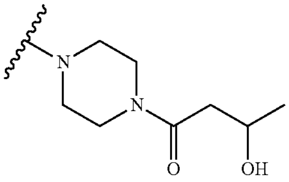

-continued

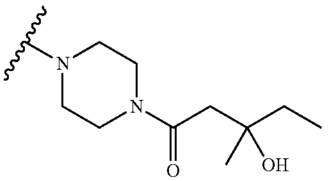

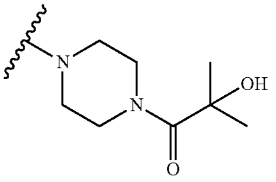

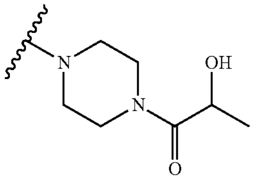

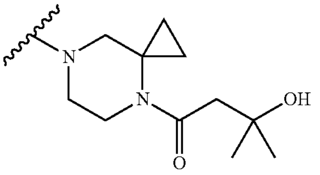

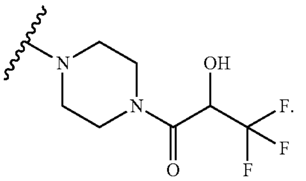

In one embodiment, D is hetCyc[1] and E is (C1-C6 alkoxy)C(═O)—. In one embodiment, hetCyc[1] is a 6-membered heterocyclic ring having 1-2 ring nitrogen atoms, wherein the heterocyclic ring is optionally substituted with cyclopropyl or C1-C3 alkyl. Non-limiting examples include the structures:

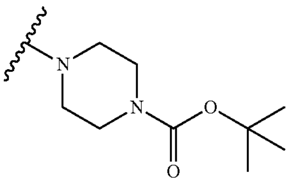

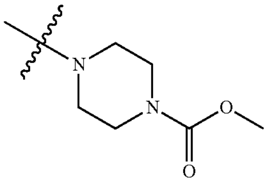

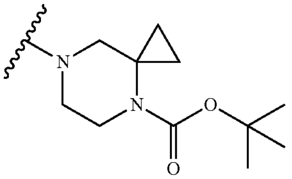

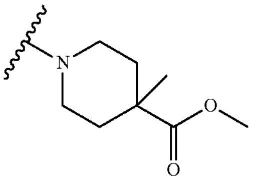

-continued

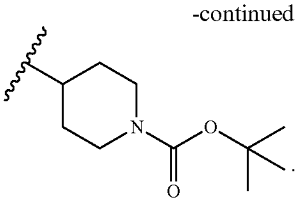

In one embodiment, D is hetCyc[1] and E is (C1-C6 alkoxy)(C1-C6 alkyl)C(═O)—. In one embodiment, hetCyc[1] is a 6-membered heterocyclic ring having two ring nitrogen atoms. Non-limiting examples include the structures:

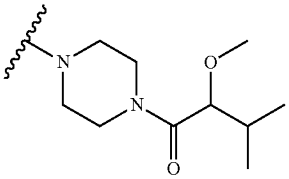

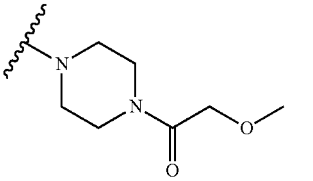

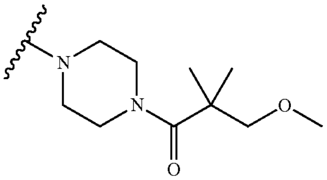

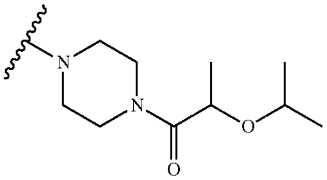

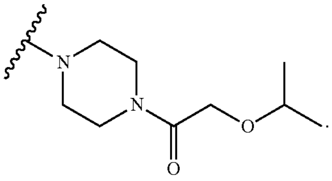

In one embodiment, D is hetCyc[1] and E is HC(═O)—. In one embodiment, hetCyc[1] is a 6-membered heterocyclic ring having one ring nitrogen atom. A non-limiting example is the structure:

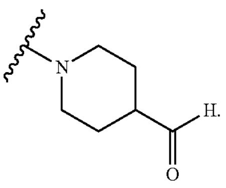

In one embodiment, D is hetCyc[1] and E is Cyc[1], where Cyc[1] is a C3-C6 cycloalkyl, wherein the cycloalkyl is optionally substituted with one or more substituents independently selected from the group consisting of OH, halogen, C1-C6 alkoxy, CN, hydroxyC1-C6 alkyl-, (C1-C6 alkoxy)C1-C6 alkyl-, and C1-C6 alkyl optionally substituted with 1-3 fluoros. In one embodiment, $Cyc^1$ is a C3-C6 cycloalkyl optionally substituted with OH. In one embodiment, $hetCyc^1$ is a 6-membered heterocyclic ring having two ring nitrogen atoms. Non-limiting examples when D is $hetCyc^1$ and E is $Cyc^1$ include the structures:

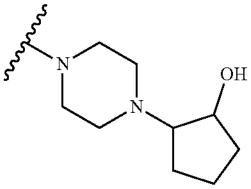

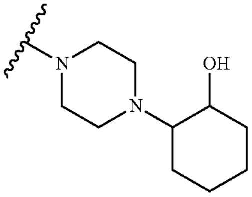

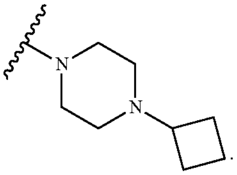

In one embodiment, D is $hetCyc^1$ and E is $Cyc^1C(=O)$— where $Cyc^1$ is as defined for Formula I. In one embodiment, $Cyc^1$ is a C3-C6 cycloalkyl, wherein the cycloalkyl is optionally substituted with one or more substituents independently selected from the group consisting of OH, halogen, CN, hydroxyC1-C6 alkyl-, (C1-C6 alkoxy)C1-C6 alkyl- or C1-C6 alkyl optionally substituted with 1-3 fluoros, or the cycloalkyl is substituted with phenyl, wherein the phenyl is optionally substituted with one or more substituents independently selected from the group consisting of halogen, C1-C3 alkyl, C1-C3 alkoxy and $CF_3$ or the cycloalkyl is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and $CF_3$. In one embodiment, the cycloalkyl is substituted with phenyl. In one embodiment, $hetCyc^1$ is a 6-membered heterocyclic ring having two ring nitrogen atoms. Non-limiting examples when D is $hetCyc^1$ and E is $Cyc^1C(=O)$— include the structures:

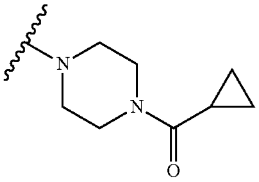

-continued

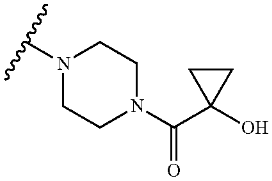

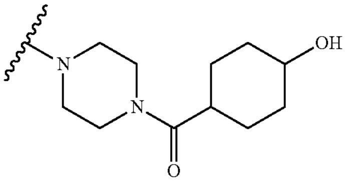

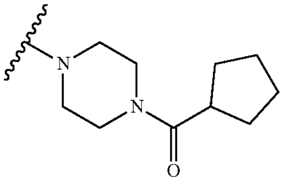

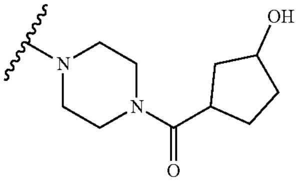

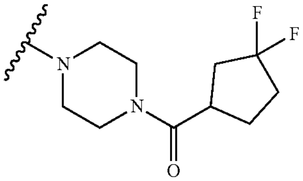

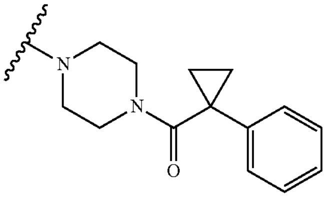

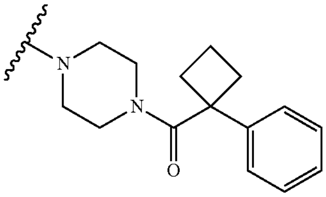

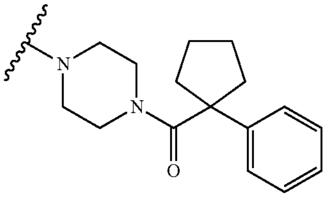

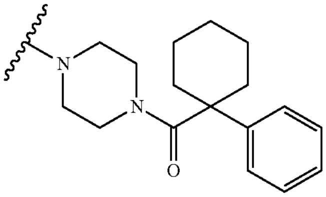

-continued

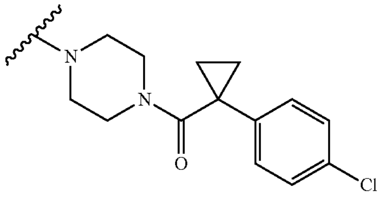

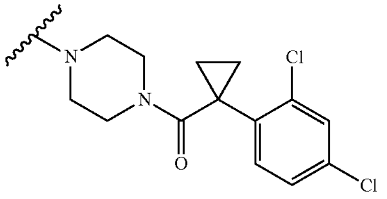

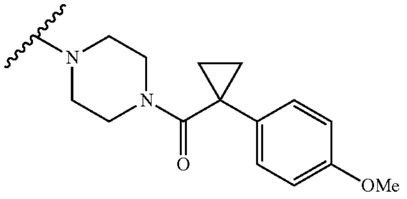

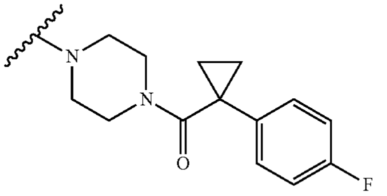

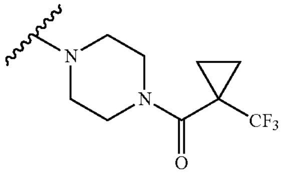

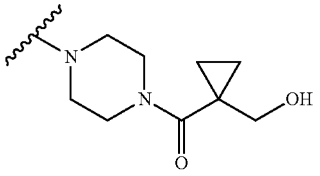

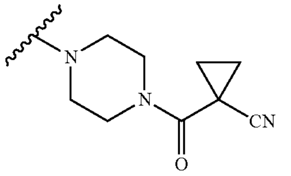

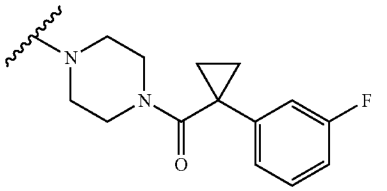

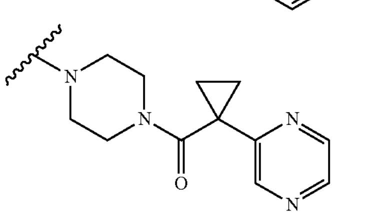

-continued

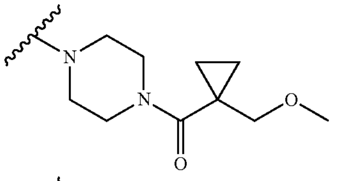

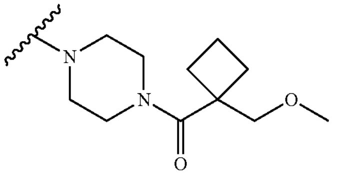

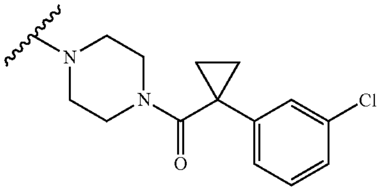

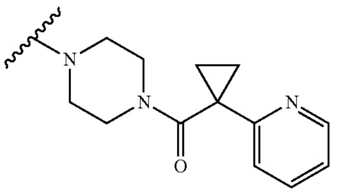

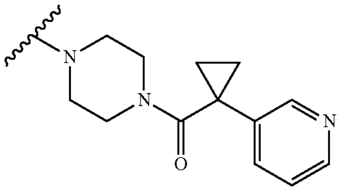

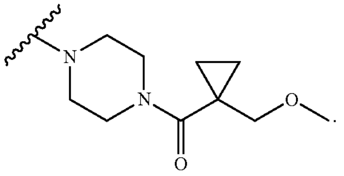

In one embodiment, D is hetCyc$^1$ and E is Cyc$^1$(C1-C6 alkyl)C(═O)— wherein the alkyl portion is optionally substituted with one or more groups independently selected from the group consisting of OH, fluoro, C1-C3 alkoxy, and $R^cR^dN$— where $R^c$ and $R^d$ are independently H or C1-C6 alkyl. In one embodiment, Cyc$^1$ is a C3-C6 cycloalkyl optionally substituted with one or more substituents independently selected from the group consisting of OH, halogen, C1-C6 alkoxy, CN, hydroxyC1-C6 alkyl-, (C1-C6 alkoxy)C1-C6 alkyl-, and C1-C6 alkyl optionally substituted with 1-3 fluoros. In one embodiment, the alkyl portion of Cyc$^1$(C1-C6 alkyl)C(═O)— is unsubstituted. In one embodiment, Cyc$^1$ is unsubstituted. In one embodiment, hetCyc$^1$ is a 6-membered heterocyclic ring having two ring nitrogen atoms. A non-limiting example when D is hetCyc$^1$ and E is Cyc$^1$(C1-C6 alkyl)C(═O)— is the structure:

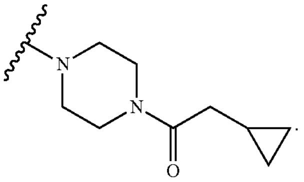 [SMILES: *N1CCN(C(=O)CC2CC2)CC1]

In one embodiment, D is $hetCyc^1$ and E is $hetCyc^4$, where $hetCyc^4$ is as defined for Formula I. In one embodiment, $hetCyc^4$ is a 4-6 membered heterocyclic ring having a ring heteroatom selected from O and S wherein the S is optionally oxidized to $SO_2$, and wherein the heterocyclic ring is optionally substituted with OH or C1-C6 alkoxy. In one embodiment, $hetCyc^1$ is a 6-membered heterocyclic ring having two ring nitrogen atoms. Non-limiting examples when D is $hetCyc^1$ and E is $hetCyc^4$ include the structures:

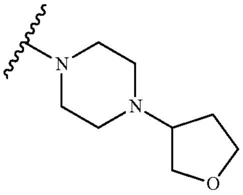

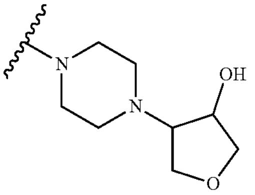

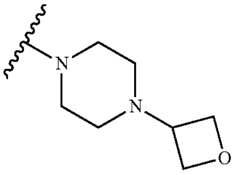

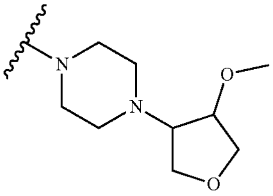

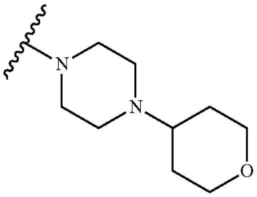

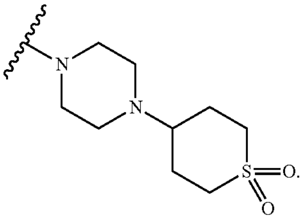

In one embodiment, D is $hetCyc^1$ and E is $hetCyc^4C(=O)$—, where $hetCyc^4$ is as defined for Formula I. In one embodiment, $hetCyc^4$ is optionally substituted with one or more substituents independently selected from the group consisting of halogen, OH, CN, C1-C6 alkyl (optionally substituted with 1-3 fluoros), C1-C6 alkoxy, (C1-C6 alkoxy) C1-C6 alkyl-, (C3-C6)cycloalkyl, a 5-6 membered heterocyclic ring having 1-2 ring heteroatoms independently selected from N and O, and phenyl wherein said phenyl is optionally substituted with one or more substituents independently selected from the group consisting of halogen, C1-C6 alkyl and C1-C6 alkoxy. In one embodiment, the ring is optionally substituted with one or more substituents independently selected from the group consisting of halogen, OH, CN, C1-C6 alkyl (optionally substituted with 1-3 fluoros), C1-C6 alkoxy and (C1-C6 alkoxy)C1-C6 alkyl-. In one embodiment, $hetCyc^1$ is a 6-membered heterocyclic ring having two ring nitrogen atoms. Non-limiting examples when D is $hetCyc^1$ and E is $hetCyc^4C(=O)$— include the structures:

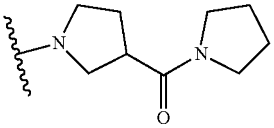

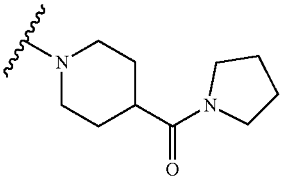

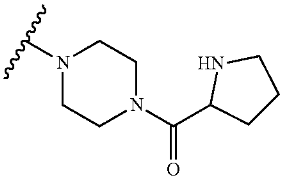

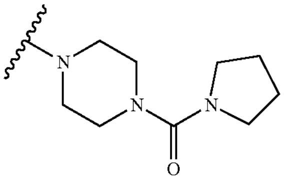

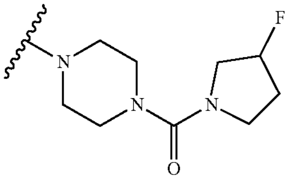

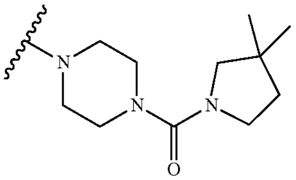

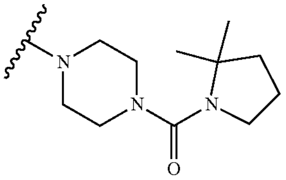

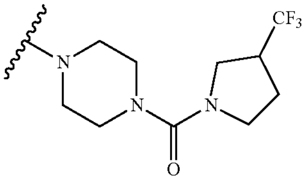

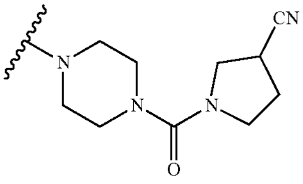

-continued
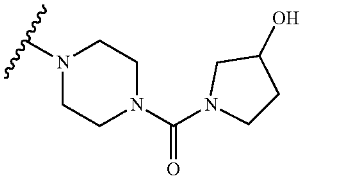
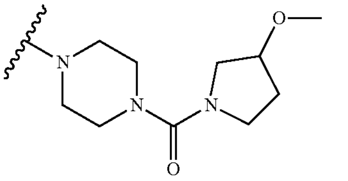
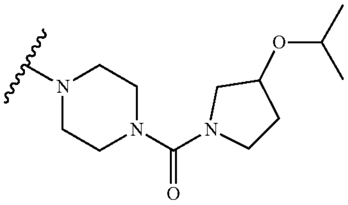
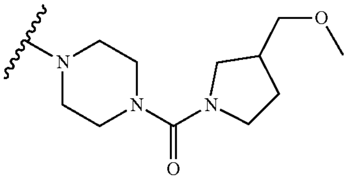
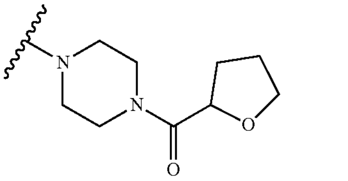
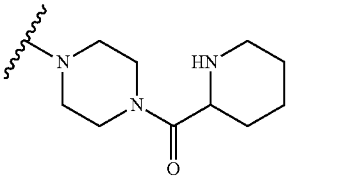
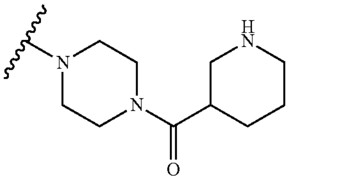
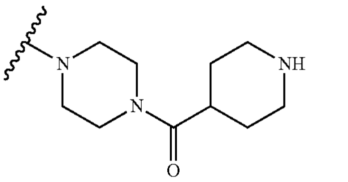
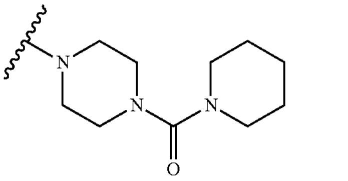
-continued
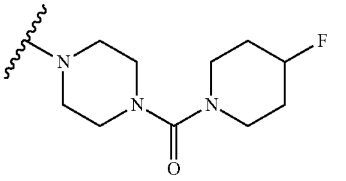
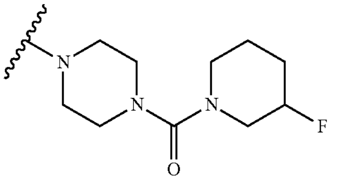
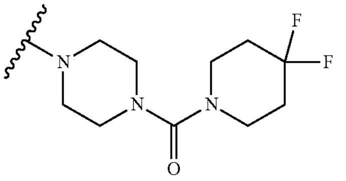
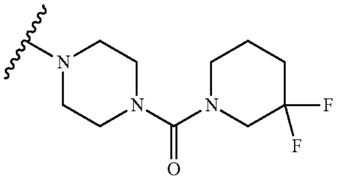
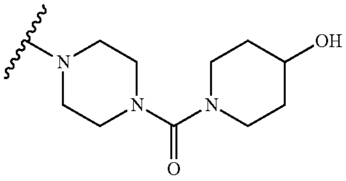
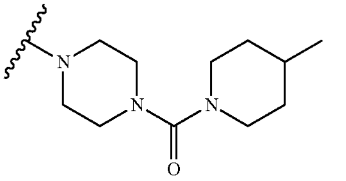
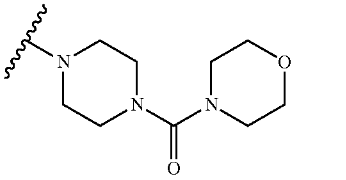
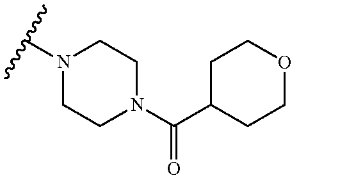
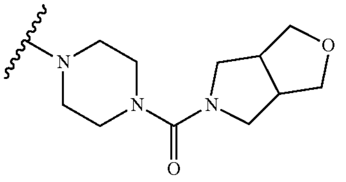

-continued
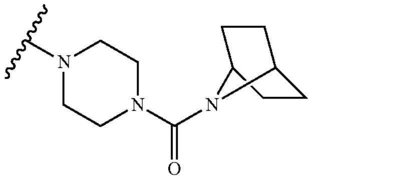
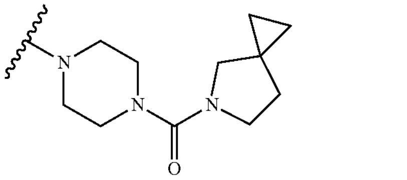
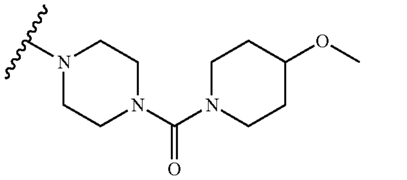
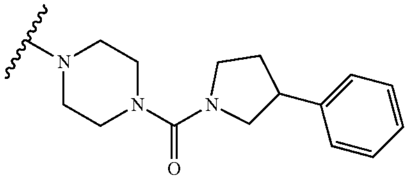
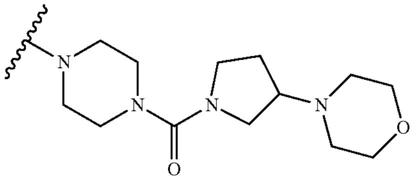
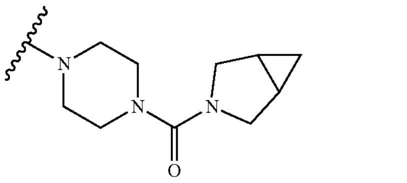
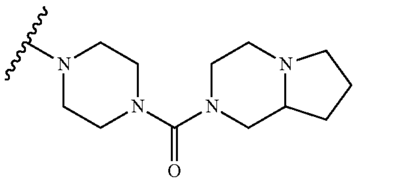
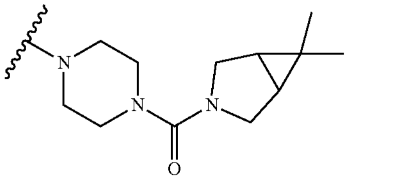
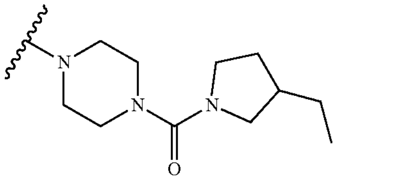
-continued
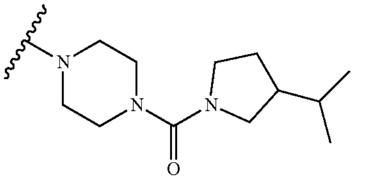
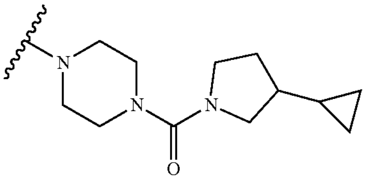
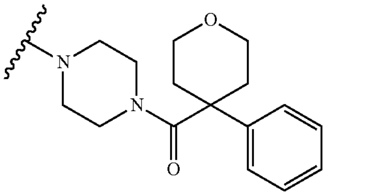
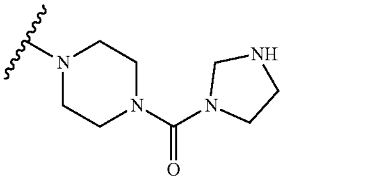
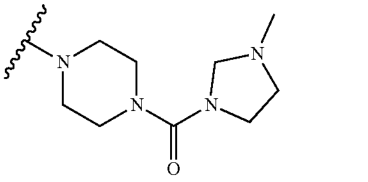
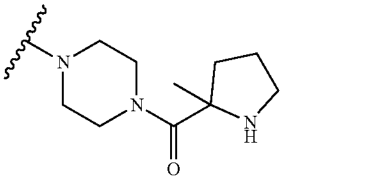
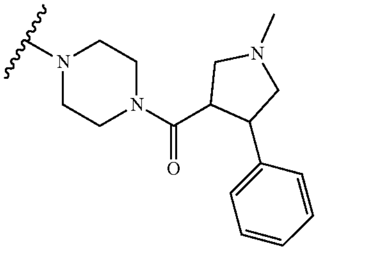
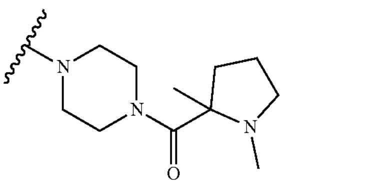

-continued

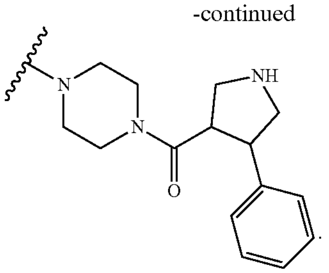

In one embodiment, D is $hetCyc^1$ and E is $hetCyc^4$(C1-C6 alkyl)C(═O)— where $hetCyc^4$ is as defined for Formula I. In one embodiment, $hetCyc^4$ is a 5-6 membered heterocyclic ring having 1-2 ring heteroatoms independently selected from N and O, wherein the heterocyclic ring is optionally substituted with C1-C6 alkyl. In one embodiment, $hetCyc^1$ is a 6-membered heterocyclic ring having two ring nitrogen atoms. Non-limiting examples when D is $hetCyc^1$ and E is $hetCyc^4$(C1-C6 alkyl)C(═O)— include the structures:

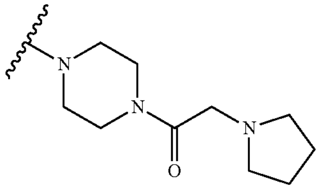

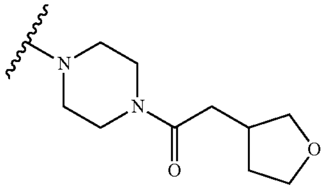

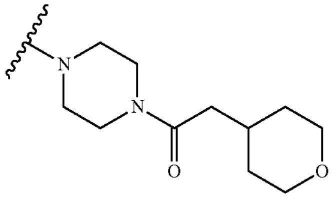

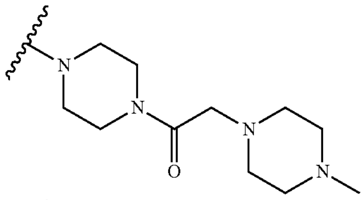

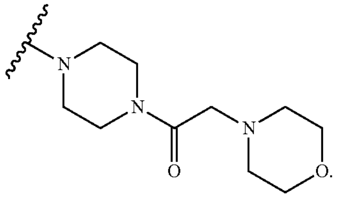

In one embodiment, D is $hetCyc^1$ and E is $hetCyc^4$C(═O) C1-C6 alkyl-, where $hetCyc^4$ is as defined for Formula I. In one embodiment, $hetCyc^4$ is a 4-6 membered heterocyclic ring having 1-2 ring heteroatoms independently selected from N and O. In one embodiment, $hetCyc^4$ is unsubstituted. In one embodiment, $hetCyc^1$ is a 6-membered heterocyclic ring having two ring nitrogen atoms. A non-limiting example when D is $hetCyc^1$ and E is $hetCyc^4$C(═O)C1-C6 alkyl- is the structure:

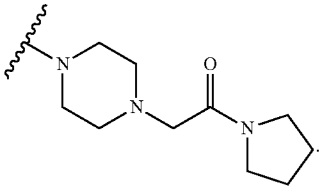 [SMILES: *N1CCN(CC(=O)N2CCCC2)CC1]

In one embodiment, D is $hetCyc^1$ and E is $hetCyc^4$C(═O) $NR^g$—, where $R^g$ is H or C1-C6 alkyl, where $hetCyc^4$ is as defined for Formula I. In one embodiment, $hetCyc^4$ is optionally substituted with one or more substituents independently selected from the group consisting of halogen, OH, CN, C1-C6 alkyl (optionally substituted with 1-3 fluoros), C1-C6 alkoxy, and (C1-C6 alkoxy)C1-C6 alkyl-. In one embodiment, $hetCyc^1$ is a 6-membered heterocyclic ring having two ring nitrogen atoms Non-limiting examples when D is $hetCyc^1$ and E is $hetCyc^4$C(═O)$NR^g$—, where $R^g$ is H or C1-C6 alkyl include the structures:

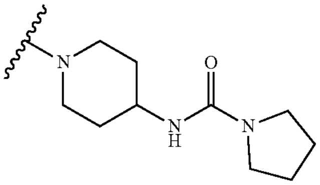

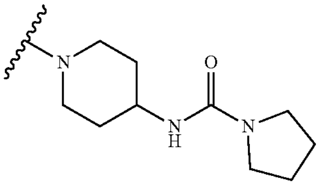

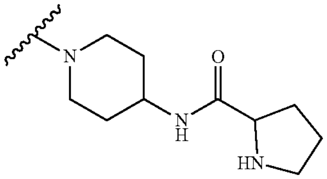

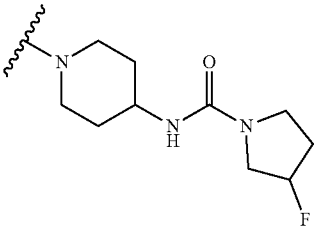

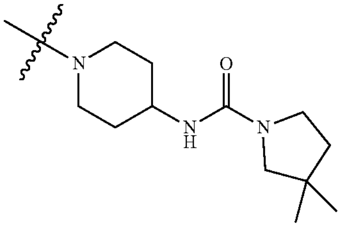

-continued
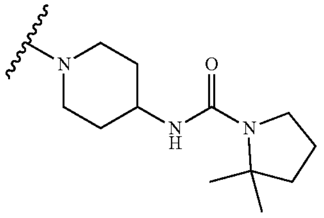
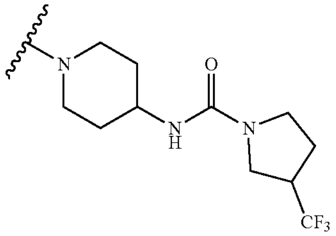
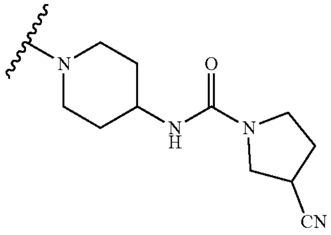
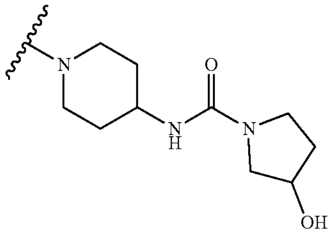
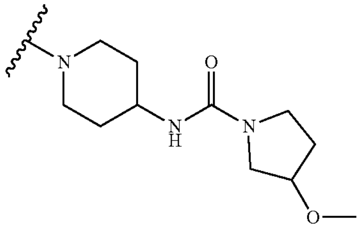
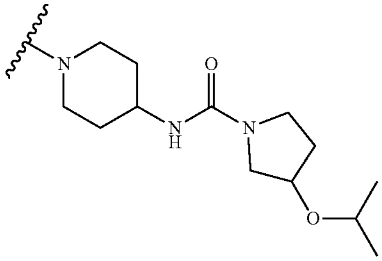
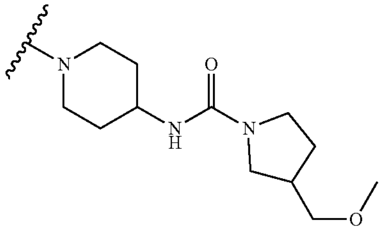
-continued
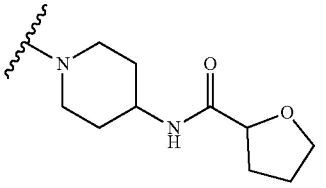
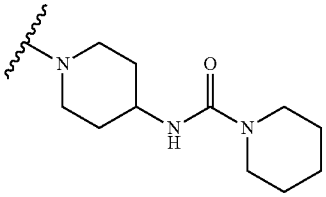
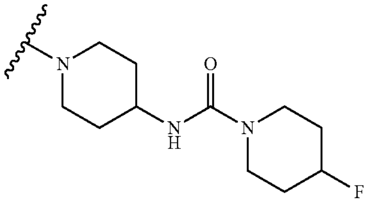
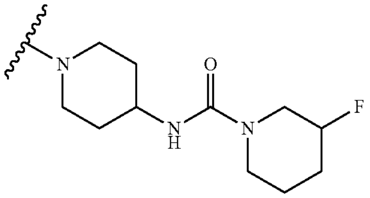
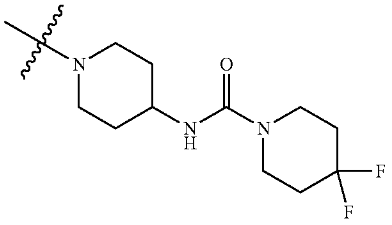
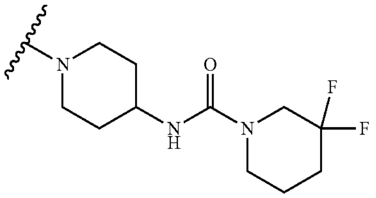
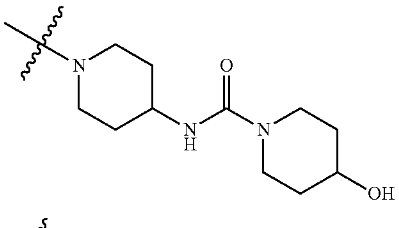
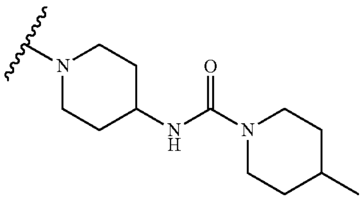

-continued

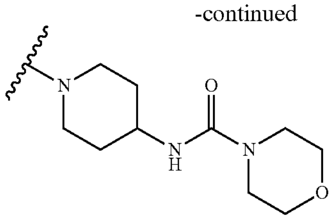

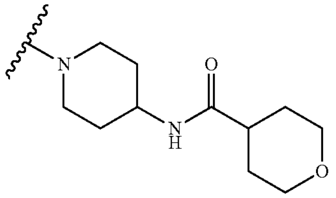

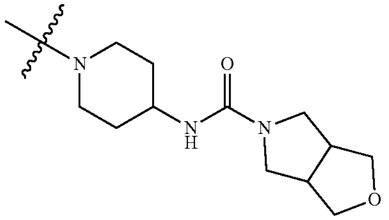

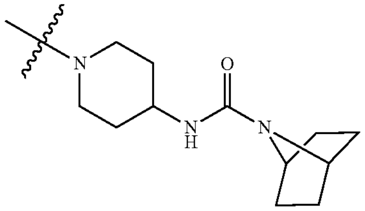

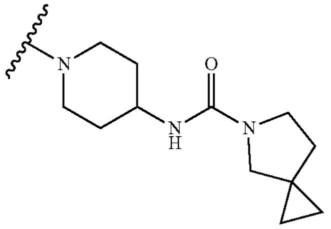

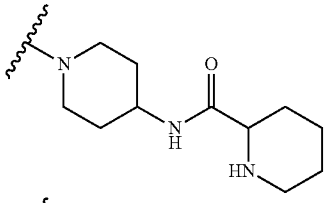

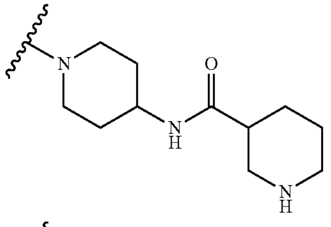

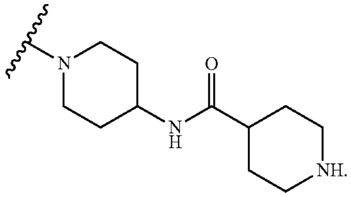

In one embodiment, D is hetCyc[1] and E is $Ar^2$ wherein $Ar^2$ is as defined for Formula I. In one embodiment, $Ar^2$ is phenyl optionally substituted with one or more substituents independently selected from the group consisting of halogen. In one embodiment, hetCyc[1] is a 4-6 membered heterocyclic ring having 1-2 ring atoms independently selected from N and O. Non-limiting examples when D is hetCyc[1] and E is $Ar^2$ include the structures:

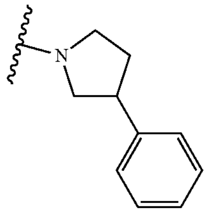

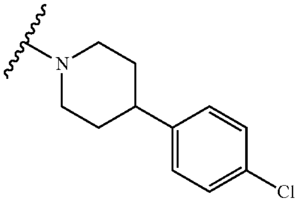

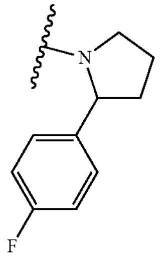

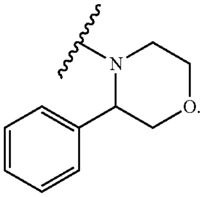

In one embodiment, D is hetCyc[1] and E is $Ar^2C(=O)$— wherein $Ar^2$ is as defined for Formula I. In one embodiment, $Ar^2$ is phenyl optionally substituted with one or more substituents independently selected from the group consisting of halogen or a 5-6 membered heterocyclic ring having 1-2 ring heteroatoms independently selected from N and O. In one embodiment, hetCyc[1] is a 6-membered ring having two ring nitrogen atoms. Non-limiting examples include the structures:

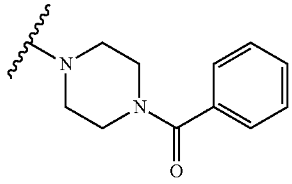

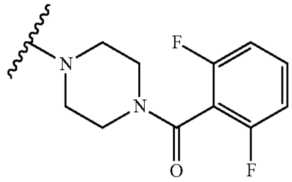

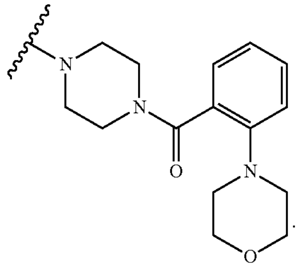

In one embodiment, D is hetCyc[1] and E is $(Ar^2)$C1-C6 alkyl- wherein $Ar^2$ is as defined for Formula I. In one embodiment, $Ar^2$ is phenyl optionally substituted with one or more substituents independently selected from the group consisting of halogen, C1-C3 alkyl, C1-C3 alkoxy, CN, and $R^iR^jN$— where $R^i$ and $R^j$ are independently selected from H and C1-C6 alkyl. In one embodiment, $Ar^2$ is phenyl optionally substituted with one or more substituents independently selected from the group consisting of halogen, C1-C6 alkyl, C1-C6 alkoxy, CN, and $R^iR^jN$— where $R^i$ and $R^j$ are independently selected from H and C1-C6 alkyl. In one embodiment, $hetCyc^1$ is a 4-6-membered ring having one or two ring nitrogen atoms wherein said ring is optionally substituted with oxo or OH. Non-limiting examples when D is $hetCyc^1$ and E is $(Ar^2)$C1-C6 alkyl-include the structures:

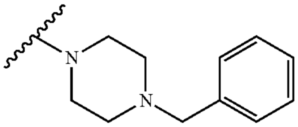

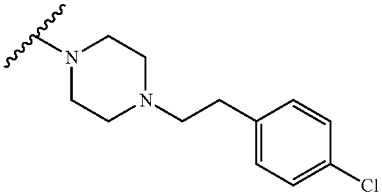

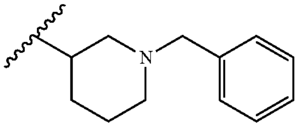

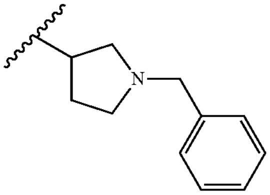

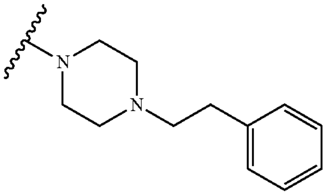

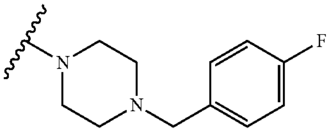

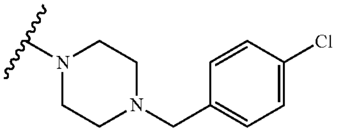

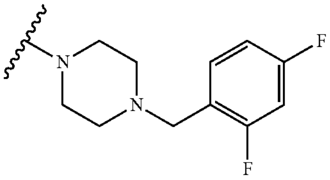

-continued

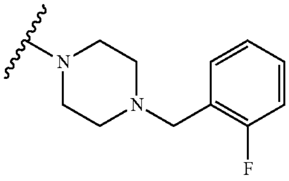

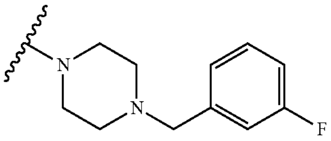

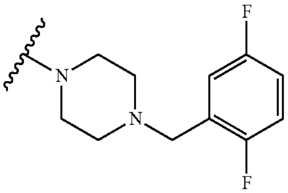

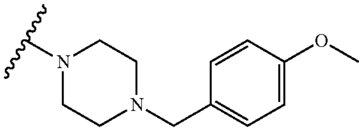

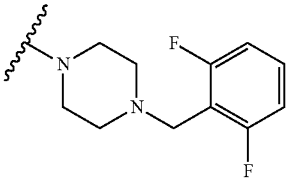

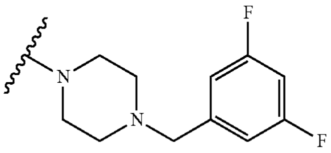

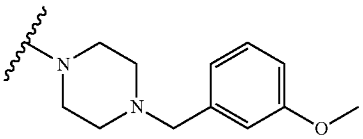

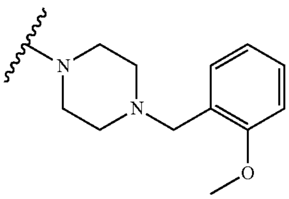

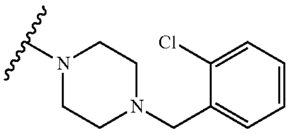

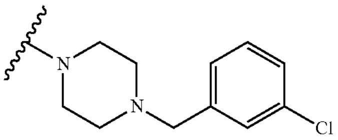

-continued

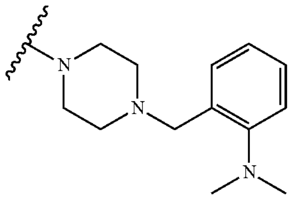

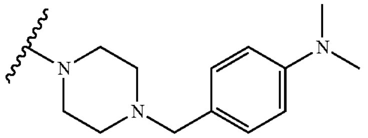

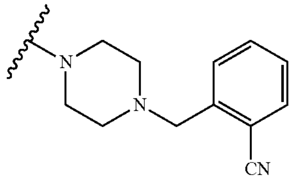

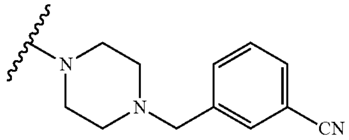

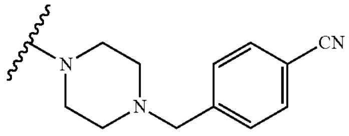

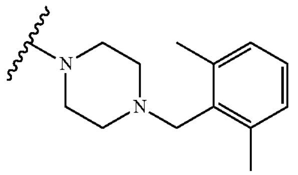

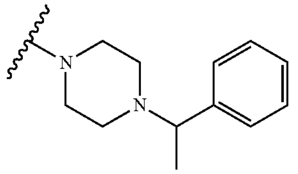

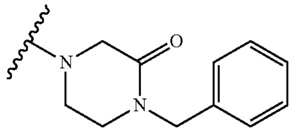

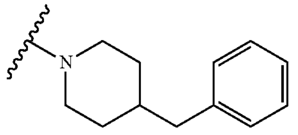

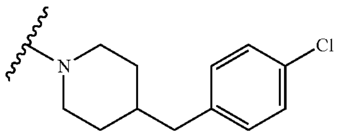

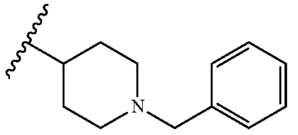

-continued

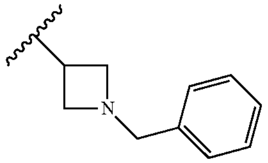

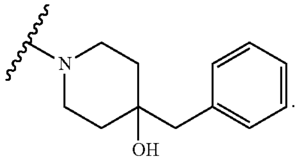

In one embodiment, D is hetCyc[1] and E is ($Ar^2$)hydroxy C2-C6 alkyl- wherein $Ar^2$ is as defined for Formula I. In one embodiment, $Ar^2$ is phenyl optionally substituted with one or more halogens. In one embodiment, hetCyc[1] is a 6-membered ring having two ring nitrogen atoms. Non-limiting examples when D is hetCyc[1] and E is ($Ar^2$)hydroxy C2-C6 alkyl- include the structures:

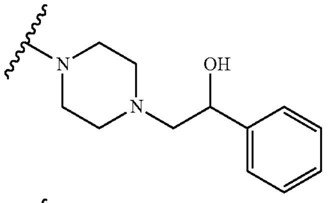

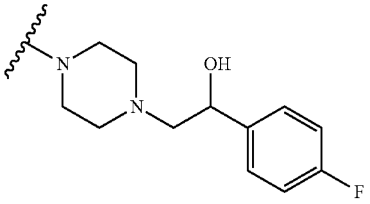

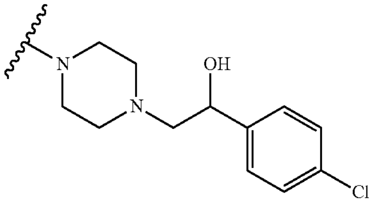

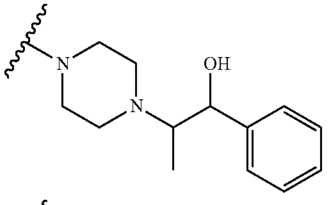

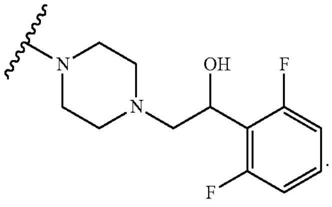

In one embodiment, D is hetCyc[1] and E is $Ar^2$(C1-C6 alkyl)C(=O)—, wherein $Ar^2$ is as defined for Formula I and the alkyl portion is optionally substituted with one or two groups independently selected from the group consisting of OH, C1-C6 alkyl (optionally substituted with 1-3 fluoros), hydroxyC1-C6 alkyl-, (C1-C6)alkoxy, $R^eR^fN$— and ($R^eR^fN$)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl. In one embodiment, hetCyc$^1$ is piperazinyl. In one embodiment, Ar$^2$ is phenyl optionally substituted with one or more substituents independently selected from halogen, CN, C1-C6 alkyl and C1-C6 alkoxy (optionally substituted with 1-3 fluoros).

In one embodiment, D is hetCyc$^1$ and E is Ar$^2$(C1-C6 alkyl)C(═O)—, wherein Ar$^2$ is as defined for Formula I and the alkyl portion is optionally substituted with one or two groups independently selected from the group consisting of OH, C1-C6 alkyl, hydroxyC1-C6 alkyl-, (C1-C6)alkoxy, $R^eR^fN$— and ($R^eR^fN$)C1-C3 alkyl- wherein $R^e$ and $R^f$ are independently H or C1-C6 alkyl. In one embodiment, hetCyc$^1$ is a 6-membered ring having two ring nitrogen atoms. Non-limiting examples when D is hetCyc$^1$ and E is Ar$^2$(C1-C6 alkyl)C(═O)— include the structures:

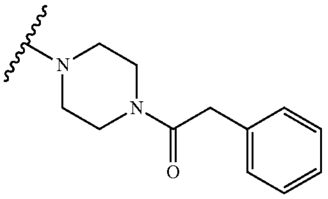

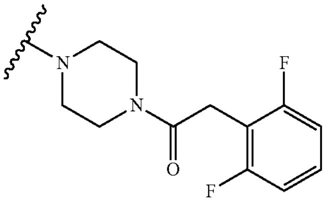

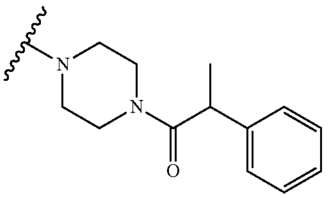

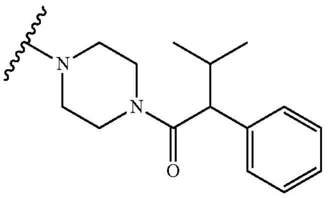

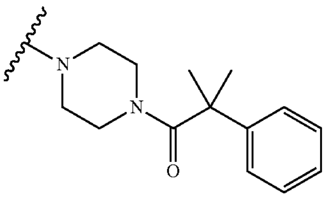

-continued

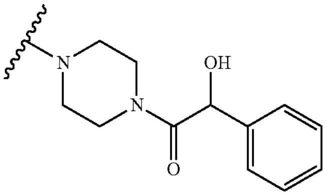

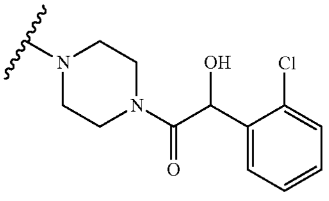

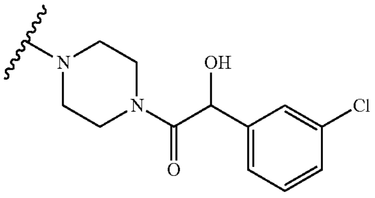

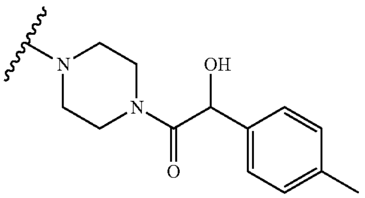

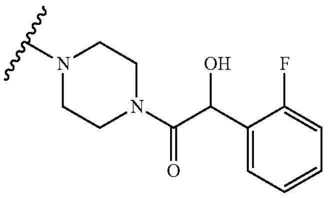

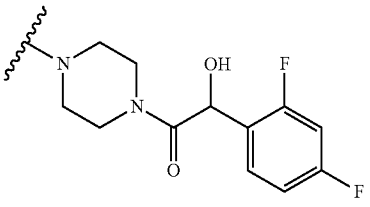

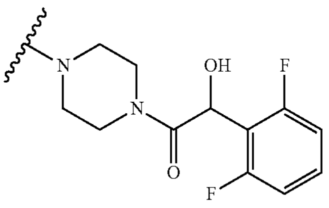

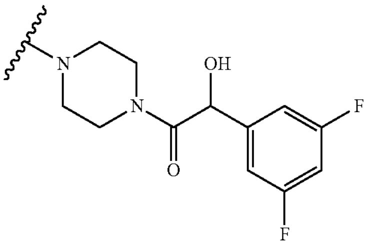

-continued
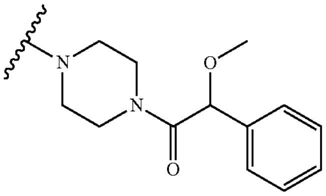
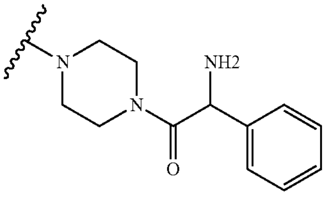
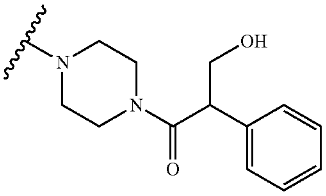
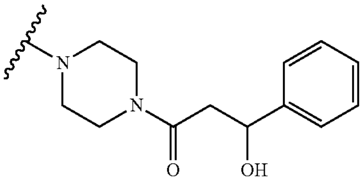
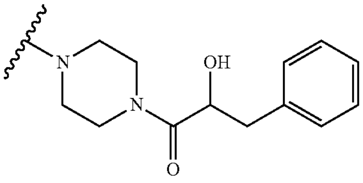
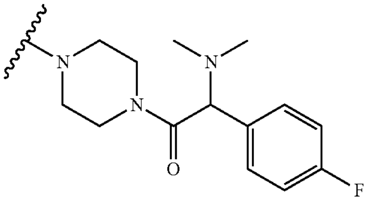
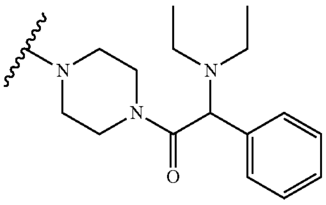
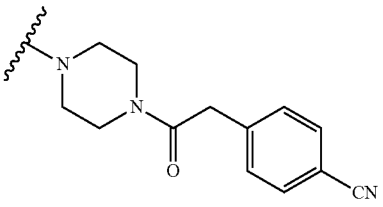
-continued
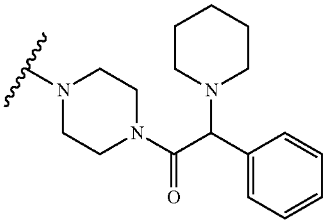
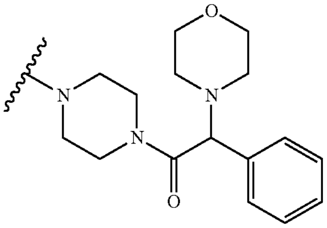
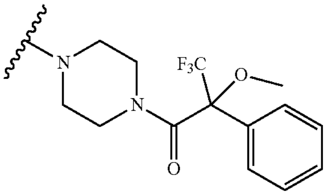
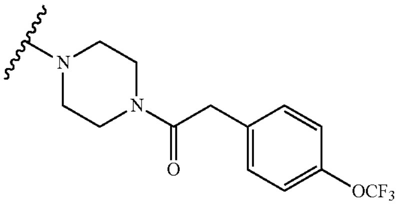
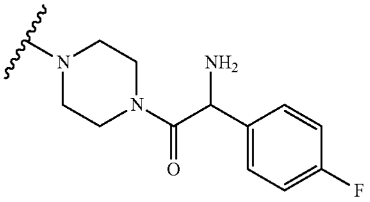
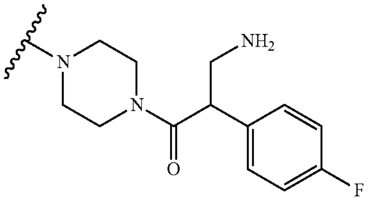
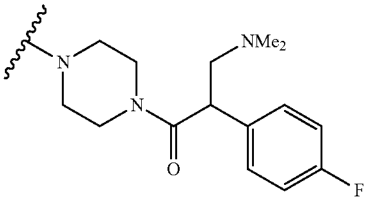
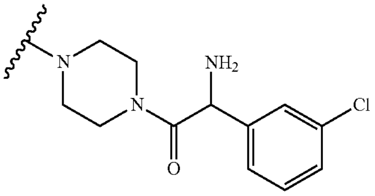

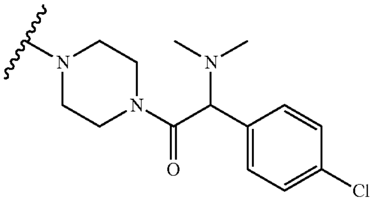

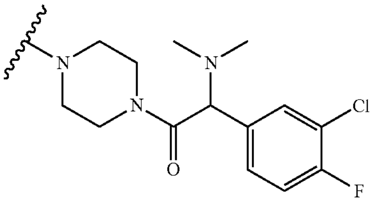

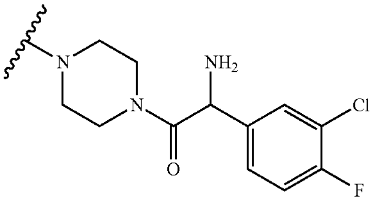

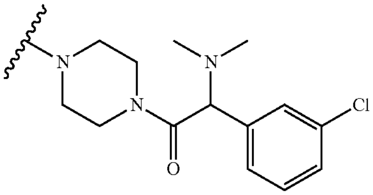

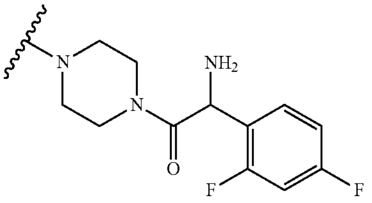

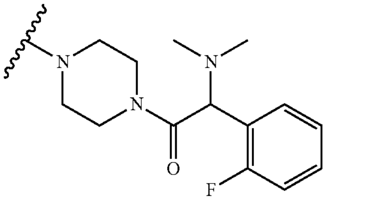

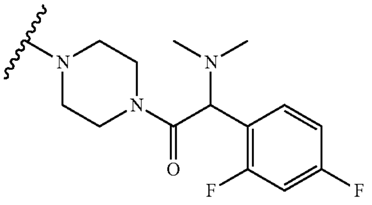

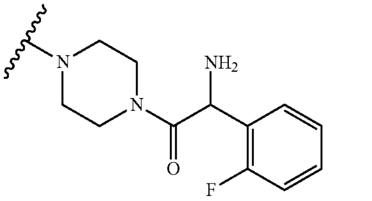

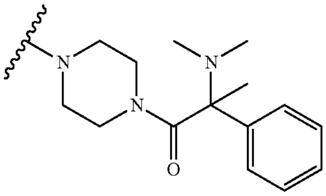

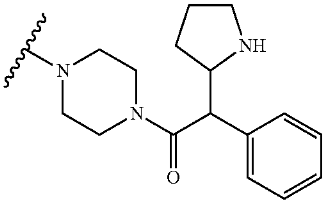

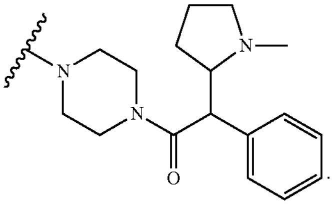

In one embodiment, D is hetCyc[1] and E is hetAr[2]C(=O)—, where hetAr[2] is as defined for Formula I. In one embodiment, hetAr[2] is optionally substituted with one or more substituents independently selected from the group consisting of C1-C3 alkyl, (C3-C6)cycloalkyl and (C1-C6 alkoxy)C1-C6 alkyl-. In one embodiment, hetCyc[1] is a 6-membered ring having two ring nitrogen atoms. Non-limiting examples when D is hetCyc[1] and E is hetAr[2]C(=O)— include the structures:

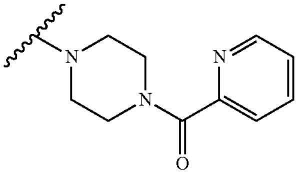

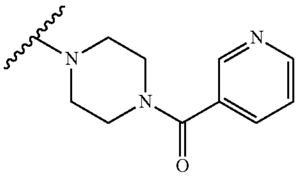

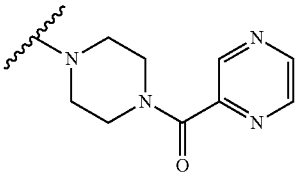

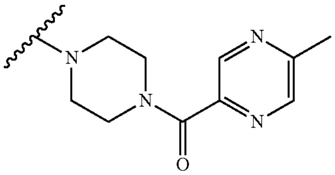

-continued

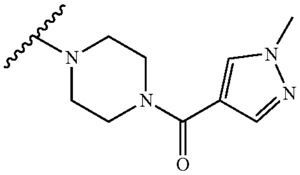

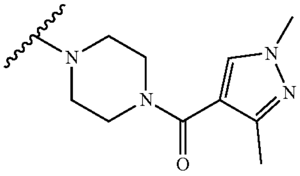

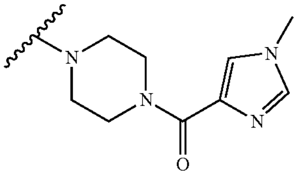

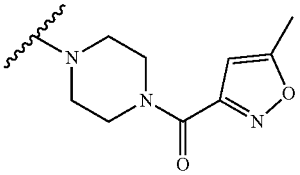

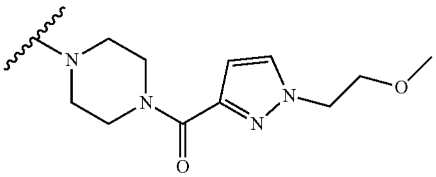

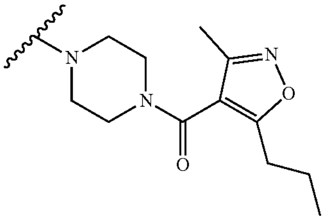

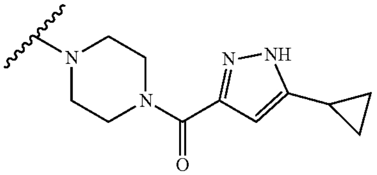

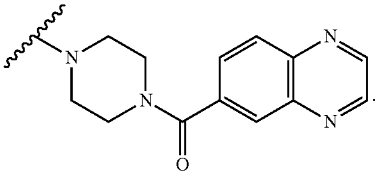

In one embodiment, D is hetCyc$^1$ and E is (hetAr$^2$) hydroxy C2-C6 alkyl- where hetAr$^2$ is as defined for Formula I. In one embodiment, hetAr$^2$ is a 5-6 membered heteroaryl ring having 1-2 ring heteroatoms independently selected from N and O wherein said ring is unsubstituted. In one embodiment, hetCyc$^1$ is a 6-membered ring having two ring nitrogen atoms. Non-limiting examples includes the structures:

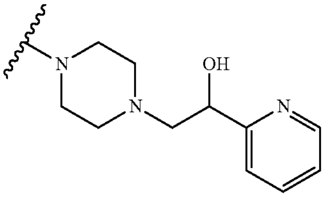

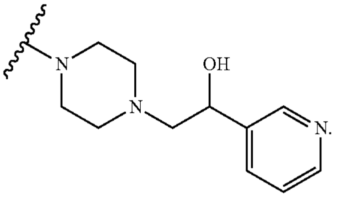

In one embodiment, D is hetCyc$^1$ and E is hetAr$^2$(C1-C6 alkyl)C(═O)—, wherein hetAr$^2$ is as defined for Formula I and the alkyl portion is optionally substituted with one or two groups independently selected from the group consisting of OH, C1-C6 alkyl, hydroxyC1-C6 alkyl-, (C1-C6) alkoxy, $R^eR^fN$— and ($R^eR^fN$)C1-C3 alkyl-, where $R^e$ and $R^f$ are independently H or C1-C6 alkyl. In one embodiment, the alkyl portion of hetAr$^2$(C1-C6 alkyl)C(═O)— is unsubstituted. In one embodiment, hetAr$^2$ is optionally substituted with one or more substituents independently selected from the group consisting of halogen and C1-C6 alkyl. In one embodiment, hetCyc$^1$ is a 6-membered ring having two ring nitrogen atoms. Non-limiting examples where D is hetCyc$^1$ and E is hetAr$^2$(C1-C6 alkyl)C(═O)— include the structures:

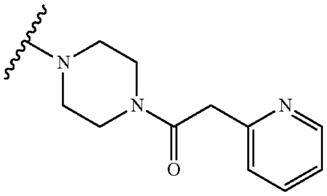

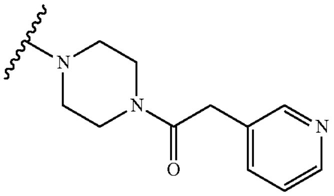

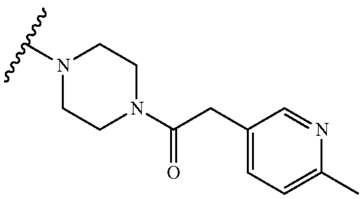

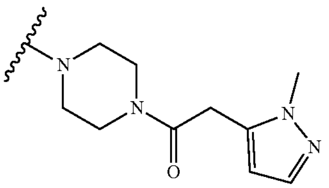

-continued

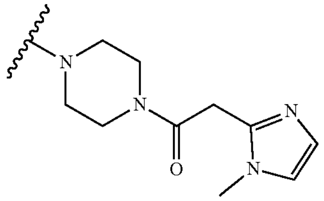

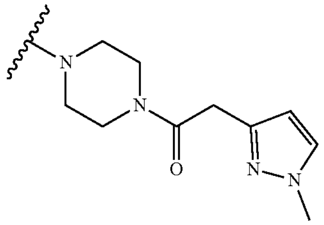

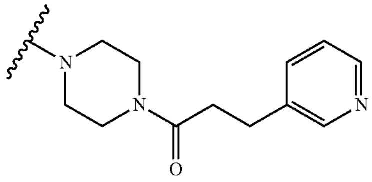

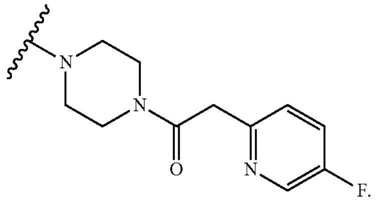

In one embodiment, D is hetCyc[1] and E is $R^1R^2NC(=O)$—, where $R^1$ is H, C1-C6 alkyl or (C1-C6 alkoxy) C1-C6 alkyl-, and $R^2$ is C1-C6 alkyl (optionally substituted with 1-3 fluoros), (C1-C6 alkoxy)C1-C6 alkyl- (optionally substituted with 1-3 fluoros), Cyc[3], hydroxyC1-C6 alkyl- (optionally substituted with 1-3 fluoros), C1-C6 alkoxy (optionally substituted with 1-3 fluoros), hetCyc[7], Ar[3], $Ar^3CH_2$—, hydroxyC1-C6 alkoxy or (C3-C6 cycloalkyl) $CH_2O$—. In one embodiment, hetCyc[1] is optionally substituted with C1-C3 alkyl. Non-limiting examples when D is hetCyc[1] and E is $R^1R^2NC(=O)$— include the structures:

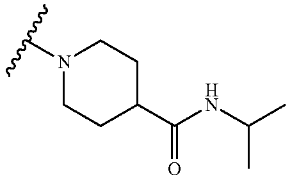

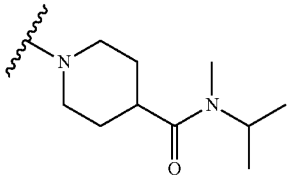

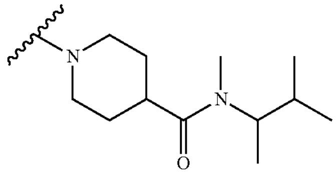

-continued

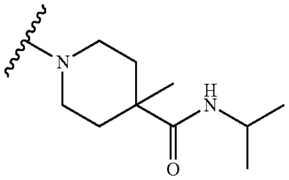

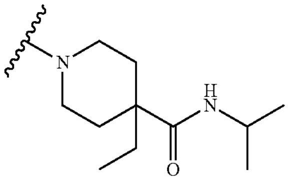

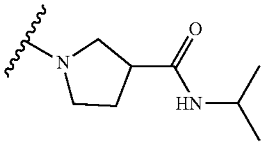

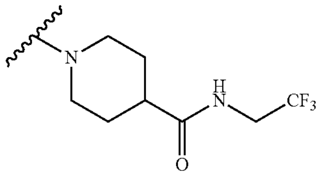

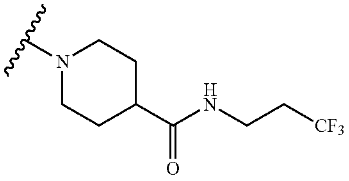

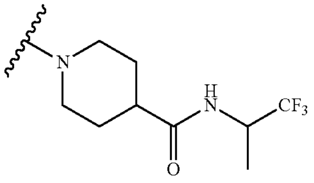

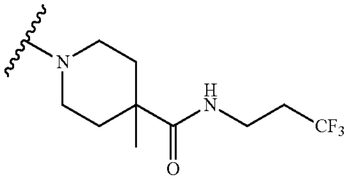

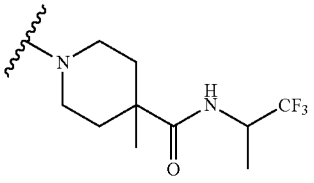

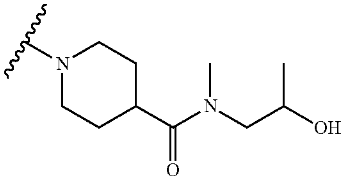

-continued
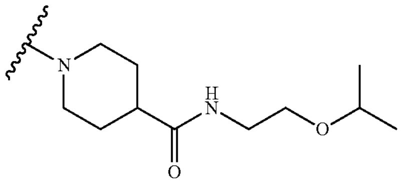
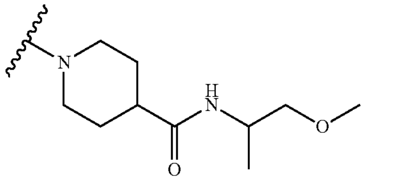
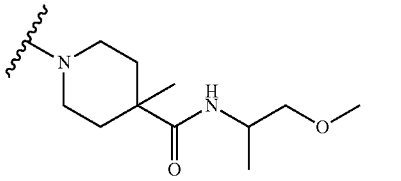
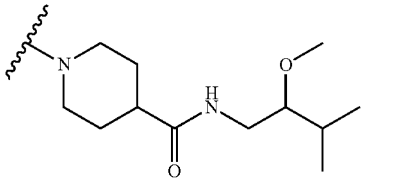
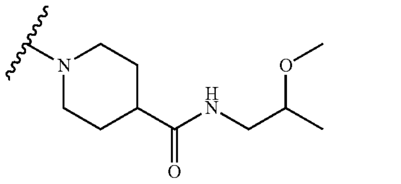
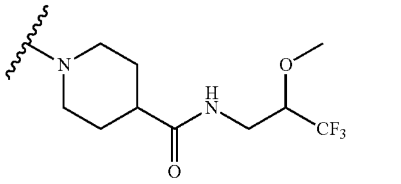
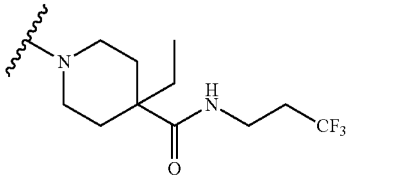
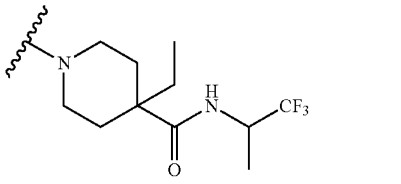
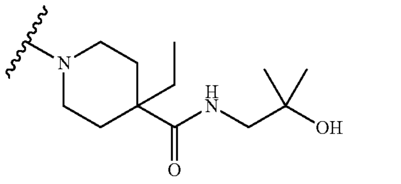
-continued
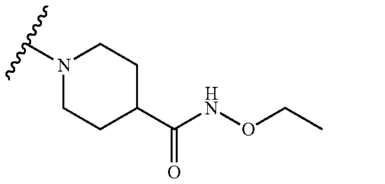
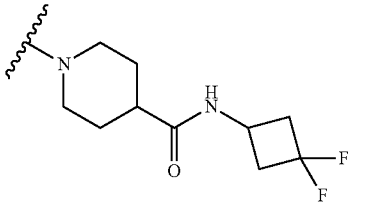
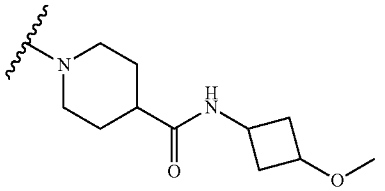
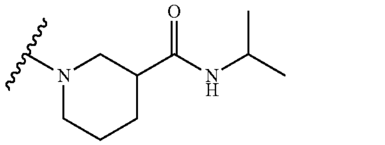
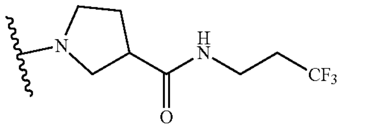
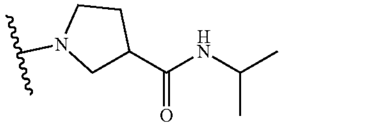
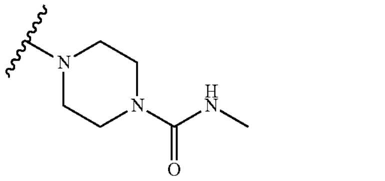
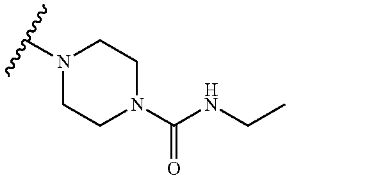
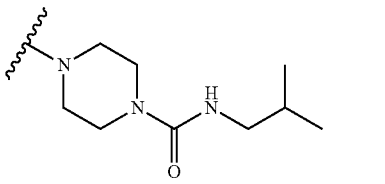
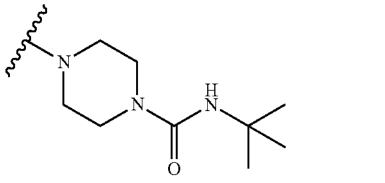

-continued
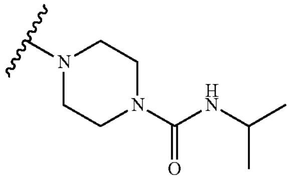
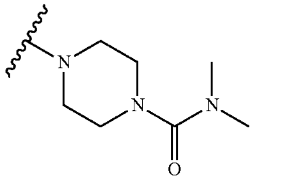
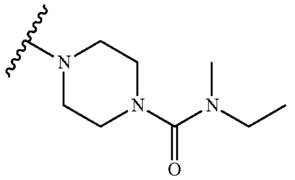
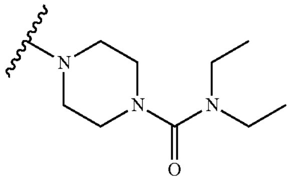
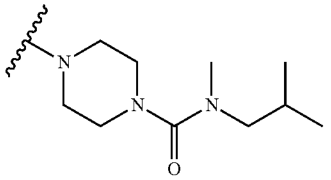
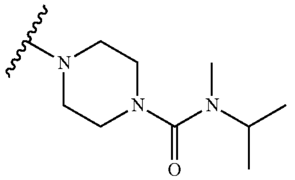
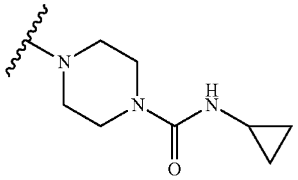
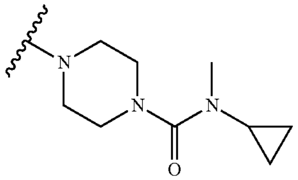
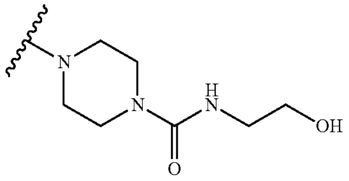
-continued
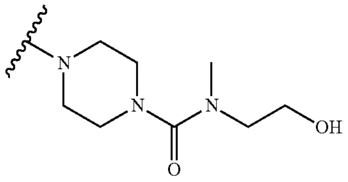
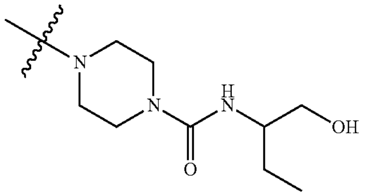
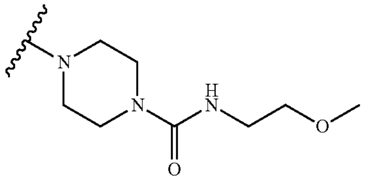
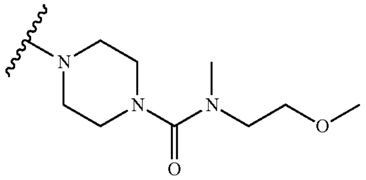
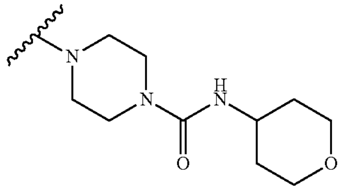
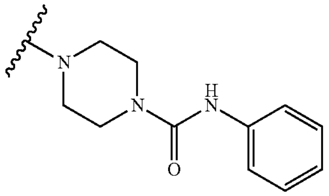
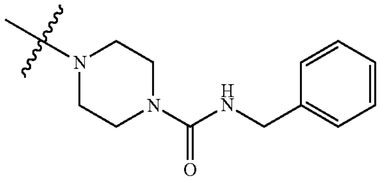
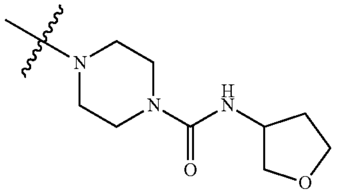
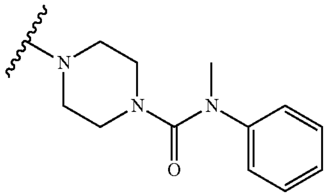

-continued
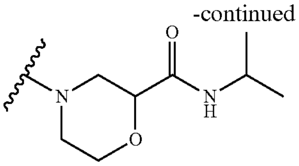
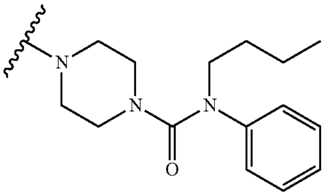
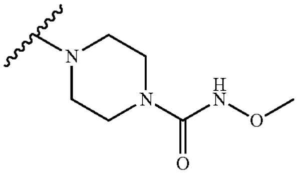
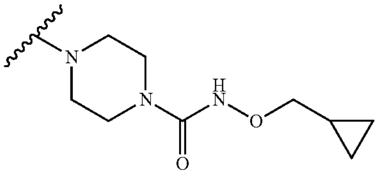
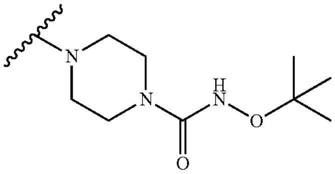
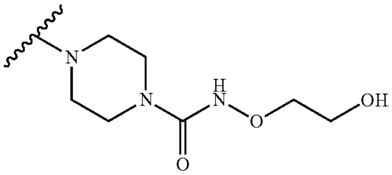
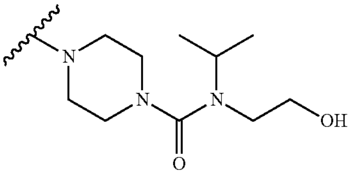
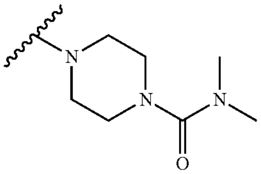
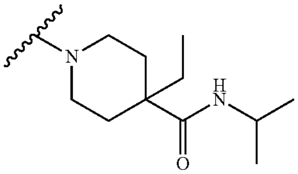
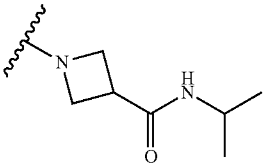
-continued
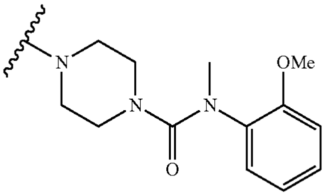
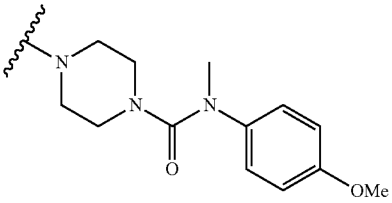
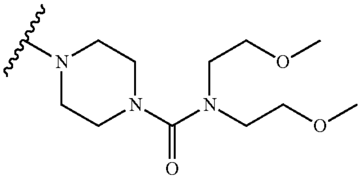
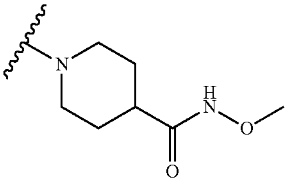
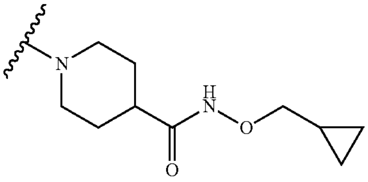
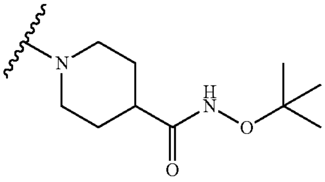
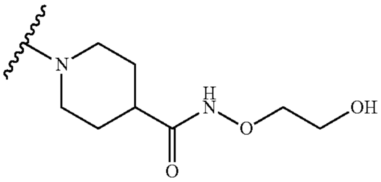
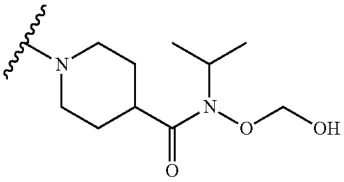
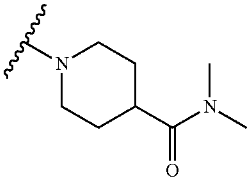

-continued

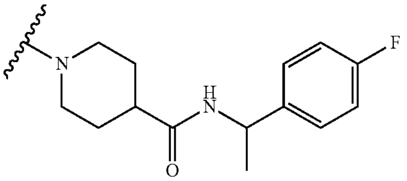

In one embodiment, D is hetCyc$^1$ and E is $R^1R^2N$(C1-C6 alkyl)C(═O)— wherein the C1-C3 alkyl portion is optionally substituted with phenyl. In one embodiment, $R^1$ is H or C1-C6 alkyl and $R^2$ is H, C1-C6 alkyl (optionally substituted with 1-3 fluoros) or (C1-C6 alkoxy)C(═O)—. In one embodiment, hetCyc$^1$ is a 6-membered ring having two ring nitrogen atoms. Non-limiting examples include the structures:

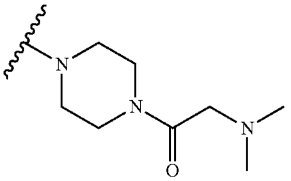

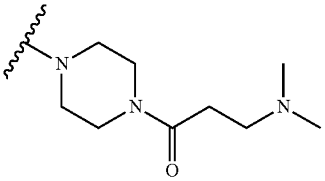

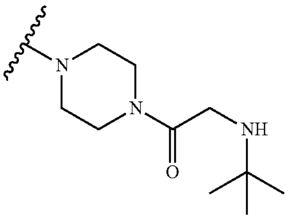

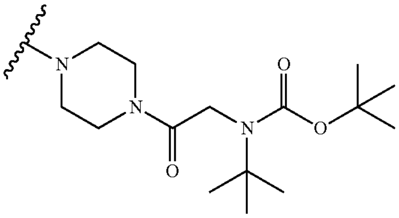

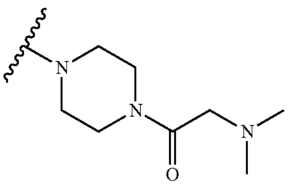

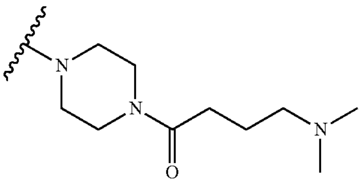

-continued

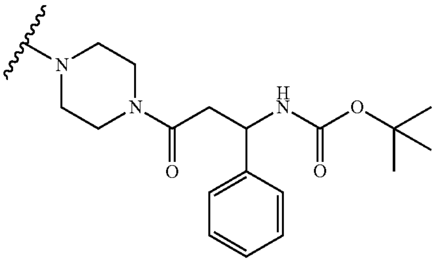

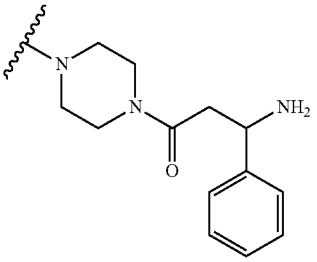

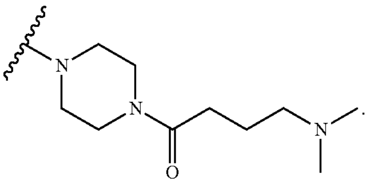

In one embodiment, D is hetCyc$^1$ and E is $R^1R^2$NC(═O) C1-C6 alkyl-. In one embodiment, $R^1$ is H or C1-C6 alkyl and $R^2$ is C1-C6 alkyl (optionally substituted with 1-3 fluoros). In one embodiment, hetCyc$^1$ is a 4-6-membered ring having one to two ring nitrogen atoms. Non-limiting examples include the structures:

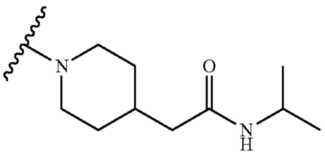

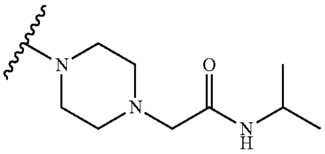

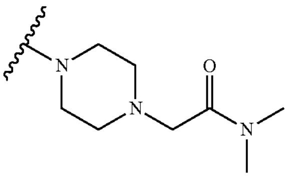

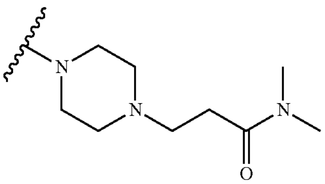

-continued

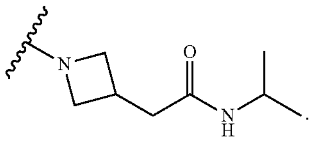

In one embodiment, D is hetCyc[1] and E is $R^1R^2NC(=O)NH-$, where $R^1$ is H or C1-C6 alkyl, and $R^2$ is C1-C6 alkyl (optionally substituted with 1-3 fluoros). In one embodiment, hetCyc[1] is a 6-membered ring having one ring nitrogen atom. Non-limiting examples include the structures:

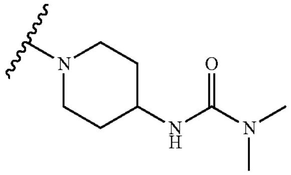

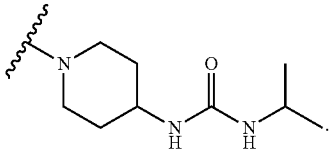

In one embodiment, D is hetCyc[1] and E is $CH_3SO_2$(C1-C6 alkyl)C(=O)—. In one embodiment, hetCyc[1] is a 6-membered ring having two ring nitrogen atoms. A non-limiting example is the structure:

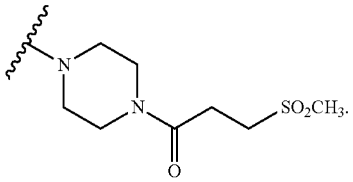 [SMILES: *N1CCN(C(=O)CCS(C)(=O)=O)CC1]

In one embodiment, D is hetCyc[1] and E is (C1-C6 alkyl)$SO_2$—. In one embodiment, hetCyc[1] is a 6-membered ring having one or two ring nitrogen atoms. Non-limiting examples include the structures:

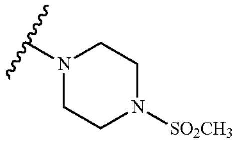

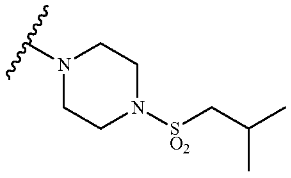

-continued

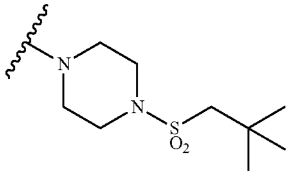

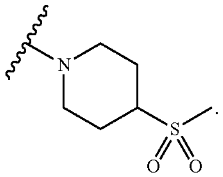

In one embodiment, D is hetCyc[1] and E is (C3-C6 cycloalkyl)$CH_2SO_2$—. In one embodiment, hetCyc[1] is a 6-membered ring having two ring nitrogen atoms. A non-limiting example is the structure:

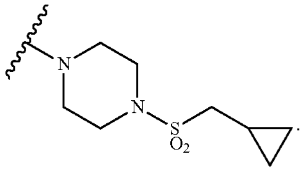 [SMILES: *N1CCN(S(=O)(=O)CC2CC2)CC1]

In one embodiment, D is hetCyc[1] and E is hetCyc[5]-$SO_2$—, where hetCyc[5] is a 5-6 membered heterocyclic ring having a ring heteroatom selected from O and N. In one embodiment, hetCyc[1] is a 6-membered ring having two ring nitrogen atoms. Non-limiting examples include the structures:

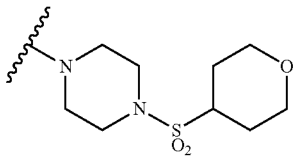

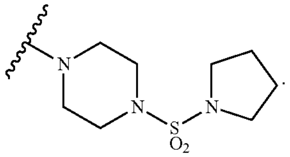

In one embodiment, D is hetCyc[1] and E is $R^4R^5NSO_2$—, where $R^4$ and $R^5$ are independently H or C1-C6 alkyl. In one embodiment, hetCyc[1] is a 6-membered ring having one or two ring nitrogen atoms. Non-limiting examples include the structures:

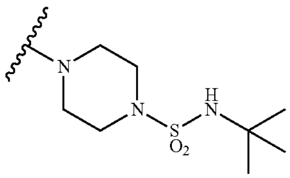

-continued

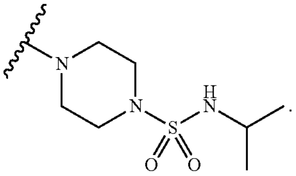

In one embodiment, D is hetCyc[1] and E is $R^6C(=O)NH-$, where $R^6$ is C1-C6 alkyl, hydroxyC1-C6 alkyl-, C1-C6 alkoxy, (C1-C6 alkoxy)C1-C6 alkyl-, phenyl or hetCyc[8]. In one embodiment, hetCyc[1] is a 6-membered ring having one ring nitrogen atom. Non-limiting examples include the structures:

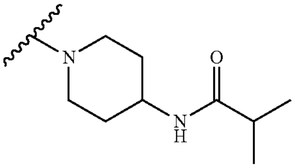

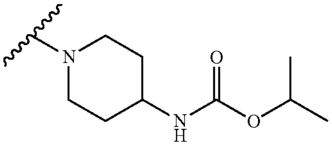

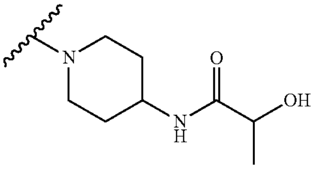

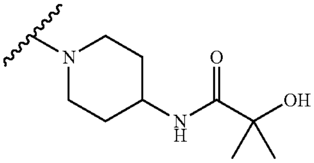

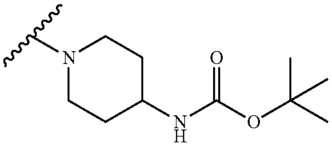

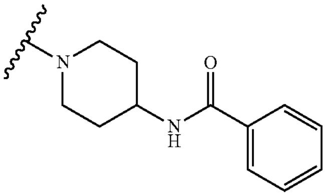

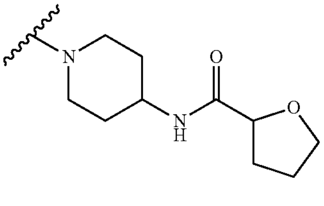

-continued

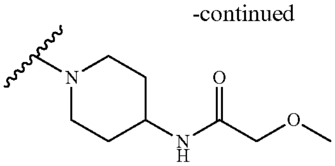

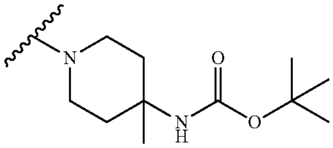

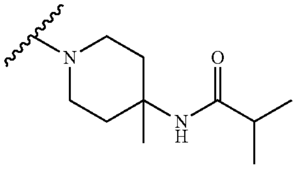

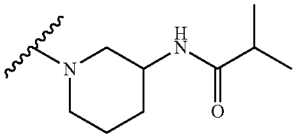

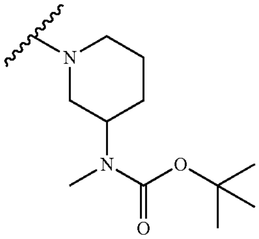

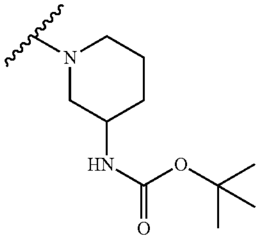

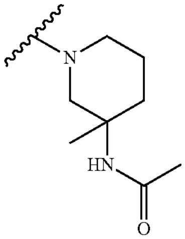

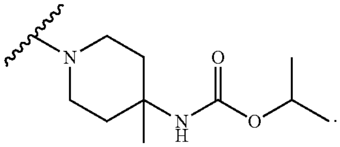

In one embodiment, D is hetCyc[1] and E is hetCyc[6], where hetCyc[6] is a 5 membered heterocyclic ring having one or two ring heteroatoms independently selected from N and O, wherein the ring is substituted with oxo and wherein the ring is further optionally substituted with one or more substituents independently selected from the group consisting of OH and C1-6 alkyl. In one embodiment, hetCyc[1] is a 6-membered ring having one or two ring nitrogen atoms. Non-limiting examples include the structures:

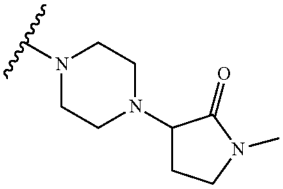

-continued

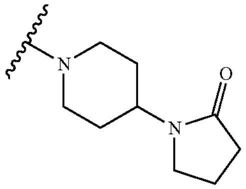

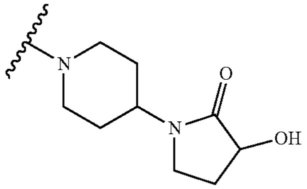

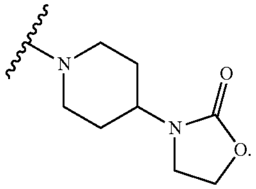

In one embodiment, D is hetCyc$^1$ and E is (hetAr$^2$)C1-C6 alkyl-, where hetAr$^2$ is as defined for Formula I. In one embodiment, hetAr$^2$ is optionally substituted with one or more substituents independently selected from the group consisting of halogen, C1-C3 alkyl and C1-C3 alkoxy. In one embodiment, hetCyc$^1$ is a 6-membered ring having one or two ring nitrogen atoms, wherein said ring is optionally substituted with OH. Non-limiting examples when D is hetCyc$^1$ and E is (hetAr$^2$)C1-C6 alkyl- include the structures:

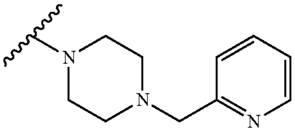

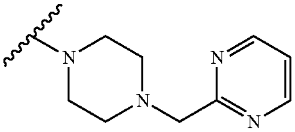

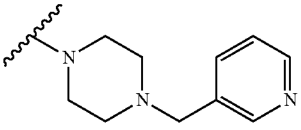

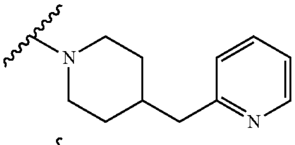

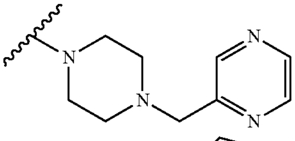

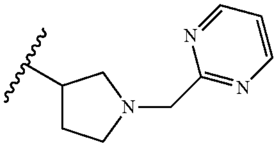

-continued

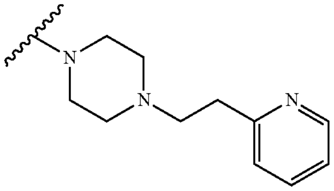

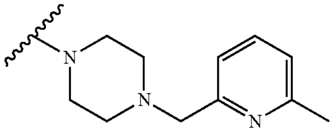

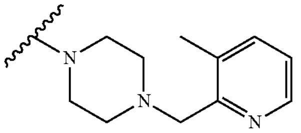

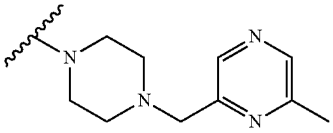

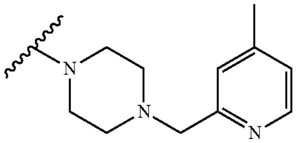

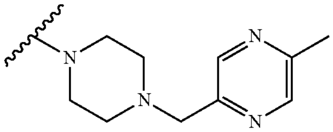

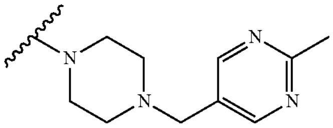

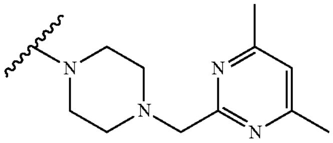

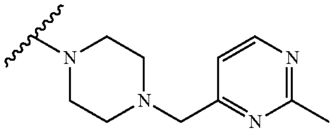

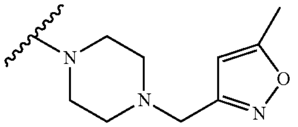

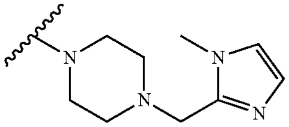

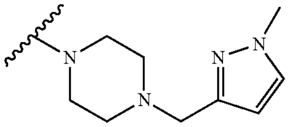

-continued

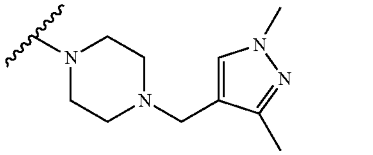

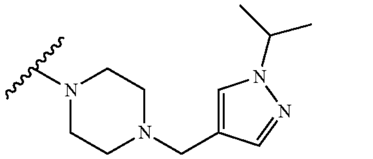

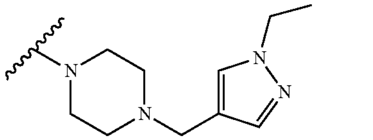

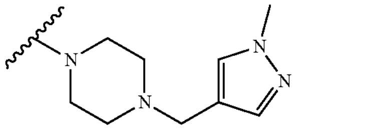

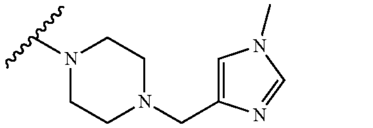

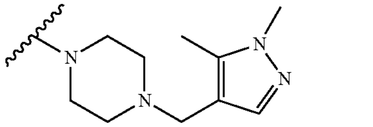

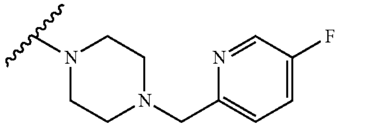

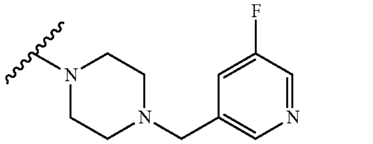

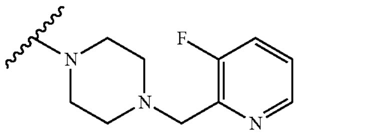

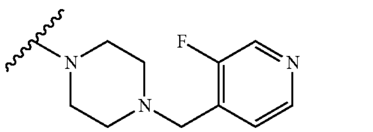

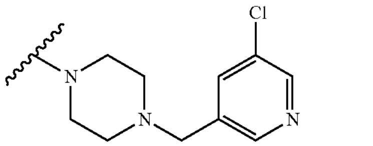

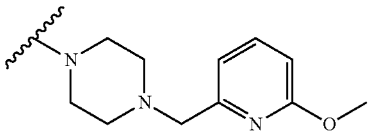

-continued

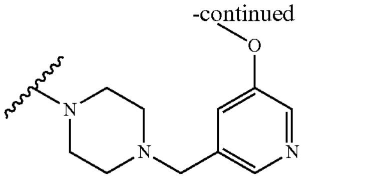

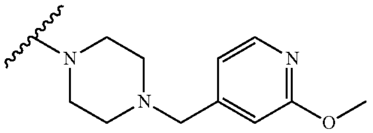

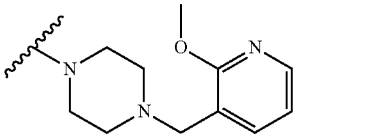

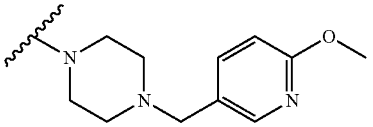

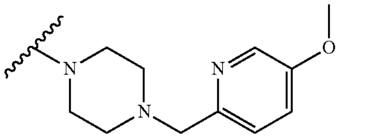

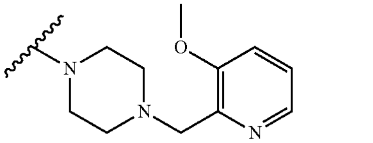

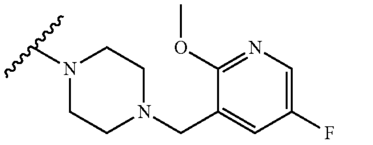

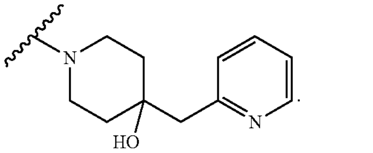

In one embodiment, D is $hetCyc^1$ and E is $(hetCyc^4)$C1-C6 alkyl-, where $hetCyc^4$ is as defined for Formula I. In one embodiment, $hetCyc^4$ is a 4-6 membered heterocyclic ring having 1-2 ring heteroatoms independently selected from N and O, wherein said heterocyclic ring is optionally substituted with (C1-C6 alkyl)C(═O)—. In one embodiment, $hetCyc^1$ is a 6-membered ring having one or two ring nitrogen atoms. Non-limiting embodiments when D is $hetCyc^1$ and E is $(hetCyc^4)$C1-C6 alkyl- include the structures:

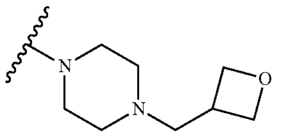

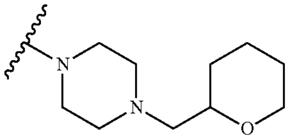

-continued

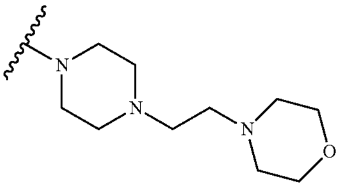

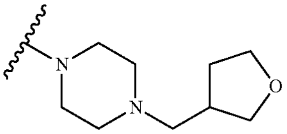

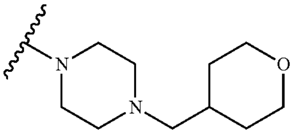

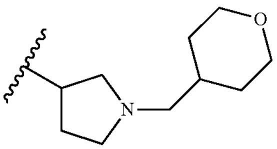

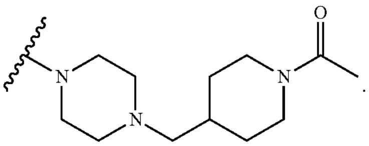

In one embodiment, D is hetCyc[1] and E is (C1-C6 alkoxy)C1-C6 alkyl- wherein said alkoxy portion is optionally substituted with 1-3 fluoros. In one embodiment, hetCyc[1] is a 6-membered ring having two ring nitrogen atoms. Non-limiting examples include the structures:

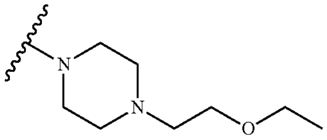

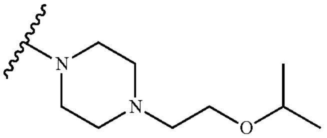

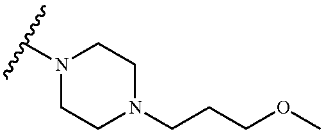

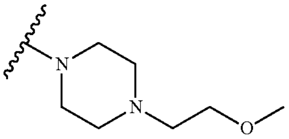

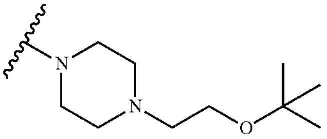

-continued

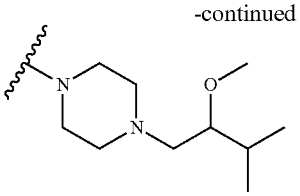

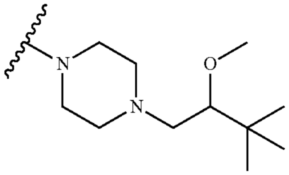

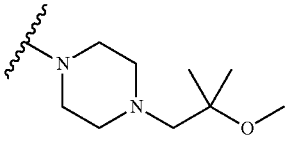

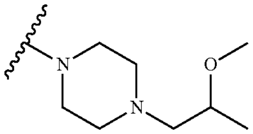

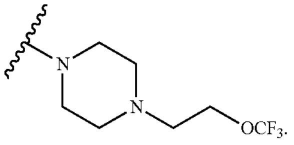

In one embodiment, D is hetCyc[1] and E is (C3-C6 cycloalkoxy)C1-C6 alkyl-. In one embodiment, hetCyc[1] is a 6-membered ring having two ring nitrogen atoms. A non-limiting example is the structure:

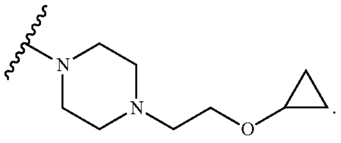 [SMILES: *N1CCN(CCOC2CC2)CC1]

In one embodiment, D is hetCyc[1] and E is (C3-C6 cycloalkyl)C1-C6 alkyl- wherein said cycloalkyl is optionally substituted with 1-2 fluoros. In one embodiment, hetCyc[1] is a 6-membered ring having two ring nitrogen atoms. Non-limiting examples include the structures:

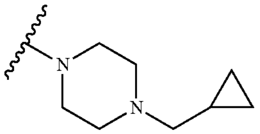

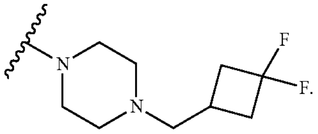

In one embodiment, D is hetCyc[1] and E is ($R^gR^hN$)C1-C6 alkyl- wherein $R^g$ and $R^h$ are independently H or C1-C6 alkyl. In one embodiment, hetCyc[1] is a 6-membered ring having one or two ring nitrogen atoms. Non-limiting examples include the structures:

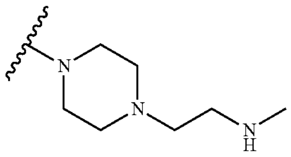

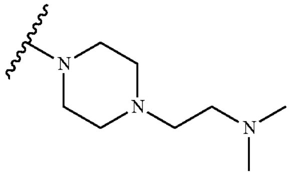

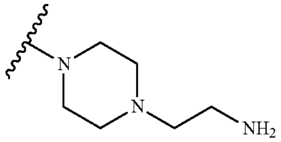

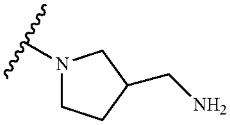

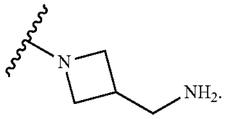

In one embodiment, D is hetCyc$^1$ and E is $Ar^2$—O—, where $Ar^2$ is as defined for Formula I. In one embodiment, $Ar^2$ is phenyl optionally substituted with one or more groups independently selected from halogen and CN. In one embodiment, hetCyc$^1$ is a 6-membered ring having one ring nitrogen atom. Non-limiting examples include the structures:

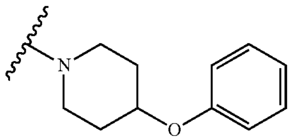

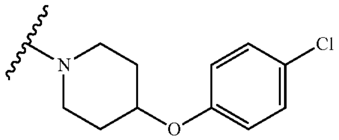

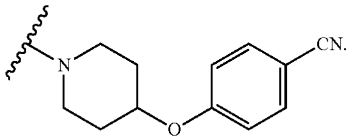

In one embodiment, D is hetCyc$^1$ and E is (C1-C6 alkyl)$SO_2$C1-C6 alkyl-. In one embodiment, hetCyc$^1$ is a 6-membered ring having two ring nitrogen atoms. A non-limiting example is the structure:

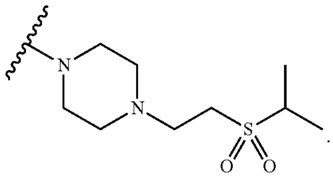 [SMILES: *N1CCN(CCS(=O)(=O)C(C)C)CC1]

In one embodiment, D is hetCyc$^1$ and E is (C1-C6 alkoxy)C(═O)NHC1-C6 alkyl-. In one embodiment, hetCyc$^1$ is a 6-membered ring having two ring nitrogen atoms. A non-limiting example is the structure:

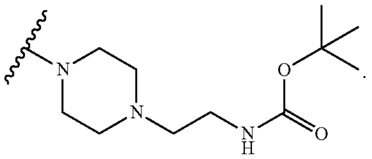 [SMILES: *N1CCN(CCNC(=O)OC(C)(C)C)CC1]

In one embodiment, D is hetCyc$^1$ and E is (C3-C6 cycloalkyl)$SO_2$— wherein said cycloalkyl is optionally substituted with C1-C6 alkyl. In one embodiment, hetCyc$^1$ is a 6-membered ring having two ring nitrogen atoms. A non-limiting example includes the structure:

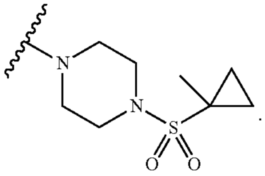 [SMILES: *N1CCN(S(=O)(=O)C2(C)CC2)CC1]

In one embodiment, D is hetCyc$^1$ and E is (N—(C1-C3 alkyl)pyridinonyl)C1-C6 alkyl-. In one embodiment, hetCyc$^1$ is a 6-membered ring having two ring nitrogen atoms. Non-limiting examples include the structures:

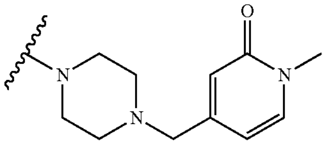

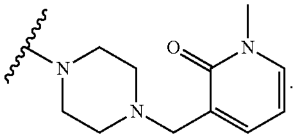

In one embodiment, D is hetCyc$^1$ and E is ($Ar^4SO_2$)C1-C6 alkyl-, where $Ar^4$ is as defined for Formula I. In one embodiment, hetCyc$^1$ is a 6-membered ring having two ring nitrogen atoms. A non-limiting example includes the structure:

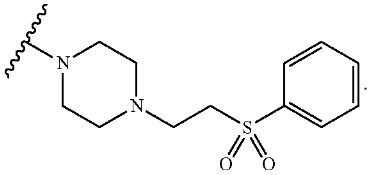 [SMILES: *N1CCN(CCS(=O)(=O)c2ccccc2)CC1]

In one embodiment, D is hetCyc$^1$ and E is (het$Ar^2$)—O—, where het$Ar^2$ is as defined for Formula I. In one embodiment, het$Ar^2$ is optionally substituted with one or more substituents independently selected from C1-C6 alkyl and C1-C6 alkoxy. In one embodiment, hetCyc$^1$ is a 6-membered ring having two ring nitrogen atoms. Non-limiting examples include the structures:

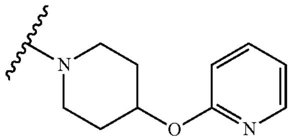

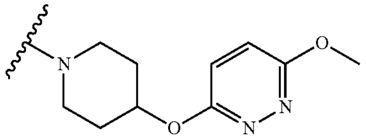

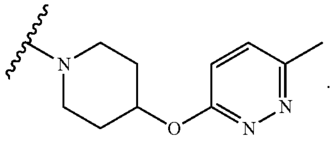

.

In one embodiment of Formula I, D is hetCyc$^2$, where hetCyc$^2$ is a 7-8 membered bridged heterocyclic ring having 1-3 ring heteroatoms independently selected from N and O, wherein the heterocyclic ring is optionally substituted with one or more substituents independently selected from the group consisting of C1-C3 alkyl. In one embodiment, hetCyc$^2$ is a 7-8 membered bridged heterocyclic ring having 1-2 ring nitrogen atoms, wherein the ring is optionally substituted with one or more substituents independently selected from the group consisting of C1-C3 alkyl. In one embodiment, hetCyc$^2$ is unsubstituted. Non-limiting examples of D when represented by hetCyc$^2$ include the structures:

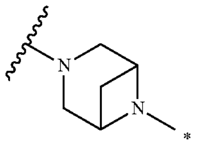 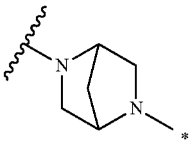

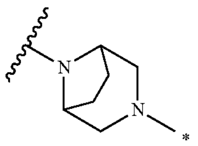 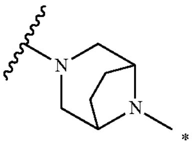

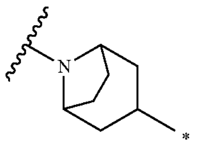 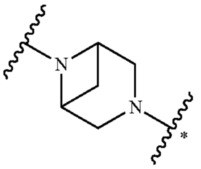

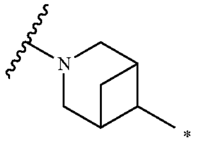

where the asterisk indicates the point of attachment to the E group and the wavy line indicates the point of attachment to the ring comprising X$^1$, X$^2$, X$^3$ and X$^4$, wherein X$^1$, X$^2$, X$^3$, X$^4$ and E are as defined for Formula I.

In one embodiment, hetCyc$^2$ is:

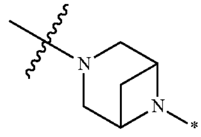 or 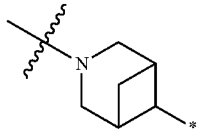

where the asterisk indicates the point of attachment to the E group and the wavy line indicates the point of attachment to the ring comprising X$^1$, X$^2$, X$^3$ and X$^4$, wherein X$^1$, X$^2$, X$^3$, X$^4$ and E are as defined for Formula I.

In one embodiment of Formula I, D is hetCyc$^2$ and E is (a) hydrogen, (b) OH, (c) R'R"N(CH$_2$)$_n$—, wherein R' is H or C1-C6 alkyl, R" is H, C1-C6 alkyl or phenyl, and n is 0 or 1, (d) C1-C6 alkyl optionally substituted with one to three fluoros, (e) hydroxyC1-C6 alkyl- optionally substituted with one to three fluoros, (f) C1-C6 alkoxy optionally substituted with one to three fluoros, (i) (C1-C6 alkyl)C(=O)— optionally substituted with one to three fluoros, (k) (C1-C6 alkoxy)C(=O)—, (o) Cyc$^1$C(=O)—, (x) (Ar$^2$)C1-C6 alkyl-, (y) (Ar$^2$)hydroxy C2-C6 alkyl-, (ee) R$^1$R$^2$N(C1-C6 alkyl)C(=O)— wherein said alkyl portion is optionally substituted with phenyl, (mm) R$^6$C(=O)NH—, or (oo) hetAr$^2$C1-C6 alkyl-, where Cyc$^1$, Ar$^2$, R$^1$, R$^2$, hetAr$^2$ and R$^6$ are as defined for Formula I.

In one embodiment of Formula I, D is hetCyc$^2$ and E is (a) hydrogen, (c) R'R"N(CH$_2$)$_n$— wherein R' is H or C1-C6 alkyl, R" is H, C1-C6 alkyl or phenyl, and n is 0 or 1, (mm) R$^6$C(=O)NH—, or (oo) hetAr$^2$C1-C6 alkyl-, where R$^6$ and hetAr$^2$ are as defined for Formula I.

In one embodiment, D is hetCyc$^2$ and E is hydrogen. In one embodiment, hetCyc$^2$ is a 7-8 membered bridged heterocyclic ring having 1-2 ring nitrogen atoms. Non-limiting examples include the structures:

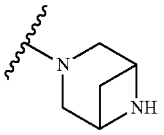 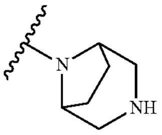 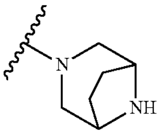

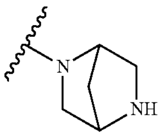 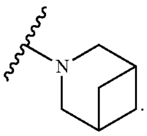

.

In one embodiment, D is hetCyc$^2$ and E is OH. In one embodiment, hetCyc$^2$ is a 7-8 membered bridged heterocyclic ring having one ring nitrogen atom. A non-limiting example is the structure:

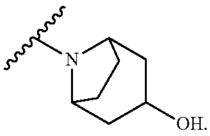 [SMILES: *N1C2CCC1CC(O)C2]

.

In one embodiment, D is hetCyc$^2$ and E is R'R"N(CH$_2$)$_n$—, wherein R' is H or C1-C6 alkyl, R" is H, C1-C6 alkyl or phenyl, and n is 0 or 1. In one embodiment, hetCyc$^2$ is a 7-8 membered bridged heterocyclic ring having one ring nitrogen atom. Non-limiting examples include the structures:

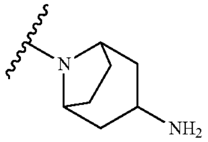
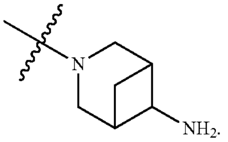

In one embodiment, D is $hetCyc^2$ and E is C1-C6 alkoxy optionally substituted with one to three fluoros. In one embodiment, $hetCyc^2$ is a 7-8 membered bridged heterocyclic ring having one ring nitrogen atom. A non-limiting example is the structure:

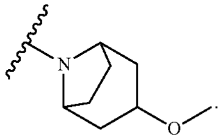 [SMILES: *N1C2CCC1CC(OC)C2]

In one embodiment, D is $hetCyc^2$ and E is (C1-C6 alkyl)C(=O)— optionally substituted with one to three fluoros. In one embodiment, $hetCyc^2$ is a 7-8 membered bridged heterocyclic ring having two ring nitrogen atoms. Non-limiting examples include the structures:

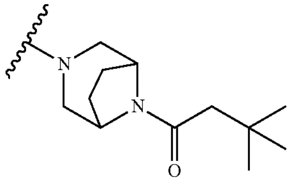
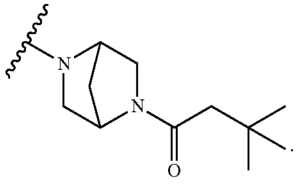

In one embodiment, D is $hetCyc^2$ and E is (C1-C6 alkoxy)C(=O)—. In one embodiment, $hetCyc^2$ is a 7-8 membered bridged heterocyclic ring having two ring nitrogen atoms. Non-limiting examples include the structures:

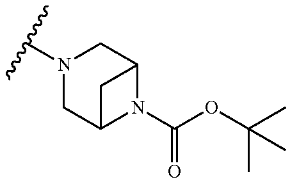
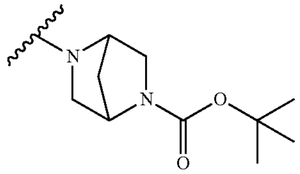

-continued

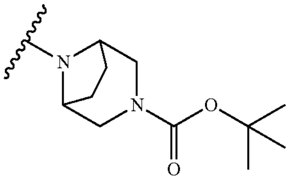
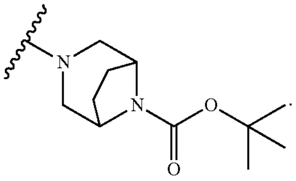

In one embodiment, D is $hetCyc^2$ and E is $(Ar^2)$C1-C6 alkyl where $Ar^2$ is as defined for Formula I. In one embodiment, $Ar^2$ is an unsubstituted phenyl. In one embodiment, $hetCyc^2$ is a 7-8 membered bridged heterocyclic ring having two ring nitrogen atoms. Non-limiting examples when D is $hetCyc^2$ and E is $(Ar^2)$C1-C6 alkyl include the structures:

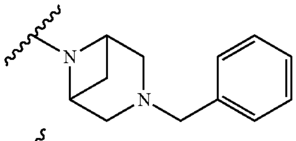
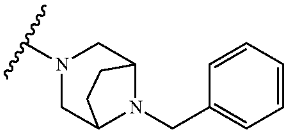
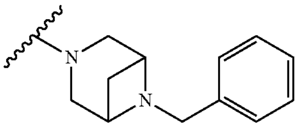
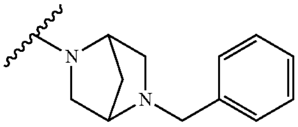
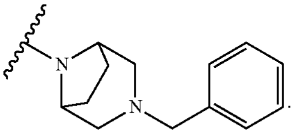

In one embodiment, D is $hetCyc^2$ and E is $R^1R^2N$(C1-C6 alkyl)C(=O)—. In one embodiment, $hetCyc^2$ is a 7-8 membered bridged heterocyclic ring having two ring nitrogen atoms. A non-limiting example is the structure:

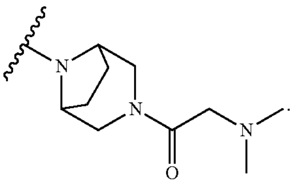 [SMILES: *N1C2CCC1CN(C(=O)CN(C)C)C2]

In one embodiment, D is $hetCyc^2$ and E is $R^6C$(=O)NH—, where $R^6$ is as defined for Formula I. In one embodiment, hetCyc$^2$ is a 7-8 membered bridged heterocyclic ring having two ring nitrogen atoms. A non-limiting example is the structure:

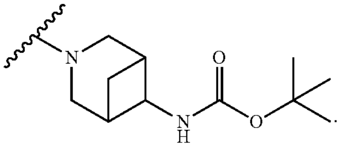 [SMILES: *N1CC2CC(C1)C2NC(=O)OC(C)(C)C]

In one embodiment, D is hetCyc$^2$ and E is hetAr$^2$C1-C6 alkyl-, where hetAr$^2$ is as defined for Formula I. In one embodiment, hetCyc$^2$ is a 7-8 membered bridged heterocyclic ring having two ring nitrogen atoms. A non-limiting example is the structure:

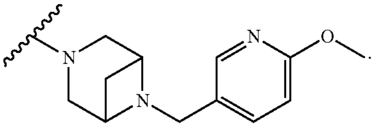 [SMILES: *N1CC2CC(C1)N2Cc1ccc(OC)nc1]

In one embodiment of Formula I, D is hetCyc$^3$, where hetCyc$^3$ is a 7-11 membered heterospirocyclic ring having 1-2 ring heteroatoms independently selected from N and O and wherein the ring is optionally substituted with C1-C3 alkyl. In one embodiment, hetCyc$^3$ is unsubstituted. Non-limiting examples when D is represented by hetCyc$^3$ include the structures:

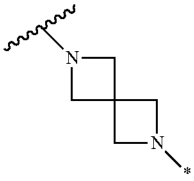
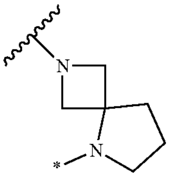
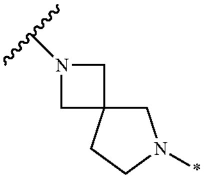
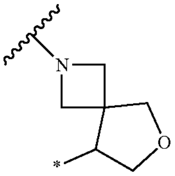
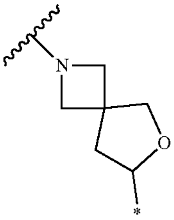
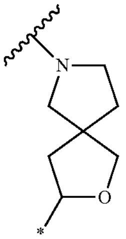
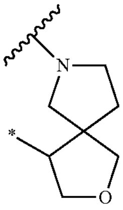
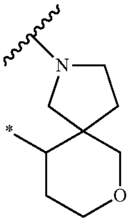
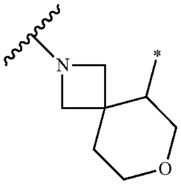

-continued

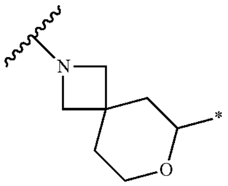
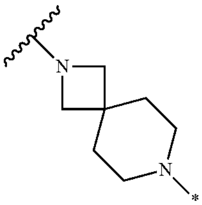
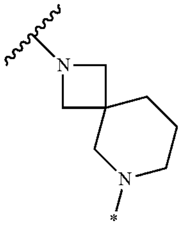
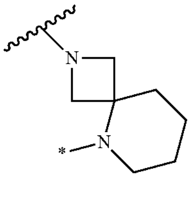
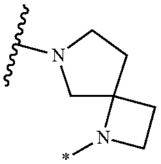
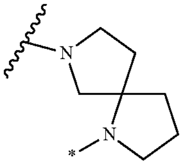
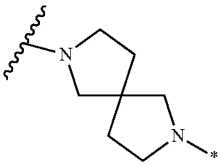
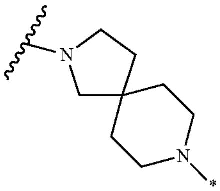
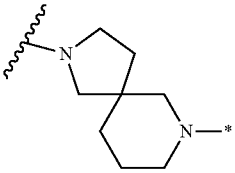
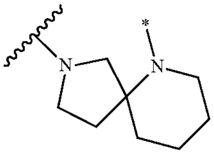
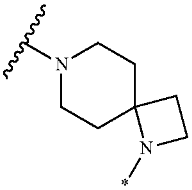
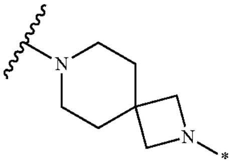
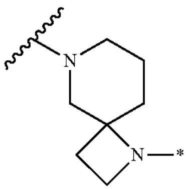
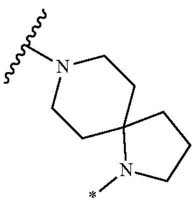
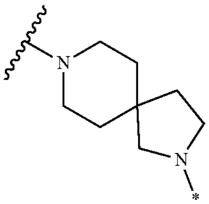
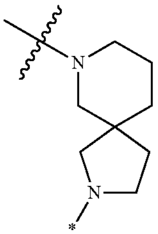

-continued

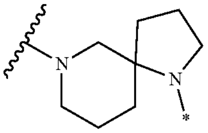 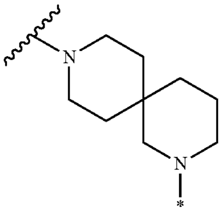

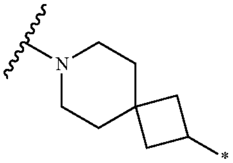 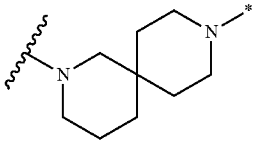

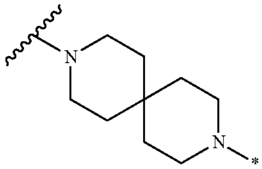 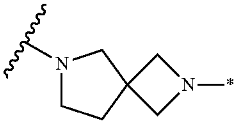

where the asterisk indicates the point of attachment to the E group and the wavy line indicates the point of attachment to the ring comprising $X^1$, $X^2$, $X^3$ and $X^4$, wherein $X^1$, $X^2$, $X^3$, $X^4$ and E are as defined for Formula I.

In one embodiment, D is hetCyc$^3$ and E is selected from (a) hydrogen, (c) R'R"N$(CH_2)_n$— wherein R' is H or C1-C6 alkyl, R" is H, C1-C6 alkyl or phenyl, and n is 0 or 1, (d) C1-C6 alkyl optionally substituted with one to three fluoros, (e) hydroxyC1-C6 alkyl optionally substituted with one to three fluoros, (i) (C1-C6 alkyl)C(═O)— optionally substituted with one to three fluoros, (j) (hydroxy C1-C6 alkyl)C(═O)— optionally substituted with one to three fluoros, (k) (C1-C6 alkoxy)C(═O)—, (o) Cyc$^1$C(═O)—, (p) Cyc$^1$(C1-C6 alkyl)C(═O), (r) hetCyc$^4$C(═O)—, (w) Ar$^2$C(═O)—, (x) (Ar$^2$)C1-C6 alkyl-, (y) (Ar$^2$)hydroxy C2-C6 alkyl-, (z) Ar$^2$(C1-C6 alkyl)C(═O)— wherein said alkyl portion is optionally substituted with one or two groups independently selected from the group consisting of OH, C1-C6 alkyl (optionally substituted with 1-3 fluoros), hydroxyC1-C6 alkyl-, (C1-C6)alkoxy, $R^eR^fN$— and ($R^eR^fN$)C1-C3 alkyl- where $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (dd) $R^1R^2$NC(═O)—, (ee) $R^1R^2$N(C1-C6 alkyl)C(═O)—, (mm) $R^6$C(═O)NH—, (xx) (C3-C6 cycloalkoxy)C(═O)— and (zz) Ar$^4CH_2$OC(═O)—.

In one embodiment, D is hetCyc$^3$ and E is hydrogen. Non-limiting examples include the structures:

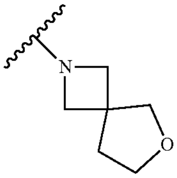 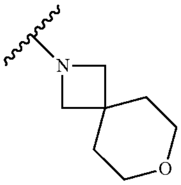 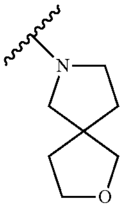

-continued

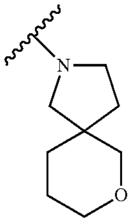 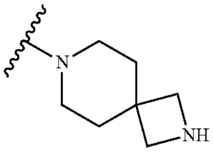

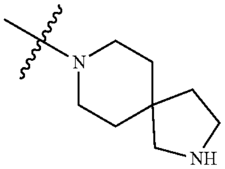 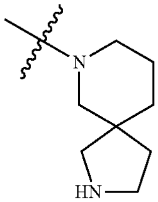

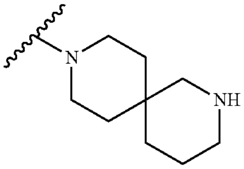 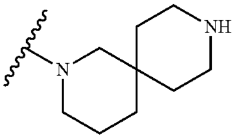

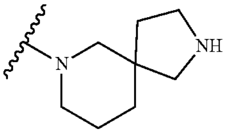 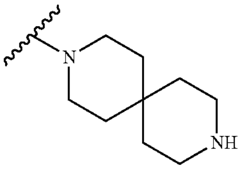

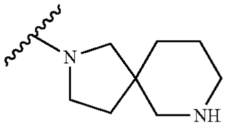 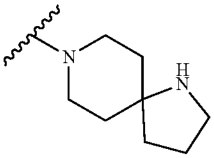

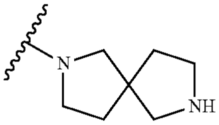 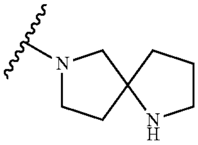

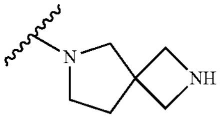 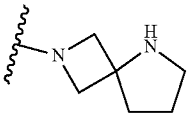

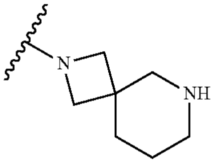 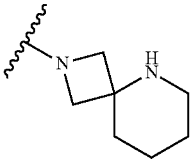

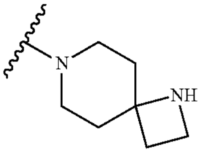 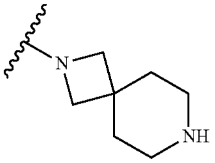

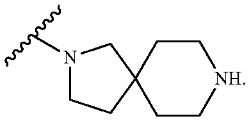

In one embodiment, D is hetCyc$^3$ and E is R'R"N$(CH_2)_n$—, wherein R' is H or C1-C6 alkyl, R" is H, C1-C6 alkyl or phenyl, and n is 0 or 1. In one embodiment, R' and R" are H. A non-limiting example is the structure:

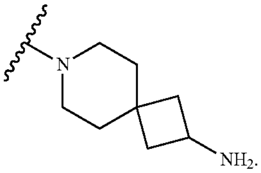 [SMILES: *N1CCC2(CC1)CC(N)C2]

In one embodiment, D is hetCyc[3] and E is C1-C6 alkyl optionally substituted with one to three fluoros. Non-limiting examples include the structures:

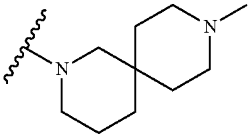
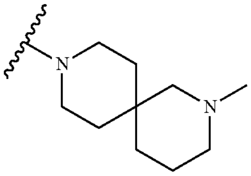
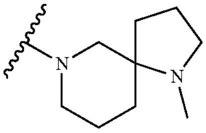
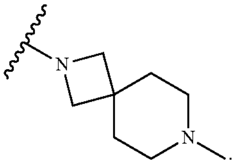

In one embodiment, D is hetCyc[3] and E is hydroxyC1-C6 alkyl- optionally substituted with one to three fluoros. Non-limiting examples include the structures:

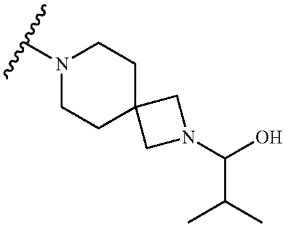

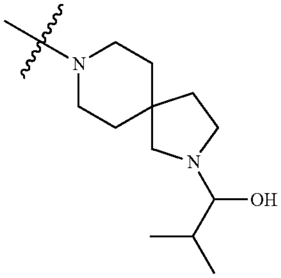
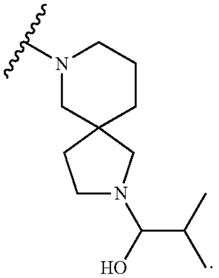

In one embodiment, D is hetCyc[3] and E is (C1-C6 alkyl)C(═O)— optionally substituted with one to three fluoros. Non-limiting examples include the structures:

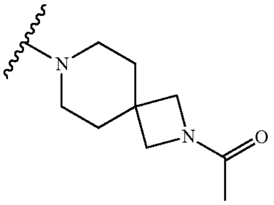

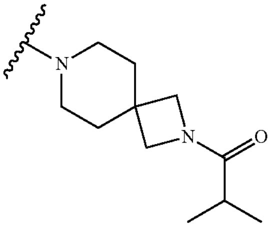

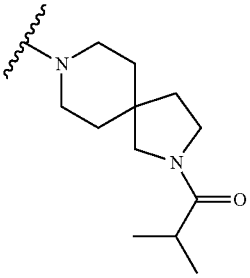
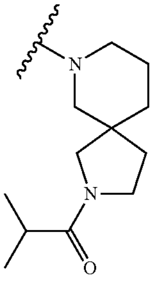

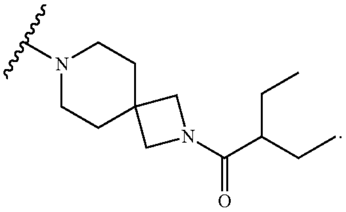

In one embodiment, D is hetCyc[3] and E is (hydroxy C1-C6 alkyl)C(═O)— optionally substituted with one to three fluoros. Non-limiting examples include the structures:

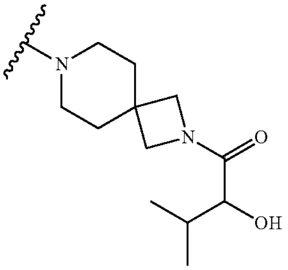

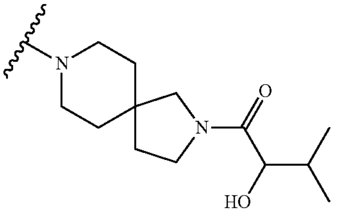

-continued
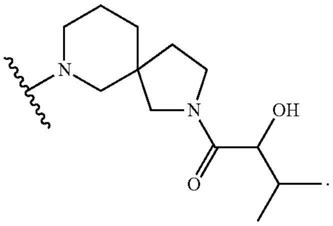
In one embodiment, D is hetCyc[3] and E is (C1-C6 alkoxy)C(=O)—. Non-limiting examples include the structures:
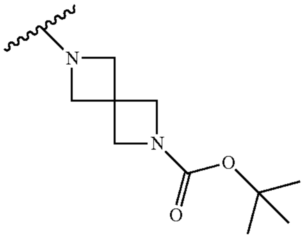
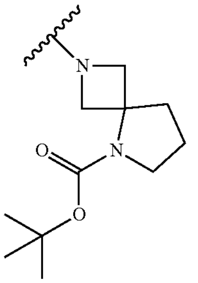
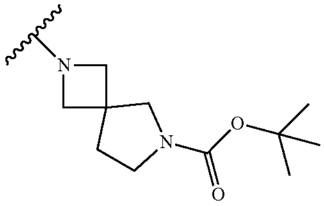
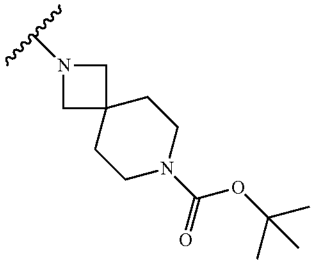
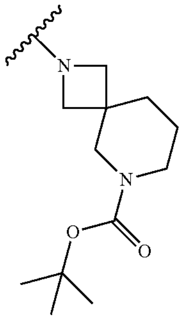
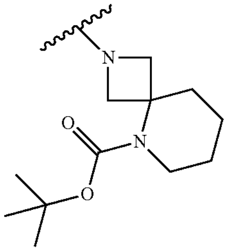
-continued
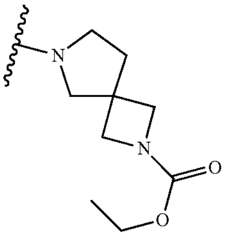
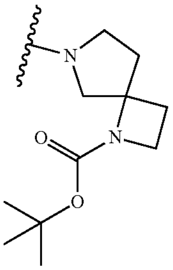
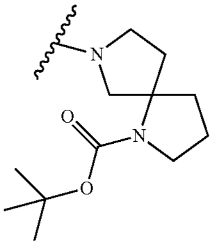
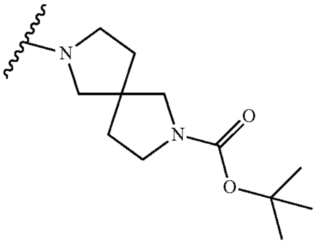
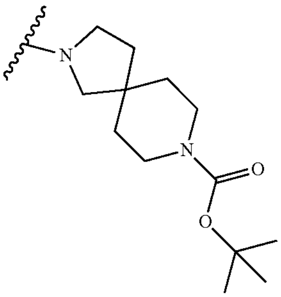
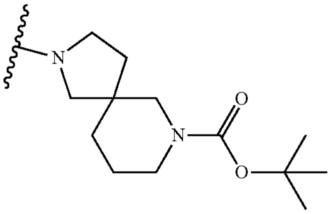
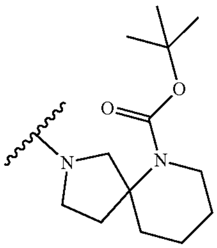
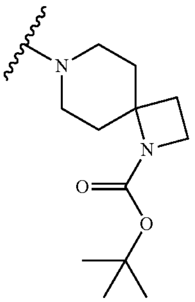

-continued
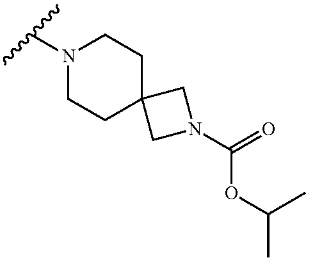
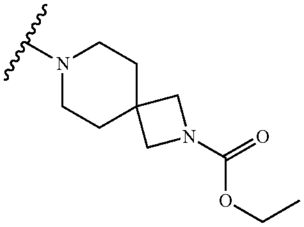
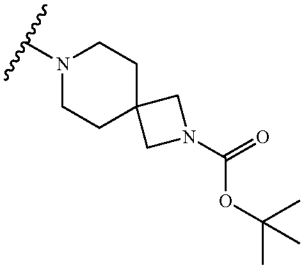
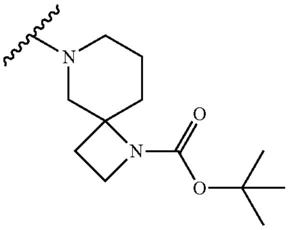
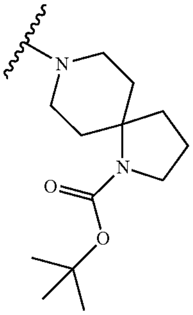
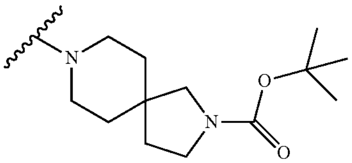
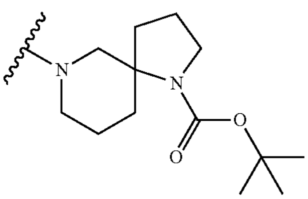
-continued
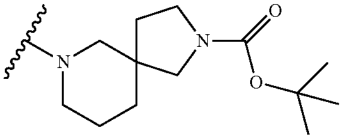
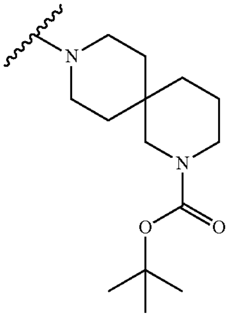
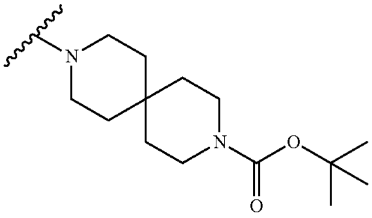
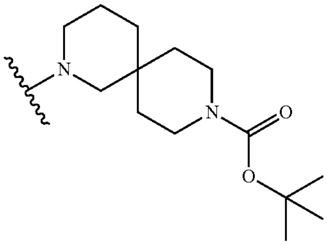
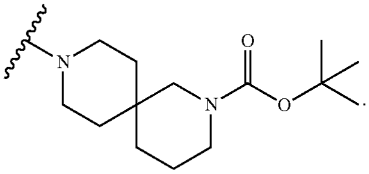
In one embodiment, D is hetCyc$^3$ and E is Cyc$^1$C(═O)—, where Cyc$^1$ is as defined for Formula I. In one embodiment, Cyc$^1$ is unsubstituted. Non-limiting examples include the structures:
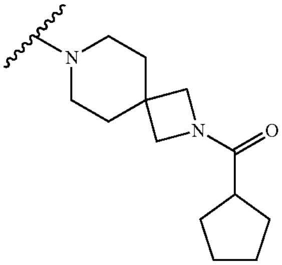

-continued

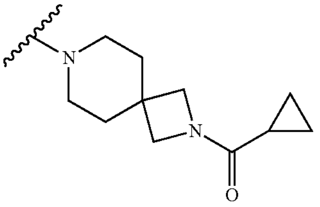

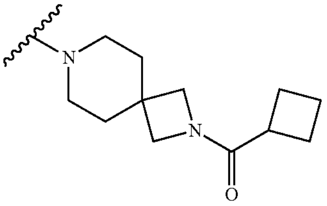

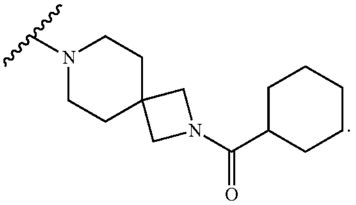

In one embodiment, D is hetCyc$^3$ and E is Cyc$^1$(C1-C6 alkyl)C(═O)— wherein said alkyl portion is optionally substituted with one or more groups independently selected from the group consisting of OH, fluoro, C1-C3 alkoxy and $R^cR^dN$—, where $R^c$ and $R^d$ are independently H or C1-C6 alkyl, and Cyc$^1$ is as defined for Formula I.

In one embodiment, D is hetCyc$^3$ and E is Cyc$^1$(C1-C6 alkyl)C(═O)— wherein said alkyl portion is unsubstituted, and Cyc$^1$ is as defined for Formula I. In one embodiment, Cyc$^1$ is an unsubstituted C3-C6 cycloalkyl.

Non-limiting examples when D is hetCyc$^3$ and E is Cyc$^1$(C1-C6 alkyl)C(═O)— include the structures:

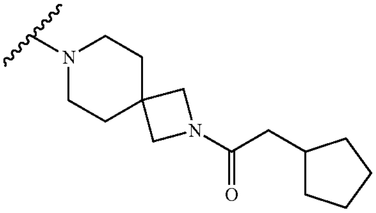

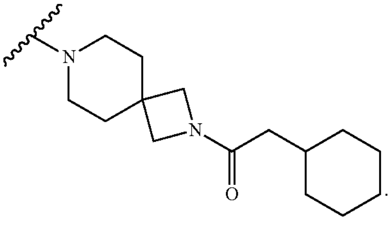

In one embodiment, D is hetCyc$^3$ and E is hetCyc$^4$C(═O)—, where hetCyc$^4$ is as defined for Formula I. In one embodiment, hetCyc$^4$ is a 4-6 membered heterocyclic ring having 1-2 ring heteroatoms independently selected from N and O, wherein said ring is unsubstituted. A non-limiting example when D is hetCyc$^3$ and E is hetCyc$^4$C(═O)— is the structure:

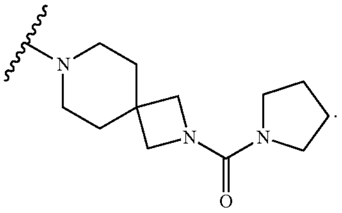 [SMILES: *N1CCC2(CC1)CN(C(=O)N1CCCC1)C2]

In one embodiment, D is hetCyc$^3$ and E is Ar$^2$C(═O)— where Ar$^2$ is as defined for Formula I. In one embodiment, Ar$^2$ is unsubstituted. A non-limiting example is the structure:

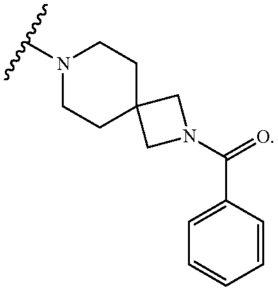 [SMILES: *N1CCC2(CC1)CN(C(=O)c1ccccc1)C2]

In one embodiment, D is hetCyc$^3$ and E is (Ar$^2$)C1-C6 alkyl-. In one embodiment, Ar$^2$ is phenyl which is unsubstituted. Non-limiting examples include the structures:

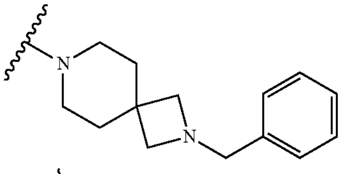

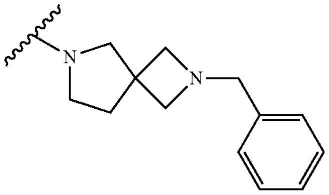

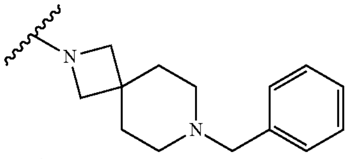

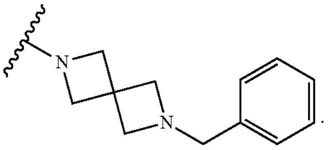

In one embodiment, D is hetCyc$^3$ and E is Ar$^2$(C1-C6 alkyl)C(═O)— wherein the alkyl portion is optionally substituted with one or two groups independently selected from the group consisting of OH, C1-C6 alkyl, hydroxyC1-C6 alkyl-, (C1-C6)alkoxy, $R^eR^fN$— and ($R^eR^fN$)C1-C3 alkyl-, where $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl, and $Ar^2$ is as defined for Formula I. In one embodiment, D is $hetCyc^3$ and E is $Ar^2$(C1-C6 alkyl)C(=O)— wherein the alkyl portion is unsubstituted. In one embodiment, $Ar^2$ is phenyl which is unsubstituted. A non-limiting example is the structure:

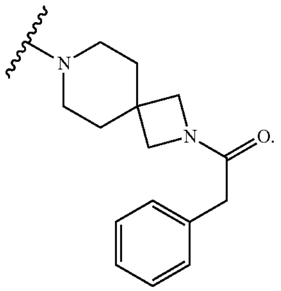 [SMILES: *N1CCC2(CC1)CN(C(=O)Cc1ccccc1)C2]

In one embodiment, D is $hetCyc^3$ and E is $R^1R^2NC$(=O)— where $R^1$ and $R^2$ are as defined for Formula I. In one embodiment, $R^1$ is H or C1-C6 alkyl and $R^2$ is H or C1-C6 alkyl optionally substituted with 1-3 fluoros. Non-limiting examples include the structures:

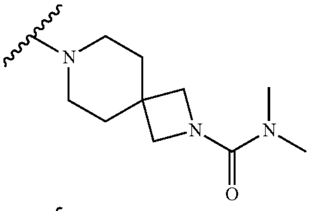

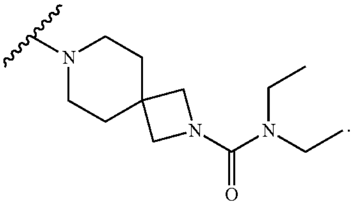

In one embodiment, D is $hetCyc^3$ and E is $R^1R^2N$(C1-C6 alkyl)C(=O)— wherein the C1-C3 alkyl portion is optionally substituted with phenyl, and $R^1$ and $R^2$ are as defined for Formula I. In one embodiment, $R^1$ is H or C1-C6 alkyl and $R^2$ is H or C1-C6 alkyl optionally substituted with 1-3 fluoros. A non-limiting example is the structure:

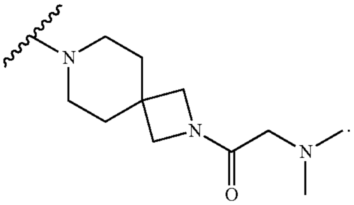 [SMILES: *N1CCC2(CC1)CN(C(=O)CN(C)C)C2]

In one embodiment, D is $hetCyc^3$ and E is $R^6C$(=O)NH—, where $R^6$ is C1-C6 alkyl, hydroxyC1-C6 alkyl-, C1-C6 alkoxy, (C1-C6 alkoxy)C1-C6 alkyl-, phenyl or $hetCyc^8$. In one embodiment, $R^6$ is C1-C6 alkoxy. A non-limiting example is the structure:

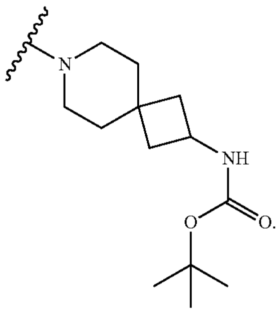 [SMILES: *N1CCC2(CC1)CC(NC(=O)OC(C)(C)C)C2]

In one embodiment, D is $hetCyc^3$ and E is (C3-C6 cycloalkoxy)C(=O)—. A non-limiting example is the structure:

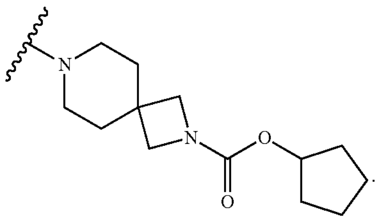 [SMILES: *N1CCC2(CC1)CN(C(=O)OC1CCCC1)C2]

In one embodiment, D is $hetCyc^3$ and E is $Ar^4CH_2OC$(=O)—. A non-limiting example is the structure:

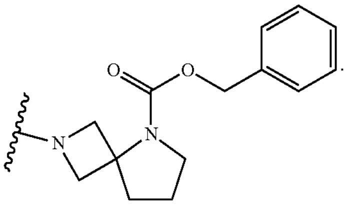 [SMILES: *N1CC2(CCCN2C(=O)OCc2ccccc2)C1]

In one embodiment, Formula I includes compounds of Formula I-A, wherein:

$X^1$ is CH or N, and each of $X^2$, $X^3$ and $X^4$ is CH;

A is H, Cl or CN;

B is $hetAr^1$;

$hetAr^1$ is pyrazolyl optionally substituted with one or more substituents independently selected from the group consisting of C1-C6 alkyl (optionally substituted with one to three fluoros), (C1-C6 alkoxy)C1-C6 alkyl-, (C1-C6 $alkylSO_2$)C1-C6 alkyl-, $hetCyc^a$, and $hetCyc^a$C1-C6 alkyl;

$hetCyc^a$ is a 4-6 membered heterocyclic ring having a ring heteroatom selected from N and O, wherein the heterocyclic ring is optionally substituted with halogen, C1-C6 alkyl (optionally substituted with one to three fluoros), (C1-C6 alkoxy)C1-C6 alkyl-, di(C1-C3 alkyl)$NCH_2C$(=O)—, (C1-C6 alkoxy)C(=O)— or (C1-C6 alkoxy)$CH_2C$(=O)—;

D is $hetCyc^1$ or $hetCyc^2$;

$hetCyc^1$ is a 4-6 membered heterocyclic ring having 1-2 ring heteroatoms independently selected from N and O, wherein the heterocyclic ring is optionally substituted with one or more substituents independently selected from the group consisting of C1-C3 alkyl (optionally substituted with one to three fluoros), or said heterocyclic ring is substituted with a cycloalkylidene ring, or said heterocyclic ring is substituted with an oxo group;

$hetCyc^2$ is a 7-8 membered bridged heterocyclic ring having 1-3 ring heteroatoms independently selected from N and O, wherein the heterocyclic ring is optionally substituted with one or more substituents independently selected from the group consisting of C1-C3 alkyl;

E is (a) hydrogen, (b) OH, (c) R'R"N($CH_2$)$_n$— wherein R' is H or C1-C6 alkyl, R" is H, C1-C6 alkyl or phenyl, and n is 0 or 1, (d) C1-C6 alkyl optionally substituted with one to three fluoros, hydroxyC1-C6 alkyl, (f) C1-C6 alkoxy optionally substituted with one to three fluoros, (g) hydroxyC1-C6 alkoxy- optionally substituted with one to three fluoros, (h) (C1-C6 alkoxy)hydroxy C1-C6 alkyl- optionally substituted with one to three fluoros, (j) (hydroxy C1-C6 alkyl)C(═O)— optionally substituted with one to three fluoros, (k) (C1-C6 alkoxy)C(═O)—, (l) (C1-C6 alkoxy)(C1-C6 alkyl)C(═O)—, (m) HC(═O)—, (n) $Cyc^1$, (o) $Cyc^1$C(═O)—, (p) $Cyc^1$(C1-C6 alkyl)C(═O)— wherein the alkyl portion is optionally substituted with one or more groups independently selected from the group consisting of OH, fluoro, C1-C3 alkoxy and $R^cR^dN$—, where $R^c$ and $R^d$ are independently H or C1-C6 alkyl, (q) $hetCyc^4$, (r) $hetCyc^4$C(═O)—, (s) $hetCyc^4$(C1-C6 alkyl)C(═O)—, (t) $hetCyc^4$C(═O)C1-C6 alkyl-, (u) $hetCyc^4$C(═O)$NR^g$—, where $R^g$ is H or C1-C6 alkyl, (v) $Ar^2$, (w) $Ar^2$C(═O)—, (x) ($Ar^2$)C1-C6 alkyl)-, (y) ($Ar^2$)hydroxy C2-C6 alkyl-, (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^fN$— and ($R^eR^fN$)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O wherein the heterocyclic ring is optionally substituted with C1-C6 alkyl, (aa) $hetAr^2$C(═O)—, (bb) ($hetAr^2$)hydroxy C2-C6 alkyl-, (cc) $hetAr^2$(C1-C6 alkyl)C(═O)— wherein the alkyl portion is optionally substituted with one or two groups independently selected from the group consisting of OH, C1-C6 alkyl, hydroxyC1-C6 alkyl, C1-C6 alkoxy, $R^eR^fN$— and ($R^eR^fN$)C1-C3 alkyl-, wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (dd) $R^1R^2$NC(═O)—, (ee) $R^1R^2$N(C1-C6 alkyl)C(═O)— wherein the alkyl portion is optionally substituted with phenyl, (ff) $R^1R^2$NC(═O)C1-C6 alkyl-, (gg) $R^1R^2$NC(═O)NH—, (hh) $CH_3SO_2$(C1-C6 alkyl)C(═O)—, (ii) (C1-C6 alkyl)$SO_2$—, (jj) (C3-C6 cycloalkyl)$CH_2SO_2$—, (kk) $hetCyc^5$-$SO_2$—, (ll) $R^4R^5NSO_2$—, (mm) $R^6$C(═O)NH—, (nn) $hetCyc^6$, (oo) ($hetAr^2$)C1-C6 alkyl-, (pp) ($hetCyc^4$)C1-C6 alkyl-, (qq) (C1-C6 alkoxy)C1-C6 alkyl- wherein said alkoxy portion is optionally substituted with 1-3 fluoros, (rr) (C3-C6 cycloalkoxy)C1-C6 alkyl-, (ss) (C3-C6 cycloalkyl)C1-C6 alkyl- wherein said cycloalkyl is optionally substituted with 1-2 fluoros, (tt) ($R^gR^hN$)C1-C6 alkyl- wherein $R^g$ and $R^h$ are independently H or C1-C6 alkyl, (uu) $Ar^2$—O—, (vv) (C1-C6 alkyl)$SO_2$C1-C6 alkyl-, (ww) (C1-C6 alkoxy)C(═O)NHC1-C6 alkyl-, (yy) (C3-C6 cycloalkyl)$SO_2$— wherein said cycloalkyl is optionally substituted with C1-C6 alkyl, (aaa) (N—(C1-C3 alkyl)pyridinonyl)C1-C6 alkyl-, (bbb) ($Ar^4SO_2$)C1-C6 alkyl- or (ccc) $hetAr^2$—O—;

$Cyc^1$ is a C3-C6 cycloalkyl, wherein (a) the cycloalkyl is optionally substituted with one or more substituents independently selected from the group consisting of OH, halogen, C1-C6 alkoxy, CN, hydroxyC1-C6 alkyl-, (C1-C6 alkoxy)C1-C6 alkyl-, and C1-C6 alkyl optionally substituted with 1-3 fluoros, or (b) the cycloalkyl is substituted with phenyl, wherein the phenyl is optionally substituted with one or more substituents independently selected from the group consisting of halogen, C1-C3 alkyl, C1-C3 alkoxy and $CF_3$, or (c) the cycloalkyl is substituted with a 5-6 membered heteroaryl ring having 1-3 ring heteroatoms independently selected from N and O, wherein the heteroaryl ring is optionally substituted with one or more substituents independently selected from the group consisting of halogen, C1-C3 alkyl, C1-C3 alkoxy and $CF_3$;

$Ar^2$ is phenyl optionally substituted with one or more substituents independently selected from the group consisting of halogen, C1-C6 alkyl (optionally substituted with one to three fluoros), C1-C6 alkoxy (optionally substituted with 1-3 fluoros), CN, a 5-6 membered heterocyclic ring having 1-2 ring heteroatoms independently selected from N and O, and $R^iR^jN$— where $R^i$ and $R^j$ are independently selected from H and C1-C6 alkyl;

$hetAr^2$ is a 5-6 membered monocyclic heteroaryl ring having 1-3 ring heteroatoms independently selected from N, O and S or a 9-10 membered bicyclic heteroaryl ring having 1-2 ring nitrogen atoms, wherein $hetAr^2$ is optionally substituted with one or more substituents independently selected from the group consisting of halogen, C1-C6 alkyl (optionally substituted with one to three fluoros), C1-C6 alkoxy (optionally substituted with 1-3 fluoros), hydroxyC1-C6 alkyl, (C3-C6)cycloalkyl, (C1-C6 alkoxy)C1-C6 alkyl-, CN and R'R"N— where R' and R" are independently H or C1-C3 alkyl;

$hetCyc^4$ is (a) a 4-6 membered heterocyclic ring having 1-2 ring heteroatoms independently selected from N, O and S wherein said S is optionally oxidized to $SO_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O wherein the heterocyclic ring is optionally independently substituted with one to two C1-C6 alkyl substituents, or (d) a 7-10 membered spirocyclic heterocyclic ring having 1-2 ring heteroatoms independently selected from N and O, wherein each of the heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl-, (C3-C6)cycloalkyl, (C1-C6 alkyl)C(═O)—, a 5-6 membered heterocyclic ring having 1-2 ring heteroatoms independently selected from N and O, and phenyl wherein said phenyl is optionally substituted with one or more substituents independently selected from halogen, C1-C6 alkyl and C1-C6 alkoxy;

$R^1$ is H, C1-C6 alkyl or (C1-C6 alkoxy)C1-C6 alkyl-;

$R^2$ is H, C1-C6 alkyl (optionally substituted with 1-3 fluoros), (C1-C6 alkoxy)C1-C6 alkyl- (optionally substituted with 1-3 fluoros), $Cyc^3$, hydroxyC1-C6 alkyl (optionally substituted with 1-3 fluoros), C1-C6 alkoxy (optionally substituted with 1-3 fluoros), (C1-C6 alkoxy)C(═O), $hetCyc^7$, $Ar^3$, $Ar^3$C1-C3 alkyl-, hydroxyC1-C6 alkoxy or (C3-C6 cycloalkyl)$CH_2O$—;

$Cyc^3$ is a 3-6 membered carbocyclic ring optionally substituted with 1-2 groups independently selected from the group consisting of C1-C6 alkoxy, OH and halogen;

$hetCyc^7$ is a 5-6 membered heterocyclic ring having a ring heteroatom selected from O and N wherein the ring is optionally substituted with C1-C6 alkyl;

$Ar^3$ is phenyl optionally substituted with one or more substituents independently selected from halogen, C1-C3 alkyl (optionally substituted with one to three fluoros), and C1-C3 alkoxy;

$R^4$ and $R^5$ are independently H or C1-C6 alkyl;

$R^6$ is C1-C6 alkyl, hydroxyC1-C6 alkyl, C1-C6 alkoxy, (C1-C6 alkoxy)C1-C6 alkyl-, phenyl or $hetCyc^8$;

$hetCyc^8$ is a 5-6 membered heterocyclic ring having a ring heteroatom selected from O and N, wherein the heterocyclic ring is optionally substituted with C1-C6 alkyl; and $Ar^4$ is phenyl optionally substituted with one or more halogens.

In one embodiment, Formula I includes compounds of Formula I-B, wherein:

$X^1$ is N and each of $X^2$, $X^3$ and $X^4$ is CH;

A is CN;

B is $hetAr^1$;

$hetAr^1$ is pyrazolyl optionally substituted with one or more substituents independently selected from C1-C6 alkyl (optionally substituted with one to three fluoros), (C1-C6 alkoxy)C1-C6 alkyl-, (C1-C6 $alkylSO_2$)C1-C6 alkyl-, $hetCyc^a$, and $hetCyc^a$C1-C6 alkyl;

$R^a$ and $R^b$ are independently H or C1-C6 alkyl;

$hetCyc^a$ is a 4-6 membered heterocyclic ring having a ring heteroatom selected from N and O, wherein the heterocyclic ring is optionally substituted with halogen, C1-C6 alkyl (optionally substituted with one to three fluoros), (C1-C6 alkoxy)C1-C6 alkyl-, di(C1-C3 alkyl)$NCH_2C$(═O)—, (C1-C6 alkoxy)C(═O)— or (C1-C6 alkoxy)$CH_2C$(═O)—;

D is $hetCyc^1$;

$hetCyc^1$ is

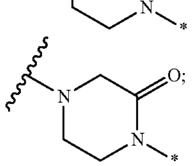

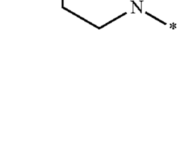

or

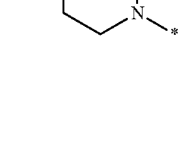

where the asterisk indicates the point of attachment to the E group and the wavy line indicates the point of attachment to the ring comprising $X^1$, $X^2$, $X^3$ and $X^4$;

E is (a) hydrogen, (d) C1-C6 alkyl optionally substituted with one to three fluoros, (e) hydroxyC1-C6 alkyl- optionally substituted with one to three fluoros, (h) (C1-C6 alkoxy)hydroxy C1-C6 alkyl-, (i) (C1-C6 alkyl)C(═O)—, wherein said alkyl portion is optionally substituted with one to three fluoros, or said alkyl portion is substituted with R'R"N— or R'R"$NCH_2$— wherein R' and R" are independently H or C1-C6 alkyl, (j) (hydroxy C1-C6 alkyl)C(═O)— optionally substituted with one to three fluoros, (k) (C1-C6 alkoxy)C(═O)—, (l) (C1-C6 alkoxy)(C1-C6 alkyl)C(═O)—, (n) $Cyc^1$, (o) $Cyc^1$C(═O)—, (p) $Cyc^1$(C1-C6 alkyl)C(═O)— wherein the alkyl portion is optionally substituted with one or more groups independently selected from the group consisting of OH, fluoro, C1-C3 alkoxy and $R^cR^dN$—, where $R^e$ and $R^d$ are independently H or C1-C6 alkyl, (q) $hetCyc^4$, (r) $hetCyc^4$C(═O)—, (s) $hetCyc^4$(C1-C6 alkyl)C(═O)—, (t) $hetCyc^4$C(═O)C1-C6 alkyl-, (w) $Ar^2$C(═O)—, (x) ($Ar^2$)C1-C6 alkyl-, (y) ($Ar^2$)hydroxy C2-C6 alkyl-, (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^fN$— and ($R^eR^fN$)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (aa) $hetAr^2$C(═O)—, (bb) ($hetAr^2$)hydroxy C2-C6 alkyl-, (cc) $hetAr^2$(C1-C6 alkyl)C(═O)— wherein the alkyl portion is optionally substituted with one or two groups independently selected from the group consisting of OH, C1-C6 alkyl, hydroxyC1-C6 alkyl, C1-C6 alkoxy, $R^eR^fN$— and ($R^eR^fN$)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl, (dd) $R^1R^2NC$(═O)—, (ee) $R^1R^2N$(C1-C6 alkyl)C(═O)— wherein the alkyl portion is optionally substituted with phenyl, (ff) $R^1R^2NC$(═O)C1-C6 alkyl-, (hh) $CH_3SO_2$(C1-C6 alkyl)C(═O)—, (ii) (C1-C6 alkyl)$SO_2$—, (jj) (C3-C6 cycloalkyl)$CH_2SO_2$—, (kk) $hetCyc^5$-$SO_2$—, (ll) $R^4R^5NSO_2$—, (oo) ($hetAr^2$)C1-C6 alkyl-, (pp) ($hetCyc^4$)C1-C6 alkyl-, (qq) (C1-C6 alkoxy)C1-C6 alkyl- wherein said alkoxy portion is optionally substituted with 1-3 fluoros, (rr) (C3-C6 cycloalkoxy)C1-C6 alkyl-, (ss) (C3-C6 cycloalkyl)C1-C6 alkyl-, (tt) ($R^gR^h$N)C1-C6 alkyl- wherein $R^g$ and $R^h$ are independently H or C1-C6 alkyl, (vv) (C1-C6 alkyl)$SO_2$C1-C6 alkyl-, (ww) (C1-C6 alkoxy)C(═O)NHC1-C6 alkyl-, (yy) (C3-C6 cycloalkyl)$SO_2$— wherein said cycloalkyl is optionally substituted with C1-C6 alkyl, (aaa) (N—(C1-C3 alkyl)pyridinonyl)C1-C6 alkyl-, or (bbb) ($Ar^4SO_2$)C1-C6 alkyl-;

and $hetCyc^1$, $Cyc^1$, $hetCyc^4$, $Ar^2$, $hetAr^2$, $R^1$, $R^2$, $hetCyc^5$, $R^4$, $R^5$, and $Ar^4$ are as defined for Formula I.

In one embodiment of Formula I-B, A is CN.

In one embodiment of Formula I-B, $hetAr^1$ is pyrazolyl optionally substituted with one or more substituents independently selected from the group consisting of C1-C6 alkyl (optionally substituted with one to three fluoros).

In one embodiment of Formula I-B, A is CN and $hetAr^1$ is pyrazolyl optionally substituted with one or more substituents independently selected from the group consisting of C1-C6 alkyl (optionally substituted with one to three fluoros).

In one embodiment of Formula I-B, E is (i) (C1-C6 alkyl)C(═O)—, wherein said alkyl portion is optionally substituted with one to three fluoros, or said alkyl portion is substituted with R'R"N— or R'R"$NCH_2$— wherein R' and R" are independently H or C1-C6 alkyl, (r) $hetCyc^4$C(═O)— where $hetCyc^4$ is as defined for Formula I, (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^f$N— and ($R^eR^f$N)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl, and where $Ar^2$ is as defined for Formula I, or (oo) ($hetAr^2$)C1-C6 alkyl-, where $hetAr^2$ is as defined for Formula I.

In one embodiment of Formula I-B, E is (i) (C1-C6 alkyl)C(═O)—, wherein said alkyl portion is optionally substituted with one to three fluoros, or said alkyl portion is substituted with R'R"N— or R'R"$NCH_2$— wherein R' and R" are independently H or C1-C6 alkyl.

In one embodiment of Formula I-B, A is CN, $hetAr^1$ is pyrazolyl optionally substituted with one or more substituents independently selected from the group consisting of C1-C6 alkyl (optionally substituted with one to three fluoros), and E is (i) (C1-C6 alkyl)C(═O)—, wherein said alkyl portion is optionally substituted with one to three fluoros, or said alkyl portion is substituted with R'R"N— or R'R"$NCH_2$— wherein R' and R" are independently H or C1-C6 alkyl.

In one embodiment of Formula I-B, E is (r) $hetCyc^4$C(═O)— where $hetCyc^4$ is as defined for Formula I.

In one embodiment of Formula I-B, A is CN, $hetAr^1$ is pyrazolyl optionally substituted with one or more substituents independently selected from the group consisting of C1-C6 alkyl (optionally substituted with one to three fluoros), and E is (r) $hetCyc^4$C(═O)— where $hetCyc^4$ is as defined for Formula I.

In one embodiment of Formula I-B, E is (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^f$N— and ($R^eR^f$N)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl, and where $Ar^2$ is as defined for Formula I.

In one embodiment of Formula I-B, A is CN, $hetAr^1$ is pyrazolyl optionally substituted with one or more substituents independently selected from the group consisting of C1-C6 alkyl (optionally substituted with one to three fluoros), and E is (z) $Ar^2$(C1-C6 alkyl)C(═O)— wherein the alkyl portion is optionally substituted with one or two groups independently selected from the group consisting of OH, C1-C6 alkyl (optionally substituted with 1-3 fluoros), hydroxyC1-C6 alkyl, C1-C6 alkoxy, $R^eR^f$N— and ($R^eR^f$N)C1-C3 alkyl- wherein $R^e$ and $R^f$ are independently H or C1-C6 alkyl, or said alkyl portion is substituted with a 5-6 membered heterocyclic ring having one or two ring heteroatoms independently selected from N and O, wherein the heterocyclic ring is optionally substituted with C1-C6 alkyl, and where $Ar^2$ is as defined for Formula I.

In one embodiment of Formula I-B, E is (oo) ($hetAr^2$)C1-C6 alkyl-, where $hetAr^2$ is as defined for Formula I.

In one embodiment of Formula I-B, A is CN, $hetAr^1$ is pyrazolyl optionally substituted with one or more substituents independently selected from the group consisting of C1-C6 alkyl (optionally substituted with one to three fluoros), and E is (oo) ($hetAr^2$)C1-C6 alkyl-, where $hetCyc^a$ and $hetAr^2$ are as defined for Formula I.

In one embodiment, Formula I includes compounds of Formula I-C, wherein:

$X^1$ is N and each of $X^2$, $X^3$ and $X^4$ is CH;

A is CN;

B is $hetAr^1$;

$hetAr^1$ is pyrazolyl optionally substituted with one or more substituents independently selected from C1-C6 alkyl (optionally substituted with one to three fluoros), (C1-C6 alkoxy)C1-C6 alkyl-, (C1-C6 alkyl$SO_2$)C1-C6 alkyl-, $hetCyc^a$, and $hetCyc^a$C1-C6 alkyl;

$R^a$ and $R^b$ are independently H or C1-C6 alkyl;

$hetCyc^a$ is a 4-6 membered heterocyclic ring having a ring heteroatom selected from N and O, wherein the heterocyclic ring is optionally substituted with halogen, C1-C6 alkyl (optionally substituted with one to three fluoros), (C1-C6 alkoxy)C1-C6 alkyl-, di(C1-C3 alkyl)$NCH_2$C(═O)—, (C1-C6 alkoxy)C(═O)— or (C1-C6 alkoxy)$CH_2$C(═O)—;

D is $hetCyc^1$;

$hetCyc^1$ is

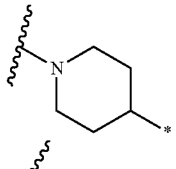
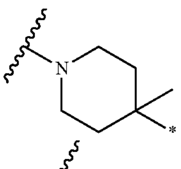
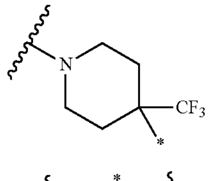
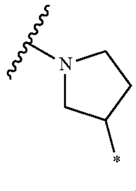
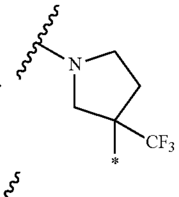
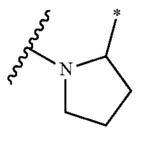
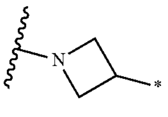
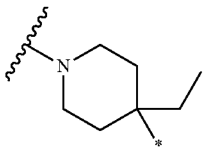

-continued

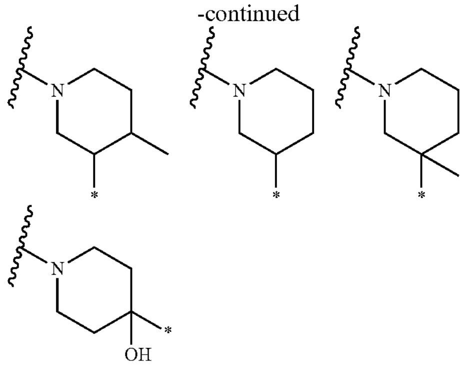

where the asterisk indicates the point of attachment to the E group and the wavy line indicates the point of attachment to the ring comprising $X^1$, $X^2$, $X^3$ and $X^4$;

E is (a) hydrogen, (b) OH, (c) $R'R''N(CH_2)_n$— wherein R' is H or C1-C6 alkyl, R" is H, C1-C6 alkyl or phenyl, and n is 0 or 1, (f) C1-C6 alkoxy optionally substituted with one to three fluoros, (g) hydroxyC1-C6 alkoxy- optionally substituted with one to three fluoros, (k) (C1-C6 alkoxy)C(═O)—, (m) HC(═O)—, (r) $hetCyc^4C$(═O)—, (u) $hetCyc^4C(═O)NR^g$—, where $R^g$ is H or C1-C6 alkyl, (v) $Ar^2$, (x) $(Ar^2)$C1-C6 alkyl-, (dd) $R^1R^2NC$(═O)—, (ff) $R^1R^2NC$(═O)C1-C6 alkyl-, (gg) $R^1R^2NC$(═O)NH—, (ll) $R^4R^5NSO_2$—, (mm) $R^6C$(═O)NH—, (nn) $hetCyc^6$, (oo) $(hetAr^2)$C1-C6 alkyl-, (tt) $(R^gR^hN)$C1-C6 alkyl- wherein $R^g$ and $R^h$ are independently H or C1-C6 alkyl, (uu) $Ar^2$—O—, or (ccc) $hetAr^2$—O—, where $hetCyc^4$, $Ar^2$, $R^1$, $R^2$, $R^4$, $R^5$, $R^6$, $hetCyc^6$, and $hetAr^2$ are as defined for Formula I.

In one embodiment of Formula I-C, A is CN.

In one embodiment of Formula I-C, $hetAr^1$ is pyrazolyl optionally substituted with one or more substituents independently selected from the group consisting of C1-C6 alkyl (optionally substituted with one to three fluoros).

In one embodiment of Formula I-C, A is CN and $hetAr^1$ is pyrazolyl optionally substituted with one or more substituents independently selected from the group consisting of C1-C6 alkyl (optionally substituted with one to three fluoros).

In one embodiment of Formula I-C, E is (x) $(Ar^2)$C1-C6 alkyl-, (mm) $R^6C$(═O)NH—, or (ccc) $hetAr^2$—O—.

In one embodiment of Formula I-C, A is CN, $hetAr^1$ is pyrazolyl optionally substituted with one or more substituents independently selected from the group consisting of C1-C6 alkyl (optionally substituted with one to three fluoros), and E is (x) $(Ar^2)$C1-C6 alkyl-.

In one embodiment of Formula I-C, A is CN, $hetAr^1$ is pyrazolyl optionally substituted with one or more substituents independently selected from the group consisting of C1-C6 alkyl (optionally substituted with one to three fluoros), and E is (mm) $R^6C$(═O)NH—.

In one embodiment of Formula I-C, A is CN, $hetAr^1$ is pyrazolyl optionally substituted with one or more substituents independently selected from the group consisting of C1-C6 alkyl (optionally substituted with one to three fluoros), and E is (ccc) $hetAr^2$—O—.

In one embodiment, Formula I includes compounds of Formula I-D, wherein:

$X^1$ is N and each of $X^2$, $X^3$ and $X^4$ is CH;

A is CN;

B is $hetAr^1$;

$hetAr^1$ is pyrazolyl optionally substituted with one or more substituents independently selected from C1-C6 alkyl (optionally substituted with one to three fluoros), (C1-C6 alkoxy)C1-C6 alkyl-, (C1-C6 $alkylSO_2$)C1-C6 alkyl-, $hetCyc^a$, and $hetCyc^a$C1-C6 alkyl;

$R^a$ and $R^b$ are independently H or C1-C6 alkyl;

$hetCyc^a$ is a 4-6 membered heterocyclic ring having a ring heteroatom selected from N and O, wherein the heterocyclic ring is optionally substituted with halogen, C1-C6 alkyl (optionally substituted with one to three fluoros), (C1-C6 alkoxy)C1-C6 alkyl-, di(C1-C3 alkyl)$NCH_2C$(═O)—, (C1-C6 alkoxy)C(═O)— or (C1-C6 alkoxy)$CH_2C$(═O)—;

D is $hetCyc^2$;

$hetCyc^2$ is:

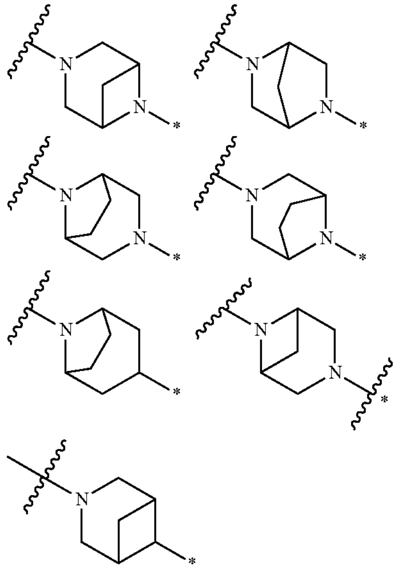

or where the asterisk indicates the point of attachment to the E group and the wavy line indicates the point of attachment to the ring comprising $X^1$, $X^2$, $X^3$ and $X^4$;

E is (a) hydrogen, (c) $R'R''N(CH_2)_n$— wherein R' is H or C1-C6 alkyl, R" is H, C1-C6 alkyl or phenyl, and n is 0 or 1;

(mm) $R^6C$(═O)NH—, or (oo) $hetAr^2$C1-C6 alkyl-;

$hetAr^2$ is a 5-6 membered monocyclic heteroaryl ring having 1-3 ring heteroatoms independently selected from N, O and S or a 9-10 membered bicyclic heteroaryl ring having 1-2 ring nitrogen atoms, wherein $hetAr^2$ is optionally substituted with one or more substituents independently selected from the group consisting of halogen, C1-C6 alkyl (optionally substituted with one to three fluoros), C1-C6 alkoxy (optionally substituted with 1-3 fluoros), hydroxyC1-C6 alkyl, (C3-C6)cycloalkyl, (C1-C6 alkoxy)C1-C6 alkyl-, CN and R'R"N— where R' and R" are independently H or C1-C3 alkyl;

$R^6$ is C1-C6 alkyl, hydroxyC1-C6 alkyl, C1-C6 alkoxy, (C1-C6 alkoxy)C1-C6 alkyl-, phenyl or hetCyc$^8$; and hetCyc$^8$ is a 5-6 membered heterocyclic ring having a ring heteroatom selected from O and N, wherein the heterocyclic ring is optionally substituted with C1-C6 alkyl.

In one embodiment of Formula I-D, A is CN.

In one embodiment of Formula I-D, hetAr$^1$ is pyrazolyl optionally substituted with one or more substituents independently selected from the group consisting of C1-C6 alkyl (optionally substituted with one to three fluoros).

In one embodiment of Formula I-D, A is CN and hetAr$^1$ is pyrazolyl optionally substituted with one or more substituents independently selected from the group consisting of C1-C6 alkyl (optionally substituted with one to three fluoros).

In one embodiment of Formula I-D, hetCyc$^2$ is:

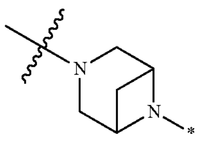
or
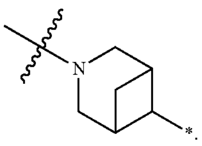

In one embodiment of Formula I-D, A is CN and hetCyc$^2$ is

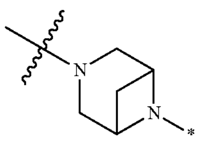
or
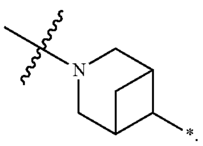

In one embodiment of Formula I-D, A is CN, hetAr$^1$ is pyrazolyl optionally substituted with one or more substituents independently selected from the group consisting of C1-C6 alkyl (optionally substituted with one to three fluoros); and hetCyc$^2$ is

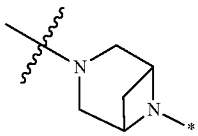
or
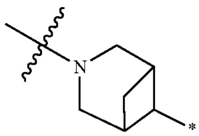

In one embodiment of Formula I-D, A is CN, hetAr$^1$ is pyrazolyl optionally substituted with one or more substituents independently selected from the group consisting of C1-C6 alkyl (optionally substituted with one to three fluoros); hetCyc$^2$ is

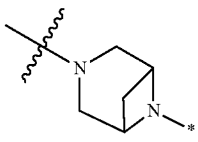
or
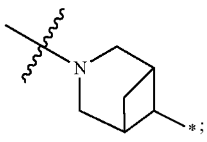

and E is (a) hydrogen.

In one embodiment of Formula I-D, A is CN, hetAr$^1$ is pyrazolyl optionally substituted with one or more substituents independently selected from the group consisting of C1-C6 alkyl (optionally substituted with one to three fluoros); hetCyc$^2$ is

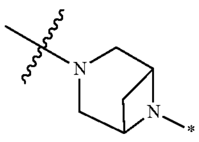
or
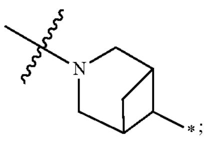

E is (c) R'R"N$(CH_2)_n$— wherein R' is H or C1-C6 alkyl, R" is H, C1-C6 alkyl or phenyl, and n is 0 or 1.

In one embodiment of Formula I-D, A is CN, hetAr$^1$ is pyrazolyl optionally substituted with one or more substituents independently selected from the group consisting of C1-C6 alkyl (optionally substituted with one to three fluoros); hetCyc$^2$ is

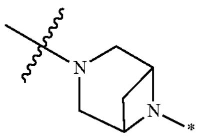
or
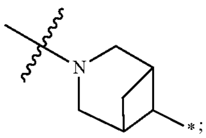

and E is (mm) $R^6C(=O)NH$—.

In one embodiment of Formula I-D, A is CN, hetAr$^1$ is pyrazolyl optionally substituted with one or more substituents independently selected from the group consisting of C1-C6 alkyl (optionally substituted with one to three fluoros); and hetCyc$^2$ is

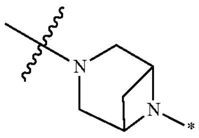
or
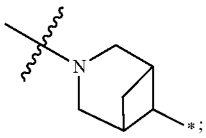

and E is (oo) hetAr$^2$C1-C6 alkyl-.

It will be appreciated that certain compounds provided herein may contain one or more centers of asymmetry and may therefore be prepared and isolated in a mixture of isomers such as a racemic mixture, or in an enantiomerically pure form.

It will further be appreciated that the compounds of Formula I or their salts may be isolated in the form of solvates, and accordingly that any such solvate is included within the scope of the present invention. For example, compounds of Formula I and salts thereof can exist in unsolvated as well as solvated forms with pharmaceutically acceptable solvents such as water, ethanol, and the like.

The compounds of Formula I include pharmaceutically acceptable salts thereof. In addition, the compounds of Formula I also include other salts of such compounds which are not necessarily pharmaceutically acceptable salts, and which may be useful as intermediates for preparing and/or purifying compounds of Formula I and/or for separating enantiomers of compounds of Formula I. Non-limiting examples of salts include monochloride, dichloride, trifluoroacetic acid, and di-trifluoroacetic acid salts of compounds of Formula I.

In one embodiment, the compounds of Formula I include the compounds of Examples 1-121 and stereoisomers and pharmaceutically acceptable salts and solvates thereof. In one embodiment, the compounds of Examples 1-121 are in the free base form. In one embodiment, the compounds of Examples 1-121 are monochloride, dichloride, trifluoroacetic acid, or di-trifluoroacetic acid salts.

The term "pharmaceutically acceptable" indicates that the substance or composition is compatible chemically and/or toxicologically, with the other ingredients comprising a formulation, and/or the patient being treated therewith.

Compounds provided herein may also contain unnatural proportions of atomic isotopes at one or more of the atoms that constitute such compounds. That is, an atom, in particular when mentioned in relation to a compound according to Formula I, comprises all isotopes and isotopic mixtures of that atom, either naturally occurring or synthetically produced, either with natural abundance or in an isotopically enriched form. For example, when hydrogen is mentioned, it is understood to refer to $^{1}H$, $^{2}H$, $^{3}H$ or mixtures thereof; when carbon is mentioned, it is understood to refer to $^{11}C$, $^{12}C$, $^{13}C$, $^{14}C$ or mixtures thereof; when nitrogen is mentioned, it is understood to refer to $^{13}N$, $^{14}N$, $^{15}N$ or mixtures thereof; when oxygen is mentioned, it is understood to refer to $^{14}O$, $^{15}O$, $^{16}O$, $^{17}O$, $^{18}O$ or mixtures thereof; and when fluoro is mentioned, it is understood to refer to $^{18}F$, $^{19}F$ or mixtures thereof. The compounds provided herein therefore also comprise compounds with one or more isotopes of one or more atom, and mixtures thereof, including radioactive compounds, wherein one or more non-radioactive atoms has been replaced by one of its radioactive enriched isotopes. Radiolabeled compounds are useful as therapeutic agents, e.g., cancer therapeutic agents, research reagents, e.g., assay reagents, and diagnostic agents, e.g., in vivo imaging agents. All isotopic variations of the compounds provided herein, whether radioactive or not, are intended to be encompassed within the scope of the present invention.

For illustrative purposes, Schemes 1-4 show general methods for preparing the compounds provided herein as well as key intermediates. For a more detailed description of the individual reaction steps, see the Examples section below. Those skilled in the art will appreciate that other synthetic routes may be used to synthesize the inventive compounds. Although specific starting materials and reagents are depicted in the Schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

Scheme 1

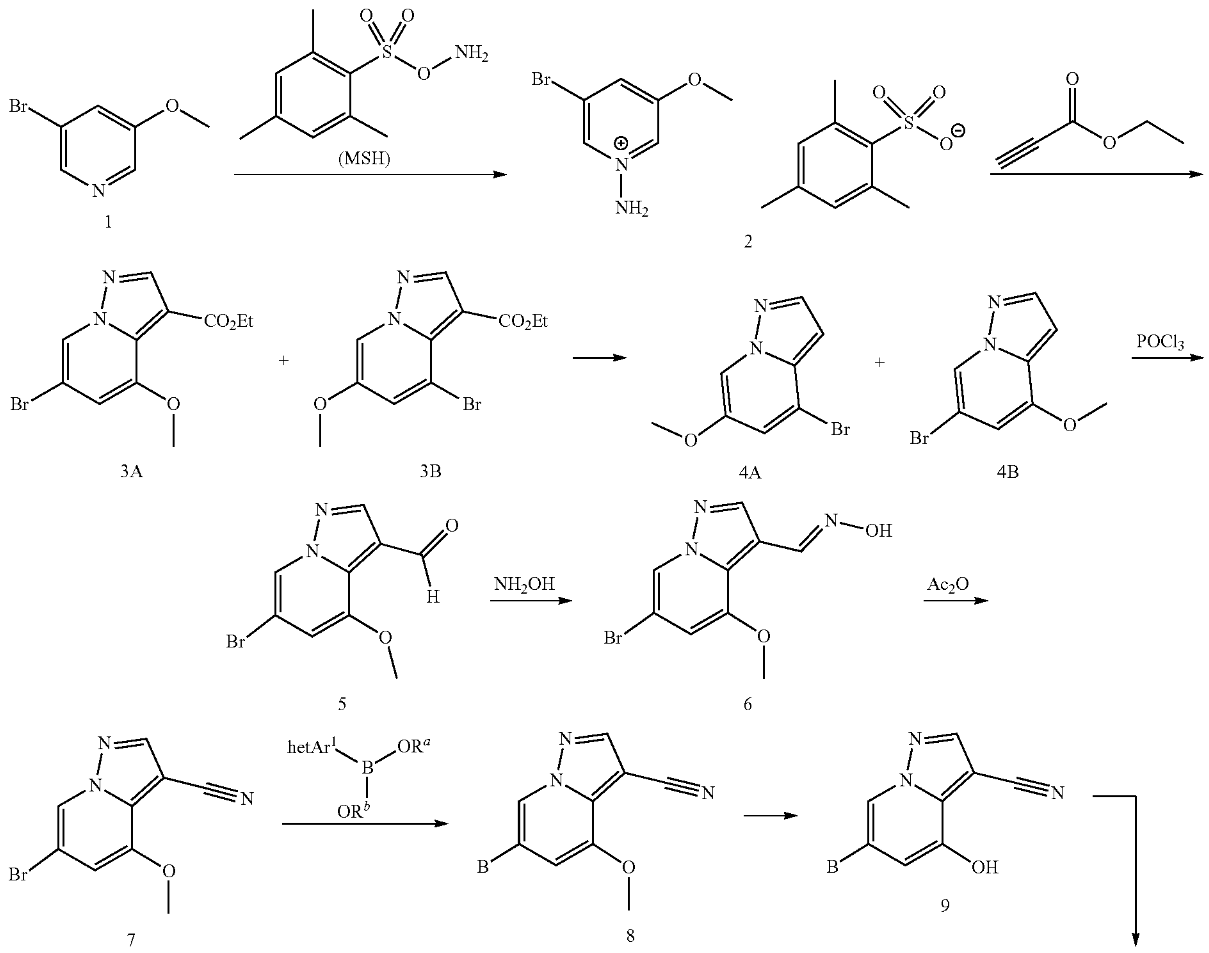

-continued

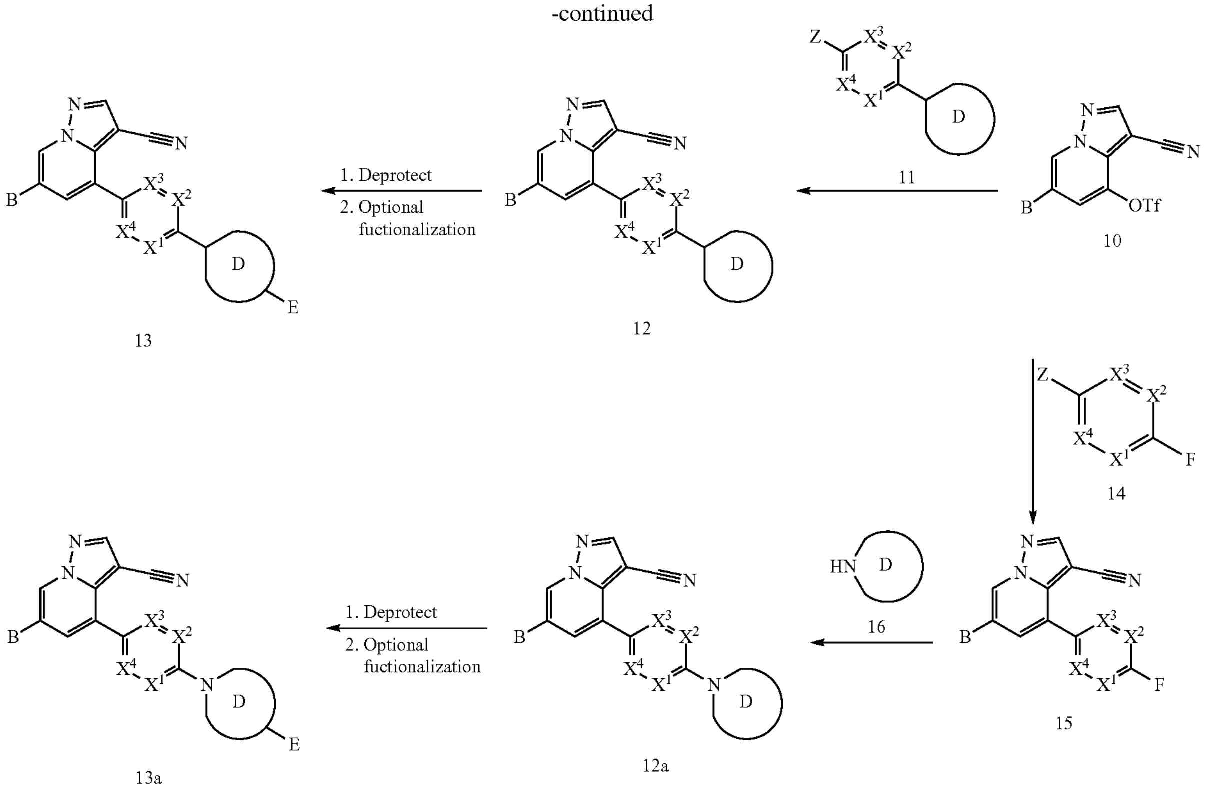

13 12 10 14 15 12a 13a

Scheme 1 shows a general scheme for the synthesis of compound 13 where A is CN, and B, $X^1$, $X^2$, $X^3$, $X^4$, and E are as defined for Formula I, and the D ring is as defined for $hetCyc^1$, $hetCyc^2$, $hetCyc^3$ or $hetCyc^9$ of Formula I, and the synthesis of compound 13a where A is CN, D is as defined for Formula I provided that the D ring is coupled to the ring defined by $X^1$, $X^2$, $X^3$ and $X^4$ through a ring nitrogen atom in the D ring, $X^1$, $X^2$, $X^3$, $X^4$ provided that at least one of $X^1$ and $X^2$ is nitrogen, and B, $X^3$, $X^4$, and E are as defined for Formula I.

Compound 2 is obtained by treating MSH reagent with 3-bromo-5-methoxypyridine, which is commercially available. The aminating reagent O-mesitylsulfonylhydroxylamine (MSH) may be prepared as described in Mendiola, J., et al., Org. Process Res. Dev. 2009, 13(2), 263-267. Compound 2 may be reacted with ethyl propiolate to provide the pyrazolo[1,5-a]pyrazine a mixture of compounds 3A and 3B, which typically are obtained in a ratio of approximately 2:1 to 9:1. The mixture of compounds 3A and 3B may be treated with 48% HBr at elevated temperatures, followed by recrystallization or chromatography purifications to isolate compound 4A as the minor isomer and compound 4B as the major isomer.

The isolated compound 4B may be functionalized with a formyl group using $POCl_3$ followed by purification to provide compound 5. The formyl group of compound 5 may be converted to an oxime group using $NH_2OH$ to provide compound 6. The oxime group of compound 6 may be converted to a nitrile group using acetic anhydride to provide compound 7. The B group may be installed by treating compound 7 with a corresponding boronic ester having the formula $hetAr^1$—$B(OR^a)(OR^b)$ where $hetAr^1$ is as defined for Formula I and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures) to provide compound 8 where B is $hetAr^1$ as defined for Formula I. The methoxy group of compound 8 may be converted to a hydroxy group by treating compound 8 with aluminum trichloride to provide compound 9. The free hydroxy group of compound 9 may be converted to a triflate group by treating compound 9 with a triflating reagent, for example 1,1,1-trifluoro-N-phenyl-N-((trifluoromethyl)sulfonyl) methanesulfonamide to provide compound 10. Compound 12 may be prepared by coupling compound 10 with the corresponding boronic ester compound 11 where Z is —$B(OR^a)(OR^b)$ and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 12 may be removed under standard conditions (for example, a Boc protecting group may be removed by treating compound 12 under acidic conditions, e.g., using HCl) to provide compound 13 where E is H. Alternatively, the deprotected D ring may be functionalized to install the E group under standard conditions such as described below to provide compound 13 where E is as defined for Formula I except that E is not H.

Alternatively, compound 10 may be coupled with compound 14 using appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$) to provide compound 15. Compound 15 may be reacted with compound 16 under appropriate $S_NAr$ conditions (for example, optionally in the presence of a base such as $K_2CO_3$ and at elevated temperature) to provide compound 12a, wherein if the D ring of compound 16 comprises a second unsubstituted ring nitrogen atom, the second nitrogen atom is protected with an appropriate amine protecting group prior to coupling. The protecting group if present on the D ring of compound 12a may be removed under standard conditions (for example, a Boc group may be removed by treating compound 12a to acidic conditions, e.g., HCl) to provide compound 13a where E is H. Alternatively, the deprotected D ring may be functionalized to install the E group under standard conditions such as described below to provide compound 13a where E is as defined for Formula I except that E is not H.

Scheme 2

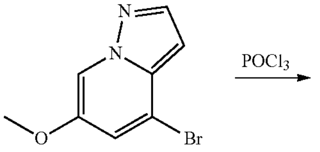

4A

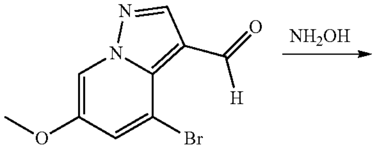

17

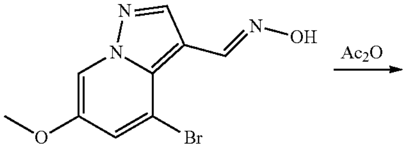

18

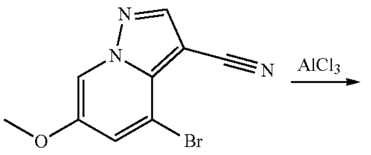

19

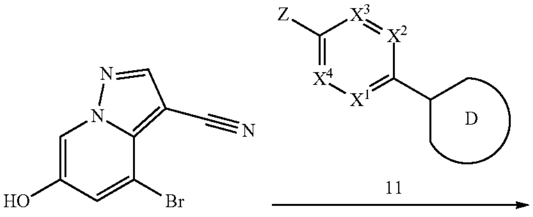

11

20

-continued

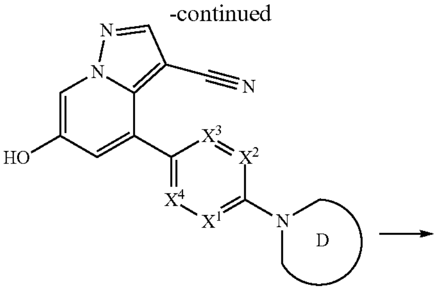

21

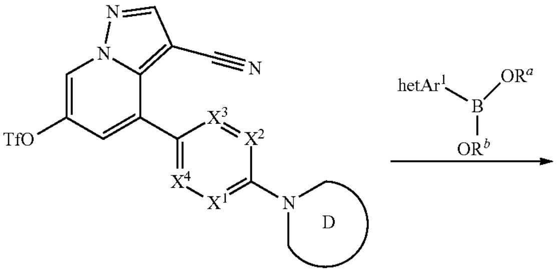

22

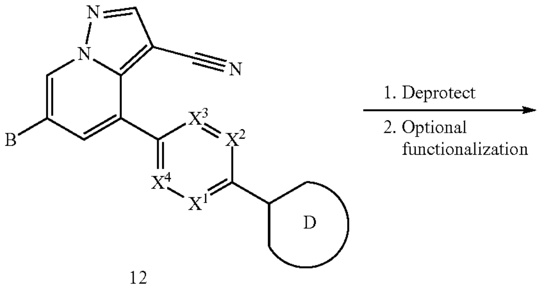

12

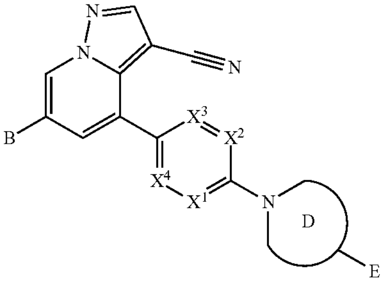

13

Scheme 2 shows an alternative route for the synthesis of compound 13, wherein A is CN, and B, $X^1$, $X^2$, $X^3$, $X^4$, and E are as defined for Formula I, and the D ring is as defined for $hetCyc^1$, $hetCyc^2$, $hetCyc^3$ or $hetCyc^9$ of Formula I. Compound 4A (prepared as in Scheme 1) may be functionalized with a formyl group using $POCl_3$ to provide compound 17. The formyl group may be converted to an oxime group using $NH_2OH$ to provide compound 18. The oxime group may be converted to a nitrile group using acetic anhydride to provide compound 19. The methoxy group of compound 19 may be converted to a hydroxy group by treating compound 19 with aluminum trichloride to provide compound 20. Compound 21 may be prepared by coupling compound 20 with the corresponding boronic ester compound 11 where Z is —$B(OR^a)(OR^b)$ and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The free hydroxy group of compound 21 may be converted to a triflate group by treating compound 21 with a triflating reagent, for example 1,1,1-trifluoro-N-phenyl-N-((trifluoromethyl)sulfonyl)methanesulfonamide to provide compound 22. The B group may be installed by treating compound 22 with the corresponding boronic ester having the formula hetAr$^1$—B(OR$^a$)(OR$^b$) where hetAr$^1$ is as defined for Formula I and R$^a$ and R$^b$ are H or (1-6C)alkyl, or R$^a$ and R$^b$ together with the atoms to which they are connected form a 5-6 membered ring optionally substituted with 1-4 substituents selected from (C1-C3 alkyl), using appropriate palladium-catalyzed cross-coupling reaction conditions, e.g., Suzuki coupling reaction conditions (for example, a palladium catalyst and optionally a ligand in the presence of an inorganic base, for example, $Pd_2(dba)_3$, X-Phos and $Na_2CO_3$ in dioxane at elevated temperatures) to provide compound 12 where B is hetAr$^1$ as defined for Formula I. The protecting group if present on the D ring of compound 12 may be removed under standard conditions (for example, a Boc group may be removed by treating compound 12 to acidic conditions, e.g., HCl in propan-2-ol) to provide compound 13 where E is H. Alternatively, the deprotected D ring may be functionalized to install the E group under standard conditions such as described below to provide compound 13 where E is as defined for Formula I except that E is not H.

-continued

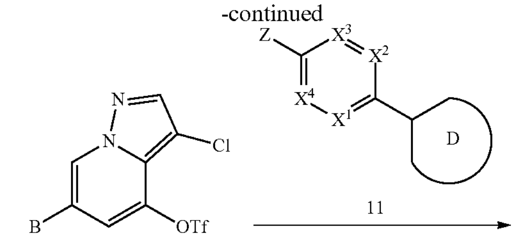

26

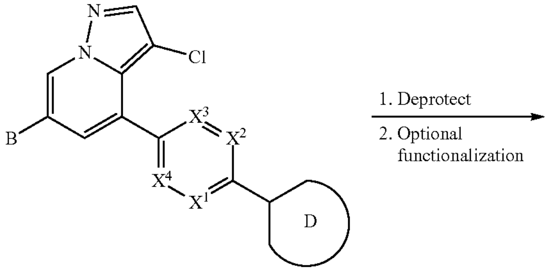

27

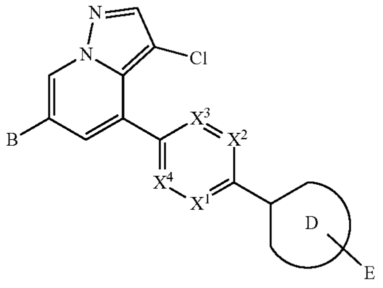

28

Scheme 3

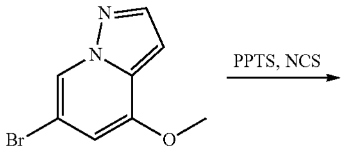

4B

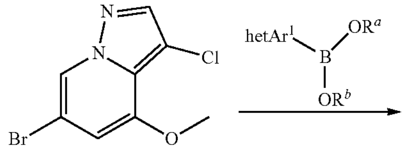

23

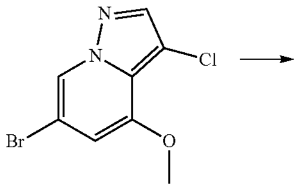

24

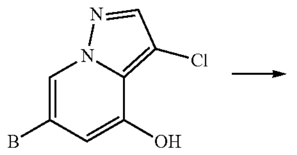

25

Scheme 3 shows a general scheme for the synthesis of compound 28 where A is Cl, and B, X$^1$, X$^2$, X$^3$, X$^4$, and E are as defined for Formula I, and the D ring is as defined for hetCyc$^1$, hetCyc$^2$, hetCyc$^3$ or hetCyc$^9$ of Formula I. Compound 4B (prepared as in Scheme 1) may be chlorinated using N-chlorosuccinimide to provide compound 23. The B group may be installed by coupling compound 23 with an appropriate boronic ester having the formula hetAr$^1$—B(OR$^a$)(OR$^b$) where hetAr$^1$ is as defined for Formula I and R$^a$ and R$^b$ are H or (1-6C)alkyl, or R$^a$ and R$^b$ together with the atoms to which they are connected form a 5-6 membered ring optionally substituted with 1-4 substituents selected from (C1-C3 alkyl), under appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures) to provide compound 24 where B is hetAr$^1$ as defined for Formula I. The methoxy group of compound 24 may be converted to a hydroxy group under standard conditions, for example by treating compound 24 with $BBr_3$, to yield compound 25. The free hydroxy group of compound 25 may be converted to a triflate group by treating compound 25 with an appropriate triflating reagent in the presence of a base, e.g., 1,1,1-trifluoro-N-phenyl-N-((trifluoromethyl)sulfonyl)methanesulfonamide and DIEA to provide compound 26. Compound 27 may be prepared by coupling compound 26 with the corresponding boronic ester compound 11 where Z is —B(OR$^a$)(OR$^b$) and R$^a$ and R$^b$ are H or (1-6C)alkyl, or R$^a$ and R$^b$ together with the atoms to which they are connected form a 5-6 membered ring optionally substituted with 1-4 substituents selected from (C1-C3 alkyl), using under standard coupling conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 27 may be removed under standard conditions (for example, a Boc group may be removed by treating compound 27 with acid (e.g., 5-6 N HCl in propan-2-ol) to provide compound 28 where E is H. Alternatively, the deprotected D ring may be functionalized to install the E group under standard conditions such as described below to provide compound 28 where E is as defined for Formula I except that E is not H.

Scheme 4

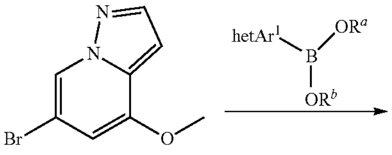

4B

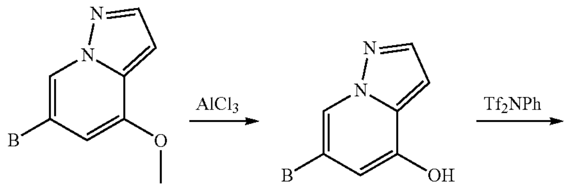

29 30

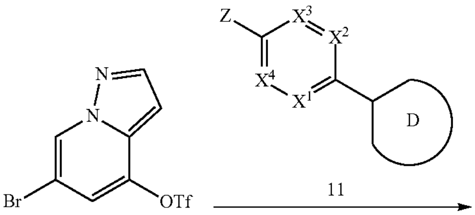

11

31

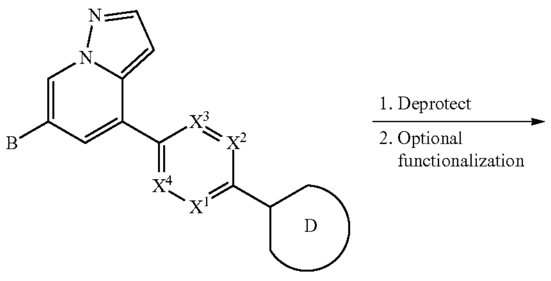

32

-continued

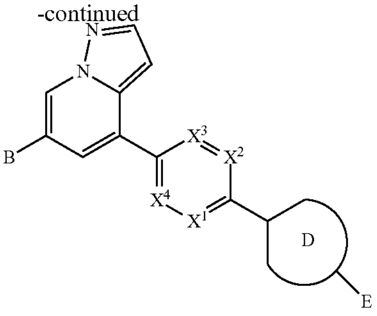

33

Scheme 4 shows a general scheme for the synthesis of compound 33, wherein A is H, and B, $X^1$, $X^2$, $X^3$, $X^4$, D and E are as defined for Formula I. Compound 4B (prepared as in Scheme 1) may be coupled with an appropriate boronic ester having the formula $hetAr^1—B(OR^a)(OR^b)$ where $hetAr^1$ is as defined for Formula I and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), under appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures) to install the B group to provide compound 29 where B is $hetAr^1$ as defined for Formula I. The methoxy group of compound 29 may be converted to a hydroxy group by treating compound 29 with aluminum trichloride to provide compound 30. The free hydroxy group of compound 30 may be converted to a triflate group by treating compound 33 with a triflating reagent in the presence of a base, e.g., 1,1,1-trifluoro-N-phenyl-N-((trifluoromethyl)sulfonyl) methanesulfonamide and DIEA in an appropriate solvent such as THF to provide compound 31. Compound 32 may be prepared by coupling compound 31 with compound 11 under appropriate palladium-catalyzed cross-coupling reaction conditions, e.g., Suzuki coupling reaction conditions (for example, a palladium catalyst and optionally a ligand in the presence of an inorganic base, for example, $Pd(PPh_3)_4$ and $Na_2CO_3$ in dioxane at elevated temperatures), wherein if the D ring of compound 11 comprises an unsubstituted ring nitrogen atom, the nitrogen atom is protected with an appropriate amine protecting group prior to coupling. The protecting group if present on the D ring of compound 32 may be removed under standard conditions (for example, a Boc group may be removed by treating compound 32 under acidic conditions, e.g., HCl in propan-2-ol) to provide compound 33 where E is H. Alternatively, the deprotected D ring may be functionalized to install the E group under standard conditions such as described below to provide compound 33 where E is as defined for Formula I except that E is not H.

The D ring of any one of compounds 13, 13a, 28, and 33 described in Schemes 1-4 may be functionalized to install an E group, where E is any of the E groups defined for Formula I with the exception of hydrogen, using standard chemistry well known to persons skilled in the art.

For example, an amide derivative (e.g., where D is $hetCyc^1$ where $hetCyc^1$ is piperazinyl and E is (C1-C6 alkyl)C(═O)— optionally substituted with one to three fluoros; (hydroxy C1-C6 alkyl)C(═O)— optionally substituted with one to three fluoros; (C1-C6 alkoxy)(C1-C6 alkyl)C(═O)—; $Cyc^1C$(═O)—; $Cyc^1$(C1-C6 alkyl)C(═O)—; $hetCyc^4$(C1-C6 alkyl)C(═O)—; $Ar^2C$(═O)—; $Ar^2$(C1-C6 alkyl)C(═O)— wherein the alkyl portion is optionally substituted with one or two groups independently selected from the group consisting of OH, C1-C6 alkyl, hydroxyC1-C6 alkyl-, (C1-C6)alkoxy, $R^eR^fN$— and ($R^eR^fN$)C1-C3 alkyl-, where $R^e$ and $R^f$ are independently selected from H and C1-C6 alkyl, or said alkyl portion is substituted with a 5-6 membered heterocyclic ring having one or two ring heteroatoms independently selected from N and O and wherein the heterocyclic ring is optionally substituted with C1-C6 alkyl; $hetAr^2C$(═O)—; or $hetAr^2$(C1-C6 alkyl)C(═O)— wherein the alkyl portion is optionally substituted with one or two groups independently selected from the group consisting of OH, C1-C6 alkyl, hydroxyC1-C6 alkyl-, (C1-C6)alkoxy, $R^eR^fN$— and ($R^eR^fN$)C1-C3 alkyl-, where $R^e$ and $R^f$ are independently H or C1-C6 alkyl), or said alkyl portion is substituted with a 5-6 membered heterocyclic ring having one or two ring heteroatoms independently selected from N and O and wherein the heterocyclic ring is optionally substituted with C1-C6 alkyl, may be obtained by treating compound 13 having a deprotected amino D ring with an carboxylic acid using conventional amide bond formation conditions, for example by treating the carboxylic acid with an activating agent (e.g., HATU), followed by addition of the compound 13 having a deprotected amino D ring in the presence of a base (e.g., an amine base such as DIEA) in an appropriate solvent (such as DMA) to provide a functionalized compound 13. The same chemistry may be utilized with compounds 13a, 28 and 33 to prepare functionalized compounds 13a, 28 and 33, respectively.

As another example, a urea derivative (e.g., where D is $hetCyc^1$ where $hetCyc^1$ is piperazinyl and E is $hetCyc^4C$(═O)— or $R^1R^2NC$(═O)—) may be prepared by first activating a ring nitrogen in the D ring of compound 13 with triphosgene in the presence of DIEA and in a solvent such as DCM, followed by addition of a primary or secondary amine reagent to provide a functionalized compound 13. The same chemistry may be utilized with compounds 13a, 28 and 33 to prepare functionalized compounds 13a, 28 and 33, respectively.

As another example, an N-alkyl derivative (e.g., where D is $hetCyc^1$ where $hetCyc^1$ is piperazinyl and E is hydroxyC1-C6 alkyl- optionally substituted with one to three fluoros; (C1-C6 alkoxy)(hydroxy C1-C6 alkyl); ($Ar^2$)C1-C6 alkyl-; ($Ar^2$)hydroxy C2-C6 alkyl-; or ($hetAr^2$)hydroxyC2-C6 alkyl-; may be prepared by treating compound 13 where E is H with an alkyl bromide, alkyl chloride or epoxide in the presence of a base such as DIEA in a solvent at ambient or elevated temperatures) to provide a functionalized compound 13. The same chemistry may be utilized with compounds 13a, 28 and 33 to prepare functionalized compounds 13a, 28 and 33, respectively.

As another example, a sulfonamide derivative may be prepared by treating compound 13 where E is H with an appropriate sulfonyl chloride in the presence of a base, such as an amine base (such as triethylamine) in an appropriate solvent to provide a functionalized compound 13. The same chemistry may be utilized with compounds 13a, 28 and 33 to prepare functionalized compounds 13a, 28 and 33, respectively.

Further provided herein is a process for preparing of a compound of Formula I or a pharmaceutically acceptable salt thereof as defined herein which comprises:

(a) for a compound of Formula I where E is H and A, B, $X^1$, $X^2$, $X^3$, $X^4$, and D are as defined for Formula I, coupling a corresponding compound having the formula

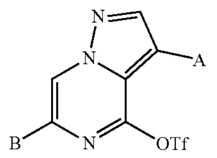

where A and B are as defined for Formula I, with a corresponding compound having the formula 11

11

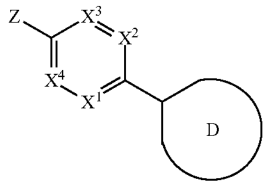

in the presence of a palladium catalyst and optionally a ligand and in the presence of a base, where Z is —B($OR^a$)($OR^b$) and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), the

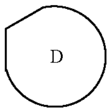

ring is as defined for $hetCyc^1$, $hetCyc^2$, $hetCyc^3$ or $hetCyc^9$ of Formula I, and $X^1$, $X^2$, $X^3$ and $X^4$ are as defined for Formula I, followed by removal of a protecting group on the D ring if present; or (b) for a compound of Formula I where A, B, $X^1$, $X^2$, $X^3$, $X^4$, D and E are as defined for Formula I with the exception that E is not hydrogen, functionalizing a corresponding compound having the formula

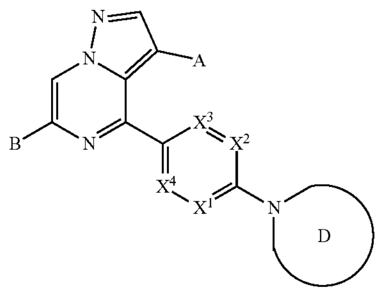

wherein the

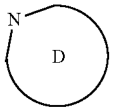

moiety is as defined for hetCyc$^1$, hetCyc$^2$, hetCyc$^3$ or hetCyc$^9$ of Formula I, and A, B, $X^1$, $X^2$, $X^3$ and $X^4$ are as defined for Formula I; or (c) for a compound of Formula I where A is CN, D is as defined for Formula I provided that the D ring is coupled to the ring defined by $X^1$, $X^2$, $X^3$ and $X^4$ through a ring nitrogen atom in the D ring, $X^1$, $X^2$, $X^3$, $X^4$ provided that at least one of $X^1$ and $X^2$ is nitrogen, and E are as defined for Formula I, reacting a corresponding compound having the formula 15

15

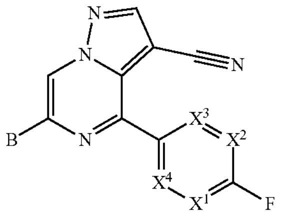

where B, $X^1$, $X^2$, $X^3$ and $X^4$ are as defined for Formula I provided that at least one of $X^1$ and $X^2$ is nitrogen, with a corresponding compound having the formula 17

17

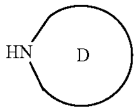

in the presence of a base, wherein the

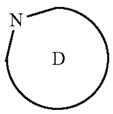

ring is as defined for hetCyc$^1$, hetCyc$^2$, hetCyc$^3$ or hetCyc$^9$ of Formula I; or (d) for a compound of Formula I where A is CN, E is H, and B, $X^1$, $X^2$, $X^3$, $X^4$, and D are as defined for Formula I, reacting a compound having the formula 22

22

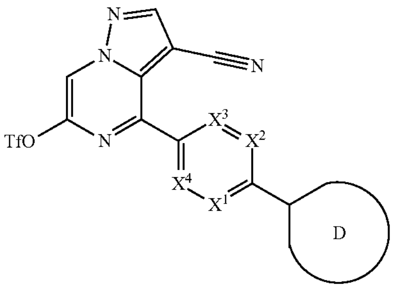

wherein the

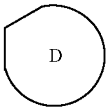

moiety is as defined for hetCyc$^1$, hetCyc$^2$, hetCyc$^3$ or hetCyc$^9$ in claim 1 and A, B, $X^1$, $X^2$, $X^3$ and $X^4$ are as defined for Formula I, with a corresponding compound having the formula

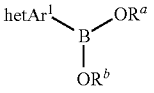

where hetAr$^1$ is as defined for Formula I and $R^a$ and $R^b$ are H or (1-6C)alkyl, or $R^a$ and $R^b$ together with the atoms to which they are connected form a 5-6 membered ring optionally substituted with 1-4 substituents selected from (C1-C3 alkyl), in the presence of a palladium catalyst and optionally a ligand and in the presence of a base; and removing any protecting groups and optionally forming a pharmaceutically acceptable salt thereof.

Referring to processes (a) and (d), suitable palladium catalysts include $Pd(PPh_3)_4$, $Pd_2(dba)_3$, $Pd(OAc)_2$, and $Pd(PPh_3)_2Cl_2$. Suitable ligands include X-PHOS (2-dicyclohexylphosphino-2',4',6'-triisopropylbiphenyl), DIPHOS (1,2-Bis(diphenylphosphino)ethane) or rac-BINAP (racemic-2,2'-Bis(diphenylphosphino)-1,1'-binaphthyl). The base may be, for example, an alkali metal carbonate, hydroxide, alkoxide or acetate, such as for example cesium carbonate, sodium carbonate, potassium carbonate, sodium hydroxide, sodium tert-butoxide or potassium acetate. Convenient solvents include aprotic solvents such as ethers (for example tetrahydrofuran or p-dioxane), toluene, DMF or DME. The reaction can be conveniently performed at a temperature ranging from ambient temperature to 120° C., for example from 80 to 110° C.

The ability of test compounds to act as RET inhibitors may be demonstrated by the assay described in Example A. $IC_{50}$ values are shown in Table 5.

In some embodiments, the compounds provided herein exhibit potent and selective RET inhibition. For example, the compounds provided herein exhibit nanomolar potency against wild type RET and select RET mutants, including, for example, the KIF5B-RET fusion, G810R and G810S ATP cleft front or linker mudations, M918T kinase domain, and V804M, V804L, and V804E gatekeeper mutations, with minimal activity against related kinases.

In some embodiments, the compounds of Formula I or a pharmaceutically acceptable salt or solvate thereof, selectively target a RET kinase. For example, a compound of Formula I or a pharmaceutically acceptable salt or solvate thereof, can selectively target a RET kinase over another kinase or non-kinase target.

In some embodiments, a compound of Formula I or a pharmaceutically acceptable salt or solvate thereof, exhibits at least a 30-fold selectivity for a RET kinase over another kinase. For example, a compound of Formula I or a pharmaceutically acceptable salt or solvate thereof, exhibits at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 200-fold selectivity; at least 300-fold selectivity; at least 400-fold selectivity; at least 500-fold selectivity; at least 600-fold selectivity; at least 700-fold selectivity; at least 800-fold selectivity; at least 900-fold selectivity; or at least 1000-fold selectivity for a RET kinase over another kinase. In some embodiments, selectivity for a RET kinase over another kinase is measured in a cellular assay (e.g., a cellular assay as provided herein).

In some embodiments, the compounds provided herein can exhibit selectivity for a RET kinase over a KDR kinase (e.g., VEGFR2). In some embodiments, the selectivity for a RET kinase over a KDR kinase is observed without loss of potency for a RET kinase encoded by a RET gene including an activating mutation or a RET kinase inhibitor resistance mutation (e.g., a gatekeeper mutant). In some embodiments, the selectivity over a KDR kinase is at least 10-fold (e.g., at least a 40-fold selectivity; at least a 50-fold selectivity; at least a 60-fold selectivity; at least a 70-fold selectivity; at least a 80-fold selectivity; at least a 90-fold selectivity; at least 100-fold selectivity; at least 150-fold selectivity; at least 200-fold selectivity; at least 250-fold selectivity; at least 300-fold selectivity; at least 350-fold selectivity; or at least 400-fold selectivity) as compared to the inhibition of KIF5B-RET (i.e. the compounds were more potent against KIF5B-RET than KDR). In some embodiments, the selectivity for a RET kinase over a KDR kinase is about 30-fold. In some embodiments, the selectivity for a RET kinase over a KDR kinase is at least 100-fold. In some embodiments, the selectivity for a RET kinase over a KDR kinase is at least 150-fold. In some embodiments, the selectivity for a RET kinase over a KDR kinase is at least 400-fold. Without being bound by any theory, potent KDR kinase inhibition is believed to be a common feature among multikinase inhibitors (MKIs) that target RET and may be the source of the dose-limiting toxicities observed with such compounds.

In some embodiments, inhibition of V804M was similar to that observed for wild-type RET. For example, inhibition of V804M was within about 2-fold (e.g., about 5-fold, about 7-fold, about 10-fold) of inhibition of wild-type RET (i.e. the compounds were similarly potent against wild-type RET and V804M). In some embodiments, selectivity for a wild-type or V804M RET kinase over another kinase is measured in an enzyme assay (e.g., an enzyme assay as provided herein). In some embodiments, the compounds provided herein exhibit selective cytotoxicity to RET-mutant cells.

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor.

In some embodiments, the compounds of Formula I or a pharmaceutically acceptable salt or solvate thereof, exhibit one or more of high GI absorption, low clearance, and low potential for drug-drug interactions.

Compounds of Formula I are useful for treating diseases and disorders which can be treated with a RET kinase inhibitor, such as RET-associated diseases and disorders, e.g., proliferative disorders such as cancers, including hematological cancers and solid tumors, and gastrointestinal disorders such as IBS.

As used herein, terms "treat" or "treatment" refer to therapeutic or palliative measures. Beneficial or desired clinical results include, but are not limited to, alleviation, in whole or in part, of symptoms associated with a disease or disorder or condition, diminishment of the extent of disease, stabilized (i.e., not worsening) state of disease, delay or slowing of disease progression, amelioration or palliation of the disease state (e.g., one or more symptoms of the disease), and remission (whether partial or total), whether detectable or undetectable. "Treatment" can also mean prolonging survival as compared to expected survival if not receiving treatment.

As used herein, the terms "subject," "individual," or "patient," are used interchangeably, refers to any animal, including mammals such as mice, rats, other rodents, rabbits, dogs, cats, swine, cattle, sheep, horses, primates, and humans. In some embodiments, the patient is a human. In some embodiments, the subject has experienced and/or exhibited at least one symptom of the disease or disorder to be treated and/or prevented. In some embodiments, the subject has been identified or diagnosed as having a cancer with a dysregulation of a RET gene, a RET protein, or expression or activity, or level of any of the same (a RET-associated cancer) (e.g., as determined using a regulatory agency-approved, e.g., FDA-approved, assay or kit). In some embodiments, the subject has a tumor that is positive for a dysregulation of a RET gene, a RET protein, or expression or activity, or level of any of the same (e.g., as determined using a regulatory agency-approved assay or kit). The subject can be a subject with a tumor(s) that is positive for a dysregulation of a RET gene, a RET protein, or expression or activity, or level of any of the same (e.g., identified as positive using a regulatory agency-approved, e.g., FDA-approved, assay or kit). The subject can be a subject whose tumors have a dysregulation of a RET gene, a RET protein, or expression or activity, or a level of the same (e.g., where the tumor is identified as such using a regulatory agency-approved, e.g., FDA-approved, kit or assay). In some embodiments, the subject is suspected of having a RET-associated cancer. In some embodiments, the subject has a clinical record indicating that the subject has a tumor that has a dysregulation of a RET gene, a RET protein, or expression or activity, or level of any of the same (and optionally the clinical record indicates that the subject should be treated with any of the compositions provided herein). In some embodiments, the patient is a pediatric patient.

The term "pediatric patient" as used herein refers to a patient under the age of 21 years at the time of diagnosis or treatment. The term "pediatric" can be further be divided into various subpopulations including: neonates (from birth through the first month of life); infants (1 month up to two years of age); children (two years of age up to 12 years of age); and adolescents (12 years of age through 21 years of age (up to, but not including, the twenty-second birthday)). Berhman R E, Kliegman R, Arvin A M, Nelson W E. Nelson *Textbook of Pediatrics,* 15th Ed. Philadelphia: W.B. Saunders Company, 1996; Rudolph A M, et al. *Rudolph's Pediatrics,* 21st Ed. New York: McGraw-Hill, 2002; and Avery M D, First L R. *Pediatric Medicine,* 2nd Ed. Baltimore: Williams & Wilkins; 1994. In some embodiments, a pediatric patient is from birth through the first 28 days of life, from 29 days of age to less than two years of age, from two years of age to less than 12 years of age, or 12 years of age through 21 years of age (up to, but not including, the twenty-second birthday). In some embodiments, a pediatric patient is from birth through the first 28 days of life, from 29 days of age to less than 1 year of age, from one month of age to less than four months of age, from three months of age to less than seven months of age, from six months of age to less than 1 year of age, from 1 year of age to less than 2 years of age, from 2 years of age to less than 3 years of age, from 2 years of age to less than seven years of age, from 3 years of age to less than 5 years of age, from 5 years of age to less than 10 years of age, from 6 years of age to less than 13 years of age, from 10 years of age to less than 15 years of age, or from 15 years of age to less than 22 years of age.

In certain embodiments, compounds of Formula I are useful for preventing diseases and disorders as defined herein (for example, autoimmune diseases, inflammatory diseases, and cancer). The term "preventing" as used herein means the prevention of the onset, recurrence or spread, in whole or in part, of the disease or condition as described herein, or a symptom thereof.

The term "RET-associated disease or disorder" as used herein refers to diseases or disorders associated with or having a dysregulation of a RET gene, a RET kinase (also called herein RET kinase protein), or the expression or activity or level of any (e.g., one or more) of the same (e.g., any of the types of dysregulation of a RET gene, a RET kinase, a RET kinase domain, or the expression or activity or level of any of the same described herein). Non-limiting examples of a RET-associated disease or disorder include, for example, cancer and gastrointestinal disorders such as irritable bowel syndrome (IBS).

The term "RET-associated cancer" as used herein refers to cancers associated with or having a dysregulation of a RET gene, a RET kinase (also called herein RET kinase protein), or expression or activity, or level of any of the same. Non-limiting examples of a RET-associated cancer are described herein.

The phrase "dysregulation of a RET gene, a RET kinase, or the expression or activity or level of any of the same" refers to a genetic mutation (e.g., a chromosomal translocation that results in the expression of a fusion protein including a RET kinase domain and a fusion partner, a mutation in a RET gene that results in the expression of a RET protein that includes a deletion of at least one amino acid as compared to a wildtype RET protein, a mutation in a RET gene that results in the expression of a RET protein with one or more point mutations as compared to a wildtype RET protein, a mutation in a RET gene that results in the expression of a RET protein with at least one inserted amino acid as compared to a wildtype RET protein, a gene duplication that results in an increased level of RET protein in a cell, or a mutation in a regulatory sequence (e.g., a promoter and/or enhancer) that results in an increased level of RET protein in a cell), an alternative spliced version of a RET mRNA that results in a RET protein having a deletion of at least one amino acid in the RET protein as compared to the wild-type RET protein), or increased expression (e.g., increased levels) of a wildtype RET kinase in a mammalian cell due to aberrant cell signaling and/or dysregulated autocrine/paracrine signaling (e.g., as compared to a control non-cancerous cell). As another example, a dysregulation of a RET gene, a RET protein, or expression or activity, or level of any of the same, can be a mutation in a RET gene that encodes a RET protein that is constitutively active or has increased activity as compared to a protein encoded by a RET gene that does not include the mutation. For example, a dysregulation of a RET gene, a RET protein, or expression or activity, or level of any of the same, can be the result of a gene or chromosome translocation which results in the expression of a fusion protein that contains a first portion of RET that includes a functional kinase domain, and a second portion of a partner protein (i.e., that is not RET). In some examples, dysregulation of a RET gene, a RET protein, or expression or activity or level of any of the same can be a result of a gene translocation of one RET gene with another non-RET gene. Non-limiting examples of fusion proteins are described in Table 1. Non-limiting examples of RET kinase protein point mutations/insertions/deletions are described in Tables 2 and 2a. Additional examples of RET kinase protein mutations (e.g., point mutations) are RET inhibitor resistance mutations. Non-limiting examples of RET inhibitor resistance mutations are described in Tables 3 and 4.

In some embodiments, dysregulation of a RET gene, a RET kinase, or the expression or activity or level of any of the same can be caused by an activating mutation in a RET gene (see, e.g., chromosome translocations that result in the expression of any of the fusion proteins listed in Table 1). In some embodiments, dysregulation of a RET gene, a RET kinase, or the expression or activity or level of any of the same can be caused by a genetic mutation that results in the expression of a RET kinase that has increased resistance to inhibition by a RET kinase inhibitor and/or a multi-kinase inhibitor (MKI), e.g., as compared to a wildtype RET kinase (see, e.g., the amino acid substitutions in Tables 3 and 4). The exemplary RET kinase point mutations, insertions, and deletions shown in Tables 2 and 2a can be caused by an activating mutation and/or can result in the expression of a RET kinase that has increased resistance to inhibition by a RET kinase inhibitor and/or a multi-kinase inhibitor (MKI).

The term "activating mutation" describes a mutation in a RET kinase gene that results in the expression of a RET kinase that has an increased kinase activity, e.g., as compared to a wildtype RET kinase, e.g., when assayed under identical conditions. For example, an activating mutation can result in the expression of a fusion protein that includes a RET kinase domain and a fusion partner. In another example, an activating mutation can be a mutation in a RET kinase gene that results in the expression of a RET kinase that has one or more (e.g., two, three, four, five, six, seven, eight, nine, or ten) amino acid substitutions (e.g., any combination of any of the amino acid substitutions described herein) that has increased kinase activity, e.g., as compared to a wildtype RET kinase, e.g., when assayed under identical conditions. In another example, an activating mutation can be a mutation in a RET kinase gene that results in the expression of a RET kinase that has one or more (e.g., two, three, four, five, six, seven, eight, nine, or ten) amino acids deleted, e.g., as compared to a wildtype RET kinase, e.g., when assayed under identical conditions. In another example, an activating mutation can be a mutation in a RET kinase gene that results in the expression of a RET kinase that has at least one (e.g., at least 2, at least 3, at least 4, at least 5, at least 6, at least 7, at least 8, at least 9, at least 10, at least 12, at least 14, at least 16, at least 18, or at least 20) amino acid inserted as compared to a wildtype RET kinase, e.g., the exemplary wildtype RET kinase described herein, e.g., when assayed under identical conditions. Additional examples of activating mutations are known in the art.

The term "wildtype" or "wild-type" describes a nucleic acid (e.g., a RET gene or a RET mRNA) or protein (e.g., a RET protein) that is found in a subject that does not have a RET-associated disease, e.g., a RET-associated cancer (and optionally also does not have an increased risk of developing a RET-associated disease and/or is not suspected of having a RET-associated disease), or is found in a cell or tissue from a subject that does not have a RET-associated disease, e.g., a RET-associated cancer (and optionally also does not have an increased risk of developing a RET-associated disease and/or is not suspected of having a RET-associated disease).

The term "regulatory agency" refers to a country's agency for the approval of the medical use of pharmaceutical agents with the country. For example, a non-limiting example of a regulatory agency is the U.S. Food and Drug Administration (FDA).

Provided herein is a method of treating cancer (e.g., a RET-associated cancer) in a patient in need of such treatment, the method comprising administering to the patient a therapeutically effective amount of a compound of Formula I or a pharmaceutically acceptable salt or solvate thereof or a pharmaceutical composition thereof. For example, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, and V804M. In some embodiments, a compound of Formula I is selected from i) Example No. 1-20; ii) Example No. 21-40; iii) Example No. 41-49; iv) Example No. 50-70; v) Example No. 71-90; vi) Example No. 91-110; vii) Example No. 111-121.

In some embodiments of any of the methods or uses described herein, the cancer (e.g., RET-associated cancer) is a hematological cancer. In some embodiments of any of the methods or uses described herein, the cancer (e.g., RET-associated cancer) is a solid tumor. In some embodiments of any of the methods or uses described herein, the cancer (e.g., RET-associated cancer) is a solid tumor. In some embodiments of any of the methods or uses described herein, the cancer (e.g., RET-associated cancer) is lung cancer (e.g., small cell lung carcinoma or non-small cell lung carcinoma), thyroid cancer (e.g., papillary thyroid cancer, medullary thyroid cancer, differentiated thyroid cancer, recurrent thyroid cancer, or refractory differentiated thyroid cancer), thyroid ademona, endocrine gland neoplasms, lung adenocarcinoma, bronchioles lung cell carcinoma, multiple endocrine neoplasia type 2A or 2B (MEN2A or MEN2B, respectively), pheochromocytoma, parathyroid hyperplasia, breast cancer, mammary cancer, mammary carcinoma, mammary neoplasm, colorectal cancer (e.g., metastatic colorectal cancer), papillary renal cell carcinoma, ganglioneuromatosis of the gastroenteric mucosa, inflammatory myofibroblastic tumor, or cervical cancer. In some embodiments of any of the methods or uses described herein, the cancer (e.g., RET-associated cancer) is selected from the group of: acute lymphoblastic leukemia (ALL), acute myeloid leukemia (AML), cancer in adolescents, adrenocortical carcinoma, anal cancer, appendix cancer, astrocytoma, atypical teratoid/rhabdoid tumor, basal cell carcinoma, bile duct cancer, bladder cancer, bone cancer, brain stem glioma, brain tumor, breast cancer, bronchial tumor, Burkitt lymphoma, carcinoid tumor, unknown primary carcinoma, cardiac tumors, cervical cancer, childhood cancers, chordoma, chronic lymphocytic leukemia (CLL), chronic myelogenous leukemia (CML), chronic myeloproliferative neoplasms, neoplasms by site, neoplasms, colon cancer, colorectal cancer, craniopharyngioma, cutaneous T-cell lymphoma, cutaneous angiosarcoma, bile duct cancer, ductal carcinoma in situ, embryonal tumors, endometrial cancer, ependymoma, esophageal cancer, esthesioneuroblastoma, Ewing sarcoma, extracranial germ cell tumor, extragonadal germ cell tumor, extrahepatic bile duct cancer, eye cancer, fallopian tube cancer, fibrous histiocytoma of bone, gallbladder cancer, gastric cancer, gastrointestinal carcinoid tumor, gastrointestinal stromal tumors (GIST), germ cell tumor, gestational trophoblastic disease, glioma, hairy cell tumor, hairy cell leukemia, head and neck cancer, thoracic neoplasms, head and neck neoplasms, CNS tumor, primary CNS tumor, heart cancer, hepatocellular cancer, histiocytosis, Hodgkin's lymphoma, hypopharyngeal cancer, intraocular melanoma, islet cell tumors, pancreatic neuroendocrine tumors, Kaposi sarcoma, kidney cancer, Langerhans cell histiocytosis, laryngeal cancer, leukemia, lip and oral cavity cancer, liver cancer, lung cancer, lymphoma, macroglobulinemia, malignant fibrous histiocytoma of bone, osteocarcinoma, melanoma, Merkel cell carcinoma, mesothelioma, metastatic squamous neck cancer, midline tract carcinoma, mouth cancer, multiple endocrine neoplasia syndromes, multiple myeloma, mycosis fungoides, myelodysplastic syndromes, myelodysplastic/myeloproliferative neoplasms, neoplasms by site, neoplasms, myelogenous leukemia, myeloid leukemia, multiple myeloma, myeloproliferative neoplasms, nasal cavity and paranasal sinus cancer, nasopharyngeal cancer, neuroblastoma, non-Hodgkin's lymphoma, non-small cell lung cancer, lung neoplasm, pulmonary cancer, pulmonary neoplasms, respiratory tract neoplasms, bronchogenic carcinoma, bronchial neoplasms, oral cancer, oral cavity cancer, lip cancer, oropharyngeal cancer, osteosarcoma, ovarian cancer, pancreatic cancer, papillomatosis, paraganglioma, paranasal sinus and nasal cavity cancer, parathyroid cancer, penile cancer, pharyngeal cancer, pheochromosytoma, pituitary cancer, plasma cell neoplasm, pleuropulmonary blastoma, pregnancy and breast cancer, primary central nervous system lymphoma, primary peritoneal cancer, prostate cancer, rectal cancer, colon cancer, colonic neoplasms, renal cell cancer, retinoblastoma, rhabdomyosarcoma, salivary gland cancer, sarcoma, Sezary syndrome, skin cancer, small cell lung cancer, small intestine cancer, soft tissue sarcoma, squamous cell carcinoma, squamous neck cancer, stomach cancer, T-cell lymphoma, testicular cancer, throat cancer, thymoma and thymic carcinoma, thyroid cancer, transitional cell cancer of the renal pelvis and ureter, unknown primary carcinoma, urethral cancer, uterine cancer, uterine sarcoma, vaginal cancer, vulvar cancer, and Wilms' tumor.

In some embodiments, a hematological cancer (e.g., hematological cancers that are RET-associated cancers) is selected from the group consisting of leukemias, lymphomas (non-Hodgkin's lymphoma), Hodgkin's disease (also called Hodgkin's lymphoma), and myeloma, for instance, acute lymphocytic leukemia (ALL), acute myeloid leukemia (AML), acute promyelocytic leukemia (APL), chronic lymphocytic leukemia (CLL), chronic myeloid leukemia (CML), chronic myelomonocytic leukemia (CMML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), and multiple myeloma (MM). Additional examples of hematological cancers include myeloproliferative disorders (MPD) such as polycythemia vera (PV), essential thrombocytopenia (ET) and idiopathic primary myelofibrosis (IMF/IPF/PMF). In one embodiment, the hematological cancer (e.g., the hematological cancer that is a RET-associated cancer) is AML or CMML.

In some embodiments, the cancer (e.g., the RET-associated cancer) is a solid tumor. Examples of solid tumors (e.g., solid tumors that are RET-associated cancers) include, for example, thyroid cancer (e.g., papillary thyroid carcinoma, medullary thyroid carcinoma), lung cancer (e.g., lung adenocarcinoma, small-cell lung carcinoma), pancreatic cancer, pancreatic ductal carcinoma, breast cancer, colon cancer, colorectal cancer, prostate cancer, renal cell carcinoma, head and neck tumors, neuroblastoma, and melanoma. See, for example, Nature Reviews Cancer, 2014, 14, 173-186.

In some embodiments, the cancer is selected from the group consisting of lung cancer, papillary thyroid cancer, medullary thyroid cancer, differentiated thyroid cancer, recurrent thyroid cancer, refractory differentiated thyroid cancer, multiple endocrine neoplasia type 2A or 2B (MEN2A or MEN2B, respectively), pheochromocytoma, parathyroid hyperplasia, breast cancer, colorectal cancer, papillary renal cell carcinoma, ganglioneuromatosis of the gastroenteric mucosa, and cervical cancer.

In some embodiments, the patient is a human.

Compounds of Formula I and pharmaceutically acceptable salts and solvates thereof are also useful for treating a RET-associated cancer.

Accordingly, also provided herein is a method for treating a patient diagnosed with or identified as having a RET-associated cancer, e.g., any of the exemplary RET-associated cancers disclosed herein, comprising administering to the patient a therapeutically effective amount of a compound of Formula I or a pharmaceutically acceptable salt or solvate thereof, or a pharmaceutical composition thereof as defined herein.

Dysregulation of a RET kinase, a RET gene, or the expression or activity or level of any (e.g., one or more) of the same can contribute to tumorigenesis. For example, a dysregulation of a RET kinase, a RET gene, or expression or activity or level of any of the same can be a translocation, overexpression, activation, amplification, or mutation of a RET kinase, a RET gene, or a RET kinase domain. Translocation can include a gene translocation resulting in the expression of a fusion protein that includes a RET kinase domain and a fusion partner. For example, a fusion protein can have increased kinase activity as compared to a wildtype RET protein. In some embodiments, a mutation in a RET gene can involve mutations in the RET ligand-binding site, extracellular domains, kinase domain, and in regions involved in protein:protein interactions and downstream signaling. In some embodiments, a mutation (e.g., an activating mutation) in a RET gene can result in the expression of a RET kinase having one or more (e.g., two, three, four, five, six, seven, eight, nine, or ten) amino acid substitutions (e.g., one or more amino acid substitutions in the kinase domain (e.g., amino acid positions 723 to 1012 in a wildtype RET protein), a gatekeeper amino acid (e.g., amino acid position 804 in a wildtype RET protein), the P-loop (e.g., amino acid positions 730-737 in a wildtype RET protein), the DFG motif (e.g., amino acid positions 892-894 in a wildtype RET protein), ATP cleft solvent front amino acids (e.g., amino acid positions 758, 811, and 892 in a wildtype RET protein), the activation loop (e.g., amino acid positions 891-916 in a wildtype RET protein), the C-helix and loop preceeding the C-helix (e.g., amino acid positions 768-788 in a wildtype RET protein), and/or the ATP binding site (e.g., amino acid positions 730-733, 738, 756, 758, 804, 805, 807, 811, 881, and 892 in a wildtype RET protein). In some embodiments, a mutation can be a gene amplification of a RET gene. In some embodiments, a mutation (e.g., an activating mutation) in a RET gene can result in the expression of a RET kinase that lacks at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) as compared to a wildtype RET protein. In some embodiments, dyregulation of a RET kinase can be increased expression (e.g., increased levels) of a wildtype RET kinase in a mammalian cell due to aberrant cell signaling and/or dysregulated autocrine/paracrine signaling (e.g., as compared to a control non-cancerous cell). In some embodiments, a mutation (e.g., an activating mutation) in a RET gene can result in the expression of a RET kinase that has at least one amino acid (e.g., at least 2, at least 3, at least 4, at least 5, at least 6, at least 7, at least 8, at least 9, at least 10, at least 12, at least 14, at least 16, at least 18, at least 20, at least 25, at least 30, at least 35, at least 40, at least 45, or at least 50 amino acids) inserted as compared to a wildtype RET protein. In some embodiments, dyregulation of a RET kinase can be increased expression (e.g., increased levels) of a wildtype RET kinase in a mammalian cell (e.g., as compared to a control non-cancerous cell), e.g., due to aberrant cell signaling and/or dysregulated autocrine/paracrine signaling. Other dysregulations can include RET mRNA splice variants. In some embodiments, the wildtype RET protein is the exemplary wildtype RET protein described herein.

In some embodiments, the dysregulation of a RET gene, a RET kinase, or expression or activity or level of any of the same, includes overexpression of wild-type RET kinase (e.g., leading to autocrine activation). In some embodiments, the dysregulation of a RET gene, a RET kinase protein, or expression or activity or level of any of the same, includes overexpression, activation, amplification, or mutation in a chromosomal segment comprising the RET gene or a portion thereof, including, for example, the kinase domain portion, or a portion capable of exhibiting kinase activity.

In some embodiments, the dysregulation of a RET gene, a RET kinase protein, or expression or activity or level of any of the same, includes one or more chromosome translocations or inversions resulting in a RET gene fusion. In some embodiments, the dysregulation of a RET gene, a RET kinase protein, or expression or activity or level of any of the same, is a result of genetic translocations in which the expressed protein is a fusion protein containing residues from a non-RET partner protein, and includes a minimum of a functional RET kinase domain.

Non-limiting examples of RET fusion proteins are shown in Table 1.

TABLE 1

Exemplary RET Fusion Partners and Cancers

| Fusion Partner | Non-limiting Exemplary RET-Associated Cancer(s) |
|---|---|
| BCR | Chronic Myelomonocytic Leukemia (CMML) |
| CLIP1 | Adenocarcinoma |
| KIF5B | NSCLC, Ovarian Cancer, Spitzoid Neoplasms; Lung Adenocarcinoma[3, 4, 14, 28]; Adenosquamous Carcinomas[15] |
| CCDC6 (also called PTC1, D10S170, or H4) | NSCLC, Colon Cancer, Papillary Thyroid Cancer; Adenocarcinomas; Lung Adenocarcinoma; Metastatic Colorectal Cancer[5]; Adenosquamous Carcinomas[15], Breast Cancer[30] |
| PTC1ex9 (a novel CCDC6 rearrangement) | Metastatic papillary thyroid cancer[2] |
| NCOA4 (also called PTC3, ELE1, and RFG) | Papillary Thyroid Cancer[21], NSCLC, Colon Cancer, Salivary Gland Cancer, Metastatic Colorectal Cancer[5]; Lung Adenocarcinoma[15]; Adenosquamous Carcinomas[15] Diffuse Sclerosing Variant of Papillary Thyroid Cancer[16], Breast Cancer[30], Acinic Cell Carcinoma[32], Mammary Analog Secretory Carcinoma[33] |
| TRIM33 (also called PTC7 and RFG7) | NSCLC, Papillary Thyroid Cancer |
| ERC1 (also called ELKS) | Papillary Thyroid Cancer, Breast Cancer |
| FGFR1OP | CMML, Primary Myelofibrosis with secondary Acute Myeloid Leukemia |
| MBD1(also known as PCM1) | Papillary Thyroid Cancer |
| RAB61P2 | Papillary Thyroid Cancer |
| PRKAR1A (also called PTC2) | Papillary Thyroid Cancer |
| TRIM24 (also called PTC6) | Papillary Thyroid Cancer |
| KTN1 (also called PTC8 ) | Papillary Thyroid Cancer |
| GOLGA5 (also called PTC5) | Papillary Thyroid Cancer, Spitzoid Neoplasms |
| HOOK3 | Papillary Thyroid Cancer |
| KIAA1468 (also called PTC9 and RFG9) | Papillary Thyroid Cancer, Lung Adenocarcinoma[8, 12] |
| TRIM27 (also called RFP) | Papillary Thyroid Cancer |
| AKAP13 | Papillary Thyroid Cancer |
| FKBP15 | Papillary Thyroid Cancer |

TABLE 1-continued

Exemplary RET Fusion Partners and Cancers

| Fusion Partner | Non-limiting Exemplary RET-Associated Cancer(s) |
|---|---|
| SPECC1L | Papillary Thyroid Cancer; Thyroid Gland Carcinoma |
| TBL1XR1 | Papillary Thyroid Cancer; Thyroid Gland Carcinoma |
| CEP55 | Diffuse Gastric Cancer[7] |
| CUX1 | Lung Adenocarcinoma |
| ACBD5 | Papillary Thyroid Carcinoma |
| MYH13 | Medullary Thyroid Carcinoma[1] |
| Uncharacterized | Inflammatory Myofibroblastic Tumor[6] |
| PIBF1 | Bronchiolus Lung Cell Carcinoma[9] |
| KIAA1217 (also called SKT) | Papillary Thyroid Cancer[10, 13] Lung Adenocarcinoma[14] NSCLC[14] |
| MPRIP | NSCLC[11] |
| HRH4-RET | Thyroid Cancer and/or Paillary Thyroid Carcinoma[17] |
| Ria-RET | Thyroid Cancer and/or Papillary Thyroid Carcinoma[17] |
| RFG8 | Papillary Thyroid Carcinoma[18] |
| FOXP4 | Lung Adenocarcinoma[19] |
| MYH10 | Infantile Myofibromatosis[20] |
| HTIF1 | Various[22] |
| TIF1G | Various[22] |
| H4L | Various[22] |
| PTC4 (a novel NCO4/ELE1 rearrangement) | Papillary Thyroid Cancer[23] |
| FRMD4A | NSCLC[24] |
| SQSTM1 | Papillary Thyroid Carcinoma[25] |
| AFAP1L2 | Papillary Thyroid Carcinoma[25] |
| AFAP1 | NSCLC[31] |
| PPFIBP2 | Papillary Thyroid Carcinoma[25] |
| EML4 | Papillary Thyroid Cancer[26] |
| PARD3 | NSCLC[27] |
| UVELD | Papillary Thyroid Cancer[29] |
| RASGEF1A | Breast Cancer[30] |
| TEL | In vitro[34] |
| RUFY1 | Colorectal Cancer[35] |
| OLFM4 | Small-Bowel Cancer[36] |
| UEVLD | Papillary Thyroid Carcinoma[29] |
| DLG5 | Non-Anaplastic Thyroid (NAT) Cancer[37] |
| RRBP1 | Colon Cancer[38] |
| ETV6 | Secretory Carcinoma[39] |

[1]Grubbs et al., *J. Clin. Endocrinol. Metab.* 100: 788-793, 2015.
[2]Halkova et al., *Human Pathology* 46: 1962-1969, 2015.
[3]U.S. Pat. No. 9,297,011
[4]U.S. Pat. No. 9,216,172
[5]Le Rolle et al., *Oncotarget.* 6(30): 28929-37, 2015.
[6]Antonescu et al., *Am J Surg Pathol.* 39(7): 957-67, 2015.
[7]U.S. Patent Application Publication No. 2015/0177246.
8U.S. Patent Application Publication No. 2015/0057335.
[9]Japanese Patent Application Publication No. 2015/109806A.
[10]Chinese Patent Application Publication No. 105255927A.
[11]Fang, et al. *Journal of Thoracic Oncology* 11.2 (2016): S21-S22.
[12]European Patent Application Publication No. EP3037547A1.
[13]Lee et al., *Oncotarget.* DOT: 10.18632/oncotarget.9137, e-published ahead of printing, 2016.
[14]Saito et al., *Cancer Science* 107: 713-720, 2016.
[15]Pirker et al., *Transl. Lung Cancer Res.* 4(6): 797-800, 2015.
[16]Joung et al., *Histopathology* 69(1): 45-53, 2016.
[17]PCT Patent Application Publication No. WO 2016/141169.
[18]Klugbauer et al., *Cancer Res.*, 60(24): 7028-32, 2000.

TABLE 1-continued

| Exemplary RET Fusion Partners and Cancers | |
|---|---|
| Fusion Partner | Non-limiting Exemplary RET-Associated Cancer(s) |

[19]Bastien et al., *Journal of Molecular Diagnostics*, 18(6): 1027, Abstract Number: S120, 2016 Annual Meeting of the Association for Molecular Pathology, Charlotte, NC, 2016.
[20]Rosenzweig et al., *Pediatr Blood Cancer*, doi: 10.1002/pbc.26377, 2016.
[21]Su et al., *PLoS One*, 11(111): e0165596, 2016.
[22]U.S. Pat. No. 9,487,491.
[23]Fugazzola et al., *Oncogene*, 13(5): 1093-7, 1996.
[24]Velcheti et al., *J Thorac Oncol.*, 12(2): e15-e16. doi: 10.1016/j.jtho.2016.11.274, 2017.
[25]Iyama et al., *Thyroid*, doi: 10.1089/thy.2016.0673, 2017.
[26]Demeure et al., *World J Surg*. 38(6): 1296-305. doi: 10.1007/s00268-014-2485-3, 2014.
[27]Sabari et al., *Oncoscience*, Advance Publications, www.impactjournals.com/oncoscience/files/papers/1/345/345.pdf, 2017.
[28]U.S. Patent Application Publication No. 2017/0014413.
[29]Lu et al., Oncotarget, 8(28): 45784-45792, doi: 10.18632/oncotarget.17412, 2017.
[30]Hirshfield et al., *Cancer Research*, (February 2017) Vol. 77, No. 4, Supp. 1. Abstract Number: P3-07-02. Meeting Info: 39th Annual CTRC-AACR San Antonio Breast Cancer Symposium. San Antonio, TX, United States. 6 Dec. 2016-10 Dec. 2016.
[31]Morgensztern et al., *Journal of Thoracic Oncology*, (January 2017) Vol. 12, No. 1, Supp. 1, pp. S717-S718, Abstract Number: P1.07-035, Meeting Info: 17th World Conference of the International Association for the Study of Lung Cancer, IASLC 2016. Vienna, Austria. 4 Dec. 2016.
[32]Dogan et al., *Laboratory Investigation*, (February 2017) Vol. 97, Supp. 1, pp. 323A. Abstract Number: 1298, Meeting Info: 106th Annual Meeting of the United States and Canadian Academy of Pathology, USCAP 2017. San Antonio, TX, United States.
[33]Dogan et al., MODERN PATHOLOGY, Vol. 30, Supp. [2], pp. 323A-323A. MA 1298, 2017.
[34]PCT Patent Application Publication No. WO 2017/146116.
[35]PCT Patent Application Publication No. WO 2017/122815.
[36]Reeser et al., *J. Mol. Diagn.*, 19(5): 682-696, doi: 10.1016/j.jmoldx.2017.05.006, 2017.
[37]Ibrahimpasic et al., *Clin. Cancer Res.*, doi: 10.1158/1078-0432.CCR-17-1183, 2017.
[38]Kloosterman et al., *Cancer Res.*, 77(14): 3814-3822. doi: 10.1158/0008-5472.CAN-16-3563, 2017.
[39]Skalova et al., *Am. J. Surg. Pathol.*, 42(2): 234-246 (2018). doi: 10.1097/PAS.0000000000000972

In some embodiments, the dysregulation of a RET gene, a RET kinase, or expression or activity or level of any of the same, includes one or more deletions (e.g., deletion of an amino acid at position 4), insertions, or point mutation(s) in a RET kinase. In some embodiments, the dysregulation of a RET gene, a RET kinase, or expression or activity or level of any of the same, includes a deletion of one or more residues from the RET kinase, resulting in constitutive activity of the RET kinase domain.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2).

TABLE 2

| Activating RET Kinase Protein Amino Acid Substitutions/Insertions/Deletions Exemplary RET Amino Acid Substitutions[A] |
|---|
| Amino acid position 2 |
| Amino acid position 3 |
| Amino acid position 4 |
| Amino acid position 5 |
| Amino acid position 6 |
| Amino acid position 7 |
| Amino acid position 8 |
| Amino acid position 11 |
| Amino acid position 12 |
| Amino acid position 13 |
| Amino acid position 20 |
| Amino acid position 32 (e.g., S32L) |
| Amino acid position 34 (e.g., D34S) |
| Amino acid position 40 (e.g., L40P) |
| Amino acid position 56 (e.g., L56M)[30] |
| Amino acid position 64 (e.g., P64L) |
| Amino acid position 67 (e.g., R67H) |

TABLE 2-continued

| Activating RET Kinase Protein Amino Acid Substitutions/Insertions/Deletions Exemplary RET Amino Acid Substitutions[A] |
|---|
| Amino acid position 114 (e.g., R114H) |
| Amino acid position 136 (e.g., glutamic acid to stop codon) |
| Amino acid position 145 (e.g., V145G) |
| Amino acid position 180 (e.g., arginine to stop codon) |
| Amino acid position 200 |
| Amino acid position 292 (e.g., V292M) |
| Amino acid position 294 |
| Amino acid position 321 (e.g., G321R) |
| Amino acid position 330 (e.g., R330Q) |
| Amino acid position 338 (e.g., T338I) |
| Amino acid position 360 (e.g., R360W) |
| Amino acid position 373 (e.g., alanine to frameshift) |
| Amino acid position 393 (e.g., F393L) |
| Amino acid position 423 (e.g., G423R)[27] |
| Amino acid position 432 |
| Amino acid position 446 (e.g., G446R)[28] |
| Δ Amino acid residues 505-506 (6-Base Pair In-Frame Germline Deletion in Exon 7)[3] |
| Amino acid position 510 (e.g., A510V) |
| Amino acid position 511 (e.g., E511K) |
| Amino acid position 513 (e.g., G513D)[7*] |
| Amino acid position 515 (e.g., C515S, C515W[4]) |
| Amino acid position 525 (e.g., R525W)[7*] |
| Amino acid position 531 (e.g., C531R, or 9 base pair duplication[2]) |
| Amino acid position 532 (e.g., duplication)[2] |
| Amino acid position 533 (e.g., G533C, G533S) |
| Amino acid position 550 (e.g., G550E) |
| Amino acid position 591 (e.g., V591I) |
| Amino acid position 593 (e.g., G593E) |
| Amino acid position 595 (e.g., E595D and E595A)[18] |
| Amino acid position 600 (e.g., R600Q) |
| Amino acid position 602 (e.g., I602V)[6] |
| Amino acid position 603 (e.g., K603Q, K603E[2]) |
| Amino acid position 606 (e.g., Y606C) |
| Amino acid position 609 (e.g., C609Y, C609S, C609G, C609R, C609F, C609W, C690C[32]) |
| Amino acid position 611 (e.g., C611R, C611S, C611G, C611Y, C611F, C611W) |
| Amino acid position 616 (e.g., E616Q)[23] |
| Amino acid position 618 (e.g., C618S, C618Y, C618R, C618Y, C618G, C618F, C618W) |
| Amino acid position 619 (e.g., F619F) |
| Amino acid position 620 (e.g., C620S, C620W, C620R, C620G, C620L, C620Y, C620F) |
| Amino acid position 623 (e.g., E623K) |
| Amino acid position 624 (e.g., D624N) |
| Amino acid position 630 (e.g., C630A, C630R, C630S, C630Y, C630F, C630W) |
| Amino acid position 631 (e.g., D631N, D631Y, D631A, D631G, D631V, D631E, ) |
| Amino acid position 632 (e.g., E632K, E632G[5, 11]) |
| Δ Amino acid residues 632-633 (6-Base Pair In-Frame Germline Deletion in Exon 11)[9] |
| Amino acid position 633 (e.g., 9 base pair duplication[2]) |
| Amino acid position 634 (e.g., C634W, C634Y, C634S, C634R, C634F, C634G, C634L, C634A, or C634T, or an insertion ELCR[2], or a 12 base pair duplication[2]) (e.g., causing MTC) |
| Amino acid position 635 (e.g., R635G) |
| Amino acid position 636 (e.g., T636P[2], T636M[4]) |
| Amino acid position 640 (e.g., A640G) |
| Amino acid position 641 (e.g., A641S, A641T[8]) |
| Amino acid position 648 (e.g., V648I) |
| Amino acid position 649 (e.g., S649L)[28] |
| Amino acid position 664 (e.g., A664D) |
| Amino acid position 665 (e.g., H665Q) |
| Amino acid position 666 (e.g., K666E, K666M, K666N, K666R) |
| Amino acid position 675 (T675T, silent nucleotide change)[18] |
| Amino acid position 686 (e.g., S686N) |
| Amino acid position 689 (e.g., S689T)[18] |
| Amino acid position 691 (e.g., G691S) |
| Amino acid position 694 (e.g., R694Q) |

TABLE 2-continued

| Activating RET Kinase Protein Amino Acid Substitutions/Insertions/Deletions Exemplary RET Amino Acid Substitutions[4] |
|---|
| Amino acid position 700 (e.g., M700L) |
| Amino acid position 706 (e.g., V706M, V706A) |
| Amino acid position 713 splice variant (e.g., E713K)[6] |
| Amino acid position 732 (e.g., E732K)[20] |
| Amino acid position 736 (e.g., G736R)[6] |
| Amino acid position 748 (e.g., G748C) |
| Amino acid position 750 (e.g., A750P) |
| Amino acid position 765 (e.g., S765P) |
| Amino acid position 766 (e.g., P766S, P766M[6]) |
| Amino acid position 768 (e.g., E768Q, E768D) |
| Amino acid position 769 (e.g., L769L) |
| Amino acid position 770 (e.g., R770Q) |
| Amino acid position 771 (e.g., D771N) |
| Amino acid position 777 (e.g., N777S) |
| Amino acid position 778 (e.g., V778I) |
| Amino acid position 781 (e.g., Q781R) |
| Amino acid position 788 (e.g., I788I[32]) |
| Amino acid position 790 (e.g., L790F) |
| Amino acid position 791 (e.g., Y791F, Y791N[24]) |
| Amino acid position 802 |
| Amino acid position 804 (e.g., V804L[15, 16], V804M[15, 16], V804E[12]) (e.g., causing MTC) |
| Amino acid position 805 (e.g., E805K) |
| Amino acid position 804/805 (e.g., V804M/E805K)[17] |
| Amino acid position 806 (e.g., Y806F, Y806S[12], Y806G, Y806C[2, 12, 14], Y806E[14], Y806H[12], Y806N[12], Y806Y[32]) |
| Amino acid position 810 (e.g., G810R[12], G810S[12], G810A[13]) |
| Amino acid position 818 (e.g., E818K) |
| Amino acid position 819 (e.g., S819I) |
| Amino acid position 823 (e.g., G823E) |
| Amino acid position 826 (e.g., Y826M, Y826S)[10] |
| Amino acid position 833 (e.g., R833C) |
| Amino acid position 836 (e.g., S836S)[19] |
| Amino acid position 841 (e.g., P841L, P841P) |
| Amino acid position 843 (e.g., E843D) |
| Amino acid position 844 (e.g., R844W, R844Q, R844L) |
| Amino acid position 848 (e.g., M848T) |
| Amino acid position 852 (e.g., I852M) |
| Amino acid position 865 (e.g., L865V)[12] |
| Amino acid position 866 (e.g., A866W)[33] |
| Amino acid position 870 (e.g., L870F)[12] |
| Amino acid position 873 (e.g., R873W) |
| Amino acid position 876 (e.g., A876V) |
| Amino acid position 881 (e.g., L881V) |
| Amino acid position 882 |
| Amino acid position 883 (e.g., A883F, A883S, A883T) |
| Amino acid position 884 (e.g., E884K) |
| Amino acid position 886 (e.g., R886W) |
| Amino acid position 891 (e.g., S891A, S891S[32]) |
| Amino acid position 897 (e.g., R897Q) |
| Amino acid position 898 (e.g., D898V) |
| Amino acid position 900 (e.g., Y900F)[22] |
| Amino acid position 901 (e.g., E901K) |
| Amino acid position 904 (e.g., S904F, S904S, S904C[2]) |
| Amino acid position 905 (e.g., Y905F)[22] |
| Amino acid position 907 (e.g., K907E, K907M) |
| Amino acid position 908 (e.g., R908K) |
| Amino acid position 911 (e.g., G911D) |
| Amino acid position 912 (e.g., R912P, R912Q) |
| Amino acid position 918 (e.g., M918T[2], M918V, M918L[6]) (e.g., causing MTC) |
| Amino acid position 919 (e.g., A919V) |
| Amino acid position 921 (e.g., E921K) |
| Amino acid position 922 (e.g., S922P, S922Y) |
| Amino acid position 930 (e.g., T930M) |
| Amino acid position 961 (e.g., F961L) |
| Amino acid position 972 (e.g., R972G) |
| Amino acid position 981 (e.g., Y981F)[22] |
| Amino acid position 982 (e.g., R982C) |
| Amino acid position 1009 (e.g., M1009V) |
| Amino acid position 1015 (e.g., Y1015F)[22] |
| Amino acid position 1017 (e.g., D1017N) |
| Amino acid position 1041 (e.g., V1041G) |
| Amino acid position 1064 (e.g., M1064T) |
| Amino acid position 1096 (e.g., Y1096F)[21] |
| Amino acid position 1109 (e.g., M1109T)[34] |
| RET + 3[1] |
| (In-Frame Deletion in Exons 6 and 11)[25] |
| (3 bp In-Frame Deletion in Exon 15)[26] |
| Nucleotide position 2136 + 2 (e.g., 2136 + 2T > G)[29] |
| (del632-636 ins6)[31] |
| Amino acid positions 791 and 852 (e.g., Y791F + I852M)[31] |
| Amino acid positions 634 and 852 (e.g., C634R + I852M)[31] |

[4]The RET kinase mutations shown may be activating mutations and/or confer increased resistance of the RET kinase to a RET kinase inhibitor and/or a multi-kinase inhibitor (MKI), e.g., as compared to a wildtype RET kinase.

[1]U.S. Patent Application Publication No. 2014/0272951.

[2]Krampitz et al., *Cancer* 120: 1920-1931, 2014.

[3]Latteyer, et al., *J. Clin. Endocrinol. Metab.* 101(3): 1016-22, 2016.

[4]Silva, et al. Endocrine 49.2: 366-372, 2015.

[5]Scollo, et al., *Endocr.* J. 63(1): 87-91, 2016.

[6]Jovanovic, et al., *Prilozi* 36(1): 93-107, 2015.

[7]Qi, et al., *Oncotarget.* 6(32): 33993-4003, 2015. *R525W and G513D appear to act in combination with S891A to enchance oncogenic activity.

[8]Kim, et al. ACTA ENDOCRINOLOGICA-BUCHAREST 11.2, 189-194, 2015.

[9]Cecchirini, et al. *Oncogene*, 14, 2609-2612, 1997.

[10]Karrasch, et al. *Eur. Thyroid J.* 5(1): 73-7, 2016.

[11]Scollo et al., *Endocr. J.* 63: 87-91, 2016.

[12]PCT Patent Application Publication No. WO 2016/127074.

[13]Huang et al., Mol. Cancer Ther., 2016 Aug. 5. pii: molcanther.0258.2016. [Epub ahead of print].

[14]Carlomagno, et al., *Endocr. Rel. Cancer* 16(1): 233-41, 2009.

[15]Yoon et al., *J. Med. Chem.* 59(1): 358-73, 2016.

[16]U.S. Pat. No. 8,629,135.

[17]Cranston, et al., *Cancer Res.* 66(20): 10179-87, 2006.

[18]Kheiroddin et al., *Clin. Lab.* 62(5): 871-6, 2016.

[19]Ceolin et al., PLoS One. 11(2): e0147840, doi: 10.1371/journal.pone.0147840, 2016.

[20]Mamedova et al., Summer Undergraduate Research Programs (SURP) Student Abstracts, University of Oklahoma Health Sciences Center, 2016.

[21]Liu et al., *J. Biol. Chem.*, 271(10): 5309-12, 1995.

[22]Kato et al., *Cancer Res.*, 62: 2414-22, 2002.

[23]Grey et al., *Endocrine Pathology*, doi: 10.1007/s12022-016-9451-6, 2016.

[24]De Almeida et al., *Endocrine Reviews*, 2016, Vol. 37, No. 2, Supp. Supplement 1. Abstract Number: SUN-068; 98th Annual Meeting and Expo of the Endocrine Society, ENDO 2016. Boston, MA, US. 1 Apr. 2016-4 Apr. 2016.

[25]Vanden et al., *Annals of Oncology*, 2016, Vol. 27, Supp. Supplement 6. Abstract Number: 427PD; 41st European Society for Medical Oncology Congress, ESMP 2016. Copenhagen, Denmark. 7 Oct. 2016-11 Oct. 2016.

[26]Romei et al., *European Thyroid Journal* (August 2016) Vol. 5, Supp. Supplement 1, pp. 75; 39th Annual Meeting of the European Thyroid Association, ETA 2016. Copenhagen, Denmark. 3 Sep. 2016-6 Sep. 2016.

[27]Lee et al., *Oncotarget*, 8(4): 6579-6588, doi: 10.18632/oncotarget.14172, 2017.

[28]Zhang et al., *Laboratory Investigation*, (February 2017) Vol. 97, Supp. 1, pp. 209A. Abstract Number: 840, Meeting Info: 106th Annual Meeting of the United States and Canadian Academy of Pathology, USCAP 2017. San Antonio, TX, United States.

[29]Borecka et al., *European Journal of Cancer*, (July 2016) Vol. 61, No. 1, pp. S26, Abstract Number: 162, Meeting Info: 24th Biennial Congress of the European Association for Cancer Research, EACR 2016. Manchester, United Kingdom.

[30]Corsello et al., *Endocrine Reviews*, (June 2014) Vol. 35, No. 3, Suppl. S, pp. SUN-0322, Meeting Info.: 96th Annual Meeting and Expo of the Endocrine-Society, Chicago, IL, USA, Jun. 21-24, 2014.

31Gazizova et al., *Endocrine Reviews*, (June 2014) Vol. 35, No. 3, Suppl. S, pp. SAT-0304, Meeting Info.: 96th Annual Meeting and Expo of the Endocrine-Society, Chicago, IL, USA, Jun. 21-24, 2014.

[32]Sromek et al., *Endocr Pathol.*, doi: 10.1007/s12022-017-9487-2, 2017.

[33]U.S. Patent Application Publication No. 2017/0267661.

[34]Davila et. al., *Rare Tumors*, 2017; 9(2): 6834. doi: 10.4081/rt.2017.6834.

In some embodiments, the dysregulation of a RET gene, a RET kinase, or expression or activity or level of any of the same, includes at least one point mutation in a RET gene that results in the production of a RET kinase that has one or more amino acid substitutions, insertions, or deletions as compared to the wild-type RET kinase (see, for example, the point mutations listed in Table 2a).

TABLE 2a

| Exemplary RET Kinase Protein Point Mutations/Insertions/Deletions Exemplary RET Point Mutations[A] |
| --- |
| Amino acid position 20 |
| Amino acid position 32 (e.g., S32L) |
| Amino acid position 34 (e.g., D34S) |
| Amino acid position 40 (e.g., L40P) |
| Amino acid position 64 (e.g., P64L) |
| Amino acid position 67 (e.g., R67H) |
| Amino acid position 114 (e.g., R114H) |
| Amino acid position 145 (e.g., V145G) |
| Amino acid position 200 |
| Amino acid position 292 (e.g., V292M) |
| Amino acid position 294 |
| Amino acid position 321 (e.g., G321R) |
| Amino acid position 330 (e.g., R330Q) |
| Amino acid position 338 (e.g., T338I) |
| Amino acid position 360 (e.g., R360W) |
| Amino acid position 393 (e.g., F393L) |
| Amino acid position 432 |
| Δ Amino acid residues 505-506 (6-Base Pair In-Frame Germline Deletion in Exon 7) |
| Amino acid position 510 (e.g., A510V) |
| Amino acid position 511 (e.g., E511K) |
| Amino acid position 513 (e.g., G513D) |
| Amino acid position 515 (e.g., C515S, C515W[4]) |
| Amino acid position 525 (e.g., R525W) |
| Amino acid position 531 (e.g., C531R, or 9 base pair duplication) |
| Amino acid position 532 (e.g., duplication) |
| Amino acid position 533 (e.g., G533C, G533S) |
| Amino acid position 550 (e.g., G550E) |
| Amino acid position 591 (e.g., V591I) |
| Amino acid position 593 (e.g., G593E) |
| Amino acid position 595 (e.g., E595D and E595A) |
| Amino acid position 600 (e.g., R600Q) |
| Amino acid position 602 (e.g., I602V) |
| Amino acid position 603 (e.g., K603Q, K603E) |
| Amino acid position 606 (e.g., Y606C) |
| Amino acid position 609 (e.g., C609Y, C609S, C609G, C609R, C609F, C609W) |
| Amino acid position 611 (e.g., C611R, C611S, C611G, C611Y, C611F, C611W) |
| Amino acid position 616 (e.g., E616Q) |
| Amino acid position 618 (e.g., C618S, C618Y, C618R, C618G, C618F, C618W) |
| Amino acid position 620 (e.g., C620S, C620W, C620R, C620G, C620L, C620Y, C620F) |
| Amino acid position 623 (e.g., E623K) |
| Amino acid position 624 (e.g., D624N) |
| Amino acid position 630 (e.g., C630A, C630R, C630S, C630Y, C630F, C630W) |
| Amino acid position 631 (e.g., D631N, D631Y, D631A, D631G, D631V, D631E,) |
| Amino acid position 632 (e.g., E632K, E632G) |
| Δ Amino acid residues 632-633 (6-Base Pair In-Frame Germline Deletion in Exon 11) |
| Amino acid position 633 (e.g., 9 base pair duplication) |
| Amino acid position 634 (e.g., C634W, C634Y, C634S, C634R, C634F, C634G, C634L, C634A, or C634T, or an insertion ELCR, or a 12 base pair duplication) (e.g., causing MTC) |
| Amino acid position 635 (e.g., R635G) |
| Amino acid position 636 (e.g., T636P, T636M) |
| Amino acid position 640 (e.g., A640G) |
| Amino acid position 641 (e.g., A641S, A641T) |
| Amino acid position 648 (e.g., V648I) |
| Amino acid position 649 (e.g., S649L) |
| Amino acid position 664 (e.g., A664D) |
| Amino acid position 665 (e.g., H665Q) |
| Amino acid position 666 (e.g., K666E, K666M, K666N, K666R) |
| Amino acid position 686 (e.g., S686N) |
| Amino acid position 689 (e.g., S689T) |
| Amino acid position 691 (e.g., G691S) |
| Amino acid position 694 (e.g., R694Q) |
| Amino acid position 700 (e.g., M700L) |
| Amino acid position 706 (e.g., V706M, V706A) |
| Amino acid position 713 splice variant (e.g., E713K) |

TABLE 2a-continued

| Exemplary RET Kinase Protein Point Mutations/Insertions/Deletions Exemplary RET Point Mutations[A] |
| --- |
| Amino acid position 732 (e.g., E732K) |
| Amino acid position 736 (e.g., G736R) |
| Amino acid position 748 (e.g., G748C) |
| Amino acid position 750 (e.g., A750P) |
| Amino acid position 765 (e.g., S765P) |
| Amino acid position 766 (e.g., P766S, P766M) |
| Amino acid position 768 (e.g., E768Q, E768D) |
| Amino acid position 769 (e.g., L769L) |
| Amino acid position 770 (e.g., R770Q) |
| Amino acid position 771 (e.g., D771N) |
| Amino acid position 777 (e.g., N777S) |
| Amino acid position 778 (e.g., V778I) |
| Amino acid position 781 (e.g., Q781R) |
| Amino acid position 790 (e.g., L790F) |
| Amino acid position 791 (e.g., Y791F, Y791N) |
| Amino acid position 802 |
| Amino acid position 804 (e.g., V804L, V804M, V804E) (e.g., causing MTC) |
| Amino acid position 805 (e.g., E805K) |
| Amino acid position 804/805 (e.g., V804M/E805K) |
| Amino acid position 806 (e.g., Y806F, Y806S, Y806G, Y806C, Y806E, Y806H, Y806N) |
| Amino acid position 810 (e.g., G810R, G810S, G810A) |
| Amino acid position 818 (e.g., E818K) |
| Amino acid position 819 (e.g., S819I) |
| Amino acid position 823 (e.g., G823E) |
| Amino acid position 826 (e.g., Y826M, Y826S) |
| Amino acid position 833 (e.g., R833C) |
| Amino acid position 836 (e.g., S836S) |
| Amino acid position 841 (e.g., P841L, P841P) |
| Amino acid position 843 (e.g., E843D) |
| Amino acid position 844 (e.g., R844W, R844Q, R844L) |
| Amino acid position 848 (e.g., M848T) |
| Amino acid position 852 (e.g., I852M) |
| Amino acid position 865 (e.g., L865V) |
| Amino acid position 870 (e.g., L870F) |
| Amino acid position 873 (e.g., R873W) |
| Amino acid position 876 (e.g., A876V) |
| Amino acid position 881 (e.g., L881V) |
| Amino acid position 882 |
| Amino acid position 883 (e.g., A883F, A883S, A883T) |
| Amino acid position 884 (e.g., E884K) |
| Amino acid position 886 (e.g., R886W) |
| Amino acid position 891 (e.g., S891A) |
| Amino acid position 897 (e.g., R897Q) |
| Amino acid position 898 (e.g., D898V) |
| Amino acid position 900 (e.g., Y900F) |
| Amino acid position 901 (e.g., E901K) |
| Amino acid position 904 (e.g., S904F, S904S, S904C) |
| Amino acid position 907 (e.g., K907E, K907M) |
| Amino acid position 908 (e.g., R908K) |
| Amino acid position 911 (e.g., G911D) |
| Amino acid position 912 (e.g., R912P, R912Q) |
| Amino acid position 918 (e.g., M918T, M918V, M918L) (e.g., causing MTC) |
| Amino acid position 919 (e.g., A919V) |
| Amino acid position 921 (e.g., E921K) |
| Amino acid position 922 (e.g., S922P, S922Y) |
| Amino acid position 930 (e.g., T930M) |
| Amino acid position 961 (e.g., F961L) |
| Amino acid position 972 (e.g., R972G) |
| Amino acid position 982 (e.g., R982C) |
| Amino acid position 1009 (e.g., M1009V) |
| Amino acid position 1015 (e.g., Y1015F) |
| Amino acid position 1017 (e.g., D1017N) |
| Amino acid position 1041 (e.g., V1041G) |
| Amino acid position 1064 (e.g., M1064T) |
| Amino acid position 1096 (e.g., Y1096F) |
| RET + 3 |

TABLE 2a-continued

| Exemplary RET Kinase Protein Point Mutations/Insertions/Deletions Exemplary RET Point Mutations[A] |
|---|
| (In-Frame Deletion in Exons 6 and 11) |
| (3bp In-Frame Deletion in Exon 15) |

[A]The RET kinase mutations shown above may be activating mutations and/or may confer increased resistance of the RET kinase to a RET inhibitor and/or a multi-kinase inhibitor (MKI), e.g., as compared to a wildtype RET kinase.

In some embodiments, the dysregulation of a RET gene, a RET kinase, or expression or activity or level of any of the same, includes a splice variation in a RET mRNA which results in an expressed protein that is an alternatively spliced variant of RET having at least one residue deleted (as compared to the wild-type RET kinase) resulting in a constitutive activity of a RET kinase domain.

A "RET kinase inhibitor" as defined herein includes any compound exhibiting RET inhibition activity. In some embodiments, a RET kinase inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitor can exhibit inhibition activity ($IC_{50}$) against a RET kinase of less than about 25 nM, less than about 10 nM, less than about 5 nM, or less than about 1 nM as measured in an assay as provided herein.

As used herein, a "first RET kinase inhibitor" or "first RET inhibitor" is a RET kinase inhibitor as defined herein, but which does not include a compound of Formula I or a pharmaceutically acceptable salt or solvate thereof as defined herein. As used herein, a "second RET kinase inhibitor" or a "second RET inhibitor" is a RET kinase inhibitor as defined herein, but which does not include a compound of Formula I or a pharmaceutically acceptable salt or solvate thereof as defined herein. When both a first and a second RET inhibitor are present in a method provided herein, the first and second RET kinase inhibitor are different.

In some embodiments, the dysregulation of a RET gene, a RET kinase, or expression or activity or level of any of the same, includes at least one point mutation in a RET gene that results in the production of a RET kinase that has one or more amino acid substitutions or insertions or deletions in a RET gene that results in the production of a RET kinase that has one or more amino acids inserted or removed, as compared to the wild-type RET kinase. In some cases, the resulting RET kinase is more resistant to inhibition of its phosphotransferase activity by one or more first RET kinase inhibitor(s), as compared to a wildtype RET kinase or a RET kinase not including the same mutation. Such mutations, optionally, do not decrease the sensitivity of the cancer cell or tumor having the RET kinase to treatment with a compound of Formula I or a pharmaceutically acceptable salt or solvate thereof (e.g., as compared to a cancer cell or a tumor that does not include the particular RET inhibitor resistance mutation). In such embodiments, a RET inhibitor resistance mutation can result in a RET kinase that has one or more of an increased $V_{max}$, a decreased $K_m$ for ATP, and an increased $K_D$ for a first RET kinase inhibitor, when in the presence of a first RET kinase inhibitor, as compared to a wildtype RET kinase or a RET kinase not having the same mutation in the presence of the same first RET kinase inhibitor.

In other embodiments, the dysregulation of a RET gene, a RET kinase, or expression or activity or level of any of the same, includes at least one point mutation in a RET gene that results in the production of a RET kinase that has one or more amino acid substitutions as compared to the wild-type RET kinase, and which has increased resistance to a compound of Formula I or a pharmaceutically acceptable salt or solvate thereof, as compared to a wildtype RET kinase or a RET kinase not including the same mutation. In such embodiments, a RET inhibitor resistance mutation can result in a RET kinase that has one or more of an increased $V_{max}$, a decreased $K_m$, and a decreased $K_D$ in the presence of a compound of Formula I or a pharmaceutically acceptable salt or solvate thereof, as compared to a wildtype RET kinase or a RET kinase not having the same mutation in the presence of the same compound of Formula I or a pharmaceutically acceptable salt or solvate thereof.

Examples of RET inhibitor resistance mutations can, e.g., include point mutations, insertions, or deletions in and near the ATP binding site in the tertiary structure of RET kinase (e.g., amino acid positions 730-733, 738, 756, 758, 804. 805, 807, 811, 881, and 892 of a wildtype RET kinase, e.g., the exemplary wildtype RET kinase described herein), including but not limited to a gatekeeper residue (e.g., amino acid position 804 in a wildtype RET kinase), P-loop residues (e.g., amino acid positions 730-737 in a wildtype RET kinase), residues in or near the DFG motif (e.g., amino acid positions 888-898 in a wildtype RET kinase), and ATP cleft solvent front amino acid residues (e.g., amino acid positions 758, 811, and 892 of a wildtype RET kinase). Additional examples of these types of mutations include changes in residues that may affect enzyme activity and/or drug binding including but are not limited to residues in the activation loop (e.g., amino acid positions 891-916 of a wildtype RET kinase), residues near or interacting with the activation loop, residues contributing to active or inactive enzyme conformations, changes including mutations, deletions, and insertions in the loop proceeding the C-helix and in the C-helix (e.g., amino acid positions 768-788 in a wildtype RET protein). In some embodiments, the wildtype RET protein is the exemplary wildtype RET kinase described herein. Specific residues or residue regions that may be changed (and are RET inhibitor resistance mutations) include but are not limited to those listed in Table 3, with numbering based on the human wildtype RET protein sequence (e.g., SEQ ID NO: 1). As can be appreciated by those skilled in the art, an amino acid position in a reference protein sequence that corresponds to a specific amino acid position in SEQ ID NO: 1 can be determined by aligning the reference protein sequence with SEQ ID NO: 1 (e.g., using a software program, such as ClustalW2). Additional examples of RET inhibitor resistance mutation positions are shown in Table 4. Changes to these residues may include single or multiple amino acid changes, insertions within or flanking the sequences, and deletions within or flanking the sequences. See also J. Kooistra, G. K. Kanev, O. P. J. Van Linden, R. Leurs, I. J. P. De Esch, and C. De Graaf, "KLIFS: A structural kinase-ligand interaction database," *Nucleic Acids Res*., vol. 44, no. D1, pp. D365-D371, 2016, which is incorporated by reference in its entirety herein.

Exemplary Sequence of Mature Human RET Protein (SEQ ID NO: 1)

```
MAKATSGAAG LRLLLLLLLP LLGKVALGLY FSRDAYWEKL YVDQAAGTPL LYVHALRDAP EEVPSFRLGQ

HLYGTYRTRL HENNWICIQE DTGLLYLNRS LDHSSWEKLS VRNRGFPLLT VYLKVFLSPT SLREGECQWP

GCARVYFSFF NTSFPACSSL KPRELCFPET RPSFRIRENR PPGTFHQFRL LPVQFLCPNI SVAYRLLEGE

GLPFRCAPDS LEVSTRWALD REQREKYELV AVCTVHAGAR EEVVMVPFPV TVYDEDDSAP TFPAGVDTAS

AVVEFKRKED TVVATLRVFD ADVVPASGEL VRRYTSTLLP GDTWAQQTFR VEHWPNETSV QANGSFVRAT

VHDYRLVLNR NLSISENRTM QLAVLVNDSD FQGPGAGVLL LHFNVSVLPV SLHLPSTYSL SVSRRARRFA

QIGKVCVENC QAFSGINVQY KLHSSGANCS TLGVVTSAED TSGILFVNDT KALRRPKCAE LHYMVVATDQ

QTSRQAQAQL LVTVEGSYVA EEAGCPLSCA VSKRRLECEE CGGLGSPTGR CEWRQGDGKG ITRNFSTCSP

STKTCPDGHC DVVETQDINI CPQDCLRGSI VGGHEPGEPR GIKAGYGTCN CFPEEEKCFC EPEDIQDPLC

DELCRTVIAA AVLFSFIVSV LLSAFCIHCY HKFAHKPPIS SAEMTFRRPA QAFPVSYSSS GARRPSLDSM

ENQVSVDAFK ILEDPKWEFP RKNLVLGKTL GEGEFGKVVK ATAFHLKGRA GYTTVAVKML KENASPSELR

DLLSEFNVLK QVNHPHVIKL YGACSQDGPL LLIVEYAKYG SLRGFLRESR KVGPGYLGSG GSRNSSSLDH

PDERALTMGD LISFAWQISQ GMQYLAEMKL VHRDLAARNI LVAEGRKMKI SDFGLSRDVY EEDSYVKRSQ

GRIPVKWMAI ESLFDHIYTT QSDVWSFGVL LWEIVTLGGN PYPGIPPERL FNLLKTGHRM ERPDNCSEEM

YRLMLQCWKQ EPDKRPVFAD ISKDLEKMMV KRRDYLDLAA STPSDSLIYD DGLSEEETPL VDCNNAPLPR

ALPSTWIENK LYGMSDPNWP GESPVPLTRA DGTNTGFPRY PNDSVYANWM LSPSAAKLMD TFDS
```

In some embodiments, compounds of Formula I and pharmaceutically acceptable salts and solvates are useful in treating patients that develop cancers with RET inhibitor resistance mutations (e.g., that result in an increased resistance to a first RET inhibitor, e.g., a substitution at amino acid position 804, e.g., V804M, V804L, or V804E, and/or one or more RET inhibitor resistance mutations listed in Tables 3 and 4) by either dosing in combination or as a subsequent or additional (e.g., follow-up) therapy to existing drug treatments (e.g., other RET kinase inhibitors; e.g., first and/or second RET kinase inhibitors). Exemplary first and second RET kinase inhibitors are described herein. In some embodiments, a first or second RET kinase inhibitor can be selected from the group consisting of cabozantinib, vandetanib, alectinib, apatinib, sitravatinib, sorafenib, lenvatinib, ponatinib, dovitinib, sunitinib, foretinib, LOXO-292, BLU667, and BLU6864.

In some embodiments, compounds of Formula I or pharmaceutically acceptable salts and solvates thereof are useful for treating a cancer that has been identified as having one or more RET inhibitor resistance mutations (that result in an increased resistance to a first or second RET inhibitor, e.g., a substitution at amino acid position 804, e.g., V804M, V804L, or V804E). Non-limiting examples of RET inhibitor resistance mutations are listed in Tables 3 and 4.

TABLE 3

| RET Inhibitor Resistance Mutations<br>Exemplary RET Resistance Mutations |
|---|
| Amino acid position 732 (e.g., E732K)[7] |
| Amino acid position 788 (e.g., I788N)[8] |
| Amino acid position 790 (e.g., L790F)[9] |
| Amino acid position 804 (e.g., V804M[1, 2], V804L[1, 2], V804E[6]) |
| Amino acid position 804/805 (e.g., V804M/E805K)[3] |
| Amino acid position 806 (e.g., Y806C[4, 6], Y806E[4], Y806S[6], Y806H[6], Y806N[6]) |
| Amino acid position 810 (e.g., G810A[5], G810R[6], G810S[6]) |

TABLE 3-continued

| RET Inhibitor Resistance Mutations<br>Exemplary RET Resistance Mutations |
|---|
| Amino acid position 865 (e.g., L865V[6]) |
| Amino acid position 870 (e.g., L870F[6]) |

[1]Yoon et al., *J. Med. Chem.* 59(1): 358-73, 2016.
[2]U.S. Pat. No. 8,629,135.
[3]Cranston, et al., *Cancer Res.* 66(20): 10179-87, 2006.
[4]Carlomagno, et al., *Endocr. Rel. Cancer* 16(1): 233-41, 2009.
[5]Huang et al., Mol. Cancer Ther., 2016 Aug. 5. pii: molcanther.0258.2016. [Epub ahead of print].
[6]PCT Patent Application Publication No. WO 2016/127074.
[7]Mamedova et al., Summer Undergraduate Research Programs (SURP) Student Abstracts, University of Oklahoma Health Sciences Center, 2016.
[8]Plenker et al., *Sci. Transl. Med.*, 9(394), doi: 10.1126/scitranslmed.aah6144, 2017.
[9]Kraft et al, *Cancer Research*, 2017, Vol. 77, No. 13, Supp. Supplement 1. Abstract Number: 4882; American Association for Cancer Research Annual Meeting 2017. Washington, DC, United States. 01 Apr. 2017-05 Apr. 2017.

TABLE 4

Additional Exemplary Amino Acid Positions of RET Inhibitor Resistance Mutations

| RET Amino Acid and Position | Exemplary Mutation | Mechanistic Resistance Rationale |
|---|---|---|
| L730 | P | Steric hindrance and/or active conformational effect |
| G731 | V | Steric hindrance and/or active conformational effect |
| E732 | K | Steric hindrance and/or active conformational effect |
| G733 | V | Steric hindrance and/or active conformational effect |
| E734 | K | Steric hindrance and/or active conformational effect |
| L760 | M | Active conformational effect |
| K761 | E | Active conformational effect |
| E762 | K | Active conformational effect |
| N763 | D | Active conformational effect |
| A764 | V | Active conformational effect |
| S765 | N | Active conformational effect |

TABLE 4-continued

Additional Exemplary Amino Acid Positions of RET Inhibitor Resistance Mutations

| RET Amino Acid and Position | Exemplary Mutation | Mechanistic Resistance Rationale |
|---|---|---|
| P766 | A | Active conformational effect |
| S767 | C | Active conformational effect |
| E768 | K | Active conformational effect |
| L779 | M | Steric hindrance and/or active conformational effect |
| I788 | M | Steric hindrance and/or active conformational effect |
| M868 | R | Steric hindrance and/or active conformational effect |
| K869 | E | Steric hindrance and/or active conformational effect |
| L870 | Q | Steric hindrance and/or active conformational effect |
| V871 | M | Steric hindrance and/or active conformational effect |
| H872 | R | Steric hindrance and/or active conformational effect |
| R873 | P | Steric hindrance and/or active conformational effect |
| D874 | Y | Steric hindrance and/or active conformational effect |
| L881 | R | Steric hindrance and/or active conformational effect |
| L895 | M | Active conformational effect |
| S896 | N | Active conformational effect |
| R897 | C | Active conformational effect |
| D898 | Y | Active conformational effect |
| V899 | G | Active conformational effect |
| Y900 | D | Active conformational effect |
| E901 | K | Active conformational effect |
| E902 | K | Active conformational effect |
| D903 | Y | Active conformational effect |
| S904 | C | Active conformational effect |
| Y905 | D | Active conformational effect |
| V906 | M | Active conformational effect |
| K907 | E | Active conformational effect |
| R908 | P | Active conformational effect |
| S909 | C | Active conformational effect |
| Q910 | R | Active conformational effect |
| G911 | C | Active conformational effect |
| R912 | P | Active conformational effect |

The oncogenic role of RET was firstly described in papillary thyroid carcinoma (PTC) (Grieco et al., *Cell,* 1990, 60, 557-63), which arises from follicular thyroid cells and is the most common thyroid malignancy. Approximately 20-30% of PTC harbor somatic chromosomal rearrangements (translocations or inversions) linking the promoter and the 5' portions of constitutively expressed, unrelated genes to the RET tyrosine kinase domain (Greco et al., Q. *J. Nucl. Med. Mol. Imaging,* 2009, 53, 440-54), therefore driving its ectopic expression in thyroid cells. Fusion proteins generated by such rearrangements are termed "RET/PTC" proteins. For example, RET/PTC 1 is a fusion between CCDD6 and RET that is commonly found in papillary thyroid carcinomas. Similarly, both RET/PTC3 and RET/PTC4 are fusions of ELE1 and RET that are commonly found in papillary thyroid carcinomas, although the fusion events resulting RET/PTC3 and RET/PTC4 lead to different proteins with different molecular weights (see e.g., Fugazzola et al., *Oncogene,* 13(5):1093-7, 1996). Some RET fusions associated with PTC are not referred to as "RET/PTC", but instead are referred to as the fusion protein inself. For example, fusion between RET and both ELKS and PCM1 are found in PTCs, but the fusion proteins are referred to as ELKS-RET and PCM1-RET (see e.g., Romei and Elisei, *Front. Endocrinol.* (*Lausanne*), 3:54, doi: 10.3389/fendo.2012.00054, 2012). The role of RET-PTC rearrangements in the pathogenesis of PTC has been confirmed in transgenic mice (Santoro et al., *Oncogene,* 1996, 12, 1821-6). To date, a variety of fusion partners have been identified, from PTC and other cancer types, all providing a protein/protein interaction domain that induces ligand-independent RET dimerization and constitutive kinase activity (see, e.g., Table 1). Recently, a 10.6 Mb pericentric inversion in chromosome 10, where RET gene maps, has been identified in about 2% of lung adenocarcinoma patients, generating different variants of the chimeric gene KIF5B-RET (Ju et al., *Genome Res.,* 2012, 22, 436-45; Kohno et al., 2012*, Nature Med.,* 18, 375-7; Takeuchi et al., *Nature Med.,* 2012, 18, 378-81; Lipson et al., 2012*, Nature Med.,* 18, 382-4). The fusion transcripts are highly expressed and all the resulting chimeric proteins contain the N-terminal portion of the coiled-coil region of KIF5B, which mediates homodimerization, and the entire RET kinase domain. None of RET positive patients harbor other known oncogenic alterations (such as EGFR or K-Ras mutation, ALK translocation), supporting the possibility that KIF5B-RET fusion could be a driver mutation of lung adenocarcinoma. The oncogenic potential of KIF5B-RET has been confirmed by transfecting the fusion gene into cultured cell lines: similarly to what has been observed with RET-PTC fusion proteins, KIF5B-RET is constitutively phosphorylated and induces NIH-3T3 transformation and IL-3 independent growth of BA-F3 cells. However, other RET fusion proteins have been identified in lung adenocarcinoma patients, such as the CCDC6-RET fusion protein, which has been found to play a key role in the proliferation of the human lung adenocarcinoma cell line LC-2/ad (*Journal of Thoracic Oncology,* 2012, 7(12):1872-1876). RET inhibitors have been shown to be useful in treating lung cancers involving RET rearrangements (Drilon, A. E. et al. *J Clin Oncol* 33, 2015 (suppl; abstr 8007)). RET fusion proteins have also been identified in patients having colorectal cancer (Song Eun-Kee, et al. *International Journal of Cancer,* 2015, 136: 1967-1975).

Besides rearrangements of the RET sequence, gain of function point mutations of RET proto-oncogene are also driving oncogenic events, as shown in medullary thyroid carcinoma (MTC), which arises from parafollicular calcitonin-producing cells (de Groot, et al., *Endocrine Rev.,* 2006, 27, 535-60; Wells and Santoro, *Clin. Cancer Res.,* 2009, 15, 7119-7122). Around 25% of MTC are associated with multiple endocrine neoplasia type 2 (MEN2), a group of inherited cancer syndromes affecting neuroendocrine organs caused by germline activating point mutations of RET. In MEN2 subtypes (MEN2A, MEN2B and Familial MTC/FMTC) RET gene mutations have a strong phenotype-genotype correlation defining different MTC aggressiveness and clinical manifestations of the disease. In MEN2A syndrome mutations involve one of the six cysteine residues (mainly C634) located in the cysteine-rich extracellular region, leading to ligand-independent homodimerization and constitutive RET activation. Patients develop MTC at a young age (onset at 5-25 years) and may also develop pheochromocytoma (50%) and hyperparathyroidism. MEN2B is mainly caused by M918T mutation, which is located in the kinase domain. This mutation constitutively activates RET in its monomeric state and alters substrate recognition by the kinase. MEN2B syndrome is characterized by an early onset (<1 year) and very aggressive form of MTC, pheochromocytoma (50% of patients) and ganglioneuromas. In FMTC the only disease manifestation is MTC, usually occurring at an adult age. Many different mutations have been detected, spanning the entire RET gene. The remaining 75% of MTC cases are sporadic and about 50% of them harbor RET somatic mutations: the most frequent mutation is M918T that, as in MEN2B, is associated with the most aggressive phenotype. Somatic point mutations of RET have also been described in other tumors such as colorectal cancer (Wood et al., *Science,* 2007, 318, 1108-13) and small cell lung carcinoma (*Jpn. J. Cancer Res.,* 1995, 86, 1127-30).

RET signaling components have been found to be expressed in primary breast tumors and to functionally interact with estrogen receptor-cc pathway in breast tumor cell lines (Boulay et al., *Cancer Res.* 2008, 68, 3743-51; Plaza-Menacho et al., *Oncogene,* 2010, 29, 4648-57), while RET expression and activation by GDNF family ligands could play an important role in perineural invasion by different types of cancer cells (Ito et al., *Surgery,* 2005, 138, 788-94; Gil et al., J. Natl. Cancer Inst., 2010, 102, 107-18; Iwahashi et al., Cancer, 2002, 94, 167-74).

RET is also expressed in 30-70% of invasive breast cancers, with expression being relatively more frequent in estrogen receptor-positive tumors (Plaza-Menacho, I., et al., *Oncogene,* 2010, 29, 4648-4657; Esseghir, S., et al., *Cancer Res.,* 2007, 67, 11732-11741; Morandi, A., et al., *Cancer Res.,* 2013, 73, 3783-3795; Gattelli, A., *EMBO Mol. Med.,* 2013, 5, 1335-1350).

The identification of RET rearrangements has been reported in a subset of (patient-derived xenograft) PDX established from colorectal cancer. Although the frequency of such events in colorectal cancer patients remains to be defined, these data suggest a role of RET as a target in this indication (Gozgit et al., AACR Annual Meeting 2014). Studies have shown that the RET promoter is frequently methylated in colorectal cancers, and heterozygous missense mutations, which are predicted to reduce RET expression, are identified in 5-10% of cases, which suggests that RET might have some features of a tumor suppressor in sporadic colon cancers (Luo, Y., et al., Oncogene, 2013, 32, 2037-2047; Sjoblom, T., et al., *Science,* 2006, 268-274; Cancer Genome Atlas Network, *Nature,* 2012, 487, 330-337).

An increasing number of tumor types are now being shown to express substantial levels of wild-type RET kinase that could have implications for tumor progression and spread. RET is expressed in 50-65% of pancreatic ductal carcinomas, and expression is more frequent in metastatic and higher grade tumors (Ito, Y, et al., *Surgery,* 2005, 138, 788-794; Zeng, Q., et al., *J. Int. Med. Res.* 2008, 36, 656-664).

In neoplasms of hematopoietic lineages, RET is expressed in acute myeloid leukemia (AML) with monocytic differentiation, as well as in CMML (Gattei, V. et al., *Blood,* 1997, 89, 2925-2937; Gattei, V., et al., *Ann. Hematol,* 1998, 77, 207-210; Camos, M., *Cancer Res.* 2006, 66, 6947-6954). Recent studies have identified rare chromosomal rearrangements that involve RET in patients with chronic myelomonocytic leukemia (CMML). CMML is frequently associated with rearrangements of several tyrosine kinases, which result in the expression of chimeric cytosolic oncoproteins that lead to activation of RAS pathways (Kohlmann, A., et al., *J. Clin. Oncol.* 2010, 28, 2858-2865). In the case of RET, gene fusions that link RET with BCR (BCR-RET) or with fibroblast growth factor receptor 1 oncogene partner (FGFR1OP-RET) were transforming in early hematopoietic progenitor cells and could shift maturation of these cells towards monocytic paths, probably through the initiation of RET-mediated RAS signaling (Ballerini, P., et al., *Leukemia,* 2012, 26, 2384-2389).

RET expression has also been shown to occur in several other tumor types, including prostate cancer, small-cell lung carcinoma, melanoma, renal cell carcinoma, and head and neck tumors (Narita, N., et al., *Oncogene,* 2009, 28, 3058-3068; Mulligan, L. M., et al., *Genes Chromosomes Cancer,* 1998, 21, 326-332; Flavin, R., et al., *Urol. Oncol.,* 2012, 30, 900-905; Dawson, D. M., *J Natl Cancer Inst,* 1998, 90, 519-523).

In neuroblastoma, RET expression and activation by GFLs has roles in tumor cell differentiation, potentially collaborating with other neurotrophic factor receptors to down regulate N-Myc, the expression of which is a marker of poor prognosis (Hofstra, R. M., W., et al., *Hum. Genet.* 1996, 97, 362-364; Petersen, S. and Bogenmann, E., *Oncogene,* 2004, 23, 213-225; Brodeur, G. M., *Nature Ref Cancer,* 2003, 3, 203-216).

Multitargeted inhibitors which cross react with RET are known (Borrello, M. G., et al., *Expert Opin. Ther. Targets,* 2013, 17(4), 403-419; International Patent Application Nos. WO 2014/141187, WO 2014/184069, and WO 2015/079251). Such multitargeted inhibitors (or multikinase inhibitors or MKIs) can also be associated with development of RET inhibitor resistance mutations. See, for example, Q. Huang et al., "Preclinical Modeling of KIF5B-RET Fusion Lung Adenocarcinoma.," *Mol. Cancer Ther., no.* 18, pp. 2521-2529, 2016; Yasuyuki Kaneta et al., Abstract B173: Preclinical characterization and antitumor efficacy of DS-5010, a highly potent and selective RET inhibitor, *Mol Cancer Ther Jan.* 1, 2018 (17) (1 Supplement) B173; DOI: 10.1158/1535-7163.TARG-17-B173, both of which are incorporated by reference in their entirety herein.

Accordingly, provided herein are methods for treating a patient diagnosed with (or identified as having) a cancer that include administering to the patient a therapeutically effective amount of a compound of Formula I or a pharmaceutically acceptable salt or solvate thereof. Also provided herein are methods for treating a patient identified or diagnosed as having a RET-associated cancer that include administering to the patient a therapeutically effective amount of a compound of Formula I or a pharmaceutically acceptable salt or solvate thereof or a pharmaceutical composition thereof. In some embodiments, the patient that has been identified or diagnosed as having a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods for treating cancer in a patient in need thereof, the method comprising: (a) detecting a RET-associated cancer in the patient; and (b) administering to the patient a therapeutically effective amount of a compound of Formula I or a pharmaceutically acceptable salt or solvate thereof or a pharmaceutical composition thereof. Some embodiments of these methods further include administering to the subject another anticancer agent (e.g., a second RET inhibitor, a second compound of Formula I or a pharmaceutically acceptable salt or solvate thereof, or an immunotherapy). In some embodiments, the subject was previously treated with a first RET inhibitor or previously treated with another anticancer treatment, e.g., resection of the tumor or radiation therapy. In some embodiments, the patient is determined to have a RET-associated cancer through the use of a regulatory agency-approved, e.g., FDA-approved test or assay for identifying dysregulation of a RET gene, a RET kinase, or expression or activity or level of any of the same, in a patient or a biopsy sample from the patient or by performing any of the non-limiting examples of assays described herein. In some embodiments, the test or assay is provided as a kit. In some embodiments, the cancer is a RET-associated cancer. For example, the RET-associated cancer can be a cancer that includes one or more RET inhibitor resistance mutations.

Also provided are methods of treating a patient that include performing an assay on a sample obtained from the patient to determine whether the patient has a dysregulation of a RET gene, a RET kinase, or expression or activity or level of any of the same, and administering (e.g., specifically or selectively administering) a therapeutically effective amount of a compound of Formula I or a pharmaceutically acceptable salt or solvate thereof or a pharmaceutical composition thereof to the patient determined to have a dysregulation of a RET gene, a RET kinase, or expression or activity or level of any of the same. Some embodiments of these methods further include administering to the subject another anticancer agent (e.g., a second RET inhibitor, a second compound of Formula I or a pharmaceutically acceptable salt or solvate thereof, or immunotherapy). In some embodiments of these methods, the subject was previously treated with a first RET inhibitor or previously treated with another anticancer treatment, e.g., resection of a tumor or radiation therapy. In some embodiments, the patient is a patient suspected of having a RET-associated cancer, a patient presenting with one or more symptoms of a RET-associated cancer, or a patient having an elevated risk of developing a RET-associated cancer. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. Additional, non-limiting assays that may be used in these methods are described herein. Additional assays are also known in the art. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof or a pharmaceutical composition thereof for use in treating a RET-associated cancer in a patient identified or diagnosed as having a RET-associated cancer through a step of performing an assay (e.g., an in vitro assay) on a sample obtained from the patient to determine whether the patient has a dysregulation of a RET gene, a RET kinase, or expression or activity or level of any of the same, where the presence of a dysregulation of a RET gene, a RET kinase, or expression or activity or level of any of the same, identifies that the patient has a RET-associated cancer. Also provided is the use of a compound of Formula I or a pharmaceutically acceptable salt or solvate thereof for the manufacture of a medicament for treating a RET-associated cancer in a patient identified or diagnosed as having a RET-associated cancer through a step of performing an assay on a sample obtained from the patient to determine whether the patient has a dysregulation of a RET gene, a RET kinase, or expression or activity or level of any of the same where the presence of dysregulation of a RET gene, a RET kinase, or expression or activity or level of any of the same, identifies that the patient has a RET-associated cancer. Some embodiments of any of the methods or uses described herein further include recording in the patient's clinical record (e.g., a computer readable medium) that the patient is determined to have a dysregulation of a RET gene, a RET kinase, or expression or activity or level of any of the same, through the performance of the assay, should be administered a compound of Formula I or a pharmaceutically acceptable salt or solvate thereof or a pharmaceutical composition thereof. In some embodiments, the assay utilizes next generation sequencing, pyrosequencing, immunohistochemistry, or break apart FISH analysis. In some embodiments, the assay is a regulatory agency-approved assay, e.g., FDA-approved kit. In some embodiments, the assay is a liquid biopsy. In some embodiments, the dysregulation of a RET gene, a RET kinase, or expression or activity or level of any of the same includes one or more RET inhibitor resistance mutations.

Also provided is a compound of Formula I or a pharmaceutically acceptable salt or solvate thereof, for use in the treatment of a cancer in a patient in need thereof or a patient identified or diagnosed as having a RET-associated cancer. Also provided is the use of a compound of Formula I or a pharmaceutically acceptable salt or solvate thereof for the manufacture of a medicament for treating a cancer in a patient identified or diagnosed as having a RET-associated cancer. In some embodiments, the cancer is a RET-associated cancer, for example, a RET-associated cancer having one or more RET inhibitor resistance mutations. In some embodiments, a patient is identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the sample. As provided herein, a RET-associated cancer includes those described herein and known in the art.

In some embodiments of any of the methods or uses described herein, the patient has been identified or diagnosed as having a cancer with a dysregulation of a RET gene, a RET kinase, or expression or activity or level of any of the same. In some embodiments of any of the methods or uses described herein, the patient has a tumor that is positive for a dysregulation of a RET gene, a RET kinase, or expression or activity or level of any of the same. In some embodiments of any of the methods or uses described herein, the patient can be a patient with a tumor(s) that is positive for a dysregulation of a RET gene, a RET kinase, or expression or activity or level of any of the same. In some embodiments of any of the methods or uses described herein, the patient can be a patient whose tumors have a dysregulation of a RET gene, a RET kinase, or expression or activity or level of any of the same. In some embodiments of any of the methods or uses described herein, the patient is suspected of having a RET-associated cancer (e.g., a cancer having one or more RET inhibitor resistance mutations). In some embodiments, provided herein are methods for treating a RET-associated cancer in a patient in need of such treatment, the method comprising a) detecting a dysregulation of a RET gene, a RET kinase, or the expression or activity or level of any of the same in a sample from the patient; and b) administering a therapeutically effective amount of a compound of Formula I or a pharmaceutically acceptable salt or solvate thereof. In some embodiments, the dysregulation of a RET gene, a RET kinase, or the expression or activity or level of any of the same includes one or more fusion proteins. Non-limiting examples of RET gene fusion proteins are described in Table 1. In some embodiments, the fusion protein is KIF5B-RET. In some embodiments, the dysregulation of a RET gene, a RET kinase, or the expression or activity or level of any of the same includes one or more RET kinase protein point mutations/insertions/deletions. Non-limiting examples of RET kinase protein point mutations/insertions/deletions are described in Tables 2 and 2a. In some embodiments, the RET kinase protein point mutations/insertions/deletions are selected from the group consisting of M918T, M918V, C634W, V804L, and V804M. In some embodiments, the dysregulation of a RET gene, a RET kinase, or the expression or activity or level of any of the same includes one or more RET inhibitor resistance mutations. Non-limiting examples of RET inhibitor resistance mutations are described in Tables 3 and 4. In some embodiments, the RET inhibitor resistance mutation is V804M. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

In some embodiments of any of the methods or uses described herein, the patient has a clinical record indicating that the patient has a tumor that has a dysregulation of a RET gene, a RET kinase, or expression or activity or level of any of the same (e.g., a tumor having one or more RET inhibitor resistance mutations). In some embodiments, the clinical record indicates that the patient should be treated with one or more of the compounds of Formula I or a pharmaceutically acceptable salts or solvates thereof or compositions provided herein. In some embodiments, the cancer with a dysregulation of a RET gene, a RET kinase, or expression or activity or level of any of the same is a cancer having one or more RET inhibitor resistance mutations. In some embodiments, the cancer with a dysregulation of a RET gene, a RET kinase, or expression or activity or level of any of the same is determined using a regulatory agency-approved, e.g., FDA-approved, assay or kit. In some embodiments, the tumor that is positive for a dysregulation of a RET gene, a RET kinase, or expression or activity or level of any of the same is a tumor positive for one or more RET inhibitor resistance mutations. In some embodiments, the tumor with a dysregulation of a RET gene, a RET kinase, or expression or activity or level of any of the same is determined using a regulatory agency-approved, e.g., FDA-approved, assay or kit.

Also provided are methods of treating a patient that include administering a therapeutically effective amount of a compound of Formula I or a pharmaceutically acceptable salt or solvate thereof to a patient having a clinical record that indicates that the patient has a dysregulation of a RET gene, a RET kinase, or expression or activity or level of any of the same. Also provided is the use of a compound of Formula I or a pharmaceutically acceptable salt or solvate thereof for the manufacture of a medicament for treating a RET-associated cancer in a patient having a clinical record that indicates that the patient has a dysregulation of a RET gene, a RET kinase, or expression or activity or level of any of the same. Some embodiments of these methods and uses can further include: a step of performing an assay (e.g., an in vitro assay) on a sample obtained from the patient to determine whether the patient has a dysregulation of a RET gene, a RET kinase, or expression or activity or level of any of the same, and recording the information in a patient's clinical file (e.g., a computer readable medium) that the patient has been identified to have a dysregulation of a RET gene, a RET kinase, or expression or activity or level of any of the same. In some embodiments, the assay is an in vitro assay. For example, an assay that utilizes next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of a RET gene, RET kinase, or expression or activity or level of any of the same includes one or more RET inhibitor resistance mutations.

Also provided herein is a method of treating a subject. In some embodiments, the method includes performing an assay on a sample obtained from the subject to determine whether the subject has a dysregulation of a RET gene, a RET protein, or expression or level of any of the same. In some such embodiments, the method also includes administering to a subject determined to have a dysregulation of a RET gene, a RET protein, or expression or activity, or level of any of the same a therapeutically effective amount of a compound of Formula I or a pharmaceutically acceptable salt or solvate thereof. In some embodiments, the method includes determining that a subject has a dysregulation of a RET gene, a RET protein, or expression or level of any of the same via an assay performed on a sample obtained from the subject. In such embodiments, the method also includes administering to a subject a therapeutically effective amount of a compound of Formula I or a pharmaceutically acceptable salt or solvate thereof. In some embodiments, the dysregulation in a RET gene, a RET kinase protein, or expression or activity of the same is a gene or chromosome translocation that results in the expression of a RET fusion protein (e.g., any of the RET fusion proteins described herein). In some embodiments, the RET fusion can be selected from a KIF5B-RET fusion and a CCDC6-RET fusion. In some embodiments, the dysregulation in a RET gene, a RET kinase protein, or expression or activity or level of any of the same is one or more point mutation in the RET gene (e.g., any of the one or more of the RET point mutations described herein). The one or more point mutations in a RET gene can result, e.g., in the translation of a RET protein having one or more of the following amino acid substitutions: M918T, M918V, C634W, V804L, and V804M. In some embodiments, the dysregulation in a RET gene, a RET kinase protein, or expression or activity or level of any of the same is one or more RET inhibitor resistance mutations (e.g., any combination of the one or more RET inhibitor resistance mutations described herein). Some embodiments of these methods further include administering to the subject another anticancer agent (e.g., a second RET inhibitor a second compound of Formula I or a pharmaceutically acceptable salt or solvate thereof, or immunotherapy).

In some embodiments, the compounds provided herein exhibit brain and/or central nervous system (CNS) penetrance. Such compounds are capable of crossing the blood brain barrier and inhibiting a RET kinase in the brain and/or other CNS structures. In some embodiments, the compounds provided herein are capable of crossing the blood brain barrier in a therapeutically effective amount. For example, treatment of a patient with cancer (e.g., a RET-associated cancer such as a RET-associated brain or CNS cancer) can include administration (e.g., oral administration) of the compound to the patient. In some such embodiments, the compounds provided herein are useful for treating a primary brain tumor or metastatic brain tumor. For example, the compounds can be used in the treatment of one or more of gliomas such as glioblastoma (also known as glioblastoma multiforme), astrocytomas, oligodendrogliomas, ependymomas, and mixed gliomas, meningiomas, medulloblastomas, gangliogliomas, schwannomas (neurilemmomas), and craniopharyngiomas (see, for example, the tumors listed in Louis, D. N. et al. *Acta Neuropathol* 131(6), 803-820 (June 2016)). In some embodiments, the brain tumor is a primary brain tumor. In some embodiments, the patient has previously been treated with another anticancer agent, e.g., another RET inhibitor (e.g., a compound that is not a compound of General Formula I) or a multi-kinase inhibitor. In some embodiments, the brain tumor is a metastatic brain tumor. In some embodiments, the patient has previously been treated with another anticancer agent, e.g., another RET inhibitor (e.g., a compound that is not a compound of General Formula I) or a multi-kinase inhibitor.

Also provided are methods (e.g., in vitro methods) of selecting a treatment for a patient identified or diagnosed as having a RET-associated cancer. Some embodiments can further include administering the selected treatment to the patient identified or diagnosed as having a RET-associated cancer. For example, the selected treatment can include administration of a therapeutically effective amount of a compound of Formula I or a pharmaceutically acceptable salt or solvate thereof. Some embodiments can further include a step of performing an assay on a sample obtained from the patient to determine whether the patient has a dysregulation of a RET gene, a RET kinase, or expression or activity or level of any of the same, and identifying and diagnosing a patient determined to have a dysregulation of a RET gene, a RET kinase, or expression or activity or level of any of the same, as having a RET-associated cancer. In some embodiments, the cancer is a RET-associated cancer having one or more RET inhibitor resistance mutations. In some embodiments, the patient has been identified or diagnosed as having a RET-associated cancer through the use of a regulatory agency-approved, e.g., FDA-approved, kit for identifying dysregulation of a RET gene, a RET kinase, or expression or activity or level of any of the same, in a patient or a biopsy sample from the patient. In some embodiments, the RET-associated cancers is a cancer described herein or known in the art. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided herein are methods of selecting a treatment for a patient, wherein the methods include a step of performing an assay on a sample obtained from the patient to determine whether the patient has a dysregulation of a RET gene, a RET kinase, or expression or activity or level of any of the same (e.g., one or more RET inhibitor resistance mutations), and identifying or diagnosing a patient determined to have a dysregulation of a RET gene, a RET kinase, or expression or activity or level of any of the same, as having a RET-associated cancer. Some embodiments further include administering the selected treatment to the patient identified or diagnosed as having a RET-associated cancer. For example, the selected treatment can include administration of a therapeutically effective amount of a compound of Formula I or a pharmaceutically acceptable salt or solvate thereof to the patient identified or diagnosed as having a RET-associated cancer. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy.

Also provided are methods of selecting a patient for treatment, wherein the methods include selecting, identifying, or diagnosing a patient having a RET-associated cancer, and selecting the patient for treatment including administration of a therapeutically-effective amount of a compound of Formula I or a pharmaceutically acceptable salt or solvate thereof. In some embodiments, identifying or diagnosing a patient as having a RET-associated cancer can include a step of performing an assay on a sample obtained from the patient to determine whether the patient has a dysregulation of a RET gene, a RET kinase, or expression or activity or level of any of the same, and identifying or diagnosing a patient determined to have a dysregulation of a RET gene, a RET kinase, or expression or activity or level of any of the same, as having a RET-associated cancer. In some embodiments, the method of selecting a patient for treatment can be used as a part of a clinical study that includes administration of various treatments of a RET-associated cancer. In some embodiments, a RET-associated cancer is a cancer having one or more RET inhibitor resistance mutations. In some embodiments, the assay is an in vitro assay. For example, an assay that utilizes the next generation sequencing, immunohistochemistry, or break apart FISH analysis. In some embodiments, the assay is a regulatory agency-approved, e.g., FDA-approved, kit. In some embodiments, the assay is a liquid biopsy. In some embodiments, the dysregulation of the RET gene, the RET kinase, or expression or activity or level of any of the same includes one or more RET inhibitor resistance mutations.

In some embodiments of any of the methods or uses described herein, an assay used to determine whether the patient has a dysregulation of a RET gene, or a RET kinase, or expression or activity or level of any of the same, using a sample from a patient can include, for example, next generation sequencing, immunohistochemistry, fluorescence microscopy, break apart FISH analysis, Southern blotting, Western blotting, FACS analysis, Northern blotting, and PCR-based amplification (e.g., RT-PCR and quantitative real-time RT-PCR). As is well-known in the art, the assays are typically performed, e.g., with at least one labelled nucleic acid probe or at least one labelled antibody or antigen-binding fragment thereof. Assays can utilize other detection methods known in the art for detecting dysregulation of a RET gene, a RET kinase, or expression or activity or levels of any of the same (see, e.g., the references cited herein). In some embodiments, the dysregulation of the RET gene, the RET kinase, or expression or activity or level of any of the same includes one or more RET inhibitor resistance mutations. In some embodiments, the sample is a biological sample or a biopsy sample (e.g., a paraffin-embedded biopsy sample) from the patient. In some embodiments, the patient is a patient suspected of having a RET-associated cancer, a patient having one or more symptoms of a RET-associated cancer, and/or a patient that has an increased risk of developing a RET-associated cancer)

In some embodiments, dysregulation of a RET gene, a RET kinase, or the expression or activity or level of any of the same can be identified using a liquid biopsy (variously referred to as a fluid biopsy or fluid phase biopsy). See, e.g., Karachialiou et al., "Real-time liquid biopsies become a reality in cancer treatment", *Ann. Transl. Med.,* 3(3):36, 2016. Liquid biopsy methods can be used to detect total tumor burden and/or the dysregulation of a RET gene, a RET kinase, or the expression or activity or level of any of the same. Liquid biopsies can be performed on biological samples obtained relatively easily from a subject (e.g., via a simple blood draw) and are generally less invasive than traditional methods used to detect tumor burden and/or dysregulation of a RET gene, a RET kinase, or the expression or activity or level of any of the same. In some embodiments, liquid biopsies can be used to detect the presence of dysregulation of a RET gene, a RET kinase, or the expression or activity or level of any of the same at an earlier stage than traditional methods. In some embodiments, the biological sample to be used in a liquid biopsy can include, blood, plasma, urine, cerebrospinal fluid, saliva, sputum, broncho-alveolar lavage, bile, lymphatic fluid, cyst fluid, stool, ascites, and combinations thereof. In some embodiments, a liquid biopsy can be used to detect circulating tumor cells (CTCs). In some embodiments, a liquid biopsy can be used to detect cell-free DNA. In some embodiments, cell-free DNA detected using a liquid biopsy is circulating tumor DNA (ctDNA) that is derived from tumor cells. Analysis of ctDNA (e.g., using sensitive detection techniques such as, without limitation, next-generation sequencing (NGS), traditional PCR, digital PCR, or microarray analysis) can be used to identify dysregulation of a RET gene, a RET kinase, or the expression or activity or level of any of the same.

In some embodiments, ctDNA derived from a single gene can be detected using a liquid biopsy. In some embodiments, ctDNA derived from a plurality of genes (e.g., 2, 3, 4, 5, 6, 7, 8, 9, 10, 15, 20, 25, 30, 35, 40, 45, 50, 55, 60, 65, 70, 75, 80, 85, 90, 95, 100 or more, or any number of genes in between these numbers) can be detected using a liquid biopsy. In some embodiments, ctDNA derived from a plurality of genes can be detected using any of a variety of commercially-available testing panels (e.g., commercially-available testing panels designed to detect dysregulation of a RET gene, a RET kinase, or the expression or activity or level of any of the same). Liquid biopsies can be used to detect dysregulation of a RET gene, a RET kinase, or the expression or activity or level of any of the same including, without limitation, point mutations or single nucleotide variants (SNVs), copy number variants (CNVs), genetic fusions (e.g., translocations or rearrangements), insertions, deletions, or any combination thereof. In some embodiments, a liquid biopsy can be used to detect a germline mutation. In some embodiments, a liquid biopsy can be used to detect a somatic mutation. In some embodiments, a liquid biopsy can be used to detect a primary genetic mutation (e.g., a primary mutation or a primary fusion that is associated with initial development of a disease, e.g., cancer). In some embodiments, a liquid biopsy can be used to detect a genetic mutation that develops after development of the primary genetic mutation (e.g., a resistance mutation that arises in response to a treatment administered to a subject). In some embodiments, a dysregulation of a RET gene, a RET kinase, or the expression or activity or level of any of the same identified using a liquid biopsy is also present in a cancer cell that is present in the subject (e.g., in a tumor). In some embodiments, any of the types of dysregulation of a RET gene, a RET kinase, or the expression or activity or level of any of the same described herein can be detected using a liquid biopsy. In some embodiments, a genetic mutation identified via a liquid biopsy can be used to identify the subject as a candidate for a particular treatment. For example, detection of dysregulation of a RET gene, a RET kinase, or the expression or activity or level of any of the same in the subject can indicate that the subject will be responsive to a treatment that includes administration of a compound of Formula I or a pharmaceutically acceptable salt thereof.

Liquid biopsies can be performed at multiple times during a course of diagnosis, a course of monitoring, and/or a course of treatment to determine one or more clinically relevant parameters including, without limitation, progression of the disease, efficacy of a treatment, or development of resistance mutations after administering a treatment to the subject. For example, a first liquid biopsy can be performed at a first time point and a second liquid biopsy can be performed at a second time point during a course of diagnosis, a course of monitoring, and/or a course of treatment. In some embodiments, the first time point can be a time point prior to diagnosing a subject with a disease (e.g., when the subject is healthy), and the second time point can be a time point after subject has developed the disease (e.g., the second time point can be used to diagnose the subject with the disease). In some embodiments, the first time point can be a time point prior to diagnosing a subject with a disease (e.g., when the subject is healthy), after which the subject is monitored, and the second time point can be a time point after monitoring the subject. In some embodiments, the first time point can be a time point after diagnosing a subject with a disease, after which a treatment is administered to the subject, and the second time point can be a time point after the treatment is administered; in such cases, the second time point can be used to assess the efficacy of the treatment (e.g., if the genetic mutation(s) detected at the first time point are reduced in abundance or are undetectable) or to determine the presence of a resistance mutation that has arisen as a result of the treatment. In some embodiments, a treatment to be administered to a subject can include a compound of Formula I or a pharmaceutically acceptable salt thereof.

In the field of medical oncology it is normal practice to use a combination of different forms of treatment to treat each patient with cancer. In medical oncology the other component(s) of such conjoint treatment or therapy in addition to compositions provided herein may be, for example, surgery, radiotherapy, and chemotherapeutic agents, such as other kinase inhibitors, signal transduction inhibitors and/or monoclonal antibodies. For example, a surgery may be open surgery or minimally invasive surgery. Compounds of Formula I therefore may also be useful as adjuvants to cancer treatment, that is, they can be used in combination with one or more additional therapies or therapeutic agents, for example a chemotherapeutic agent that works by the same or by a different mechanism of action.

In some embodiments of any the methods described herein, the compound of Formula I (or a pharmaceutically acceptable salt or solvate thereof) is administered in combination with a therapeutically effective amount of at least one additional therapeutic agent selected from one or more additional therapies or therapeutic (e.g., chemotherapeutic) agents.

Non-limiting examples of additional therapeutic agents include: other RET-targeted therapeutic agents (i.e. a first or second RET kinase inhibitor), receptor tyrosine kinase-targeted therapeutic agents, signal transduction pathway inhibitors, checkpoint inhibitors, modulators of the apoptosis pathway (e.g. obataclax); cytotoxic chemotherapeutics, angiogenesis-targeted therapies, immune-targeted agents, including immunotherapy, and radiotherapy. In some embodiments, the other RET-targeted therapeutic is a multikinase inhibitor exhibiting RET inhibition activity. In some embodiments, the other RET-targeted therapeutic inhibitor is selective for a RET kinase. Exemplary RET kinase inhibitors can exhibit inhibition activity ($IC_{50}$) against a RET kinase of less than about 1000 nM, less than about 500 nM, less than about 200 nM, less than about 100 nM, less than about 50 nM, less than about 25 nM, less than about 10 nM, or less than about 1 nM as measured in an assay as described herein. In some embodiments, a RET kinase inhibitors can exhibit inhibition activity ($IC_{50}$) against a RET kinase of less than about 25 nM, less than about 10 nM, less than about 5 nM, or less than about 1 nM as measured in an assay as provided herein.

Non-limiting examples of RET-targeted therapeutic agents (e.g., a first RET inhibitor or a second RET inhibitor) include alectinib (9-Ethyl-6,6-dimethyl-8-[4-(morpholin-4-yl)piperidin-1-yl]-11-oxo-6,11-dihydro-5H-benzo[b]carbazole-3-carbonitrile); amuvatinib (MP470, HPK56) (N-(1,3-benzodioxol-5-ylmethyl)-4-([1]benzofuro[3,2-d]pyrimidin-4-yl)piperazine-1-carbothioamide); apatinib (YN968D1) (N-[4-(1-cyanocyclopentyl) phenyl-2-(4-picolyl)amino-3-Nicotinamide methanesulphonate); cabozantinib (Cometriq XL-184) (N-(4-((6,7-Dimethoxyquinolin-4-yl)oxy)phenyl)-N'-(4-fluorophenyl)cyclopropane-1,1-dicarboxamide); dovitinib (TKI258; GFKI-258; CHIR-258) ((3Z)-4-amino-5-fluoro-3-[5-(4-methylpiperazin-1-yl)-1,3-dihydrobenzimidazol-2-ylidene]quinolin-2-one); famitinib (5-[2-(diethylamino)ethyl]-2-[(Z)-(5-fluoro-2-oxo-1H-indol-3-ylidene) methyl]-3-methyl-6,7-dihydro-1H-pyrrolo[3,2-c]pyridin-4-one); fedratinib (SAR302503, TG101348) (N-(2-Methyl-2-propanyl)-3-{[5-methyl-2-({4-[2-(1-pyrrolidinyl)ethoxy] phenyl}amino)-4-pyrimidinyl] amino}benzenesulfonamide); foretinib (XL880, EXEL-2880, GSK1363089, GSK089) (N1'-[3-fluoro-4-[[6-methoxy-7-(3-morpholinopropoxy)-4-quinolyl]oxy] phenyl]-N1-(4-fluorophenyl)cyclopropane-1,1-dicarboxamide); fostamantinib (R788) (2H-Pyrido[3,2-b]-1,4-oxazin-3(4H)-one, 6-[[5-fluoro-2-[(3,4,5-trimethoxyphenyl)amino]-4-pyrimidinyl]amino]-2,2-dimethyl-4-[(phosphonooxy)methyl]-, sodium salt (1:2)); ilorasertib (ABT-348) (1-(4-(4-amino-7-(1-(2-hydroxyethyl)-1H-pyrazol-4-yl)thieno[3,2-c]pyridin-3-yl)phenyl)-3-(3-fluorophenyl)urea); lenvatinib (E7080, Lenvima) (4-[3-chloro-4-(cyclopropylaminocarbonyl)aminophenoxy]-7-methoxy-6-quinolinecarboxamide); motesanib (AMG 706) (N-(3,3-Dimethyl-2,3-dihydro-1H-indol-6-yl)-2-[(pyridin-4-ylmethyl)amino]pyridine-3-carboxamide); nintedanib (3-Z-[1-(4-(N-((4-methyl-piperazin-1-yl)-methylcarbonyl)-N-methyl-amino)-anilino)-1-phenyl-methylene]-6-methyoxycarbonyl-2-indolinone); ponatinib (AP24534) (3-(2-Imidazo[1,2-b]pyridazin-3-ylethynyl)-4-methyl-N-[4-[(4-methylpiperazin-1-yl)methyl]-3-(trifluoromethyl) phenyl]benzamide); PP242 (a TORKinib) (2-[4-Amino-1-(1-methylethyl)-1H-pyrazolo[3,4-d]pyrimidin-3-yl]-1H-indol-5-ol); quizartinib (1-(5-(tert-Butyl)isoxazol-3-yl)-3-(4-(7-(2-morpholinoethoxy)benzo[d]imidazo[2,1-b]thiazol-2-yl)phenyl)urea); regorfenib (BAY 73-4506, stivarga) (4-[4-({[4-Chloro-3-(trifluoromethyl)phenyl] carbamoyl}amino)-3-fluorophenoxy]-N-methylpyridine-2-carboxamide hydrate); RXDX-105 (CEP-32496, agerafenib) (1-(3-((6,7-dimethoxyquinazolin-4-yl)oxy)phenyl)-3-(5-(1,1,1-trifluoro-2-methylpropan-2-yl)isoxazol-3-yl)urea); semaxanib (SU5416) ((3Z)-3-[(3,5-dimethyl-1H-pyrrol-2-yl)methylidene]-1,3-dihydro-2H-indol-2-one); sitravatinib (MGCD516, MG516) (N-(3-Fluoro-4-{[2-(5-{[(2-methoxyethyl)amino]methyl}-2-pyridinyl)thieno[3,2-b] pyridin-7-yl]oxy}phenyl)-N?-(4-fluorophenyl)-1,1-cyclopropanedicarboxamide); sorafenib (BAY 43-9006) (4-[4-[[[[4-chloro-3-(trifluoromethyl)phenyl]amino]carbonyl] amino]phenoxy]-N-methyl-2-pyridinecarboxamide); vandetanib (N-(4-bromo-2-fluorophenyl)-6-methoxy-7-[(1-methylpiperidin-4-yl)methoxy]quinazolin-4-amine); vatalanib (PTK787, PTK/ZK, ZK222584) (N-(4-chlorophenyl)-4-(pyridin-4-ylmethyl)phthalazin-1-amine); AD-57 (N-[4-[4-amino-1-(1-methylethyl)-1H-pyrazolo[3,4-d]pyrimidin-3-yl]phenyl]-N'-[3-(trifluoromethyl)phenyl]-urea); AD-80 (1-[4-(4-amino-1-propan-2-ylpyrazolo[3,4-d]pyrimidin-3-yl)phenyl]-3-[2-fluoro-5-(trifluoromethyl)phenyl]urea); AD-81 (1-(4-(4-amino-1-isopropyl-1H-pyrazolo[3,4-d]pyrimidin-3-yl)phenyl)-3-(4-chloro-3-(trifluoromethyl)phenyl)urea); ALW-II-41-27 (N-(5-((4-((4-ethylpiperazin-1-yl) methyl)-3-(trifluoromethyl)phenyl)carbamoyl)-2-methylphenyl)-5-(thiophen-2-yl)nicotinamide); BPR1K871 (1-(3-chlorophenyl)-3-(5-(2-((7-(3-(dimethylamino) propoxy)quinazolin-4-yl)amino)ethyl)thiazol-2-yl)urea); CLM3 (1-phenethyl-N-(1-phenylethyl)-1H-pyrazolo[3,4-d] pyrimidin-4-amine); EBI-907 (N-(2-chloro-3-(1-cyclopropyl-8-methoxy-3H-pyrazolo[3,4-c]isoquinolin-7-yl)-4-fluorophenyl)-3-fluoropropane-1-sulfonamide); NVP-AST-487 (N-[4-[(4-ethyl-1-piperazinyl)methyl]-3-(trifluoromethyl) phenyl]-N'-[4-[[6-(methylamino)-4-pyrimidinyl]oxy]phenyl]-urea); NVP-BBT594 (BBT594) (5-((6-acetamidopyrimidin-4-yl)oxy)-N-(4-((4-methylpiperazin-1-yl)methyl)-3-(trifluoromethyl)phenyl)indoline-1-carboxamide); PD173955 (6-(2,6-dichlorophenyl)-8-methyl-2-(3-methylsulfanylanilino)pyrido[2,3-d]pyrimidin-7-one); PP2 (4-amino-5-(4-chlorophenyl)-7-(dimethylethyl)pyrazolo[3,4-d]pyrimidine); PZ-1 (N-(5-(tert-butyl)isoxazol-3-yl)-2-(4-(5-(1-methyl-1H-pyrazol-4-yl)-1Hbenzo[d]imidazol-1-yl) phenyl)acetamide); RPI-1 (1,3-dihydro-5,6-dimethoxy-3-[(4-hydroxyphenyl)methylene]-H-indol-2-one; (3E)-3-[(4-hydroxyphenyl)methylidene]-5,6-dimethoxy-1H-indol-2-one); SGI-7079 (3-[2-[[3-fluoro-4-(4-methyl-1-piperazinyl) phenyl]amino]-5-methyl-7H-pyrrolo[2,3-d]pyrimidin-4-yl]-benzeneacetonitrile); SPP86 (1-Isopropyl-3-(phenylethynyl)-1H-pyrazolo[3,4-d]pyrimidin-4-amine); SU4984 (4-[4-[(E)-(2-oxo-1H-indol-3-ylidene)methyl]phenyl]piperazine-1-carbaldehyde); sunitinb (SU11248) (N-(2-Diethylaminoethyl)-5-[(Z)-(5-fluoro-2-oxo-1H-indol-3-ylidene)methyl]-2,4-dimethyl-1H-pyrrole-3-carboxamide); TG101209 (N-tert-butyl-3-(5-methyl-2-(4-(4-methylpiperazin-1-yl)phenylamino)pyrimidin-4-ylamino)benzenesulfonamide); Withaferin A ((4β,5β,6β,22R)-4,27-Dihydroxy-5,6:22,26-diepoxyergosta-2,24-diene-1,26-dione); XL-999 ((Z)-5-((1-ethylpiperidin-4-yl)amino)-3-((3-fluorophenyl) (5-methyl-1H-imidazol-2-yl)methylene)indolin-2-one); BPR1J373 (a 5-phenylthiazol-2-ylamine-pyriminide derivative); CG-806 (CG'806); DCC-2157; GTX-186; HG-6-63-01 ((E)-3-(2-(4-chloro-1H-pyrrolo[2,3-b]pyridin-5-yl)vinyl)-N-(4-((4-ethylpiperazin-1-yl)methyl)-3-(trifluoromethyl)phenyl)-4-methylbenzamide); SW-01 (Cyclobenzaprine hydrochloride); XMD 15-44 (N-(4-((4-ethylpiperazin-1-yl)methyl)-3-(trifluoromethyl)phenyl)-4-methyl-3-(pyridin-3-ylethynyl)benzamide (generated from structure)); Y078-DM1 (an antibody drug conjugate composed of a RET antibody (Y078) linked to a derivative of the cytotoxic agent maytansine); Y078-DM4 (an antibody drug conjugate composed of a RET antibody (Y078) linked to a derivative of the cytotoxic agent maytansine); ITRI-305 (DON5 TB, DIB003599); BLU-667; BLU6864; DS-5010; GSK3179106; GSK3352589; and NMS-E668.

Further examples of RET-targeted therapeutics (e.g., a first RET kinase inhibitor aor a second RET kinase inhibitor) include 5-amino-3-(5-cyclopropylisoxazol-3-yl)-1-isopropyl-1H-pyrazole-4-carboxamide; 3-(5-cyclopropylisoxazol-3-yl)-1-isopropyl-1H-pyrazolo[3,4-d]pyrimidin-4-amine; 3-((6,7-Dimethoxyquinazolin-4-yl)amino)-4-fluoro-2- methylphenol; N-(5-(tert-butyl)isoxazol-3-yl)-2-(4-(imidazo[1,2-a]pyridin-6-yl)phenyl)acetamide; N-(5-(tert-butyl) isoxazol-3-yl)-2-(3-(imidazo[1,2-b]pyridazin-6-yloxy) phenyl)acetamide; N-(2-fluoro-5-trifluoromethylphenyl)-N'-{4'-[(2"-benzamido)pyridin-4"-ylamino]phenyl}urea; 2-amino-6-{[2-(4-chlorophenyl)-2-oxoethyl]sulfanyl}-4-(3-thienyl)pyridine-3,5-dicarbonitrile; and 3-arylureidobenzylidene-indolin-2-ones.

Additional examples of other RET kinase inhibitors include those described in U.S. Pat. Nos. 9,150,517 and 9,149,464, and International Publication No. WO 2014075035, all of which are hereby incorporated by reference. For example, in some embodiments the other RET inhibitor is a compound of formula I:

I

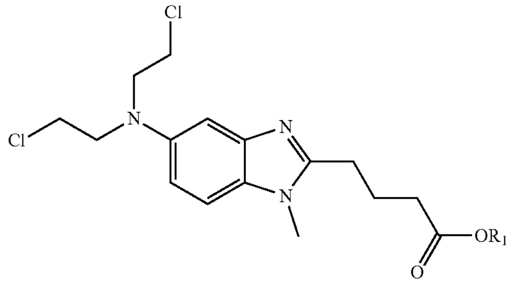

wherein $R_1$ is $C_6$-$C_{24}$alkyl or polyethylene glycol; or a pharmaceutically acceptable salt form thereof. In some embodiments, the other RET inhibitor is 4-{5-[bis-(chloroethyl)-amino]-1-methyl-1H-benzimidazol-2-yl}butyric acid dodecyl ester.

Additional examples of other RET kinase inhibitors include those described in International Publication No. WO 2016127074, which is hereby incorporated by reference. For example, in some embodiments, the other RET inhibitor is a compound of Formula (I) or a pharmaceutically acceptable salt thereof, wherein:

(I)

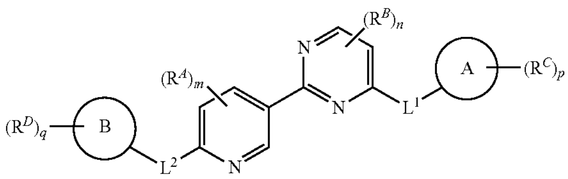

wherein Rings A and B are each independently selected from aryl, heteroaryl, cycloalkyl and heterocyclyl;

each $L^1$ and $L^2$ is independently selected from a bond, —(C1-C6 alkylene)-, —(C2-C6 alkenylene)-, —(C2-C6 alkynylene)-, —(C1-C6 haloalkylene)-, —(C1-C6 heteroalkylene)-, —C(O)—, —O—, —S—, —S(O), —$S(O)_2$—, —$N(R^1)$—, —O—(C1-C6 alkylene)-, —(C1-C6 alkylene)-O—, —$N(R^1)$—C(O)—, —C(O)$N(R^1)$—, —(C1-C6 alkylene)-$N(R^1)$—, —$N(R^1)$—(C1-C6 alkylene)-, —$N(R^1)$—C(O)—(C1-C6 alkylene)-, —(C1-C6 alkylene)-$N(R^1)$—C(O)—, —C(O)—$N(R^1)$—(C1-C6 alkylene)-, —(C1-C6 alkylene)-C(O)—$N(R^1)$—, —$N(R^1)$—$S(O)_2$—, —$S(O)_2$—$N(R^1)$—, —$N(R^1)$—$S(O)_2$—(C1-C6 alkylene)-, and —$S(O)_2$—$N(R^1)$—(C1-C6 alkylene)-; wherein each alkylene, alkenylene, alkynylene, haloalkylene, and heteroalkylene is independently substituted with 0-5 occurrences of R';

each $R^A$ and $R^B$ is independently selected from C1-C6 alkyl, C1-C6 alkoxy, halo, C1-C6 haloalkyl, C1-C6 hydroxyalkyl, C1-C6 heteroalkyl, and —$N(R^1)(R^1)$; wherein each alkyl, alkoxy, haloalkyl, hydroxyalkyl, and hydroxyalkyl is independently substituted with 0-5 occurrences of Ra;

each $R^C$ and $R^D$ is independently selected from C1-C6 alkyl, C2-C6 alkenyl, C2-C6 alkynyl, C1-C6 alkoxy, halo, C1-C6 heteroalkyl, C1-C6 haloalkyl, C1-C6 haloalkoxy, C1-C6 hydroxyalkyl, cycloalkyl, aryl, heteroaryl, aryloxy, aralkyl, heterocyclyl, heterocyclylalkyl, nitro, cyano, —$C(O)R^1$, —$OC(O)R^1$, —$C(O)OR^1$, —(C1-C6 alkylene)-$C(O)R^1$, —$SR^1$, —$S(O)_2R^1$, —$S(O)_2$—$N(R^1)(R^1)$, —(C1-C6 alkylene)-$S(O)_2R^1$, —(C1-C6 alkylene)-$S(O)_2$—$N(R^1)(R^1)$, —$N(R^1)(R^1)$—C(O)—$N(R^1)(R^1)$—$N(R^1)$—$C(O)R^1$, —$N(R^1)$—$C(O)OR^1$, —(C1-C6 alkylene)-$N(R^1)$—$C(O)R^1$, —$N(R^1)S(O)_2R^1$, and —$P(O)(R^1)(R^1)$; wherein each of alkyl, alkenyl, alkynyl, alkoxy, heteroalkyl, haloalkyl, haloalkoxy, hydroxyalkyl, cycloalkyl, aryl, heteroaryl, aryloxy, aralkyl, heterocyclyl, and heterocyclylalkyl is independently substituted with 0-5 occurrences of $R^a$; or 2 $R^C$ or 2 $R^D$ together with the carbon atom(s) to which they are attached form a cycloalkyl or heterocyclyl ring independently substituted with 0-5 occurrences of $R^a$;

each $R^1$ is independently selected from hydrogen, hydroxyl, halo, thiol, C1-C6 alkyl, C1-C6 thioalkyl, C1-C6 alkoxy, C1-C6 haloalkyl, C1-C6 hydroxyalkyl, C1-C6 heteroalkyl, cycloalkyl, cycloalkylalkyl, heteroarylalkyl, heterocyclyl, and heterocyclylalkyl, wherein each of alkyl, thioalkyl, alkoxy, haloalkyl, hydroxyalkyl, heteroalkyl, cycloalkyl, cycloalkylalkyl, heteroarylalkyl, heterocyclyl, and heterocyclylalkyl is independently substituted with 0-5 occurrences of $R^b$, or 2 $R^1$ together with the atom(s) to which they are attached form a cycloalkyl or heterocyclyl ring independently substituted with 0-5 occurrences of $R^b$;

each $R^a$ and $R^b$ is independently C1-C6 alkyl, halo, hydroxyl, C1-C6 haloalkyl, C1-C6 heteroalkyl, C1-C6 hydroxyalkyl, C1-C6 alkoxy, cycloalkyl, heterocyclyl, or cyano, wherein each of alkyl, haloalkyl, heteroalkyl, hydroxyalkyl, alkoxy, cycloalkyl and heterocyclyl is independently substituted with 0-5 occurrences of R';

each R' is C1-C6 alkyl, C1-C6 heteroalkyl, halo, hydroxyl, C1-C6 haloalkyl, C1-C6 hydroxyalkyl, cycloalkyl or cyano; or 2 R', together with the atom(s) to which they are attached form a cycloalkyl or heterocyclyl ring;

m is 0, 1, 2, or 3;

n is 0, 1, or 2; and p and q are each independently 0, 1, 2, 3, or 4. For example, a RET inhibitor can be selected from the group consisting of:

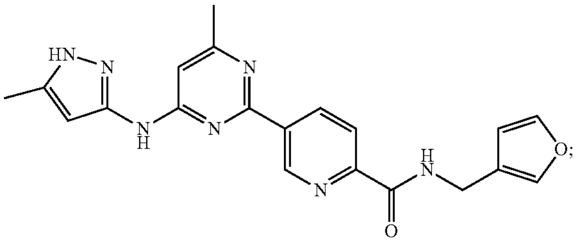
;
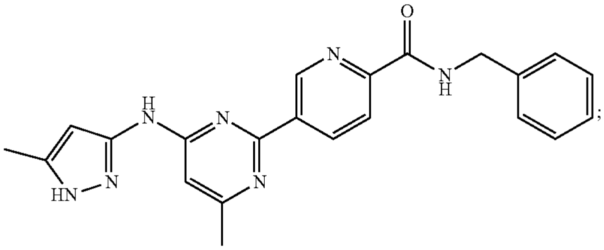
;
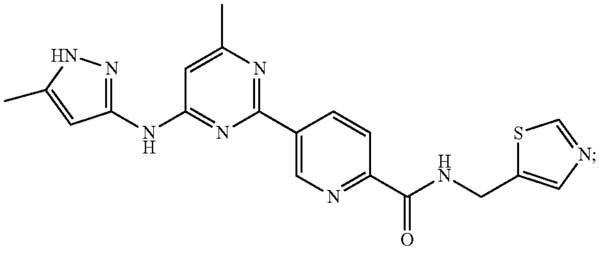
;
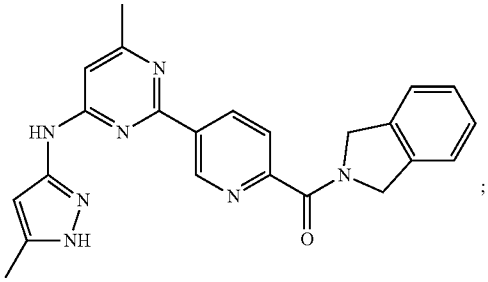
;
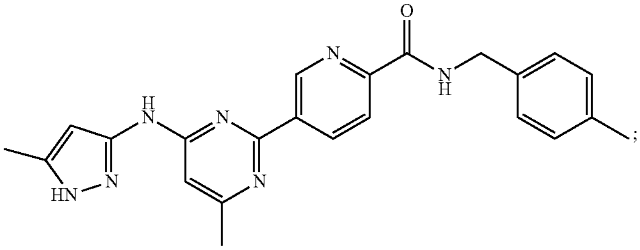
;
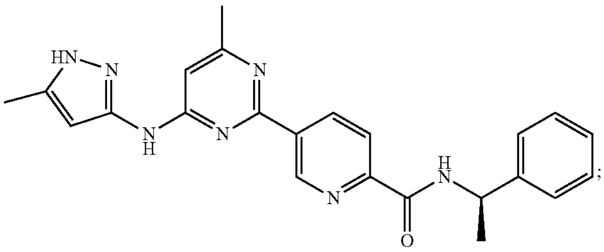
;
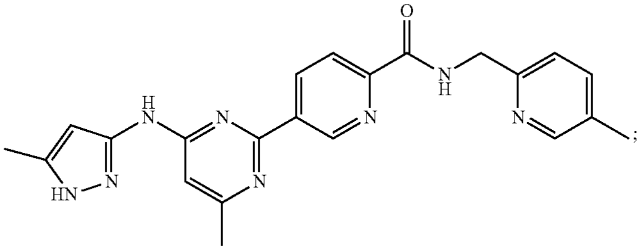
;

-continued
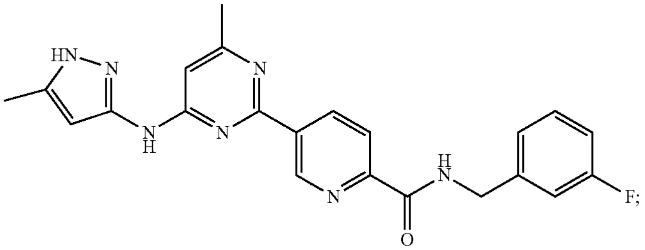
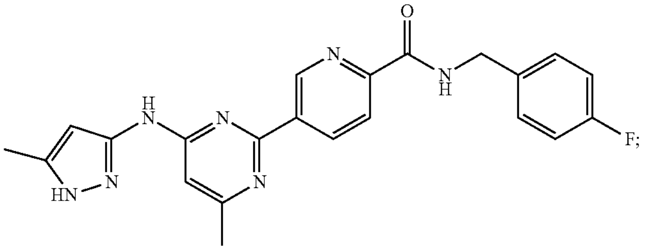
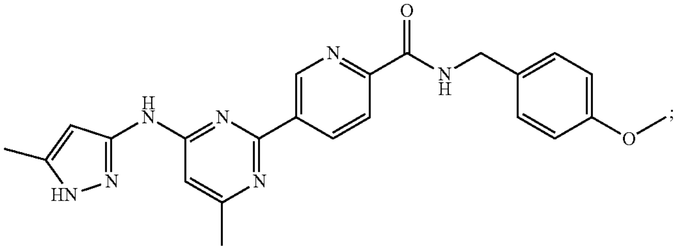
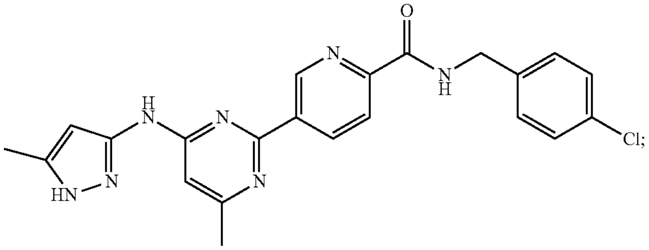
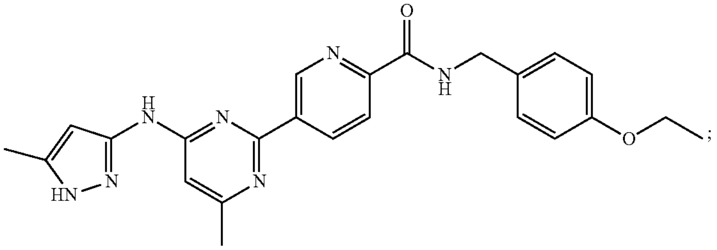
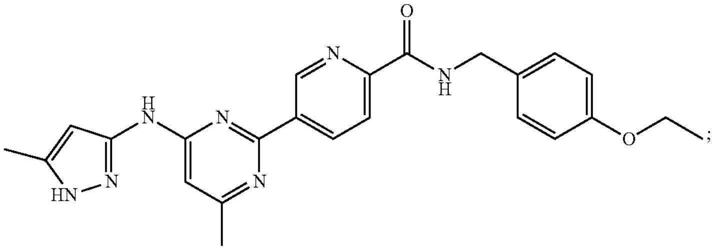

-continued
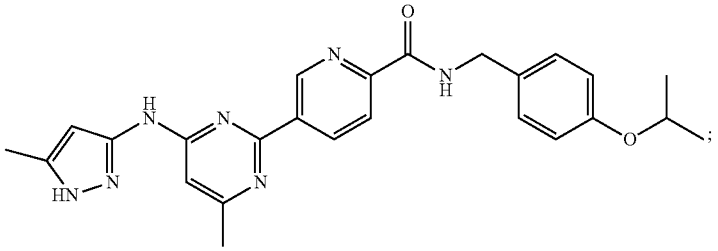
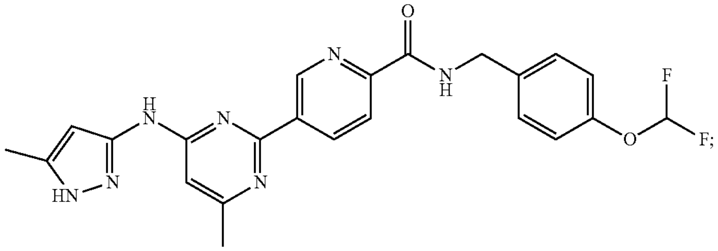
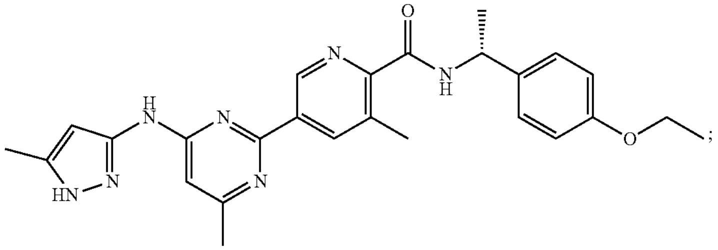
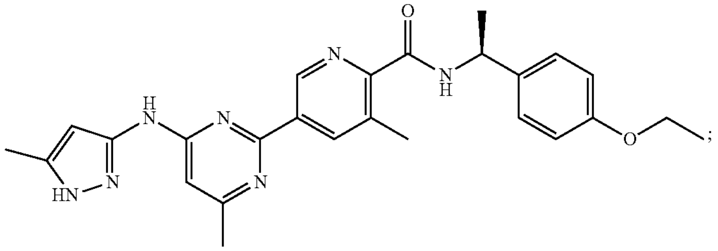
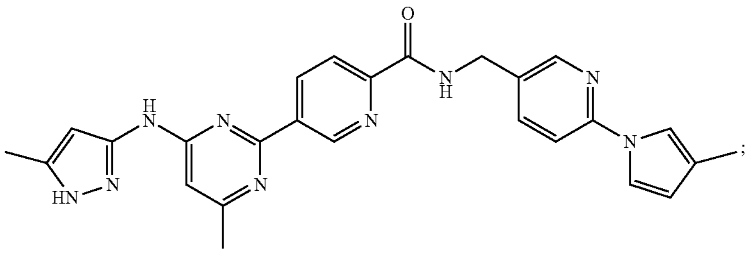
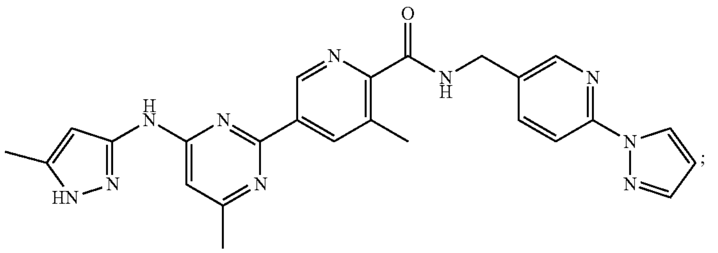

-continued
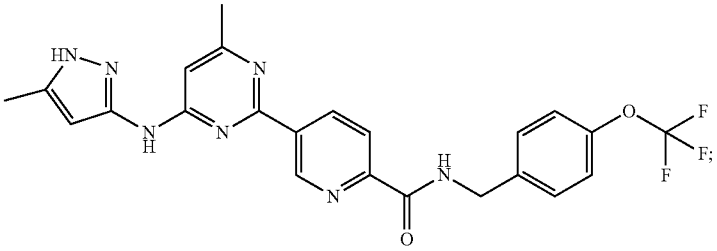
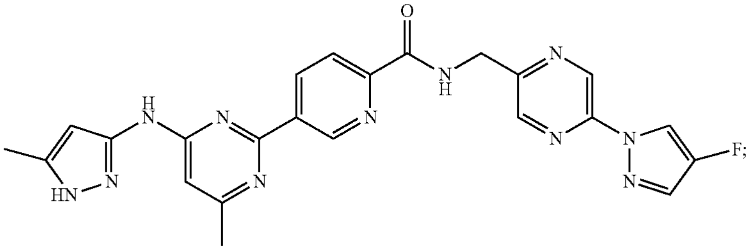
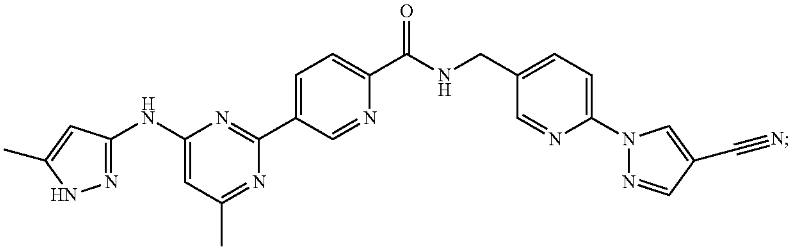
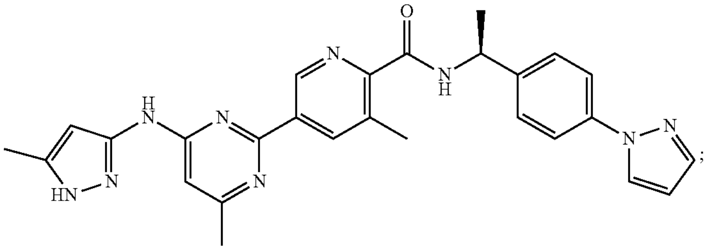
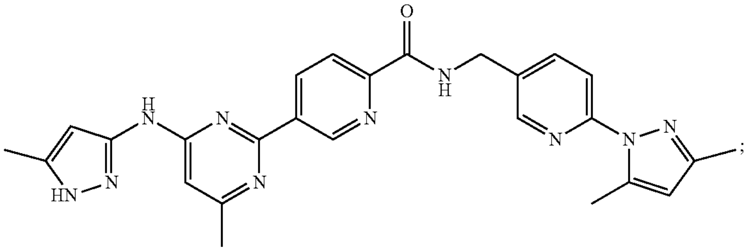
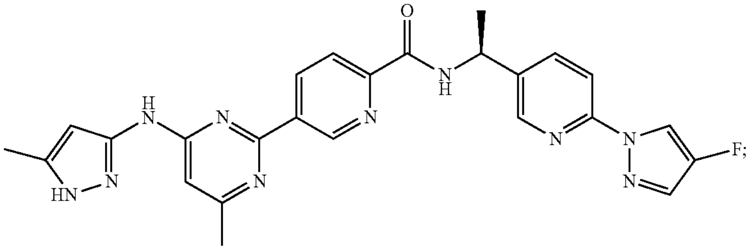

-continued
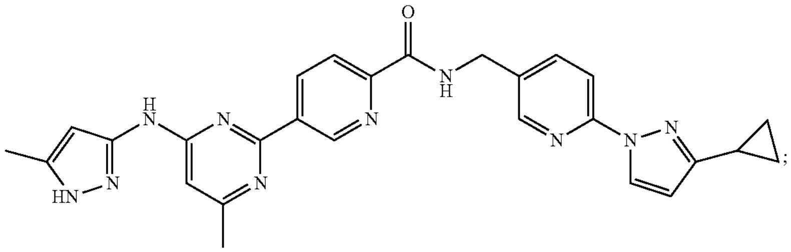
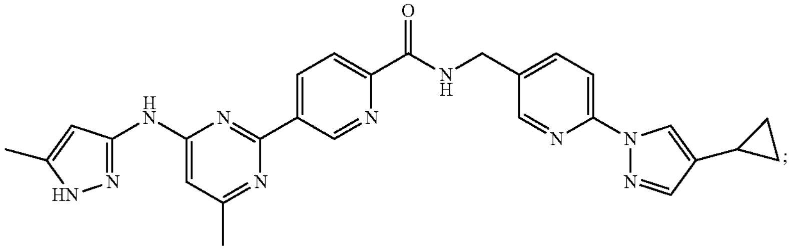
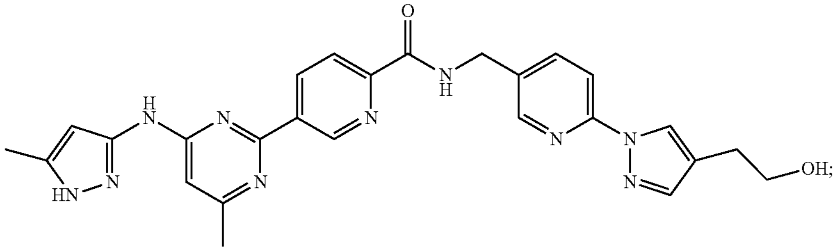
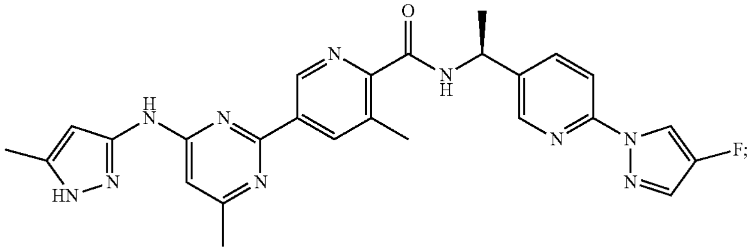
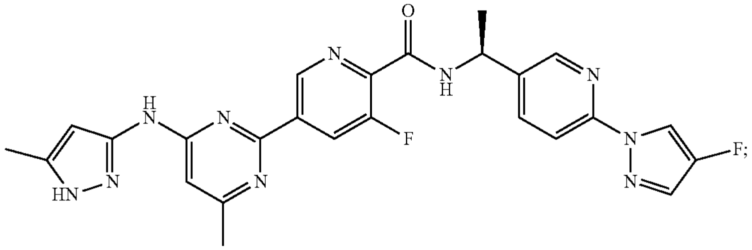
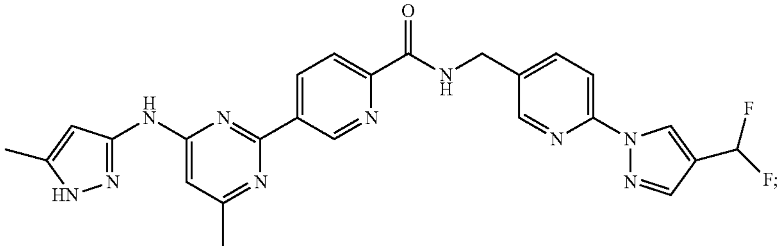

-continued

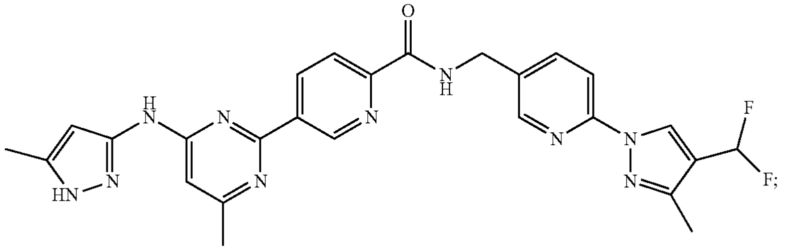

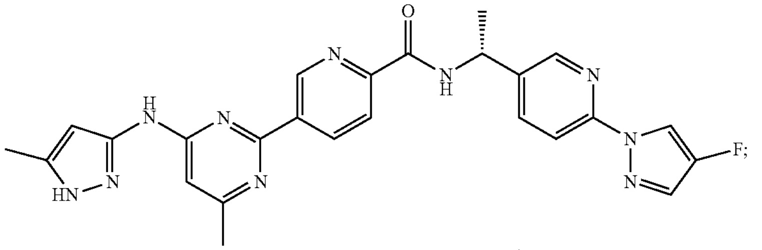

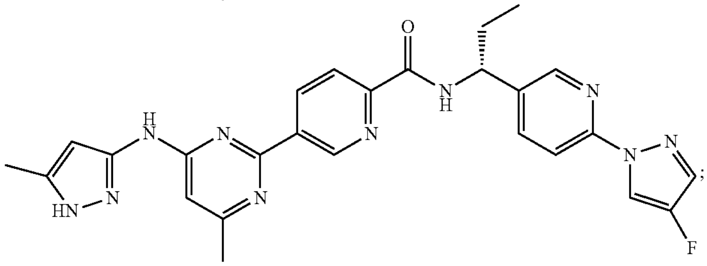

; and

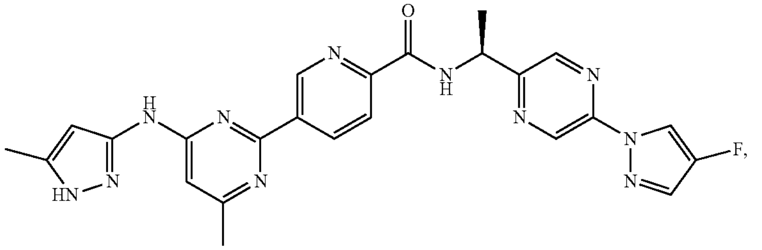

or a pharmaceutically acceptable salt thereof.

Additional examples of other RET kinase inhibitors include those described in International Publication No WO 2016075224, which is hereby incorporated by reference. For example, in some embodiments, the other RET inhibitor is a compound of Formula (II) or a pharmaceutically acceptable salt thereof, wherein:

(II)

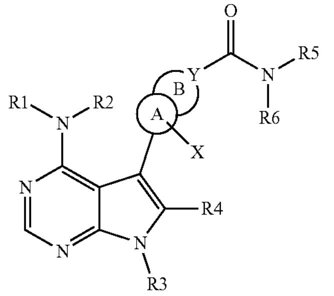

R1 and R2 are independently hydrogen or an optionally substituted group selected from straight or branched ($C_1$-$C_6$) alkyl, ($C_3$-$C_6$) cycloalkyl and COR', wherein R' is an optionally substituted group selected from straight or branched ($C_1$-$C_6$) alkyl and ($C_3$-$C_6$) cycloalkyl;

R3 is hydrogen or an optionally substituted group selected from straight or branched ($C_1$-$C_6$) alkyl, ($C_2$-$C_6$) alkenyl, ($C_2$-$C_6$) alkynyl, ($C_3$-$C_6$) cycloalkyl, aryl, heteroaryl and a 3- to 7-membered heterocyclyl ring;

R4 is hydrogen or an optionally substituted group selected from straight or branched ($C_1$-$C_6$) alkyl, ($C_2$-$C_6$) alkenyl, aryl, heteroaryl or heterocyclyl;

A is a 5- or 6-membered heteroaryl ring or a phenyl ring;

B is a 5- or 6-membered ring selected from heteroaryl, ($C_5$-$C_6$) cycloalkyl and heterocyclyl ring or a phenyl ring; wherein ring A and ring B are fused together to form a bicyclic system comprising a 6-membered aromatic or 5- to 6-membered heteroaromatic ring fused with a 6-membered aromatic or 5- to 6-membered heteroaromatic, ($C_5$-$C_6$) cycloalkyl or heterocyclyl ring;

Y is carbon or nitrogen;

X is hydrogen, halogen, hydroxyl, cyano or an optionally substituted group selected from straight or branched ($C_1$-$C_6$) alkyl and ($C_1$-$C_6$) alkoxyl; and R5 and R6 are independently hydrogen or an optionally substituted group selected from straight or branched ($C_1$-$C_6$) alkyl, ($C_3$-$C_6$) cycloalkyl, heterocyclyl, aryl and heteroaryl.

Additional examples of other RET kinase inhibitors include those described in International Publication No. WO 2015079251, which is hereby incorporated by reference. For example, in some embodiments, the other RET inhibitor is a compound of Formula (III) or a pharmaceutically acceptable salt or solvate thereof, wherein:

(III)

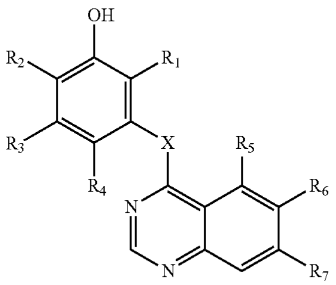

X is NH, $NR_x$, 0 or S, wherein $R_x$ is (1-3C)alkyl;

$R_1$ is selected from halo (e.g., fluoro, chloro, or bromo), trifluoromethyl, (1-4C)alkyl (e.g., methyl), (1-4C)alkoxy or (3-6C)cycloalkyl, wherein an alkyl, alkoxy or cycloalkyl group is optionally substituted with one or more fluoro;

$R_2$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C) alkoxy (e.g., OMe), wherein an alkyl, cycloalkyl or alkoxy group is optionally substituted with one or more fluoro;

$R_3$ is selected from hydrogen, halo (e.g. fluoro, chloro or bromo), hydroxyl, cyano, trifluoromethyl, trifluoromethoxy, (1-6C)alkyl (e.g., methyl), (3-8C)cycloalkyl, or (1-4C) alkoxy (e.g., OMe), wherein an alkyl, cycloalkyl or alkoxy group is optionally substituted with one or more fluoro;

$R_4$ is selected from hydrogen, halo (e.g., fluoro, chloro or bromo), hydroxyl, cyano, trifluoromethyl, trifluoromethoxy, (1-6C)alkyl (e.g., methyl), (3-8C)cycloalkyl, or (1-4C) alkoxy (e.g., OMe), wherein an alkyl, cycloalkyl or alkoxy group is optionally substituted with one or more fluoro;

$R_5$ is selected from hydrogen or a group defined by the formula:

$—O-L_5-X_5-Q_5$;

wherein $L_5$ is absent or a linear or branched (1-4C)alkylene;

$X_5$ is absent or —C(O)O—, —O—, —C(O)—, —OC(O)—, $—CH(QR_{5L})—$, $—N(R^j)—$, $—N(R_{5L})—C(O)—$, $—N(R_{5L})—C(O)O—$, $—C(O)—N(R_{5L})—$, —S—, —SO—, $—SO_2—$, $—S(O)_2N(R_{5L})—$, or $—N(R_{5L})SO_2—$ wherein $R_{5L}$ is selected from hydrogen or methyl; and $Q_5$ is (1-6C)alkyl, (2-6C)alkenyl, (2-6C)alkynyl, (3-8C) cycloalkyl, (3-8C)cycloalkyl-(1-4C)alkyl, aryl, aryl-(1-4C)alkyl, heteroaryl, heteroaryl-(1-4C)alkyl, heterocyclyl or heterocyclyl-(1-4C)alkyl;

$R_6$ is selected from hydrogen, or a group defined by the formula:

$—O-L_6-X_6-Q_6$ wherein $L_6$ is absent or a linear or branched (1-4C)alkylene;

$X_6$ is absent or selected from —O—, —C(O)—, —C(O)O—, —OC(O)—, $—CH(OR_{6L})—$, $—N(R_{6L})$, $—N(R_{6L})—C(O)—$, $—N(R_{6L})—C(O)O—$, $—C(O)—N(R_{6L})—$, —S—, —SO—, $—SO_2—$, $—S(O)_2N(R_{6L})—$, or $—N(R_{6L})SO_2—$ wherein $R_{6L}$ is selected from hydrogen or (1-3C)alkyl;

$Q_6$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or $Q_6$ and $R_{L6}$ are linked such that, together with the nitrogen atom to which they are attached, they form a heterocyclic ring;

wherein $R_6$ is optionally substituted (e.g. substituted on $L_6$ and/or $Q_6$) with one or more (1-6C)alkyl, (1-6C)alkanoyl, $OR_{6X}$, $SR_{6X}$, $S(O)R_{6X}$, $S(O)_2R_{6X}$, $C(O)OR_{6X}$ or $C(O)NR_{6X}R'_{6X}$, wherein $R_{6X}$ and $R'_{6X}$ are independently hydrogen, (1-8C)alkyl, or $R_{6X}$ and $R'_{6X}$ are linked such that, together with the nitrogen atom to which they are attached, they form a heterocyclic ring; and $R_7$ is selected from hydrogen, (1-6C)alkoxy, or a group defined by the formula:

$—O-L_7-X_7-Q_7-$ wherein $L_7$ is absent or a linear or branched (1-4C)alkylene;

$X_7$ is absent or selected from —O—, —C(O)—, —C(O)O—, —OC(O)—, $—CH(OR_{6L})—$, $—N(R_{7L})—$, $—N(R_{7L})—C(O)—$, $—N(R_{7L})—C(O)O—$, $—C(O)—N(R_{7L})—$, —S—, —SO—, $—SO_2—$, $—S(O)_2N(R_{7L})—$, or $—N(R_{7L})SO_2—$ wherein $R_{7L}$ is selected from hydrogen or (1-3C)alkyl;

$Q_7$ is hydrogen, (1-8C)alkyl, (2-8C)alkenyl, (2-8C)alkynyl, (3-8C)cycloalkyl, (3-8C)cycloalkyl-(1-6C)alkyl, aryl, aryl-(1-6C)alkyl, heteroaryl, heteroaryl-(1-6C)alkyl, heterocyclyl, heterocyclyl-(1-6C)alkyl, or $Q_7$ and $R_{7L}$ are linked such that, together with the nitrogen atom to which they are attached, they form a heterocyclic ring;

wherein $R_7$ is optionally substituted (e.g., substituted on $L_7$ and/or $Q_7$) with one or more halo, hydroxyl, nitro, cyano, (1-8C)alkyl, (1-8C)alkanoyl, $OR_{7X}$, $SR_{7X}$, $S(O)R_{7X}$, $S(O)_2R_{7X}$, $C(O)OR_{7X}$ or $C(O)NR_{7X}R'_{7X}$, wherein $R_{7X}$ and $R'_{7X}$ are independently hydrogen, (1-8C)alkyl, or $R_{7X}$ and $R'_{7X}$ are linked such that, together with the nitrogen atom to which they are attached, they form a heterocyclic ring; or $R_7$ is optionally substituted with one or more groups selected from oxo, (1-4C)haloalkyl, (1-4C)hydroxyalkyl, $C(O)R_{7y}$ or $NR_{7y}R'_{7y}$, wherein $R_{7y}$ and $R'_{7y}$ are independently hydrogen or (1-8C)alkyl.

Additional examples of other RET kinase inhibitors include those described in International Publication No. WO2017178845, which is hereby incorporated by reference. For example, in some embodiments, the other RET inhibitor is a compound of Formula (IV) or a pharmaceutically acceptable salt thereof, wherein:

(IV)

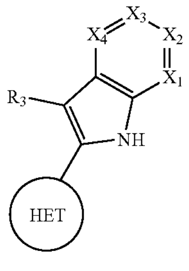

HET is selected from one of the following:

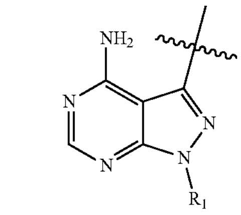
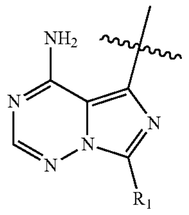
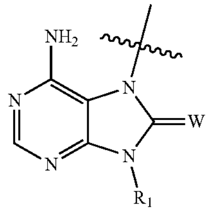
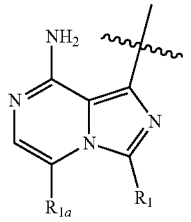
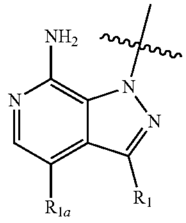
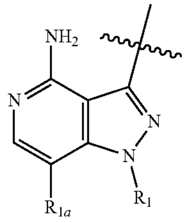
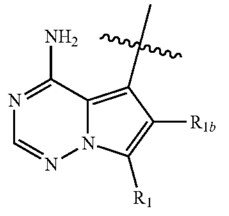
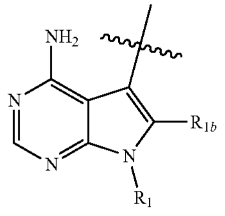
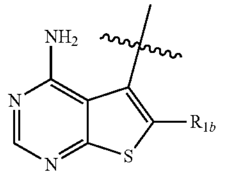
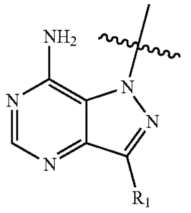
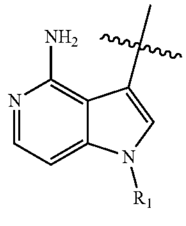
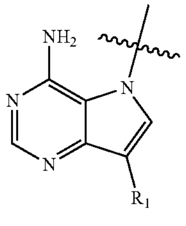

wherein

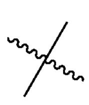

denotes the point of attachment;

$R_1$ is selected from hydrogen, (1-4C)haloalkyl, (1-4C)haloalkoxy or a group of the formula:

-L-Y-Q wherein:

L is absent or (1-5C)alkylene optionally substituted by one or more substituents selected from (1-2C)alkyl or oxo;

Y is absent or O, S, SO, $SO_2$, $N(R_a)$, C(O), C(O)O, OC(O), $C(O)N(R_a)$, $N(R_a)C(O)$, $N(R_a)C(O)N(R_b)$, $N(R_a)C(O)O$, $OC(O)N(R_a)$, $S(O)_2N(R_a)$, or $N(R_a)SO_2$, wherein $R_a$ and $R_b$ are each independently selected from hydrogen or (1-4C)alkyl; and Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_pR_c$ (where p is 0, 1 or 2), $SO_2N(R_d)R_c$, $N(R_d)SO_2R_c$, $Si(R_e)(R_d)R_c$ or $(CH_2)_qNR_cR_d$ (where q is 1, 2 or 3); wherein $R_c$, $R_d$ and $R_e$ are each independently selected from hydrogen, (1-6C)alkyl or (3-6C)cycloalkyl; or $R_c$ and $R_d$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxy; or Q is optionally substituted by a group of the formula:

$-L_1-L_{Q1}-W_1$ wherein:

$L_1$ is absent or (1-3C)alkylene optionally substituted by one or more substituents selected from (1-2C)alkyl or oxo;

$L_{Q1}$ is absent or selected from O, S, SO, $SO_2$, $N(R_f)$, C(O), C(O)O, OC(O), $C(O)N(R_f)$, $N(R_f)C(O)$, $N(R_f)C(O)N(R_g)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $W_1$ is hydrogen, (1-6C)alkyl, aryl, aryl(1-2C)alkyl, (3-8C)cycloalkyl, (3-8C)cycloalkenyl, heteroaryl or heterocyclyl; wherein $W_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_rR_h$ (where r is 0, 1 or 2), $SO_2N(R_i)R_h$, $N(R_i)SO_2R_h$ or $(CH_2)_sNR_iR_h$ (where s is 1, 2 or 3); wherein $R_h$ and $R_i$ are each independently selected from hydrogen, (1-4C)alkyl or (3-6C)cycloalkyl;

$R_{1a}$ and $R_{1b}$ are each selected from H, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;

W is selected from 0, S or $NR_{W1}$, wherein $R_{W1}$ is selected from H or (1-2C)alkyl;

$X_1$, $X_2$, $X_3$ and $X_4$ are independently selected from CH, $CR_2$ or N;

$R_2$ is selected from hydrogen, halo, (1-4C)alkyl, (1-4C)alkoxy, (1-4C)haloalkyl, (1-4C)haloalkoxy, amino, cyano, nitro, aryl, heteroaryl, heterocyclyl, cycloalkyl, (2-4C)alkynyl, $NR_jR_k$, $OR_j$, $C(O)R_j$, $C(O)OR_j$, $OC(O)R_j$, $C(O)N(R_k)R_j$, $N(R_k)C(O)R_j$, $N(R_k)C(O)N(R_j)$, $S(O)_{r1}R_k$ (where $r_1$ is 0, 1 or 2), $SO_2N(R_j)R_k$, $N(R_j)SO_2R_k$ or $(CH_2)_vNR_jR_k$ (where v is 1, 2 or 3); wherein $R_j$ and $R_k$ are each independently selected from hydrogen or (1-4C)alkyl; and wherein said (1-4C)alkyl, aryl, heteroaryl, heterocycyl or cycloalkyl is optionally substituted by one or more substituents selected from halo, (1-4C)alkyl, (1-4C)alkoxy, (1-4C)haloalkyl, (1-4C)haloalkoxy, amino, cyano, nitro, phenyl, (2-4C)alkynyl, $NR_{j1}R_{k1}$, $OR_{j1}$, $C(O)R_{j1}$, $C(O)OR_{j1}$, $OC(O)R_{j1}$, $C(O)N(R_{k1})R_{j1}$, $N(R_{k1})C(O)R_{j1}$, $S(O)_{r2}R_h$ (where $r_2$ is 0, 1 or 2), $SO_2N(R_{j1})R_{k1}$, $N(R_{j1})SO_2R_{k1}$ or $(CH_2)_{v1}NR_{j1}R_{k1}$ (where $v_1$ is 1, 2 or 3); and wherein $R_{j1}$ and $R_{k1}$ are each independently selected from hydrogen or (1-4C)alkyl; and $R_3$ is selected from halo, (1-4C)alkyl, (1-4C)alkoxy, (1-4C)haloalkyl, (1-4C)haloalkoxy, amino, cyano, nitro, (2-4C)alkynyl, $NR_lR_m$, $OR_l$, $C(O)R_l$, $C(O)OR_l$, $OC(O)R_l$, $C(O)N(R_m)R_l$, $N(R_m)C(O)R_l$, or $(CH_2)_yNR_lR_m$ (where y is 1, 2 or 3); wherein said (1-4C)alkyl is optionally substituted by one or more substituents selected from amino, hydroxy, (1-2C)alkoxy or halo; and wherein $R_l$ and $R_m$ are each independently selected from hydrogen or (1-4C)alkyl.

Additional examples of other RET kinase inhibitors include those described in International Publication No. WO2017178844, which is hereby incorporated by reference. For example, in some embodiments, the other RET inhibitor is a compound of Formula (V) or a pharmaceutically acceptable salt thereof, wherein:

(V)

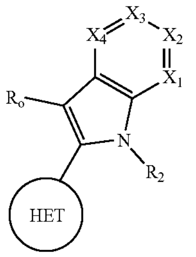

HET is selected from one of the following:

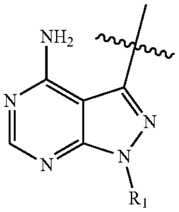
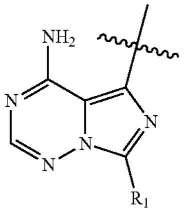
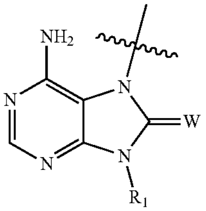
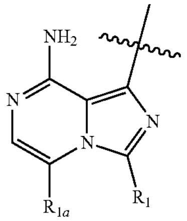
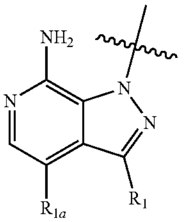
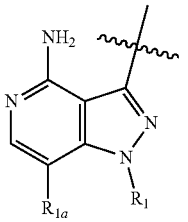

-continued

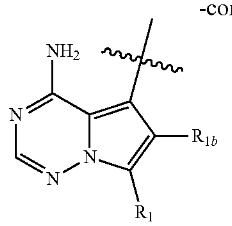
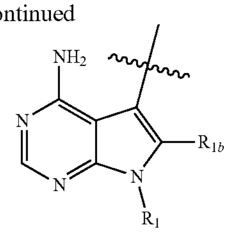
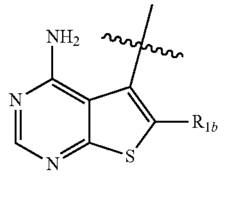
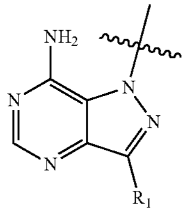
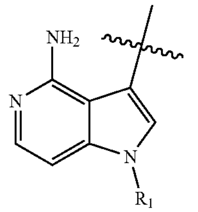
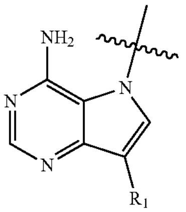

wherein

denotes the point of attachment;

$R_1$ is selected from hydrogen, (1-4C)haloalkyl, (1-4C) haloalkoxy or a group of the formula:

-L-Y-Q wherein:

L is absent or (1-5C)alkylene optionally substituted by one or more substituents selected from (1-2C)alkyl or oxo;

Y is absent or O, S, SO, $SO_2$, $N(R_a)$, C(O), C(O)O, OC(O), $C(O)N(R_a)$, $N(R_a)C(O)$, $N(R_a)C(O)N(R_b)$, $N(R_a)C(O)O$, $OC(O)N(R_a)$, $S(O)_2N(R_a)$, or $N(R_a)SO_2$, wherein $R_a$ and $R_b$ are each independently selected from hydrogen or (1-4C)alkyl; and Q is hydrogen, (1-6C)alkyl, (2-6C)alkenyl, (2-6C)alkynyl, aryl, (3-10C)cycloalkyl, (3-10C)cycloalkenyl, heteroaryl or heterocyclyl; wherein Q is optionally further substituted by one or more substituent groups independently selected from (1-4C)alkyl, halo, (1-4C)haloalkyl, (1-4C)haloalkoxy, amino, (1-4C)aminoalkyl, cyano, hydroxy, carboxy, carbamoyl, sulphamoyl, mercapto, ureido, $NR_cR_d$, $OR_c$, $C(O)R_c$, $C(O)OR_c$, $OC(O)R_c$, $C(O)N(R_d)R_c$, $N(R_d)C(O)R_c$, $S(O)_yR_c$ (where y is 0, 1 or 2), $SO_2N(R_d)R_c$, $N(R_d)SO_2R_c$, $Si(R_d)(R_c)R_e$ or $(CH_2)_zNR_cR_d$ (where z is 1, 2 or 3); wherein $R_c$, $R_d$ and $R_e$ are each independently selected from hydrogen, (1-6C)alkyl or (3-6C)cycloalkyl; or $R_c$ and $R_d$ can be linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl; or Q is optionally substituted by a group of the formula:

$-L_1-L_{Q1}-Z_1$ wherein:

$L_1$ is absent or (1-3C)alkylene optionally substituted by one or more substituents selected from (1-2C)alkyl or oxo;

$L_{Q1}$ is absent or selected from O, S, SO, $SO_2$, $N(R_f)$, C(O), C(O)O, OC(O), $C(O)N(R_f)$, $N(R_f)C(O)$, $N(R_g)C(O)N(R_f)$, $N(R_f)C(O)O$, $OC(O)N(R_f)$, $S(O)_2N(R_f)$, or $N(R_f)SO_2$, wherein $R_f$ and $R_g$ are each independently selected from hydrogen or (1-2C)alkyl; and $Z_1$ is hydrogen, (1-6C)alkyl, aryl, aryl(1-2C)alkyl, (3-8C)cycloalkyl, (3-8C)cycloalkenyl, heteroaryl or heterocyclyl; wherein $Z_1$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_hR_i$, $OR_h$, $C(O)R_h$, $C(O)OR_h$, $OC(O)R_h$, $C(O)N(R_i)R_h$, $N(R_i)C(O)R_h$, $S(O)_{ya}R_h$ (where $y^a$ is 0, 1 or 2), $SO_2N(R_i)R_h$, $N(R_i)SO_2R_h$ or $(CH_2)_{za}NR_iR_h$ (where $z^a$ is 1, 2 or 3); wherein $R_h$ and $R_i$ are each independently selected from hydrogen, (1-4C)alkyl or (3-6C)cycloalkyl;

$R_{1a}$ and $R_{1b}$ are each selected from hydrogen, (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl or mercapto;

W is selected from O, So r $NR_j$, wherein $R_j$ is selected from H or (1-2C)alkyl;

$X_1$ and $X_2$ are each independently selected from N or $CR_k$; wherein $R_k$ is selected from hydrogen, halo, (1-4C)alkyl, (1-4C)alkoxy, amino, (1-4C)alkylamino, (1-4C)dialkylamino, cyano, (2C)alkynyl, $C(O)R_{k1}$, $C(O)OR_{k1}$, $OC(O)R_{k1}$, $C(O)N(R_{k2})R_{k1}$, $N(R_{k2})C(O)R_{k1}$, $S(O)_{yb}R_{k1}$ (where $y^b$ is 0, 1 or 2), $SO_2N(R_{k2})R_{k1}$, $N(R_{k2})SO_2R_{k1}$ or $(CH_2)_{zb}NR_{k1}R_{k2}$ (where $z^b$ is 1, 2 or 3); wherein said (1-4C)alkyl is optionally substituted by one or more substituents selected from amino, hydroxy, (1-2C)alkoxy or halo; and $R_{k1}$ and $R_{k2}$ are each independently selected from hydrogen or (1-4C)alkyl;

$X_3$ is selected from N or $CR_m$;

wherein $R_m$ is selected from hydrogen, halo, (1-4C)alkyl, (1-4C)alkoxy, amino, (1-4C)alkylamino, (1-4C)dialkylamino, cyano, (2C)alkynyl, $C(O)R_{m1}$, $C(O)OR_{m1}$, $OC(O)R_{m1}$, $C(O)N(R_{m2})R_{m1}$, $N(R_{m2})C(O)R_{m1}$, $S(O)_{yc}R_{m1}$ (where $y^c$ is 0, 1 or 2), $SO_2N(R_{m2})R_{m1}$, $N(R_{m2})SO_2R_{m1}$ or $(CH_2)_{zc}NR_{m1}R_{m2}$ (where zc is 1, 2 or 3); wherein said (1-4C)alkyl is optionally substituted by one or more substituents selected from amino, hydroxy, (1-2C)alkoxy or halo; and $R_{m1}$ and $R_{m2}$ are each independently selected from hydrogen or (1-4C)alkyl;

$R_o$ is selected from halo, (1-4C)alkyl, (1-4C)alkoxy, amino, (1-4C)alkylamino, (1-4C)dialkylamino, cyano, (2C)alkynyl, $C(O)R_{o1}$, $C(O)OR_{o1}$, $OC(O)R_{o1}$, $C(O)N(R_{o2})R_{o1}$, $N(R_{o2})C(O)R_{o1}$, $S(O)_{yd}R_{o1}$ (where $y^d$ is 0, 1 or 2), $SO_2N(R_{o2})R_{o1}$, $N(R_{o2})SO_2R_{o1}$ or $(CH_2)_{zd}NR_{o1}R_{o2}$ (where $z^d$ is 1, 2 or 3); wherein said (1-4C)alkyl is optionally substituted by one or more substituents selected from amino, hydroxy, (1-2C)alkoxy or halo; and $R_{o1}$ and $R_{o2}$ are each independently selected from hydrogen or (1-4C)alkyl;

$R_2$ is selected from hydrogen, (1-4C)alkyl or a group of the formula:

$-L_2-Y_2-Q_2$ wherein:

$L_2$ is absent or (1-3C)alkylene optionally substituted by one or more substituents selected from (1-2C)alkyl or oxo;

$Y_2$ is absent or C(O), C(O)O, $C(O)N(R_p)$, wherein $R_p$ is selected from hydrogen or (1-4C)alkyl; and $Q_2$ is hydrogen, (1-6C)alkyl, aryl, (3-8C)cycloalkyl, (3-8C)cycloalkenyl, heteroaryl or heterocyclyl; wherein $Q_2$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_qR_r$, $OR_q$, wherein $R_q$ and $R_r$ are each independently selected from hydrogen, (1-4C)alkyl or (3-6C)cycloalkyl; $R_3$ is selected from a group of the formula:

$—Y_3-Q_3$ wherein:

$Y_3$ is C(O), $C(O)N(R_y)$, $C(O)N(R_y)O$, $N(R_y)(O)C$, C(O)O, OC(O), $N(R_y)C(O)N(R_{y1})$, $SO_2N(R_y)$, $N(R_y)SO_2$, oxazolyl, triazolyl, oxadiazolyl, thiazolyl, imidazolyl, thiadiazolyl, pyridinyl, pyrazolyl, pyrrolyl or tetrazolyl, wherein $R_y$ and $R_{y1}$ are independently selected from hydrogen or (1-2C)alkyl; and $Q_3$ is hydrogen, (1-6C)alkyl, aryl, aryl(1-2C)alkyl, (3-8C)cycloalkyl, (3-8C)cycloalkenyl, heteroaryl or heterocyclyl; wherein $Q_3$ is optionally further substituted by one or more substituent groups independently selected from (1-4C)alkyl, halo, (1-4C)haloalkyl, (1-4C)haloalkoxy, amino, cyano, hydroxy, carboxy, carbamoyl, sulphamoyl, $NR_zR_{aa}$, $OR_z$, wherein $R_z$ and $R_{aa}$ are each independently selected from hydrogen, (1-4C)alkyl or (3-6C)cycloalkyl; or $Q_3$ is optionally substituted by a group of the formula:

$-L_4-L_{Q4}-Z_4$ wherein:

$L_4$ is absent or (1-3C)alkylene optionally substituted by one or more substituents selected from (1-2C)alkyl or oxo;

$L_{Q4}$ is absent or selected from or O, S, SO, $SO_2$, $N(R_{ab})$, C(O), C(O)O, OC(O), $C(O)N(R_{ab})$, $N(R_{ab})C(O)$, $N(R_{ac})C(O)N(R_{ab})$, $N(R_{ab})C(O)O$, $OC(O)N(R_{ab})$, $S(O)_2N(R_{ab})$, or $N(R_{ab})SO_2$, wherein $R_{ab}$ and $R_{ac}$ are each independently selected from hydrogen or (1-2C)alkyl; and $Z_4$ is hydrogen, (1-6C)alkyl, aryl, aryl(1-2C)alkyl, (3-8C)cycloalkyl, (3-8C)cycloalkenyl, heteroaryl or heterocyclyl; wherein $Z_4$ is optionally substituted by one or more substituents selected from (1-4C)alkyl, halo, (1-4C)haloalkyl, (1-4C)haloalkoxy, (1-4C)alkoxy, (1-4C)alkylamino, amino, cyano, hydroxy, carboxy, carbamoyl, sulphamoyl, mercapto, ureido, aryl, heteroaryl, heterocycyl, (3-6C)cycloalkyl, $NR_{ad}R_{ae}$, $OR_{ad}$, $C(O)R_{ad}$, $C(O)OR_{ad}$, $OC(O)R_{ad}$, $C(O)N(R_{ae})R_{ad}$, $N(R_{ae})C(O)R_{ad}$, $S(O)_{ye}R_{ad}$ (where $y^e$ is 0, 1 or 2), $SO_2N(R_{ae})R_{ad}$, $N(R_{ae})SO_2R_{ad}$ or $(CH_2)_{ze}NR_{ad}R_{ae}$ (where $z^e$ is 1, 2 or 3); wherein $R_{ad}$ and $R_{ae}$ are each independently selected from hydrogen, (1-4C)alkyl or (3-6C)cycloalkyl; or $Q_3$ and $R_y$ are linked such that, together with the nitrogen atom to which they are attached, they form a 4-7 membered heterocyclic ring which is optionally substituted by one or more substituents selected from (1-4C)alkyl, halo, (1-4C)haloalkyl, (1-4C)haloalkoxy, (1-4C)alkoxy, (1-4C)alkylamino, amino, cyano or hydroxyl;

with the proviso that only one or two of $X_1$, $X_2$ or $X_3$ can be N.

Additional examples of other RET kinase inhibitors include those described in International Publication No. WO 2017145050, which is hereby incorporated by reference. For example, in some embodiments, the other RET has the Formula (VI) or is a pharmaceutically acceptable salt thereof.

(VI)

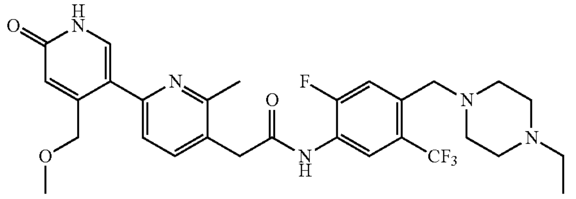

Additional examples of other RET kinase inhibitors include those described in International Publication No. WO 2016038552 is hereby incorporated by reference. For example, in some embodiments, the other RET has the Formula (VII), or the Formula (VIII), or is a pharmaceutically acceptable salt thereof.

(VII)

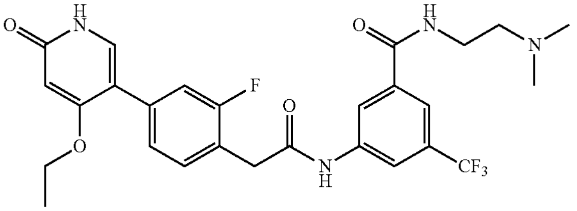

(VIII)

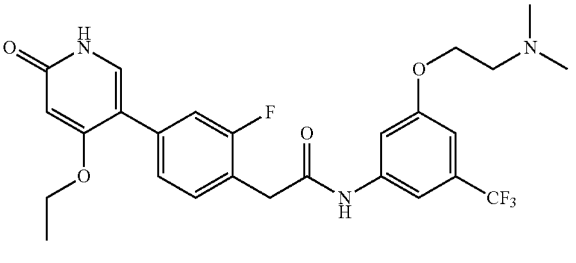

Yet other therapeutic agents include RET inhibitors such as those described, for example, in U.S. Pat. Nos. 9,738,660; 9,801,880; 9,682,083; 9,789,100; 9,550,772; 9,493,455; 9,758,508; 9,604,980; 9,321,772; 9,522,910; 9,669,028; 9,186,318; 8,933,230; 9,505,784; 8,754,209; 8,895,744; 8,629,135; 8,815,906; 8,354,526; 8,741,849; 8,461,161; 8,524,709; 8,129,374; 8,686,005; 9,006,256; 8,399,442; 7,795,273; 7,863,288; 7,465,726; 8,552,002; 8,067,434; 8,198,298; 8,106,069; 6,861,509; 8,299,057; 9,150,517; 9,149,464; 8,299,057; and 7,863,288; U.S. Publication Nos. 2018/0009817; 2018/0009818; 2017/0283404; 2017/0267661; 2017/0298074; 2017/0114032; 2016/0009709; 2015/0272958; 2015/0238477; 2015/0099721; 2014/0371219; 2014/0137274; 2013/0079343; 2012/0283261; 2012/0225057; 2012/0065233; 2013/0053370; 2012/0302567; 2011/0189167; 2016/0046636; 2013/0012703; 2011/0281841; 2011/0269739; 2012/0271048; 2012/0277424; 2011/0053934; 2011/0046370; 2010/0280012; 2012/0070410; 2010/0081675; 2010/0075916; 2011/0212053; 2009/0227556; 2009/0209496; 2009/0099167; 2010/0209488; 2009/0012045; 2013/0303518; 2008/0234267; 2008/0199426; 2010/0069395; 2009/0312321; 2010/0173954; 2011/0195072; 2010/0004239; 2007/0149523; 2017/0281632; 2017/0226100; 2017/0121312; 2017/0096425; 2017/0044106; 2015/0065468; 2009/0069360; 2008/0275054; 2007/0117800; 2008/0234284; 2008/0234276; 2009/0048249; 2010/0048540; 2008/0319005; 2009/0215761; 2008/0287427; 2006/0183900; 2005/0222171; 2005/0209195; 2008/0262021; 2008/0312192; 2009/0143399; 2009/0130229; 2007/0265274; 2004/0185547; and 2016/0176865; and International Publication Nos. WO 2017/145050; WO 2017/097697; WO 2017/049462; WO 2017/043550; WO 2017/027883; WO 2017/013160; WO 2017/009644; WO 2016/168992; WO 2016/137060; WO 2016/127074; WO 2016/075224; WO 2016/038552; WO 2015/079251; WO 2014/086284; WO 2013/042137; WO 2013/036232; WO 2013/016720; WO 2012/053606; WO 2012/047017; WO 2007/109045; WO 2009/042646; WO 2009/023978; WO 2009/017838; WO 2017/178845; WO 2017/178844; WO 2017/146116; WO 2017/026718; WO 2016/096709; WO 2007/057397; WO 2007/057399; WO 2007/054357; WO 2006/130613; WO 2006/089298; WO 2005/070431; WO 2003/020698; WO 2001/062273; WO 2001/016169; WO 1997/044356; WO 2007/087245; WO 2005/044835; WO 2014/075035; and WO 2016/038519; and *J. Med. Chem.* 2012, 55 (10), 4872-4876, all of which are hereby incorporated by reference in their entireties.

In some embodiments, a RET inhibitor (e.g., a first RET inhibitor or a second RET inhibitor) is a compound of the Formula II:

II

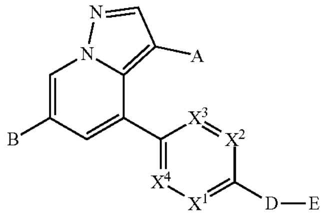

or a pharmaceutically acceptable salt or solvate thereof, wherein:

$X^1$ is CH, $CCH_3$, CF, CCl or N;

$X^2$ is CH, CF or N;

$X^3$ is CH, CF or N;

$X^4$ is CH, CF or N;

wherein zero, one or two of $X^1$, $X^2$, $X^3$ and $X^4$ is N;

A is H, Cl, CN, Br, $CH_3$, $CH_2CH_3$ or cyclopropyl;

B is $hetAr^1$;

$hetAr^1$ is a 5-membered heteroaryl ring having 1-3 ring heteroatoms independently selected from N, S and O, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)$CH_2$C(═O)—, (C1-C4 alkoxy)C(═O)C1-C3 alkyl, C3-C6 cycloalkyl, ($R^aR^b$N)C1-C6 alkyl, ($R^aR^b$N)C(═O)C1-C6 alkyl, (C1-C6 alkyl$SO_2$)C1-C6 alkyl, hetCyc$^a$, and 4-methoxybenzyl;

$R^a$ and $R^b$ are independently H or C1-C6 alkyl;

hetCyc$^a$ is a 4-6 membered heterocyclic ring having a ring heteroatom selected from N and O, wherein said heterocyclic ring is optionally substituted with halogen, C1-C6 alkyl, fluoroC1-C6 alkyl, difluoroC1-C6 alkyl, trifluoroC1-C6 alkyl, (C1-C6 alkoxy)C1-C6 alkyl, di(C1-C3 alkyl)N$CH_2$C(═O), (C1-C6 alkoxy)C(═O) or (C1-C6 alkoxy)$CH_2$C(═O);

D is hetCyc$^1$, hetCyc$^2$, hetCyc$^3$ or hetCyc$^9$;

hetCyc$^1$ is a 4-6 membered heterocyclic ring having 1-2 ring atoms selected from N and O, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group; hetCyc$^2$ is a 7-8 membered bridged heterocyclic ring having 1-3 ring heteroatoms independently selected from N and O, wherein said heterocyclic ring is optionally substituted with C1-C3 alkyl;

hetCyc$^3$ is a 7-11 membered heterospirocyclic ring having 1-2 ring heteroatoms independently selected from N and O, wherein said ring is optionally substituted with C1-C3 alkyl;

hetCyc$^9$ is a fused 9-10 membered heterocyclic ring having 1-3 ring nitrogen atoms and optionally substituted with oxo;

E is (a) hydrogen, (b) OH, (c) $R^aR^b$N—, wherein $R^a$ is H or C1-C6 alkyl and $R^b$ is H, C1-C6 alkyl or phenyl;

(d) C1-C6 alkyl optionally substituted with one to three fluoros, (e) hydroxyC1-C6 alkyl- optionally substituted with one to three fluoros, (f) C1-C6 alkoxy optionally substituted with one to three fluoros, (g) hydroxy(C1-C6 alkoxy) optionally substituted with one to three fluoros, (h) (C1-C6 alkoxy)hydroxy C1-C6 alkyl- optionally substituted with one to three fluoros, (i) (C1-C6 alkyl)C(═O)— optionally substituted with one to three fluoros, (j) (hydroxy C1-C6 alkyl)C(═O)— optionally substituted with one to three fluoros, (k) (C1-C6 alkoxy)C(═O)—, (l) (C1-C6 alkoxy)(C1-C6 alkyl)C(═O)—, (m) HC(═O)—, (n) Cyc$^1$, (o) Cyc$^1$C(═O)—, (p) Cyc$^1$(C1-C6 alkyl)C(═O)— wherein said alkyl portion is optionally substituted with one or more groups independently selected from the group consisting of OH, fluoro, C1-C3 alkoxy and $R^cR^d$N—, where R and $R^d$ are independently H or C1-C6 alkyl, (q) hetCyc$^4$, (r) hetCyc$^4$C(═O)—, (s) hetCyc$^4$(C1-C3 alkyl)C(═O)—, (t) (hetCyc$^4$)C(═O)C1-C2 alkyl-, (u) hetCyc$^4$C(═O)NH—, (v) $Ar^2$, (w) $Ar^2$C(═O)—, (x) $Ar^2$C1-C6 alkyl-, (y) ($Ar^2$)hydroxy C2-C6 alkyl-, (z) $Ar^2$(C1-C3 alkyl)C(═O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^f$N—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O, (aa) hetAr$^2$C(═O)—, (bb) (hetAr$^2$)hydroxyC2-C6 alkyl-, (cc) hetAr$^2$(C1-C3 alkyl)C(═O)—, wherein said alkyl portion is optionally substituted with one or two groups independently selected from the group consisting of OH, C1-C6 alkyl, hydroxyC1-C6 alkyl, C1-C6 alkoxy and $R^eR^f$N—, wherein $R^e$ and $R^f$ are independently H or C1-C6 alkyl or $R^e$ and $R^f$ together with the nitrogen to which they are attached form a 5-6 membered azacyclic ring optionally having an additional ring heteroatom selected from N and O, (dd) $R^1R^2$NC(═O)—, (ee) $R^1R^2$N(C1-C3 alkyl)C(═O)—, wherein said alkyl portion is optionally substituted with phenyl, (ff) $R^1R^2$NC(═O)C1-C2 alkyl-, (gg) $R^1R^2$NC(═O)NH—, (hh) $CH_3SO_2$(C1-C6 alkyl)C(═O)—, (ii) (C1-C6 alkyl)$SO_2$—, (jj) (C3-C6 cycloalkyl)$CH_2SO_2$—, (kk) hetCyc$^5$-$SO_2$—, (ll) $R^4R^5NSO_2$—, (mm) $R^6$C(═O)NH—, (nn) hetCyc$^6$, (oo) hetAr$^2$C1-C6 alkyl-, (pp) (hetCyc$^4$)C1-C6 alkyl-, (qq) (C1-C6 alkoxy)C1-C6 alkyl- optionally substituted with 1-3 fluoros, (rr) (C3-C6 cycloalkoxy)C1-C6 alkyl-, (ss) (C3-C6 cycloalkyl)C1-C6 alkyl-, wherein said cycloalkyl is optionally substituted with 1-2 fluoros, (tt) ($R^gR^h$N)C1-C6 alkyl-, wherein $R^g$ and $R^h$ are independently H or C1-C6 alkyl, (uu) $Ar^2$—O—, (vv) (C1-C6 alkyl$SO_2$)C1-C6 alkyl-, (ww) (C1-C6 alkoxy)C(═O)NHC1-C6 alkyl-, (xx) (C3-C6 cycloalkoxy)C(═O)—, (yy) (C3-C6 cycloalkyl)$SO_2$—, wherein said cycloalkyl is optionally substituted with C1-C6 alkyl, (zz) $Ar^4CH_2$OC(═O)—, (aaa) (N—(C1-C3 alkyl)pyridinonyl)C1-C3 alkyl-, and (bbb) ($Ar^4SO_2$)C1-C6 alkyl-;

Cyc$^1$ is a C3-C6 cycloalkyl, wherein (a) said cycloalkyl is optionally substituted with one or more substituents independently selected from the group consisting of OH, halogen, C1-C6 alkoxy, CN, hydroxyC1-C6 alkyl, (C1-C6 alkoxy)C1-C6 alkyl, and C1-C6 alkyl optionally substituted with 1-3 fluoros, or (b) said cycloalkyl is substituted with phenyl, wherein said phenyl is optionally substituted with one or more substituents independently selected from the group consisting of halogen, C1-C3 alkyl, C1-C3 alkoxy and CF, or (c) said cycloalkyl is substituted with a 5-6 membered heteroaryl ring having 1-3 ring heteroatoms independently selected from N and O, wherein said heteroaryl ring is optionally substituted with one or more substituents independently selected from the group consisting of halogen, C1-C3 alkyl, C1-C3 alkoxy and $CF_3$;

$Ar^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and $R^iR^jN$— wherein $R^i$ and $R^j$ are independently H or C1-C6 alkyl;

$hetAr^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;

$hetCyc^4$ is (a) a 4-6 membered heterocyclic ring having 1-2 ring heteroatoms independently selected from N, O and S wherein said S is optionally oxidized to $SO_2$, (b) a 7-8 membered bridged heterocyclic ring having 1-2 ring heteroatoms independently selected from N and O, (c) a 6-12 membered fused bicyclic heterocyclic ring having 1-2 ring heteroatoms independently selected from N and O and optionally independently substituted with 1-2 C1-C6 alkyl substitutents, or (d) a 7-10 membered spirocyclic heterocyclic ring having 1-2 ring heteroatoms independently selected from N and O, wherein each of said heterocyclic rings is optionally substituted with one or more substituents independently selected from the group consisting of halogen, OH, CN, C1-C6 alkyl (optionally substituted with 1-3 fluoros), C1-C6 alkoxy, (C1-C6 alkoxy)C1-C6 alkyl, (C3-C6)cycloalkyl, (C1-C6 alkyl)C(═O)—, a 5-6 membered heterocyclic ring having 1-2 ring heteroatoms independently selected from N and O, and phenyl wherein said phenyl is optionally substituted with one or more substituents selected from halogen, C1-C6 alkyl and C1-C6 alkoxy;

$hetCyc^5$ is a 5-6 membered heterocyclic ring having a ring heteroatom selected from O and N;

$hetCyc^6$ is a 5 membered heterocyclic ring having one or two ring heteroatoms independently selected from N and O, wherein said ring is substituted with oxo and wherein said ring is further optionally substituted with one or more substituents independently selected from the group consisting of OH and C1-C6 alkyl;

$R^1$ is H, C1-C6 alkyl or (C1-C6 alkoxy)C1-C6 alkyl;

$R^2$ is H, C1-C6 alkyl (optionally substituted with 1-3 fluoros), (C1-C6 alkoxy)C1-C6 alkyl (optionally substituted with 1-3 fluoros), $Cyc^3$, hydroxyC1-C6 alkyl (optionally substituted with 1-3 fluoros), C1-C6 alkoxy (optionally substituted with 1-3 fluoros), (C1-C6 alkoxy)C(═O), $hetCyc^7$, $Ar^3$, $Ar^3$C1-C3 alkyl-, hydroxyC1-C6 alkoxy or (3-6C cycloalkyl)$CH_2O$—;

$Cyc^3$ is a 3-6 membered carbocyclic ring optionally substituted with 1-2 groups independently selected from the group consisting of C1-C6 alkoxy, OH and halogen;

$hetCyc^7$ is a 5-6 membered heterocyclic ring having a ring heteroatom selected from O and N wherein said ring is optionally substituted with C1-C6 alkyl;

$Ar^3$ is phenyl optionally substituted with one or more substituents independently selected from halogen, C1-C3 alkyl, C1-C3 alkoxy, fluoroC1-C3 alkyl, difluoroC1-C3 alkyl and trifluoroC1-C3 alkyl;

$R^4$ and $R^5$ are independently H or C1-C6 alkyl;

$R^6$ is C1-C6 alkyl, hydroxyC1-C6 alkyl, C1-C6 alkoxy, (C1-C6 alkoxy)C1-C6 alkyl, phenyl or $hetCyc^8$;

$hetCyc^8$ is a 5-6 membered heterocyclic ring having a ring heteroatom selected from O and N, wherein said heterocyclic ring is optionally substituted with C1-C6 alkyl; and $Ar^4$ is phenyl optionally substituted with one or more halogens.

In some embodiments, a RET inhibitor (e.g., a first RET inhibitor or a second RET inhibitor) is a compound of the Formula III:

III

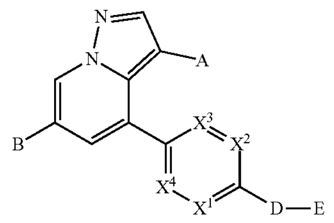

or a pharmaceutically acceptable salt or solvate thereof, wherein:

$X^1$ is CH or N;

$X^2$ is CH or N;

$X^3$ is CH or N;

$X^4$ is CH or N;

wherein one or two of $X^1$, $X^2$, $X^3$ and $X^4$ is N;

A is CN;

B is $hetAr^1$;

$hetAr^1$ is a 5-membered heteroaryl ring having 1-3 ring nitrogen atoms, wherein said heteroaryl ring is optionally substituted with one or more substituents independently selected from the group consisting of halogen, C1-C6 alkyl, hydroxyC1-C6 alkyl, fluoroC1-C6 alkyl, difluoroC1-C6 alkyl, trifluoroC1-C6 alkyl, cyanoC1-C6 alkyl, (C1-C6 alkoxy)C1-C6 alkyl, (C1-C4 alkoxy)$CH_2C$(═O)—, (C1-C4 alkoxy)C(═O)C1-C3 alkyl, C3-C6 cycloalkyl, ($R^aR^b$N)C1-C6 alkyl, ($R^aR^b$N)C(═O)C1-C6 alkyl, (C1-C6 alkyl$SO_2$)C1-C6 alkyl, and 4-methoxybenzyl;

$R^a$ and $R^b$ are independently H or C1-C6 alkyl;

D is $hetCyc^1$;

$hetCyc^1$ is a 4-6 membered heterocyclic ring having 1-2 ring nitrogen atoms, wherein said heterocyclic ring is optionally substituted with one or more substituents independently selected from the group consisting of C1-C3 alkyl, fluoroC1-C3 alkyl, difluoroC1-C3 alkyl, trifluoroC1-C3 alkyl and OH, or said heterocyclic ring is substituted with a C3-C6 cycloalkylidene ring, or said heterocyclic ring is substituted with an oxo group;

E is (w) $Ar^2$C(═O)—, (x) $Ar^2$C1-C6 alkyl-, (z) $Ar^2$(C1-C3 alkyl)C(═O)— wherein said alkyl portion is optionally substituted with one or two groups independently selected from the group consisting of OH, C1-C6 alkyl (optionally substituted with 1-3 fluoros), hydroxyC1-C6 alkyl, C1-C6 alkoxy and $R^eR^f$N—, where $R^e$ and $R^f$ are independently H or C1-C6 alkyl, or $R^e$ and $R^f$ together with the nitrogen to which they are attached form a 5-6 membered azacyclic ring optionally having an additional ring heteroatom selected from N and O, (cc) $hetAr^2$(C1-C3 alkyl)C(═O)—, wherein said alkyl portion is optionally substituted with one or two groups independently selected from the group consisting of OH, C1-C6 alkyl, hydroxyC1-C6 alkyl, C1-C6 alkoxy and $R^eR^fN$—, wherein $R^e$ and $R^f$ are independently H or C1-C6 alkyl or $R^e$ and $R^f$ together with the nitrogen to which they are attached form a 5-6 membered azacyclic ring optionally having an additional ring heteroatom selected from N and O, (dd) $R^1R^2NC(=O)$—, (oo) $hetAr^2$C1-C6 alkyl-, $Ar^2$ is phenyl optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, CN, a 5-6 membered heterocyclic ring having 1-2 ring heteroatoms independently selected from N and O, and $R^iR^jN$— wherein $R^i$ and $R^j$ are independently H or C1-C6 alkyl;

$hetAr^2$ is a 5-6 membered heteroaryl ring having 1-3 ring heteroatoms independently selected from N, O and S and optionally substituted with one or more substituents independently selected from the group consisting of halogen, C1-C6 alkyl, C1-C6 alkoxy (optionally substituted with 1-3 fluoros), fluoroC1-C6 alkyl, difluoroC1-C6 alkyl, trifluoroC1-C6 alkyl, hydroxyC1-C6 alkyl, (C3-C6)cycloalkyl, (C1-C6 alkoxy)C1-C6 alkyl, CN, OH, and R'R"N—, wherein R' and R" are independently H or C1-C3 alkyl;

$R^1$ is H, C1-C6 alkyl or (C1-C6 alkoxy)C1-C6 alkyl; and $R^2$ is H, C1-C6 alkyl (optionally substituted with 1-3 fluoros), (C1-C6 alkoxy)C1-C6 alkyl (optionally substituted with 1-3 fluoros), hydroxyC1-C6 alkyl (optionally substituted with 1-3 fluoros), C1-C6 alkoxy (optionally substituted with 1-3 fluoros), (C1-C6 alkoxy)C(=O), hydroxyC1-C6 alkoxy or (3-6C cycloalkyl)$CH_2O$.

In some embodiments, a RET inhibitor (e.g., a first RET inhibitor or a second RET inhibitor) is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of the Formula IV:

IV

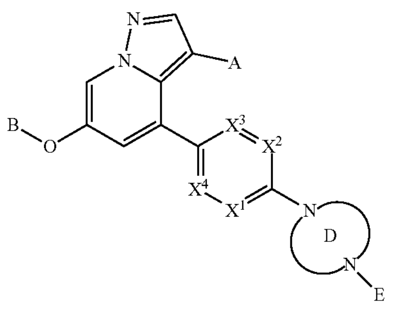

or a pharmaceutically acceptable salt or solvate thereof, wherein:

$X^1$, $X^2$, $X^3$ and $X^4$ are independently CH, CF, $CCH_3$ or N, wherein zero, one or two of $X^1$, $X^2$, $X^3$ and $X^4$ is N;

A is H, CN, Cl, $CH_3$—, $CH_3CH_2$—, cyclopropyl, —$CH_2CN$ or —$CH(CN)CH_3$;

B is (a) hydrogen, (b) C1-C6 alkyl optionally substituted with 1-3 fluoros, (c) hydroxyC2-C6 alkyl-, wherein the alkyl portion is optionally substituted with 1-3 fluoros or a C3-C6 cycloalkylidene ring, (d) dihydroxyC3-C6 alkyl-, wherein the alkyl portion is optionally substituted with a C3-C6 cycloalkylidene ring, (e) (C1-C6 alkoxy)C1-C6 alkyl- optionally substituted with 1-3 fluoros, (f) $(R^1R^2N)$C1-C6 alkyl- wherein said alkyl portion is optionally substituted with OH and wherein $R^1$ and $R^2$ are independently H or C1-C6 alkyl (optionally substituted with 1-3 fluoros);

(g) $hetAr^1$C1-C3 alkyl-, wherein $hetAr^1$ is a 5-6 membered heteroaryl ring having 1-3 ring heteroatoms independently selected from N, O and S and is optionally substituted with one or more independently selected C1-C6 alkyl substituents;

(h) (C3-C6 cycloalkyl)C1-C3 alkyl-, wherein said cycloalkyl is optionally substituted with OH, (i) $(hetCyc^a)$C1-C3 alkyl-, (j) $hetCyc^a$-, (k) C3-C6 cycloalkyl-, wherein said cycloalkyl is optionally substituted with OH, (l) (C1-C4 alkyl)C(=O)O—C1-C6 alkyl-, wherein each of the C1-C4 alkyl and C1-C6 alkyl portions is optionally and independently substituted with 1-3 fluoros, or (m) $(R^1R^2N)C(=O)$C1-C6 alkyl-, wherein $R^1$ and $R^2$ are independently H or C1-C6 alkyl (optionally substituted with 1-3 fluoros);

$hetCyc^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(=O)—, (C1-C6 alkoxy)C1-C6 alkyl-, and fluoro, or wherein $hetCyc^a$ is substituted with oxo;

Ring D is (i) a saturated 4-7 membered heterocyclic ring having two ring nitrogen atoms, (ii) a saturated 7-8 membered bridged heterocyclic ring having two ring nitrogen atoms and optionally having a third ring heteroatom which is oxygen, (iii) a saturated 7-11 membered heterospirocyclic ring having two ring nitrogen atoms, or (iv) a saturated 9-10 membered bicyclic fused heterocyclic ring having two ring nitrogen atoms, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is (a) hydrogen, (b) C1-C6 alkyl optionally substituted with 1-3 fluoros, (c) (C1-C6 alkoxy)C1-C6 alkyl- optionally substituted with 1-3 fluoros, (d) (C1-C6 alkyl)C(=O)—, wherein said alkyl portion is optionally substituted with 1-3 fluoros or with a $R^gR^hN$— substituent wherein $R^g$ and $R^h$ are independently H or C1-C6 alkyl, (e) (hydroxyC2-C6 alkyl)C(=O)— optionally substituted with 1-3 fluoros, (f) (C1-C6 alkoxy)C(=O)—, (g) (C3-C6 cycloalkyl)C(=O)—, wherein said cycloalkyl is optionally substituted with one or more substituents independently selected from C1-C6 alkyl, C1-C6 alkoxy, OH, and (C1-C6 alkoxy)C1-C6 alkyl-, or said cycloalkyl is substituted with a 5-6 membered heteroaryl ring having 1-3 ring heteroatoms independently selected from N and O, (h) $Ar^1$C1-C6 alkyl-, (i) $Ar^1$(C1-C6 alkyl)C(=O)—, wherein said alkyl portion is optionally substituted with OH, hydroxyC1-C6 alkyl-, C1-C6 alkoxy, $R^{m}R^{n}N$— or $R^{m}R^{n}N$—$CH_2$—, wherein each $R^m$ and $R^n$ is independently H or C1-C6 alkyl, (j) $hetAr^2$C1-C6 alkyl-, wherein said alkyl portion is optionally substituted with 1-3 fluoros, (k) $hetAr^2$(C1-C6 alkyl)C(=O)— wherein said alkyl portion is optionally substituted with OH, hydroxyC1-C6 alkyl- or C1-C6 alkoxy, (l) $hetAr^2$C(=O)—, (m) $hetCyc^1$C(=O)—, (n) $hetCyc^1$C1-C6 alkyl-, (o) $R^3R^4$NC(=O)—, (p) $Ar^1N(R^3)$C(=O)—, (q) $hetAr^2N(R^3)$C(=O)—, (r) (C1-C6 alkyl)$SO_2$—, wherein the alkyl portion is optionally substituted with 1-3 fluoros, (s) $Ar^1SO_2$—, (t) $hetAr^2SO_2$—, (u) N—(C1-C6 alkyl)pyridinonyl, (v) $Ar^1$C(=O)—;

(w) $Ar^1$O—C(=O)—, (x) (C3-C6 cycloalkyl)(C1-C6 alkyl)C(=O)—, (y) (C3-C6 cycloalkyl)(C1-C6 alkyl)$SO_2$—, wherein the alkyl portion is optionally substituted with 1-3 fluoros, (z) $Ar^1$(C1-C6 alkyl)$SO_2$—, (aa) $hetCyc^1$-O—C(=O)—, (bb) $hetCyc^1CH_2$C(=O)—, (cc) $hetAr^2$, or (dd) C3-C6 cycloalkyl;

$Ar^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), $R^eR^fN$— wherein $R^e$ and $R^f$ are independently H, C1-C6 alkyl, $(R^pR^qN)$C1-C6 alkoxy- wherein $R^p$ and $R^q$ are independently H or C1-C6 alkyl, and $(hetAr^a)$C1-C6 alkyl- wherein $hetAr^a$ is a 5-6 membered heteroaryl ring having 1-2 ring nitrogen atoms, or $Ar^1$ is a phenyl ring fused to a 5-6 membered heterocyclic ring having 1-2 ring heteroatoms independently selected from N and 0;

$hetAr^2$ is a 5-6 membered heteroaryl ring having 1-3 ring heteroatoms independently selected from N, O and S or a 9-10 membered bicyclic heteroaryl ring having 1-3 ring nitrogen atoms, wherein $hetAr^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), $R^eR^fN$— wherein $R^e$ and $R^f$ are independently H or C1-C6 alkyl, OH, (C1-C6 alkoxy)C1-C6 alkoxy- and C3-C6 cycloalkyl;

$hetCyc^1$ is a 4-6 membered saturated heterocyclic ring having 1-2 ring heteroatoms independently selected from N, O and S wherein said heterocyclic ring is optionally substituted with one or more substituents independently selected from C1-C6 alkoxy and halogen;

$R^3$ is H or C1-C6 alkyl; and $R^4$ is C1-C6 alkyl.

In some embodiments, a RET inhibitor (e.g., a first RET inhibitor or a second RET inhibitor) is a compound of the Formula V:

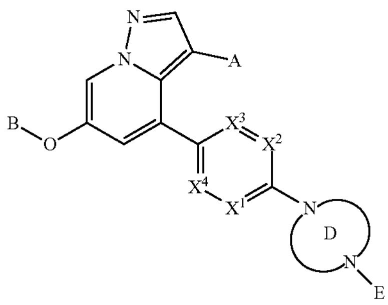

V or a pharmaceutically acceptable salt and solvate thereof, wherein:

$X^1$, $X^2$, $X^3$ and $X^4$ are independently CH or N, wherein zero, one or two of $X^1$, $X^2$, $X^3$ and $X^4$ is N;

A is CN;

B is (b) C1-C6 alkyl optionally substituted with 1-3 fluoros, (c) hydroxyC2-C6 alkyl-, wherein the alkyl portion is optionally substituted with 1-3 fluoros or a C3-C6 cycloalkylidene ring, (e) (C1-C6 alkoxy)C1-C6 alkyl- optionally substituted with 1-3 fluoros, (f) $(R^1R^2N)$C1-C6 alkyl-, wherein said alkyl portion is optionally substituted with OH and wherein $R^1$ and $R^2$ are independently H or C1-C6 alkyl (optionally substituted with 1-3 fluoros);

(g) $hetAr^1$C1-C3 alkyl-, wherein $hetAr^1$ is a 5-6 membered heteroaryl ring having 1-3 ring heteroatoms independently selected from N, O and S and is optionally substituted with one or more independently selected C1-C6 alkyl substituents; or (i) $(hetCyc^a)$C1-C3 alkyl-, $hetCyc^a$- is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl-, C1-C6 alkoxy, (C1-C6 alkyl)C(═O)—, (C1-C6 alkoxy)C1-C6 alkyl- and fluoro, or wherein hetCyc$^a$ is substituted with oxo;

Ring D is (i) a saturated 4-7 membered heterocyclic ring having two ring nitrogen atoms, or (ii) a saturated 7-9 membered bridged heterocyclic ring having two ring nitrogen atoms and optionally having a third ring heteroatom which is oxygen, wherein each of said rings is optionally substituted with (a) one to four groups independently selected from halogen, OH, C1-C3 alkyl which is optionally substituted with 1-3 fluoros, or C1-C3 alkoxy which is optionally substituted with 1-3 fluoros, (b) a C3-C6 cycloalkylidene ring, or (c) an oxo group;

E is (h) Ar$^1$C1-C6 alkyl-, (j) hetAr$^2$C1-C6 alkyl-, wherein the alkyl portion is optionally substituted with 1-3 fluoros, or (l) hetAr$^2$C(═O)—, Ar$^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), $R^eR^fN$— wherein $R^e$ and $R^f$ are independently H or C1-C6 alkyl, ($R^pR^qN$)C1-C6 alkoxy- wherein $R^p$ and $R^q$ are independently H or C1-C6 alkyl, and (hetAr$^a$)C1-C6 alkyl- wherein hetAr$^a$ is a 5-6 membered heteroaryl ring having 1-2 ring nitrogen atoms, or Ar$^1$ is a phenyl ring fused to a 5-6 membered heterocyclic ring having 1-2 ring heteroatoms independently selected from N and O; and hetAr$^2$ is a 5-6 membered heteroaryl ring having 1-3 ring heteroatoms independently selected from N, O and S or a 9-10 membered bicyclic heteroaryl ring having 1-3 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), $R^eR^fN$— wherein $R^e$ and $R^f$ are independently H or C1-C6 alkyl, OH, (C1-C6 alkoxy)C1-C6 alkoxy- and C3-C6 cycloalkyl.

In some embodiments, a RET inhibitor which is not a compound of Formula I is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof.

In some embodiments, a RET inhibitor (e.g., a first RET inhibitor or a second RET inhibitor) is a compound of Formula VI:

VI

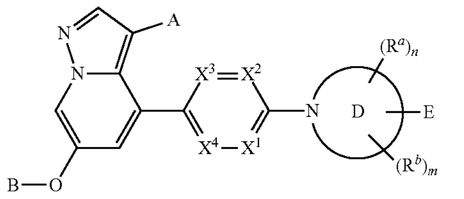

or a pharmaceutically acceptable salt or solvate thereof, wherein:

$X^1$, $X^2$, $X^3$ and $X^4$ are independently CH, $CCH_3$, CF or N, wherein zero, one or two of $X^1$, $X^2$, $X^3$ and $X^4$ is N;

A is H, CN, Cl, methyl, ethyl or cyclopropyl;

B is:

(a) hydrogen, (b) C1-C6 alkyl optionally substituted with 1-3 fluoros, (c) hydroxyC2-C6 alkyl- wherein the alkyl portion is optionally substituted with a C3-C6 cycloalkylidene ring, (d) dihydroxyC3-C6 alkyl- wherein the alkyl portion is optionally substituted with a C3-C6 cycloalkylidene ring, (e) (C1-C6 alkoxy)C1-C6 alkyl- optionally substituted with 1-3 fluoros, (f) ($R^1R^2N$)C1-C6 alkyl- where $R^1$ and $R^2$ are independently selected from H, C1-C6 alkyl (optionally substituted with 1-3 fluoros), (C1-C6 alkoxy)C1-C6 alkyl-, (C1-C6 alkyl)C(═O)— and (C1-C6 alkoxy)C(═O)—;

(g) hetAr$^1$C1-C3 alkyl-, where hetAr$^1$ is a 5-6 membered heteroaryl ring having 1-3 ring heteroatoms independently selected from N, O and S and is optionally substituted with one or more independently selected C1-C6 alkyl substituents;

(h) (C3-C6 cycloalkyl)C1-C3 alkyl-, wherein said cycloalkyl is optionally substituted with OH, (i) (hetCyc$^a$)C1-C3 alkyl-, (j) hetCyc$^a$, (k) ($R^1R^2N$)C(═O)C1-C6 alkyl-, where $R^1$ and $R^2$ are independently selected from H and C1-C6 alkyl;

(l) ($R^1R^2N$)C(═O)—, where $R^1$ and $R^2$ are independently selected from H and C1-C6 alkyl, or (m) hetCyc$^a$C(═O)C1-C6 alkyl-;

hetCyc$^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(═O)—, C1-C6 alkoxy, oxo and (C1-C6 alkoxy)C(═O)—;

Ring D is (i) a saturated monocyclic 4-7 membered heterocyclic ring having one ring heteroatom which is nitrogen, (ii) a saturated 7-8 membered bridged heterocyclic ring having one ring heteroatom which is nitrogen, or (iii) a saturated 7-11 membered heterospirocyclic ring system having one ring heteroatom which is nitrogen;

each $R^a$ is independently C1-C6 alkyl (optionally substituted with 1-3 fluoros), hydroxyC1-C6 alkyl or (C1-C6 alkoxy)C1-C6 alkyl-;

$R^b$ is (a) hydroxy, (b) cyclopropyl, (c) hetCyc$^b$$CH_2$—, (d) $R^iR^jNC(=O)CH_2OCH_2$— where $R^i$ and $R^j$ are independently H or C1-C6 alkyl, (e) $R^cR^dN$—, (f) $R^cR^dNCH_2$—, (g) C1-C6 alkoxy-, (h) (C1-C4 alkyl)-C(=O)NH— wherein said alkyl portion is optionally substituted with hetCyc$^b$, hetAr$^a$, C1-C6 alkoxy- or R'R"N—, or said alkyl portion is optionally substituted with two substituents independently selected from R'R"N— and OH, where each R' and R" is independently hydrogen or C1-C6 alkyl, (i) (R'R"N)C1-C6 alkoxy$(CH_2)_n$— where n is 0 or 1 and R' and R" are independently hydrogen or C1-C6 alkyl, (j) hetCyc$^b$(C1-C3 alkyl)$OCH_2$—, (k) hetCyc$^b$C(=O)NH— or (l) hetAr$^a$C(=O)NH—;

hetCyc$^b$ is a 4-6 membered heterocyclic ring, a 7-8 membered bridged heterocyclic ring, or a 7-10 membered heterospirocyclic ring, each ring having 1-2 ring heteroatoms independently selected from N and O, wherein hetCyc$^b$ is optionally substituted with one or more substituents independently selected from OH, fluoro, C1-C6 alkyl (optionally substituted with 1-3 fluoros), hydroxyC1-C6 alkyl-(optionally substituted with 1-3 fluoros), (C1-C6 alkoxy) C1-C6 alkyl-, (C1-C6 alkoxy)C(=O)—, C1-C6 alkoxy, and R'R"N— where R' and R" are independently hydrogen or C1-C6 alkyl;

hetAr$^a$ is a 5-6 membered heteroaryl ring having 1-3 ring heteroatoms independently selected from N, O and S wherein hetAr$^a$ is optionally substituted with one or more substituents independently selected from the group consisting of halogen, CN, C1-C6 alkyl (optionally substituted with 1-3 fluoros), and C1-C6 alkoxy (optionally substituted with 1-3 fluoros), $R^c$ is hydrogen or C1-C6 alkyl;

$R^d$ is hydrogen, C1-C6 alkyl (optionally substituted with 1-3 fluoros), (C1-C6 alkoxy)C(=O)—, hydroxyC1-C6 alkyl (optionally substituted with 1-3 fluoros), (hydroxyC1-C6 alkyl)C(=O)—, (C1-C6 alkyl)C(=O)—, $(R^kR^lN)$C1-C6 alkyl- where $R^k$ and $R^l$ are independently H or C1-C6 alkyl, $R^mR^nNC(=O)$C1-C6 alkyl- where $R^m$ and $R^n$ are independently H or C1-C6 alkyl, $PhCH_2$— wherein the phenyl is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)$SO_2$—, $R^eR^fN$— and $(R^eR^fN)$C1-C6 alkyl- where each $R^e$ and $R^f$ is independently H or C1-C6 alkyl, (C1-C6 alkoxy)C1-C6 alkyl-, or hetCyc$^c$ where hetCyc$^c$ is a 4-6 membered heterocyclic ring having a ring heteroatom selected from N and O and optionally substituted with C1-C6 alkyl;

n is 0, 1, 2, 3, 4, 5 or 6;

m is 0 or 1;

E is:

(a) hydrogen, (b) hydroxy, (c) C1-C6 alkyl optionally substituted with 1-3 fluoros, (d) $Ar^1$C1-C6 alkyl- wherein said alkyl portion is optionally substituted with 1-3 fluoros, (e) hetAr$^2$C1-C6 alkyl-, (f) (C1-C6 alkoxy)C1-C6 alkoxy-, (g) $Ar^1O$—, (h) hetAr$^2$—O—, (i) $Ar^1NR^g$— where $R^g$ is H or C1-C6 alkyl, (j) hetAr$^2NR^g$— where $R^g$ is H or C1-C6 alkyl, (k) $R^3C(=O)NR^g$— where $R^g$ is H or C1-C6 alkyl;

(l) $Ar^1C(=O)NR^g$— where $R^g$ is H or C1-C6 alkyl, (m) hetAr$^2C(=O)NR^g(CH_2)_p$— where p is 0 or 1 and $R^g$ is H or C1-C6 alkyl, (n) $R^4R^5NC(=O)$—, (o) $Ar^1NR^gC(=O)$—, where $R^g$ is H or C1-C6 alkyl, (p) hetAr$^2NR^gC(=O)$—, where $R^g$ is H or C1-C6 alkyl, (q) $Ar^1$(C1-C6 alkyl)C(=O)— wherein said alkyl portion is optionally substituted with OH, hydroxy(C1-C6 alkyl), C1-C6 alkoxy or $NH_2$, (r) hetCyc$^5$C(=O)—, (s) $R^4R^5NC(=O)NR^g$— where $R^g$ is H or C1-C6 alkyl, or (t) (C1-C6 alkyl)$SO_2$—;

(u) $Ar^1$(C1-C6 alkyl)C(=O)$NR^g$— where $R^g$ is H or C1-C6 alkyl, (v) hetAr$^4C(=O)NR^g$— where $R^g$ is H or C1-C6 alkyl, (w) hetAr$^2$—S(=O)—, (x) (C3-C6 cycloalkyl)$CH_2SO_2$—, (y) $Ar^1$(C1-C6 alkyl)$SO_2$—, (z) hetAr$^2SO_2$—, (aa) $Ar^1$, (bb) hetAr$^2$, (cc) hetCyc$^5$, (dd) C1-C6 alkoxy, (ee) $Ar^1$(C1-C6 alkyl)-O—, (ff) hetAr$^2$(C1-C6 alkyl)-O—, (gg) hetAr$^2$—O—C1-C6 alkyl-, (hh) $Ar^1$(C1-C6 alkyl)$NR^g$— where $R^g$ is H or C1-C6 alkyl, (ii) hetAr$^2$—S—, (jj) $Ar^2SO_2NR^g(CH_2)_p$— where p is 0 or 1 and $R^g$ is H or C1-C6 alkyl, (kk) (C1-C6 alkoxy)C(=O)—, (ll) (C1-C6 alkyl)$NR^gC(=O)O$— where $R^g$ is H or C1-C6 alkyl, (mm) (C1-C6 alkyl)$NR^gSO_2$— where $R^g$ is H or C1-C6 alkyl, (nn) hetCyc$^5C(=O)NR^g$— where $R^g$ is H or C1-C6 alkyl, (oo) Q-$NR^h$(C1-C3 alkyl)C(=O)$NR^g$— where $R^g$ and $R^h$ are independently H or C1-C6 alkyl and Q is H, C1-C6 alkyl or (C1-C6 alkyl)OC(=O)—, (pp)

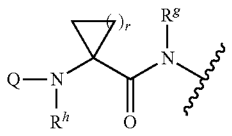

where $R^g$ and $R^h$ are independently H or C1-C6 alkyl, Q is H, C1-C6 alkyl or (C1-C6 alkyl)OC(=O)— and r is 1, 2, 3 or 4, (qq)

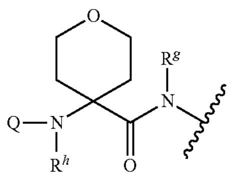

where $R^g$ and $R^h$ are independently H or C1-C6 alkyl and Q is H, C1-C6 alkyl or (C1-C6 alkyl)OC(=O)—, (rr)

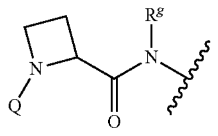

where $R^g$ is H or C1-C6 alkyl and Q is H, C1-C6 alkyl or (C1-C6 alkyl)OC(=O)—, or (ss) $R^gR^hN$— where $R^g$ and $R^h$ are independently H or C1-C6 alkyl, (tt) (C3-C6 cycloalkyl)C(=O)$NR^g$— where the cycloalkyl is optionally and independently substituted with one or more halogens, (uu) (C1-C6 alkyl)C(=O)$NR^gCH_2$— where $R^g$ is H or C1-C6 alkyl, or (vv) C1-C6 alkyl)$SO_2NR^g$— where $R^g$ is H or C1-C6 alkyl;

$Ar^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)$SO_2$—, $R^eR^fN$—and ($R^eR^fN$)C1-C6 alkyl- where each $R^e$ and $R^f$ is independently H or C1-C6 alkyl;

$hetAr^2$ is a 5-6 membered heteroaryl ring having 1-3 ring heteroatoms independently selected from N, O and S, or a 9-10 membered bicyclic heteroaryl having 1-2 ring nitrogen atoms, wherein $hetAr^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-;

$hetCyc^5$ is a 4-6 membered saturated heterocyclic ring having 1-2 ring heteroatoms independently selected from N, O and S wherein said heterocyclic ring is optionally substituted with one or more substituents independently selected from C1-C6 alkoxy and oxo;

$R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)$CH_2$—, (C3-C6 cycloalkyl)O—, (C3-C6 cycloalkyl)$CH_2O$—, $hetCyc^7O$—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH or R'R"N— where R' and R" are independently hydrogen or C1-C6 alkyl;

$R^4$ is H or C1-C6 alkyl;

$R^5$ is $Ar^2$, $hetAr^3$, $Ar^2CH_2$—, $hetCyc^6$-$CH_2$—, hydroxyC1-C6 alkyl-, (C3-C6 cycloalkyl)$CH_2$—, or C1-C6 alkyl optionally substituted with 1-3 fluoros;

$Ar^2$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, and $R^gR^hN$— where $R^g$ and $R^h$ are independently H or C1-C6 alkyl, or $Ar^2$ is phenyl fused to a 6 membered heterocyclic ring having a ring nitrogen atom and optionally substituted with C1-C6 alkyl;

$hetAr^3$ is a 5-6 membered heteroaryl ring having 1-3 ring heteroatoms independently selected from N, O and S and optionally substituted with one or more substituents independently selected from the group consisting of halogen, CN, C1-C6 alkyl (optionally substituted with 1-3 fluoros), C1-C6 alkoxy (optionally substituted with 1-3 fluoros), and (C1-C6 alkoxy)C1-C6 alkyl-(optionally substituted with 1-3 fluoros);

$hetAr^4$ is pyridin-4(1H)-onyl or pyridin-2(1H)-onyl optionally substituted with one or more substituents independently selected from C1-C6 alkyl and halogen;

$hetCyc^6$ is a 5-7 membered heterocyclic ring having 1-3 ring heteroatoms independently selected from N, O and S; and $hetCyc^7$ is a 5-7 membered heterocyclic ring having 1-3 ring heteroatoms independently selected from N, O and S.

In some embodiments, a RET inhibitor (e.g., a first RET inhibitor or a second RET inhibitor) is a compound of the Formula VII:

VII

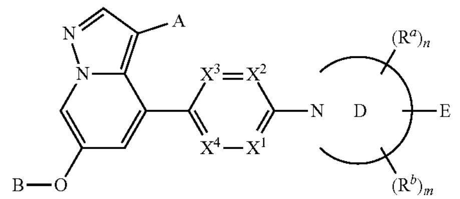

or a pharmaceutically acceptable salt or solvate thereof, wherein:

$X^1$, $X^2$, $X^3$ and $X^4$ are independently CH or N, wherein zero, one or two of $X^1$, $X^2$, $X^3$ and $X^4$ is N;

A is CN;

B is:

(b) C1-C6 alkyl optionally substituted with 1-3 fluoros, (c) hydroxyC2-C6 alkyl- wherein the alkyl portion is optionally substituted with a C3-C6 cycloalkylidene ring, or (i) ($hetCyc^a$)C1-C3 alkyl-;

$hetCyc^a$ is a 4-6 membered heterocyclic ring having 1-2 ring heteroatoms independently selected from N and O and optionally substituted with one or more substituents independently selected from OH, C1-C6 alkyl (optionally substituted with 1-3 fluoros), hydroxyC1-C6 alkyl, halogen, (C1-C6 alkyl)C(=O)—, C1-C6 alkoxy, oxo, and (C1-C6 alkoxy)C(=O)—;

Ring D is a saturated monocyclic 4-7 membered heterocyclic ring having one ring heteroatom which is nitrogen;

each $R^a$ is independently C1-C6 alkyl (optionally substituted with 1-3 fluoros);

$R^b$ is (a) hydroxy;

n is 0 or 1;

m is 0 or 1;

E is:

(e) $hetAr^2$C1-C6 alkyl-, (h) $hetAr^2$—O—, (k) $R^3C$(=O)$NR^g$— where $R^g$ is H or C1-C6 alkyl, (l) $Ar^1C$(=O)$NR^g$— where $R^g$ is H or C1-C6 alkyl, or (m) $hetAr^2C$(=O)$NR^g(CH_2)_p$— where p is 0 or 1 and $R^g$ is H or C1-C6 alkyl;

$Ar^1$ is phenyl optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros), C3-C6 cycloalkyl, hydroxyC1-C6 alkyl, (C1-C6 alkyl)$SO_2$—, $R^eR^fN$— and ($R^eR^fN$)C1-C6 alkyl- where each $R^e$ and $R^f$ is independently H or C1-C6 alkyl;

hetAr$^2$ is a 5-6 membered heteroaryl ring having 1-3 ring heteroatoms independently selected from N, O and S, or a 9-10 membered bicyclic heteroaryl having 1-2 ring nitrogen atoms, wherein hetAr$^2$ is optionally substituted with one or more substituents independently selected from the group consisting of halogen, CN, C1-C6 alkyl (optionally substituted with 1-3 fluoros), C1-C6 alkoxy (optionally substituted with 1-3 fluoros), (C1-C6 alkoxy)C1-C6 alkyl- (optionally substituted with 1-3 fluoros) and hydroxyC1-C6 alkoxy-; and $R^3$ is C1-C6 alkyl (optionally substituted with 1-3 fluoros), hydroxyC1-C6 alkyl-, C1-C6 alkoxy, C3-C6 cycloalkyl, (C3-C6 cycloalkyl)$CH_2$—, (C3-C6 cycloalkyl)O—, (C3-C6 cycloalkyl)$CH_2O$—, hetCyc$^7$O—, Ph-O—, or (C1-C6 alkoxy)C1-C6 alkyl-; wherein each of said C3-C6 cycloalkyl moieties is optionally substituted with C1-C6 alkyl (optionally substituted with 1-3 fluoros), C1-C6 alkoxy, OH, or R'R"N— where R' and R" are independently hydrogen or C1-C6 alkyl.

In some embodiments, a RET inhibitor which is not a compound of Formula I is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof.

Non-limiting examples of receptor tyrosine kinase (e.g., Trk) targeted therapeutic agents, include afatinib, cabozantinib, cetuximab, crizotinib, dabrafenib, entrectinib, erlotinib, gefitinib, imatinib, lapatinib, lestaurtinib, nilotinib, pazopanib, panitumumab, pertuzumab, sunitinib, trastuzumab, 1-((3S,4R)-4-(3-fluorophenyl)-1-(2-methoxyethyl)pyrrolidin-3-yl)-3-(4-methyl-3-(2-methylpyrimidin-5-yl)-1-phenyl-1H-pyrazol-5-yl)urea, AG 879, AR-772, AR-786, AR-256, AR-618, AZ-23, AZ623, DS-6051, Go 6976, GNF-5837, GTx-186, GW 441756, LOXO-101, MGCD516, PLX7486, RXDX101, VM-902A, TPX-0005, and TSR-011. Additional Trk targeted therapeutic agents include those described in U.S. Pat. Nos. 8,450,322; 8,513,263; 8,933,084; 8,791,123; 8,946,226; 8,450,322; 8,299,057; and 8,912,194; U.S. Publication No. 2016/0137654; 2015/0166564; 2015/0051222; 2015/0283132; and 2015/0306086; International Publication No. WO 2010/033941; WO 2010/048314; WO 2016/077841; WO 2011/146336; WO 2011/006074; WO 2010/033941; WO 2012/158413; WO 2014078454; WO 2014078417; WO 2014078408; WO 2014078378; WO 2014078372; WO 2014078331; WO 2014078328; WO 2014078325; WO 2014078323; WO 2014078322; WO 2015175788; WO 2009/013126; WO 2013/174876; WO 2015/124697; WO 2010/058006; WO 2015/017533; WO 2015/112806; WO 2013/183578; and WO 2013/074518, all of which are hereby incorporated by reference in their entireties.

Further examples of Trk inhibitors can be found in U.S. Pat. No. 8,637,516, International Publication No. WO 2012/034091, U.S. Pat. No. 9,102,671, International Publication No. WO 2012/116217, U.S. Publication No. 2010/0297115, International Publication No. WO 2009/053442, U.S. Pat. No. 8,642,035, International Publication No. WO 2009092049, U.S. Pat. No. 8,691,221, International Publication No. WO2006131952, all of which are incorporated by reference in their entireties herein. Exemplary Trk inhibitors include GNF-4256, described in *Cancer Chemother. Pharmacol.* 75(1):131-141, 2015; and GNF-5837 (N-[3-[[2,3-dihydro-2-oxo-3-(1H-pyrrol-2-ylmethylene)-1H-indol-6-yl]amino]-4-methylphenyl]-N'-[2-fluoro-5-(trifluoromethyl)phenyl]-urea), described in *ACS Med. Chem. Lett.* 3(2):140-145, 2012, each of which is incorporated by reference in its entirety herein.

Additional examples of Trk inhibitors include those disclosed in U.S. Publication No. 2010/0152219, U.S. Pat. No. 8,114,989, and International Publication No. WO 2006/123113, all of which are incorporated by reference in their entireties herein. Exemplary Trk inhibitors include AZ623, described in Cancer 117(6):1321-1391, 2011; AZD6918, described in *Cancer Biol. Ther.* 16(3):477-483, 2015; AZ64, described in *Cancer Chemother. Pharmacol.* 70:477-486, 2012; AZ-23 ((S)-5-Chloro-N2-(1-(5-fluoropyridin-2-yl)ethyl)-N4-(5-isopropoxy-1H-pyrazol-3-yl)pyrimidine-2,4-diamine), described in *Mol. Cancer Ther.* 8:1818-1827, 2009; and AZD7451; each of which is incorporated by reference in its entirety.

A Trk inhibitor can include those described in U.S. Pat. Nos. 7,615,383; 7,384,632; 6,153,189; 6,027,927; 6,025,166; 5,910,574; 5,877,016; and 5,844,092, each of which is incorporated by reference in its entirety.

Further examples of Trk inhibitors include CEP-751, described in *Int. J. Cancer* 72:672-679, 1997; CT327, described in *Acta Derm. Venereol.* 95:542-548, 2015; compounds described in International Publication No. WO 2012/034095; compounds described in U.S. Pat. No. 8,673,347 and International Publication No. WO 2007/022999; compounds described in U.S. Pat. No. 8,338,417; compounds described in International Publication No. WO 2016/027754; compounds described in U.S. Pat. No. 9,242,977; compounds described in U.S. Publication No. 2016/0000783; sunitinib (N-(2-diethylaminoethyl)-5-[(Z)-(5-fluoro-2-oxo-1H-indol-3-ylidene)methyl]-2,4-dimethyl-1H-pyrrole-3-carboxamide), as described in *PLoS One* 9:e95628, 2014; compounds described in International Publication No. WO 2011/133637; compounds described in U.S. Pat. No. 8,637,256; compounds described in *Expert. Opin. Ther. Pat.* 24(7):731-744, 2014; compounds described in *Expert Opin. Ther. Pat.* 19(3):305-319, 2009; (R)-2-phenylpyrrolidine substituted imidazopyridazines, e.g., GNF-8625, (R)-1-(6-(6-(2-(3-fluorophenyl)pyrrolidin-1-yl)imidazo[1,2-b]pyridazin-3-yl)-[2,4'-bipyridin]-2'-yl)piperidin-4-ol as described in ACS Med. Chem. Lett. 6(5):562-567, 2015; GTx-186 and others, as described in *PLoS One*

8(12):e83380, 2013; K252a ((9S-(9α,10β,12α))-2,3,9,10,11,12-hexahydro-10-hydroxy-10-(methoxycarbonyl)-9-methyl-9,12-epoxy-1H-diindolo[1,2,3-fg:3',2',1'-kl]pyrrolo[3,4-i][1,6]benzodiazocin-1-one), as described in *Mol. Cell Biochem.* 339(1-2):201-213, 2010; 4-aminopyrazolylpyrimidines, e.g., AZ-23 (((S)-5-chloro-N2-(1-(5-fluoropyridin-2-yl)ethyl)-N4-(5-isopropoxy-1H-pyrazol-3-yl)pyrimidine-2,4-diamine)), as described in *J. Med. Chem.* 51(15): 4672-4684, 2008; PHA-739358 (danusertib), as described in *Mol. Cancer Ther.* 6:3158, 2007; Gö 6976 (5,6,7,13-tetrahydro-13-methyl-5-oxo-12H-indolo[2,3-a]pyrrolo[3,4-c]carbazole-12-propanenitrile), as described in J. Neurochem. 72:919-924, 1999; GW441756 ((3Z)-3-[(1-methylindol-3-yl)methylidene]-1H-pyrrolo[3,2-b]pyridin-2-one), as described in *IJAE* 115:117, 2010; milciclib (PHA-848125AC), described in *J. Carcinog.* 12:22, 2013; AG-879 ((2E)-3-[3,5-Bis(1,1-dimethylethyl)-4-hydroxyphenyl]-2-cyano-2-propenethioamide); altiratinib (N-(4-((2-(cyclopropanecarboxamido)pyridin-4-yl)oxy)-2,5-difluorophenyl)-N-(4-fluorophenyl)cyclopropane-1,1-dicarboxamide); cabozantinib (N-(4-((6,7-Dimethoxyquinolin-4-yl)oxy)phenyl)-N'-(4-fluorophenyl)cyclopropane-1,1-dicarboxamide); lestaurtinib ((5S,6S,8R)-6-Hydroxy-6-(hydroxymethyl)-5-methyl-7,8,14,15-tetrahydro-5H-16-oxa-4b,8a, 14-triaza-5,8-methanodibenzo[b,h]cycloocta[jkl]cyclopenta[e]-as-indacen-13(6H)-one); dovatinib (4-amino-5-fluoro-3-[6-(4-methylpiperazin-1-yl)-1H-benzimidazol-2-yl]quinolin-2(1H)-one mono 2-hydroxypropanoate hydrate); sitravatinib (N-(3-fluoro-4-((2-(5-(((2-methoxyethyl)amino)methyl)pyridin-2-yl)thieno[3,2-b]pyridin-7-yl)oxy)phenyl)-N-(4-fluorophenyl)cyclopropane-1,1-dicarboxamide); ONO-5390556; regorafenib (4-[4-({[4-Chloro-3-(trifluoromethyl)phenyl]carbamoyl}amino)-3-fluorophenoxy]-N-methylpyridine-2-carboxamide hydrate); and VSR-902A; all of the references above are incorporated by reference in their entireties herein.

The ability of a Trk inhibitor to act as a TrkA, TrkB, and/or Trk C inhibitor may be tested using the assays described in Examples A and B in U.S. Pat. No. 8,513,263, which is incorporated herein by reference.

In some embodiments, signal transduction pathway inhibitors include Ras-Raf-MEK-ERK pathway inhibitors (e.g., binimetinib, selumetinib, encorafinib, sorafenib, trametinib, and vemurafenib), PI3K-Akt-mTOR-S6K pathway inhibitors (e.g. everolimus, rapamycin, perifosine, temsirolimus), and other kinase inhibitors, such as baricitinib, brigatinib, capmatinib, danusertib, ibrutinib, milciclib, quercetin, regorafenib, ruxolitinib, semaxanib, AP32788, BLU285, BLU554, INCB39110, INCB40093, INCB50465, INCB52793, INCB54828, MGCD265, NMS-088, NMS-1286937, PF 477736 ((R)-amino-N-[5,6-dihydro-2-(1-methyl-1H-pyrazol-4-yl)-6-oxo-1Hpyrrolo[4,3,2-ef][2,3]benzodiazepin-8-yl]-cyclohexaneacetamide), PLX3397, PLX7486, PLX8394, PLX9486, PRN1008, PRN1371, RXDX103, RXDX106, RXDX108, and TG101209 (N-tert-butyl-3-(5-methyl-2-(4-(4-methylpiperazin-1-yl)phenylamino)pyrimidin-4-ylamino)benzenesulfonamide).

Non-limiting examples of checkpoint inhibitors include ipilimumab, tremelimumab, nivolumab, pidilizumab, MPDL3208A, MEDI4736, MSB0010718C, BMS-936559, BMS-956559, BMS-935559 (MDX-1105), AMP-224, and pembrolizumab.

In some embodiments, cytotoxic chemotherapeutics are selected from arsenic trioxide, bleomycin, cabazitaxel, capecitabine, carboplatin, cisplatin, cyclophosphamide, cytarabine, dacarbazine, daunorubicin, docetaxel, doxorubicin, etoposide, fluorouracil, gemcitabine, irinotecan, lomustine, methotrexate, mitomycin C, oxaliplatin, paclitaxel, pemetrexed, temozolomide, and vincristine.

Non-limiting examples of angiogenesis-targeted therapies include aflibercept and bevacizumab.

The term "immunotherapy" refers to an agent that modulates the immune system. In some embodiments, an immunotherapy can increase the expression and/or activity of a regulator of the immune system. In some embodiments, an immunotherapy can decrease the expression and/or activity of a regulator of the immune system. In some embodiments, an immunotherapy can recruit and/or enhance the activity of an immune cell.

In some embodiments, the immunotherapy is a cellular immunotherapy (e.g., adoptive T-cell therapy, dendritic cell therapy, natural killer cell therapy). In some embodiments, the cellular immunotherapy is sipuleucel-T (APC8015; Provenge™; Plosker (2011) Drugs 71(1): 101-108). In some embodiments, the cellular immunotherapy includes cells that express a chimeric antigen receptor (CAR). In some embodiments, the cellular immunotherapy is a CAR-T cell therapy. In some embodiments, the CAR-T cell therapy is tisagenlecleucel (Kymriah™).

In some embodiments, the immunotherapy is an antibody therapy (e.g., a monoclonal antibody, a conjugated antibody). In some embodiments, the antibody therapy is bevacizumab (Mvasti™, Avastin®), trastuzumab (Herceptin®), avelumab (Bavencio®), rituximab (MabThera™, Rituxan®), edrecolomab (Panorex), daratumuab (Darzalex®), olaratumab (Lartruvo™), ofatumumab (Arzerra®), alemtuzumab (Campath®), cetuximab (Erbitux®), oregovomab, pembrolizumab (Keytruda®), dinutiximab (Unituxin®), obinutuzumab (Gazyva®), tremelimumab (CP-675,206), ramucirumab (Cyramza®), ublituximab (TG-1101), panitumumab (Vectibix®), elotuzumab (Empliciti™), avelumab (Bavencio®), necitumumab (Portrazza™), cirmtuzumab (UC-961), ibritumomab (Zevalin®), isatuximab (SAR650984), nimotuzumab, fresolimumab (GC1008), lirilumab (INN), mogamulizumab (Poteligeo®), ficlatuzumab (AV-299), denosumab (Xgeva®), ganitumab, urelumab, pidilizumab or amatuximab.

In some embodiments, the immunotherapy is an antibody-drug conjugate. In some embodiments, the antibody-drug conjugate is gemtuzumab ozogamicin (Mylotarg™), inotuzumab ozogamicin (Besponsa®), brentuximab vedotin (Adcetris®), ado-trastuzumab emtansine (TDM-1; Kadcyla®), mirvetuximab soravtansine (IMGN853) or anetumab ravtansine In some embodiments, the immunotherapy includes blinatumomab (AMG103; Blincyto®) or midostaurin (Rydapt).

In some embodiments, the immunotherapy includes a toxin. In some embodiments, the immunotherapy is denileukin diftitox (Ontak®).

In some embodiments, the immunotherapy is a cytokine therapy. In some embodiments, the cytokine therapy is an interleukin 2 (IL-2) therapy, an interferon alpha (IFNα) therapy, a granulocyte colony stimulating factor (G-CSF) therapy, an interleukin 12 (IL-12) therapy, an interleukin 15 (IL-15) therapy, an interleukin 7 (IL-7) therapy or an erythropoietin-alpha (EPO) therapy. In some embodiments, the IL-2 therapy is aldesleukin (Proleukin®). In some embodiments, the IFNα therapy is IntronA® (Roferon-A®). In some embodiments, the G-CSF therapy is filgrastim (Neupogen®).

In some embodiments, the immunotherapy is an immune checkpoint inhibitor. In some embodiments, the immunotherapy includes one or more immune checkpoint inhibitors.

In some embodiments, the immune checkpoint inhibitor is a CTLA-4 inhibitor, a PD-1 inhibitor or a PD-L1 inhibitor. In some embodiments, the CTLA-4 inhibitor is ipilimumab (Yervoy®) or tremelimumab (CP-675,206). In some embodiments, the PD-1 inhibitor is pembrolizumab (Keytruda®) or nivolumab (Opdivo®). In some embodiments, the PD-L1 inhibitor is atezolizumab (Tecentriq®), avelumab (Bavencio®) or durvalumab (Imfinzi™).

In some embodiments, the immunotherapy is mRNA-based immunotherapy. In some embodiments, the mRNA-based immunotherapy is CV9104 (see, e.g., Rausch et al. (2014) Human Vaccin Immunother 10(11): 3146-52; and Kubler et al. (2015) J. Immunother Cancer 3:26).

In some embodiments, the immunotherapy is bacillus Calmette-Guerin (BCG) therapy.

In some embodiments, the immunotherapy is an oncolytic virus therapy. In some embodiments, the oncolytic virus therapy is talimogene alherparepvec (T-VEC; Imlygic®).

In some embodiments, the immunotherapy is a cancer vaccine. In some embodiments, the cancer vaccine is a human papillomavirus (HPV) vaccine. In some embodiments, the HPV vaccine is Gardasil®, Gardasil9® or Cervarix®. In some embodiments, the cancer vaccine is a hepatitis B virus (HBV) vaccine. In some embodiments, the HBV vaccine is Engerix-B®, Recombivax HB® or GI-13020 (Tarmogen®). In some embodiments, the cancer vaccine is Twinrix® or Pediarix®. In some embodiments, the cancer vaccine is BiovaxID®, Oncophage®, GVAX, ADXS11-001, ALVAC-CEA, PROSTVAC®, Rindopepimut®, CimaVax-EGF, lapuleucel-T (APC8024; Neuvenge™), GRNVAC1, GRNVAC2, GRN-1201, hepcortespenlisimut-L (Hepko-V5), DCVAX®, SCIB 1, BMT CTN 1401, PrCa VBIR, PANVAC, ProstAtak®, DPX-Survivac, or viagenpumatucel-L (HS-110).

In some embodiments, the immunotherapy is a peptide vaccine. In some embodiments, the peptide vaccine is nelipepimut-S (E75) (NeuVax™), IMA901, or SurVaxM (SVN53-67). In some embodiments, the cancer vaccine is an immunogenic personal neoantigen vaccine (see, e.g., Ott et al. (2017) Nature 547: 217-221; Sahin et al. (2017) Nature 547: 222-226). In some embodiments, the cancer vaccine is RGSH4K, or NEO-PV-01. In some embodiments, the cancer vaccine is a DNA-based vaccine. In some embodiments, the DNA-based vaccine is a mammaglobin-A DNA vaccine (see, e.g., Kim et al. (2016) OncoImmunology 5(2): e1069940).

In some embodiments, immune-targeted agents are selected from aldesleukin, interferon alfa-2b, ipilimumab, lambrolizumab, nivolumab, prednisone, and sipuleucel-T.

Non-limiting examples of radiotherapy include radioiodide therapy, external-beam radiation, and radium 223 therapy.

Additional kinase inhibitors include those described in, for example, U.S. Pat. Nos. 7,514,446; 7,863,289; 8,026,247; 8,501,756; 8,552,002; 8,815,901; 8,912,204; 9,260,437; 9,273,051; U.S. Publication No. US 2015/0018336; International Publication No. WO 2007/002325; WO 2007/002433; WO 2008/080001; WO 2008/079906; WO 2008/079903; WO 2008/079909; WO 2008/080015; WO 2009/007748; WO 2009/012283; WO 2009/143018; WO 2009/143024; WO 2009/014637; 2009/152083; WO 2010/111527; WO 2012/109075; WO 2014/194127; WO 2015/112806; WO 2007/110344; WO 2009/071480; WO 2009/118411; WO 2010/031816; WO 2010/145998; WO 2011/092120; WO 2012/101032; WO 2012/139930; WO 2012/143248; WO 2012/152763; WO 2013/014039; WO 2013/102059; WO 2013/050448; WO 2013/050446; WO 2014/019908; WO 2014/072220; WO 2014/184069; and WO 2016/075224 all of which are hereby incorporated by reference in their entireties.

Further examples of kinase inhibitors include those described in, for example, WO 2016/081450; WO 2016/022569; WO 2016/011141; WO 2016/011144; WO 2016/011147; WO 2015/191667; WO 2012/101029; WO 2012/113774; WO 2015/191666; WO 2015/161277; WO 2015/161274; WO 2015/108992; WO 2015/061572; WO 2015/058129; WO 2015/057873; WO 2015/017528; WO/2015/017533; WO 2014/160521; and WO 2014/011900, each of which is hereby incorporated by reference in its entirety.

Further examples of kinase inhibitors include luminespib (AUY-922, NVP-AUY922) (5-(2,4-dihydroxy-5-isopropylphenyl)-N-ethyl-4-(4-(morpholinomethyl)phenyl)isoxazole-3-carboxamide) and doramapimod (BIRB-796) (1-[5-tert-butyl-2-(4-methylphenyl)pyrazol-3-yl]-3-[4-(2-morpholin-4-ylethoxy)naphthalen-1-yl]urea).

Accordingly, also provided herein is a method of treating cancer, comprising administering to a patient in need thereof a pharmaceutical combination for treating cancer which comprises (a) a compound of Formula I or a pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or a pharmaceutically acceptable salt or solvate thereof and the additional therapeutic agent are together effective in treating the cancer.

In some embodiments, the additional therapeutic agent(s) includes any one of the above listed therapies or therapeutic agents which are standards of care in cancers wherein the cancer has a dysregulation of a RET gene, a RET protein, or expression or activity, or level of any of the same.

These additional therapeutic agents may be administered with one or more doses of the compound of Formula I, or a pharmaceutically acceptable salt or solvate thereof, or pharmaceutical composition thereof, as part of the same or separate dosage forms, via the same or different routes of administration, and/or on the same or different administration schedules according to standard pharmaceutical practice known to one skilled in the art.

Also provided herein is (i) a pharmaceutical combination for treating a cancer in a patient in need thereof, which comprises (a) a compound of Formula I or a pharmaceutically acceptable salt or solvate thereof, (b) at least one additional therapeutic agent (e.g., any of the exemplary additional therapeutic agents described herein or known in the art), and (c) optionally at least one pharmaceutically acceptable carrier for simultaneous, separate or sequential use for the treatment of cancer, wherein the amounts of the compound of Formula I or pharmaceutically acceptable salt or solvate thereof and of the additional therapeutic agent are together effective in treating the cancer; (ii) a pharmaceutical composition comprising such a combination; (iii) the use of such a combination for the preparation of a medicament for the treatment of cancer; and (iv) a commercial package or product comprising such a combination as a combined preparation for simultaneous, separate or sequential use; and to a method of treatment of cancer in a patient in need thereof. In one embodiment the patient is a human. In some embodiments, the cancer is a RET-associated cancer. For example, a RET-associated cancer having one or more RET inhibitor resistance mutations.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., a chemotherapeutic agent), are both administered to a patient simultaneously in the form of a single composition or dosage. The term "non-fixed combination" means that a compound of Formula I or a pharmaceutically acceptable salt or solvate thereof and at least one additional therapeutic agent (e.g., chemotherapeutic agent) are formulated as separate compositions or dosages such that they may be administered to a patient in need thereof simultaneously, concurrently or sequentially with variable intervening time limits, wherein such administration provides effective levels of the two or more compounds in the body of the patient. These also apply to cocktail therapies, e.g. the administration of three or more active ingredients Accordingly, also provided herein is a method of treating a cancer, comprising administering to a patient in need thereof a pharmaceutical combination for treating cancer which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of cancer, wherein the amounts of the compound of Formula I or pharmaceutically acceptable salt or solvate thereof and the additional therapeutic agent are together effective in treating the cancer. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, the compound of Formula I or pharmaceutically acceptable salt or solvate thereof, and the additional therapeutic agent are administered simultaneously as a combined dosage. In some embodiments, the cancer is a RET-associated cancer. For example, a RET-associated cancer having one or more RET inhibitor resistance mutations.

Also provided herein is a method of treating a disease or disorder mediated by RET in a patient in need of such treatment, the method comprising administering to the patient a therapeutically effective amount of a compound of Formula I or a pharmaceutically acceptable salt or solvate thereof or a pharmaceutical composition thereof. In some embodiments, the disease or disorder mediated by RET is a dysregulation of RET gene, a RET kinase, or expression or activity or level of any of the same. For example the dysregulation of a RET gene, a RET kinase, or expression or activity or level of any of the same includes one or more RET inhibitor resistance mutations. A disease or disorder mediated by RET can include any disease, disorder or condition that is directly or indirectly linked to expression or activity of RET, including overexpression and/or abnormal activity levels. In one embodiment, the disease is cancer (e.g., a RET-associated cancer). In one embodiment, the cancer is any of the cancers or RET-associated cancers described herein.

Although the genetic basis of tumorigenesis may vary between different cancer types, the cellular and molecular mechanisms required for metastasis appear to be similar for all solid tumor types. During a metastatic cascade, the cancer cells lose growth inhibitory responses, undergo alterations in adhesiveness and produce enzymes that can degrade extracellular matrix components. This leads to detachment of tumor cells from the original tumor, infiltration into the circulation through newly formed vasculature, migration and extravasation of the tumor cells at favorable distant sites where they may form colonies. A number of genes have been identified as being promoters or suppressors of metastasis. For example, overexpression of glial cell-derived neurotrophic factor (GDNF) and its RET receptor tyrosine kinase have been correlated with cancer proliferation and metastasis. See, e.g., Zeng, Q. et al. *J. Int. Med. Res*. (2008) 36(4): 656-64.

Accordingly, also provided herein are methods for inhibiting, preventing, aiding in the prevention, or decreasing the symptoms of metastasis of a cancer in a patient in need thereof, the method comprising administering to the patient a therapeutically effective amount of a compound of Formula I or a pharmaceutically acceptable salt or solvate thereof or a pharmaceutical composition thereof. Such methods can be used in the treatment of one or more of the cancers described herein. See, e.g., US Publication No. 2013/0029925; International Publication No. WO 2014/083567; and U.S. Pat. No. 8,568,998. See also, e.g., Hezam K et al., *Rev Neurosci* 2018 Jan. 26; 29:93-98; Gao L, et al., *Pancreas* 2015 January; 44:134-143; Ding K et al., *J Biol Chem* 2014 Jun. 6; 289:16057-71; and Amit M et al., *Oncogene* 2017 Jun. 8; 36:3232-3239. In some embodiments, the cancer is a RET-associated cancer. In some embodiments, the compound of Formula I or a pharmaceutically acceptable salt or solvate thereof is used in combination with an additional therapy or another therapeutic agent, including a chemotherapeutic agent, such as a kinase inhibitor. For example, a first or second RET kinase inhibitor.

The term "metastasis" is an art known term and means the formation of an additional tumor (e.g., a solid tumor) at a site distant from a primary tumor in a subject or patient, where the additional tumor includes the same or similar cancer cells as the primary tumor.

Also provided are methods of decreasing the risk of developing a metastasis or an additional metastasis in a patient having a RET-associated cancer that include: selecting, identifying, or diagnosing a patient as having a RET-associated cancer, and administering a therapeutically effective amount of a compound of Formula I or a pharmaceutically acceptable salt or solvate thereof to the patient selected, identified, or diagnosed as having a RET-associated cancer. Also provided are methods of decreasing the risk of developing a metastasis or an additional metastasis in a patient having a RET-associated cancer that includes administering a therapeutically effective amount of a compound of Formula I or a pharmaceutically acceptable salt or solvent thereof to a patient having a RET-associated cancer. The decrease in the risk of developing a metastasis or an additional metastasis in a patient having a RET-associated cancer can be compared to the risk of developing a metastasis or an additional metastasis in the patient prior to treatment, or as compared to a patient or a population of patients having a similar or the same RET-associated cancer that has received no treatment or a different treatment. In some embodiments, the RET-associated cancer is a RET-associated cancer having one or more RET inhibitor resistance mutations.

The phrase "risk of developing a metastasis" means the risk that a subject or patient having a primary tumor will develop an additional tumor (e.g., a solid tumor) at a site distant from a primary tumor in a subject or patient over a set period of time, where the additional tumor includes the same or similar cancer cells as the primary tumor. Methods for reducing the risk of developing a metastasis in a subject or patient having a cancer are described herein.

The phrase "risk of developing additional metastases" means the risk that a subject or patient having a primary tumor and one or more additional tumors at sites distant from the primary tumor (where the one or more additional tumors include the same or similar cancer cells as the primary tumor) will develop one or more further tumors distant from the primary tumor, where the further tumors include the same or similar cancer cells as the primary tumor. Methods for reducing the risk of developing additional metastasis are described herein.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-

(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl- 1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of: ((S)-4-(6-(4-(2-hydroxy-3-phenylpropanoyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(2-(pyridin-2-yl)acetyl)piperazin-1-yl)pyridin-3-yl)pyrazolo[1,5-a]pyridine-3-carbonitrile; 4-(6-(4-(2,6-difluorobenzoyl)piperazin-1-yl)pyridin-3-yl)-6-(1-methyl-1H-pyrazol-4-yl)pyrazolo[1,5-a]pyridine-3-carbonitrile 2,2,2-trifluoroacetate; 4-(5-(3-cyano-6-(1-methyl-1H-pyrazol-4-yl)pyrazolo[1,5-a]pyridin-4-yl)pyridin-2-yl)-N,N-diethylpiperazine-1-carboxamide; 1-(5-(3-cyano-6-(1-methyl-1H-pyrazol-4-yl)pyrazolo[1,5-a]pyridin-4-yl)pyridin-2-yl)-N-(2-methoxy-3-methylbutyl)piperidine-4-carboxamide; 4-(6-(4-(2-(5-fluoropyridin-2-yl)acetyl)piperazin-1-yl)pyridin-3-yl)-6-(1-methyl-1H-pyrazol-4-yl)pyrazolo[1,5-a]pyridine-3-carbonitrile bis(2,2,2-trifluoroacetate); 4-(6-(4-(2,6-difluorobenzyl)piperazin-1-yl)pyridine-3-yl)-6-(1-methyl-1H-pyrazol-4-yl)pyrazolo[1,5-a]pyridine-3-carbonitrile; 4-(6-(4-(2-methoxybenzyl)piperazin-1-yl)pyridin-3-yl)-6-(1-methyl-1H-pyrazol-4-yl)pyrazolo[1,5-a]pyridine-3-carbonitrile; 6-(1-methyl-1H-pyrazol-4-yl)-4-(6-(4-(pyridine-2-ylmethyl)piperazin-1-yl)pyridin-3-yl)pyrazolo[1,5-a]pyridine-3-carbonitrile; 4-(6-(4-((6-methoxypyridin-3-yl)methyl)piperazin-1-yl)pyridin-3-yl)-6-(1-methyl-1H-pyrazol-4-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2- hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of: 4-(6-(4-benzylpiperazin-1-yl)pyridin-3-yl)-6-(2-morpholinoethoxy)pyrazolo[1,5-a]pyridine-3-carbonitrile; 6-(2-hydroxyethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; (R)-6-(2-hydroxypropoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 6-(2-methoxyethoxy)-4-(6-(4-((6-methoxypyridin-3-yl)methyl)piperazin-1-yl)pyridin-3-yl)pyrazolo[1,5-a]pyridine-3-carbonitrile; 6-(2-hydroxy-2-methylpropoxy)-4-(6-(6-(6-methoxynicotinoyl)-3,6-diazabicyclo[3.1.1]heptan-3-yl)pyridin-3-yl)pyrazolo[1,5-a]pyridine-3-carbonitrile; 6-(2-

(dimethylamino)ethoxy)-4-(6-(6-((6-methoxypyridin-3-yl)methyl)-3,6-diazabicyclo[3.1.1]heptan-3-yl)pyridin-3-yl)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-(2-morpholinoethoxy)pyrazolo[1,5-a]pyridine-3-carbonitrile; 4-(6-(6-((6-methoxypyridin-3-yl)methyl)-3,6-diazabicyclo[3.1.1]heptan-3-yl)pyridin-3-yl)-6-((1-methyl-1H-imidazol-4-yl)methoxy)pyrazolo[1,5-a]pyridine-3-carbonitrile; and 6-ethoxy-4-(5-(6-((5-fluoro-6-methoxypyridin-3-yl)methyl)-3,6-diazabicyclo[3.1.1]heptan-3-yl)pyrazin-2-yl)pyrazolo[1,5-a]pyridine-3-carbonitrile; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

In some embodiments, the presence of one or more RET inhibitor resistance mutations in a tumor causes the tumor to be more resistant to treatment with a first RET inhibitor. Methods useful when a RET inhibitor resistance mutation causes the tumor to be more resistant to treatment with a first RET inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the first RET inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl) pyrazolo[1,5-a]pyridine-3-carbonitrile; 6-(2-hydroxy-2-methylpropoxy)-4-(6-(3-(pyridin-2-yloxy)azetidin-1-yl) pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a] pyridine-3-carbonitrile; (S)-6-(2-hydroxy-2-methylpropoxy)-4-(6-(3-(pyridin-2-yloxy)pyrrolidin-1-yl) pyridin-3-yl)pyrazolo[1,5-a]pyridine-3-carbonitrile; N-(1-(5-(3-cyano-6-((3-fluoro-1-methylazetidin-3-yl)methoxy) pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl) piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a first RET inhibitor, wherein the first RET inhibitor is selected from the group consisting of: N-(1-(5-(3-cyano-6-(2-hydroxy-2-methylpropoxy)pyrazolo[1,5-a] pyridin-4-yl)pyridin-2-yl)-4-methylpiperidin-4-yl)benzamide; 6-ethoxy-4-(6-(4-hydroxy-4-(pyridin-2-ylmethyl) piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a] pyridine-3-carbonitrile; 6-(2-hydroxy-2-methylpropoxy)-4-(6-(4-((6-methoxypyridazin-3-yl)oxy)piperidin-1-yl) pyridin-3-yl)pyrazolo[1,5-a]pyridine-3-carbonitrile; (S)-6-(2-hydroxy-2-methylpropoxy)-4-(6-(3-(pyridin-2-yloxy) pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl) pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl) pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the first RET inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl) pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl) pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2-methylpropoxy)-4-(6-(3-(pyridin-2-yloxy)pyrrolidin-1-yl)pyridin-3-yl)pyrazolo[1,5-a]pyridine-3-carbonitrile; N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl)piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a second RET inhibitor, wherein the second RET inhibitor is selected from the group consisting of: N-(1-(5-(3-cyano-6-(2-hydroxy-2-methylpropoxy)pyrazolo[1,5-a]pyridin-4-yl)pyridin-2-yl)-4-methylpiperidin-4-yl)benzamide; 6-ethoxy-4-(6-(4-hydroxy-4-(pyridin-2-ylmethyl)piperidin-1-yl)pyridin-3-yl)pyrazolo[1,5-a]pyridine-3-carbonitrile; 6-(2-hydroxy-2-methylpropoxy)-4-(6-(3-(pyridin-2-yloxy)azetidin-1-yl)pyridin-3-yl)pyrazolo[1,5-a]pyridine-3-carbonitrile; 6-(2-hydroxy-2-methylpropoxy)-4-(6-(4-((6-methoxypyridazin-3-yl)oxy)piperidin-1-yl)pyridin-3-yl)pyrazolo[1,5-a]pyridine-3-carbonitrile; (S)-6-(2-hydroxy-2- methylpropoxy)-4-(6-(3-(pyridin-2-yloxy)pyrrolidin-1-yl) pyridin-3-yl)pyrazolo[1,5-a]pyridine-3-carbonitrile; N-(1-(5-(3-cyano-6-((3-fluoro-1-methylazetidin-3-yl)methoxy) pyrazolo[1,5-a]pyridin-4-yl)pyridin-2-yl)-4-methylpiperidin-4-yl)-5-fluoro-2-methylbenzamide; 3-chloro-N-(1-(5-(3-cyano-6-((3-fluoro-1-methylazetidin-3-yl)methoxy)pyrazolo[1,5-a]pyridin-4-yl)pyridin-2-yl)-4-methylpiperidin-4-yl)picolinamide; N-((3S,4S)-1-(5-(3-cyano-6-ethoxypyrazolo[1,5-a]pyridin-4-yl)pyridin-2-yl)-3-hydroxypiperidin-4-yl)-3-methylbutanamide; 6-(2-hydroxy-2-methylpropoxy)-4-(6-(4-hydroxy-4-(pyridin-2-ylmethyl) piperidin-1-yl)pyridin-3-yl)pyrazolo[1,5-a]pyridine-3-carbonitrile; and 3-chloro-N-((3S,4S)-1-(5-(3-cyano-6-ethoxypyrazolo[1,5-a]pyridin-4-yl)pyrazin-2-yl)-3-hydroxypiperidin-4-yl)picolinamide; or a pharmaceutically acceptable salt or solvate thereof, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

In some embodiments, the presence of one or more RET inhibitor resistance mutations in a tumor causes the tumor to be more resistant to treatment with a multikinase inhibitor. Methods useful when a RET inhibitor resistance mutation causes the tumor to be more resistant to treatment with a multikinase inhibitor are described below. For example, provided herein are methods of treating a subject having a cancer that include: identifying a subject having a cancer cell that has one or more RET inhibitor resistance mutations; and administering to the identified subject a compound of Formula I or a pharmaceutically acceptable salt or solvate thereof. In some embodiments, the compound of Formula I or a pharmaceutically acceptable salt or solvate thereof is administered in combination with the multikinase inhibitor. Also provided are methods of treating a subject identified as having a cancer cell that has one or more RET inhibitor resistance mutations that include administering to the subject a compound of Formula I or a pharmaceutically acceptable salt or solvate thereof. In some embodiments, the compound of Formula I or a pharmaceutically acceptable salt or solvate thereof is administered in combination with the multikinase inhibitor. In some embodiments, the one or more RET inhibitor resistance mutations confer increased resistance to a cancer cell or tumor to treatment with the multikinase inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

For example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a multikinase inhibitor, wherein the multikinase inhibitor is selected from vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a first multikinase inhibitor, wherein the multikinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a multikinase inhibitor, wherein the multikinase inhibitor is selected from the group consisting of: vandetanib or cabozantinib; or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a multikinase inhibitor, wherein the multikinase inhibitor is selected from the group consisting of vandetanib or cabozantinib; or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof as a monotherapy or in conjunction with another anticancer agent to the subject if the subject has a cancer cell that has at least one RET inhibitor resistance mutation; or (e) administering additional doses of the multikinase inhibitor of step (b) to the subject if the subject has a cancer cell that does not have a RET inhibitor resistance mutation.

As another example, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib, as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering a multikinase inhibitor (e.g., vandetanib or cabozantinib), as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation. In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering a multikinase inhibitor (e.g., vandetanib or cabozantinib) as a monotherapy or in conjunction with another anticancer agent to the subject if the subject has a cancer cell that has at least one RET inhibitor resistance mutation; or (e) administering additional doses of the compound of Formula I or a pharmaceutically acceptable salt or solvate thereof of step (b) to the subject if the subject has a cancer cell that does not have a RET inhibitor resistance mutation.

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has at least one RET inhibitor resistance mutation of Tables 3 or 4; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) determining whether a cancer cell in a sample obtained from the subject has the RET inhibitor resistance mutation V804M; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation) if the subject has a cancer cell that has at least one RET inhibitor resistance mutation. In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668 is administered in step (d).

Also, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I or a pharmaceutically acceptable salt or solvate thereof. In some embodiments, the methods further comprise (after (b)) (c) detecting at least one RET inhibitor resistance mutation in a cancer cell in a sample obtained from the subject; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation). In some embodiments, provided herein are methods for treating a RET-associated cancer in a subject in need of such treatment, the method comprising (a) detecting a dysregulation of a RET gene, a RET kinase, or the expression or activity or level of any of the same in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) detecting at least one RET inhibitor resistance mutation in a cancer cell in a sample obtained from the subject; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation). In some embodiments, provided herein are methods for treating a RET-associated cancer in a subject in need of such treatment, the method comprising (a) detecting one or more fusion proteins of Table 1 and/or one or more RET kinase protein point mutations/insertions/deletions of Tables 2 and 2a in a sample from the subject; and (b) administering to the subject a therapeutically effective amount of a compound of Formula I or a pharmaceutically acceptable salt or solvate thereof selected from the group consisting of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) detecting at least one RET inhibitor resistance mutation of Tables 3 or 4 in a cancer cell in a sample obtained from the subject; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668 is administered in step (d). In some embodiments, provided herein are methods for treating a RET-associated cancer in a subject in need of such treatment, the method comprising (a) detecting the fusion protein KIF5B-RET in a sample from the subject; and (b) administering to the subject a therapeutically effective amount of a compound of Formula I selected from i) Example No. 1-20; ii) Example No. 21-40; iii) Example No. 41-49; iv) Example No. 50-70; v) Example No. 71-90; vi) Example No. 91-110; vii) Example No. 111-121, or a pharmaceutically acceptable salt or solvate thereof. In some embodiments, the methods further comprise (after (b)) (c) detecting the RET inhibitor resistance mutation V804M in a cancer cell in a sample obtained from the subject; and (d) administering additional doses of the compound of Formula I or a pharmaceutically acceptable salt or solvate thereof of step (b) to the subject as a monotherapy or in conjunction with another anticancer agent (e.g., a second RET inhibitor, a second compound of Formula I or a pharmaceutically acceptable salt thereof, or immunotherapy) or anticancer therapy (e.g., surgery or radiation). In some embodiments, a second RET inhibitor selected from the group consisting of alectinib, cabozantinib, lenvatinib, nintedanib, ponatinib, regorfenib, sorafenib, sunitinib, vandetanib, RXDX-105 (agerafenib), LOXO-292, BLU-667, BLU6864, DS-5010, GSK3179106, GSK3352589, and NMS-E668 is administered in step (d).

Also provided are methods of selecting a treatment for a subject having a cancer that include: identifying a subject having a cancer cell that has one or more RET inhibitor resistance mutations; and selecting a treatment that includes administration of a compound of Formula I or a pharmaceutically acceptable salt or solvate thereof. In some embodiments, the one or more RET inhibitor resistance mutations confer increased resistance to a cancer cell or tumor to treatment with a first RET inhibitor. In some embodiments, the compound of Formula I or a pharmaceutically acceptable salt or solvate thereof is administered in combination with the first RET inhibitor. Also provided are methods of selecting a treatment for a subject having a cancer that include: selecting a treatment that includes administration of a compound of Formula I or a pharmaceutically acceptable salt or solvate thereof for a subject identified as having a cancer cell that has one or more RET inhibitor resistance mutations. Also provided are methods of selecting a subject having a cancer for a treatment that does not include a first RET inhibitor as a monotherapy that include: identifying a subject having a cancer cell that has one or more RET inhibitor resistance mutations; and selecting the identified subject for a treatment that includes a compound of Formula I or a pharmaceutically acceptable salt or solvate thereof. Also provided are methods of selecting a subject having a cancer for a treatment that does not include a first RET inhibitor as a monotherapy that include: selecting a subject identified as having a cancer cell that has one or more RET inhibitor resistance mutations for a treatment that includes administration of a compound of Formula I or a pharmaceutically acceptable salt or solvate thereof. In some embodiments, the one or more RET inhibitor resistance mutations include one or more RET inhibitor resistance mutations listed in Tables 3 and 4. In some embodiments, the one or more RET inhibitor resistance mutations can include a substitution at amino acid position 804, e.g., V804M, V804L, or V804E.

Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject having a cancer cell that has one or more RET inhibitor resistance mutations has a decreased likelihood of having a positive response (i.e. an increased likelihood of having a negative response) to treatment with a first RET inhibitor as a monotherapy. Also provided are methods of determining the likelihood that a subject having a cancer (e.g., a RET-associated cancer) will have a positive response to treatment with a first RET inhibitor as a monotherapy that include: determining whether a cancer cell in a sample obtained from the subject has one or more RET inhibitor resistance mutations; and determining that a subject not having a cancer cell that has one or more RET inhibitor resistance mutations has an increased likelihood of having a positive response to treatment with a first RET inhibitor as a monotherapy as compared to a subject having a cancer cell that has one or more RET inhibitor resistance mutations. Also provided are methods of predicting the efficacy of treatment with a first RET inhibitor as a monotherapy in a subject having cancer that include: determining whether a cancer cell in a sample obtained from the subject has one or more RET inhibitor resistance mutations; and determining that treatment with a first RET inhibitor as a monotherapy is less likely to be effective in a subject having a cancer cell in a sample obtained from the subject that has one or more RET inhibitor resistance mutations. Also provided are methods of predicting the efficacy of treatment with a first RET inhibitor as a monotherapy in a subject having cancer that include: determining that treatment with a first RET inhibitor as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (d) administering additional doses of the first RET inhibitor of step (a) to the subject if the subject has a cancer cell that does not have a RET inhibitor resistance mutation. In some embodiments, where the subject is administered additional doses of the first RET inhibitor of step (a), the subject can also be administered another anticancer agent (e.g., a second RET inhibitor or a compound of Formula I or a pharmaceutically acceptable salt or solvate thereof, or immunotherapy). In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

Also provided are methods of treating a subject having a cancer that include: (a) administering one or more doses of a first RET inhibitor to the subject for a period of time; (b) after (a), determining whether a cancer cell in a sample obtained from the subject has at least one RET inhibitor resistance mutation; and (c) administering a second RET inhibitor as a monotherapy or in conjunction with another anticancer agent to the subject if the subject has a cancer cell that has at least one RET inhibitor resistance mutation; or (d) administering additional doses of the first RET inhibitor step (a) to the subject if the subject has a cancer cell that does not have a RET inhibitor resistance mutation. In some embodiments, where the subject is administered additional doses of the first RET inhibitor of step (a), the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy.

Also provided are methods of treating a subject having a cancer (e.g., a RET-associated cancer) that include: (a) determining whether a cancer cell in a sample obtained from a subject having a cancer and previously administered one or more doses of a first RET inhibitor, has one or more RET inhibitor resistance mutations; and (b) administering a compound of Formula I or a pharmaceutically acceptable salt or solvate thereof as a monotherapy or in conjunction with another anticancer agent to the subject if the subject has a cancer cell that has at least one RET inhibitor resistance mutation; or (c) administering additional doses of the first RET inhibitor previously administered to the subject if the subject has cancer cell that does not have a RET inhibitor resistance mutation. In some embodiments, where the subject is administered additional doses of the first RET inhibitor previously administered to the subject, the subject can also be administered another anticancer agent (e.g., a compound of Formula I or a pharmaceutically acceptable salt or solvate thereof, or immunotherapy). In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (b), another anticancer agent can be the first RET inhibitor administered in step (a).

Also provided are methods of treating a subject having a cancer that include: (a) determining whether a cancer cell in a sample obtained from a subject having a cancer and previously administered one or more doses of a first RET inhibitor has one or more RET inhibitor resistance mutations; and (b) administering a second RET inhibitor as a monotherapy or in conjunction with another anticancer agent to the subject if the subject has a cancer cell that has at least one RET inhibitor resistance mutation; or (c) administering additional doses of the first RET inhibitor previously administered to the subject if the subject has a cancer cell that does not have a RET inhibitor resistance mutation. In some embodiments, where the subject is administered additional doses of the first RET inhibitor previously administered to the subject, the subject can also be administered another anticancer agent. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments of (b), another anticancer agent can be the first RET inhibitor administered in step (a).

Treatment of a patient having a cancer with a multi-kinase inhibitor (MKI) or target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can result in dysregulation of a RET gene, a RET kinase, or the expression or activity or level of the same in the cancer, and/or resistance to a RET inhibitor. See, e.g., Bhinge et al., *Oncotarget* 8:27155-27165, 2017; Chang et al., *Yonsei Med. J.* 58:9-18, 2017; and Lopez-Delisle et al., doi: 10.1038/s41388-017-0039-5, Oncogene 2018.

Treatment of a patient having a cancer with a RET inhibitor in combination with a multi-kinase inhibitor or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) can have increased therapeutic efficacy as compared to treatment of the same patient or a similar patient with the RET inhibitor as a monotherapy, or the multi-kinase inhibitor or the target-specific kinase inhibitor as a monotherapy. See, e.g., Tang et al., doi: 10.1038/modpathol.2017.109, *Mod. Pathol.* 2017; Andreucci et al., *Oncotarget* 7:80543-80553, 2017; Nelson-Taylor et al., *Mol. Cancer Ther.* 16:1623-1633, 2017; and Kato et al., *Clin. Cancer Res.* 23:1988-1997, 2017.

Provided herein are methods of treating a patient having a cancer (e.g., any of the cancers described herein) and previously administered a multi-kinase inhibitor (MKI) or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: administering to the patient (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) previously administered a MKI or a target specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) that include: identifying a patient having a cancer cell that has a dysregulation of a RET gene, a RET kinase, or the expression or activity or level of the same; and administering to the identified patient (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) that include: administering to a patient a therapeutically effective amount of a MKI or a target-specific kinase inhibitor (e.g., a BRAF inhibitor, a EGFR inhibitor, a MEK inhibitor, an ALK inhibitor, a ROS1 inhibitor, a MET inhibitor, an aromatase inhibitor, a RAF inhibitor, or a RAS inhibitor) (e.g., as a monotherapy) for a first period of time; after the period of time, identifying a patient having a cancer cell that has a dysregulation of a RET gene, a RET kinase, or the expression or activity or level of the same; and administering to the identified patient (i) a therapeutically effective dose of a compound of Formula I or a pharmaceutically acceptable salt or solvate thereof as a monotherapy, or (ii) a therapeutically effective dose of a compound of Formula I or a pharmaceutically acceptable salt or solvate thereof, and a therapeutically effective dose of the previously administered MKI or the previously administered target-specific kinase inhibitor.

Provided herein are methods of treating a patient having a cancer (e.g., any of the cancers described herein) that has dysregulation of a BRAF gene, a BRAF kinase, or the expression or activity or level of the same that include administering to the patient (i) a therapeutically effective amount of a compound of Formula I or a pharmaceutically acceptable salt or solvate thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that include: identifying a patient having a cancer cell that has dysregulation of a BRAF gene, a BRAF kinase, or the expression or activity or level of the same; and administering to the identified patient (i) a therapeutically effective amount of a compound of Formula I or a pharmaceutically acceptable salt or solvate thereof and (ii) a therapeutically effective amount of a BRAF inhibitor (e.g., any of the BRAF inhibitors described herein or known in the art).

Provided herein are methods of treating a patient having a cancer (e.g., any of the cancers described herein) that has dysregulation of an EGFR gene, an EGFR protein, or the expression or activity or level of the same that include administering to the patient (i) a therapeutically effective amount of a compound of Formula I or a pharmaceutically acceptable salt or solvate thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that include: identifying a patient having a cancer cell that has dysregulation of an EGFR gene, an EGFR protein, or the expression or activity or level of the same; and administering to the identified patient (i) a therapeutically effective amount of a compound of Formula I or a pharmaceutically acceptable salt or solvate thereof and (ii) a therapeutically effective amount of an EGFR inhibitor (e.g., any of the EGFR inhibitors described herein or known in the art).

Provided herein are methods of treating a patient having a cancer (e.g., any of the cancers described herein) that has dysregulation of a MEK gene, a MEK protein, or the expression or activity or level of the same that include administering to the patient (i) a therapeutically effective amount of a compound of Formula I or a pharmaceutically acceptable salt or solvate thereof and (ii) a therapeutically effective amount of a MEK inhibitor (e.g., any of the MEK inhibitors described herein or known in the art).

Provided herein are methods of treating a patient having a cancer (e.g., any of the cancers described herein) that include: identifying a patient having a cancer cell that has dysregulation of a MEK gene, a MEK protein, or the expression or activity or level of the same; and administering to the identified patient (i) a therapeutically effective amount of a compound of Formula I or a pharmaceutically acceptable salt or solvate thereof and (ii) a therapeutically effective amount of a MEK inhibitor (e.g., any of the MEK inhibitors described herein or known in the art).

Provided herein are methods of treating a patient having a cancer (e.g., any of the cancers described herein) that has dysregulation of an ALK gene, an ALK protein, or the expression or activity or level of the same that include administering to the patient (i) a therapeutically effective amount of a compound of Formula I or a pharmaceutically acceptable salt or solvate thereof and (ii) a therapeutically effective amount of an ALK inhibitor (e.g., any of the ALK inhibitors described herein or known in the art).

Provided herein are methods of treating a patient having a cancer (e.g., any of the cancers described herein) that include: identifying a patient having a cancer cell that has dysregulation of an ALK gene, an ALK protein, or the expression or activity or level of the same; and administering to the identified patient (i) a therapeutically effective amount of a compound of Formula I or a pharmaceutically acceptable salt or solvate thereof and (ii) a therapeutically effective amount an ALK inhibitor (e.g., any of the ALK inhibitors described herein or known in the art).

Provided herein are methods of treating a patient having a cancer (e.g., any of the cancers described herein) that has dysregulation of a ROS gene, a ROS protein, or the expression or activity or level of the same that include administering to the patient (i) a therapeutically effective amount of a compound of Formula I or a pharmaceutically acceptable salt or solvate thereof and (ii) a therapeutically effective amount of a ROS inhibitor (e.g., any of the ROS inhibitors described herein or known in the art).

Provided herein are methods of treating a patient having a cancer (e.g., any of the cancers described herein) that include: identifying a patient having a cancer cell that has dysregulation of a ROS gene, a ROS protein, or the expression or activity or level of the same; and administering to the identified patient (i) a therapeutically effective amount of a compound of Formula I or a pharmaceutically acceptable salt or solvate thereof and (ii) a therapeutically effective amount a ROS inhibitor (e.g., any of the ROS inhibitors described herein or known in the art).

Provided herein are methods of treating a patient having a cancer (e.g., any of the cancers described herein) that has dysregulation of a MET gene, a MET protein, or the expression or activity or level of the same that include administering to the patient (i) a therapeutically effective amount of a compound of Formula I or a pharmaceutically acceptable salt or solvate thereof and (ii) a therapeutically effective amount of a MET inhibitor (e.g., any of the MET inhibitors described herein or known in the art).

Provided herein are methods of treating a patient having a cancer (e.g., any of the cancers described herein) that include: identifying a patient having a cancer cell that has dysregulation of a MET gene, a MET protein, or the expression or activity or level of the same; and administering to the identified patient (i) a therapeutically effective amount of a compound of Formula I or a pharmaceutically acceptable salt or solvate thereof and (ii) a therapeutically effective amount a MET inhibitor (e.g., any of the MET inhibitors described herein or known in the art).

Provided herein are methods of treating a patient having a cancer (e.g., any of the cancers described herein) that has dysregulation of an aromatase gene, an aromatase protein, or the expression or activity or level of the same that include administering to the patient (i) a therapeutically effective amount of a compound of Formula I or a pharmaceutically acceptable salt or solvate thereof and (ii) a therapeutically effective amount of an aromatase inhibitor (e.g., any of the aromatase inhibitors described herein or known in the art).

Provided herein are methods of treating a patient having a cancer (e.g., any of the cancers described herein) that include: identifying a patient having a cancer cell that has dysregulation of an aromatase gene, an aromatase protein, or the expression or activity or level of the same; and administering to the identified patient (i) a therapeutically effective amount of a compound of Formula I or a pharmaceutically acceptable salt or solvate thereof and (ii) a therapeutically effective amount an aromatase inhibitor (e.g., any of the aromatase inhibitors described herein or known in the art).

Provided herein are methods of treating a patient having a cancer (e.g., any of the cancers described herein) that has dysregulation of a RAF gene, a RAF protein, or the expression or activity or level of the same that include administering to the patient (i) a therapeutically effective amount of a compound of Formula I or a pharmaceutically acceptable salt or solvate thereof and (ii) a therapeutically effective amount of a RAF inhibitor (e.g., any of the RAF inhibitors described herein or known in the art).

Provided herein are methods of treating a patient having a cancer (e.g., any of the cancers described herein) that include: identifying a patient having a cancer cell that has dysregulation of a RAF gene, a RAF protein, or the expression or activity or level of the same; and administering to the identified patient (i) a therapeutically effective amount of a compound of Formula I or a pharmaceutically acceptable salt or solvate thereof and (ii) a therapeutically effective amount a RAF inhibitor (e.g., any of the RAF inhibitors described herein or known in the art).

Provided herein are methods of treating a patient having a cancer (e.g., any of the cancers described herein) that has dysregulation of a RAS gene, a RAS protein, or the expression or activity or level of the same that include administering to the patient (i) a therapeutically effective amount of a compound of Formula I or a pharmaceutically acceptable salt or solvate thereof and (ii) a therapeutically effective amount of a RAS inhibitor (e.g., any of the RAS inhibitors described herein or known in the art).

Provided herein are methods of treating a patient having a cancer (e.g., any of the cancers described herein) that include: identifying a patient having a cancer cell that has dysregulation of a RAS gene, a RAS protein, or the expression or activity or level of the same; and administering to the identified patient (i) a therapeutically effective amount of a compound of Formula I or a pharmaceutically acceptable salt or solvate thereof and (ii) a therapeutically effective amount a RAS inhibitor (e.g., any of the RAS inhibitors described herein or known in the art).

The phrase "dysregulation of a BRAF gene, a BRAF protein, or the expression or activity or level of any of the same" refers to a genetic mutation (e.g., a chromosomal translocation that results in the expression of a fusion protein including a BRAF kinase domain and a fusion partner, a mutation in a BRAF gene that results in the expression of a BRAF protein that includes a deletion of at least one amino acid as compared to a wildtype BRAF protein, a mutation in a BRAF gene that results in the expression of a BRAF protein with one or more point mutations as compared to a wildtype BRAF protein, a mutation in a BRAF gene that results in the expression of a BRAF protein with at least one inserted amino acid as compared to a wildtype BRAF protein, a gene duplication that results in an increased level of BRAF protein in a cell, or a mutation in a regulatory sequence (e.g., a promoter and/or enhancer) that results in an increased level of BRAF protein in a cell), an alternative spliced version of a BRAF mRNA that results in a BRAF protein having a deletion of at least one amino acid in the BRAF protein as compared to the wild-type BRAF protein), or increased expression (e.g., increased levels) of a wildtype BRAF protein in a mammalian cell due to aberrant cell signaling and/or dysregulated autocrine/paracrine signaling (e.g., as compared to a control non-cancerous cell). As another example, a dysregulation of a BRAF gene, a BRAF protein, or expression or activity, or level of any of the same, can be a mutation in a BRAF gene that encodes a BRAF protein that is constitutively active or has increased activity as compared to a protein encoded by a BRAF gene that does not include the mutation. For example, a dysregulation of a BRAF gene, a BRAF protein, or expression or activity, or level of any of the same, can be the result of a gene or chromosome translocation which results in the expression of a fusion protein that contains a first portion of a BRAF protein that includes a functional kinase domain, and a second portion of a partner protein (i.e., that is not BRAF). In some examples, dysregulation of a BRAF gene, a BRAF protein, or expression or activity or level of any of the same can be a result of a gene translocation of one BRAF gene with another non-BRAF gene.

Non-limiting examples of a BRAF inhibitor include dabrafenib, vemurafenib (also called RG7204 or PLX4032), sorafenib tosylate, PLX-4720, GDC-0879, BMS-908662 (Bristol-Meyers Squibb), LGX818 (Novartis), PLX3603 (Hofmann-LaRoche), RAF265 (Novartis), RO5185426 (Hofmann-LaRoche), and GSK2118436 (GlaxoSmithKline). Additional examples of a BRAF inhibitor are known in the art.

The phrase "dysregulation of an EGFR gene, an EGFR protein, or the expression or activity or level of any of the same" refers to a genetic mutation (e.g., a chromosomal translocation that results in the expression of a fusion protein including an EGFR kinase domain and a fusion partner, a mutation in an EGFR gene that results in the expression of an EGFR protein that includes a deletion of at least one amino acid as compared to a wildtype EGFR protein, a mutation in an EGFR gene that results in the expression of an EGFR protein with one or more point mutations as compared to a wildtype EGFR protein, a mutation in an EGFR gene that results in the expression of an EGFR protein with at least one inserted amino acid as compared to a wildtype EGFR protein, a gene duplication that results in an increased level of EGFR protein in a cell, or a mutation in a regulatory sequence (e.g., a promoter and/or enhancer) that results in an increased level of EGFR protein in a cell), an alternative spliced version of a EGFR mRNA that results in an EGFR protein having a deletion of at least one amino acid in the EGFR protein as compared to the wild-type EGFR protein), or increased expression (e.g., increased levels) of a wildtype EGFR protein in a mammalian cell due to aberrant cell signaling and/or dysregulated autocrine/paracrine signaling (e.g., as compared to a control non-cancerous cell). As another example, a dysregulation of an EGFR gene, an EGFR protein, or expression or activity, or level of any of the same, can be a mutation in an EGFR gene that encodes an EGFR protein that is constitutively active or has increased activity as compared to a protein encoded by an EGFR gene that does not include the mutation. For example, a dysregulation of an EGFR gene, an EGFR protein, or expression or activity, or level of any of the same, can be the result of a gene or chromosome translocation which results in the expression of a fusion protein that contains a first portion of a EGFR protein that includes a functional kinase domain, and a second portion of a partner protein (i.e., that is not EGFR). In some examples, dysregulation of an EGFR gene, an EGFR protein, or expression or activity or level of any of the same can be a result of a gene translocation of one EGFR gene with another non-EGFR gene.

Non-limiting examples of an EGFR inhibitor include gefitinib, erlotinib, brigatinib, lapatinib, neratinib, icotinib, afatinib, dacomitinib, poziotinib, vandetanib, afatinib, AZD9291, CO-1686, HM61713, AP26113, CI-1033, PKI-166, GW-2016, EKB-569, PDI-168393, AG-1478, CGP-59326A. Additional examples of an EGFR inhibitor are known in the art.

The phrase "dysregulation of a MEK gene, a MEK protein, or the expression or activity or level of any of the same" refers to a genetic mutation (e.g., a chromosomal translocation that results in the expression of a fusion protein including a MEK kinase domain and a fusion partner, a mutation in a MEK gene that results in the expression of a MEK protein that includes a deletion of at least one amino acid as compared to a wildtype MEK protein, a mutation in a MEK gene that results in the expression of a MEK protein with one or more point mutations as compared to a wildtype MEK protein, a mutation in a MEK gene that results in the expression of a MEK protein with at least one inserted amino acid as compared to a wildtype MEK protein, a gene duplication that results in an increased level of MEK protein in a cell, or a mutation in a regulatory sequence (e.g., a promoter and/or enhancer) that results in an increased level of MEK protein in a cell), an alternative spliced version of a MEK mRNA that results in a MEK protein having a deletion of at least one amino acid in the MEK protein as compared to the wild-type MEK protein), or increased expression (e.g., increased levels) of a wildtype MEK protein in a mammalian cell due to aberrant cell signaling and/or dysregulated autocrine/paracrine signaling (e.g., as compared to a control non-cancerous cell). As another example, a dysregulation of a MEK gene, a MEK protein, or expression or activity, or level of any of the same, can be a mutation in a MEK gene that encodes a MEK protein that is constitutively active or has increased activity as compared to a protein encoded by a MEK gene that does not include the mutation. For example, a dysregulation of a MEK gene, a MEK protein, or expression or activity, or level of any of the same, can be the result of a gene or chromosome translocation which results in the expression of a fusion protein that contains a first portion of a MEK protein that includes a functional kinase domain, and a second portion of a partner protein (i.e., that is not MEK). In some examples, dysregulation of a MEK gene, a MEK protein, or expression or activity or level of any of the same can be a result of a gene translocation of one MEK gene with another non-MEK gene.

Non-limiting examples of a MEK inhibitor include mekinist, trametinib (GSK 1120212), cobimetinib (XL518), binimetinib (MEK162), selumetinib, PD-325901, CI-1040, PD035901, TAK-733, PD098059, U0126, AS703026/MSC1935369, XL-518/GDC-0973, BAY869766/RDEA119, and GSK11120212. Additional examples of a MEK inhibitor are known in the art.

The phrase "dysregulation of an ALK gene, an ALK protein, or the expression or activity or level of any of the same" refers to a genetic mutation (e.g., a chromosomal translocation that results in the expression of a fusion protein including an ALK kinase domain and a fusion partner, a mutation in an ALK gene that results in the expression an ALK protein that includes a deletion of at least one amino acid as compared to a wildtype ALK protein, a mutation in an ALK gene that results in the expression of an ALK protein with one or more point mutations as compared to a wildtype ALK protein, a mutation in an ALK gene that results in the expression of an ALK protein with at least one inserted amino acid as compared to a wildtype ALK protein, a gene duplication that results in an increased level of ALK protein in a cell, or a mutation in a regulatory sequence (e.g., a promoter and/or enhancer) that results in an increased level of ALK protein in a cell), an alternative spliced version of an ALK mRNA that results in an ALK protein having a deletion of at least one amino acid in the ALK protein as compared to the wild-type ALK protein), or increased expression (e.g., increased levels) of a wildtype ALK protein in a mammalian cell due to aberrant cell signaling and/or dysregulated autocrine/paracrine signaling (e.g., as compared to a control non-cancerous cell). As another example, a dysregulation of an ALK gene, an ALK protein, or expression or activity, or level of any of the same, can be a mutation in an ALK gene that encodes an ALK protein that is constitutively active or has increased activity as compared to a protein encoded by an ALK gene that does not include the mutation. For example, a dysregulation of an ALK gene, an ALK protein, or expression or activity, or level of any of the same, can be the result of a gene or chromosome translocation which results in the expression of a fusion protein that contains a first portion of an ALK protein that includes a functional kinase domain, and a second portion of a partner protein (i.e., that is not ALK). In some examples, dysregulation of an ALK gene, an ALK protein, or expression or activity or level of any of the same can be a result of a gene translocation of one ALK gene with another non-ALK gene.

Non-limiting examples of an ALK inhibitor include crizotinib (Xalkori), ceritinib (Zykadia), alectinib (Alecensa), dalantercept, ACE-041 (Brigatinib) (AP26113), entrectinib (NMS-E628), PF-06463922 (Pfizer), TSR-011 (Tesaro), CEP-37440 (Teva), CEP-37440 (Teva), X-396 (Xcovery), and ASP-3026 (Astellas). Additional examples of an ALK inhibitor are known in the art.

The phrase "dysregulation of a ROS1 gene, a ROS1 protein, or the expression or activity or level of any of the same" refers to a genetic mutation (e.g., a chromosomal translocation that results in the expression of a fusion protein including a ROS1 kinase domain and a fusion partner, a mutation in a ROS1 gene that results in the expression a ROS1 protein that includes a deletion of at least one amino acid as compared to a wildtype ROS1 protein, a mutation in a ROS1 gene that results in the expression of a ROS1 protein with one or more point mutations as compared to a wildtype ROS1 protein, a mutation in a ROS1 gene that results in the expression of a ROS1 protein with at least one inserted amino acid as compared to a wildtype ROS1 protein, a gene duplication that results in an increased level of ROS1 protein in a cell, or a mutation in a regulatory sequence (e.g., a promoter and/or enhancer) that results in an increased level of ROS1 protein in a cell), an alternative spliced version of a ROS1 mRNA that results in a ROS1 protein having a deletion of at least one amino acid in the ROS1 protein as compared to the wild-type ROS1 protein), or increased expression (e.g., increased levels) of a wildtype ROS1 protein in a mammalian cell due to aberrant cell signaling and/or dysregulated autocrine/paracrine signaling (e.g., as compared to a control non-cancerous cell). As another example, a dysregulation of a ROS1 gene, a ROS1 protein, or expression or activity, or level of any of the same, can be a mutation in a ROS1 gene that encodes a ROS1 protein that is constitutively active or has increased activity as compared to a protein encoded by a ROS1 gene that does not include the mutation. For example, a dysregulation of a ROS1 gene, a ROS1 protein, or expression or activity, or level of any of the same, can be the result of a gene or chromosome translocation which results in the expression of a fusion protein that contains a first portion of a ROS1 protein that includes a functional kinase domain, and a second portion of a partner protein (i.e., that is not ROS1). In some examples, dysregulation of a ROS1 gene, a ROS1 protein, or expression or activity or level of any of the same can be a result of a gene translocation of one ROS1 gene with another non-ROS1 gene.

Non-limiting examples of a ROS1 inhibitor include crizotinib, entrectinib (RXDX-101), lorlatinib (PF-06463922), certinib, TPX-0005, DS-605, and cabozantinib. Additional examples of a ROS1 inhibitor are known in the art.

The phrase "dysregulation of a MET gene, a MET protein, or the expression or activity or level of any of the same" refers to a genetic mutation (e.g., a chromosomal translocation that results in the expression of a fusion protein including a MET kinase domain and a fusion partner, a mutation in a MET gene that results in the expression a MET protein that includes a deletion of at least one amino acid as compared to a wildtype MET protein, a mutation in a MET gene that results in the expression of a MET protein with one or more point mutations as compared to a wildtype MET protein, a mutation in a MET gene that results in the expression of a MET protein with at least one inserted amino acid as compared to a wildtype MET protein, a gene duplication that results in an increased level of MET protein in a cell, or a mutation in a regulatory sequence (e.g., a promoter and/or enhancer) that results in an increased level of MET protein in a cell), an alternative spliced version of a MET mRNA that results in a MET protein having a deletion of at least one amino acid in the MET protein as compared to the wild-type MET protein), or increased expression (e.g., increased levels) of a wildtype MET protein in a mammalian cell due to aberrant cell signaling and/or dysregulated autocrine/paracrine signaling (e.g., as compared to a control non-cancerous cell). As another example, a dysregulation of a MET gene, a MET protein, or expression or activity, or level of any of the same, can be a mutation in a MET gene that encodes a MET protein that is constitutively active or has increased activity as compared to a protein encoded by a MET gene that does not include the mutation. For example, a dysregulation of a MET gene, a MET protein, or expression or activity, or level of any of the same, can be the result of a gene or chromosome translocation which results in the expression of a fusion protein that contains a first portion of a MET protein that includes a functional kinase domain, and a second portion of a partner protein (i.e., that is not MET). In some examples, dysregulation of a MET gene, a MET protein, or expression or activity or level of any of the same can be a result of a gene translocation of one MET gene with another non-MET gene.

Non-limiting examples of a MET inhibitor include crizotinib, cabozantinib, JNJ-38877605, PF-04217903 (Pfizer), MK-2461, GSK 1363089, AMG 458 (Amgen), tivantinib, INCB28060 (Incyte), PF-02341066 (Pfizer), E7050 (Eisai), BMS-777607 (Bristol-Meyers Squibb), JNJ-38877605 (Johnson & Johnson), ARQ197 (ArQule), GSK/1363089/XL880 (GSK/Exeilixis), and XL174 (BMS/Exelixis). Additional examples of a MET inhibitor are known in the art.

The phrase "dysregulation of a aromatase gene, an aromatase protein, or the expression or activity or level of any of the same" refers to a genetic mutation (e.g., a mutation in an aromatase gene that results in the expression an aromatase protein that includes a deletion of at least one amino acid as compared to a wildtype aromatase protein, a mutation in an aromatase gene that results in the expression of an aromatase protein with one or more point mutations as compared to a wildtype aromatase protein, a mutation in an aromatase gene that results in the expression of an aromatase protein with at least one inserted amino acid as compared to a wildtype aromatase protein, a gene duplication that results in an increased level of aromatase protein in a cell, or a mutation in a regulatory sequence (e.g., a promoter and/or enhancer) that results in an increased level of aromatase protein in a cell), an alternative spliced version of an aromatase mRNA that results in an aromatase protein having a deletion of at least one amino acid in the aromatase protein as compared to the wild-type aromatase protein), or increased expression (e.g., increased levels) of a wildtype aromatase in a mammalian cell due to aberrant cell signaling and/or dysregulated autocrine/paracrine signaling (e.g., as compared to a control non-cancerous cell). As another example, a dysregulation of an aromatase gene, an aromatase protein, or expression or activity, or level of any of the same, can be a mutation in an aromatase gene that encodes an aromatase protein that is constitutively active or has increased activity as compared to a protein encoded by an aromatase gene that does not include the mutation.

Non-limiting examples of an aromatase inhibitor include Arimidex (anastrozole), Aromasin (exemestane), Femara (letrozole), Teslac (testolactone), and formestane. Additional examples of an aromatase inhibitor are known in the art.

The phrase "dysregulation of a RAF gene, a RAF protein, or the expression or activity or level of any of the same" refers to a genetic mutation (e.g., a chromosomal translocation that results in the expression of a fusion protein including a RAF kinase domain and a fusion partner, a mutation in a RAF gene that results in the expression a RAF protein that includes a deletion of at least one amino acid as compared to a wildtype RAF protein, a mutation in a RAF gene that results in the expression of a RAF protein with one or more point mutations as compared to a wildtype RAF protein, a mutation in a RAF gene that results in the expression of a RAF protein with at least one inserted amino acid as compared to a wildtype RAF protein, a gene duplication that results in an increased level of RAF protein in a cell, or a mutation in a regulatory sequence (e.g., a promoter and/or enhancer) that results in an increased level of RAF protein in a cell), an alternative spliced version of a RAF mRNA that results in a RAF protein having a deletion of at least one amino acid in the RAF protein as compared to the wild-type RAF protein), or increased expression (e.g., increased levels) of a wildtype RAF protein in a mammalian cell due to aberrant cell signaling and/or dysregulated autocrine/paracrine signaling (e.g., as compared to a control non-cancerous cell). As another example, a dysregulation of a RAF gene, a RAF protein, or expression or activity, or level of any of the same, can be a mutation in a RAF gene that encodes a RAF protein that is constitutively active or has increased activity as compared to a protein encoded by a RAF gene that does not include the mutation. For example, a dysregulation of a RAF gene, a RAF protein, or expression or activity, or level of any of the same, can be the result of a gene or chromosome translocation which results in the expression of a fusion protein that contains a first portion of a RAF protein that includes a functional kinase domain, and a second portion of a partner protein (i.e., that is not RAF). In some examples, dysregulation of a RAF gene, a RAF protein, or expression or activity or level of any of the same can be a result of a gene translocation of one RAF gene with another non-RAF gene.

Non-limiting examples of a RAF inhibitor include sorafenib, vemurafenib, dabrafenib, BMS-908662/XL281, GSK2118436, RAF265, RO5126766, and RO4987655. Additional examples of a RAF inhibitor are known in the art.

The phrase "dysregulation of a RAS gene, a RAS protein, or the expression or activity or level of any of the same" refers to a genetic mutation (e.g., a chromosomal translocation that results in the expression of a fusion protein including a RAS kinase domain and a fusion partner, a mutation in a RAS gene that results in the expression a RAS protein that includes a deletion of at least one amino acid as compared to a wildtype RAS protein, a mutation in a RAS gene that results in the expression of a RAS protein with one or more point mutations as compared to a wildtype RAS protein, a mutation in a RAS gene that results in the expression of a RAS protein with at least one inserted amino acid as compared to a wildtype RAS protein, a gene duplication that results in an increased level of RAS protein in a cell, or a mutation in a regulatory sequence (e.g., a promoter and/or enhancer) that results in an increased level of RAS protein in a cell), an alternative spliced version of a RAS mRNA that results in a RAS protein having a deletion of at least one amino acid in the RAS protein as compared to the wild-type RAS protein), or increased expression (e.g., increased levels) of a wildtype RAS protein in a mammalian cell due to aberrant cell signaling and/or dysregulated autocrine/paracrine signaling (e.g., as compared to a control non-cancerous cell). As another example, a dysregulation of a RAS gene, a RAS protein, or expression or activity, or level of any of the same, can be a mutation in a RAS gene that encodes a RAS protein that is constitutively active or has increased activity as compared to a protein encoded by a RAS gene that does not include the mutation. For example, a dysregulation of a RAS gene, a RAS protein, or expression or activity, or level of any of the same, can be the result of a gene or chromosome translocation which results in the expression of a fusion protein that contains a first portion of a RAS protein that includes a functional kinase domain, and a second portion of a partner protein (i.e., that is not RAS). In some examples, dysregulation of a RAS gene, a RAS protein, or expression or activity or level of any of the same can be a result of a gene translocation of one RAS gene with another non-RAS gene.

Non-limiting examples of a RAS inhibitor include Kobe0065 and Kobe2602. Additional examples of a RAS inhibitor are known in the art.

Non-limiting examples of multi-kinase inhibitors (MKIs) include dasatinib and sunitinib.

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a compound of Formula I or a pharmaceutically acceptable salt or solvate thereof as a monotherapy or in conjunction with another anticancer agent for the subject if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) administering one or more doses of a first RET inhibitor to the subject for a period of time; (b) after (a), determining whether a cancer cell in a sample obtained from the subject has at least one RET inhibitor resistance mutation; and (c) selecting a second RET inhibitor as a monotherapy or in conjunction with another anticancer agent if the subject has a cancer cell that has one or more RET inhibitor resistance mutations; or (d) selecting additional doses of the first RET inhibitor of step (a) for the subject if the subject has a cancer cell that does not have a RET inhibitor resistance mutation. In some embodiments, when additional doses of the first RET inhibitor of step (a) are selected for the subject, the method can further include selecting doses of another anticancer agent for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a compound of Formula I or a pharmaceutically acceptable salt or solvate thereof as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof. or an immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments of step (c), another RET inhibitor can be the first RET inhibitor administered in step (a).

Also provided are methods of selecting a treatment for a subject having a cancer that include (a) determining whether a cancer cell in a sample obtained from a subject having a cancer and previously administered one or more doses of a first RET inhibitor has one or more RET inhibitor resistance mutations; (b) selecting a second RET inhibitor as a monotherapy or in conjunction with another anticancer agent for the subject if the subject has a cancer cell that has at least one RET inhibitor resistance mutation; or (c) selecting additional doses of the first RET inhibitor previously administered to the subject if the subject has a cancer cell that does not have a RET inhibitor resistance mutation. In some embodiments, when additional doses of the first RET inhibitor previously administered to the subject are selected for the subject, the method can further include selecting doses of another anticancer agent (e.g., a compound of Formula I or a pharmaceutically acceptable salt or solvate thereof, or an immunotherapy) for the subject. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E. In some embodiments, the additional anticancer agent is any anticancer agent known in the art. For example, the additional anticancer agent is another RET inhibitor (e.g., a compound of Formula I or a pharmaceutically acceptable salt or solvate thereof). In some embodiments, the additional anticancer agent is an immunotherapy. In some embodiments, another RET can be the first RET inhibitor administered in step (a).

Also provided are methods of determining a subject's risk for developing a cancer that has some resistance to a first RET inhibitor that include: determining whether a cell in a sample obtained from the subject has one or more RET inhibitor resistance mutations; and identifying a subject having a cell that has one or more RET inhibitor resistance mutations, as having an increased likelihood of developing a cancer that has some resistance to the first RET inhibitor. Also provided are methods of determining a subject's risk for developing a cancer that has some resistance to a first RET inhibitor that include: identifying a subject having a cell that has one or more RET inhibitor resistance mutations, as having an increased likelihood of developing a cancer that has some resistance to the first RET inhibitor. Also provided are methods of determining the presence of a cancer that has some resistance to a first RET inhibitor that include: determining whether a cancer cell in a sample obtained from the subject has one or more RET inhibitor resistance mutations; and determining that the subject having a cancer cell that has one or more RET inhibitor resistance mutations has a cancer that has some resistance to the first RET inhibitor. Also provided are methods of determining the presence of a cancer that has some resistance to a first RET inhibitor in a subject that include: determining that a subject having a cancer cell that has one or more RET inhibitor resistance mutations, has a cancer that has some resistance to the first RET inhibitor. In some embodiments, the one or more RET inhibitor resistance mutations confer increased resistance to a cancer cell or tumor to treatment with the first RET inhibitor. In some embodiments, the one or more RET inhibitor resistance mutations include one or more RET inhibitor resistance mutations listed in Tables 3 and 4. For example, the one or more RET inhibitor resistance mutations can include a substitution at amino acid position 804, e.g., V804M, V804L, or V804E.

In some embodiments of any of the methods described herein, a RET inhibitor resistance mutation that confers increased resistance to a cancer cell or tumor to treatment with a first RET inhibitor can be any of the RET inhibitor resistance mutations listed in Table 3 or 4 (e.g., a substitution at amino acid position 804, e.g., V804M, V804L, or V804E).

In some embodiments, the presence of one or more RET inhibitor resistance mutations in a tumor causes the tumor to be more resistant to treatment with a compound of Formula I or a pharmaceutically acceptable salt or solvate thereof. Methods useful when a RET inhibitor resistance mutation causes the tumor to be more resistant to treatment with a compound of Formula I or a pharmaceutically acceptable salt or solvate thereof are described below. For example, provided herein are methods of treating a subject having a cancer that include: identifying a subject having a cancer cell that has one or more RET inhibitor resistance mutations; and administering to the identified subject a treatment that does not include a compound of Formula I or a pharmaceutically acceptable salt or solvate thereof as a monotherapy (e.g., a second RET kinase inhibitor). Also provided are methods of treating a subject identified as having a cancer cell that has one or more RET inhibitor resistance mutations that include administering to the subject a treatment that does not include a compound of Formula I or a pharmaceutically acceptable salt or solvate thereof as a monotherapy (e.g., a second RET kinase inhibitor). In some embodiments, the one or more RET inhibitor resistance mutations confer increased resistance to a cancer cell or tumor to treatment with a compound of Formula I or a pharmaceutically acceptable salt or solvate thereof.

Also provided are methods of selecting a treatment for a subject having a cancer that include: identifying a subject having a cancer cell that has one or more RET inhibitor resistance mutations; and selecting a treatment that does not include a compound of Formula I or a pharmaceutically acceptable salt or solvate thereof as a monotherapy for the identified subject (e.g., a second RET kinase inhibitor). Also provided are methods of selecting a treatment for a subject having a cancer that include: selecting a treatment that does not include a compound of Formula I or a pharmaceutically acceptable salt or solvate thereof as a monotherapy (e.g., a second RET kinase inhibitor) for a subject identified as having a cancer cell that has one or more RET inhibitor resistance mutations. Also provided are methods of selecting a subject having a cancer for a treatment that does not include a compound of Formula I or a pharmaceutically acceptable salt or solvate thereof as a monotherapy (e.g., a second RET kinase inhibitor) that include: identifying a subject having a cancer cell that has one or more RET inhibitor resistance mutations; and selecting the identified subject for a treatment that does not include a compound of Formula I or a pharmaceutically acceptable salt or solvate thereof as a monotherapy (e.g., a second RET kinase inhibitor). Also provided are methods of selecting a subject having a cancer for a treatment that does not include a compound of Formula I or a pharmaceutically acceptable salt or solvate thereof as a monotherapy (e.g., a second RET kinase inhibitor) that include: selecting a subject identified as having a cancer cell that has one or more RET inhibitor resistance mutations for a treatment that does not include a compound of Formula I or a pharmaceutically acceptable salt or solvate thereof as a monotherapy. In some embodiments, the one or more RET inhibitor resistance mutations confer increased resistance to a cancer cell or tumor to treatment with a compound of Formula I or a pharmaceutically acceptable salt or solvate thereof.

Also provided are methods of determining the likelihood that a subject having a cancer will have a positive response to treatment with a compound of Formula I or a pharmaceutically acceptable salt or solvate thereof as a monotherapy that include: determining whether a cancer cell in a sample obtained from the subject has one or more RET inhibitor resistance mutations; and determining that the subject having the cancer cell that has one or more RET inhibitor resistance mutations has a decreased likelihood of having a positive response to treatment with a compound of Formula I or a pharmaceutically acceptable salt or solvate thereof as a monotherapy. Also provided are methods of determining the likelihood that a subject having cancer will have a positive response to treatment with a compound of Formula I or a pharmaceutically acceptable salt or solvate thereof as a monotherapy that include: determining that a subject having a cancer cell that has one or more RET inhibitor resistance mutations has a decreased likelihood of having a positive response to treatment with a compound of Formula I or a pharmaceutically acceptable salt or solvate thereof as a monotherapy. Also provided are methods of predicting the efficacy of treatment with a compound of Formula I or a pharmaceutically acceptable salt or solvate thereof as a monotherapy in a subject having cancer that include: determining whether a cancer cell in a sample obtained from the subject has one or more RET inhibitor resistance mutations; and determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. Also provided are methods of predicting the efficacy of treatment with a compound of Formula I or a pharmaceutically acceptable salt or solvate thereof as a monotherapy in a subject having cancer that include: determining that treatment with a compound of Formula I or a pharmaceutically acceptable salt or solvate thereof as a monotherapy is less likely to be effective in a subject having a cancer cell in a sample obtained from the subject that has one or more RET inhibitor resistance mutations. In some embodiments, the one or more RET inhibitor resistance mutations confer increased resistance to a cancer cell or tumor to treatment with a compound of Formula I or a pharmaceutically acceptable salt or solvate thereof.

Also provided are methods of treating a subject having a cancer that include: (a) administering one or more doses of a compound of Formula I or a pharmaceutically acceptable salt or solvate thereof for a period of time; (b) after (a), determining whether a cancer cell in a sample obtained from the subject has one or more RET inhibitor resistance mutations; and (c) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (d) administering additional doses of the compound of Formula I or a pharmaceutically acceptable salt or solvate thereof of step (a) to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent or a second compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of treating a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) administering a second RET inhibitor or a second compound of Formula I or a pharmaceutically acceptable salt or solvate thereof as a monotherapy or in conjunction with another anticancer agent to a subject having a cancer cell that has one or more RET inhibitor resistance mutations; or (c) administering additional doses of the compound of Formula I or a pharmaceutically acceptable salt or solvate thereof previously administered to a subject having a cancer cell that does not have a RET inhibitor resistance mutation. In some embodiments, where the subject is administered additional doses of the compound of Formula I or a pharmaceutically acceptable salt or solvate thereof of step (a), the subject can also be administered another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) administering one or more doses of a compound of Formula I or a pharmaceutically acceptable salt or solvate thereof to the subject for a period of time; (b) after (a), determining whether a cancer cell in a sample obtained from the subject has one or more RET inhibitor resistance mutations; and (c) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (d) selecting additional doses of the compound of Formula I or a pharmaceutically acceptable salt or solvate thereof of step (a) for the subject if the subject has a cancer cell that does not have a RET inhibitor resistance mutation. In some embodiments, where additional doses of a compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of selecting a treatment for a subject having a cancer that include: (a) determining whether a cancer cell in a sample obtained from a subject having a cancer and previously administered one or more doses of a compound of Formula I or a pharmaceutically acceptable salt or solvate thereof, has one or more RET inhibitor resistance mutations; (b) selecting a second RET inhibitor or a second compound of Formula I or a pharmaceutically acceptable salt or solvate thereof as a monotherapy or in conjunction with another anticancer agent for the subject if the subject has a cancer cell that has a RET inhibitor resistance mutation; or (c) selecting additional doses of the compound of Formula I or a pharmaceutically acceptable salt or solvate thereof previously administered to the subject if the subject has a cancer cell that does not have a RET inhibitor resistance mutation. In some embodiments, where additional doses of the compound of Formula I or a pharmaceutically acceptable salt or solvate thereof of step (a) are selected for the subject, the method can also include further selecting another anticancer agent. In some embodiments, the one or more RET inhibitor resistance mutations confer increased resistance to a cancer cell or tumor to treatment with a compound of Formula I or a pharmaceutically acceptable salt or solvate thereof. In some embodiments, the additional anticancer agent is any anticancer agent known in the art. For example, the additional anticancer agent is another RET inhibitor (e.g., a second RET inhibitor). In some embodiments, the additional anticancer agent is an immunotherapy. In some embodiments, another RET can be the compound of Formula I or a pharmaceutically acceptable salt or solvate thereof administered in step (a).

Also provided are methods of determining a subject's risk for developing a cancer that has some resistance to a compound of Formula I or a pharmaceutically acceptable salt or solvate thereof that include: determining whether a cell in a sample obtained from the subject has one or more RET inhibitor resistance mutations; and identifying the subject if the subject has a cell that has one or more RET inhibitor resistance mutations as having an increased likelihood of developing a cancer that has some resistance to a compound of Formula I or a pharmaceutically acceptable salt or solvate thereof. Also provided are methods of determining a subject's risk for developing a cancer that has some resistance to a compound of Formula I or a pharmaceutically acceptable salt or solvate thereof that include: identifying a subject having a cell that has one or more RET inhibitor resistance mutations as having an increased likelihood of developing a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof that includes: determining whether a cancer cell in a sample obtained from the subject has one or more RET inhibitor resistance mutations; and determining that the subject having the cancer cell that has one or more RET inhibitor resistance mutations has a cancer that has some resistance to a compound of Formula I or a pharmaceutically acceptable salt or solvate thereof. Also provided are methods of determining the presence of a cancer that has some resistance to a compound of Formula I or a pharmaceutically acceptable salt or solvate thereof in a subject that include: determining that a subject having a cancer cell that has one or more RET inhibitor resistance mutations has a cancer that has some resistance to a compound of Formula I or a pharmaceutically acceptable salt or solvate thereof. In some embodiments, the one or more RET inhibitor resistance mutations confer increased resistance to a cancer cell or tumor to treatment with a compound of Formula I or a pharmaceutically acceptable salt or solvate thereof.

In some embodiments of any of the methods described herein, a RET inhibitor resistance mutation that confers increased resistance to a cancer cell or tumor to treatment with a compound of Formula I or a pharmaceutically acceptable salt or solvate thereof, can be any of the RET inhibitor resistance mutations listed in Table 3 or 4.

Methods of determining the level of resistance of a cancer cell or a tumor to a RET inhibitor (e.g., any of the RET inhibitors described herein or known in the art) can be determined using methods known in the art. For example, the level of resistance of a cancer cell to a RET inhibitor can be assessed by determining the $IC_{50}$ of a RET inhibitor (e.g., any of the RET inhibitors described herein or known in the art) on the viability of a cancer cell. In other examples, the level of resistance of a cancer cell to a RET inhibitor can be assessed by determining the growth rate of the cancer cell in the presence of a RET inhibitor (e.g., any of the RET inhibitors described herein). In other examples, the level of resistance of a tumor to a RET inhibitor can be assessed by determining the mass or size of one or more tumors in a subject over time during treatment with a RET inhibitor (e.g., any of the RET inhibitors described herein). In other examples, the level of resistance of a cancer cell or a tumor to a RET inhibitor can be indirectly assessed by determining the activity of a RET kinase including one or more of the RET inhibitor resistance mutations (i.e., the same RET kinase expressed in a cancer cell or a tumor in a subject). The level of resistance of a cancer cell or tumor having one or more RET inhibitor resistance mutations to a RET inhibitor is relative to the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein). For example, the determined level of resistance of a cancer cell or a tumor having one or more RET inhibitor resistance mutations can be greater than about 1%, greater than about 2%, greater than about 3%, greater than about 4%, greater than about 5%, greater than about 6%, greater than about 7%, greater than about 8%, greater than about 9%, greater than about 10%, greater than about 11%, greater than about 12%, greater than about 13%, greater than about 14%, greater than about 15%, greater than about 20%, greater than about 25%, greater than about 30%, greater than about 35%, greater than about 40%, greater than about 45%, greater than about 50%, greater than about 60%, greater than about 70%, greater than about 80%, greater than about 90%, greater than about 100%, greater than about 110%, greater than about 120%, greater than about 130%, greater than about 140%, greater than about 150%, greater than about 160%, greater than about 170%, greater than about 180%, greater than about 190%, greater than about 200%, greater than about 210%, greater than about 220%, greater than about 230%, greater than about 240%, greater than about 250%, greater than about 260%, greater than about 270%, greater than about 280%, greater than about 290%, or greater than about 300% of the level of resistance in a cancer cell or tumor that does not have a RET inhibitor resistance mutation (e.g., a cancer cell or tumor that does not have the same RET inhibitor resistance mutations, a cancer cell or a tumor that does not have any RET inhibitor resistance mutations, or a cancer cell or a tumor that expresses a wildtype RET protein).

RET is thought to play an important role in the development and survival of afferent nociceptors in the skin and gut. RET kinase knock-out mice lack enteric neurons and have other nervous system anomalies suggesting that a functional RET kinase protein product is necessary during development (Taraviras, S. et al., *Development,* 1999, 126:2785-2797). Moreover population studies of patients with Hirschsprung's disease characterized by colonic obstruction due to lack of normal colonic enervation have a higher proportion of both familial and sporadic loss of function RET mutations (Butler Tjaden N., et al., *Transl. Res.,* 2013, 162: 1-15). Irritable bowel syndrome (IBS) is a common illness affecting 10-20% of individuals in developed countries and is characterized by abnormal bowel habits, bloating and visceral hypersensitivity (Camilleri, M., *N. Engl. J. Med.,* 2012, 367: 1626-1635). While the etiology of IBS is unknown it is thought to result from either a disorder between the brain and gastrointestinal tract, a disturbance in the gut microbiome or increased inflammation. The resulting gastrointestinal changes affect normal bowel transit resulting in either diarrhea or constipation. Furthermore in many IBS patients the sensitization of the peripheral nervous system results in visceral hypersensitivity or allodynia (Keszthelyi, D., *Eur. J. Pain,* 2012, 16: 1444-1454). See, e.g., U.S. Publication No. 2015/0099762.

Accordingly, provided herein are methods for treating a patient diagnosed with (or identified as having) an irritable bowel syndrome (IBS) including diarrhea-predominant, constipation-predominant or alternating stool pattern, functional bloating, functional constipation, functional diarrhea, unspecified functional bowel disorder, functional abdominal pain syndrome, chronic idiopathic constipation, functional esophageal disorders, functional gastroduodenal disorders, functional anorectal pain, and inflammatory bowel disease that include administering to the patient a therapeutically effective amount of a compound of Formula I or a pharmaceutically acceptable salt or solvate thereof.

Also provided herein are methods for treating a patient identified or diagnosed as having a RET-associated irritable bowel syndrome (IBS) (e.g., a patient that has been identified or diagnosed as having a RET-associated irritable bowel syndrome (IBS) through the use of a regulatory agency-approved, e.g., FDA-approved, kit for identifying dysregulation of a RET gene, a RET kinase, or expression or activity or level of any of the same, in a patient or a biopsy sample from the patient) that include administering to the patient a therapeutically effective amount of a compound of Formula I or a pharmaceutically acceptable salt or solvate thereof.

Also provided herein are methods for treating pain associated with IBS that include administering to the patient a therapeutically effective amount of a compound of Formula I or a pharmaceutically acceptable salt or solvate thereof. In some embodiments, a compound of Formula I or a pharmaceutically acceptable salt or solvate thereof is administered in combination with another therapeutic agent useful for treating one or more symptoms of IBS.

Also provided are methods for treating an irritable bowel syndrome (IBS) in a patient in need thereof, the method comprising: (a) determining if the irritable bowel syndrome (IBS) in the patient is a RET-associated IBS (e.g., using a regulatory-agency approved, e.g., FDA-approved, kit for identifying dysregulation of a RET gene, a RET kinase, or expression or activity or level of any of the same, in a patient or a biopsy sample from the patient, or by performing any of the non-limiting examples of assays described herein); and (b) if the IBS is determined to be a RET-associated IBS, administering to the patient a therapeutically effective amount of a compound of Formula I or a pharmaceutically acceptable salt or solvate thereof.

In some embodiments, the compounds of the present invention are useful for treating irritable bowel syndrome (IBS) in combination with one or more additional therapeutic agents or therapies effective in treating the irritable bowel syndrome that work by the same or a different mechanism of action. The at least one additional therapeutic agent may be administered with a compound of Formula I or a pharmaceutically acceptable salt or solvate thereof as part of the same or separate dosage forms, via the same or different routes of administration, and on the same or different administration schedules according to standard pharmaceutical practice known to one skilled in the art.

Non-limiting examples of additional therapeutics for the treatment of irritable bowel syndrome (IBS) include probiotics, fiber supplements (e.g., psyllium, methylcellulose), anti-diarrheal medications (e.g., loperamide), bile acid binders (e.g., cholestyramine, colestipol, colesevelam), anticholinergic and antispasmodic medications (e.g., hyoscyamine, dicyclomine), antidepressant medications (e.g., tricyclic antidepressant such as imipramine or notriptyline or a selective serotonin reuptake inhibitor (SSRI) such as fluoxetine or paroxetine), antibiotics (e.g., rifaximin), alosetron, and lubiprostone.

Accordingly, also provided herein are methods of treating irritable bowel syndrome (IBS), comprising administering to a patient in need thereof a pharmaceutical combination for treating IBS which comprises (a) a compound of Formula I or pharmaceutically acceptable salt or solvate thereof, (b) an additional therapeutic agent, and (c) optionally at least one pharmaceutically acceptable carrier for simultaneous, separate or sequential use for the treatment of IBS, wherein the amounts of the compound of Formula I or pharmaceutically acceptable salt or solvate thereof and the additional therapeutic agent are together effective in treating the IBS. In one embodiment, the compound of Formula I or pharmaceutically acceptable salt or solvate thereof, and the additional therapeutic agent are administered simultaneously as separate dosages. In one embodiment, the compound of Formula I or pharmaceutically acceptable salt or solvate thereof, and the additional therapeutic agent are administered as separate dosages sequentially in any order, in jointly therapeutically effective amounts, e.g. in daily or intermittently dosages. In one embodiment, compound of Formula I or pharmaceutically acceptable salt or solvate thereof, and the additional therapeutic agent are administered simultaneously as a combined dosage.

Also provided herein is (i) a pharmaceutical combination for treating irritable bowel syndrome in a patient in need thereof, which comprises (a) a compound of Formula I or a pharmaceutically acceptable salt or solvate thereof, (b) at least one additional therapeutic agent (e.g., any of the exemplary additional therapeutic agents described herein for treating irritable bowel syndrome or known in the art), and (c) optionally at least one pharmaceutically acceptable carrier for simultaneous, separate or sequential use for the treatment of irritable bowel syndrome, wherein the amounts of the compound of Formula I or pharmaceutically acceptable salt or solvate thereof and of the additional therapeutic agent are together effective in treating the irritable bowel syndrome; (ii) a pharmaceutical composition comprising such a combination; (iii) the use of such a combination for the preparation of a medicament for the treatment of irritable bowel syndrome; and (iv) a commercial package or product comprising such a combination as a combined preparation for simultaneous, separate or sequential use; and to a method of treatment of irritable bowel syndrome in a patient in need thereof. In one embodiment the patient is a human.

The term "pharmaceutical combination", as used herein, refers to a pharmaceutical therapy resulting from the mixing or combining of more than one active ingredient and includes both fixed and non-fixed combinations of the active ingredients. The term "fixed combination" means that a compound of Formula I or a pharmaceutically acceptable salt or solvate thereof and at least one additional therapeutic agent (e.g., an agent effective in treating irritable bowel syndrome), are both administered to a patient simultaneously in the form of a single composition or dosage. The term "non-fixed combination" means that a compound of Formula I or a pharmaceutically acceptable salt or solvate thereof and at least one additional therapeutic agent (e.g., an agent effective in treating irritable bowel syndrome) are formulated as separate compositions or dosages, such that they may be administered to a patient in need thereof simultaneously, concurrently or sequentially with variable intervening time limits, wherein such administration provides effective levels of the two or more compounds in the body of the patient. In one embodiment, the compound of Formula I and the additional therapeutic agent are formulated as separate unit dosage forms, wherein the separate dosages forms are suitable for either sequential or simultaneous administration. These also apply to cocktail therapies, e.g. the administration of three or more active ingredients.

In some embodiments, a compound provided herein can be used as an agent for supportive care for a patient undergoing cancer treatment. For example, a compound of Formula I or a pharmaceutically acceptable salt or solvate thereof, can be useful to reduce one or more symptoms associated with treatment with one or more cancer therapies such as diarrheal or constipations complications and/or abdominal pain. See, for example, U.S. Publication No. 2015/0099762 and Hoffman, J. M. et al. *Gastroenterology* (2012) 142:844-854. Accordingly, a compound, or a pharmaceutically acceptable salt thereof, or composition provided herein can be administered to a patient to address one or more complications associated with cancer treatment (e.g., gastrointestinal complications such as diarrhea, constipation, or abdominal pain).

In some embodiments, a therapeutically effective amount of a compound of Formula I or a pharmaceutically acceptable salt or solvate thereof, can be administered to a patient undergoing cancer treatment (e.g., a patient experiencing an adverse event associated with cancer treatment such as an immune-related adverse event or a gastrointestinal complication including diarrhea, constipation, and abdominal pain). For example, a compound provided herein, or a pharmaceutically acceptable salt thereof, can be used in the treatment of colitis or IBS associated with administration of a checkpoint inhibitor; see, e.g., Postow, M. A. et al. *Journal of Clinical Oncology* (2015) 33: 1974-1982. In some such embodiments, a compound provided herein, or a pharmaceutically acceptable salt thereof, can be formulated to exhibit low bioavailability and/or be targeted for delivery in the gastrointestinal tract. See, for example, U.S. Pat. No. 6,531,152.

Also provided is a method for inhibiting RET kinase activity in a cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a subject having a cell having RET kinase activity. In some embodiments, the cell is a cancer cell. In one embodiment, the cancer cell is any cancer as described herein. In some embodiments, the cancer cell is a RET-associated cancer cell. In some embodiments, the cell is a gastrointestinal cell.

Also provided is a method for inhibiting RET kinase activity in a mammalian cell, comprising contacting the cell with a compound of Formula I. In one embodiment, the contacting is in vitro. In one embodiment, the contacting is in vivo. In one embodiment, the contacting is in vivo, wherein the method comprises administering an effective amount of a compound of Formula I or a pharmaceutically acceptable salt or solvate thereof to a mammal having a cell having RET kinase activity. In some embodiments, the mammalian cell is a mammalian cancer cell. In one embodiment, the mammalian cancer cell is any cancer as described herein. In some embodiments, the mammalian cancer cell is a RET-associated cancer cell. In some embodiments, the mammalian cell is a gastrointestinal cell.

As used herein, the term "contacting" refers to the bringing together of indicated moieties in an in vitro system or an in vivo system. For example, "contacting" a RET kinase with a compound provided herein includes the administration of a compound provided herein to an individual or patient, such as a human, having a RET kinase, as well as, for example, introducing a compound provided herein into a sample containing a cellular or purified preparation containing the RET kinase.

Also provided herein is a method of inhibiting cell proliferation, in vitro or in vivo, the method comprising contacting a cell with an effective amount of a compound of Formula I or a pharmaceutically acceptable salt or solvate thereof, or a pharmaceutical composition thereof as defined herein.

The phrase "effective amount" means an amount of compound that, when administered to a patient in need of such treatment, is sufficient to (i) treat a RET kinase-associated disease or disorder, (ii) attenuate, ameliorate, or eliminate one or more symptoms of the particular disease, condition, or disorder, or (iii) delay the onset of one or more symptoms of the particular disease, condition, or disorder described herein. The amount of a compound of Formula I that will correspond to such an amount will vary depending upon factors such as the particular compound, disease condition and its severity, the identity (e.g., weight) of the patient in need of treatment, but can nevertheless be routinely determined by one skilled in the art.

When employed as pharmaceuticals, the compounds of Formula I can be administered in the form of pharmaceutical compositions. These compositions can be prepared in a manner well known in the pharmaceutical art, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Oral administration can include a dosage form formulated for once-daily or twice-daily (BID) administration. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, for example, by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

Also provided herein are pharmaceutical compositions which contain, as the active ingredient, a compound of Formula I or a pharmaceutically acceptable salt or solvate thereof, in combination with one or more pharmaceutically acceptable carriers (excipients). In some embodiments, the composition is suitable for topical administration. In making the compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders. In one embodiment, the composition is formulated for oral administration. In one embodiment, the composition is formulated as a tablet or capsule.

The compositions comprising a compound of Formula I or a pharmaceutically acceptable salt or solvate thereof can be formulated in a unit dosage form, each dosage containing from about 5 to about 1,000 mg (1 g), more usually about 100 mg to about 500 mg, of the active ingredient. The term "unit dosage form" refers to physically discrete units suitable as unitary dosages for human subjects and other patients, each unit containing a predetermined quantity of active material (i.e., a compound for Formula I as provided herein) calculated to produce the desired therapeutic effect, in association with a suitable pharmaceutical excipient.

In some embodiments, the compositions provided herein contain from about 5 mg to about 50 mg of the active ingredient. One having ordinary skill in the art will appreciate that this embodies compounds or compositions containing about 5 mg to about 10 mg, about 10 mg to about 15 mg, about 15 mg to about 20 mg, about 20 mg to about 25 mg, about 25 mg to about 30 mg, about 30 mg to about 35 mg, about 35 mg to about 40 mg, about 40 mg to about 45 mg, or about 45 mg to about 50 mg of the active ingredient.

In some embodiments, the compositions provided herein contain from about 50 mg to about 500 mg of the active ingredient. One having ordinary skill in the art will appreciate that this embodies compounds or compositions containing about 50 mg to about 100 mg, about 100 mg to about 150 mg, about 150 mg to about 200 mg, about 200 mg to about 250 mg, about 250 mg to about 300 mg, about 350 mg to about 400 mg, or about 450 mg to about 500 mg of the active ingredient.

In some embodiments, the compositions provided herein contain from about 500 mg to about 1,000 mg of the active ingredient. One having ordinary skill in the art will appreciate that this embodies compounds or compositions containing about 500 mg to about 550 mg, about 550 mg to about 600 mg, about 600 mg to about 650 mg, about 650 mg to about 700 mg, about 700 mg to about 750 mg, about 750 mg to about 800 mg, about 800 mg to about 850 mg, about 850 mg to about 900 mg, about 900 mg to about 950 mg, or about 950 mg to about 1,000 mg of the active ingredient.

The active compound may be effective over a wide dosage range and is generally administered in a pharmaceutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms, and the like.

In some embodiments, the compounds provided herein can be administered in an amount ranging from about 1 mg/kg to about 100 mg/kg. In some embodiments, the compound provided herein can be administered in an amount of about 1 mg/kg to about 20 mg/kg, about 5 mg/kg to about 50 mg/kg, about 10 mg/kg to about 40 mg/kg, about 15 mg/kg to about 45 mg/kg, about 20 mg/kg to about 60 mg/kg, or about 40 mg/kg to about 70 mg/kg. For example, about 5 mg/kg, about 10 mg/kg, about 15 mg/kg, about 20 mg/kg, about 25 mg/kg, about 30 mg/kg, about 35 mg/kg, about 40 mg/kg, about 45 mg/kg, about 50 mg/kg, about 55 mg/kg, about 60 mg/kg, about 65 mg/kg, about 70 mg/kg, about 75 mg/kg, about 80 mg/kg, about 85 mg/kg, about 90 mg/kg, about 95 mg/kg, or about 100 mg/kg. In some embodiments, such administration can be once-daily or twice-daily (BID) administration.

Provided herein are pharmaceutical kits useful, for example, in the treatment of RET-associated diseases or disorders, such as cancer or irritable bowel syndrome (IBS), which include one or more containers containing a pharmaceutical composition comprising a therapeutically effective amount of a compound provided herein. Such kits can further include, if desired, one or more of various conventional pharmaceutical kit components, such as, for example, containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

EXAMPLES

The following examples illustrate the invention.

Biological Examples

Example A

RET Enzyme Assay

Compounds of Formula I were screened for their ability to inhibit wildtype and V804M mutant RET kinase using CisBio's HTRF® KinEASE™-TK assay technology. Briefly, N-terminal GST tagged recombinant human RET cytoplasmic domain (aa 658-end) from Eurofins (0.25 nM RET; Catalog No. 14-570M) or N-terminal GST tagged recombinant human V804M mutant RET cytoplasmic domain (aa 658-end) from Millipore (0.25 nM enzyme; Catalog No. 14-760) was incubated with 250 nM TK-substrate biotin (CisBio, part of Catalog No. 62TKOPEC) and 1 mM ATP along with test compound in a buffer consisting of 25 mM HEPES pH 7.4, 10 mM $MgCl_2$, 0.01% Triton X-100, and 2% DMSO in a volume of 8 μL. Compounds were typically prepared in a threefold serial dilution in DMSO and added to the assay to give the appropriate final concentration. After a 30-minute incubation at 22° C., the reaction was quenched by adding 8 μL of quench solution containing 31.25 nM Sa-XL665 and 1× TK-ab-Cryptate in HTRF detection buffer (all from CisBio, part of Cat. No. 62TKOPEC). After a 1 hour incubation at 22° C., the extent of reaction was determined using a PerkinElmer EnVision multimode plate reader via HTRF dual wavelength detection, and the percent of control (POC) was calculated using a ratiometric emission factor. 100 POC was determined using no test compounds and 0 POC was determined using pre-quenched control reactions. The POC values were fit to a 4 parameter logistic curve, and the $IC_{50}$ is defined as the concentration of inhibitor at which the POC equals 50 for the fitted curve. The $IC_{50}$ values for the compounds tested in this assay are provided in Table 5.

Example B

RET Cell Assay

The cellular potency of a compound inhibiting RET kinase was determined in HEK-293 cells expressing a Kif5b-RET fusion protein. Briefly, HEK-293 cells expressing a Kif5b-RET fusion protein were plated at 50K cells/well in 96 well poly-D-Lysine coated plates the day prior to the assay. The cells were incubated for 1 hour with test compound in DMEM (Dulbecco's Modified Eagle Medium) at a final DMSO concentration of 0.5%. Compounds were typically prepared in a three-fold serial dilution in DMSO and added to the assay to give the appropriate final concentration. After 1 hour the media was removed, the cells were fixed with 3.8% formaldehyde for 20 min, washed with PBS, and permeabilized for 10 min with 100% methanol. The plates were then washed with PBS-0.05% Tween20, and blocked with LI-COR Blocking solution (LI-COR catalog #927-40000) for 1 hour. Plates were washed with PBS-0.05% Tween20, then incubated with anti-phospho-RET (Tyr1062) (Santa Cruz catalog #sc-20252-R) antibody and anti-GAPDH (Millipore catalog #MAB374) antibody for 2 hours. The plates were washed with PBS-0.05% Tween20, and incubated with anti-rabbit 680 (Molecular Probes catalog No. A21109) and anti-mouse 800 (LI-COR catalog No. 926-32210) secondary antibodies for 1 hour. All antibodies were diluted in LI-COR Block containing 0.05% Tween. The plates were washed with PBS-0.05% Tween20, 100 μL PBS was added to each well, and the plates were read on a LI-COR Aerius fluorescent plate reader. The phospho-RET signal was normalized to the GAPDH signal. 100 POC (percent of control) was determined using no test compounds and 0 POC was determined using 1 μM of a control inhibitor. The POC values were fit to a 4 parameter logistic curve. The $IC_{50}$ value is the point where the curve crosses 50 POC. The $IC_{50}$ values for the compounds tested in this assay are provided in Table 5.

TABLE 5

$IC_{50}$'s of compounds tested in the assay of Examples A and B

| Ex# | RET Enzyme (wild type) $IC_{50}$ (nM) | RET enzyme (V804M) $IC_{50}$ (nM) | KIF5B-RET pTYR1062 Cell $IC_{50}$ (nM) |
|---|---|---|---|
| 1 | 368.8 | N/A | N/A |
| 2 | 36.4 | N/A | 62.7 |
| 3 | 52.2 | N/A | 153.1 |
| 4 | 64.5 | 39.4 | 209.9 |
| 5 | 23.7 | 56.4 | 35.4 |
| 6 | 42.7 | 100.6 | 72.6 |
| 7 | 141.3 | 1095.6 | N/A |
| 8 | 144.2 | 1006.7 | N/A |
| 9 | 10.1 | N/A | 27.8 |
| 10 | 35.0 | N/A | 70.7 |
| 11 | 18.6 | 79.9 | 20.7 |
| 12 | 5.2 | 17.1 | 7.0 |
| 13 | 14.1 | N/A | 30.0 |
| 14 | 11.2 | 37.6 | 8.9 |
| 15 | 24.9 | 88.3 | 24.3 |
| 16 | 70.0 | 309.5 | 84.2 |
| 17 | 30.4 | 91.7 | 25.8 |
| 18 | 10.7 | 56.7 | 7.3 |
| 19 | 12.3 | 117.0 | 28.5 |

TABLE 5-continued

| IC$_{50}$'s of compounds tested in the assay of Examples A and B | | | |
|---|---|---|---|
| Ex# | RET Enzyme (wild type) IC$_{50}$ (nM) | RET enzyme (V804M) IC$_{50}$ (nM) | KIF5B-RET pTYR1062 Cell IC$_{50}$ (nM) |
| 20 | 30.2 | 159.7 | 27.6 |
| 21 | 54.6 | 308.8 | 74.2 |
| 22 | 73.1 | 343.8 | 84.1 |
| 23 | 5.5 | 16.6 | 5.3 |
| 24 | 20.9 | 67.6 | 11.0 |
| 25 | 16.4 | 83.8 | 12.9 |
| 26 | 168.0 | 924.0 | N/A |
| 27 | 7.1 | 14.0 | 7.0 |
| 28 | 13.2 | 18.5 | 6.5 |
| 29 | 16.6 | 41.3 | 10.7 |
| 30 | 16.8 | 164.0 | 32.0 |
| 31 | 162.0 | 927.5 | N/A |
| 32 | 21.6 | 75.6 | 7.0 |
| 33 | 77.2 | 352.1 | 52.2 |
| 34 | 138.6 | 624.2 | N/A |
| 35 | 25.7 | 112.8 | 16.7 |
| 36 | 39.3 | 179.3 | 31.0 |
| 37 | 52.4 | 435.5 | 88.2 |
| 38 | 9.0 | 29.6 | 7.7 |
| 39 | 17.0 | 91.0 | 14.4 |
| 40 | 4.5 | 31.8 | 2.7 |
| 41 | 142.1 | 875.2 | N/A |
| 42 | 8.3 | 16.6 | 5.2 |
| 43 | 39.3 | 208.7 | 102.1 |
| 44 | 4195.9 | 10000.0 | N/A |
| 45 | 53.0 | 414.6 | 57.5 |
| 46 | 31.1 | 335.2 | 15.4 |
| 47 | 13.8 | 58.4 | 17.6 |
| 48 | 19.0 | 47.5 | 21.5 |
| 49 | 25.5 | 83.3 | 9.1 |
| 50 | 7.0 | 22.4 | 5.0 |
| 51 | 26.6 | 68.6 | 6.4 |
| 52 | 8.9 | 29.6 | 3.8 |
| 53 | 6.8 | 28.1 | 4.0 |
| 54 | 18.9 | 64.3 | 6.2 |
| 55 | 31.5 | 112.8 | 16.6 |
| 56 | 26.0 | 61.9 | 7.1 |
| 57 | 40.8 | 105.1 | 21.9 |
| 58 | 32.4 | 47.2 | 75.4 |
| 59 | 16.8 | 29.0 | 24.4 |
| 60 | 9.9 | 76.1 | 21.1 |
| 62 | 13.1 | 60.7 | 24.0 |
| 63 | 2.8 | 18.0 | 12.2 |
| 64 | 4.2 | 20.8 | 6.9 |
| 65 | 13.9 | 66.2 | 21.4 |
| 67 | 13.1 | 190.7 | 67.9 |
| 68 | 6.6 | 26.3 | 69.6 |
| 69 | 19.4 | 369.8 | 146.0 |
| 70 | 292.2 | 1914.2 | N/A |
| 71 | 154.2 | 1324.1 | N/A |
| 72 | 24.8 | 179.5 | 778.5 |
| 73 | 127.1 | 504.4 | N/A |
| 74 | 31.3 | 83.7 | 188.6 |
| 75 | 11.4 | 192.3 | 53.2 |
| 76 | 59.7 | 500.0 | 350.7 |
| 77 | 9.3 | 46.6 | 6.2 |
| 78 | 10.5 | 28.1 | 4.2 |
| 79 | 5.7 | 45.1 | 22.7 |
| 80 | 23.0 | 86.5 | 29.7 |
| 81 | 223.6 | 2344.3 | N/A |
| 82 | 29.6 | 215.8 | 37.2 |
| 83 | 34.9 | 280.0 | 106.9 |
| 84 | 386.4 | 2757.1 | N/A |
| 85 | 284.6 | 2617.1 | N/A |
| 86 | 43.9 | 342.7 | 181.5 |
| 87 | 123.4 | 998.6 | N/A |
| 88 | 20.0 | 104.4 | 14.1 |
| 89 | 11.1 | 55.5 | 20.7 |
| 90 | 42.5 | 193.2 | 79.8 |
| 91 | 49.7 | 479.2 | 20.3 |
| 92 | 17.8 | 78.1 | 12.4 |
| 93 | 28.4 | 61.3 | 5.6 |
| 94 | 6.5 | 13.7 | 2.7 |
| 95 | 25.9 | 152.0 | 33.9 |

TABLE 5-continued

| IC$_{50}$'s of compounds tested in the assay of Examples A and B | | | |
|---|---|---|---|
| Ex# | RET Enzyme (wild type) IC$_{50}$ (nM) | RET enzyme (V804M) IC$_{50}$ (nM) | KIF5B-RET pTYR1062 Cell IC$_{50}$ (nM) |
| 96 | 27.5 | 229.9 | 25.8 |
| 97 | 150.8 | 1382.2 | N/A |
| 98 | 4.4 | 5.8 | 2.1 |
| 99 | 4.8 | 9.0 | 2.9 |
| 100 | 7.1 | 11.7 | 2.3 |
| 101 | 3.9 | 8.7 | 2.3 |
| 102 | 7.2 | 20.1 | 4.8 |
| 103 | 112.9 | 2526.4 | N/A |
| 104 | 84.3 | 711.7 | 164.1 |
| 105 | 735.4 | 10000.0 | N/A |
| 106 | 112.0 | 957.6 | N/A |
| 107 | 130.2 | 420.0 | N/A |
| 108 | 247.9 | 849.5 | N/A |
| 109 | 11.0 | 51.4 | 7.8 |
| 110 | 85.7 | 1581.2 | 302.1 |
| 111 | 33.3 | 209.7 | 131.7 |
| 112 | 30.7 | 229.3 | 61.7 |
| 113 | 224.9 | 1328.0 | N/A |
| 114 | 68.5 | 1267.9 | 198.5 |
| 115 | 55.1 | 856.0 | 79.3 |
| 116 | 223.0 | 3846.9 | 1068.7 |
| 117 | 121.2 | 699.5 | N/A |
| 118 | 19.8 | 34.8 | 6.4 |
| 119 | 47.7 | 364.3 | 83.1 |
| 120 | 57.4 | 320.9 | 82.6 |
| 121 | 31.7 | 273.4 | 63.8 |

Synthetic Examples

Synthesis of Synthetic Intermediates

Intermediate P1

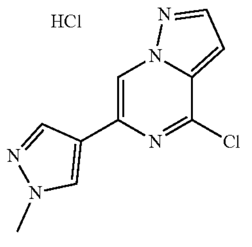 [SMILES: Cn1cc(-c2cn3nccc3c(Cl)n2)cn1 ; Cl]

4-Chloro-6-(1-methyl-1H-pyrazol-4-yl)pyrazolo[1,5-a]pyrazine hydrochloride

Step 1: Preparation of Diethyl 1-(2-(1-methyl-1H-pyrazol-4-yl)-2-oxoethyl)-1H-pyrazole-3,5-dicarboxylate In 250 mL of acetonitrile was dissolved 2-chloro-1-(1-methyl-1H-pyrazol-4-yl)ethanone (18.3 g, 115 mmol) and diethyl 1H-pyrazole-3,5-dicarboxylate (24.5 g, 115 mmol) before finely ground $K_2CO_3$ (31.9 g, 231 mmol) was added in one portion. The reaction mixture was stirred at ambient temperature overnight. The reaction mixture was filtered, and the cake was washed with acetonitrile (100 mL). The filtrate was concentrated in vacuo to a thick oil. The oil was dissolved in EtOAc (80 mL), and heptane (200 mL) was added slowly with stirring. The resultant solids were stirred for 2 h, then filtered and washed with heptane. The solids were dried in a vacuum oven to afford the title compound (26.4 g, 67% yield).

Step 2: Preparation of Ethyl 4-hydroxy-6-(1-methyl-1H-pyrazol-4-yl)pyrazolo[1,5-a]pyrazine-2-carboxylate and 4-Hydroxy-6-(1-methyl-1H-pyrazol-4-yl)pyrazolo[1,5-a]pyrazine-2-carboxylic acid In 320 mL of acetic acid were combined diethyl 1-(2-(1-methyl-1H-pyrazol-4-yl)-2-oxoethyl)-1H-pyrazole-3,5-dicarboxylate (8.0 g, 23.9 mmol) and $NH_4OAc$ (55.3 g, 718 mmol) in a 500 mL glass pressure vessel. The vessel was sealed and the reaction mixture was heated to 120° C. overnight, followed by heating at 160° C. for 48 hours. The reaction mixture was cooled to ambient temperature and then poured into a 2 L flask. Water (960 mL) was slowly added and the mixture was stirred with cooling for 2 hours. The fine pink suspension that resulted after stirring overnight was collected by vacuum filtration. The solids were collected and dried in a vacuum oven to afford a 1:2 mixture of the title compounds, ethyl 4-hydroxy-6-(1-methyl-1H-pyrazol-4-yl)pyrazolo[1,5-a]pyrazine-2-carboxylate (5.45 g, 26% yield) and 4-hydroxy-6-(1-methyl-1H-pyrazol-4-yl)pyrazolo[1,5-a]pyrazine-2-carboxylic acid (5.45 g, 58% yield).

Step 3: Preparation of 6-(1-Methyl-1H-pyrazol-4-yl)-4-oxo-4,5-dihydropyrazolo[1,5-a]pyrazine-2-carboxylic acid Crude ethyl 4-hydroxy-6-(1-methyl-1H-pyrazol-4-yl)pyrazolo[1,5-a]pyrazine-2-carboxylate (10.00 g, 34.81 mmol) was charged to a 500 mL flask equipped with mechanical stirring, a thermocouple, and a reflux condenser equipped with a nitrogen balloon. 6 N HCl (100 mL) was added, and the reaction mixture was heated at 65° C. for 32 h. The reaction mixture was cooled to ambient temperature overnight, and water (100 mL) was added. The reaction mixture was stirred for 1 h, and then filtered. The resulting solids were rinsed with water and dried in the vacuum oven overnight to afford the title compound (8.8 g, 98% yield).

Step 4: Preparation of 6-(1-Methyl-1H-pyrazol-4-yl)pyrazolo[1,5-a]pyrazin-4(5H)-one 6-(1-Methyl-1H-pyrazol-4-yl)-4-oxo-4,5-dihydropyrazolo[1,5-a]pyrazine-2-carboxylic acid (10.0 g, 38.6 mmol) was added to a 500 mL flask equipped with mechanical stirring, a thermocouple, a reflux condenser and static nitrogen pressure. $Cu(OAc)_2$ (3.5 g, 19.3 mmol), 1,10-phenanthroline (3.5 g, 19.3 mmol) and N-methylpyrrolidone (100 mL) were added. The reaction mixture was heated to 165° C. overnight. The reaction mixture was cooled to ambient temperature, and 3 M HCl (200 mL) was added to afford a slurry, which was stirred overnight. The product was collected by vacuum filtration, rinsed with water, and dried in the vacuum oven overnight to afford the title compound (8.0 g, 96% yield).

Step 5: Preparation of 4-Chloro-6-(1-methyl-1H-pyrazol-4-yl)pyrazolo[1,5-a]pyrazine hydrochloride To a 100 mL 3-neck flask fitted with a magnetic stir bar, internal temperature probe, and reflux condenser was added 6-(1-methyl-1H-pyrazol-4-yl)pyrazolo[1,5-a]pyrazin-4(5H)-one (5.0 g, 23.2 mmol), followed by phosphoryl trichloride (34.6 mL, 371 mmol). The reaction mixture was heated to 80° C. under nitrogen for 7 h. The reaction mixture was cooled to 50° C., then charged with 40 mL of acetonitrile, and cooled to ambient temperature. The resulting solids were filtered, washed with 20 mL of acetonitrile, and dried in a vacuum oven to afford the title compound (2.65 g). The filtrates were diluted with 80 mL of methyl tert-butyl ether and the reaction mixture was stirred at ambient temperature overnight. The resultant solids were filtered and dried to afford additional amounts of the title compound (2.97 g). The total yield of 4-chloro-6-(1-methyl-1H-pyrazol-4-yl)pyrazolo[1,5-a]pyrazine hydrochloride was 4.55 g (16.8 mmol, 72.5% yield).

Intermediate P2

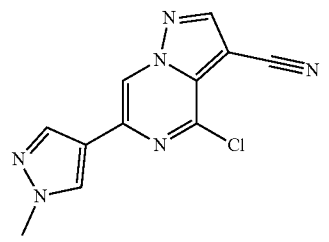 [SMILES: Cn1cc(-c2cn3ncc(C#N)c3c(Cl)n2)cn1]

4-Chloro-6-(1-methyl-1H-pyrazol-4-yl)pyrazolo[1,5-a]pyrazine-3-carbonitrile

Step 1: Preparation of 4-Chloro-3-iodo-6-(1-methyl-1H-pyrazol-4-yl)pyrazolo[1,5-a]pyrazine Under a $N_{2(g)}$ atmosphere, a mixture of 4-chloro-6-(1-methyl-1H-pyrazol-4-yl)pyrazolo[1,5-a]pyrazine (80.2 g, 343 mmol) and NIS (92.7 g, 412 mmol) in DMF (2000 mL) was mechanically stirred for 30 min at ambient temperature. Additional NIS (92.7 g, 412 mmol) was introduced as a solution in DMF (350 mL). The mixture was stirred for an additional 30 min at ambient temperature, then for 90 min at 50° C., before cooling to ambient temperature over 16 h. The resulting slurry was filtered, and the filter cake was rinsed with EtOAc (400 mL) and dried in a vacuum oven overnight at 40° C. to afford the title compound (87 g, 71% yield). MS (apci) m/z=359.96 (M+1), 361.96 (M+2).

Step 2: Preparation of 4-Chloro-6-(1-methyl-1H-pyrazol-4-yl)pyrazolo[1,5-a]pyrazine-3-carbonitrile Under a $N_{2(g)}$ atmosphere, a cold (−20 to −25° C.) slurry of 4-chloro-3-iodo-6-(1-methyl-1H-pyrazol-4-yl)pyrazolo[1,5-a]pyrazine (43.0 g, 120 mmol) in THF (430 mL) was treated slowly with 1.65 M i-PrMgCl in THF (76.1 mL, 125.6 mmol) while maintaining the internal temperature at or below −19° C. during the addition. After stirring 20 min at −25° C., additional i-PrMgCl (2 mL, 3.3 mmol; 1.65 M) was introduced, and the reaction was stirred for 2 min at −25° C. Immediately thereafter, a solution of 1-cyanato-4-methoxybenzene (21.65 g, 138.3 mmol) in THF (60 mL) was introduced at a rate that allowed internal temperature to be maintained at or below −19° C. during the addition. The reaction was allowed to warm to 20° C. over 16 h, and the resultant slurry was filtered. The filter cake was rinsed with EtOAc (70 mL), then dried in a vacuum oven for 2 h at 40° C. to afford the title compound (22.2 g, 72% yield). MS (apci) m/z=258.8 (M+H). $^1H$ NMR (400 MHz, DMSO-$d_6$) δ: 9.41 (s, 1H), 8.82 (s, 1H), 8.32 (s, 1H), 8.06 (s, 1H), 3.87 (s, 3H).

Intermediate P3

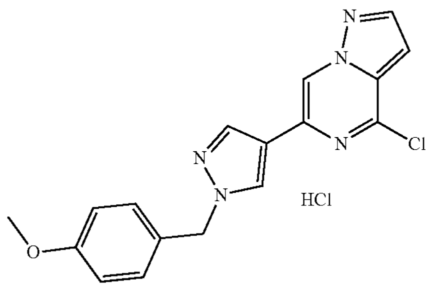 [SMILES: COc1ccc(Cn2cc(-c3cn4nccc4c(Cl)n3)cn2)cc1 ; Cl]

4-Chloro-6-(1-(4-methoxybenzyl)-1H-pyrazol-4-yl)pyrazolo[1,5-a]pyrazine hydrochloride Step 1: Preparation of 4-Iodo-1-(4-methoxybenzyl)-1H-pyrazole 4-Iodo-1H-pyrazole (5.0 g, 25.8 mmol) was dissolved in DMF (50 mL), and $K_2CO_3$ (4.27 g, 30.9 mmol) was added followed by 1-(chloromethyl)-4-methoxybenzene (3.86 mL, 28.4 mmol). The reaction mixture was stirred at ambient temperature overnight. The reaction mixture was then poured into water and extracted with $Et_2O$, washed with brine, dried over sodium sulfate, filtered, and concentrated to afford the title compound (8.3 g, 103% yield)

Step 2: Preparation of 2-Chloro-1-(1-(4-methoxybenzyl)-1H-pyrazol-4-yl)ethanone

4-Iodo-1-(4-methoxybenzyl)-1H-pyrazole (8.1 g, 26 mmol) was dissolved in THF (50 mL) and cooled in an ice bath. Isopropylmagnesium chloride (2.9 M, 8.9 mL, 26 mmol) was added slowly. The reaction mixture was stirred for 10 min, and then 2-chloro-N-methoxy-N-methylacetamide (3.5 g, 26 mmol) dissolved in THF (15 mL) was added slowly by syringe. The reaction mixture was warmed to ambient temperature and stirred for 1 h. The reaction mixture was partitioned between EtOAc and 1N HCl, and the organic layer was dried over sodium sulfate, filtered, and concentrated to afford the crude title compound (7.1 g, 104% yield) as an amber oil that slowly solidified.

Step 3: Preparation of Diethyl 1-(2-(1-(4-methoxybenzyl)-1H-pyrazol-4-yl)-2-oxoethyl)-1H-pyrazole-3,5-dicarboxylate Crude 2-chloro-1-(1-(4-methoxybenzyl)-1H-pyrazol-4-yl)ethanone (7.1 g, 21 mmol) was dissolved in acetonitrile (100 mL). Diethyl 1H-pyrazole-3,5-dicarboxylate (4.6 g, 21 mmol) was added, followed by $K_2CO_3$ (5.9 g, 43 mmol), and the reaction mixture was stirred at 45° C. for 1 h. The reaction mixture was cooled to ambient temperature, diluted with EtOAc, filtered, and concentrated. The residue was purified over silica gel to afford the title compound (8.7 g, 92% yield) as a white solid Step 4: Preparation of Ethyl 4-hydroxy-6-(1-(4-methoxybenzyl)-1H-pyrazol-4-yl)pyrazolo[1,5-a]pyrazine-2-carboxylate Diethyl 1-(2-(1-(4-methoxybenzyl)-1H-pyrazol-4-yl)-2-oxoethyl)-1H-pyrazole-3,5-dicarboxylate (8.2 g, 18.6 mmol) was dissolved in HOAc (100 mL) and $NH_4OAc$ (43.1 g, 559 mmol) was added. The reaction mixture heated in a sealed tube at 120° C. for 48 h. The reaction mixture was cooled to ambient temperature, poured into water (200 mL), filtered and dried to afford the title compound (5.65 g, 77% yield) as a white solid Step 5: Preparation of 4-Hydroxy-6-(1-(4-methoxybenzyl)-1H-pyrazol-4-yl)pyrazolo[1,5-a]pyrazine-2-carboxylic acid Ethyl 4-hydroxy-6-(1-(4-methoxybenzyl)-1H-pyrazol-4-yl)pyrazolo[1,5-a]pyrazine-2-carboxylate (5.4 g, 14 mmol) was suspended in THF (60 mL), and 1M lithium hydroxide (30 mL, 30 mmol) was added. The reaction mixture was heated to 50° C. for 30 min. The reaction mixture was quenched with slow addition of 1M HCl (35 mL) with vigorous stirring. Additional water (10 mL) was added to aid in stirring. The mixture was stirred vigorously at 50° C. for 15 min, then cooled and filtered. The isolated solids were washed with water and dried in vacuum oven to afford the title compound (4.6 g, 92% yield) as a white solid Step 6: Preparation of 6-(1-(4-Methoxybenzyl)-1H-pyrazol-4-yl)pyrazolo[1,5-a]pyrazin-4-ol 4-Hydroxy-6-(1-(4-methoxybenzyl)-1H-pyrazol-4-yl)pyrazolo[1,5-a]pyrazine-2-carboxylic acid (4.6 g, 13 mmol) was charged to a 25 mL flask and 1,10-phenanthroline (1.00 g, 5.5 mmol) and diacetoxycopper (1.0 g, 5.5 mmol) were added. The reaction mixture was diluted with N-methylpyrrolidone (12 mL) and then heated to 165° C. under nitrogen for 6 h. The reaction mixture was cooled to ambient temperature overnight, transferred to a flask with 1N HCl (20 mL) and stirred at 50° C. for 45 min. The reaction mixture was then filtered, and the isolated solids were washed with water and dried in vacuum oven to afford 4.7 g of a dark brown solid. The dried solid was suspended in 1N HCl (60 mL), and N-methylpyrrolidone (10 mL) was added to aid in wetting. The mixture was stirred at 65° C. for 1 h. The mixture was filtered and the isolated solids were washed with water until the resulting filtrate was colorless. The isolated solids were dried in vacuum oven to afford the title compound (3.7 g, 91% yield) as a brown solid.

Step 7: Preparation of 4-Chloro-6-(1-(4-methoxybenzyl)-1H-pyrazol-4-yl)pyrazolo[1,5-a]pyrazine hydrochloride 6-(1-(4-Methoxybenzyl)-1H-pyrazol-4-yl)pyrazolo[1,5-a]pyrazin-4-ol (3.7 g, 11.5 mmol) was suspended in phosphoryl trichloride (10.6 mL, 115 mmol) and heated to 80° C. under nitrogen for 3 h. The reaction mixture was cooled to ambient temperature and poured into methyl tert-butyl ether (80 mL) with vigorous stirring. The mixture was stirred for 10 min and then filtered. The isolated solids were washed with methyl tert-butyl ether and dried in vacuum oven to afford the title compound (2.7 g), as a tan solid. After sitting for 2 d, the filtrate contained solids. The solids were isolated by filtration and dried to afford additional title compound (Total yield: 3.9 g, 90% yield).

Intermediate P4

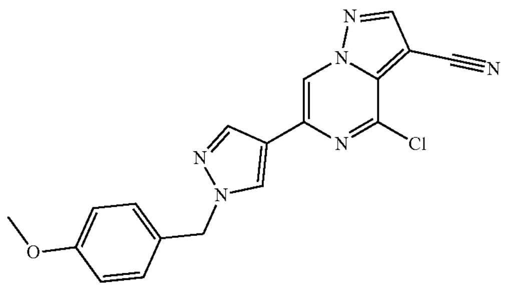 [SMILES: COc1ccc(Cn2cc(-c3cn4ncc(C#N)c4c(Cl)n3)cn2)cc1]

4-Chloro-6-(1-(4-methoxybenzyl)-1H-pyrazol-4-yl)pyrazolo[1,5-a]pyrazine-3-carbonitrile Step 1: Preparation of 4-Chloro-3-iodo-6-(1-(4-methoxybenzyl)-1H-pyrazol-4-yl)pyrazolo[1,5-a]pyrazine Under a $N_{2(g)}$ atmosphere, a mixture of 4-chloro-6-(1-(4-methoxybenzyl)-1H-pyrazol-4-yl)pyrazolo[1,5-a]pyrazine (10.0 g, 29.4 mmol) and NIS (7.95 g, 35.3 mmol) in DMF (200 mL) was stirred for 30 min at ambient temperature. Additional NIS (7.95 g, 35.3 mmol) was introduced as a solution in DMF (10 mL). The reaction mixture was stirred for 30 min at ambient temperature and then for 16 h at 50° C. before filtering the resultant suspension. The filter cake was rinsed with EtOAc (50 mL) and dried in a vacuum oven at 40° C. to afford the title compound (11.0 g, 80%). MS (apci) m/z=465.5 (M+H).

Step 2: Preparation of 4-Chloro-6-(1-(4-methoxybenzyl)-1H-pyrazol-4-yl)pyrazolo[1,5-a]pyrazine-3-carbonitrile Under a $N_{2(g)}$ atmosphere, a cold (−19 to −25° C.) solution of 4-chloro-3-iodo-6-(1-(4-methoxybenzyl)-1H-pyrazol-4-yl)pyrazolo[1,5-a]pyrazine (2.0 g, 4.29 mmol) in THF (28 mL), was treated slowly with 1.68 M i-PrMgCl in THF (2.8 mL, 4.7 mmol), maintaining the internal temperature at or below −19° C. during the addition. The reaction was stirred for 20 min at −25° C., and then 1-cyanato-4-methoxybenzene (0.77 g, 5.15 mmol) was introduced as a solution in THF (2 mL), again maintaining the internal temperature at or below −19° C. during the addition. The reaction mixture was allowed to warm to 20° C. over 12 h, and then the resulting slurry was vacuum filtered. The isolated solids were purified by silica chromatography (stepped gradient eluent of 7:3, then 1:1, then 3:7 heptane-EtOAc) to afford the title compound (0.8 g, 52% yield). MS (apci) m/z=364.8 (M+H).

Intermediate P5

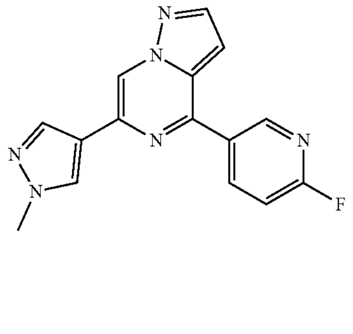 [SMILES: Cn1cc(-c2cn3nccc3c(-c3ccc(F)nc3)n2)cn1]

4-(6-Fluoropyridin-3-yl)-6-(i-methyl-1H-pyrazol-4-yl)pyrazolo[1,5-a]pyrazine

A mixture of 4-chloro-6-(1-methyl-1H-pyrazol-4-yl)pyrazolo[1,5-a]pyrazine hydrochloride (Intermediate P1; 3.5 g, 13.0 mmol), (6-fluoropyridin-3-yl)boronic acid (2.28 g, 16.2 mmol), X-phos (1.24 g, 2.59 mmol), and $Pd_2(dba)_3$ (0.593 g, 0.648 mmol) in THF (40 mL) was sparged with $Ar_{(g)}$ for 30 seconds before adding 2 M $K_2CO_{3(aq)}$ (19.4 mL, 38.9 mmol). The mixture was sparged with $Ar_{(g)}$ for an additional 5 min, then sealed, and stirred overnight at 70° C. The reaction mixture was diluted with DCM (250 mL) and saturated $NaHCO_{3(aq)}$ (50 mL). This resulted in an emulsion which was resolved with the addition of 10% iPrOH in $CHCl_3$ (100 mL). The resultant biphasic mixture was separated, and the organic extracts were retained, while the aqueous extracts containing solid were washed with a mixture of DCM (3×250 mL) and 10% iPrOH in $CHCl_3$ (3×100 mL). All organic extracts were combined, then dried over anhydrous $MgSO_{4(s)}$, filtered, and concentrated in vacuo. The residue was solubilized in DCM and MeOH, and purified by silica chromatography (using 60-75% EtOAc in DCM with 0.1% $NH_4OH$ as the gradient eluent) to afford the title compound (0.800 g, 21% yield). MS (apci) m/z=295.1 (M+H). $^1H$ NMR (400 MHz, $CDCl_3$) δ: 8.95 (m, 1H), 8.56 (m, 1H), 8.50-8.54 (m, 1H), 8.06 (m, 1H), 7.94 (s, 2H), 7.11-7.14 (m, 1H), 6.92 (m, 1H), 3.98 (s, 3H).

Intermediate P6

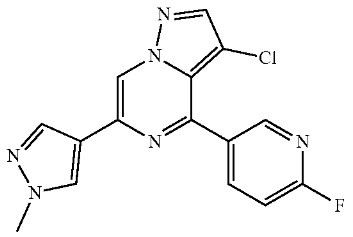 [SMILES: Cn1cc(-c2cn3ncc(Cl)c3c(-c3ccc(F)nc3)n2)cn1]

3-Chloro-4-(6-fluoropyridin-3-yl)-6-(1-methyl-1H-pyrazol-4-yl)pyrazolo[1,5-a]pyrazine A thick suspension of 4-(6-fluoropyridin-3-yl)-6-(1-methyl-1H-pyrazol-4-yl)pyrazolo[1,5-a]pyrazine (Intermediate P5; 0.523 g, 1.78 mmol) and NCS (0.237 g, 1.78 mmol) in DMF (20 mL) was stirred overnight at 50° C., then for another day at 60° C. Additional NCS (0.237 g, 1.78 mmol) was introduced, and the reaction was allowed to stir for 5 d at 60° C. The reaction mixture was quenched with water and vigorously stirred. The mixture was vacuum filtered. The filter cake was air dried overnight, then washed with $Et_2O$. The solids were dried in a vacuum oven for 2 d at 45° C., affording a mixture of the title compound and 4-(6-fluoropyridin-3-yl)-6-(1-methyl-1H-pyrazol-4-yl)pyrazolo[1,5-a]pyrazine (Intermediate P5) (0.554 g, ~1:1 ratio by HPLC). This mixture was directly used in the next step without further purification.

Intermediate P7

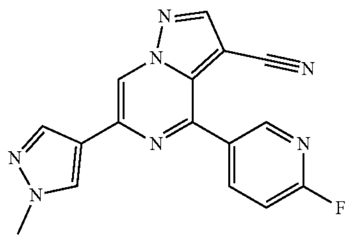 [SMILES: Cn1cc(-c2cn3ncc(C#N)c3c(-c3ccc(F)nc3)n2)cn1]

4-(6-Fluoropyridin-3-yl)-6-(1-methyl-1H-pyrazol-4-yl)pyrazolo[1,5-a]pyrazine-3-carbonitrile In a pressure vessel, 4-chloro-6-(1-methyl-1H-pyrazol-4-yl)pyrazolo[1,5-a]pyrazine-3-carbonitrile (Intermediate P2; 0.503 g, 1.94 mmol), 2-fluoro-5-(4,4,5,5-tetramethyl-1,3,2-dioxaborolan-2-yl)pyridine (0.520 g, 2.33 mmol), and $Pd(PPh_3)_4$ (0.0674 g, 0.0583 mmol) were suspended in 2 M $Na_2CO_{3(aq)}$ (5.83 mL, 11.7 mmol) and 1,4-dioxane (9.72 mL). The mixture was sparged with $N_{2(g)}$ for 15 min, then sealed and stirred overnight at 80° C. The reaction mixture was cooled for 20 minutes before adding additional $Pd(PPh_3)_4$ (0.0674 g, 0.0583 mmol) and 2-fluoro-5-(4,4,5,5-tetramethyl-1,3,2-dioxaborolan-2-yl)pyridine (0.075 g, 0.34 mmol) were introduced. The reaction mixture was sparged again with $N_{2(g)}$ for 15 min, then sealed and stirred for 24 hrs at 80° C. The reaction mixture was cooled to room temperature, then poured into water (100 mL). The resulting suspension was filtered, and the filter cake was washed successively with water (2×5 mL) and Hexanes (2×5 mL). The solids were air dried to cleanly afford the title compound (0.44 g, 71% yield). MS (apci) m/z=320.1 (M+H).

Intermediate P9

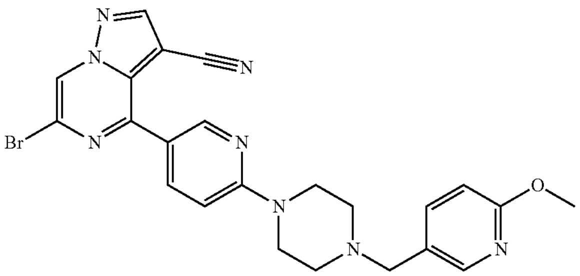 [SMILES: COc1ccc(CN2CCN(c3ccc(-c4nc(Br)cn5ncc(C#N)c45)cn3)CC2)cn1]

6-bromo-4-(6-(4-((6-methoxypyridin-3-yl)methyl)piperazin-1-yl)pyridin-3-yl)pyrazolo[1,5-a]pyrazine-3-carbonitrile A mixture of 4,6-dibromopyrazolo[1,5-a]pyrazine-3-carbonitrile (Intermediate R9; 153 mg, 0.507 mmol), 1-((6-methoxypyridin-3-yl)methyl)-4-(5-(4,4,5,5-tetramethyl-1,3,2-dioxaborolan-2-yl)pyridin-2-yl)piperazine (Intermediate R1; 208 mg, 0.507 mmol), $Cs_2CO_{3(s)}$ (330 mg, 1.01 mmol) and $PdCl_2(dppf).CH_2Cl_2$ (41.4 mg, 0.0507 mmol) in 4:1 dioxane:water (1.5 mL) was sparged with $N_{2(g)}$, then stirred overnight at ambient temperature. The reaction mixture was diluted with DCM and washed with saturated $NaHCO_{3(aq)}$. The organic extracts were washed with brine, then dried over anhydrous $Na_2SO_{4(s)}$, filtered, and concentrated in vacuo. The crude residue was purified by silica chromatography (using 1-9% DCM/MeOH with 1% $NH_4OH$ as the gradient eluent) to cleanly afford the title compound (204 mg, 80% yield). MS (apci) m/z=505.1 (M+H).

Intermediate R1

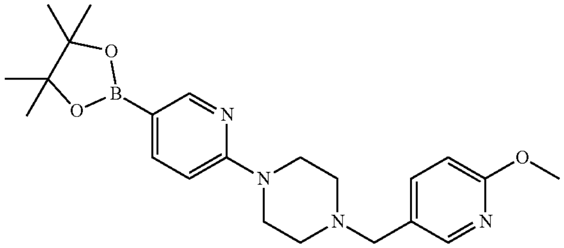

1-((6-Methoxypyridin-3-yl)methyl)-4-(5-(4,4,5,5-tetramethyl-1,3,2-dioxaborolan-2-yl)pyridin-2-yl)piperazine A mixture of 1-(5-(4,4,5,5-tetramethyl-1,3,2-dioxaborolan-2-yl)pyridin-2-yl)piperazine (5 g, 17.3 mmol) and 6-methoxynicotinaldehyde (2.85 g, 20.7 mmol) in DCE (85 mL) was treated portionwise with $NaBH(AcO)_3$ (7.3 g, 35 mmol). The mixture was stirred 2.5 h at ambient temperature, and then concentrated in vacuo to reduce the volume by half. The mixture was diluted with EtOAc, and washed sequentially with saturated $NaHCO_{3(aq)}$ and brine. The organic extracts were dried over anhydrous $Na_2SO_{4(s)}$, filtered, and concentrated in vacuo to afford the title compound (4.86 g, 69% yield). MS (apci) m/z=411.2 (M+H).

Intermediate R2

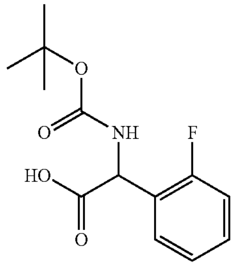 [SMILES: CC(C)(C)OC(=O)NC(C(=O)O)c1ccccc1F]

2-((tert-butoxycarbonyl)amino)-2-(2-fluorophenyl)acetic acid

A solution of 2-amino-2-(2-fluorophenyl)acetic acid (300 mg, 1.77 mmol) in THF (1.8 mL) was treated sequentially with 1 M $NaOH_{(aq)}$ (2.66 mL, 5.32 mmol) and di-tert-butyl dicarbonate (387 mg, 1.77 mmol). The resulting mixture was stirred overnight at ambient temperature before introducing additional di-tert-butyl dicarbonate (387 mg, 1.77 mmol). The reaction mixture was concentrated in vacuo. The residue was suspended in DCM, and washed sequentially with saturated $NaHCO_{3(aq)}$, water and brine (2×2 mL each). The combined organic extracts were dried over anhydrous $Na_2SO_{4(s)}$, filtered, and concentrated in vacuo. The residue was triturated with DCM/Hexanes (1:10) and dried under high vacuum to afford the title compound (486 mg, quantitative yield). MS (apci) m/z=268.1 (M+H)

Intermediate R3

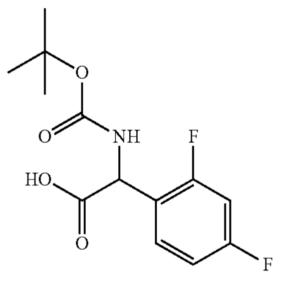 [SMILES: CC(C)(C)OC(=O)NC(C(=O)O)c1ccc(F)cc1F]

2-((tert-butoxycarbonyl)amino)-2-(2,4-difluorophenyl)acetic acid

A solution of 2-amino-2-(2,4-difluorophenyl)acetic acid (300 mg, 1.60 mmol) in THF (1.6 mL) was treated sequentially with 2 M $NaOH_{(aq)}$ (2.41 mL, 4.81 mmol) and di-tert-butyl dicarbonate (385 mg, 1.76 mmol). After stirring the resulting mixture for 2 h at ambient temperature, additional di-tert-butyl dicarbonate (387 mg, 1.77 mmol) was introduced, and the reaction was stirred an additional 1.5 h. The reaction mixture was concentrated in vacuo. The residue was suspended in DCM and washed sequentially with saturated $NaHCO_{3(aq)}$, water and brine (2×2 mL each). The combined organic extracts were dried over anhydrous $Na_2SO_{4(s)}$, filtered, and concentrated in vacuo. The residue was triturated twice with DCM/Hexanes (1:10) and dried under high vacuum to afford the title compound (383 mg, 83% yield). MS (apci) m/z=286.1 (M−H)

Intermediate R4

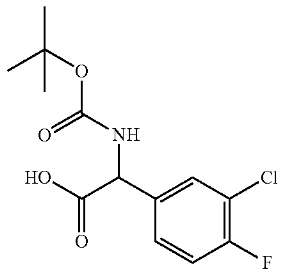 [SMILES: CC(C)(C)OC(=O)NC(C(=O)O)c1ccc(F)c(Cl)c1]

2-((tert-butoxycarbonyl)amino)-2-(3-chloro-4-fluorophenyl)acetic acid

A solution of racemic 2-amino-2-(3-chloro-4-fluorophenyl)acetic acid (1 g, 4.9 mmol) in THF (50 mL) was treated sequentially with 2 M $NaOH_{(aq)}$ (7 mL, 15 mmol) and di-tert-butyl dicarbonate (1.18 g, 5.40 mmol). After stirring overnight at ambient temperature, the reaction mixture was concentrated in vacuo to approximately 10 mL. The concentrated mixture was neutralized with 1 M $HCl_{(aq)}$ (15 mL) then extracted with EtOAc (2×50 mL). The combined organic extracts were washed with brine (50 mL), dried over anhydrous $MgSO_{4(s)}$, filtered, and concentrated in vacuo to afford the title compound (383 mg, 83% yield). MS (apci) m/z=301.9 (M+H).

Intermediate R5

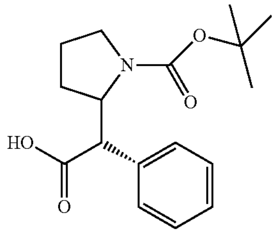

(2 S)-2-(1-(tert-butoxycarbonyl)pyrrolidin-2-yl)-2-phenyl acetic acid

Step 1: Preparation of (R)-4-benzyl-3-(2-phenylacetyl)oxazolidin-2-one

A solution of (R)-(+)-4-Benzyl-2-oxazolidinone (2.80 g, 15.8 mmol) in THF (100 mL) was cooled to −78° C., then treated with 1M $[(CH_3)_3Si]_2NLi$ in THF (15.8 mL, 15.8 mmol). The reaction mixture was stirred at −78° C. for 15 min before treating with (R)-(+)-4-benzyl-2-oxazolidinone (2.80 g, 15.8 mmol). After allowing the resulting mixture to slowly warm to ambient temperature over 2 h, the reaction mixture was stirred for an additional 60 h at ambient temperature. The reaction mixture was treated with saturated $NaHCO_{3(aq)}$ then extracted with EtOAc (2×). The combined organic extracts were extracted with water (3×) and brine (1×), and then dried over anhydrous $Na_2SO_{4(s)}$, filtered, and concentrated in vacuo. The residue was purified by silica chromatography (using 5-60% Hexanes-EtOAc as the gradient eluent) to afford the title compound (3.53 g, 79% yield). $^1H$ NMR (400 MHz, DMSO-$d_6$) δ 7.36-7.12 (m, 10H), 4.70-4.65 (m, 1H), 4.36-4.11 (m, 4H), 3.01-2.88 (m, 2H).

Step 2: Preparation of tert-butyl 2-((S)-2-((R)-4-benzyl-2-oxooxazolidin-3-yl)-2-oxo-1-phenylethyl)pyrrolidine-1-carboxylate A solution of (R)-4-benzyl-3-(2-phenylacetyl)oxazolidin-2-one (Step 1; 1.11 g, 3.76 mmol) in DCM (38 mL) was cooled to −78° C., and then sequentially treated with DIEA (786 μL, 4.51 mmol) and $TiCl_4$ (495 μL, 4.51 mmol). After stirring at −78° C. for 30 min, tert-butyl 2-methoxypyrrolidine-1-carboxylate (1.14 g, 5.64 mmol) was introduced. The cooling bath was removed, and the reaction mixture was stirred 16 h at ambient temperature. The reaction mixture then was cooled to 0° C., quenched with saturated $NaHCO_{3(aq)}$ and stirred at 0° C. for 15 min. The quenched mixture was extracted with EtOAc (2×), and the combined organic extracts were washed with water (2×) and brine (1×). The organic extracts were dried over anhydrous $Na_2SO_{4(s)}$, filtered, and concentrated in vacuo. The residue was purified by silica chromatography (using 5-60% Hexanes-EtOAc as the gradient eluent) to afford the title compound (374.5 mg, 21% yield). MS (apci) m/z=365.2 (M+H-Boc).

Step 3: Preparation of (2S)-2-(1-(tert-butoxycarbonyl)pyrrolidin-2-yl)-2-phenylacetic acid A solution of 1 M $LiOH_{(aq)}$ (806.1 μL, 1.612 mmol) in 1:1 THF:water (4.0 mL) was cooled to 0° C. The resulting cold solution was treated with 32 wt % $H_2O_{2(aq)}$ (205.9 μL, 2.015 mmol). After stirring at 0° C. for 15 min, tert-butyl 2-((S)-2-((R)-4-benzyl-2-oxooxazolidin-3-yl)-2-oxo-1-phenylethyl)pyrrolidine-1-carboxylate (Step 2; 374.5 mg, 0.8061 mmol) was introduced. The resulting mixture was stirred 16 h at ambient temperature. The reaction mixture was quenched with 10% $Na_2S_2O_{3(aq)}$, diluted with $Et_2O$ and washed with 1 M $NaOH_{(aq)}$ (2×). The combined aqueous extracts were back extracted with $Et_2O$ (2×). The aqueous extracts were acidified to pH 4 using 4 M $HCl_{(aq)}$ and extracted with 4:1 DCM:iPrOH (2×). The combined DCM: iPrOH extracts were dried over anhydrous $Na_2SO_{4(s)}$, filtered, and concentrated in vacuo to afford the title compound (246.2 mg, quantitative yield). MS (apci) m/z=206.2 (M+H-Boc).

Intermediate R6

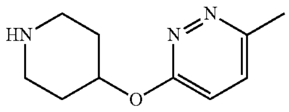

3-methyl-6-(piperidin-4-yloxy)pyridazine

Step 1: Preparation of tert-butyl 4-((6-methylpyridazin-3-yl)oxy)piperidine-1-carboxylate A solution of tert-butyl 4-hydroxypiperidine-1-carboxylate (10.22 g, 50.75 mmol) in DMF (56.39 mL) was treated with 60% w/w NaH (2.165 g, 54.14 mmol) at ambient temperature and allowed to stir for 10 min. The reaction mixture was treated with 3-chloro-6-methylpyridazine (4.350 g, 33.84 mmol). The reaction mixture was stirred for 10 min at ambient temperature and then at 90° C. for 48 h. The reaction mixture was cooled to ambient temperature and quenched with saturated $NaHCO_{3(aq)}$ (20 mL) and water (20 mL). The quenched mixture was extracted with DCM (3×40 mL), and the combined organic extracts were washed with water (3×100 mL) and brine (3×100 mL). The combined organic extracts were dried over anhydrous $Na_2SO_{4(s)}$, filtered, and concentrated in vacuo to afford the title compound (quantitative yield assumed). MS (apci) m/z=294.20 (M+H).

Step 2: Preparation of 3-methyl-6-(piperidin-4-yloxy)pyridazine

A solution of tert-butyl 4-((6-methylpyridazin-3-yl)oxy) piperidine-1-carboxylate (Step 1; 9.93 g, 33.8 mmol) in DCM (10.9 mL) was treated with TFA (13.0 mL, 169 mmol). After stirring for 20 min at ambient temperature, the reaction mixture was treated with additional TFA (13 mL). The reaction mixture was stirred for an additional 1.5 h at ambient temperature before concentrating the mixture in vacuo. The residue was purified by silica chromatography (using 1-9% MeOH in DCM with 0.1% $NH_4OH$ as the gradient eluent). The fractions containing the desired product were combined and concentrated in vacuo. The residue was triturated with DCM (10 mL) and Hexanes (20 mL) and then concentrated in vacuo to afford the title compound (5.51 g, 84% yield). MS (apci) m/z=194.2 (M+H).

Intermediate R7

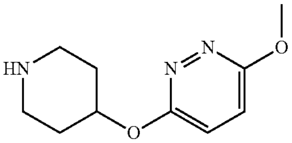

3-methoxy-6-(piperidin-4-yloxy)pyridazine

Step 1: Preparation of tert-butyl 4-((6-methoxypyridazin-3-yl)oxy)piperidine-1-carboxylate A room temperature solution of tert-butyl 4-hydroxypiperidine-1-carboxylate (2.0 g, 9.94 mmol) in DMF (16.6 mL) was treated with 60% w/w NaH (0.437 g, 10.9 mmol). After stirring for 15 min at ambient temperature, reaction mixture was treated with 3-chloro-6-methoxypyridazine (1.44 g, 9.94 mmol). The resulting mixture was stirred for 15 min at ambient temperature then overnight at 90° C. The reaction was incomplete at this point, therefore, the reaction mixture was cooled to 0° C., and treated with additional 60% w/w NaH (0.437 g, 10.9 mmol) and tert-butyl 4-hydroxypiperidine-1-carboxylate (2.0 g, 9.94 mmol) The resulting mixture was stirred for 15 min at 0° C., then brought to ambient temperature and finally heated at 90° C. for an additional 24 h. This process of cooling the reaction to introduce supplemental reagent was repeated once more before the reaction mixture was quenched at ambient temperature with the addition of saturated $NaHCO_{3(aq)}$ (4 mL) and water (4 mL). The quenched mixture was extracted with EtOAc (3×8 mL), and the combined organic extracts were washed with water (3×20 mL) and brine (1×20 mL). The organic extracts were dried over anhydrous $Na_2SO_{4(s)}$, filtered, and concentrated in vacuo. The crude residue was purified by silica chromatography (using 5-50% EtOAc in Hexanes as the gradient eluent) to afford title compound (1.57 g, 51% yield). MS (apci) m/z=310.20 (M+H).

Step 2: Preparation of 3-methoxy-6-(piperidin-4-yloxy)pyridazine

A solution of tert-butyl 4-((6-methoxypyridazin-3-yl)oxy) piperidine-1-carboxylate (Step 1; 0.706 g, 2.28 mmol) in DCM (0.734 mL) was treated with TFA (0.879 mL, 11.4 mmol). After stirring for 15 min at ambient temperature, the reaction mixture concentrated in vacuo. The residue was purified by silica chromatography (using 1-9% MeOH in DCM with 0.1% $NH_4OH$ as the gradient eluent) to afford the title compound (0.390 g, 82% yield). MS (apci) m/z=210.1 (M+H).

Intermediate R8

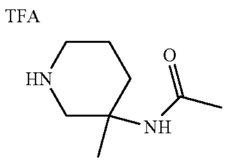

N-(3-methylpiperidin-3-yl)acetamide 2,2,2-trifluoroacetate

Step 1: Preparation of tert-butyl 3-acetamido-3-methylpiperidine-1-carboxylate

A solution of tert-butyl 3-amino-3-methylpiperidine-1-carboxylate (0.1091 g, 0.5091 mmol) and TEA (0.1419 mL, 1.018 mmol) in DCM (5.1 mL) was treated with acetic anhydride (72.05 μL, 0.7636 mmol). The reaction was monitored for completion by TLC (EtOAc/silica, using ninhydrin stain). Upon completion, the reaction mixture was diluted with DCM (40 mL) and washed with brine (3×20 mL). The organic extracts were dried over anhydrous $MgSO_{4(s)}$, filtered, and concentrated in vacuo. The crude residue was purified by silica chromatography using DCM as eluent to afford title compound (0.104 g, 80% yield). MS (apci) m/z=157.2 (M+H-Boc).

Step 2: Preparation of N-(3-methylpiperidin-3-yl)acetamide 2,2,2-trifluoroacetate A solution of tert-butyl 3-acetamido-3-methylpiperidine-1-carboxylate (Step 1; 0.104 g, 0.407 mmol) in $CHCl_3$ (0.734 mL) was treated with TFA (1.6 mL, 20 mmol). The reaction was monitored for completion by TLC (EtOAc/silica, using ninhydrin stain). Upon completion the reaction mixture was concentrated in vacuo to afford the title compound (112 mg, quantitative yield). MS=157.2 (M+H-BOC).

Intermediate R9

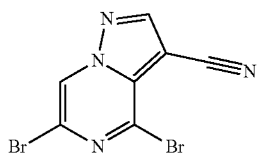 [SMILES: N#Cc1cnn2cc(Br)nc(Br)c12]

4,6-dibromopyrazolo[1,5-a]pyrazine-3-carbonitrile

Step 1: Preparation of 1-amino-3,5-dibromopyrazin-1-ium 2,4,6-trimethylbenzenesulfonate Under an inert atmosphere ($N_{2(g)}$) a cold (0° C.) solution of O-(mesitylsulfonyl)hydroxylamine (Intermediate R10; 9.8 g, 45 mmol) in DCM (300 mL) was treated portion-wise with 2,6-dibromopyrazine (9.0 g, 38 mmol). The resulting mixture was stirred for 48 h at ambient temperature and concentrated to minimal DCM to provide the title compound (17 g, 99% yield) which was used crude in the next step. MS (apci) m/z=235.9.2 (M+H).

Step 2: Preparation of 4,6-dibromopyrazolo[1,5-a]pyrazine-3-carbonitrile

The DCM slurry of 1-amino-3,5-dibromopyrazin-1-ium 2,4,6-trimethylbenzenesulfonate (Step 1; 17 g, 37.5 mmol) was diluted with 1,4-dioxane (200 mL) then treated with acrylonitrile (5.65 mL, 86.3 mmol) and DIEA (8.52 mL, 48.8 mmol). After stirring the resulting mixture for 3 h at ambient temperature, 2,3-dichloro-5,6-dicyano-1,4-benzoquinone (DDQ) (17.9 g, 78.8 mmol) was added, and the reaction was stirred for an additional 3 h at ambient temperature. The reaction mixture was extracted with EtOAc (500 mL) and water (400 mL). The organic extracts were treated with silica gel (40 g). The resulting slurry was concentrated in vacuo, then loaded on top of a silica gel plug (200 g) and rinsed with 20% ethyl acetate/hexanes. The filtrate was concentrated in vacuo and purified by silica chromatography (using 10-40% EtOAc/Hexanes as the gradient eluent) to cleanly afford the title compound (2.3 g, 20% yield). $^1H$ NMR (400 MHz, DMSO-$d_6$) δ 9.60 (s, 1H), 8.91 (s, 1H).

Intermediate R10

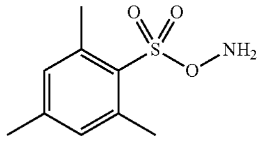

O-(mesitylsulfonyl)hydroxylamine

Step 1: Preparation of tert-butyl (mesitylsulfonyl)oxycarbamate

To a 0° C. solution of 2,4,6-trimethylbenzene-1-sulfonyl chloride (10.0 g, 45.72 mmol) and tert-butyl hydroxycarbamate (6.088 g, 45.72 mmol) in MTBE (100 mL) was added TEA (14.46 mL, 48.01 mmol) drop-wise while stirring. The resulting suspension was stirred at 0° C. for an additional 30 min and then warmed to ambient temperature. The reaction was diluted with water (100 mL), adjusted to pH 4 with 1 N $HCl_{(aq)}$. The organic layer was dried ($Na_2SO_4$), filtered and concentrated to yield the title compound initially as a yellowish oil, which upon drying overnight under high vacuum became a white solid (12.89 g, 89% yield). $^1H$ NMR ($CDCl_3$) δ 7.66 (br s, 1H), 6.98 (s, 2H), 2.67 (s, 6H), 2.32 (s, 3H), 1.31 (s, 9H).

Step 2: Preparation of O-(mesitylsulfonyl)hydroxylamine (Intermediate R1, MSH)

To TFA (117 mL, 1521 mmol) at 0° C. was slowly added tert-butyl (mesitylsulfonyl)oxycarbamate (39.0 g, 124 mmol) over 25 min. The reaction mixture was stirred at 0° C. for 1.5 h and then quenched with the sequential addition of crushed ice (5×200 mL) and water (2×125 mL). The resulting thick suspension was vigorously stirred at ambient temperature for 5 min. Without allowing the filter cake to run dry, the solids were collected by careful vacuum filtration followed by subsequent rinsing with water (4 L) until the filtrate reached pH 6 (Caution: explosion risk exists with dry compound at ambient temperature). The wet filter cake was taken up in DCM (150 mL) and the resulting biphasic solution was separated. The DCM layer was dried over $MgSO_4$ for 30 min and then filtered and rinsed with DCM (420 mL) to provide the title compound as a 0.22 M solution in DCM.

Intermediate R11

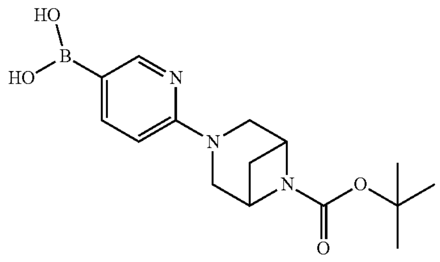 [SMILES: CC(C)(C)OC(=O)N1C2CC1CN(c1ccc(B(O)O)cn1)C2]

(6-(6-(tert-butoxycarbonyl)-3,6-diazabicyclo[3.1.1]heptan-3-yl)pyridin-3-yl)boronic acid Method 1

Step 1: Preparation of tert-butyl 3-(5-bromopyridin-2-yl)-3,6-diazabicyclo[3.1.1]heptane-6-carboxylate A suspension of 3,6-diaza-bicyclo[3.1.1]heptane-6-carboxylic acid tert-butyl ester (1.046 g, 5.27 mmol), 5-bromo-2-fluoropyridine (919 mg, 5.22 mmol) and $K_2CO_{3(s)}$ (3.61 g, 26.1 mmol) in DMSO (5.22 mL) was stirred for 1 day at 90° C. After cooling to ambient temperature, the reaction mixture was partitioned between EtOAc and water. The organic extracts were washed with additional water, then dried over anhydrous $Na_2SO_{4(s)}$, filtered, and concentrated in vacuo. Purification of the crude residue by silica chromatography (0-50% Hexanes/EtOAc as gradient eluent) provided the title compound (1.80 g, 97% yield). MS (apci) m/z=354.0 (M+1), 356.1 (M+2).

Step 2: Preparation of (6-(6-(tert-butoxycarbonyl)-3,6-diazabicyclo[3.1.1]heptan-3-yl)pyridin-3-yl)boronic acid A mixture of tert-butyl 3-(5-bromopyridin-2-yl)-3,6-diazabicyclo[3.1.1]heptane-6-carboxylate (1.80 g, 5.08 mmol), bis(pinacolato)diboron (3.87 g, 15.2 mmol), $PdCl_2$(dppf).$CH_2Cl_2$ (414 mg, 0.508 mmol), and KOAc (1.50 g, 15.2 mmol) in dioxane (5.75 mL) was sparged with $N_{2(g)}$, then stirred for 3 h at 80° C. After cooling to room temperature, the reaction mixture was diluted with DCM and washed with water. The aqueous extracts were washed with DCM. The DCM extracts were combined and dried over anhydrous $Na_2SO_{4(s)}$, filtered, and concentrated in vacuo. The crude residue was sonicated with hexanes (200 mL) and ether (50 mL) for 5 min, and the resulting gray suspension was filtered. The collected solids were triturated with MeOH, and the resulting suspension was filtered to afford the title compound as a white solid (840 mg, 52% yield). MS (apci) m/z=320.2 (M+H).

Method 2

A suspension of 3,6-diaza-bicyclo[3.1.1]heptane-6-carboxylic acid tert-butyl ester (182 mg, 0.918 mmol), 2-fluoro-5-(4,4,5,5-tetramethyl-1,3,2-dioxaborolan-2-yl)pyridine (819 mg, 3.67 mmol) and $K_2CO_{3(s)}$ (634 mg, 4.59 mmol) in DMSO (918 μL) was heated to 90° C., then treated with water (5 mL). The resulting mixture was stirred for 1 hour at 90° C., then cooled to ambient temperature and filtered to cleanly provide the title compound (1.0 g, 41% yield). MS (apci) m/z=320.1 (M+H).

Preparation of Synthetic Examples

Example 1

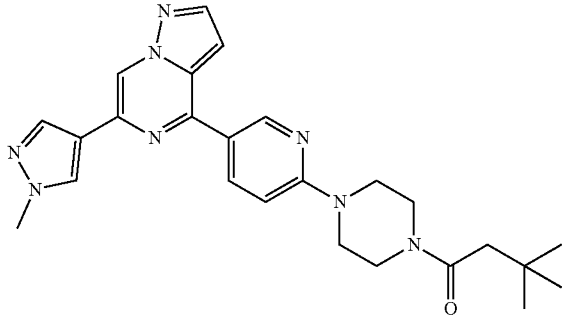 [SMILES: Cn1cc(-c2cn3nccc3c(-c3ccc(N4CCN(C(=O)CC(C)(C)C)CC4)nc3)n2)cn1]

3,3-Dimethyl-1-(4-(4-(6-(1-methyl-1H-pyrazol-4-yl)pyrazolo[1,5-a]pyrazin-4-yl)phenyl)piperazin-1-yl)butan-1-one Step 1: Preparation of tert-Butyl 4-(5-(6-(1-methyl-1H-pyrazol-4-yl)pyrazolo[1,5-a]pyrazin-4-yl)pyridin-2-yl)piperazine-1-carboxylate and tert-Butyl 4-(5-(3-chloro-6-(1-methyl-1H-pyrazol-4-yl)pyrazolo[1,5-a]pyrazin-4-yl)pyri din-2-yl)piperazine-1-carboxylate A mixture (1:1) of 4-(6-fluoropyridin-3-yl)-6-(1-methyl-1H-pyrazol-4-yl)pyrazolo[1,5-a]pyrazine (Intermediate P5; 242 mg, 0.821 mmol), 3-chloro-4-(6-fluoropyridin-3-yl)-6-(1-methyl-1H-pyrazol-4-yl)pyrazolo[1,5-a]pyrazine (Intermediate P6; 900 mg, 0.821 mmol) and tert-butyl piperazine-1-carboxylate (1530 mg, 8.213 mmol) in dioxane (5 mL) was stirred for 2 d at 90° C. The reaction was cooled to ambient temperature, then diluted with saturated $NH_4Cl_{(aq)}$ (20 mL) and brine (2 mL). The mixture was extracted with EtOAc (3×), and the combined organic extracts were concentrated in vacuo. The residue was purified by C18 reverse phase chromatography (using 0-70% ACN/water as the gradient eluent) to cleanly isolate tert-Butyl 4-(5-(3-chloro-6-(1-methyl-1H-pyrazol-4-yl)pyrazolo[1,5-a]pyrazin-4-yl)pyridin-2-yl)piperazine-1-carboxylate (102 mg, 25% yield), MS (apci) m/z=495.0 (M+H), 497.1, (M+H+2) with Cl pattern, as well as a mixture (1:1) of the both title compounds (130 mg, 34% yield), MS (apci) m/z=461.1 (M+H).

Step 2: Preparation of 3,3-Dimethyl-1-(4-(4-(6-(1-methyl-1H-pyrazol-4-yl)pyrazolo[1,5-a]pyrazin-4-yl)phenyl)piperazin-1-yl)butan-1-one A mixture (1:1) of tert-butyl 4-(5-(6-(1-methyl-1H-pyrazol-4-yl)pyrazolo[1,5-a]pyrazin-4-yl)pyridin-2-yl)piperazine-1-carboxylate and tert-butyl 4-(5-(3-chloro-6-(1-methyl-1H-pyrazol-4-yl)pyrazolo[1,5-a]pyrazin-4-yl)pyridin-2-yl)piperazine-1-carboxylate (130 mg, 0.282 mmol) in DCM (10 mL) was treated with 5 M HCl in iPrOH (135 μL, 0.67 mmol). The mixture was stirred overnight at ambient temperature then concentrated in vacuo to afford the crude product as a mixture (1:1) of 6-(1-methyl-1H-pyrazol-4-yl)-4-(6-(piperazin-1-yl)pyridin-3-yl)pyrazolo[1,5-a]

pyrazine dihydrochloride and 3-chloro-6-(1-methyl-1H-pyrazol-4-yl)-4-(6-(piperazin-1-yl)pyridin-3-yl)pyrazolo[1,5-a]pyrazine dihydrochloride. A portion of this crude product mixture (40 mg, 0.10 mmol) in DMF (0.5 mL) was treated sequentially with 3,3-dimethylbutanoyl chloride (41 mg, 0.30 mmol) and TEA (70 μL, 0.50 mmol). The mixture was stirred for 4 h at ambient temperature, then directly purified by C18 reverse phase chromatography (using 0-70% ACN/water as the gradient eluent) to separately afford the title compound, 3,3-dimethyl-1-(4-(4-(6-(1-methyl-1H-pyrazol-4-yl)pyrazolo[1,5-a]pyrazin-4-yl)phenyl)piperazin-1-yl)butan-1-one (6.5 mg, 28% yield), MS (apci) m/z=459.1 (M+H). In addition, compound 1-(4-(4-(3-chloro-6-(1-methyl-1H-pyrazol-4-yl)pyrazolo[1,5-a]pyrazin-4-yl)phenyl)piperazin-1-yl)-3,3-dimethylbutan-1-one (Example 2; 8.9 mg, 36% yield) was also isolated during chromatography purification.

Example 2

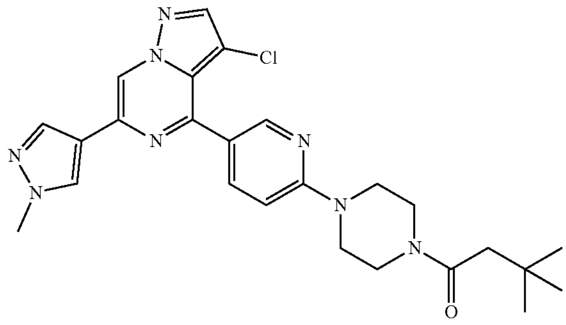 [SMILES: Cn1cc(-c2cn3ncc(Cl)c3c(-c3ccc(N4CCN(C(=O)CC(C)(C)C)CC4)nc3)n2)cn1]

1-(4-(4-(3-Chloro-6-(1-methyl-1H-pyrazol-4-yl)pyrazolo[1,5-a]pyrazin-4-yl)phenyl)piperazin-1-yl)-3,3-dimethylbutan-1-one The title compound was isolated during the preparation of Example 1. MS (apci) m/z=493.1 (M+H), 495.1 (M+H+2) with Cl pattern.

Examples 3

1-(4-(5-(3-Chloro-6-(1-methyl-1H-pyrazol-4-yl)pyrazolo[1,5-a]pyrazin-4-yl)pyridin-2-yl)piperazin-1-yl)ethan-1-one

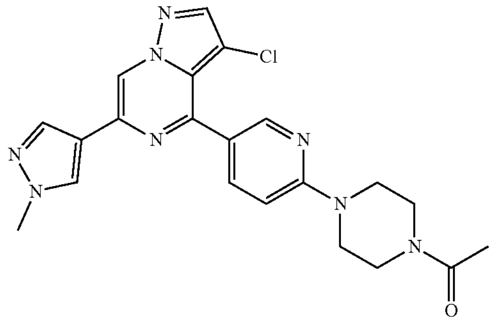 [SMILES: CC(=O)N1CCN(c2ccc(-c3nc(-c4cnn(C)c4)cn4ncc(Cl)c34)cn2)CC1]

A mixture (1:1) of 6-(1-methyl-1H-pyrazol-4-yl)-4-(6-(piperazin-1-yl)pyridin-3-yl)pyrazolo[1,5-a]pyrazine dihydrochloride and 3-chloro-6-(1-methyl-1H-pyrazol-4-yl)-4-(6-(piperazin-1-yl)pyridin-3-yl)pyrazolo[1,5-a]pyrazine dihydrochloride (Example 1; Step 2; 33 mg, 0.083 mmol) in DMF (0.5 mL) was treated sequentially with acetyl chloride (249 μL, 0.25 mmol) and TEA (58 μL, 0.42 mmol). The mixture was stirred for 2 h at ambient temperature then directly purified by C18 reverse phase chromatography (using 0-70% ACN/water as the gradient eluent) to separately afford the title compound (8 mg, 44% yield). MS (apci) m/z=437.0 (M+H), 439.1 (M+H+2).

Example 4

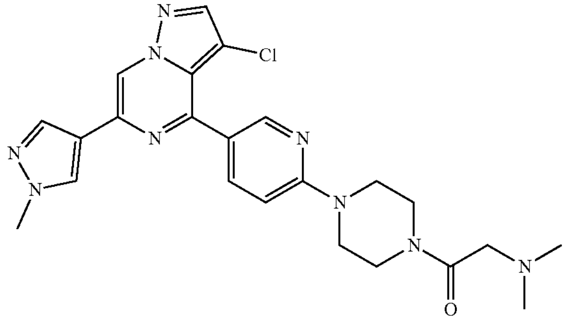 [SMILES: CN(C)CC(=O)N1CCN(c2ccc(-c3nc(-c4cnn(C)c4)cn4ncc(Cl)c34)cn2)CC1]

1-(4-(5-(3-Chloro-6-(1-methyl-1H-pyrazol-4-yl)pyrazolo[1,5-a]pyrazin-4-yl)pyridin-2-yl)piperazin-1-yl)-2-(dimethylamino)ethan-1-one Step 1: Preparation of 3-Chloro-6-(1-methyl-1H-pyrazol-4-yl)-4-(6-(piperazin-1-yl)pyridin-3-yl)pyrazolo[1,5-a]pyrazine dihydrochloride A solution of 4-(5-(3-chloro-6-(1-methyl-1H-pyrazol-4-yl)pyrazolo[1,5-a]pyrazin-4-yl)pyridin-2-yl)piperazine-1-carboxylate (Example 1, Step 1; 202 mg, 0.408 mmol) in DCM (10 mL) was treated with 5 M HCl in iPrOH (408 μL, 2.04 mmol). The mixture was stirred overnight at ambient temperature then concentrated in vacuo to afford the title compound (177 mg, quantitative yield). MS (apci) m/z=395.0 (M+H), 397.0 (M+H+2) with Cl pattern.

Step 2: Preparation of 1-(4-(5-(3-Chloro-6-(1-methyl-1H-pyrazol-4-yl)pyrazolo[1,5-a]pyrazin-4-yl)pyridin-2-yl)piperazin-1-yl)-2-(dimethylamino)ethan-1-one A solution of 3-chloro-6-(1-methyl-1H-pyrazol-4-yl)-4-(6-(piperazin-1-yl)pyridin-3-yl)pyrazolo[1,5-a]pyrazine dihydrochloride (30 mg, 0.070 mmol) in DMF (0.5 mL) was treated sequentially with 2-(dimethylamino)acetyl chloride (25 mg, 0.21 mmol) and TEA (48 μL, 0.35 mmol). The mixture was stirred for 2 h at ambient temperature then directly purified by C18 reverse phase chromatography (using 0-70% ACN/water as the gradient eluent) to afford the title compound (26 mg, 78% yield). MS (apci) m/z=480.1 (M+H), 481.1 (M+H+2) with Cl pattern.

Example 5

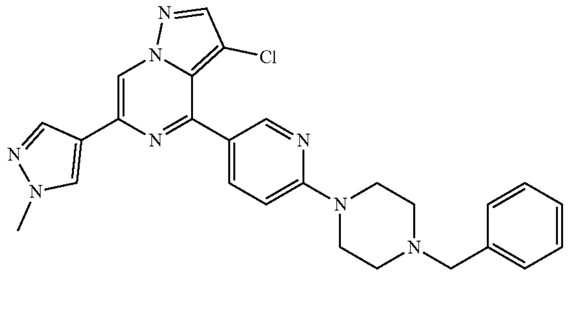 [SMILES: Cn1cc(-c2cn3ncc(Cl)c3c(-c3ccc(N4CCN(Cc5ccccc5)CC4)nc3)n2)cn1]

4-(6-(4-Benzylpiperazin-1-yl)pyridin-3-yl)-3-chloro-6-(1-methyl-1H-pyrazol-4-yl)pyrazolo[1,5-a]pyrazine A solution of 3-chloro-6-(1-methyl-1H-pyrazol-4-yl)-4-(6-(piperazin-1-yl)pyridin-3-yl)pyrazolo[1,5-a]pyrazine dihydrochloride, contaminated with 6-(1-methyl-1H-pyrazol-4-yl)-4-(6-(piperazin-1-yl)pyridin-3-yl)pyrazolo[1,5-a]pyrazine dihydrochloride (Example 4, Step 1; 20 mg, 0.043 mmol) in DMF (0.2 mL) was treated with (bromomethyl)benzene (11 mg, 0.064 mmol) and TEA (18 μL, 0.13 mmol). The reaction mixture was allowed to stir for 1 h at ambient temperature, and then directly purified by C18 reverse phase chromatography (using 0-60% ACN/water as the gradient eluent) to afford the title compound (2.9 mg, 14% yield). MS (apci) m/z=485.1 (M+H), 487.1 (M+H+2) with Cl pattern.

Example 6

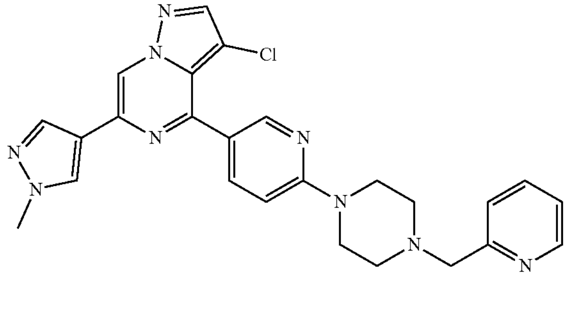 [SMILES: Cn1cc(-c2cn3ncc(Cl)c3c(-c3ccc(N4CCN(Cc5ccccn5)CC4)nc3)n2)cn1]

3-Chloro-6-(i-methyl-1H-pyrazol-4-yl)-4-(6-(4-(pyridin-2-ylmethyl)piperazin-1-yl)pyridin-3-yl)pyrazolo[1,5-a]pyrazine A solution of 3-chloro-6-(1-methyl-1H-pyrazol-4-yl)-4-(6-(piperazin-1-yl)pyridin-3-yl)pyrazolo[1,5-a]pyrazine dihydrochloride, contaminated with 6-(1-methyl-1H-pyrazol-4-yl)-4-(6-(piperazin-1-yl)pyridin-3-yl)pyrazolo[1,5-a]pyrazine dihydrochloride (Example 4, Step 1; 18.5 mg, 0.0428 mmol in DMF (0.2 mL) was treated with picolinaldehyde (6.87 mg, 0.0641 mmol), $Me_4N(AcO)_3BH$ (22.5 mg, 0.0855 mmol) and TEA (17.9 μL, 0.128 mmol). The reaction mixture was allowed to stir overnight at ambient temperature and then directly purified by C18 reverse phase chromatography (using 0-60% ACN/water as the gradient eluent) to afford the title compound (14.8 mg, 71% yield). MS (apci) m/z=486.1 (M+H), 487.1 (M+H+2) with Cl pattern.

Example 7

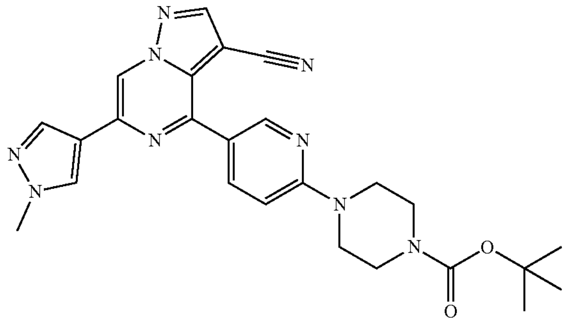 [SMILES: Cn1cc(-c2cn3ncc(C#N)c3c(-c3ccc(N4CCN(C(=O)OC(C)(C)C)CC4)nc3)n2)cn1]

tert-Butyl 4-(5-(3-cyano-6-(1-methyl-1H-pyrazol-4-yl)pyrazolo[1,5-a]pyrazin-4-yl)pyridin-2-yl)piperazine-1-carboxylate In a pressure vessel, a mixture of 4-chloro-6-(1-methyl-1H-pyrazol-4-yl)pyrazolo[1,5-a]pyrazine-3-carbonitrile (Intermediate P2; 2.85 g, 11.0 mmol) and tert-butyl 4-(5-(4,4,5,5-tetramethyl-1,3,2-dioxaborolan-2-yl)pyridin-2-yl)piperazine-1-carboxylate (6.43 g, 16.5 mmol) in 1,4-dioxane (44.1 mL) and 2 N $K_2CO_{3(aq)}$ (33.1 mL, 66.1 mmol) was sparged with $N_{2(g)}$ for 5 min. The mixture was treated with $Pd(PPh_3)_4$ (0.0674 g, 0.0583 mmol), then sealed and stirred 30 h at 90° C. After cooling to ambient temperature, the resultant biphasic suspension was vacuum filtered, and the filter cake was rinsed sequentially with 2 N $K_2CO_{3(aq)}$ (ca. 20 mL) and water (3×20 mL). The solids were air dried for 4 h, then dried under high vacuum overnight to cleanly afford the title compound (5.94 g, quantitative yield). MS (apci) m/z=486.2 (M+H).

Example 8

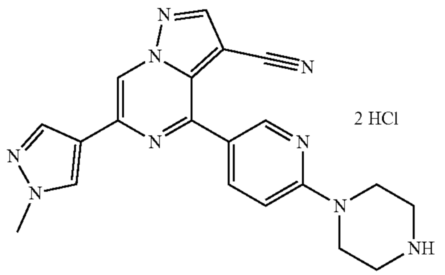 [SMILES: Cn1cc(-c2cn3ncc(C#N)c3c(-c3ccc(N4CCNCC4)nc3)n2)cn1]

6-(1-Methyl-1H-pyrazol-4-yl)-4-(6-(piperazin-1-yl)pyridin-3-yl)pyrazolo[1,5-a]pyrazine-3-carbonitrile dihydrochloride A mixture of tert-butyl 4-(5-(3-cyano-6-(1-methyl-1H-pyrazol-4-yl)pyrazolo[1,5-a]pyrazin-4-yl)pyridin-2-yl)piperazine-1-carboxylate (Example 7; 433 mg, 0.892 mmol) and TFA (687 μL, 8.92 mmol) in DCM (10 mL) was stirred for 90 min at ambient temperature, then concentrated in vacuo. The residue was purified by silica chromatography (using 0-10% $CHCl_3$/MeOH with 0.1% $NH_4OH$ as the gradient eluent to afford the title compound (384 mg, quantitative yield). MS (apci) m/z=386.2 (M+H-Boc).

Example 9

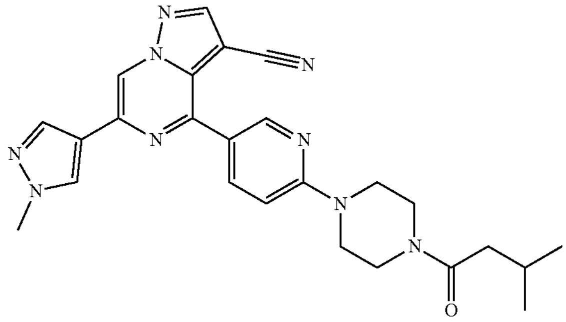 [SMILES: CC(C)CC(=O)N1CCN(c2ccc(-c3nc(-c4cnn(C)c4)cn4ncc(C#N)c34)cn2)CC1]

6-(1-Methyl-1H-pyrazol-4-yl)-4-(6-(4-(3-methylbutanoyl)piperazin-1-yl)pyridin-3-yl)pyrazolo[1,5-a]pyrazine-3-carbonitrile A solution of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 15 mg, 0.039 mmol) in DCM (2 mL) was treated sequentially with 3-methylbutanoyl chloride (7.0 mg, 0.058 mmol) and TEA (54 μL, 0.39 mmol). The mixture was stirred overnight at ambient temperature, then quenched with water and extracted with DCM (3×) in a PS frit. The combined organic extracts were concentrated in vacuo, and the residue was purified by C18 reverse phase chromatography (using 0-70% ACN/water as the gradient eluent) to afford the title compound (12 mg, 66% yield). MS (apci) m/z=470.1 (M+H).

Example 10

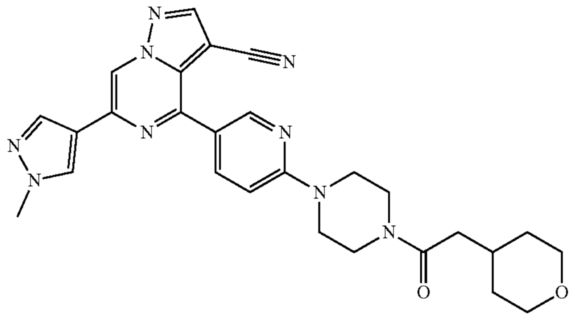 [SMILES: Cn1cc(-c2cn3ncc(C#N)c3c(-c3ccc(N4CCN(C(=O)CC5CCOCC5)CC4)nc3)n2)cn1]

6-(1-Methyl-1H-pyrazol-4-yl)-4-(6-(4-(2-(tetrahydro-2H-pyran-4-yl)acetyl)piperazin-1-yl)pyridin-3-yl)pyrazolo[1,5-a]pyrazine-3-carbonitrile A solution of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 10 mg, 0.026 mmol) in DCM (2 mL) was treated sequentially with 2-(tetrahydro-2H-pyran-4-yl)acetyl chloride (6.3 mg, 0.039 mmol) and TEA (36 μL, 0.26 mmol). The mixture was stirred overnight at ambient temperature, then quenched with water, and extracted with DCM (3×) in a PS frit. The combined organic extracts were concentrated in vacuo, and the residue was purified by C18 reverse phase chromatography (using 0-70% ACN/water as the gradient eluent) to afford the title compound (2.6 mg, 20% yield). MS (apci) m/z=512.2 (M+H).

Example 11

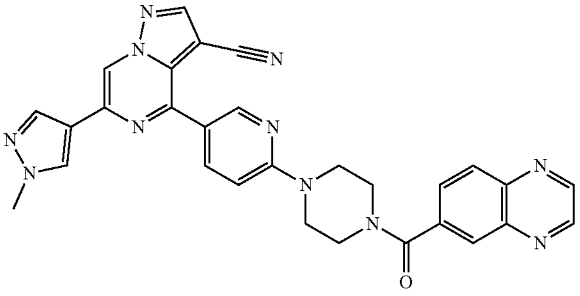 [SMILES: Cn1cc(-c2cn3ncc(C#N)c3c(-c3ccc(N4CCN(C(=O)c5ccc6nccnc6c5)CC4)nc3)n2)cn1]

6-(1-Methyl-1H-pyrazol-4-yl)-4-(6-(4-(quinoxaline-6-carbonyl)piperazin-1-yl)pyridin-3-yl)pyrazolo[1,5-a]pyrazine-3-carbonitrile A solution of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 30 mg, 0.078 mmol), 6-quinoxalinecarbonyl chloride (30 mg, 0.16 mmol) and DIEA (68 μL, 0.39 mmol) in DMF (156 L) was stirred overnight at ambient temperature. The mixture was partitioned between EtOAc and water. The aqueous extracts were extracted with EtOAc (3×). The combined organic extracts were washed with brine (1×), then dried over anhydrous $Na_2SO_{4(s)}$, filtered, and concentrated in vacuo. The residue was purified by C18 reverse phase chromatography (using 5-95% ACN/water with 0.1% TFA as the gradient eluent) to provide the TFA salt of the title compound. The TFA salt was treated with saturated $NaHCO_{3(aq)}$, and extracted into EtOAc (2×). The combined organic extracts were dried over anhydrous $Na_2SO_{4(s)}$, filtered, and concentrated in vacuo to afford the title compound (1.0 mg, 2.4% yield). MS (apci) m/z=542.2 (M+H).

Example 12

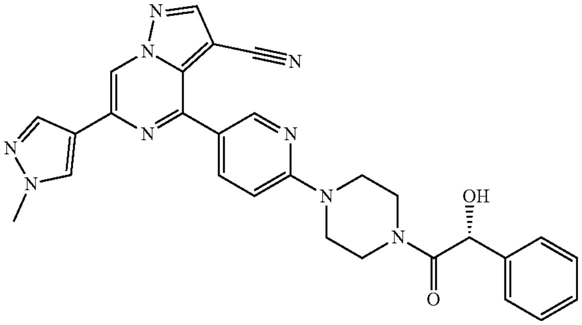 [SMILES: Cn1cc(-c2cn3ncc(C#N)c3c(-c3ccc(N4CCN(C(=O)[C@H](O)c5ccccc5)CC4)nc3)n2)cn1]

(R)-4-(6-(4-(2-Hydroxy-2-phenylacetyl)piperazin-1-yl)pyridin-3-yl)-6-(1-methyl-1H-pyrazol-4-yl)pyrazolo[1,5-a]pyrazine-3-carbonitrile A solution of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 10 mg, 0.026 mmol) in DCM (2 mL) was treated sequentially with (R)-2-hydroxy-2-phenylacetic acid (5.0 mg, 0.033 mmol), TEA (30 μL, 0.22 mmol) and HATU (8.3 mg, 0.022 mmol). The mixture was stirred 1 h at ambient temperature before concentrating in vacuo. The residue was purified by C18 reverse phase chromatography (using 0-75% ACN/water as the gradient eluent) to afford the title compound (3.0 mg, 26% yield). MS (apci) m/z=520.1 (M+H).

Example 13

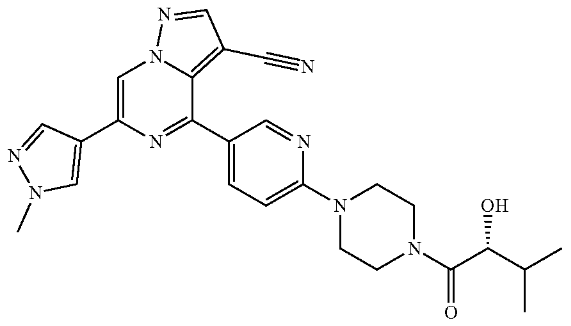 [SMILES: CC(C)[C@@H](O)C(=O)N1CCN(c2ccc(-c3nc(-c4cnn(C)c4)cn4ncc(C#N)c34)cn2)CC1]

(R)-4-(6-(4-(2-Hydroxy-3-methylbutanoyl)piperazin-1-yl)pyridin-3-yl)-6-(1-methyl-1H-pyrazol-4-yl)pyrazolo[1,5-a]pyrazine-3-carbonitrile The title compound (2.2 mg, 21% yield) was prepared and purified using a similar procedure to that described for Example 12, replacing (R)-2-hydroxy-2-phenylacetic acid with (R)-2-hydroxy-3-methylbutanoic acid, and replacing the DCM with DMF. MS (apci) m/z=520.1 (M+H).

Example 14

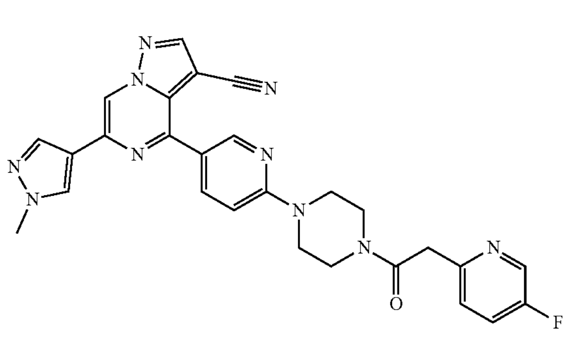 [SMILES: Cn1cc(-c2cn3ncc(C#N)c3c(-c3ccc(N4CCN(C(=O)Cc5ccc(F)cn5)CC4)nc3)n2)cn1]

4-(6-(4-(2-(5-Fluoropyridin-2-yl)acetyl)piperazin-1-yl)pyridin-3-yl)-6-(1-methyl-1H-pyrazol-4-yl)pyrazolo[1,5-a]pyrazine-3-carbonitrile A solution of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 30 mg, 0.078 mmol) in DCM (1 mL) was treated sequentially with DIEA (27 μL, 0.16 mmol), 2-(5-fluoropyridin-2-yl)acetic acid (14 mg, 0.093 mmol) and HATU (30 mg, 0.078 mmol). The mixture was stirred overnight at ambient temperature before concentrating in vacuo. The residue was purified by C18 reverse phase chromatography (using 5-95% ACN/water with 0.1% TFA as the gradient eluent) to provide the TFA salt of the title compound. The TFA salt was treated with saturated $NaHCO_{3(aq)}$, and subsequently extracted into DCM. The combined organic extracts were dried over anhydrous $Na_2SO_{4(s)}$, filtered, and concentrated in vacuo. The residue was further purified by silica chromatography (using 0-20% MeOH in DCM as the gradient eluent) to cleanly afford the title compound (2.6 mg, 6.2% yield). MS (apci) m/z=522.8 (M+H).

Example 15

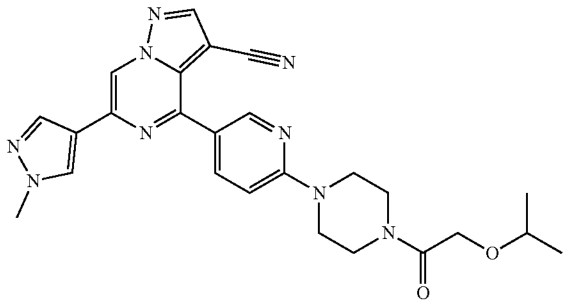 [SMILES: CC(C)OCC(=O)N1CCN(c2ccc(-c3nc(-c4cnn(C)c4)cn4ncc(C#N)c34)cn2)CC1]

4-(6-(4-(2-Isopropoxyacetyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 20 mg, 0.0436 mmol) in anhydrous DMA (0.4 mL) was treated sequentially with DIEA (22.7 μL, 0.131 mmol), HATU (24.9 mg, 0.0655 mmol) and 2-isopropoxyacetic acid (7.73 mg, 0.0655 mmol). The mixture was stirred overnight at ambient temperature. Additional DIEA (15 μL, 0.087 mmol) and HATU (15 mg, 0.040 mmol) were added twice over a period of 24 h while stirring at ambient temperature. The reaction mixture was quenched with the addition of water in $CHCl_3$. The quenched mixture was stirred 30 min at room temperature, then extracted with $CHCl_3$ (3×) in a PS frit. The combined organic extracts were concentrated in vacuo, and the residue was purified by C18 reverse phase chromatography (using 15-80% ACN/water as the gradient eluent) to cleanly afford the title compound (3.6 mg, 17% yield). MS (apci) m/z=486.2 (M+H).

The compounds in Table A were prepared using a similar method to that described for the synthesis of Example 15, replacing 2-isopropoxyacetic acid with the appropriate carboxylic acid. Reactions were monitored for completion by LCMS, and reaction durations, along with the timing (and quantities) of the introduction of additional DIEA and HATU, were adjusted accordingly. In all cases reactions were quenched with water and $CHCl_3$ or DCM, and title compounds were cleanly isolated following C18 reverse phase chromatography using an appropriate gradient.

TABLE A

| Ex # | Structure | Chemical Name | MS (apci) m/z |
|---|---|---|---|
| 16 | 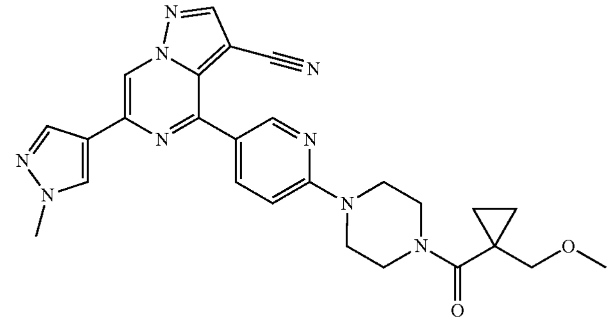 [SMILES: COCC1(C(=O)N2CCN(c3ccc(-c4nc(-c5cnn(C)c5)cn5ncc(C#N)c45)cn3)CC2)CC1] | 4-(6-(4-(1-(methoxymethyl)cyclopropane-1-carbonyl)piperazin-1-yl)pyridin-3-yl)-6-(1-methyl-1H-pyrazol-4-yl)pyrazolo[1,5-a]pyrazine-3-carbonitrile | 498.2 (M + H) |
| 17 | 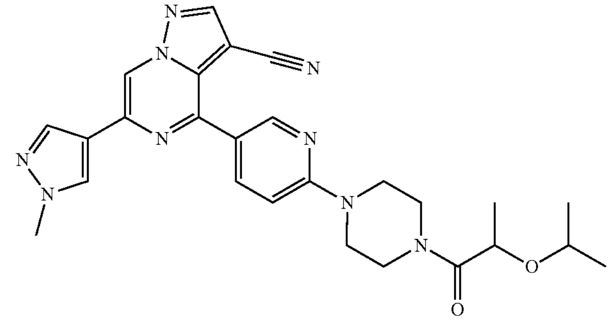 [SMILES: CC(C)OC(C)C(=O)N1CCN(c2ccc(-c3nc(-c4cnn(C)c4)cn4ncc(C#N)c34)cn2)CC1] | 4-(6-(4-(2-isopropoxypropanoyl)piperazin-1-yl)pyridin-3-yl)-6-(1-methyl-1H-pyrazol-4-yl)pyrazolo[1,5-a]pyrazine-3-carbonitrile | 500.2 (M + H) |

Example 18

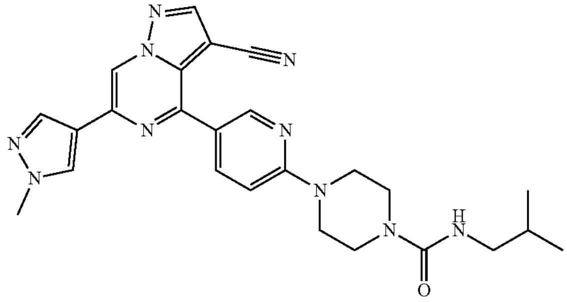 [SMILES: CC(C)CNC(=O)N1CCN(c2ccc(-c3nc(-c4cnn(C)c4)cn4ncc(C#N)c34)cn2)CC1]

4-(5-(3-Cyano-6-(1-methyl-1H-pyrazol-4-yl)pyrazolo[1,5-a]pyrazin-4-yl)pyridin-2-yl)-N-isobutylpiperazine-1-carboxamide A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 0.101 g, 0.220 mmol) in anhydrous DMA (3 mL) was treated with TEA (0.154 mL, 1.10 mmol) and 1-isocyanato-2-methylpropane (0.0262 g, 0.264 mmol). The mixture was stirred for 4 h at ambient temperature before an additional drop of 1-isocyanato-2-methylpropane was added. The reaction mixture was stirred for an additional 2 hrs at ambient temperature before directly purifying by C18 reverse phase chromatography (using 20-80% ACN/water with 0.1% formic acid as the gradient eluent) to cleanly afford the title compound (50 mg, 47% yield). MS (apci) m/z=485.2 (M+H).

Example 19

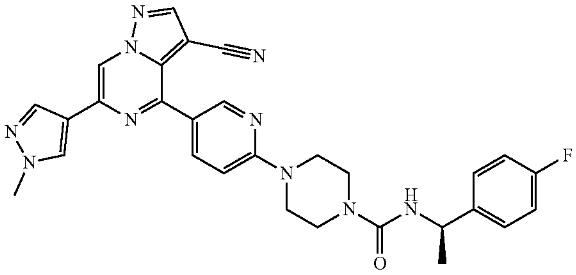 [SMILES: C[C@@H](NC(=O)N1CCN(c2ccc(-c3nc(-c4cnn(C)c4)cn4ncc(C#N)c34)cn2)CC1)c1ccc(F)cc1]

(R)-4-(5-(3-Cyano-6-(1-methyl-1H-pyrazol-4-yl)pyrazolo[1,5-a]pyrazin-4-yl)pyridin-2-yl)-N-(1-(4-fluorophenyl)ethyl)piperazine-1-carboxamide The title compound (24.2 mg, 59% yield) was prepared and purified using a similar procedure to that described for Example 18, replacing 1-isocyanato-2-methylpropane with (R)-1-fluoro-4-(1-isocyanatoethyl)benzene. As the reaction was monitored for completion by LCMS, the addition of supplemental isocyanate was omitted, and the reaction was complete within 6 hrs. MS (apci) m/z=550.2 (M+H).

Example 20

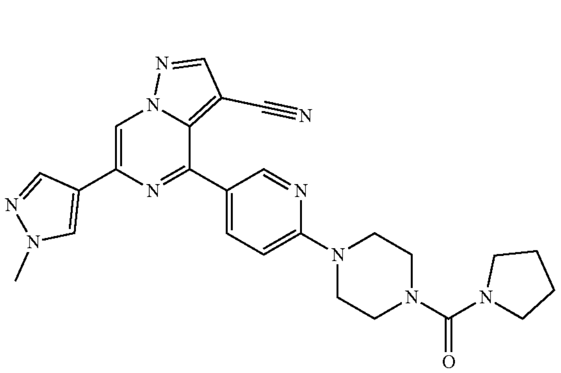 [SMILES: Cn1cc(-c2cn3ncc(C#N)c3c(-c3ccc(N4CCN(C(=O)N5CCCC5)CC4)nc3)n2)cn1]

6-(1-Methyl-1H-pyrazol-4-yl)-4-(6-(4-(pyrrolidine-1-carbonyl)piperazin-1-yl)pyridin-3-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 20 mg, 0.044 mmol) and DIEA (38 μL, 0.22 mmol) in DCM (218 μL) was treated with pyrrolidine-1-carbonyl chloride (6.4 mg, 0.048 mmol). The reaction mixture was stirred overnight at ambient temperature, then concentrated in vacuo. The residue was purified by C18 reverse phase chromatography (using 5-95% ACN/water with 0.1% TFA as the gradient eluent) to provide the TFA salt of the title compound. The TFA salt was treated with saturated $NaHCO_{3(aq)}$, and subsequently extracted into EtOAc. The combined organic extracts were dried over anhydrous $Na_2SO_{4(s)}$, filtered, and concentrated in vacuo. The residue was further purified by silica chromatography (using 0-20% MeOH in EtOAc as the gradient eluent) to cleanly afford the title compound (2.6 mg, 12% yield). MS (apci) m/z=483.2 (M+H).

Example 21

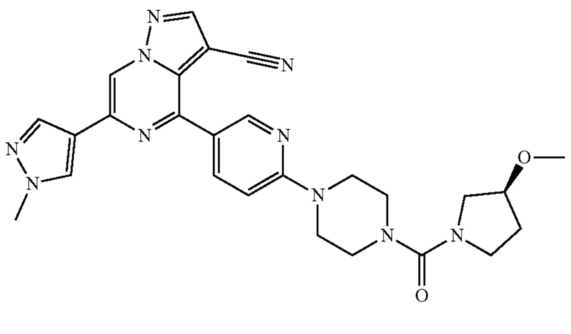 [SMILES: CO[C@H]1CCN(C(=O)N2CCN(c3ccc(-c4nc(-c5cnn(C)c5)cn5ncc(C#N)c45)cn3)CC2)C1]

(S)-4-(6-(4-(3-Methoxypyrrolidine-1-carbonyl)piperazin-1-yl)pyridin-3-yl)-6-(1-methyl-1H-pyrazol-4-yl)pyrazolo[1,5-a]pyrazine-3-carbonitrile Step 1: Preparation of 4-Nitrophenyl 4-(5-(3-cyano-6-(1-methyl-1H-pyrazol-4-yl)pyrazolo[1,5-a]pyrazin-4-yl)pyridin-2-yl)piperazine-1-carboxylate A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 100 mg, 0.218 mmol) in DMA (2.18 mL) was treated sequentially with DIEA (114 μL, 0.655 mmol) and 4-nitrophenyl carbonochloridate (48.4 mg, 0.240 mmol). The reaction mixture was stirred 6 h at ambient temperature before introducing additional 4-nitrophenyl carbonochloridate (22 mg, 0.109 mmol). The resultant mixture was stirred 2 h at ambient temperature. LCMS analysis of the mixture indicated clean conversion to the title compound (120 mg, quantitative yield is assumed). MS (apci) m/z=551.2 (M+H). The mixture was divided into 5 equal parts for immediate use in subsequent reactions.

Step 2: Preparation of (S)-4-(6-(4-(3-Methoxypyrrolidine-1-carbonyl)piperazin-1-yl)pyridin-3-yl)-6-(1-methyl-1H-pyrazol-4-yl)pyrazolo[1,5-a]pyrazine-3-carbonitrile A solution of (S)-3-methoxypyrrolidine (5.5 mg, 0.054 mmol) and DIEA (19 μL, 0.11 mmol) in DMA (0.1 mL) was treated with a suspension 4-nitrophenyl 4-(5-(3-cyano-6-(1-methyl-1H-pyrazol-4-yl)pyrazolo[1,5-a]pyrazin-4-yl)pyridin-2-yl)piperazine-1-carboxylate (Example 21, Step 1; 20 mg, 0.036 mmol) in DIEA (23 μL, 0.13 mmol) and DMA (0.44 mL). The reaction mixture was stirred overnight at 80° C. After cooling to ambient temperature, the reaction mixture was diluted with water and extracted with EtOAc (3×). The combined organic extracts were dried over anhydrous $Na_2SO_{4(s)}$, filtered, and concentrated in vacuo. The residue was purified by C18 reverse phase chromatography (using 5-95% ACN/water with 0.1% TFA as the gradient eluent) to provide the TFA salt of the title compound. The TFA salt was treated with saturated $NaHCO_{3(aq)}$ and extracted into EtOAc (3×). The combined organic extracts were concentrated in vacuo, and the residue was purified by silica chromatography (using 0-100% (20% MeOH/2% $NH_4OH$/78% DCM) in DCM as the gradient eluent) to cleanly afford the title compound (5.6 mg, 29% yield). MS (apci) m/z=513.2 (M+H).

Example 22

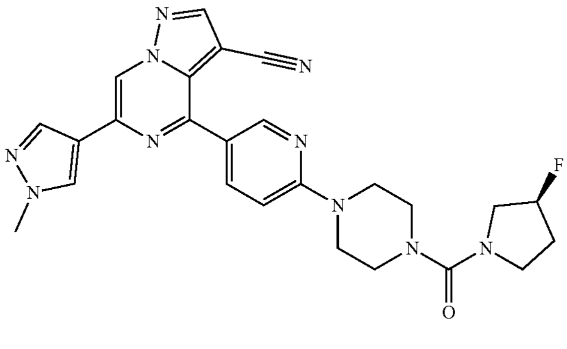 [SMILES: Cn1cc(-c2cn3ncc(C#N)c3c(-c3ccc(N4CCN(C(=O)N5CC[C@H](F)C5)CC4)nc3)n2)cn1]

(S)-4-(6-(4-(3-Fluoropyrrolidine-1-carbonyl)piperazin-1-yl)pyridin-3-yl)-6-(1-methyl-1H-pyrazol-4-yl)pyrazolo[1,5-a]pyrazine-3-carbonitrile The title compound was prepared and purified using a similar procedure to that described for Example 21, replacing (S)-3-methoxypyrrolidine with (S)-3-fluoropyrrolidine. The reaction was monitored for completion by LCMS. Additional (S)-3-fluoropyrrolidine (4.9 mg, 0.054 mmol) was introduced, and the reaction duration was adjusted to ensure reaction completion. Additionally, the gradient eluent in the final silica chromatography was altered (0-20% MeOH in DCM) to allow clean isolation of the title compound (1 mg, 6% yield) MS (apci) m/z=501.2 (M+H).

Example 23

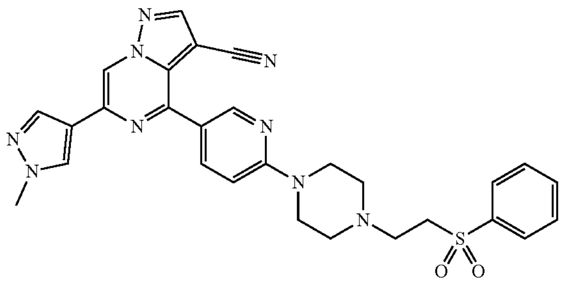 [SMILES: Cn1cc(-c2cn3ncc(C#N)c3c(-c3ccc(N4CCN(CCS(=O)(=O)c5ccccc5)CC4)nc3)n2)cn1]

6-(1-Methyl-1H-pyrazol-4-yl)-4-(6-(4-(2-(phenylsulfonyl)ethyl)piperazin-1-yl)pyridin-3-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 21 mg, 0.046 mmol) in anhydrous DMA (0.5 mL) was treated with TEA (46.4 μL, 0.458 mmol) and ((2-chloroethyl)sulfonyl)benzene (28.1 mg, 0.137 mmol). The mixture was stirred overnight at 75° C. before cooling to ambient temperature. The reaction mixture was purified directly by C18 reverse phase chromatography (using 20-80% ACN/water as the gradient eluent) to cleanly afford the title compound (3.7 mg, 15% yield). MS (apci) m/z=554.2 (M+H).

The compounds in Table B were prepared using a similar method to that described for the synthesis of Example 23, replacing ((2-chloroethyl)sulfonyl)benzene with the appropriate alkyl halide. Reactions were conducted at 70° C., and monitored for completion by LCMS, adjusting reaction durations accordingly. The title compounds were cleanly isolated following C18 reverse phase chromatography using an appropriate gradient.

TABLE B

| Ex # | Structure | Chemical Name | MS (apci) m/z |
|---|---|---|---|
| 24 | 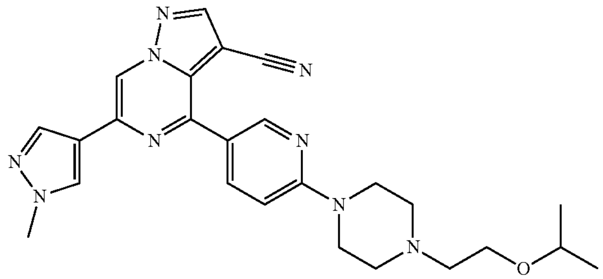 [SMILES: CC(C)OCCN1CCN(c2ccc(-c3nc(-c4cnn(C)c4)cn4ncc(C#N)c34)cn2)CC1] | 4-(6-(4-(2-isopropoxyethyl)piperazin-1-yl)pyridin-3-yl)-6-(1-methyl-1H-pyrazol-4-yl)pyrazolo[1,5-a]pyrazine-3-carbonitrile | 472.2 (M + H) |
| 25 | 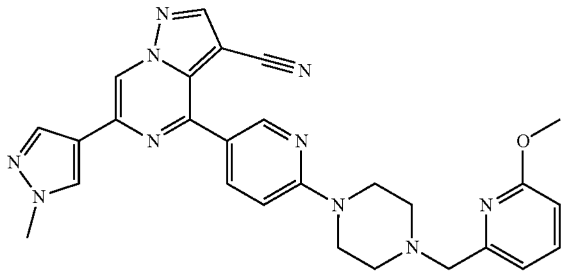 [SMILES: COc1cccc(CN2CCN(c3ccc(-c4nc(-c5cnn(C)c5)cn5ncc(C#N)c45)cn3)CC2)n1] | 4-(6-(4-((6-methoxypyridin-2-yl)methyl)piperazin-1-yl)pyridin-3-yl)-6-(1-methyl-1H-pyrazol-4-yl)pyrazolo[1,5-a]pyrazine-3-carbonitrile | 507.2 (M + H) |
| 26 | 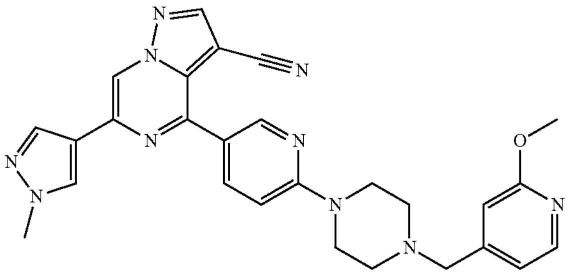 [SMILES: COc1cc(CN2CCN(c3ccc(-c4nc(-c5cnn(C)c5)cn5ncc(C#N)c45)cn3)CC2)ccn1] | 4-(6-(4-((2-methoxypyridin-4-yl)methyl)piperazin-1-yl)pyridin-3-yl)-6-(1-methyl-1H-pyrazol-4-yl)pyrazolo[1,5-a]pyrazine-3-carbonitrile | 507.2 (M + H) |

Example 27

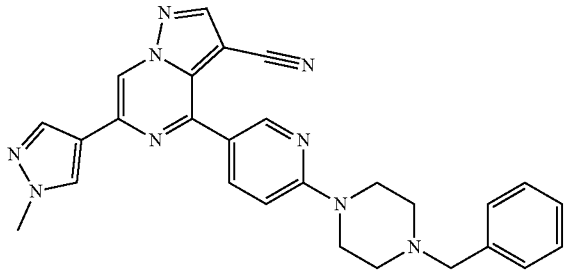 [SMILES: Cn1cc(-c2cn3ncc(C#N)c3c(-c3ccc(N4CCN(Cc5ccccc5)CC4)nc3)n2)cn1]

4-(6-(4-Benzylpiperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 20 mg, 0.044 mmol) in anhydrous DMF (0.1 mL) was treated with TEA (18.2 μL, 0.131 mmol) and (bromomethyl)benzene (6.74 μL, 0.0567 mmol). The mixture was stirred 1 h at RT, then purified directly by C18 reverse phase chromatography (using 0-80% ACN/water as the gradient eluent) to afford the title compound (10 mg, 48% yield). MS (apci) m/z=476.2 (M+H).

Example 28

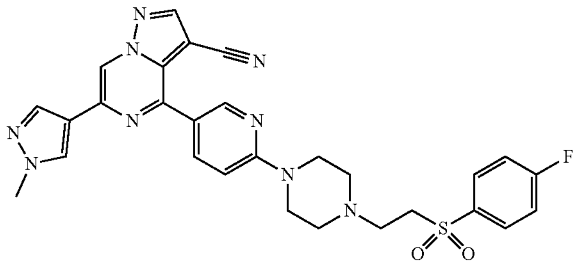 [SMILES: Cn1cc(-c2cn3ncc(C#N)c3c(-c3ccc(N4CCN(CCS(=O)(=O)c5ccc(F)cc5)CC4)nc3)n2)cn1]

4-(6-(4-(2-((4-Fluorophenyl)sulfonyl)ethyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 19 mg, 0.042 mmol) in anhydrous DMA (0.5 mL) was treated with TEA (57.8 μL, 0.415 mmol) and 1-((2-chloroethyl)sulfonyl)-4-fluorobenzene (27.7 mg, 0.124 mmol). The mixture was stirred at 70° C. until LCMS indicated complete consumption of carbonitrile. After cooling to ambient temperature, the reaction mixture was quenched by partitioning between water and $CHCl_3$. The quenched mixture was extracted with $CHCl_3$ (3×) in a PS Frit, and the combined organic extracts were concentrated in vacuo. The residue was purified by C18 reverse phase chromatography (using 15-80% ACN/water as the gradient eluent) to cleanly afford the title compound (18.7 mg, 79% yield). MS (apci) m/z=572.2 (M+H).

Example 29

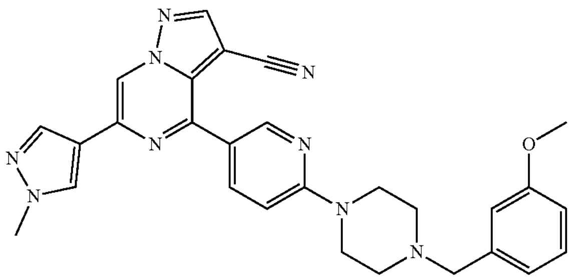 [SMILES: COc1cccc(CN2CCN(c3ccc(-c4nc(-c5cnn(C)c5)cn5ncc(C#N)c45)cn3)CC2)c1]

4-(6-(4-(3-Methoxybenzyl)piperazin-1-yl)pyridin-3-yl)-6-(1-methyl-1H-pyrazol-4-yl)pyrazolo[1,5-a]pyrazine-3-carbonitrile A cold (0° C.) suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 15.3 mg, 0.0334 mmol) in anhydrous DMA (0.4 mL) was treated with TEA (18.6 μL, 0.134 mmol) and stirred for 4 min at 0° C. 1-(Bromomethyl)-3-methoxybenzene (0.007011 ml, 0.05007 mmol) was introduced, and the mixture was stirred 3 d at ambient temperature. The reaction mixture was quenched by partitioning between water and $CHCl_3$. The quenched mixture was extracted with $CHCl_3$ (3×) in a PS Frit, and the combined organic extracts were concentrated in vacuo. The residue was purified by C18 reverse phase chromatography (using 20-80% ACN/water as the gradient eluent) to cleanly afford the title compound (5.8 mg, 33% yield). MS (apci) m/z=506.2 (M+H).

Example 30

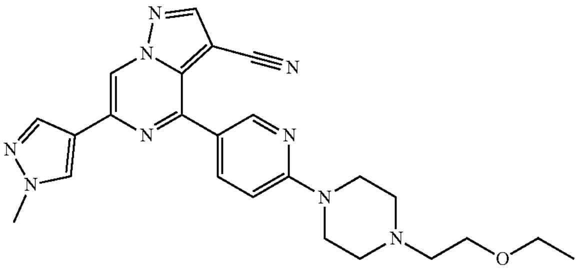 [SMILES: CCOCCN1CCN(c2ccc(-c3nc(-c4cnn(C)c4)cn4ncc(C#N)c34)cn2)CC1]

4-(6-(4-(2-Ethoxyethyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 30 mg, 0.078 mmol) in DMF (778 μL) was treated with $K_2CO_{3(s)}$ (32.3 mg, 0.234 mmol) and 1-bromo-2-ethoxyethane (10.5 μL, 0.0934 mmol). The reaction mixture was stirred overnight at 50° C. After cooling to ambient temperature, the reaction mixture was diluted with MeOH, and filtered. The filtrate was concentrated in vacuo, and the residue was purified by C18 reverse phase chromatography (using 5-95% ACN/water with 0.1% TFA as the gradient eluent) to provide the TFA salt of the title compound. The TFA salt was neutralized by treatment with saturated $NaHCO_{3(aq)}$, and subsequent extraction with EtOAc (3×). The combined organic extracts were dried over anhydrous $Na_2SO_{4(s)}$, filtered, and concentrated in vacuo cleanly afford the title compound (7 mg, 18% yield). MS (apci) m/z=458.2 (M+H).

Example 31

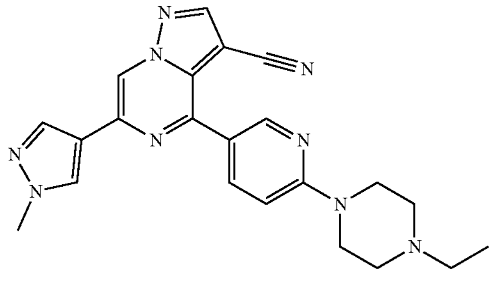 [SMILES: CCN1CCN(c2ccc(-c3nc(-c4cnn(C)c4)cn4ncc(C#N)c34)cn2)CC1]

4-(6-(4-Ethylpiperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 10 mg, 0.0259 mmol in DMF (259 μL) was treated sequentially with $K_2CO_{3(s)}$ (10.8 mg, 0.0778 mmol) and bromoethane (2.31 μL, 0.0311 mmol). The reaction mixture was stirred for 7 d at 50° C. before additional bromoethane (1.93 μL, 0.0259 mmol) was added. After stirring for an additional 4 h at 50° C., the reaction mixture was cooled to ambient temperature and partitioned between DCM (5 mL) and water (5 mL). The mixture was extracted with DCM (3×10 mL). The combined organic extracts were washed with brine, then dried over anhydrous $Na_2SO_{4(s)}$, filtered, and concentrated in vacuo. The residue was purified by silica chromatography (using 5-95% ACN/water with 0.1% TFA as the gradient eluent) to provide the TFA salt of the title compound. The TFA salt was treated with saturated $NaHCO_{3(aq)}$, and subsequently extracted into EtOAc (3×). The combined organic extracts were dried over anhydrous $Na_2SO_{4(s)}$, filtered, and concentrated in vacuo. The residue was purified by silica chromatography (using 0-100% (20% MeOH/2% $NH_4OH$/78% DCM) in DCM as the gradient eluent) to cleanly afford the title compound (3.9 mg, 36% yield). MS (apci) m/z=414.2 (M+H).

Example 32

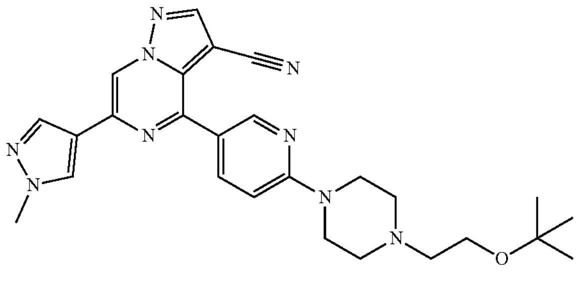 [SMILES: Cn1cc(-c2cn3ncc(C#N)c3c(-c3ccc(N4CCN(CCOC(C)(C)C)CC4)nc3)n2)cn1]

4-(6-(4-(2-(tert-butoxy)ethyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 18 mg, 0.039 mmol) in anhydrous DMF (0.4 mL) was treated with 2-(tert-butoxy)ethyl methanesulfonate (23.1 mg, 0.118 mmol) and TEA (54.7 μL, 0.393 mmol). The mixture was stirred for 4 d at 70° C., then cooled to ambient temperature and purified directly by C18 reverse phase chromatography (using 30-85% ACN/water as the gradient eluent) to afford the title compound (3.6 mg, 19% yield). MS (apci) m/z=486.2 (M+H).

Example 33

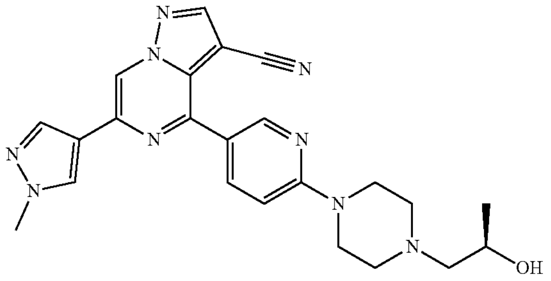 [SMILES: C[C@@H](O)CN1CCN(c2ccc(-c3nc(-c4cnn(C)c4)cn4ncc(C#N)c34)cn2)CC1]

(R)-4-(6-(4-(2-Hydroxypropyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 32.5 mg, 0.0709 mmol) in dry MeOH (0.35 mL) was treated sequentially with DIEA (24.8 μL, 0.142 mmol) and (R)-2-methyloxirane (6 μL, 0.0851 mmol). The mixture was stirred for 20 min each first at 75° C., then at ambient temperature. Additional DIEA (24.8 μL, 0.142 mmol), (R)-2-methyloxirane (10 μL, 0.142 mmol) and dry MeOH (0.35 mL) were introduced. The reaction mixture was stirred 3 d at 75° C., then cooled to ambient temperature and concentrated in vacuo. The residue was purified by C18 reverse phase chromatography (using 10-70% ACN/water with 0.1% formic acid as the gradient eluent) to afford the title compound (17 mg, 54% yield). MS (apci) m/z=444.1 (M+H).

Example 34

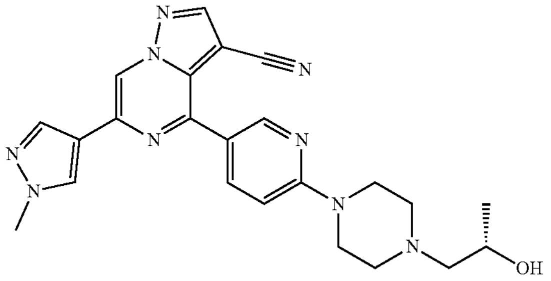 [SMILES: C[C@H](O)CN1CCN(c2ccc(-c3nc(-c4cnn(C)c4)cn4ncc(C#N)c34)cn2)CC1]

(S)-4-(6-(4-(2-Hydroxypropyl)piperazin-1-yl)pyridin-3-yl)-6-(1-methyl-1H-pyrazol-4-yl)pyrazolo[1,5-a]pyrazine-3-carbonitrile The title compound (13 mg, 41% yield) was prepared and purified using a similar procedure to that described for Example 33, replacing (R)-2-methyloxirane with (S)-2-methyloxirane. MS (apci) m/z=501.2 (M+H).

Example 35

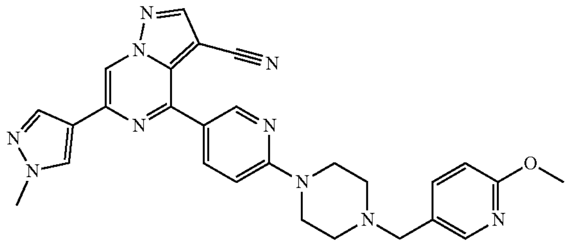 [SMILES: COc1ccc(CN2CCN(c3ccc(-c4nc(-c5cnn(C)c5)cn5ncc(C#N)c45)cn3)CC2)cn1]

4-(6-(4-((6-Methoxypyridin-3-yl)methyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 115 mg, 0.251 mmol) in dry DMA (2 mL) was treated with TEA (24.8 μL, 0.142 mmol), $Me_4N(AcO)_3BH$ (132 mg, 0.502 mmol) and 6-methoxynicotinaldehyde (72.4 mg, 0.502 mmol). The mixture was stirred for 2 d at ambient temperature before introducing additional TEA (24.8 μL, 0.142 mmol) and $Me_4N(AcO)_3BH$ (132 mg, 0.502 mmol). The reaction mixture was stirred at ambient temperature until starting material had been consumed as determined by LCMS. The reaction mixture was quenched with water/$CHCl_3$ and extracted with $CHCl_3$ in a PS Frit. The combined organic extracts were concentrated in vacuo, and the residue was purified by C18 reverse phase chromatography (using 15-80% ACN/water as the gradient eluent) to afford the title compound (6.7 mg, 53% yield). MS (apci) m/z=507.2 (M+H).

The compounds in Table C were prepared using a similar method to that described for the synthesis of Example 35, replacing 6-methoxynicotinaldehyde with the appropriate aldehyde. Reactions were monitored for completion by LCMS, and the timing of the introduction of supplemental reagent amounts, and reaction durations were adjusted accordingly. The title compounds were cleanly isolated following C18 reverse phase chromatography using an appropriate gradient.

TABLE C

| Ex # | Structure | Chemical Name | MS (apci) m/z |
|---|---|---|---|
| 36 | 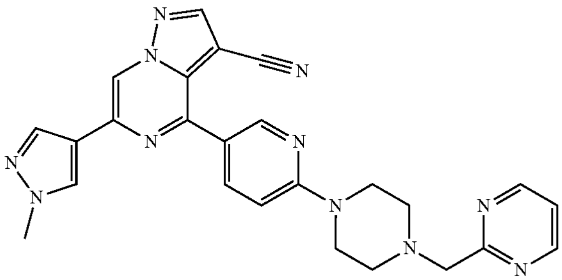 [SMILES: Cn1cc(-c2cn3ncc(C#N)c3c(-c3ccc(N4CCN(Cc5ncccn5)CC4)nc3)n2)cn1] | 6-(1-methyl-1H-pyrazol-4-yl)-4-(6-(4-(pyrimidin-2-ylmethyl)piperazin-1-yl)pyridin-3-yl)pyrazolo[1,5-a]pyrazine-3-carbonitrile | 478.2 (M + H) |
| 37 | 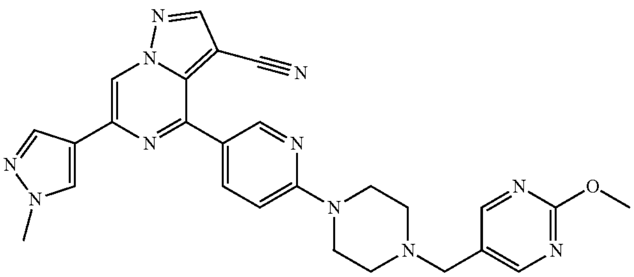 [SMILES: COc1ncc(CN2CCN(c3ccc(-c4nc(-c5cnn(C)c5)cn5ncc(C#N)c45)cn3)CC2)cn1] | 4-(6-(4-((2-methoxypyrimidin-5-yl)methyl)piperazin-1-yl)pyridin-3-yl)-6-(1-methyl-1H-pyrazol-4-yl)pyrazolo[1,5-a]pyrazine-3-carbonitrile | 508.2 (M + H) |

TABLE C-continued

| Ex # | Structure | Chemical Name | MS (apci) m/z |
|---|---|---|---|
| 38 | 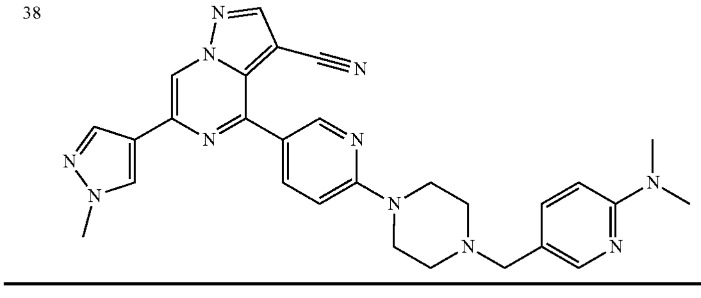 | 4-(6-(4-((6-(dimethylamino)pyridin-3-yl)methyl)piperazin-1-yl)pyridin-3-yl)-6-(1-methyl-1H-pyrazol-4-yl)pyrazolo[1,5-a]pyrazine-3-carbonitrile | 520.3 (M + H) |

Example 39

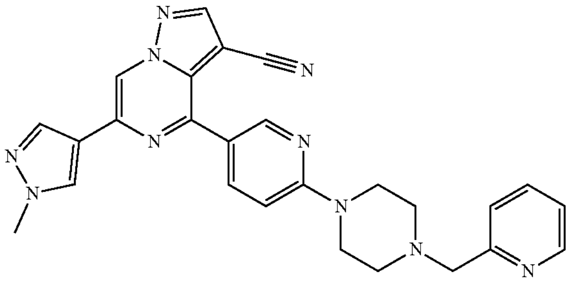 [SMILES: Cn1cc(-c2cn3ncc(C#N)c3c(-c3ccc(N4CCN(Cc5ccccn5)CC4)nc3)n2)cn1]

6-(1-Methyl-1H-pyrazol-4-yl)-4-(6-(4-(pyridin-2-ylmethyl)piperazin-1-yl)pyridin-3-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 2.0 g, 4.4 mmol) in dry DMA (44 mL) was treated sequentially with TEA (1.82 mL, 13.1 mmol) and $NaBH(AcO)_3$ (132 mg, 0.502 mmol). The mixture was treated, in dropwise fashion, with picolinaldehyde (0.935 g, 8.73 mmol), and stirred for 4 h at ambient temperature. The reaction mixture was poured slowly into cold (0° C.) DI water (500 mL), and the quenched mixture was stirred overnight at ambient temperature before vacuum filtering. The resultant filter cake was rinsed with water (100 mL) and MTBE (100 mL). The solids then were dissolved in DCM, dried over anhydrous $Na_2SO_{4(s)}$, filtered, and concentrated in vacuo to cleanly afford the title compound (1.70 g, 82% yield). MS (apci) m/z=477.2 (M+H).

Example 40

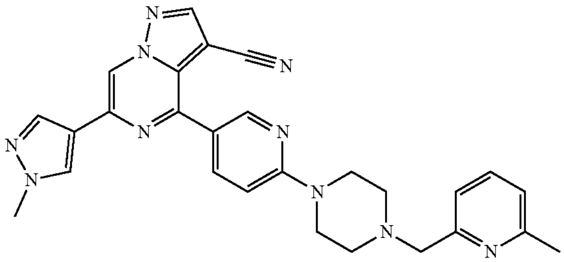 [SMILES: Cc1cccc(CN2CCN(c3ccc(-c4nc(-c5cnn(C)c5)cn5ncc(C#N)c45)cn3)CC2)n1]

6-(1-Methyl-1H-pyrazol-4-yl)-4-(6-(4-((6-methylpyridin-2-yl)methyl)piperazin-1-yl)pyridin-3-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol) in dry DMA (1.1 mL) was treated sequentially with TEA (1.82 mL, 13.1 mmol), 6-methylpicolinaldehyde (26.4 mg, 0.218 mmol) and $NaBH(AcO)_3$ (132 mg, 0.502 mmol). The mixture was stirred for 18 h at ambient temperature. The reaction mixture was poured dropwise into rapidly stirring DI water (20 mL), and the quenched mixture was stirred overnight at ambient temperature before vacuum filtering. The resultant filter cake was rinsed with water (3×5 mL) and MTBE (3×5 mL). The solids were dissolved in DCM, dried over anhydrous $Na_2SO_{4(s)}$, filtered, and concentrated in vacuo to cleanly afford the title compound (43.4 mg, 77% yield). MS (apci) m/z=491.3 (M+H).

Example 41

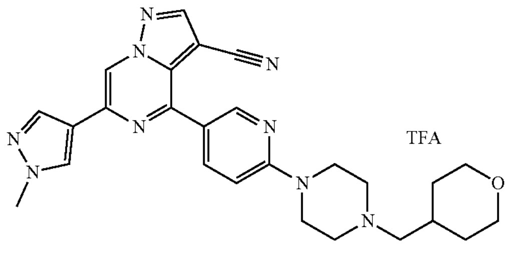 [SMILES: Cn1cc(-c2cn3ncc(C#N)c3c(-c3ccc(N4CCN(CC5CCOCC5)CC4)nc3)n2)cn1]

TFA 6-(1-Methyl-1H-pyrazol-4-yl)-4-(6-(4-((tetrahydro-2H-pyran-4-yl)methyl)piperazin-1-yl)pyridin-3-yl)pyrazolo[1,5-a]pyrazine-3-carbonitrile 2,2,2-trifluoroacetate A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol) in DCE (259 μL) was treated sequentially with tetrahydro-2H-pyran-4-carbaldehyde (6 μL, 0.052 mmol) and NaBH$(AcO)_3$ (132 mg, 0.502 mmol). The mixture was stirred for 5 h at ambient temperature. The reaction mixture was concentrated in vacuo, and the residue was purified by C18 reverse phase chromatography (using 5-95% ACN/water with 0.1% TFA the gradient eluent) to cleanly afford the title compound (2.7 mg, 22% yield). MS (apci) m/z=484.2 (M+H).

Example 42

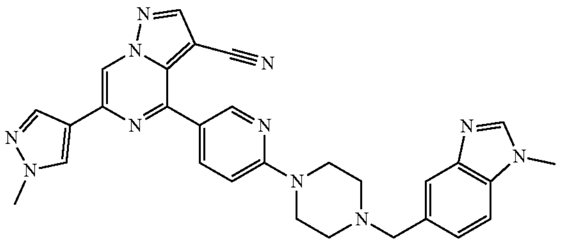 [SMILES: Cn1cc(-c2cn3ncc(C#N)c3c(-c3ccc(N4CCN(Cc5ccc6c(c5)ncn6C)CC4)nc3)n2)cn1]

4-(6-(4-((1-Methyl-1H-benzo[d]imidazol-5-yl)methyl)piperazin-1-yl)pyridin-3-yl)-6-(1-methyl-1H-pyrazol-4-yl)pyrazolo[1,5-a]pyrazine-3-carbonitrile A suspension of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 30 mg, 0.078 mmol) in DCE (778 μL) was treated sequentially with 1-methyl-1H-benzimidazole-5-carboxaldehyde (25 mg, 0.16 mmol) and NaBH$(AcO)_3$ (49 mg, 0.23 mmol). The mixture was stirred overnight at ambient temperature, and then concentrated in vacuo. The residue was purified first by silica chromatography (using 0-20% MeOH in DCM as the gradient eluent) and then by C18 reverse phase chromatography (using 5-95% ACN/water with 0.1% TFA the gradient eluent) to cleanly afford the title compound as its TFA salt. The TFA salt was treated with saturated $NaHCO_{3(aq)}$, and subsequently extracted into EtOAc (3×). The combined organic extracts were dried over anhydrous $Na_2SO_{4(s)}$, filtered, and concentrated in vacuo to cleanly afford the title compound (1.5 mg, 3.6% yield). MS (apci) m/z=529.8 (M+H).

Example 43

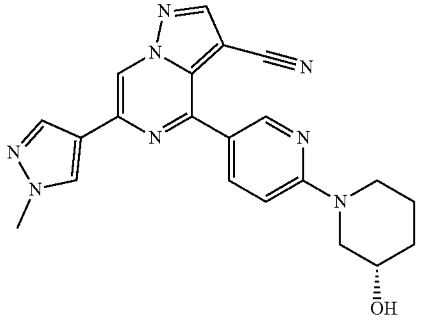 [SMILES: Cn1cc(-c2cn3ncc(C#N)c3c(-c3ccc(N4CCC[C@H](O)C4)nc3)n2)cn1]

(S)-4-(6-(3-Hydroxypiperidin-1-yl)pyridin-3-yl)-6-(1-methyl-1H-pyrazol-4-yl)pyrazolo[1,5-a]pyrazine-3-carbonitrile A solution of 4-(6-fluoropyridin-3-yl)-6-(1-methyl-H-pyrazol-4-yl)pyrazolo[1,5-a]pyrazine-3-carbonitrile (Intermediate P7; 50 mg, 0.16 mmol) in DMSO (3.1 mL) was treated with (S)-piperidin-3-ol (79 mg, 0.78 mmol) and $K_2CO_{3(s)}$ (87 mg, 0.63 mmol) then stirred overnight at 110° C. After cooling to ambient temperature, the reaction mixture was diluted with water (10 mL), and extracted with DCM (4×10 mL) in a PS Frit. The combined organic extracts were concentrated in vacuo, and purified by C18 reverse phase chromatography (using 0-60% ACN/water as the gradient eluent) to afford the title compound (35 mg, 56% yield). MS (apci) m/z=401.1 (M+H).

Example 44

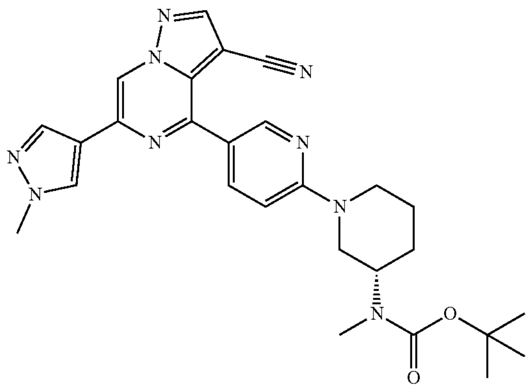 [SMILES: CN(C(=O)OC(C)(C)C)[C@H]1CCCN(c2ccc(-c3nc(-c4cnn(C)c4)cn4ncc(C#N)c34)cn2)C1]

tert-Butyl (S)-(1-(5-(3-cyano-6-(1-methyl-1H-pyrazol-4-yl)pyrazolo[1,5-a]pyrazin-4-yl)pyridin-2-yl)piperidin-3-yl)(methyl)carbamate A solution of 4-(6-fluoropyridin-3-yl)-6-(1-methyl-H-pyrazol-4-yl)pyrazolo[1,5-a]pyrazine-3-carbonitrile (Intermediate P7; 0.100 g, 0.313 mmol) in DMSO (6.26 mL) was treated with (S)-tert-butyl methyl(piperidin-3-yl)carbamate (0.268 g, 1.25 mmol) and $K_2CO_{3(s)}$ (0.173 g, 1.25 mmol) and stirred overnight at 110° C. After cooling to ambient temperature, the reaction mixture was diluted with water (10 mL) and extracted with DCM (4×10 mL) in a PS Frit. The combined organic extracts were concentrated in vacuo, and purified by C18 reverse phase chromatography (using 0-60% ACN/water as the gradient eluent) to afford the title compound (106 mg, 66% yield). MS (apci) m/z=514.2 (M+H).

Example 45

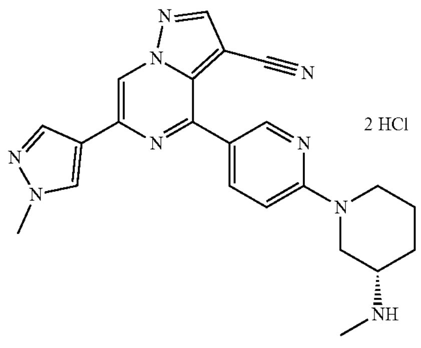 [SMILES: CN[C@H]1CCCN(c2ccc(-c3nc(-c4cnn(C)c4)cn4ncc(C#N)c34)cn2)C1]

(S)-6-(1-Methyl-1H-pyrazol-4-yl)-4-(6-(3-(methylamino)piperidin-1-yl)pyridin-3-yl)pyrazolo[1,5-a]pyrazine-3-carbonitrile dihydrochloride A solution of tert-butyl (S)-(1-(5-(3-cyano-6-(1-methyl-1H-pyrazol-4-yl)pyrazolo[1,5-a]pyrazin-4-yl)pyridin-2-yl)piperidin-3-yl)(methyl)carbamate (Example 44; 100 mg, 0.195 mmol) in $CHCl_3$ (2 mL) was treated 5 M HCl in iPrOH (195 μL, 0.974 mmol). The mixture was stirred 2 h at ambient temperature, and then concentrated in vacuo to afford the title compound (80 mg, 99% yield). MS (apci) m/z=414.2 (M+H).

Example 46

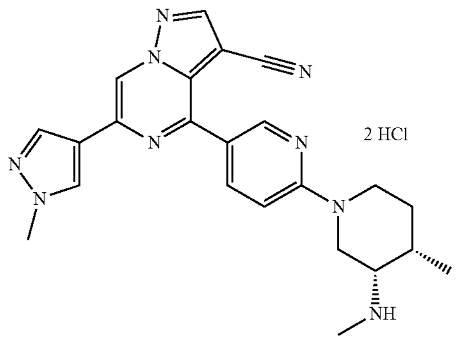 [SMILES: CN[C@@H]1CN(c2ccc(-c3nc(-c4cnn(C)c4)cn4ncc(C#N)c34)cn2)CC[C@@H]1C]

6-(1-Methyl-1H-pyrazol-4-yl)-4-(6-((3S,4S)-4-methyl-3-(methylamino)piperidin-1-yl)pyridin-3-yl)pyrazolo[1,5-a]pyrazine-3-carbonitrile dihydrochloride Step 1: Preparation of tert-Butyl ((3S,4S)-1-(5-(3-cyano-6-(1-methyl-1H-pyrazol-4-yl)pyrazolo[1,5-a]pyrazin-4-yl)pyridin-2-yl)-4-methylpiperidin-3-yl)(methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.100 g, 0.313 mmol) in DMSO (6.26 mL) was treated with tert-butyl methyl((3S,4S)-4-methylpiperidin-3-yl)carbamate (0.100 g, 0.438 mmol) and $K_2CO_{3(s)}$ (0.173 g, 1.25 mmol) and stirred overnight at 110° C. After cooling to ambient temperature, the reaction mixture was diluted with water (10 mL) and extracted with DCM (4×10 mL) in a PS Frit. The combined organic extracts were concentrated in vacuo and purified by C18 reverse phase chromatography (using 0-80% ACN/water as the gradient eluent) to afford the title compound (32 mg, 19% yield). MS (apci) m/z=528.3 (M+H).

Step 2: Preparation of 6-(1-Methyl-1H-pyrazol-4-yl)-4-(6-((3S,4S)-4-methyl-3-(methylamino)piperidin-1-yl)pyridin-3-yl)pyrazolo[1,5-a]pyrazine-3-carbonitrile dihydrochloride A solution of tert-butyl ((3S,4S)-1-(5-(3-cyano-6-(1-methyl-1H-pyrazol-4-yl)pyrazolo[1,5-a]pyrazin-4-yl)pyridin-2-yl)-4-methylpiperidin-3-yl)(methyl)carbamate (Example 46. Step 1; 10 mg, 0.020 mmol) in $CHCl_3$ (2 mL) was treated 5 M HCl in iPrOH (11 μL, 0.057 mmol). The mixture was stirred overnight at ambient temperature, and then concentrated in vacuo. The residue was washed with $Et_2O$ (2×1 mL) and air-dried to afford the title compound (6 mg, 74% yield). MS (apci) m/z=414.2 (M+H).

Example 47

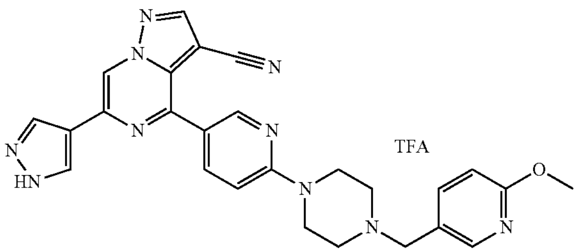 [SMILES: COc1ccc(CN2CCN(c3ccc(-c4nc(-c5cn[nH]c5)cn5ncc(C#N)c45)cn3)CC2)cn1]

4-(6-(4-((6-Methoxypyridin-3-yl)methyl)piperazin-1-yl)pyridin-3-yl)-6-(1H-pyrazol-4-yl)pyrazolo[1,5-a]pyrazine-3-carbonitrile 2,2,2-trifluoroacetate Step 1: Preparation of 6-(1-(4-Methoxybenzyl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile A mixture of 4-chloro-6-(1-(4-methoxybenzyl)-1H-pyrazol-4-yl)pyrazolo[1,5-a]pyrazine-3-carbonitrile (Intermediate P4; 270 mg, 0.740 mmol), 1-((6-methoxypyridin-3-yl)methyl)-4-(5-(4,4,5,5-tetramethyl-1,3,2-dioxaborolan-2-yl)pyridin-2-yl)piperazine (456 mg, 1.11 mmol), $Na_2CO_{3(s)}$ (0.392 g, 3.70 mmol) and $Pd(PPh_3)_4$ (0.0428 g, 0.0370 mmol) was suspended in 1,4-dioxane (9.72 mL) and sparged with $Ar_{(g)}$. The mixture was stirred 2 h at 80° C. before water (0.5 mL) and additional $Pd(PPh_3)_4$ were introduced. The reaction mixture was sparged again with $Ar_{(g)}$ and stirred for 2 d at 80° C. The reaction mixture was cooled to ambient temperature, then diluted with DCM and washed with water. The organic extracts were purified by silica chromatography (10% to 100% EtOAc in DCM) to cleanly afford the title compound (291 mg, 64% yield). MS (apci) m/z=612.8 (M+H).

Step 2: Preparation of 4-(6-(4-((6-Methoxypyridin-3-yl)methyl)piperazin-1-yl)pyridin-3-yl)-6-(1H-pyrazol-4-yl)pyrazolo[1,5-a]pyrazine-3-carbonitrile 2,2,2-trifluoroacetate Under $N_{2(g)}$, 6-(1-(4-methoxybenzyl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile (291 mg, 0.475 mmol) was suspended in TFA (20 mL) then stirred overnight at 90° C. After cooling to ambient temperature, the reaction mixture was azeotroped with toluene (2×5 mL) in vacuo. The residue was purified by C18 reverse phase chromatography (using 2-50% ACN/water with 0.1% TFA as the gradient eluent) and dried under high vacuum overnight to afford the title compound (296 mg, quantitative yield). MS (apci) m/z=493.2 (M+H).

Example 48

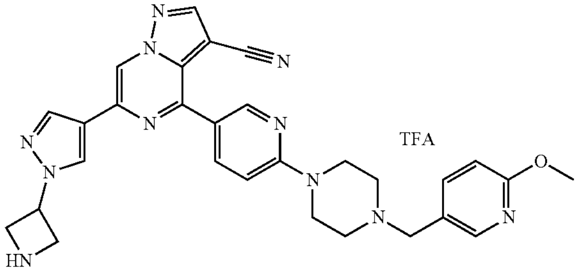 [SMILES: COc1ccc(CN2CCN(c3ccc(-c4nc(-c5cnn(C6CNC6)c5)cn5ncc(C#N)c45)cn3)CC2)cn1]

6-(1-(Azetidin-3-yl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile 2,2,2-trifluoroacetate A solution of 4-(6-(4-((6-methoxypyridin-3-yl)methyl)piperazin-1-yl)pyridin-3-yl)-6-(1H-pyrazol-4-yl)pyrazolo[1,5-a]pyrazine-3-carbonitrile 2,2,2-trifluoroacetate (Example 47; 29 mg, 0.059 mmol) in DMA (1 mL) was treated sequentially with $Cs_2CO_{3(s)}$ (58 mg, 0.18 mmol) and tert-butyl 3-iodoazetidine-1-carboxylate (20.0 mg, 0.0707 mmol). The mixture was stirred 1.5 h at 80° C. before introducing additional tert-butyl 3-iodoazetidine-1-carboxylate (6.7 mg, 0.071 mmol). The reaction was stirred for 3 d at 80° C., then concentrated in vacuo and suspended 1:1 DCM: water (2 mL). The organic extracts were separated, then washed with water (2×1 mL), dried over anhydrous $MgSO_{4(s)}$, filtered, and concentrated in vacuo. The residue was dissolved in 1:1 TFA:DCM (2 mL), stirred 30 min at ambient temperature, and concentrated in vacuo to cleanly afford the title compound (37.2 mg, 96% yield). MS (apci) m/z=548.2 (M+H).

Example 49

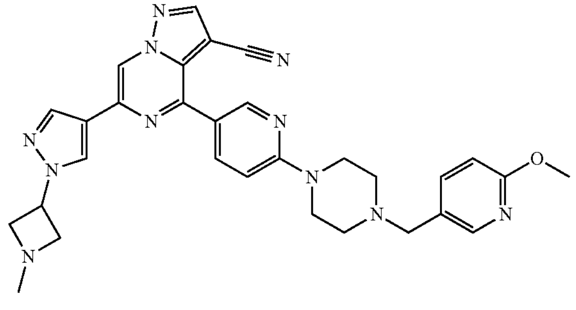 [SMILES: COc1ccc(CN2CCN(c3ccc(-c4nc(-c5cnn(C6CN(C)C6)c5)cn5ncc(C#N)c45)cn3)CC2)cn1]

4-(6-(4-((6-Methoxypyridin-3-yl)methyl)piperazin-1-yl)pyridin-3-yl)-6-(1-(1-methylazetidin-3-yl)-1H-pyrazol-4-yl)pyrazolo[1,5-a]pyrazine-3-carbonitrile A solution of 6-(1-(azetidin-3-yl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile 2,2,2-trifluoroacetate 2,2,2-trifluoroacetate (Example 48; 28 mg, 0.042 mmol) in MeOH (1.0 mL) and formaldehyde (6.9 μL, 0.093 mmol) was stirred for 30 min at ambient temperature, then treated with $NaBH(AcO)_3$ (27 mg, 0.13 mmol). The mixture was stirred for 3 h at ambient temperature before introducing additional $NaBH(AcO)_3$ (28 mg, 0.13 mmol) and formaldehyde (6.9 μL, 0.093 mmol). The reaction was stirred for 18 h at ambient temperature, then concentrated in vacuo and suspended 1:1 DCM: water (2 mL). The organic extracts were separated, then washed with water (2×1 mL), dried over anhydrous $MgSO_{4(s)}$, filtered, and concentrated in vacuo to cleanly afford the title compound (4.8 mg, 20% yield). MS (apci) m/z=562.3 (M+H).

Example 50

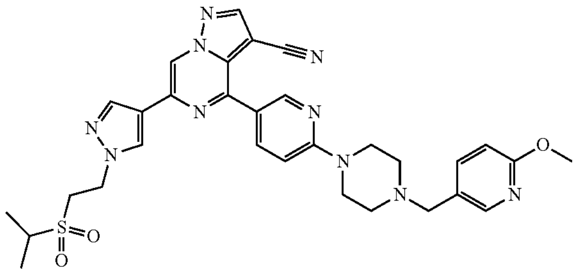 [SMILES: COc1ccc(CN2CCN(c3ccc(-c4nc(-c5cnn(CCS(=O)(=O)C(C)C)c5)cn5ncc(C#N)c45)cn3)CC2)cn1]

6-(1-(2-(Isopropylsulfonyl)ethyl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile A solution of 4-(6-(4-((6-methoxypyridin-3-yl)methyl)piperazin-1-yl)pyridin-3-yl)-6-(1H-pyrazol-4-yl)pyrazolo[1,5-a]pyrazine-3-carbonitrile 2,2,2-trifluoroacetate (Example 47; 29 mg, 0.059 mmol) in DMA (1 mL) was treated sequentially with $Cs_2CO_{3(s)}$ (58 mg, 0.18 mmol) and 2-((2-chloroethyl)sulfonyl)propane (12.1 mg, 0.0707 mmol). The mixture was stirred for 1 h at 80° C., then concentrated in vacuo and suspended 1:1 DCM: water (2 mL). The organic extracts were separated, then washed with water (2×1 mL), dried over anhydrous $MgSO_{4(s)}$, filtered, concentrated in vacuo to cleanly afford the title compound (16.4 mg, 44% yield). MS (apci) m/z=627.2 (M+H).

The compounds in Table D were prepared using a similar method to that described for the synthesis of Example 50, replacing 2-((2-chloroethyl)sulfonyl)propane with the appropriate alkyl halide (except where noted *). Reactions were monitored for completion by LCMS, and reaction durations were adjusted accordingly.

TABLE D

| Ex # | Structure | Chemical Name | MS (apci) m/z |
|---|---|---|---|
| 51 | 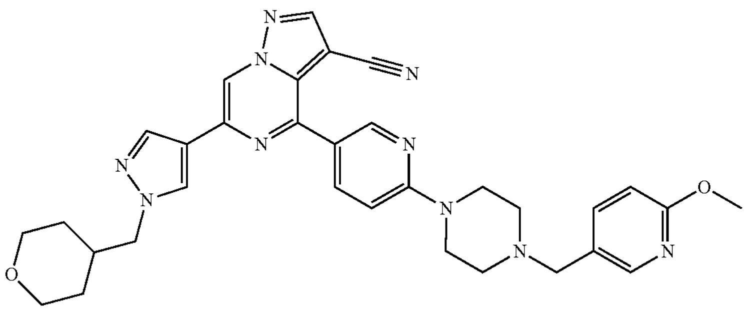 [SMILES: COc1ccc(CN2CCN(c3ccc(-c4nc(-c5cnn(CC6CCOCC6)c5)cn5ncc(C#N)c45)cn3)CC2)cn1] | 4-(6-(4-((6-methoxypyridin-3-yl)methyl)piperazin-1-yl)pyridin-3-yl)-6-(1-((tetrahydro-2H-pyran-4-yl)methyl)-1H-pyrazol-4-yl)pyrazolo[1,5-a]pyrazine-3-carbonitrile | 591.3 (M + H) |
| 52 | 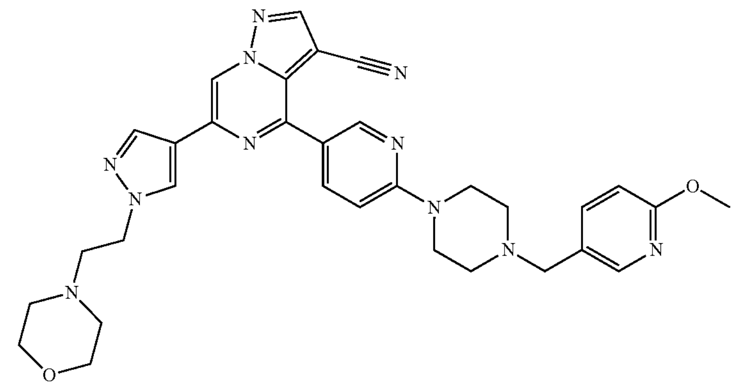 [SMILES: COc1ccc(CN2CCN(c3ccc(-c4nc(-c5cnn(CCN6CCOCC6)c5)cn5ncc(C#N)c45)cn3)CC2)cn1] | 4-(6-(4-((6-methoxypyridin-3-yl)methyl)piperazin-1-yl)pyridin-3-yl)-6-(1-(2-morpholinoethyl)-1H-pyrazol-4-yl)pyrazolo[1,5-a]pyrazine-3-carbonitrile | 606.3 (M + H) |
| 53 | 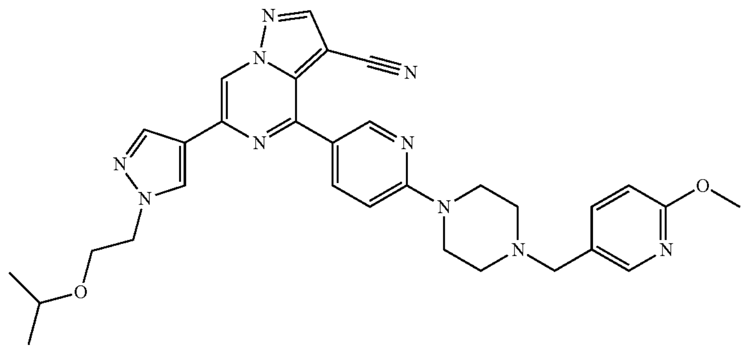 [SMILES: COc1ccc(CN2CCN(c3ccc(-c4nc(-c5cnn(CCOC(C)C)c5)cn5ncc(C#N)c45)cn3)CC2)cn1] | 6-(1-(2-isopropoxyethyl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile | 579.3 (M + H) |

* after 1.5 h reaction, required the introduction of supplemental alkylating agent (1.2 equivalents) and additional stirring (3 d) at ambient temperature to achieve completion Example 54

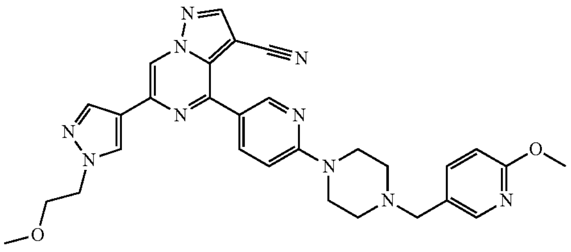

6-(1-(2-Methoxyethyl)-1H-pyrazol-4-yl)-4-(6-(4-((6-methoxypyridin-3-yl)methyl)piperazin-1-yl)pyridin-3-yl)pyrazolo[1,5-a]pyrazine-3-carbonitrile A solution of 4-(6-(4-((6-methoxypyridin-3-yl)methyl)piperazin-1-yl)pyridin-3-yl)-6-(1H-pyrazol-4-yl)pyrazolo

[1,5-a]pyrazine-3-carbonitrile 2,2,2-trifluoroacetate (Example 47; 29 mg, 0.059 mmol) in DMA (1 mL) was treated sequentially with $Cs_2CO_{3(s)}$ (58 mg, 0.18 mmol) and 1-chloro-2-methoxyethane (6.7 mg, 0.071 mmol). The mixture was stirred 1.5 h at 80° C. before introducing additional 1-chloro-2-methoxyethane (6.7 mg, 0.071 mmol). The reaction was stirred 3 d at 80° C., then directly purified by preparative thin layer silica chromatography (using 1:1:8 MeOH/Acetone/DCM as eluent) to cleanly afford the title compound (7.7 mg, 24% yield). MS (apci) m/z=551.3 (M+H).

The compounds in Table E were prepared using a similar method to that described for the synthesis of Example 54, replacing 1-chloro-2-methoxyethane with the appropriate alkyl halide. Reactions were monitored for completion by LCMS, and reaction durations were adjusted accordingly. Title compounds were cleanly isolated following preparative thin layer silica chromatography using an appropriate eluent.

TABLE E

| Ex # | Structure | Chemical Name | MS (apci) m/z |
|---|---|---|---|
| 55 | 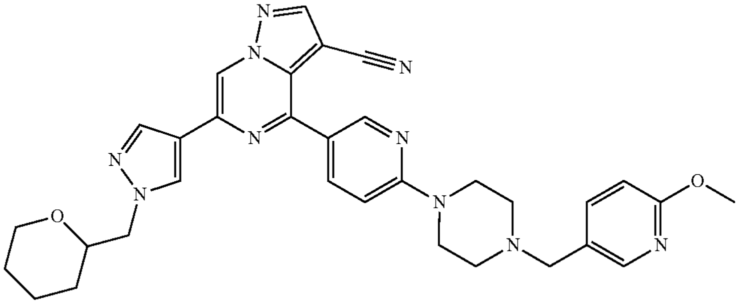 [SMILES: COc1ccc(CN2CCN(c3ccc(-c4nc(-c5cnn(CC6CCCCO6)c5)cn5ncc(C#N)c45)cn3)CC2)cn1] | 4-(6-(4-((6-methoxypyridin-3-yl)methyl)piperazin-1-yl)pyridin-3-yl)-6-(1-((tetrahydro-2H-pyran-2-yl)methyl)-1H-pyrazol-4-yl)pyrazolo[1,5-a]pyrazine-3-carbonitrile | 591.3 (M + H) |
| 56 | 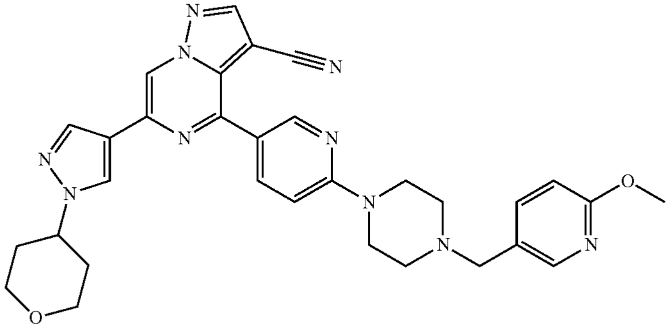 [SMILES: COc1ccc(CN2CCN(c3ccc(-c4nc(-c5cnn(C6CCOCC6)c5)cn5ncc(C#N)c45)cn3)CC2)cn1] | 4-(6-(4-((6-methoxypyridin-3-yl)methyl)piperazin-1-yl)pyridin-3-yl)-6-(1-(tetrahydro-2H-pyran-4-yl)-1H-pyrazol-4-yl)pyrazolo[1,5-a]pyrazine-3-carbonitrile | 577.3 (M + H) |
| 57 | 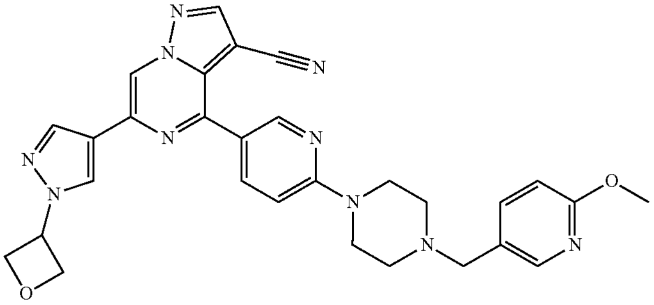 [SMILES: COc1ccc(CN2CCN(c3ccc(-c4nc(-c5cnn(C6COC6)c5)cn5ncc(C#N)c45)cn3)CC2)cn1] | 4-(6-(4-((6-methoxypyridin-3-yl)methyl)piperazin-1-yl)pyridin-3-yl)-6-(1-(oxetan-3-yl)-1H-pyrazol-4-yl)pyrazolo[1,5-a]pyrazine-3-carbonitrile | 549.3 (M + H) |

Example 58

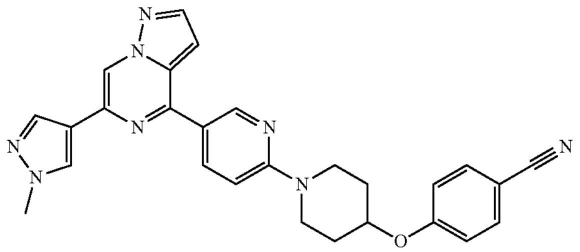 [SMILES: Cn1cc(-c2cn3nccc3c(-c3ccc(N4CCC(Oc5ccc(C#N)cc5)CC4)nc3)n2)cn1]

4-((1-(5-(6-(1-methyl-1H-pyrazol-4-yl)pyrazolo[1,5-a]pyrazin-4-yl)pyridin-2-yl)piperidin-4-yl)oxy)benzonitrile A solution of 4-(6-fluoropyridin-3-yl)-6-(1-methyl-1H-pyrazol-4-yl)pyrazolo[1,5-a]pyrazine (Intermediate P5; 14.2 mg, 0.0482 mmol) in DMA (0.1 mL) was treated with TEA (6.72 μL, 0.0482 mmol) and 4-(piperidin-4-yloxy)benzonitrile (20 mg, 0.0989 mmol) then stirred overnight at 110° C. After cooling to ambient temperature, the reaction mixture was diluted with water (10 mL), and extracted with DCM (4×10 mL) in a PS Frit. The combined organic extracts were concentrated in vacuo, and purified by C18 reverse phase chromatography (using 0-60% ACN/water as the gradient eluent) to afford the title compound (3.0 mg, 13.1% yield). MS (apci) m/z=477.2 (M+H).

Example 59

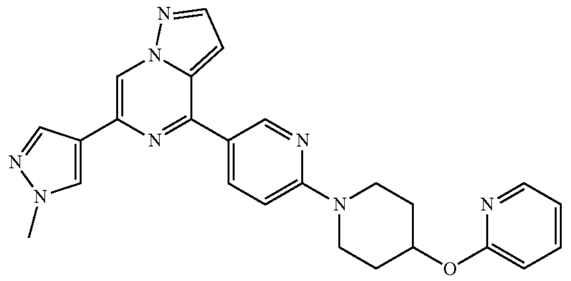 [SMILES: Cn1cc(-c2cn3nccc3c(-c3ccc(N4CCC(Oc5ccccn5)CC4)nc3)n2)cn1]

6-(1-methyl-1H-pyrazol-4-yl)-4-(6-(4-(pyridin-2-yloxy)piperidin-1-yl)pyridin-3-yl)pyrazolo[1,5-a]pyrazine A solution of 4-(6-fluoropyridin-3-yl)-6-(1-methyl-1H-pyrazol-4-yl)pyrazolo[1,5-a]pyrazine (Intermediate P5; 31.5 mg, 0.107 mmol) in DMA (0.1 mL) was treated with TEA (74.5 μL, 0.534 mmol) and 2-(piperidin-4-yloxy)pyridine (20 mg, 0.112 mmol), then stirred overnight at 110° C. After cooling to ambient temperature, the reaction mixture was diluted with water (10 mL), and extracted with DCM (4×10 mL) in a PS Frit. The combined organic extracts were concentrated in vacuo, and purified by C18 reverse phase chromatography (using 0-60% ACN/water as the gradient eluent) to afford the title compound (8.4 mg, 17% yield). MS (apci) m/z=453.3 (M+H).

Example 60

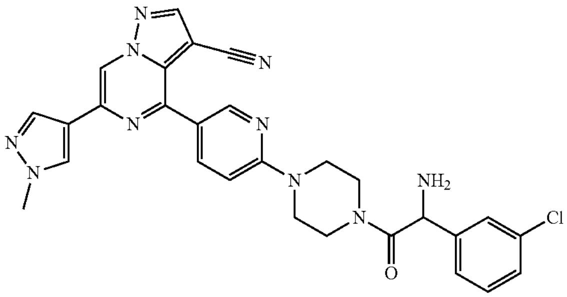 [SMILES: Cn1cc(-c2cn3ncc(C#N)c3c(-c3ccc(N4CCN(C(=O)C(N)c5cccc(Cl)c5)CC4)nc3)n2)cn1]

4-(6-(4-(2-amino-2-(3-chlorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (1-(3-chlorophenyl)-2-(4-(5-(3-cyano-6-(1-methyl-1H-pyrazol-4-yl)pyrazolo[1,5-a]pyrazin-4-yl)pyridin-2-yl)piperazin-1-yl)-2-oxoethyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile (Example 8; 400 mg, 0.802 mmol), N-Boc-(3'-chlorophenyl)glycine (229 mg, 0.802 mmol) and HATU (915 mg, 2.41 mmol) in anhydrous DCM (0.4 mL) was treated sequentially with DIEA (140 μL, 0.802 mmol) and anhydrous DMF (250 μL). The resulting mixture was stirred for 1 h at ambient temperature and then concentrated in vacuo. The crude material was purified by reverse phase chromatography (5-95% ACN in water with 0.1% TFA), and fractions containing the desired product were combined and extracted with 4:1 DCM:iPrOH. The organic extracts were concentrated in vacuo to afford the title compound in sufficient purity for subsequent use (524 mg, quantitative yield). MS (apci) m/z=653.3 (M+H).

Step 2: Preparation of 4-(6-(4-(2-amino-2-(3-chlorophenyl)acetyl)piperazin-1-yl)pyridin-3-yl)-6-(1-methyl-1H-pyrazol-4-yl)pyrazolo[1,5-a]pyrazine-3-carbonitrile A solution of tert-butyl (1-(3-chlorophenyl)-2-(4-(5-(3-cyano-6-(1-methyl-1H-pyrazol-4-yl)pyrazolo[1,5-a]pyrazin-4-yl)pyridin-2-yl)piperazin-1-yl)-2-oxoethyl)carbamate (Step 1; 1.0 g, 1.5 mmol) in DCM (15 mL) was treated with TFA (1.2 mL, 15 mmol). The reaction mixture was stirred for a period of 5 h at ambient temperature, introducing additional TFA (5 equivalents) at the 1 h and 4 h time intervals. The resulting mixture then was stirred overnight at ambient temperature, and concentrated in vacuo. The residue was purified by C18 reverse phase chromatography (using 5-95% water:ACN as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford the semi-pure title compound. The semi-pure material was triturated with DCM/Hexanes (1:10) to afford the title compound (435 mg, 51% yield). MS (apci) m/z=554.2 (M+H).

Example 61

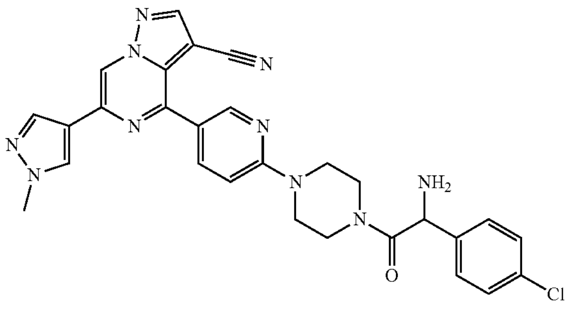 [SMILES: Cn1cc(-c2cn3ncc(C#N)c3c(-c3ccc(N4CCN(C(=O)C(N)c5ccc(Cl)cc5)CC4)nc3)n2)cn1]

4-(6-(4-(2-amino-2-(4-chlorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (1-(4-chlorophenyl)-2-(4-(5-(3-cyano-6-(1-methyl-1H-pyrazol-4-yl) pyrazolo[1,5-a]pyrazin-4-yl)pyridin-2-yl)piperazin-1-yl)-2-oxoethyl)carbamate A suspension of 6-(1-methyl-1H-pyrazol-4-yl)-4-(6-(piperazin-1-yl)pyridin-3-yl)pyrazolo[1,5-a]pyrazine-3-carbonitrile 2,2,2-trifluoroacetate (Example 8; 60 mg, 0.12 mmol), (S)-2-((tert-butoxycarbonyl)amino)-2-(4-chlorophenyl)acetic acid (34 mg, 0.12 mmol) and HATU (137 mg, 0.36 mmol) in anhydrous DCM (0.6 mL) was treated with 4-methylmorpholine (40 μL, 0.36 mmol). The reaction mixture was stirred overnight at ambient temperature, and then filtered. The resultant filtrate was subjected to C18 reverse phase chromatography (using 5-95% water:ACN as the gradient eluent to cleanly afford the title compound (72 mg, 92% yield). MS (apci) m/z=653.3 (M+H).

Step 2: Preparation of 4-(6-(4-(2-amino-2-(4-chlorophenyl)acetyl)piperazin-1-yl)pyridin-3-yl)-6-(1-methyl-1H-pyrazol-4-yl)pyrazolo[1,5-a]pyrazine-3-carbonitrile A solution of tert-butyl (1-(4-chlorophenyl)-2-(4-(5-(3-cyano-6-(1-methyl-1H-pyrazol-4-yl)pyrazolo[1,5-a] pyrazin-4-yl)pyridin-2-yl)piperazin-1-yl)-2-oxoethyl)carbamate (Step 1; 72 mg, 0.11 mmol) in DCM (1.1 mL) was treated with TFA (85 μL, 1.1 mmol). The resulting mixture was stirred for 3 h at ambient temperature, and subsequently concentrated in vacuo. The residue was purified by C18 reverse phase chromatography (using 5-95% water:ACN as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford semi-pure title compound. The semi-pure material was triturated with DCM/Hexanes (1:10) to afford the title compound (37 mg, 61% yield). MS (apci) m/z=553.2 (M+H).

Example 62

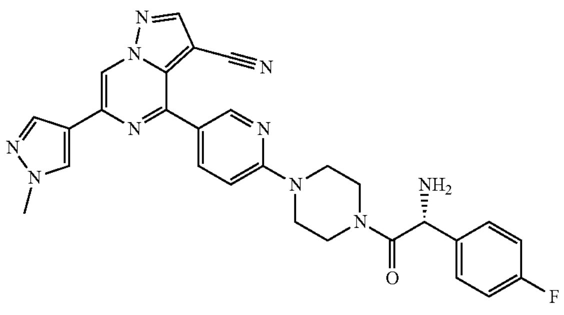 [SMILES: Cn1cc(-c2cn3ncc(C#N)c3c(-c3ccc(N4CCN(C(=O)[C@H](N)c5ccc(F)cc5)CC4)nc3)n2)cn1]

(R)-4-(6-(4-(2-amino-2-(4-fluorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (R)-(2-(4-(5-(3-cyano-6-(1-methyl-1H-pyrazol-4-yl)pyrazolo[1,5-a] pyrazin-4-yl)pyridin-2-yl)piperazin-1-yl)-1-(4-fluorophenyl)-2-oxoethyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol), (R)-2-((tert-butoxycarbonyl)amino)-2-(4-fluorophenyl)acetic acid (29 mg, 0.11 mmol) and HATU (50 mg, 0.13 mmol) in anhydrous DCM (7.0 μL) was treated with DIEA (19 μL, 0.11 mmol). The reaction mixture was stirred overnight at ambient temperature, and then was concentrated in vacuo. The residue was purified by silica chromatography (using 0-10% $CHCl_3$/MeOH with 0.1% $NH_4OH$ as the gradient eluent) to afford the title compound which was used directly in Step 2 (75 mg, quantitative yield). MS (apci) m/z=537.2 (M+H).

Step 2: Preparation of (R)-4-(6-(4-(2-amino-2-(4-fluorophenyl)acetyl)piperazin-1-yl)pyridin-3-yl)-6-(1-methyl-1H-pyrazol-4-yl)pyrazolo[1,5-a]pyrazine-3-carbonitrile A solution of tert-butyl (R)-(2-(4-(5-(3-cyano-6-(1-methyl-1H-pyrazol-4-yl)pyrazolo[1,5-a]pyrazin-4-yl)pyridin-2-yl)piperazin-1-yl)-1-(4-fluorophenyl)-2-oxoethyl)carbamate (Step 1; 75 mg, 0.12 mmol) in DCM (236 μL) was treated with TFA (91 μL, 1.2 mmol). The resulting mixture was stirred 30 min at ambient temperature before introducing additional TFA (10 equivalents). The reaction mixture was stirred for 1 h at ambient temperature, and then concentrated in vacuo. The residue was purified by silica chromatography (using 0-10% $CHCl_3$/MeOH with 0.1% $NH_4OH$ as the gradient eluent) to afford the title compound (37 mg, 59% yield). MS (apci) m/z=537.2 (M+H).

Example 63

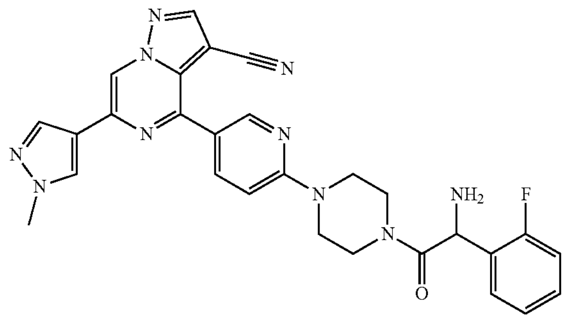 [SMILES: Cn1cc(-c2cn3ncc(C#N)c3c(-c3ccc(N4CCN(C(=O)C(N)c5ccccc5F)CC4)nc3)n2)cn1]

4-(6-(4-(2-amino-2-(2-fluorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (2-(4-(5-(3-cyano-6-(1-methyl-1H-pyrazol-4-yl)pyrazolo[1,5-a]pyrazin-4-yl)pyridin-2-yl)piperazin-1-yl)-1-(2-fluorophenyl)-2-oxoethyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile (Example 8; 100 mg, 0.259 mmol), 2-((tert-butoxycarbonyl)amino)-2-(2-fluorophenyl)acetic acid (Intermediate R2; 69.9 mg, 0.259 mmol) and HATU (296 mg, 0.778 mmol) in anhydrous DCM (1.3 mL) was treated with DIEA (181 μL, 1.04 mmol). The resulting mixture was stirred for 1 h at ambient temperature. The resulting suspension was filtered, and the filtrate was purified by C18 reverse phase chromatography (using 5-95% water:ACN with 0.1% TFA as the gradient eluent). Fractions containing the desired product were combined, diluted with 4:1 DCM:iPrOH and washed with brine. The organic extracts were dried over anhydrous $Na_2SO_{4(s)}$, filtered, and concentrated in vacuo to afford the title compound in sufficient purity for subsequent use (165 mg, quantitative yield). MS (apci) m/z=637.3 (M+H).

Step 2: Preparation of 4-(6-(4-(2-amino-2-(2-fluorophenyl)acetyl)piperazin-1-yl)pyridin-3-yl)-6-(1-methyl-1H-pyrazol-4-yl)pyrazolo[1,5-a]pyrazine-3-carbonitrile tert-Butyl (2-(4-(5-(3-cyano-6-(1-methyl-1H-pyrazol-4-yl)pyrazolo[1,5-a]pyrazin-4-yl)pyridin-2-yl)piperazin-1-yl)-1-(2-fluorophenyl)-2-oxoethyl)carbamate (Step 1; 165 mg, 0.259 mmol) was dissolved in 1:1 TFA:DCM (2.6 mL). The resulting mixture was stirred overnight at ambient temperature and subsequently concentrated in vacuo. The residue was purified by C18 reverse phase chromatography (using 5-95% water:ACN with 0.1% TFA as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford semi-pure title compound. The semi-pure material was triturated with DCM/Hexanes (1:10) to afford the title compound (46.5 mg, 33.4% yield). MS (apci) m/z=537.2 (M+H).

Example 64

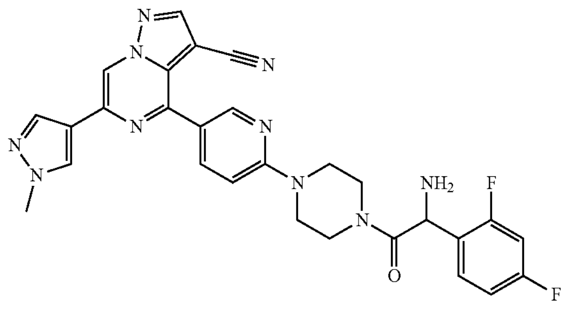 [SMILES: Cn1cc(-c2cn3ncc(C#N)c3c(-c3ccc(N4CCN(C(=O)C(N)c5ccc(F)cc5F)CC4)nc3)n2)cn1]

4-(6-(4-(2-amino-2-(2,4-difluorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (2-(4-(5-(3-cyano-6-(1-methyl-1H-pyrazol-4-yl)pyrazolo[1,5-a]pyrazin-4-yl)pyridin-2-yl)piperazin-1-yl)-1-(2,4-difluorophenyl)-2-oxoethyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile (Example 8; 100 mg, 0.259 mmol), 2-((tert-butoxycarbonyl)amino)-2-(2,4-difluorophenyl)acetic acid (Intermediate R3; 74.5 mg, 0.259 mmol) and HATU (296 mg, 0.778 mmol) in anhydrous DCM (1.3 mL) was treated with DIEA (181 μL, 1.04 mmol). The resulting mixture was stirred for 1 h at ambient temperature, then concentrated in vacuo to afford the title compound in sufficient purity for subsequent use (170 mg, quantitative yield). MS (apci) m/z=655.3 (M+H).

Step 2: Preparation of 4-(6-(4-(2-amino-2-(2,4-difluorophenyl)acetyl)piperazin-1-yl)pyridin-3-yl)-6-(1-methyl-1H-pyrazol-4-yl)pyrazolo[1,5-a]pyrazine-3-carbonitrile Crude tert-butyl (2-(4-(5-(3-cyano-6-(1-methyl-1H-pyrazol-4-yl)pyrazolo[1,5-a]pyrazin-4-yl)pyridin-2-yl)piperazin-1-yl)-1-(2,4-difluorophenyl)-2-oxoethyl)carbamate (Step 1; 170 mg, 0.260 mmol) was dissolved in 1:1 TFA:DCM (2.6 mL). The resulting mixture was stirred overnight at ambient temperature and subsequently concentrated in vacuo. The residue was purified by C18 reverse phase chromatography (using 5-95% ACN in water with 0.1% TFA as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford semi-pure title compound. The semi-pure material was triturated with DCM/Hexanes (1:10) to afford the title compound (89 mg, 62% yield). MS (apci) m/z=555.2 (M+H).

Example 65

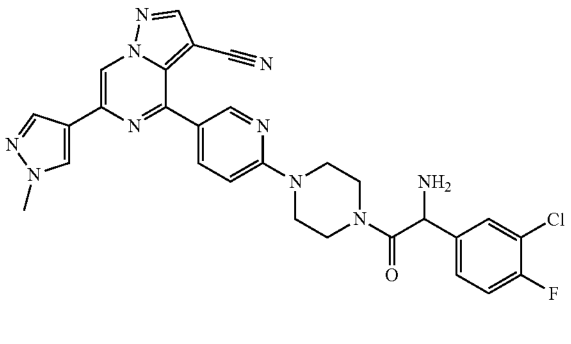 [SMILES: Cn1cc(-c2cn3ncc(C#N)c3c(-c3ccc(N4CCN(C(=O)C(N)c5ccc(F)c(Cl)c5)CC4)nc3)n2)cn1]

4-(6-(4-(2-amino-2-(3-chloro-4-fluorophenyl)acetyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (1-(3-chloro-4-fluorophenyl)-2-(4-(5-(3-cyano-6-(1-methyl-1H-pyrazol-4-yl)pyrazolo[1,5-a]pyrazin-4-yl)pyridin-2-yl)piperazin-1-yl)-2-oxoethyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 200 mg, 0.436 mmol), 2-((tert-butoxycarbonyl)amino)-2-(3-chloro-4-fluorophenyl)acetic acid (Intermediate R4; 133 mg, 0.436 mmol) and HATU (498 mg, 1.31 mmol) in anhydrous DCM (2.2 mL) was treated with DIEA (76.2 μL, 0.436 mmol). The reaction mixture was stirred overnight at ambient temperature. The resulting suspension was filtered, and the filtrate was concentrated in vacuo to provide the desired compound (293 mg, quantitative yield). MS (apci) m/z=571.2 (M+H).

Step 2: Preparation of 4-(6-(4-(2-amino-2-(3-chloro-4-fluorophenyl acetyl)piperazin-1-yl)pyridin-3-yl)-6-(1-methyl-1H-pyrazol-4-yl)pyrazolo[1,5-a]pyrazine-3-carbonitrile A solution of tert-butyl (1-(3-chloro-4-fluorophenyl)-2-(4-(5-(3-cyano-6-(1-methyl-1H-pyrazol-4-yl)pyrazolo[1,5-a]pyrazin-4-yl)pyridin-2-yl)piperazin-1-yl)-2-oxoethyl)carbamate (Step 1; 293 mg, 0.437 mmol) in DCM (4.4 mL) was treated with TFA (336 μL, 4.37 mmol). The resulting mixture was stirred for 1 h at ambient temperature, and then before additional TFA (10 equivalents) was added. The reaction mixture was stirred for an additional 2 h at ambient temperature, introducing additional TFA (2 mL) after the first additional 1 h of stirring at ambient temperature. The reaction mixture was concentrated in vacuo. The residue was purified by C18 reverse phase chromatography (using 5-95% water:ACN with 0.1% TFA as the gradient eluent). The solid isolated was re-purified by silica chromatography (using 0-10% DCM/MeOH with 0.1% $NH_4OH$ as the gradient eluent) and Fractions containing the desired product were combined and concentrated in vacuo. The residue was triturated with DCM/MeOH (1:10) and the solvents were removed in vacuo to afford the title compound (152 mg, 61% yield). MS (apci) m/z=571.2 (M+H).

Example 66

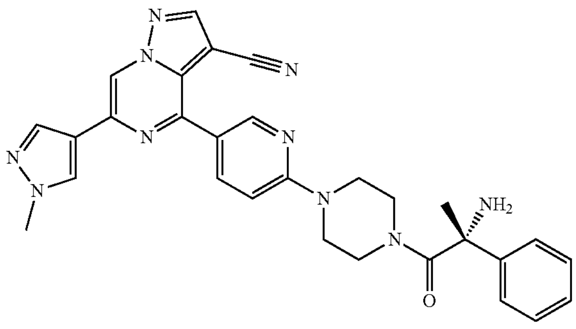 [SMILES: Cn1cc(-c2cn3ncc(C#N)c3c(-c3ccc(N4CCN(C(=O)[C@](C)(N)c5ccccc5)CC4)nc3)n2)cn1]

(R)-4-(6-(4-(2-amino-2-phenylpropanoyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (R)-(1-(4-(5-(3-cyano-6-(1-methyl-1H-pyrazol-4-yl)pyrazolo[1,5-a]pyrazin-4-yl)pyridin-2-yl)piperazin-1-yl)-1-oxo-2-phenylpropan-2-yl)carbamate A mixture of 6-(1-methyl-1H-pyrazol-4-yl)-4-(6-(piperazin-1-yl)pyridin-3-yl)pyrazolo[1,5-a]pyrazine-3-carbonitrile (Example 8; 60 mg, 0.16 mmol), (R)-2-((tert-butoxycarbonyl)amino)-2-phenylpropanoic acid (41 mg, 0.16 mmol) and HATU (71 mg, 0.19 mmol) in anhydrous DCM (1.6 mL) was treated with DIEA (82 μL, 0.47 mmol). The reaction mixture was stirred overnight at ambient temperature. The resulting suspension was concentrated in vacuo to afford the title compound in sufficient purity for subsequent use (98 mg, 99% yield). MS (apci) m/z=633.3 (M+H).

Step 2: Preparation of (R)-4-(6-(4-(2-amino-2-phenylpropanoyl)piperazin-1-yl)pyridin-3-yl)-6-(1-methyl-1H-pyrazol-4-yl)pyrazolo[1,5-a]pyrazine-3-carbonitrile A solution of tert-butyl (R)-(1-(4-(5-(3-cyano-6-(1-methyl-1H-pyrazol-4-yl)pyrazolo[1,5-a]pyrazin-4-yl)pyridin-2-yl)piperazin-1-yl)-1-oxo-2-phenylpropan-2-yl)carbamate (Step 1; 98 mg, 0.15 mmol) in 1:1 TFA:DCM (155 μL) was stirred overnight at ambient temperature, and then concentrated in vacuo. The residue was purified by C18 reverse phase chromatography (using 5-95% water:ACN with 0.1% TFA as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford semi-pure title compound (79 mg, 96% yield) which was carried on without further purification. MS (apci) m/z=533.2 (M+H).

Example 67

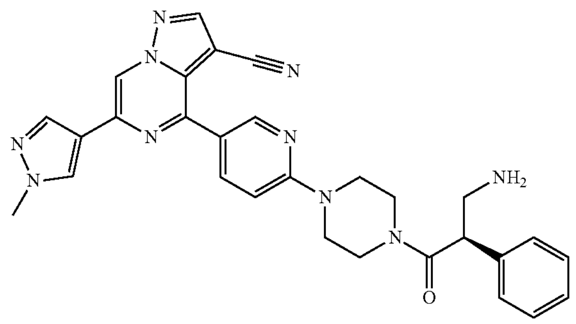 [SMILES: Cn1cc(-c2cn3ncc(C#N)c3c(-c3ccc(N4CCN(C(=O)[C@@H](CN)c5ccccc5)CC4)nc3)n2)cn1]

(R)-4-(6-(4-(3-amino-2-phenylpropanoyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (R)-(3-(4-(5-(3-cyano-6-(1-methyl-1H-pyrazol-4-yl)pyrazolo[1,5-a]pyrazin-4-yl)pyridin-2-yl)piperazin-1-yl)-3-oxo-2-phenylpropyl)carbamate A suspension of 6-(1-methyl-1H-pyrazol-4-yl)-4-(6-(piperazin-1-yl)pyridin-3-yl)pyrazolo[1,5-a]pyrazine-3-carbonitrile (Example 8; 40 mg, 0.10 mmol), (R)-3-(Boc-amino)-2-phenylpropionic acid (28 mg, 0.10 mmol) and HATU (118 mg, 0.31 mmol) in anhydrous DCM (519 μL) was treated with DIEA (73 μL, 0.42 mmol). The reaction mixture was stirred overnight at ambient temperature. The resulting suspension was filtered, and the filtrate was concentrated in vacuo. The residue was purified by silica chromatography (using 0-10% DCM/MeOH with 0.1% $NH_4OH$ as the gradient eluent) to afford the title compound in sufficient purity for subsequent use (78 mg, quantitative yield). MS (apci) m/z=633.3 (M+H).

Step 2: Preparation of (R)-4-(6-(4-(3-amino-2-phenylpropanoyl)piperazin-1-yl)pyridin-3-yl)-6-(1-methyl-1H-pyrazol-4-yl)pyrazolo[1,5-a]pyrazine-3-carbonitrile A solution of tert-butyl (R)-(3-(4-(5-(3-cyano-6-(1-methyl-1H-pyrazol-4-yl)pyrazolo[1,5-a]pyrazin-4-yl)pyridin-2-yl)piperazin-1-yl)-3-oxo-2-phenylpropyl)carbamate (Step 1; 78 mg, 0.12 mmol) in DCM (7.0 mL) was treated with TFA (95 μL, 1.2 mmol) and stirred overnight at ambient temperature. The resulting suspension was concentrated in vacuo, and the residue was purified by silica chromatography (using 0-10% DCM/MeOH as the gradient eluent). Fractions containing the desired product were combined, concentrated in vacuo and triturated with DCM/Hexanes to cleanly afford the title compound (54 mg, 82% yield). MS (apci) m/z=533.3 (M+H).

Example 68

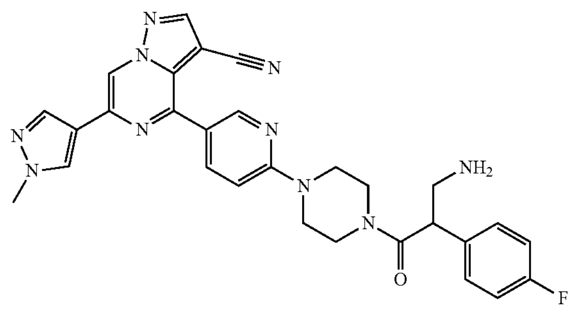 [SMILES: Cn1cc(-c2cn3ncc(C#N)c3c(-c3ccc(N4CCN(C(=O)C(CN)c5ccc(F)cc5)CC4)nc3)n2)cn1]

4-(6-(4-(3-amino-2-(4-fluorophenyl)propanoyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (3-(4-(5-(3-cyano-6-(1-methyl-1H-pyrazol-4-yl)pyrazolo[1,5-a]pyrazin-4-yl)pyridin-2-yl)piperazin-1-yl)-2-(4-fluorophenyl)-3-oxopropyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile (Example 8; 100 mg, 0.259 mmol), 3-{[(tert-butoxy)carbonyl]amino}-2-(4-fluorophenyl)propanoic acid (73.5 mg, 0.259 mmol) and HATU (296 mg, 0.778 mmol) in anhydrous DCM (1.3 mL) was treated with DIEA (181 μL, 1.04 mmol). The reaction mixture was stirred for 1 h at ambient temperature. The resulting suspension was filtered, and the filtrate was concentrated in vacuo to afford the title compound in sufficient purity for subsequent use (169 mg, quantitative yield). MS (apci) m/z=651.3 (M+H).

Step 2: Preparation of 4-(6-(4-(3-amino-2-(4-fluorophenyl)propanoyl)piperazin-1-yl)pyridin-3-yl)-6-(1-methyl-1H-pyrazol-4-yl)pyrazolo[1,5-a]pyrazine-3-carbonitrile A solution of tert-butyl (3-(4-(5-(3-cyano-6-(1-methyl-1H-pyrazol-4-yl)pyrazolo[1,5-a]pyrazin-4-yl)pyridin-2-yl)piperazin-1-yl)-2-(4-fluorophenyl)-3-oxopropyl)carbamate (Step 1; 169 mg, 0.260 mmol) in DCM (2.6 mL) was treated with TFA (0.2 mL, 2.60 mmol). The resulting mixture was stirred for 1 h at ambient temperature and then concentrated in vacuo. The residue was purified by C18 reverse phase chromatography (using 5-95% water:ACN with 0.1% TFA as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to afford semi-pure title compound. The semi-pure material was triturated with DCM/Hexanes (1:10) to afford the title compound (143 mg, quantitative yield). MS (apci) m/z=551.3 (M+H).

Example 69

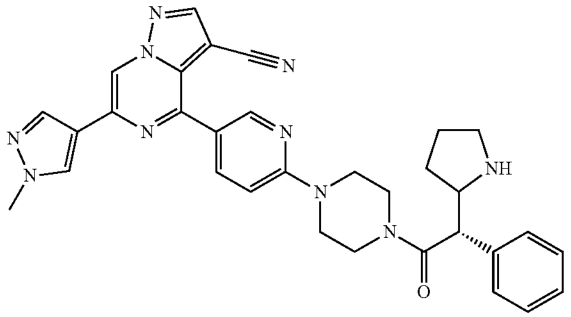 [SMILES: Cn1cc(-c2cn3ncc(C#N)c3c(-c3ccc(N4CCN(C(=O)[C@@H](c5ccccc5)C5CCCN5)CC4)nc3)n2)cn1]

6-(1-methyl-1H-pyrazol-4-yl)-4-(6-(4-((2S)-2-phenyl-2-(pyrrolidin-2-yl)acetyl)piperazin-1-yl)pyridin-3-yl)pyrazolo[1,5-a]pyrazine-3-carbonitrile Step 1: Preparation of tert-butyl 2-((S)-2-(4-(5-(3-cyano-6-(1-methyl-1H-pyrazol-4-yl)pyrazolo[1,5-a]pyrazin-4-yl)pyridin-2-yl)piperazin-1-yl)-2-oxo-1-phenylethyl)pyrrolidine-1-carboxylate A suspension of 6-(1-methyl-1H-pyrazol-4-yl)-4-(6-(piperazin-1-yl)pyridin-3-yl)pyrazolo[1,5-a]pyrazine-3-carbonitrile (Example 8; 275.0 mg, 0.7135 mmol) in anhydrous DCM (7.0 mL) was treated with (2S)-2-(1-(tert-butoxycarbonyl)pyrrolidin-2-yl)-2-phenylacetic acid (Intermediate R5; 239.7 mg, 0.7848 mmol), HATU (298.4 mg, 0.7848 mmol) and DIEA (497 µL, 2.85 mmol). The reaction mixture was stirred 16 h at ambient temperature. The resulting solution was concentrated in vacuo, and the residue was purified by silica chromatography (using 5-95% DCM:Acetone as the gradient eluent) to afford the title compound which was used directly in Step 2. MS (apci) m/z=573.3 (M+H).

Step 2: Preparation of 6-(1-methyl-1H-pyrazol-4-yl)-4-(6-(4-((2S)-2-phenyl-2-(pyrrolidin-2-yl)acetyl)piperazin-1-yl)pyridin-3-yl)pyrazolo[1,5-a]pyrazine-3-carbonitrile A solution of tert-butyl 2-((S)-2-(4-(5-(3-cyano-6-(1-methyl-1H-pyrazol-4-yl)pyrazolo[1,5-a]pyrazin-4-yl)pyridin-2-yl)piperazin-1-yl)-2-oxo-1-phenylethyl)pyrrolidine-1-carboxylate (Step 1; 0.713 mmol) in 1:1 TFA:DCM (7.0 mL) was stirred 30 min at ambient temperature, and subsequently concentrated in vacuo. The residue was purified by C18 reverse phase chromatography (using 5-95% water:ACN with 0.1% TFA as the gradient eluent). Fractions containing the desired product were combined, diluted with 4:1 DCM:iPrOH, and sequentially washed with saturated $NaHCO_{3(aq)}$ and brine. The combined organic extracts were dried over anhydrous $Na_2SO_{4(s)}$, filtered, and concentrated in vacuo to cleanly afford the title compound as about 97% of a single enantiomer (250.0 mg, 61% yield). MS (apci) m/z=573.3 (M+H).

Example 70

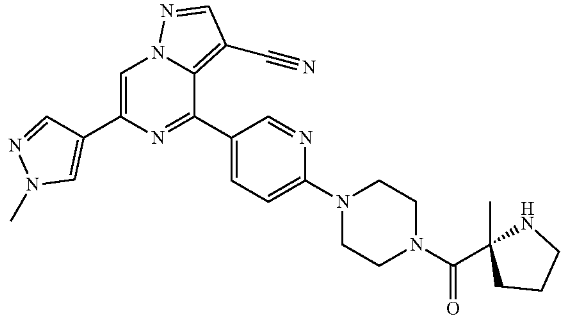 [SMILES: Cn1cc(-c2cn3ncc(C#N)c3c(-c3ccc(N4CCN(C(=O)[C@@]5(C)CCCN5)CC4)nc3)n2)cn1]

(R)-6-(1-methyl-1H-pyrazol-4-yl)-4-(6-(4-(2-methylpyrrolidine-2-carbonyl)piperazin-1-yl)pyridin-3-yl)pyrazolo[1,5-a]pyrazine-3-carbonitrile Step 1: Preparation of tert-butyl (R)-2-(4-(5-(3-cyano-6-(1-methyl-1H-pyrazol-4-yl)pyrazolo[1,5-a]pyrazin-4-yl)pyridin-2-yl)piperazine-1-carbonyl)-2-methylpyrrolidine-1-carboxylate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol), R-1-(tert-butoxycarbonyl)-2-methylpyrrolidine-2-carboxylic acid (25 mg, 0.11 mmol) and HATU (124 mg, 0.33 mmol) in anhydrous DCM (545 µL) was treated with DIEA (19 µL, 0.11 mmol). The resulting mixture was stirred overnight at ambient temperature. The reaction mixture was filtered, and the filtrate was concentrated in vacuo. The residue was purified by silica chromatography (using 0-20% DCM:MeOH with 0-2% $NH_4OH$ as the gradient eluent). Fractions containing the desired product were combined, concentrated and triturated with DCM/Hexanes (1:10) to afford the title compound (65 mg, quantitative yield) which was used directly in Step 2. MS (apci) m/z=597.3 (M+H).

Step 2: Preparation of (R)-6-(1-methyl-1H-pyrazol-4-yl)-4-(6-(4-(2-methylpyrrolidine-2-carbonyl)piperazin-1-yl)pyridin-3-yl)pyrazolo[1,5-a]pyrazine-3-carbonitrile A solution of tert-butyl (R)-2-(4-(5-(3-cyano-6-(1-methyl-1H-pyrazol-4-yl)pyrazolo[1,5-a]pyrazin-4-yl)pyridin-2-yl)piperazine-1-carbonyl)-2-methylpyrrolidine-1-carboxylate (Step 1; 65 mg, 0.11 mmol) in 1:1 TFA:DCM (1.2 mL) was stirred 2 h at ambient temperature. The reaction mixture was quenched with saturated $NaHCO_{3(aq)}$ and then washed with water and brine. The organic extracts were dried over anhydrous $Na_2SO_{4(s)}$, filtered, and concentrated in vacuo. The residue was purified by C18 reverse phase chromatography (using 5-95% water:ACN with 0.1% TFA as the gradient eluent). Fractions containing the desired product were combined and re-purified using silica chromatography (0-20% DCM:MeOH with 0-2% $NH_4OH$ as the gradient eluent). The fractions containing the desired compound were combined and concentrated in vacuo. The residue was triturated with DCM/Hexanes 1:10) and dried in vacuo to cleanly afford the title compound (15 mg, 28% yield). MS (apci) m/z=497.3 (M+H).

Example 71

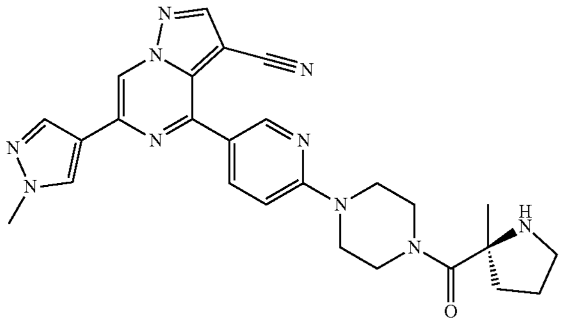 [SMILES: Cn1cc(-c2cn3ncc(C#N)c3c(-c3ccc(N4CCN(C(=O)[C@]5(C)CCCN5)CC4)nc3)n2)cn1]

(S)-6-(1-methyl-1H-pyrazol-4-yl)-4-(6-(4-(2-methylpyrrolidine-2-carbonyl)piperazin-1-yl)pyridin-3-yl)pyrazolo[1,5-a]pyrazine-3-carbonitrile Step 1: Preparation of tert-butyl (S)-2-(4-(5-(3-cyano-6-(1-methyl-1H-pyrazol-4-yl)pyrazolo[1,5-a]pyrazin-4-yl)pyridin-2-yl)piperazine-1-carbonyl)-2-methylpyrrolidine-1-carboxylate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol), (S)-1-(tert-butoxycarbonyl)-2-methylpyrrolidine-2-carboxylic acid (25 mg, 0.11 mmol) and HATU (124 mg, 0.33 mmol) in anhydrous DCM (545 μL) was treated with DIEA (76 μL, 0.44 mmol). After stirring the reaction mixture for 3 h at ambient temperature, DMF (1 mL) and additional DIEA (76 μL, 0.44 mmol) were added, and the resulting mixture was stirred for 24 h at ambient temperature. The reaction mixture was filtered, and the filtrate was concentrated in vacuo. The residue was purified by silica chromatography (using 0-20% DCM:MeOH with 0-1% $NH_4OH$ as the gradient eluent). Fractions containing the desired product were combined, concentrated, triturated with DCM/Hexanes (1:10) and concentrated in vacuo to afford the title compound (65 mg, quantitative yield) which was used directly in Step 2. MS (apci) m/z=597.3 (M+H).

Step 2: Preparation of (S)-6-(1-methyl-1H-pyrazol-4-yl)-4-(6-(4-(2-methylpyrrolidine-2-carbonyl)piperazin-1-yl)pyridin-3-yl)pyrazolo[1,5-a]pyrazine-3-carbonitrile A solution of tert-butyl (S)-2-(4-(5-(3-cyano-6-(1-methyl-1H-pyrazol-4-yl)pyrazolo[1,5-a]pyrazin-4-yl)pyridin-2-yl)piperazine-1-carbonyl)-2-methylpyrrolidine-1-carboxylate (Step 1; 65 mg, 0.11 mmol) in DCM (1.1 mL) was treated with TFA (84 μL, 1.1 mmol), then stirred overnight at ambient temperature. The reaction mixture was concentrated in vacuo, and the residue was purified by C18 reverse phase chromatography (using 5-95% water:ACN with 0.1% TFA as the gradient eluent). Fractions containing the desired product were combined, diluted with 4:1 DCM:iPrOH and washed sequentially with saturated $NaHCO_{3(aq)}$ and brine. The organic extracts were dried over anhydrous $Na_2SO_{4(s)}$, filtered, and concentrated in vacuo. The residue was triturated with DCM/Hexanes (1:10) and dried in vacuo to cleanly afford the title compound (17 mg, 31% yield). MS (apci) m/z=497.3 (M+H).

Example 72

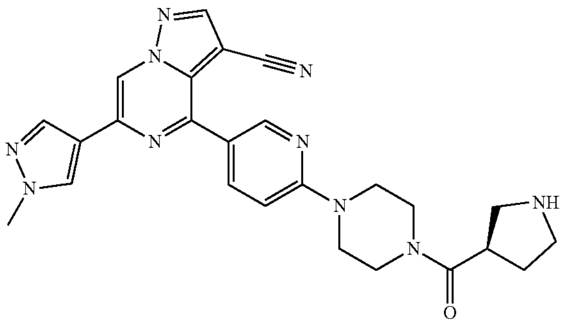 [SMILES: Cn1cc(-c2cn3ncc(C#N)c3c(-c3ccc(N4CCN(C(=O)[C@@H]5CCNC5)CC4)nc3)n2)cn1]

(R)-6-(1-methyl-1H-pyrazol-4-yl)-4-(6-(4-(pyrrolidine-3-carbonyl)piperazin-1-yl)pyridin-3-yl)pyrazolo[1,5-a]pyrazine-3-carbonitrile Step 1: Preparation of tert-butyl (R)-3-(4-(5-(3-cyano-6-(1-methyl-1H-pyrazol-4-yl)pyrazolo[1,5-a]pyrazin-4-yl)pyridin-2-yl)piperazine-1-carbonyl)pyrrolidine-1-carboxylate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 195 mg, 0.425 mmol), (R)-1-(tert-butoxycarbonyl)pyrrolidine-3-carboxylic acid (91.6 mg, 0.425 mmol) and HATU (485 mg, 1.28 mmol) in anhydrous DCM (2.1 mL) was treated with DIEA (73.4 μL, 0.425 mmol). After stirring for 2 h at ambient temperature, the reaction mixture was filtered, and the filtrate was concentrated in vacuo. The residue was purified by silica chromatography (using (0-10% DCM:MeOH with 0-1% $NH_4OH$ as the gradient eluent). Fractions containing the desired product were combined, concentrated and triturated with DCM/Hexanes (1:10) and dried in vacuo for 1 h to afford the title compound (248 mg, quantitative yield) which was used directly in Step 2. MS (apci) m/z=583.3 (M+H).

Step 2: Preparation of (R)-6-(1-methyl-1H-pyrazol-4-yl)-4-(6-(4-(pyrrolidine-3-carbonyl)piperazin-1-yl)pyridin-3-yl)pyrazolo[1,5-a]pyrazine-3-carbonitrile A solution tert-butyl (R)-3-(4-(5-(3-cyano-6-(1-methyl-1H-pyrazol-4-yl)pyrazolo[1,5-a]pyrazin-4-yl)pyridin-2-yl)piperazine-1-carbonyl)pyrrolidine-1-carboxylate (Step 1; 248 mg, 0.426 mmol) in DCM (4.3 mL) was treated with TFA (328 μL, 4.26 mmol), and stirred for 45 min at ambient temperature. Additional TFA (328 μL, 4.26 mmol) was introduced, and the reaction mixture was stirred overnight at ambient temperature. The reaction mixture was concentrated in vacuo, and the residue was purified by C18 reverse phase chromatography (using 5-95% water:ACN with 0.1% TFA as the gradient eluent). Fractions containing the desired product were combined, diluted with 4:1 DCM:iPrOH and washed sequentially with saturated $NaHCO_{3(aq)}$ and brine. The combined organic extracts were dried over anhydrous $Na_2SO_{4(s)}$, filtered, and concentrated in vacuo. The residue was triturated with DCM/Hexanes (1:10) and dried in vacuo to cleanly afford the title compound (39.1 mg, 19% yield). MS (apci) m/z=483.2 (M+H).

Example 73

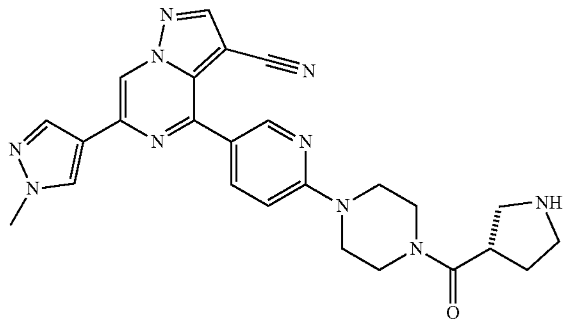

(S)-6-(1-methyl-1H-pyrazol-4-yl)-4-(6-(4-(pyrrolidine-3-carbonyl)piperazin-1-yl)pyridin-3-yl)pyrazolo[1,5-a]pyrazine-3-carbonitrile Step 1: Preparation of tert-butyl (S)-3-(4-(5-(3-cyano-6-(1-methyl-1H-pyrazol-4-yl)pyrazolo[1,5-a]pyrazin-4-yl)pyridin-2-yl)piperazine-1-carbonyl)pyrrolidine-1-carboxylate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 50 mg, 0.11 mmol), (S)-1-(tert-butoxycarbonyl)pyrrolidine-3-carboxylic acid (23 mg, 0.11 mmol) and HATU (124 mg, 0.33 mmol) in anhydrous DCM (545 μL) was treated with DIEA (76 μL, 0.44 mmol). After stirring for 3 h at ambient temperature, the reaction mixture was filtered, and the filtrate was concentrated in vacuo. The residue was purified by silica chromatography (using (0-20% DCM:MeOH with 0-1% $NH_4OH$ as the gradient eluent). Fractions containing the desired product were combined, concentrated and triturated with DCM/Hexanes (1:10) and dried in vacuo for 1 h to afford the title compound (64 mg, quantitative yield) which was used directly in Step 2. MS (apci) m/z=583.3 (M+H).

Step 2: Preparation of (S)-6-(1-methyl-1H-pyrazol-4-yl)-4-(6-(4-(pyrrolidine-3-carbonyl)piperazin-1-yl)pyridin-3-yl)pyrazolo[1,5-a]pyrazine-3-carbonitrile A solution tert-butyl (S)-3-(4-(5-(3-cyano-6-(1-methyl-1H-pyrazol-4-yl)pyrazolo[1,5-a]pyrazin-4-yl)pyridin-2-yl)piperazine-1-carbonyl)pyrrolidine-1-carboxylate (Step 1; 64 mg, 0.11 mmol) in DCM (1.1 mL) was treated with TFA (85 μL, 1.1 mmol), then stirred for 1 h at ambient temperature. The reaction mixture was diluted with 4:1 DCM:iPrOH and washed sequentially with saturated $NaHCO_{3(aq)}$ and brine. The combined organic extracts were dried over anhydrous $Na_2SO_{4(s)}$, filtered, and concentrated in vacuo. The residue was triturated with DCM/Hexanes (1:10) and dried in vacuo to cleanly afford the title compound (48 mg, 91% yield). MS (apci) m/z=483.3 (M+H).

Example 74

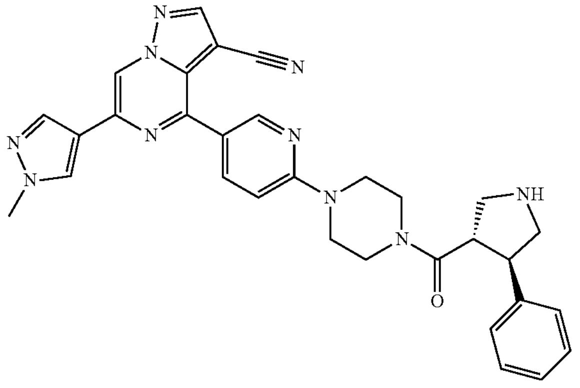 [SMILES: Cn1cc(-c2cn3ncc(C#N)c3c(-c3ccc(N4CCN(C(=O)[C@@H]5CNC[C@H]5c5ccccc5)CC4)nc3)n2)cn1]

6-(1-methyl-1H-pyrazol-4-yl)-4-(6-(4-((trans-(+))-4-phenylpyrrolidine-3-carbonyl)piperazin-1-yl)pyridin-3-yl)pyrazolo[1,5-a]pyrazine-3-carbonitrile Step 1: Preparation of tert-butyl-trans-(±)-3-(4-(5-(3-cyano-6-(1-methyl-1H-pyrazol-4-yl)pyrazolo[1,5-a]pyrazin-4-yl)pyridin-2-yl)piperazine-1-carbonyl)-4-phenylpyrrolidine-1-carboxylate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 200 mg, 0.436 mmol), trans-(±)-1-(tert-butoxycarbonyl)-4-phenylpyrrolidine-3-carboxylic acid (127 mg, 0.436 mmol) and HATU (498 mg, 1.31 mmol) in anhydrous DCM (2.2 mL) was treated with DIEA (76.2 μL, 0.436 mmol). After stirring for 3 h at ambient temperature, the reaction mixture was filtered, and the filtrate was concentrated in vacuo. The residue was purified by silica chromatography (using 0-20% DCM: MeOH as the gradient eluent). Fractions containing the desired product were combined, concentrated and triturated with DCM/Hexanes (1:10) and dried in vacuo for 1 h to afford the title compound (287 mg, quantitative yield) which was used directly in Step 2. MS (apci) m/z=659.3 (M+H).

Step 2: Preparation of 6-(1-methyl-1H-pyrazol-4-yl)-4-(6-(4-(-trans-(±)-4-phenylpyrrolidine-3-carbonyl)piperazin-1-yl)pyridin-3-yl)pyrazolo[1,5-a]pyrazine-3-carbonitrile A solution of tert-butyl-trans-(±)-3-(4-(5-(3-cyano-6-(1-methyl-1H-pyrazol-4-yl)pyrazolo[1,5-a]pyrazin-4-yl)pyridin-2-yl)piperazine-1-carbonyl)-4-phenylpyrrolidine-1-carboxylate (Step 1; 287 mg, 0.436 mmol) in DCM (4.4 mL) was treated with TFA (336 μL, 4.36 mmol) and stirred overnight at ambient temperature. The resulting mixture was concentrated in vacuo, and the residue was purified by C18 reverse phase chromatography (using 5-95% water:ACN with 0.1% TFA as the gradient eluent). Fractions containing the desired product were combined, diluted with 4:1 DCM: iPrOH and washed sequentially with saturated $NaHCO_{3(aq)}$, water and brine. The combined organic extracts were dried over anhydrous $Na_2SO_{4(s)}$, filtered, and concentrated in vacuo. The residue was triturated with DCM/Hexanes (1:10) and dried in vacuo overnight to cleanly afford the title compound (242 mg, 99% yield). MS (apci) m/z=559.3 (M+H).

Example 75

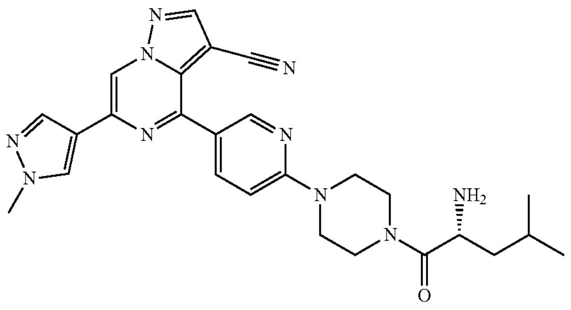 [SMILES: CC(C)C[C@@H](N)C(=O)N1CCN(c2ccc(-c3nc(-c4cnn(C)c4)cn4ncc(C#N)c34)cn2)CC1]

4-(6-(4-(D-leucyl)piperazin-1-yl)pyridin-3-yl)-6-(1-methyl-H-pyrazol-4-yl)pyrazolo[1,5-a]pyrazine-3-carbonitrile Step 1: Preparation of tert-butyl (R)-(1-(4-(5-(3-cyano-6-(1-methyl-1H-pyrazol-4-yl)pyrazolo[1,5-a]pyrazin-4-yl)pyridin-2-yl)piperazin-1-yl)-4-methyl-1-oxopentan-2-yl)carbamate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 55 mg, 0.120 mmol), HATU (54.8 mg, 0.144 mmol) and 2(tert-butoxycarbonyl)-D-leucine (30.5 mg, 0.132 mmol) in anhydrous DCM (4 mL) was treated with DIEA (83.6 μL, 0.480 mmol). The reaction mixture was stirred for 3 d at ambient temperature. The resulting mixture was purified by silica phase chromatography (using 30-100% ethyl acetate in hexanes as the gradient eluent) to afford the title compound (70 mg, 97% yield). MS (apci) m/z=599.3 (M+H).

Step 2: Preparation of 4-(6-(4-(D-leucyl)piperazin-1-yl)pyridin-3-yl)-6-(1-methyl-1H-pyrazol-4-yl)pyrazolo[1,5-a]pyrazine-3-carbonitrile A solution of tert-butyl (R)-(1-(4-(5-(3-cyano-6-(1-methyl-1H-pyrazol-4-yl)pyrazolo[1,5-a]pyrazin-4-yl)pyridin-2-yl)piperazin-1-yl)-4-methyl-1-oxopentan-2-yl)carbamate (Step 1; 0.070 g, 0.12 mmol) was dissolved in DCM (4 mL) and treated with TFA (2 mL). The resulting mixture was stirred for 1 h at ambient temperature and then concentrated in vacuo. The residue was purified by C18 reverse phase chromatography (using 5-95% ACN in water with 0.1% TFA as the gradient eluent). Fractions containing the desired product were combined, diluted with 4:1 DCM:iPrOH and washed sequentially with saturated $NaHCO_{3(aq)}$ and brine. The combined organic extracts were dried over anhydrous $Na_2SO_{4(s)}$, filtered, and concentrated in vacuo to afford the title compound (43 mg, 74% yield). MS (apci) m/z=499.3 (M+H).

Example 76

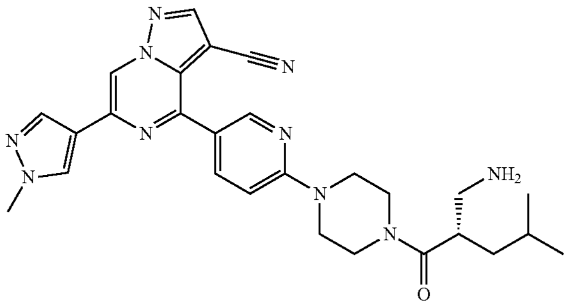 [SMILES: CC(C)C[C@@H](CN)C(=O)N1CCN(c2ccc(-c3nc(-c4cnn(C)c4)cn4ncc(C#N)c34)cn2)CC1]

(S)-4-(6-(4-(2-(aminomethyl)-4-methylpentanoyl)piperazin-1-yl)pyridin-3-yl)-6-(1-methyl-1H-pyrazol-4-yl)pyrazolo[1,5-a]pyrazine-3-carbonitrile Step 1: Preparation of tert-butyl (S)-(2-(4-(5-(3-cyano-6-(1-methyl-1H-pyrazol-4-yl)pyrazolo[1,5-a]pyrazin-4-yl)pyridin-2-yl)piperazine-1-carbonyl)-4-methylpentyl)carbamate A mixture of 6-(1-methyl-1H-pyrazol-4-yl)-4-(6-(piperazin-1-yl)pyridin-3-yl)pyrazolo[1,5-a]pyrazine-3-carbonitrile dihydrochloride (Example 8; 55 mg, 0.120 mmol), HATU (54.8 mg, 0.144 mmol) and (S)-2-(((tert-Butoxycarbonyl)amino)methyl)-4-methylpentanoic acid (32.4 mg, 0.132 mmol) in anhydrous DCM (4 mL) was treated with DIEA (83.6 μl, 0.480 mmol). The reaction mixture was stirred overnight at ambient temperature. The resulting mixture was concentrated in vacuo to afford the title compound in sufficient purity for subsequent use (73 mg, 99% yield). MS (apci) m/z=613.4 (M+H).

Step 2: Preparation of (S)-4-(6-(4-(2-(aminomethyl)-4-methylpentanoyl)piperazin-1-yl)pyridin-3-yl)-6-(1-methyl-1H-pyrazol-4-yl)pyrazolo[1,5-a]pyrazine-3-carbonitrile A solution of tert-butyl (S)-(2-(4-(5-(3-cyano-6-(1-methyl-1H-pyrazol-4-yl)pyrazolo[1,5-a]pyrazin-4-yl)pyridin-2-yl)piperazine-1-carbonyl)-4-methylpentyl)carbamate (Step 1; 73 mg, 0.12 mmol) was dissolved in DCM (4 mL) and treated with TFA (2 mL). The resulting mixture was stirred for 30 min at ambient temperature and then concentrated in vacuo. The residue was purified by C18 reverse phase chromatography (using 5-95% ACN in water with 0.1% TFA as the gradient eluent). Fractions containing the desired product were combined, diluted with 4:1 DCM:iPrOH and washed sequentially with saturated $NaHCO_{3(aq)}$ and brine. The combined organic extracts were dried over anhydrous $Na_2SO_{4(s)}$, filtered, and concentrated in vacuo to afford the title compound (43 mg, 70% yield). MS (apci) m/z=513.2 (M+H).

Example 77

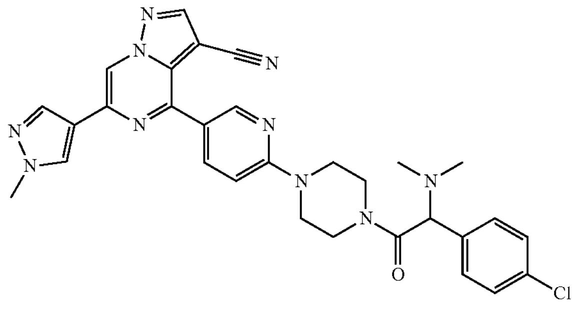 [SMILES: CN(C)C(C(=O)N1CCN(c2ccc(-c3nc(-c4cnn(C)c4)cn4ncc(C#N)c34)cn2)CC1)c1ccc(Cl)cc1]

4-(6-(4-(2-(4-chlorophenyl)-2-(dimethylamino) acetyl)piperazin-1-yl)pyridin-3-yl)-6-(1-methyl-1H-pyrazol-4-yl)pyrazolo[1,5-a]pyrazine-3-carbonitrile A solution of 4-(6-(4-(2-amino-2-(4-chlorophenyl)acetyl) piperazin-1-yl)pyridin-3-yl)-6-(1-methyl-1H-pyrazol-4-yl) pyrazolo[1,5-a]pyrazine-3-carbonitrile (Example 61; 37 mg, 0.067 mmol) and formaldehyde (20 μL, 0.27 mmol) in dry DCM (669 μL) was treated with $NaBH(AcO)_3$ (132 mg, 0.502 mmol). The resulting mixture was stirred for 2 h at ambient temperature. The reaction mixture was filtered, and the filtrate was concentrated in vacuo. The residue was purified by C18 reverse phase chromatography (using 5-95% water:ACN with 0.1% TFA as the gradient eluent). Fractions containing the desired product were combined, diluted with 4:1 DCM:iPrOH and washed sequentially with saturated $NaHCO_{3(aq)}$, water and brine. The combined organic extracts were dried over anhydrous $Na_2SO_{4(s)}$, filtered, and concentrated in vacuo. The residue was triturated with DCM/Hexanes (1:10) and dried in vacuo to cleanly afford the title compound (27.2 mg, 70% yield). MS (apci) m/z=581.2 (M+H).

Example 78

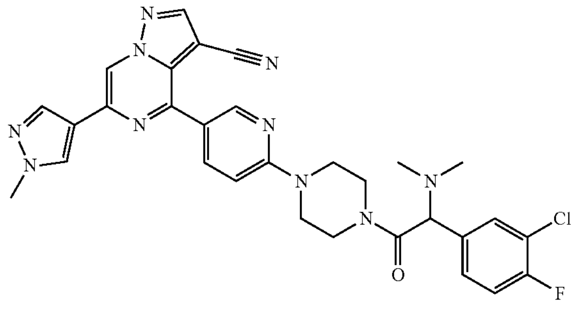 [SMILES: CN(C)C(C(=O)N1CCN(c2ccc(-c3nc(-c4cnn(C)c4)cn4ncc(C#N)c34)cn2)CC1)c1ccc(F)c(Cl)c1]

4-(6-(4-(2-(3-chloro-4-fluorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile A solution of 4-(6-(4-(2-amino-2-(3-chloro-4-fluorophenyl)acetyl)piperazin-1-yl)pyridin-3-yl)-6-(1-methyl-1H-pyrazol-4-yl)pyrazolo[1,5-a]pyrazine-3-carbonitrile (Example 65; 152 mg, 0.266 mmol) and formaldehyde (79.3 μL, 1.06 mmol) in dry DCM (2.66 mL) was treated with $NaBH(AcO)_3$ (282 mg, 1.33 mmol). The resulting mixture was stirred overnight at ambient temperature. The reaction mixture was concentrated in vacuo, and the residue was purified by C18 reverse phase chromatography (using 5-95% water:ACN with 0.1% TFA as the gradient eluent). Fractions containing the desired product were combined, concentrated in vacuo, suspended in DCM and washed sequentially with saturated $NaHCO_{3(aq)}$, water and brine. The combined organic extracts were dried over anhydrous $Na_2SO_{4(s)}$, filtered, and concentrated in vacuo to cleanly afford the title compound (74.3 mg, 47% yield). MS (apci) m/z=599.2 (M+H).

Example 79

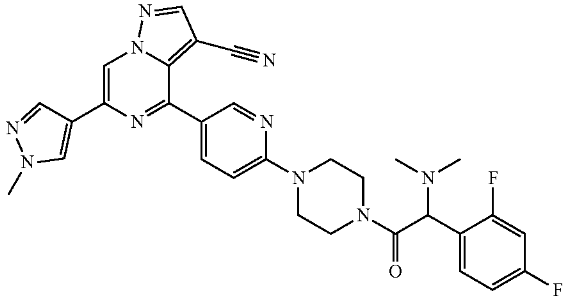 [SMILES: CN(C)C(C(=O)N1CCN(c2ccc(-c3nc(-c4cnn(C)c4)cn4ncc(C#N)c34)cn2)CC1)c1ccc(F)cc1F]

4-(6-(4-(2-(2,4-difluorophenyl)-2-(dimethylamino) acetyl)piperazin-1-yl)pyridin-3-yl)-6-(1-methyl-1H-pyrazol-4-yl)pyrazolo[1,5-a]pyrazine-3-carbonitrile A solution of 4-(6-(4-(2-amino-2-(2,4-difluorophenyl) acetyl)piperazin-1-yl)pyridin-3-yl)-6-(1-methyl-1H-pyrazol-4-yl)pyrazolo[1,5-a]pyrazine-3-carbonitrile (Example 64; 89 mg, 0.16 mmol) and formaldehyde (48 μL, 0.64 mmol) in dry DCM (1.6 mL) was treated with $NaBH(AcO)_3$ (170 mg, 0.802 mmol). The resulting mixture was stirred for 1 h at ambient temperature. The reaction mixture was concentrated in vacuo, and the residue was purified by C18 reverse phase chromatography (using 5-95% water:ACN with 0.1% TFA as the gradient eluent). Fractions containing the desired product were combined, diluted with 4:1 DCM: iPrOH, and washed sequentially with saturated $NaHCO_{3(aq)}$ and brine. The combined organic extracts were dried over anhydrous $Na_2SO_{4(s)}$, filtered, and concentrated in vacuo. The residue was triturated with DCM/Hexanes (1:10) and dried overnight in vacuo to cleanly afford the title compound (56.2 mg, 60% yield). MS (apci) m/z=583.3 (M+H).

The compounds in Table F were prepared and purified using a similar method to that described for the synthesis of Example 79, replacing 4-(6-(4-(2-amino-2-(2,4-difluorophenyl)acetyl)piperazin-1-yl)pyridin-3-yl)-6-(1-methyl-1H-pyrazol-4-yl)pyrazolo[1,5-a]pyrazine-3-carbonitrile with the appropriate amine (source noted in table). Reactions were monitored for completion by LCMS, and reaction durations, and where noted, quantities of formaldehyde and NaBH(AcO)3, were adjusted accordingly. The title compounds were cleanly isolated following a similar C18 reverse phase chromatography using an appropriate gradient and free basing extraction sequence to that used in the synthesis of Example 79.

TABLE F

| Ex. # | Starting material | Structure | Chemical Name | MS (apci) m/z |
|---|---|---|---|---|
| 80 | Ex. 63 | 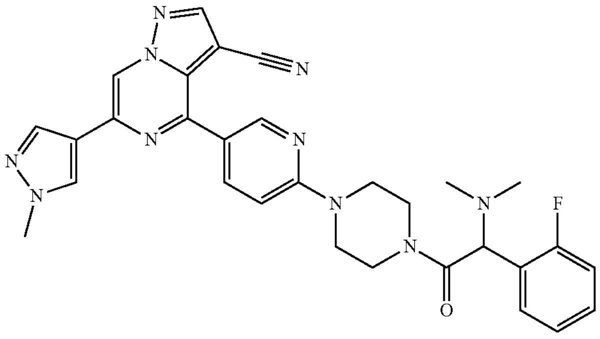 [SMILES: CN(C)C(C(=O)N1CCN(c2ccc(-c3nc(-c4cnn(C)c4)cn4ncc(C#N)c34)cn2)CC1)c1ccccc1F] | 4-(6-(4-(2-(dimethylamino)-2-(2-fluorophenyl)acetyl)piperazin-1-yl)pyridin-3-yl)-6-(1-methyl-1H-pyrazol-4-yl)pyrazolo[1,5-a]pyrazine-3-carbonitrile | 565.30 (M + H) |
| 81 | Ex. 66 | 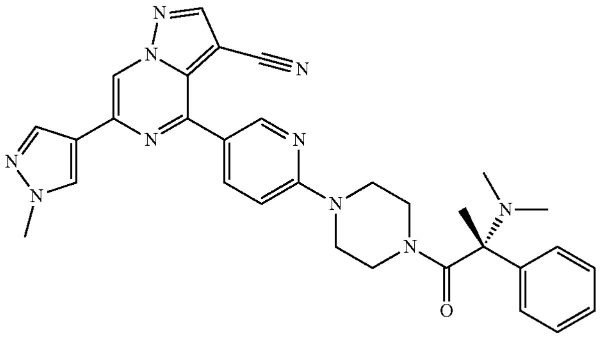 [SMILES: CN(C)[C@@](C)(C(=O)N1CCN(c2ccc(-c3nc(-c4cnn(C)c4)cn4ncc(C#N)c34)cn2)CC1)c1ccccc1] | (R)-4-(6-(4-(2-(dimethylamino)-2-phenylpropanoyl)piperazin-1-yl)pyridin-3-yl)-6-(1-methyl-1H-pyrazol-4-yl)pyrazolo[1,5-a]pyrazine-3-carbonitrile | 561.30 (M + H) |
| 82 | Ex. 68 | 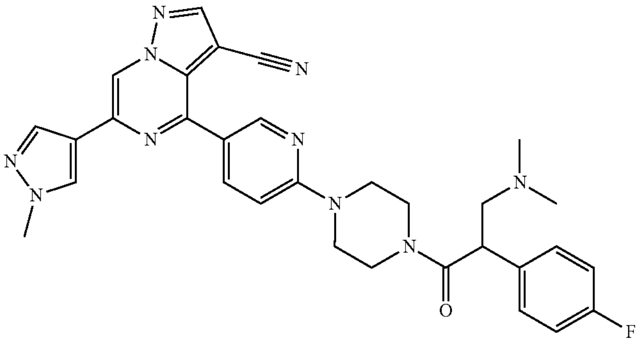 [SMILES: CN(C)CC(C(=O)N1CCN(c2ccc(-c3nc(-c4cnn(C)c4)cn4ncc(C#N)c34)cn2)CC1)c1ccc(F)cc1] | 4-(6-(4-(3-(dimethylamino)-2-(4-fluorophenyl)propanoyl)piperazin-1-yl)pyridin-3-yl)-6-(1-methyl-1H-pyrazol-4-yl)pyrazolo[1,5-a]pyrazine-3-carbonitrile | 579.30 (M + H) |
| 83 | Ex. 69 | 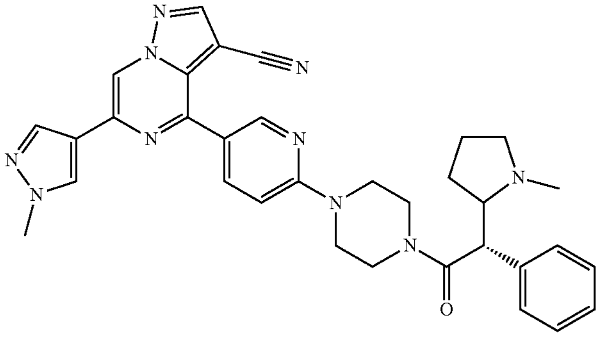 [SMILES: CN1CCCC1[C@@H](C(=O)N1CCN(c2ccc(-c3nc(-c4cnn(C)c4)cn4ncc(C#N)c34)cn2)CC1)c1ccccc1] | 6-(1-methyl-1H-pyrazol-4-yl)-4-(6-(4-((2S)-2-(1-methylpyrrolidin-2-yl)-2-phenylacetyl)piperazin-1-yl)pyridin-3-yl)pyrazolo[1,5-a]pyrazine-3-carbonitrile | 587.30 (M + H) |

TABLE F-continued

| Ex. # | Starting material | Structure | Chemical Name | MS (apci) m/z |
|---|---|---|---|---|
| 84 | Ex. 70 | 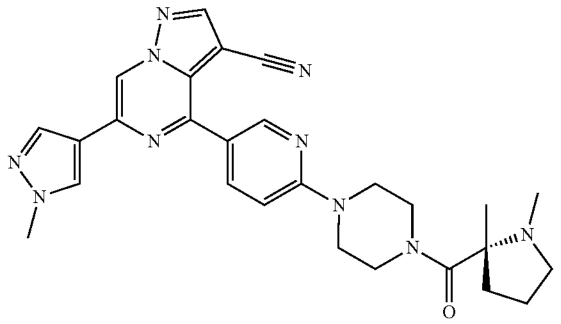 [SMILES: CN1CCC[C@]1(C)C(=O)N1CCN(c2ccc(-c3nc(-c4cnn(C)c4)cn4ncc(C#N)c34)cn2)CC1] | (R)-4-(6-(4-(1,2-dimethylpyrrolidine-2-carbonyl)piperazin-1-yl)pyridin-3-yl)-6-(1-methyl-1H-pyrazol-4-yl)pyrazolo[1,5-a]pyrazine-3-carbonitrile | 511.30 (M + H) |
| 85 | Ex. 71 | 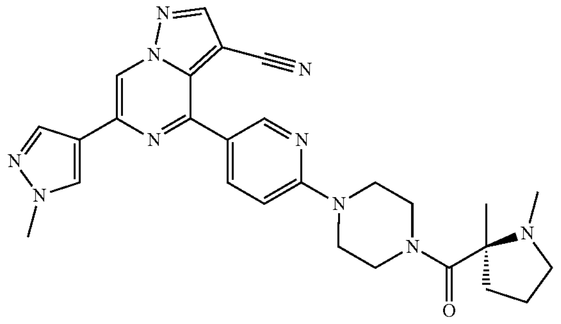 [SMILES: CN1CCC[C@@]1(C)C(=O)N1CCN(c2ccc(-c3nc(-c4cnn(C)c4)cn4ncc(C#N)c34)cn2)CC1] | (S)-4-(6-(4-(1,2-dimethylpyrrolidine-2-carbonyl)piperazin-1-yl)pyridin-3-yl)-6-(1-methyl-1H-pyrazol-4-yl)pyrazolo[1,5-a]pyrazine-3-carbonitrile | 511.30 (M + H) |
| 86 | Ex. 72 | 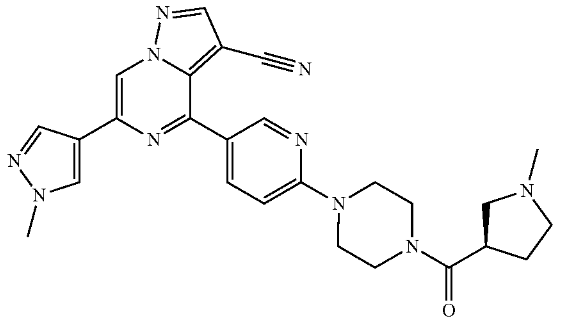 [SMILES: CN1CC[C@@H](C(=O)N2CCN(c3ccc(-c4nc(-c5cnn(C)c5)cn5ncc(C#N)c45)cn3)CC2)C1] | (R)-6-(1-methyl-1H-pyrazol-4-yl)-4-(6-(4-(1-methylpyrrolidine-3-carbonyl)piperazin-1-yl)pyridin-3-yl)pyrazolo[1,5-a]pyrazine-3-carbonitrile | 497.30 (M + H) |
| 87 | Ex. 73 | 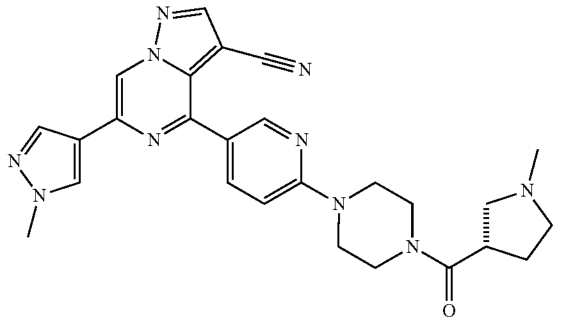 [SMILES: CN1CC[C@H](C(=O)N2CCN(c3ccc(-c4nc(-c5cnn(C)c5)cn5ncc(C#N)c45)cn3)CC2)C1] | (S)-6-(1-methyl-1H-pyrazol-4-yl)-4-(6-(4-(1-methylpyrrolidine-3-carbonyl)piperazin-1-yl)pyridin-3-yl)pyrazolo[1,5-a]pyrazine-3-carbonitrile | 497.30 (M + H) |

TABLE F-continued

| Ex. # | Starting material | Structure | Chemical Name | MS (apci) m/z |
|---|---|---|---|---|
| 88 | Ex. 74 | 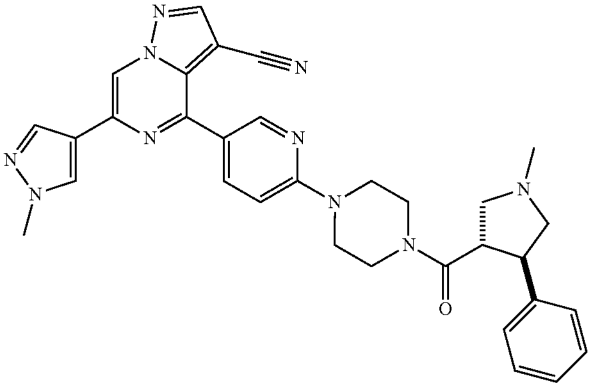 [SMILES: CN1C[C@@H](C(=O)N2CCN(c3ccc(-c4nc(-c5cnn(C)c5)cn5ncc(C#N)c45)cn3)CC2)[C@H](c2ccccc2)C1] | 6-(1-methyl-1H-pyrazol-4-yl)-4-(6-(4-((trans-(±))-4-phenylpyrrolidine-3-carbonyl)piperazin-1-yl)pyridin-3-yl)pyrazolo[1,5-a]pyrazine-3-carbonitrile | 573.20 (M + H) |

*10 equivalents of formaldehyde and 5 equivalents of $NaBH(AcO)_3$ were used in this reaction

**5 equivalents of formaldehyde and 5 equivalents of $NaBH(AcO)_3$ were used in this reaction; trituration was skipped in this example

Examples 89 and 90

6-(1-methyl-1H-pyrazol-4-yl)-4-(6-(4-((3S,4R)-1-methyl-4-phenylpyrrolidine-3-carbonyl)piperazin-1-yl)pyridin-3-yl)pyrazolo[1,5-a]pyrazine-3-carbonitrile (Ex. 89) and 6-(1-methyl-1H-pyrazol-4-yl)-4-(6-(4-((3R,4S)-1-methyl-4-phenylpyrrolidine-3-carbonyl)piperazin-1-yl)pyridin-3-yl)pyrazolo[1,5-a]pyrazine-3-carbonitrile (Ex. 90)

Ex. 89

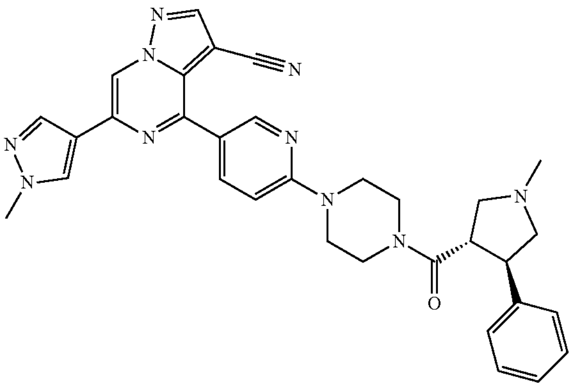

Ex. 90

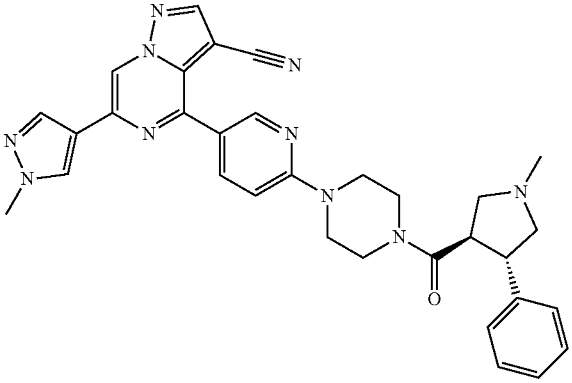

A solution of the racemate 6-(1-methyl-1H-pyrazol-4-yl)-4-(6-(4-((trans-(±))-4-phenylpyrrolidine-3-carbonyl)piperazin-1-yl)pyridin-3-yl)pyrazolo[1,5-a]pyrazine-3-carbonitrile (Ex. 88; 142 mg, 0.25 mmol) was separated into the respective enantiomers by Super-Critical Fluid Chromatography (SFC) utilizing an isocratic mobile phase consisting of A: 28% (Methanol:Isopropyl alcohol:diethylamine [80:20:1]) and B: 72% (super critical Carbon Dioxide), with a flow rate of 4 mL/min. achieved upon a stationary phase OD-H column (Chiral Technology, Inc.; cellulose—α-D 1-4 Glucose(tris[3,5-dimethylphenylcarbamate]); 4.6 mm×250 mm, 5 u). Injections and chromatography were monitored with fixed wavelength UV @ 220 nm and 254 nm. Fractions containing each enantiomer were isolated and independently concentrated in vacuo to cleanly afford the two title compounds: Peak 1, Example 89: 6-(1-methyl-1H-pyrazol-4-yl)-4-(6-(4-((3S,4R)-1-methyl-4-phenylpyrrolidine-3-carbonyl)piperazin-1-yl)pyridin-3-yl)pyrazolo[1,5-a]pyrazine-3-carbonitrile. MS (apci) m/z=572.3 (M+H). Peak 2, Example 90: 6-(1-methyl-1H-pyrazol-4-yl)-4-(6-(4-((3R,4S)-1-methyl-4-phenylpyrrolidine-3-carbonyl)piperazin-1-yl)pyridin-3-yl)pyrazolo[1,5-a]pyrazine-3-carbonitrile. MS (apci) m/z=572.3 (M+H).

Example 91

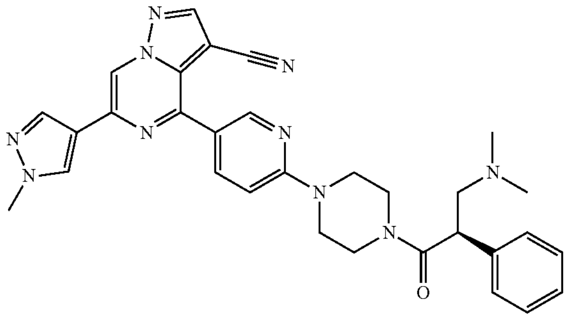 [SMILES: CN(C)C[C@H](C(=O)N1CCN(c2ccc(-c3nc(-c4cnn(C)c4)cn4ncc(C#N)c34)cn2)CC1)c1ccccc1]

(R)-4-(6-(4-(3-(dimethylamino)-2-phenylpropanoyl)piperazin-1-yl)pyridin-3-yl)-6-(1-methyl-1H-pyrazol-4-yl)pyrazolo[1,5-a]pyrazine-3-carbonitrile A solution of (R)-4-(6-(4-(3-amino-2-phenylpropanoyl)piperazin-1-yl)pyridin-3-yl)-6-(1-methyl-1H-pyrazol-4-yl)pyrazolo[1,5-a]pyrazine-3-carbonitrile (Example 67; 43 mg, 0.081 mmol) and formaldehyde (22 μL, 0.81 mmol) in dry DCM (0.81 mL) was treated with $NaBH(AcO)_3$ (86 mg, 0.40 mmol). After stirring the mixture overnight additional formaldehyde (22 μL, 0.81 mmol) and $NaBH(AcO)_3$ (86 mg, 0.40 mmol) were added, and the reaction was again allowed to stir overnight at ambient temperature. The reaction mixture was purified by silica chromatography (using 0-10% $CHCl_3$:MeOH with 0-1% $NH_4OH$ as the gradient eluent). Fractions containing the desired product were combined, concentrated in vacuo, and triturated with DCM/Hexanes (1:10) to cleanly afford the title compound (11.6 mg, 26% yield). MS (apci) m/z=561.3 (M+H).

Example 92

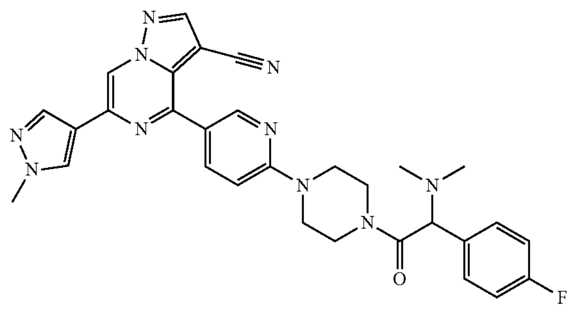 [SMILES: CN(C)C(C(=O)N1CCN(c2ccc(-c3nc(-c4cnn(C)c4)cn4ncc(C#N)c34)cn2)CC1)c1ccc(F)cc1]

(4-(6-(4-(2-(dimethylamino)-2-(4-fluorophenyl)acetyl)piperazin-1-yl)pyridin-3-yl)-6-(1-methyl-1H-pyrazol-4-yl)pyrazolo[1,5-a]pyrazine-3-carbonitrile The title compound was prepared and purified using a similar procedure to that described for Example 91, replacing (R)-4-(6-(4-(3-amino-2-phenylpropanoyl)piperazin-1-yl)pyridin-3-yl)-6-(1-methyl-1H-pyrazol-4-yl)pyrazolo[1,5-a]pyrazine-3-carbonitrile with (R)-4-(6-(4-(2-amino-2-(4-fluorophenyl)acetyl)piperazin-1-yl)pyridin-3-yl)-6-(1-methyl-1H-pyrazol-4-yl)pyrazolo[1,5-a]pyrazine-3-carbonitrile (Example 62). MS (apci) m/z=565.3 (M+H).

Example 93

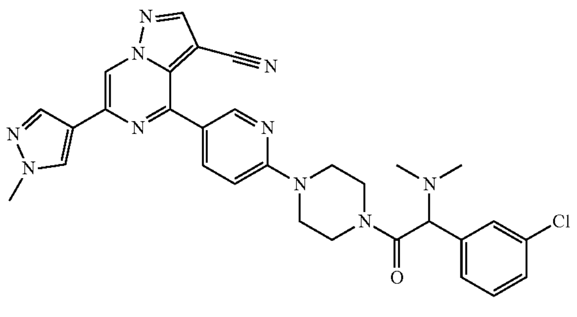 [SMILES: CN(C)C(C(=O)N1CCN(c2ccc(-c3nc(-c4cnn(C)c4)cn4ncc(C#N)c34)cn2)CC1)c1cccc(Cl)c1]

4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile A solution of 4-(6-(4-(2-amino-2-(3-chlorophenyl)acetyl)piperazin-1-yl)pyridin-3-yl)-6-(1-methyl-1H-pyrazol-4-yl)pyrazolo[1,5-a]pyrazine-3-carbonitrile (Example 60; 430 mg, 0.778 mmol) and formaldehyde (232 μL, 3.11 mmol) in 1:1 DCM:MeOH (8 mL) was treated with $NaBH(AcO)_3$ (824 mg, 3.89 mmol). After stirring the mixture overnight at ambient temperature, the resulting suspension was filtered, and the filtrate was concentrated in vacuo. The residue was subsequently purified by C18 reverse phase chromatography (using 5-95% water:ACN as the gradient eluent). Fractions containing the desired product were combined, concentrated in vacuo, and triturated with DCM/Hexanes (1:10) then dried again in vacuo for 5 d to cleanly afford the title compound (154 mg, 34% yield). MS (apci) m/z=581.2 (M+H).

Examples 94 and 95

(R)-4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile (Ex. 94) and (S)-4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile (Ex. 95)

Ex. 94

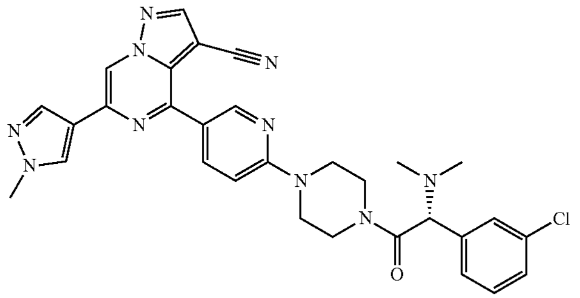

Ex. 95

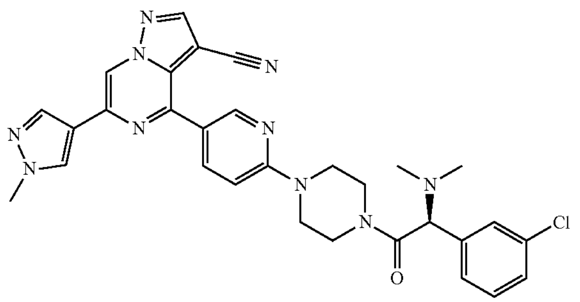

A solution of the racemate 4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile (Example 93; 147 mg, 0.260 mmol) was separated into the respective enantiomers by Super-Critical Fluid Chromatography (SFC) utilizing an isocratic mobile phase consisting of A: 28% (Methanol:Isopropyl alcohol:diethylamine [80:20:1]) and B: 72% (super critical Carbon Dioxide), with a flow rate of 4 mL/min. achieved upon a stationary phase (Chiral Technology, Inc., OD-H column (cellulose—α-D 1-4 Glucose(tris[3,5-dimethylphenylcarbamate]), 4.6 mm×250 mm, 5 u). Injections and chromatography were monitored with fixed wavelength UV @ 220 nm and 254 nm.

Fractions containing the enantiomer in Peak 1 were isolated and independently concentrated in vacuo to provide Example 94: (R)-4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile (14.1 mg, 10% recovery). MS (apci) m/z=581.3 (M+H). $^1$H NMR (400 MHz, $CDCl_3$) δ 8.76 (d, J=1.9 Hz, 1H), 8.52 (s, 1H), 8.33 (s, 1H), 8.05 (dd, J=8.9, 2.5 Hz, 1H), 7.96 (d, J=6.9 Hz, 2H), 7.47 (s, 1H), 7.37-7.28 (m, 3H), 6.73 (d, J=8.5 Hz, 1H), 4.22 (s, 1H), 3.98 (s, 3H), 3.71 (m, 7H), 3.41 (m, 1H), 2.32 (s, 6H).

Fractions containing the enantiomer in Peak 2 were combined, concentrated in vacuo but found to be impure. This material was re-purified by C18 reverse phase chromatography (using 5-95% water:ACN with 0.1% TFA as the gradient eluent). Fractions containing the desired product were combined, diluted with 4:1 DCM:iPrOH and washed sequentially with saturated $NaHCO_{3(aq)}$ and brine. The organic extracts were dried over anhydrous $Na_2SO_{4(s)}$, filtered, and concentrated in vacuo. The residue was triturated with DCM/Hexanes (1:10) and dried overnight in vacuo to cleanly afford Example 95: (S)-4-(6-(4-(2-(3-chlorophenyl)-2-(dimethylamino)acetyl)piperazin-1-yl)pyridin-3-yl)-6-(1-methyl-1H-pyrazol-4-yl)pyrazolo[1,5-a]pyrazine-3-carbonitrile (12.7 mg, 9% recovery). MS (apci) m/z=581.3 (M+H).

Example 96

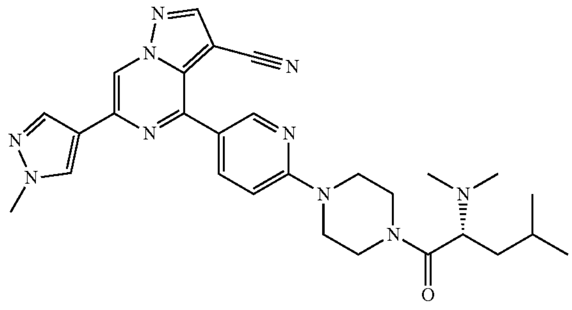 [SMILES: CC(C)C[C@H](C(=O)N1CCN(c2ccc(-c3nc(-c4cnn(C)c4)cn4ncc(C#N)c34)cn2)CC1)N(C)C]

4-(6-(4-(dimethyl-D-leucyl)piperazin-1-yl)pyridin-3-yl)-6-(1-methyl-1H-pyrazol-4-yl)pyrazolo[1,5-a]pyrazine-3-carbonitrile A solution of 4-(6-(4-(D-leucyl)piperazin-1-yl)pyridin-3-yl)-6-(1-methyl-1H-pyrazol-4-yl)pyrazolo[1,5-a]pyrazine-3-carbonitrile (Example 75; 37.4 mg, 0.0750 mmol) and formaldehyde (55.8 μL, 0.750 mmol) in DCM (750 μL) was treated with $NaBH(AcO)_3$ (79.5 mg, 0.375 mmol). After stirring the mixture 3 h at ambient temperature, the reaction mixture was concentrated in vacuo. The residue was subsequently purified by C18 reverse phase chromatography (using 5-95% water:ACN with 0.1% TFA as the gradient eluent). Fractions containing the desired product were combined, diluted with 4:1 DCM:iPrOH and washed sequentially with saturated $NaHCO_{3(aq)}$ and brine. The organic extracts were dried over anhydrous $Na_2SO_{4(s)}$, filtered, and concentrated in vacuo to afford the title compound (21 mg, 53% yield). MS (apci) m/z=527.3 (M+H).

Example 97

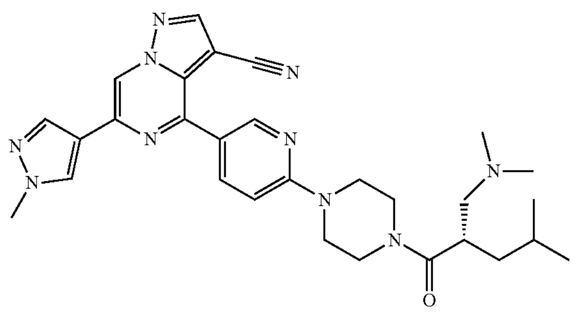 [SMILES: CC(C)C[C@@H](CN(C)C)C(=O)N1CCN(c2ccc(-c3nc(-c4cnn(C)c4)cn4ncc(C#N)c34)cn2)CC1]

(S)-4-(6-(4-(2-((dimethylamino)methyl)-4-methylpentanoyl)piperazin-1-yl)pyridin-3-yl)-6-(1-methyl-1H-pyrazol-4-yl)pyrazolo[1,5-a]pyrazine-3-carbonitrile The title compound was prepared and purified using a similar procedure to that described for Example 96, replacing 4-(6-(4-(D-leucyl)piperazin-1-yl)pyridin-3-yl)-6-(1-methyl-1H-pyrazol-4-yl)pyrazolo[1,5-a]pyrazine-3-carbonitrile (Example 75), with (S)-4-(6-(4-(2-(aminomethyl)-4-methylpentanoyl)piperazin-1-yl)pyridin-3-yl)-6-(1-methyl-1H-pyrazol-4-yl)pyrazolo[1,5-a]pyrazine-3-carbonitrile (Example 76). MS (apci) m/z=541.3 (M+H).

Example 98

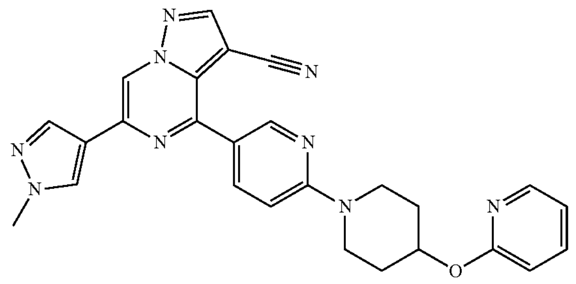 [SMILES: Cn1cc(-c2cn3ncc(C#N)c3c(-c3ccc(N4CCC(Oc5ccccn5)CC4)nc3)n2)cn1]

6-(1-methyl-1H-pyrazol-4-yl)-4-(6-(4-(pyridin-2-yloxy)piperidin-1-yl)pyridin-3-yl)pyrazolo[1,5-a]pyrazine-3-carbonitrile A solution of 4-(6-fluoropyridin-3-yl)-6-(1-methyl-H-pyrazol-4-yl)pyrazolo[1,5-a]pyrazine-3-carbonitrile (Intermediate P7; 52.3 mg, 0.208 mmol) in DMSO (1 mL) was treated with 2-(piperidin-4-yloxy)pyridine dihydrochloride (79 mg, 0.78 mmol) and $Cs_2CO_{3(s)}$ (280 mg, 0.858 mmol) then stirred overnight at 60° C. After cooling to ambient temperature, the reaction mixture was diluted with water, and extracted with DCM (4×). The combined organic extracts were washed with water, then dried over anhydrous $Na_2SO_{4(s)}$, filtered, and concentrated in vacuo. The residue was purified by silica chromatography (using 0-100% Hexanes/EtOAc as the gradient eluent) to afford the title compound (19.7 mg, 39% yield). MS (apci) m/z=478.2 (M+H).

Example 99

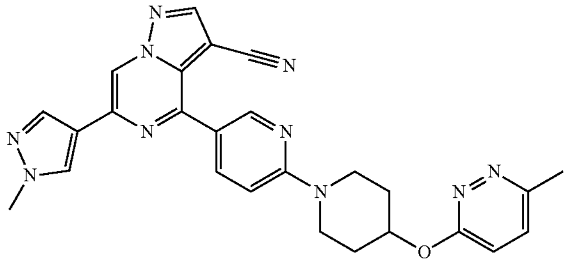

6-(1-methyl-1H-pyrazol-4-yl)-4-(6-(4-((6-methylpyridazin-3-yl)oxy)piperidin-1-yl)pyridin-3-yl) pyrazolo[1,5-a]pyrazine-3-carbonitrile A solution of 4-(6-fluoropyridin-3-yl)-6-(1-methyl-H-pyrazol-4-yl)pyrazolo[1,5-a]pyrazine-3-carbonitrile (Intermediate P7; 26.1 mg, 0.0817 mmol) in DMSO (1 mL) was treated with 3-methyl-6-(piperidin-4-yloxy)pyridazine (Intermediate R6; 39.6 mg, 0.205 mmol) and $Cs_2CO_{3(s)}$ (266 mg, 0.817 mmol) then stirred overnight at 60° C. After cooling to ambient temperature, the reaction mixture was diluted with water, and extracted with DCM (4×). The combined organic extracts were washed with water, then dried over anhydrous $Na_2SO_{4(s)}$, filtered, and concentrated in vacuo. The residue was purified by silica chromatography (using 0-100% Hexanes/EtOAc as the gradient eluent) to afford the title compound (15.5 mg, 33% yield). MS (apci) m/z=493.2 (M+H).

Example 100

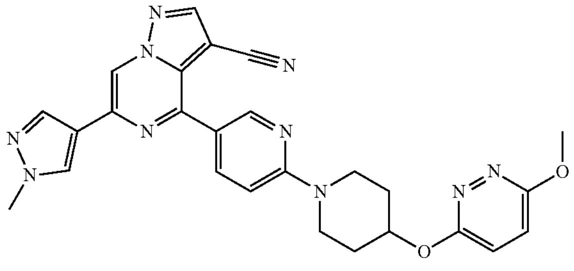

4-(6-(4-((6-methoxypyridazin-3-yl)oxy)piperidin-1-yl)pyridin-3-yl)-6-(1-methyl 1H-pyrazol-4-yl)pyrazolo[1,5-a]pyrazine-3-carbonitrile A solution of 4-(6-fluoropyridin-3-yl)-6-(1-methyl-H-pyrazol-4-yl)pyrazolo[1,5-a]pyrazine-3-carbonitrile (Intermediate P7; 25.3 mg, 0.0792 mmol) in DMSO (1 mL) was treated with 3-methoxy-6-(piperidin-4-yloxy)pyridazine (Intermediate R7; 33.2 mg, 0.159 mmol) and $Cs_2CO_{3(s)}$ (258 mg, 0.792 mmol) then stirred overnight at 60° C. After cooling to ambient temperature, the reaction mixture was diluted with water and extracted with DCM (4×). The combined organic extracts were washed with water, then dried over anhydrous $Na_2SO_{4(s)}$, filtered, and concentrated in vacuo. The residue was purified by silica chromatography (using 0-100% Hexanes/EtOAc as the gradient eluent) to afford the title compound (1.9 mg, 4.7% yield). MS (apci) m/z=509.2 (M+H).

Example 101

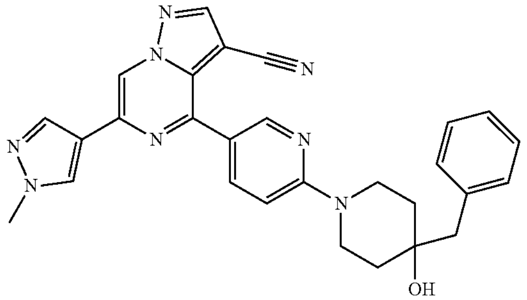 [SMILES: Cn1cc(-c2cn3ncc(C#N)c3c(-c3ccc(N4CCC(O)(Cc5ccccc5)CC4)nc3)n2)cn1]

4-(6-(4-benzyl-4-hydroxypiperidin-1-yl)pyridin-3-yl)-6-(1-methyl-1H-pyrazol-4-yl)pyrazolo[1,5-a] pyrazine-3-carbonitrile A solution of 4-(6-fluoropyridin-3-yl)-6-(1-methyl-1H-pyrazol-4-yl)pyrazolo[1,5-a]pyrazine-3-carbonitrile (Intermediate P7; 28.5 mg, 0.0893 mmol) in DMSO (0.5 mL) was treated with 4-benzylpiperidin-4-ol (51.2 mg, 0.268 mmol) and $Cs_2CO_{3(s)}$ (174 mg, 0.536 mmol) then stirred overnight at 60° C. The reaction mixture was diluted with water, and extracted with DCM (3×). The combined organic extracts were dried over anhydrous $Na_2SO_{4(s)}$, filtered, and concentrated in vacuo. The residue was purified by silica chromatography (using 0-100% Hexanes/EtOAc as the gradient eluent) to afford the title compound (11.7 mg, 27% yield). MS (apci) m/z=491.2 (M+H).

Example 102

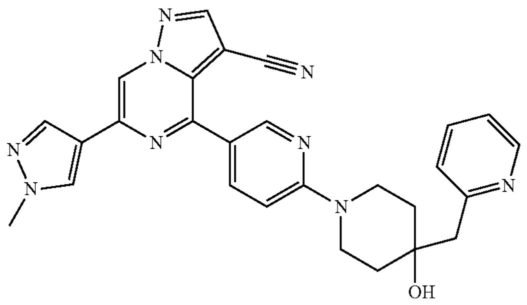 [SMILES: Cn1cc(-c2cn3ncc(C#N)c3c(-c3ccc(N4CCC(O)(Cc5ccccn5)CC4)nc3)n2)cn1]

4-(6-(4-hydroxy-4-(pyridin-2-ylmethyl)piperidin-1-yl)pyridin-3-yl)-6-(1-methyl-1H-pyrazol-4-yl)pyrazolo[1,5-a]pyrazine-3-carbonitrile A solution of 4-(6-fluoropyridin-3-yl)-6-(l-methyl-1H-pyrazol-4-yl)pyrazolo[1,5-a]pyrazine-3-carbonitrile (Intermediate P7; 35.6 mg, 0.111 mmol) in DMSO (0.5 mL) was treated with 4-(pyridin-2-ylmethyl)piperidin-4-ol (64.3 mg, 0.334 mmol) and $Cs_2CO_{3(s)}$ (218 mg, 0.669 mmol) then stirred overnight at 60° C. After cooling to ambient temperature, the reaction mixture was diluted with water and extracted with DCM (3×). The combined organic extracts were dried over anhydrous $Na_2SO_{4(s)}$, filtered, and concentrated in vacuo. The residue was purified by silica chromatography (using 0-100% Hexanes/EtOAc as the gradient eluent) to afford the title compound (29.8 mg, 45% yield). MS (apci) m/z=492.2 (M+H).

Example 103

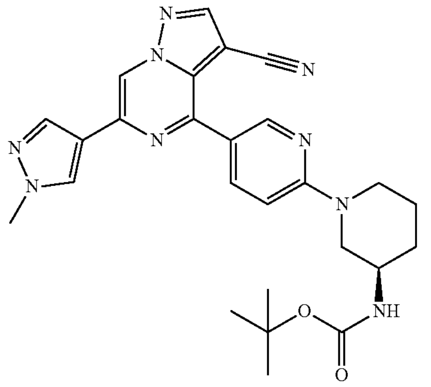 [SMILES: Cn1cc(-c2cn3ncc(C#N)c3c(-c3ccc(N4CCC[C@@H](NC(=O)OC(C)(C)C)C4)nc3)n2)cn1]

tert-butyl (R)-(1-(5-(3-cyano-6-(1-methyl-1H-pyrazol-4-yl)pyrazolo[1,5-a]pyrazin-4-yl)pyridin-2-yl)piperidin-3-yl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 69 mg, 0.20 mmol) in DMA (10 mL) was treated with tert-butyl (R)-piperidin-3-ylcarbamate (122 mg, 0.609 mmol) and TEA (142 μL, 1.02 mmol) then stirred 4 h at 60° C. After cooling to ambient temperature, the reaction mixture was purified by silica chromatography (using 0-100% Hexanes/EtOAc as the gradient eluent) to afford the title compound (38.9 mg, 36% yield). MS (apci) m/z=500.2 (M+H).

Example 104

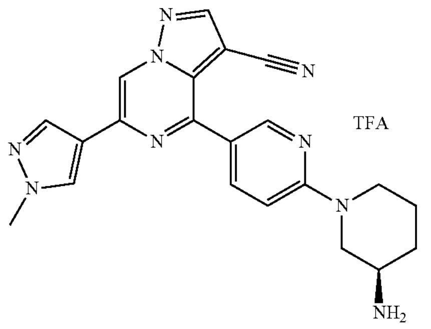 [SMILES: Cn1cc(-c2cn3ncc(C#N)c3c(-c3ccc(N4CCC[C@@H](N)C4)nc3)n2)cn1 ; "TFA"]

(R)-4-(6-(3-aminopiperidin-1-yl)pyridin-3-yl)-6-(1-methyl-1H-pyrazol-4-yl)pyrazolo[1,5-a]pyrazine-3-carbonitrile 2,2,2-trifluoroacetate A solution of tert-butyl (R)-(1-(5-(3-cyano-6-(1-methyl-1H-pyrazol-4-yl)pyrazolo[1,5-a]pyrazin-4-yl)pyridin-2-yl)piperidin-3-yl)carbamate (Example 103; 23.7 mg, 0.0474 mmol) in DCM (47.4 μL) was treated dropwise with TFA (36.5 μL, 0.474 mmol). The resulting mixture was stirred for 1 h at ambient temperature and then concentrated in vacuo overnight to afford the title compound as the TFA salt (43 mg, 74% yield). MS (apci) m/z=400.1 (M+H).

Example 105

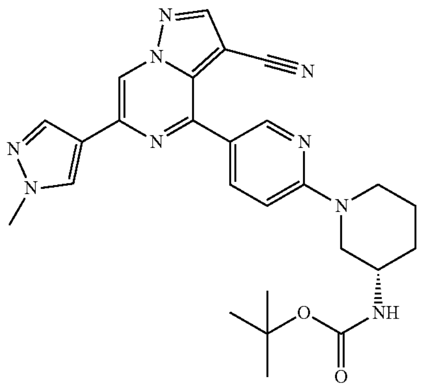 [SMILES: Cn1cc(-c2cn3ncc(C#N)c3c(-c3ccc(N4CCC[C@H](NC(=O)OC(C)(C)C)C4)nc3)n2)cn1]

tert-butyl (S)-(1-(5-(3-cyano-6-(1-methyl-1H-pyrazol-4-yl)pyrazolo[1,5-a]pyrazin-4-yl)pyridin-2-yl)piperidin-3-yl)carbamate A solution of 4-(6-fluoropyridin-3-yl)-6-(1-methyl-H-pyrazol-4-yl)pyrazolo[1,5-a]pyrazine-3-carbonitrile (Intermediate P7; 64 mg, 0.18 mmol) in DMA (10 mL) was treated with tert-butyl (S)-piperidin-3-ylcarbamate (111 mg, 0.553 mmol) and TEA (129 μL, 0.922 mmol) and stirred for 4 h at 60° C. After cooling to ambient temperature, the reaction mixture was purified by silica chromatography (using 0-100% Hexanes/EtOAc as the gradient eluent) to afford the title compound (74.3 mg, 77% yield). MS (apci) m/z=500.2 (M+H).

Example 106

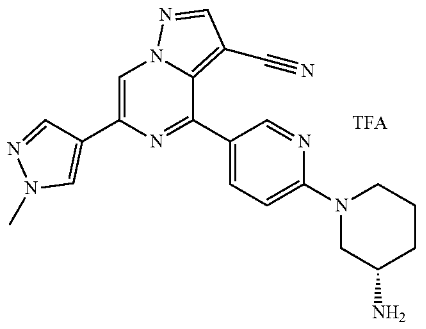 [SMILES: Cn1cc(-c2cn3ncc(C#N)c3c(-c3ccc(N4CCC[C@H](N)C4)nc3)n2)cn1 ; "TFA"]

(S)-4-(6-(3-aminopiperidin-1-yl)pyridin-3-yl)-6-(1-methyl-1H-pyrazol-4-yl)pyrazolo[1,5-a]pyrazine-3-carbonitrile 2,2,2-trifluoroacetate A solution of tert-butyl (S)-(1-(5-(3-cyano-6-(1-methyl-1H-pyrazol-4-yl)pyrazolo[1,5-a]pyrazin-4-yl)pyridin-2-yl)piperidin-3-yl)carbamate (Example 105; 42.8 mg, 0.0857 mmol) in DCM (85.7 μL) was treated dropwise with TFA (66.0 μL, 0.857 mmol). The resulting mixture was stirred for 1 h at ambient temperature and then concentrated in vacuo overnight to afford the title compound as the TFA salt (43 mg, 74% yield). MS (apci) m/z=400.0 (M+H).

Example 107

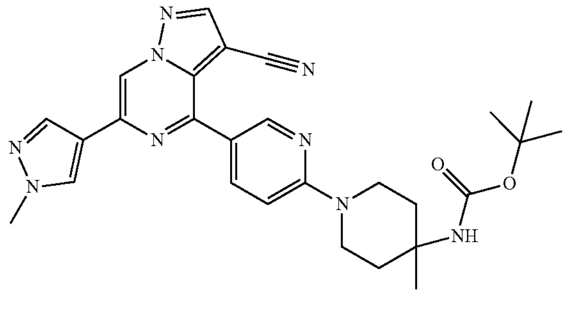 [SMILES: Cn1cc(-c2cn3ncc(C#N)c3c(-c3ccc(N4CCC(C)(NC(=O)OC(C)(C)C)CC4)nc3)n2)cn1]

tert-butyl (1-(5-(3-cyano-6-(1-methyl-1H-pyrazol-4-yl)pyrazolo[1,5-a]pyrazin-4-yl)pyridin-2-yl)-4-methylpiperidin-4-yl)carbamate A solution of 4-(6-fluoropyridin-3-yl)-6-(1-methyl-H-pyrazol-4-yl)pyrazolo[1,5-a]pyrazine-3-carbonitrile (Intermediate P7; 252.1 mg, 0.7895 mmol) in DMSO (1 mL) was treated with 4-(pyridin-2-ylmethyl)piperidin-4-ol (64.3 mg, 0.334 mmol) and $Cs_2CO_{3(s)}$ (1.80 g, 5.53 mmol) then stirred overnight at 60° C. After cooling to ambient temperature, the reaction mixture was diluted with water, and extracted with DCM (4×). The combined organic extracts were dried over anhydrous $Na_2SO_{4(s)}$, filtered, and concentrated in vacuo. The residue was purified by silica chromatography (using 0-100% Hexanes/EtOAc as the gradient eluent) to afford the title compound (271.8 mg, 62% yield). MS (apci) m/z=514.2 (M+H).

Example 108

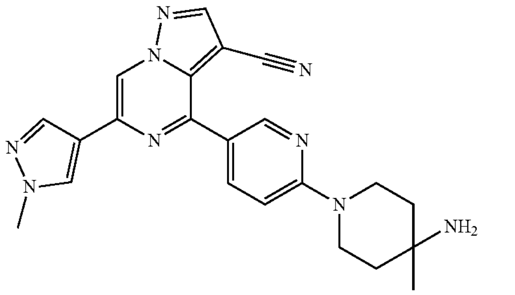 [SMILES: Cn1cc(-c2cn3ncc(C#N)c3c(-c3ccc(N4CCC(C)(N)CC4)nc3)n2)cn1]

4-(6-(4-amino-4-methylpiperidin-1-yl)pyridin-3-yl)-6-(1-methyl-1H-pyrazol-4-yl)pyrazolo[1,5-a]pyrazine-3-carbonitrile A solution of tert-butyl (1-(5-(3-cyano-6-(1-methyl-1H-pyrazol-4-yl)pyrazolo[1,5-a]pyrazin-4-yl)pyridin-2-yl)-4-methylpiperidin-4-yl)carbamate (Example 105; 250 mg, 0.487 mmol) in DCM (4 mL) and treated with TFA (4 mL, 0.487 mmol). The reaction mixture was stirred for 4 d at ambient temperature and then concentrated in vacuo. The residue was dissolved in DCM and washed with saturated $NaHCO_{3(aq)}$. The aqueous extracts were extracted with DCM. The combined organic extracts were dried over anhydrous $Na_2SO_{4(s)}$, filtered, and concentrated in vacuo to afford the title compound (25.9 mg, 12% yield). MS (apci) m/z=414.2 (M+H).

Example 109

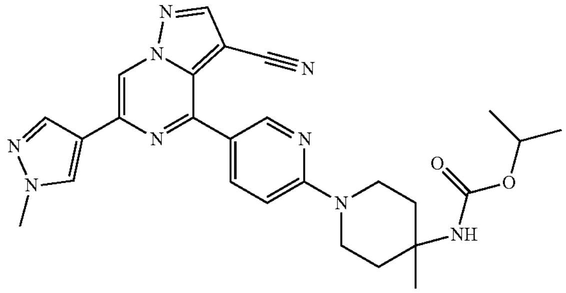 [SMILES: CC(C)OC(=O)NC1(C)CCN(c2ccc(-c3nc(-c4cnn(C)c4)cn4ncc(C#N)c34)cn2)CC1]

isopropyl (1-(5-(3-cyano-6-(1-methyl-1H-pyrazol-4-yl)pyrazolo[1,5-a]pyrazin-4-yl)pyridin-2-yl)-4-methylpiperidin-4-yl)carbamate A solution of 4-(6-(4-amino-4-methylpiperidin-1-yl)pyridin-3-yl)-6-(1-methyl-1H-pyrazol-4-yl)pyrazolo[1,5-a]pyrazine-3-carbonitrile (Example 108; 6.5 mg, 0.016 mmol) and DIEA (4.06 mg, 0.0314 mmol) was dissolved in DCM (500 μL) and treated with isopropyl carbonochloridate (2.31 mg, 0.0189 mmol). The reaction mixture was stirred overnight at ambient temperature. The residue was treated with iPrOH and stirred at 60° C. for 3 h. The reaction mixture was cooled to ambient temperature, concentrated in vacuo and purified by silica chromatography (using 0-100% Hexanes/EtOAc as the gradient eluent) to afford the title compound (5.3 mg, 68% yield). MS (apci) m/z=500.2 (M+H).

Example 110

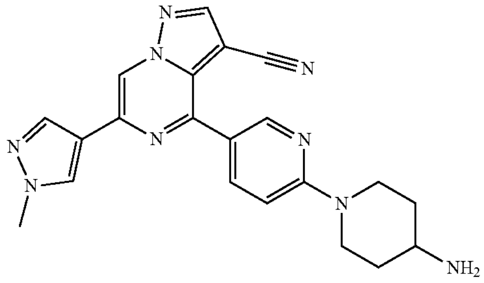 [SMILES: Cn1cc(-c2cn3ncc(C#N)c3c(-c3ccc(N4CCC(N)CC4)nc3)n2)cn1]

4-(6-(4-aminopiperidin-1-yl)pyridin-3-yl)-6-(1-methyl-1H-pyrazol-4-yl)pyrazolo[1,5-a]pyrazine-3-carbonitrile Step 1: Preparation of tert-butyl (1-(5-(3-cyano-6-(1-methyl-1H-pyrazol-4-yl)pyrazolo[1,5-a]pyrazin-4-yl)pyridin-2-yl)piperidin-4-yl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1054 g, 0.3301 mmol) in DMSO (6.6 mL) was treated with tert-butyl piperidin-4-ylcarbamate (0.2644 g, 1.320 mmol) and $K_2CO_{3(s)}$ (0.1825 g, 1.320 mmol) then stirred 3 d at 110° C. After cooling to ambient temperature, the reaction mixture was diluted with water (10 mL), and extracted with DCM (2×20 mL). The combined organic extracts were dried over anhydrous $MgSO_{4(s)}$, filtered, and concentrated in vacuo. The residue was purified by silica chromatography (using 0-100% EtOAc/Hexanes as the gradient eluent). Fractions containing the desired product were concentrated in vacuo, then suspended in water (to remove residual DMSO), filtered and dried in vacuo to afford the title compound (115.2 mg, 70% yield). MS (apci) m/z=500.3 (M+H).

Step 2: Preparation of 4-(6-(4-aminopiperidin-1-yl)pyridin-3-yl)-6-(1-methyl-1H-pyrazol-4-yl)pyrazolo[1,5-a]pyrazine-3-carbonitrile A solution of tert-butyl (1-(5-(3-cyano-6-(1-methyl-1H-pyrazol-4-yl)pyrazolo[1,5-a]pyrazin-4-yl)pyridin-2-yl)piperidin-4-yl)carbamate (Step 1; 0.1152 g, 0.2306 mmol) was dissolved in $CHCl_3$ (3.1 mL) and treated with 5 M HCl in iPrOH (0.23 mL, 1.2 mmol). The reaction mixture was stirred for 8 h at ambient temperature and then concentrated in vacuo. The residue was dissolved in DCM and washed with saturated $Na_2CO_{3(aq)}$. The aqueous extracts were extracted with DCM (2×40 mL). The combined organic extracts were dried over anhydrous $MgSO_{4(s)}$, filtered, and concentrated in vacuo to afford the title compound (20 mg, 22% yield). MS (apci) m/z=400.2 (M+H).

Example 111

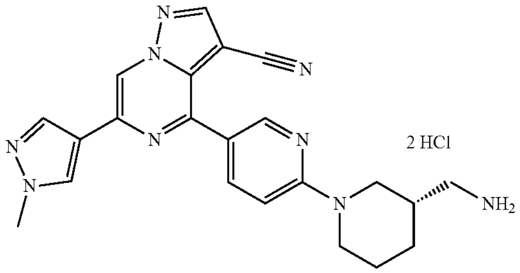 [SMILES: Cn1cc(-c2cn3ncc(C#N)c3c(-c3ccc(N4CCC[C@@H](CN)C4)nc3)n2)cn1]

(S)-4-(6-(3-(aminomethyl)piperidin-1-yl)pyridin-3-yl)-6-(1-methyl-1H-pyrazol-4-yl)pyrazolo[1,5-a]pyrazine-3-carbonitrile dihydrochloride Step 1: Preparation of tert-butyl (S)-((1-(5-(3-cyano-6-(1-methyl-1H-pyrazol-4-yl)pyrazolo[1,5-a]pyrazin-4-yl)pyridin-2-yl)piperidin-3-yl)methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1007 g, 0.3154 mmol) in DMSO (6.3 mL) was treated with tert-butyl (R)-(piperidin-3-ylmethyl)carbamate (0.2703 g, 1.261 mmol) and $K_2CO_{3(s)}$ (0.1743 g, 1.261 mmol) and stirred for 30 min at 110° C. After cooling to ambient temperature, the reaction mixture was diluted with water (50 mL) and stirred for 1 h before filtering to afford the title compound (0.1527 mg, 94% yield). MS (apci) m/z=514.3 (M+H).

Step 2: Preparation of (S)-4-(6-(3-(aminomethyl)piperidin-1-yl)pyridin-3-yl)-6-(1-methyl-1H-pyrazol-4-yl)pyrazolo[1,5-a]pyrazine-3-carbonitrile dihydrochloride A solution of tert-butyl (S)-((1-(5-(3-cyano-6-(1-methyl-1H-pyrazol-4-yl)pyrazolo[1,5-a]pyrazin-4-yl)pyridin-2-yl)piperidin-3-yl)methyl)carbamate (Step 1; 0.1527 g, 0.2973 mmol) was dissolved in $CHCl_3$ (4.0 mL) and treated with 5 M HCl in iPrOH (0.30 mL, 1.5 mmol). The resulting mixture was stirred 4 h at ambient temperature and then concentrated in vacuo to afford the title compound (0.1633 g, quantitative yield). MS (apci) m/z=414.2 (M+H).

Example 112

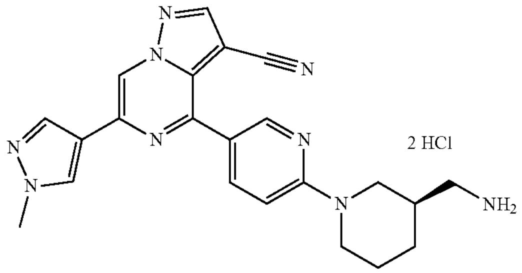 [SMILES: Cn1cc(-c2cn3ncc(C#N)c3c(-c3ccc(N4CCC[C@H](CN)C4)nc3)n2)cn1]

(R)-4-(6-(3-(aminomethyl)piperidin-1-yl)pyridin-3-yl)-6-(1-methyl-1H-pyrazol-4-yl)pyrazolo[1,5-a]pyrazine-3-carbonitrile dihydrochloride Step 1: Preparation of tert-butyl (R)-((1-(5-(3-cyano-6-(1-methyl-1H-pyrazol-4-yl)pyrazolo[1,5-a]pyrazin-4-yl)pyridin-2-yl)piperidin-3-yl)methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1003 g, 0.3141 mmol) in DMSO (6.3 mL) was treated with tert-butyl (S)-(piperidin-3-ylmethyl)carbamate (0.2693 g, 1.256 mmol) and $K_2CO_{3(s)}$ (0.1737 g, 1.256 mmol) then stirred 30 min at 110° C. After cooling to ambient temperature, the reaction mixture was diluted with water (50 mL), and stirred for 1 h before filtering to afford the title compound (0.1381 mg, 86% yield). MS (apci) m/z=514.3 (M+H).

Step 2: Preparation of (R)-4-(6-(3-(aminomethyl)piperidin-1-yl)pyridin-3-yl)-6-(1-methyl-1H-pyrazol-4-yl)pyrazolo[1,5-a]pyrazine-3-carbonitrile dihydrochloride A solution of tert-butyl (R)-((1-(5-(3-cyano-6-(1-methyl-1H-pyrazol-4-yl)pyrazolo[1,5-a]pyrazin-4-yl)pyridin-2-yl)

piperidin-3-yl)methyl)carbamate (Step 1; 0.1381 g, 0.2689 mmol) was dissolved in $CHCl_3$ (3.6 mL) and treated with 5 M HCl in iPrOH (0.27 mL, 1.3 mmol). The resulting mixture was stirred 4 h at ambient temperature and then concentrated in vacuo to afford the title compound (0.1425 g, quantitative yield). MS (apci) m/z=414.2 (M+H).

Example 113

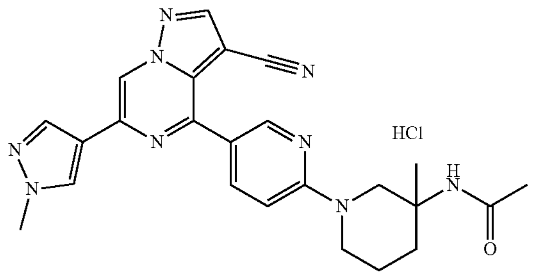 [SMILES: CC(=O)NC1(C)CCCN(c2ccc(-c3nc(-c4cnn(C)c4)cn4ncc(C#N)c34)cn2)C1 ; Cl]

N-(1-(5-(3-cyano-6-(1-methyl-1H-pyrazol-4-yl)pyrazolo[1,5-a]pyrazin-4-yl)pyridin-2-yl)-3-methylpiperidin-3-yl)acetamide hydrochloride Step 1: Preparation of N-(1-(5-(3-cyano-6-(1-methyl-1H-pyrazol-4-yl)pyrazolo[1,5-a]pyrazin-4-yl)pyridin-2-yl)-3-methylpiperidin-3-yl)acetamide A solution of 4-(6-fluoropyridin-3-yl)-6-(1-methyl-1H-pyrazol-4-yl)pyrazolo[1,5-a]pyrazine-3-carbonitrile (Intermediate P7; 0.0.035 g, 0.110 mmol) in DMSO (2.19 mL) was treated with N-(3-methylpiperidin-3-yl)acetamide 2,2,2-trifluoroacetate (Intermediate R8; 68.5 mg, 0.438 mmol) and $K_2CO_{3(s)}$ (0.0606 g, 0.438 mmol) and stirred overnight at 110° C. After cooling to ambient temperature, the reaction mixture was diluted with water (50 mL), and stirred for 1 h before filtering to afford the title compound (0.0432 mg, 87% yield). MS (apci) m/z=456.2 (M+H).

Step 2: Preparation of N-(1-(5-(3-cyano-6-(1-methyl-1H-pyrazol-4-yl)pyrazolo[1,5-a]pyrazin-4-yl)pyridin-2-yl)-3-methylpiperidin-3-yl)acetamide hydrochloride A solution of N-(1-(5-(3-cyano-6-(1-methyl-1H-pyrazol-4-yl)pyrazolo[1,5-a]pyrazin-4-yl)pyridin-2-yl)-3-methylpiperidin-3-yl)acetamide (Step 1; 0.0432 g, 0.0948 mmol) was dissolved in $CHCl_3$ (1.3 mL), and treated with 5 M HCl in iPrOH (0.09 mL, 0.47 mmol). The resulting mixture was stirred 4 h at ambient temperature and then concentrated in vacuo to afford the title compound (0.043 g, 75% yield). MS (apci) m/z=456.2 (M+H).

Example 114

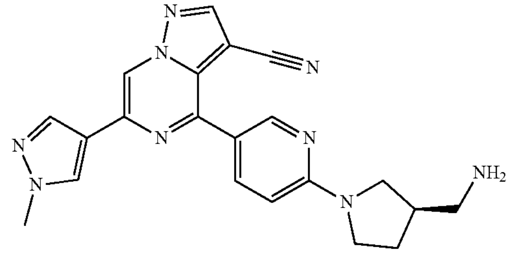 [SMILES: Cn1cc(-c2cn3ncc(C#N)c3c(-c3ccc(N4CC[C@H](CN)C4)nc3)n2)cn1]

(R)-4-(6-(3-(aminomethyl)pyrrolidin-1-yl)pyridin-3-yl)-6-(1-methyl-1H-pyrazol-4-yl)pyrazolo[1,5-a]pyrazine-3-carbonitrile Step 1: Preparation of tert-butyl (R)-((1-(5-(3-cyano-6-(1-methyl-1H-pyrazol-4-yl)pyrazolo[1,5-a]pyrazin-4-yl)pyridin-2-yl)pyrrolidin-3-yl)methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1019 g, 0.3191 mmol) in DMSO (6.4 mL) was treated with tert-butyl (S)-(pyrrolidin-3-ylmethyl)carbamate (0.2557 g, 1.277 mmol) and $K_2CO_{3(s)}$ (0.1767 g, 1.277 mmol) and stirred 3 d at 110° C. After cooling to ambient temperature, the reaction mixture was diluted with water (10 mL), and extracted with DCM (2×20 mL). The combined organic extracts were dried over anhydrous $MgSO_{4(s)}$, filtered, and concentrated in vacuo. The residue was purified by silica chromatography (using 0-100% EtOAc/Hexanes as the gradient eluent). Fractions containing the desired product were concentrated in vacuo, then suspended in water (to remove residual DMSO), filtered and dried in vacuo to afford the title compound (67 mg, 42% yield). MS (apci) m/z=500.2 (M+H).

Step 2: Preparation of (R)-4-(6-(3-(aminomethyl)pyrrolidin-1-yl)pyridin-3-yl)-6-(1-methyl-1H-pyrazol-4-yl)pyrazolo[1,5-a]pyrazine-3-carbonitrile A solution of tert-butyl (R)-((1-(5-(3-cyano-6-(1-methyl-1H-pyrazol-4-yl)pyrazolo[1,5-a]pyrazin-4-yl)pyridin-2-yl)pyrrolidin-3-yl)methyl)carbamate (Step 1; 0.1019 g, 0.2040 mmol) was dissolved in $CHCl_3$ (2.7 mL) and treated with 5 M HCl in iPrOH (0.20 mL, 1.0 mmol). The reaction mixture was stirred 4 h at ambient temperature and then concentrated in vacuo. The residue was dissolved in DCM then washed with saturated $Na_2CO_{3(aq)}$. The aqueous extracts were extracted with DCM (2×40 mL). The combined organic extracts were dried over anhydrous $MgSO_{4(s)}$, filtered, and concentrated in vacuo to afford the title compound (5.7 mg, 7% yield). MS (apci) m/z=400.2 (M+H).

Example 115

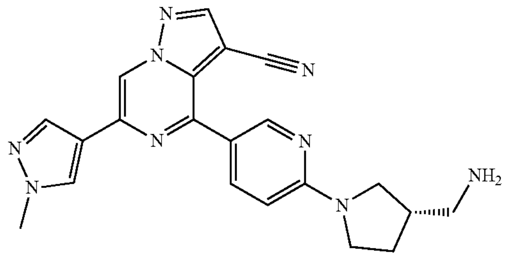 [SMILES: Cn1cc(-c2cn3ncc(C#N)c3c(-c3ccc(N4CC[C@@H](CN)C4)nc3)n2)cn1]

(S)-4-(6-(3-(aminomethyl)pyrrolidin-1-yl)pyridin-3-yl)-6-(1-methyl-1H-pyrazol-4-yl)pyrazolo[1,5-a]pyrazine-3-carbonitrile Step 1: Preparation of tert-butyl (S)-((1-(5-(3-cyano-6-(1-methyl-1H-pyrazol-4-yl)pyrazolo[1,5-a]pyrazin-4-yl)pyridin-2-yl)pyrrolidin-3-yl)methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1020 g, 0.3194 mmol) in DMSO (6.4 mL) was treated with tert-butyl (R)-(pyrrolidin-3-ylmethyl)carbamate (0.2559 g, 1.278 mmol) and $K_2CO_{3(s)}$ (0.1766 g, 1.278 mmol) then stirred 3 d at 110° C. After cooling to ambient temperature, the reaction mixture was diluted with water (10 mL), and extracted with DCM (2×20 mL). The combined organic extracts were dried over anhydrous $MgSO_{4(s)}$, filtered, and concentrated in vacuo. The residue was purified by silica chromatography (using 0-100% EtOAc/Hexanes as the gradient eluent). Fractions containing the desired product were concentrated in vacuo, then suspended in water (to remove residual DMSO), filtered and dried in vacuo to afford the title compound (76.7 mg, 48% yield). MS (apci) m/z=500.2 (M+H).

Step 2: Preparation of (S)-4-(6-(3-(aminomethyl)pyrrolidin-1-yl)pyridin-3-yl)-6-(1-methyl-1H-pyrazol-4-yl)pyrazolo[1,5-a]pyrazine-3-carbonitrile A solution of tert-butyl (S)-((1-(5-(3-cyano-6-(1-methyl-1H-pyrazol-4-yl)pyrazolo[1,5-a]pyrazin-4-yl)pyridin-2-yl)pyrrolidin-3-yl)methyl)carbamate (Step 1; 0.0767 g, 0.1535 mmol) was dissolved in $CHCl_3$ (2.0 mL) and treated with 5 M HCl in iPrOH (0.15 mL, 0.77 mmol). The reaction mixture was stirred 4 h at ambient temperature and then concentrated in vacuo. The residue was dissolved in DCM then washed with saturated $Na_2CO_{3(aq)}$. The aqueous extracts were extracted with DCM (2×40 mL). The combined organic extracts were dried over anhydrous $MgSO_{4(s)}$, filtered, and concentrated in vacuo to afford the title compound (18.9 mg, 31% yield). MS (apci) m/z=400.2 (M+H).

Example 116

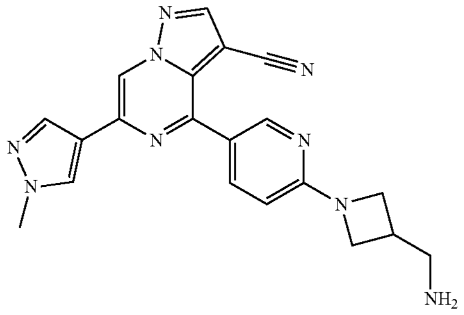 [SMILES: Cn1cc(-c2cn3ncc(C#N)c3c(-c3ccc(N4CC(CN)C4)nc3)n2)cn1]

4-(6-(3-(aminomethyl)azetidin-1-yl)pyridin-3-yl)-6-(1-methyl-1H-pyrazol-4-yl)pyrazolo[1,5-a]pyrazine-3-carbonitrile Step 1: Preparation of tert-butyl ((1-(5-(3-cyano-6-(1-methyl-1H-pyrazol-4-yl)pyrazolo[1,5-a]pyrazin-4-yl)pyridin-2-yl)azetidin-3-yl)methyl)carbamate A solution of 4-(6-fluoropyridin-3-yl)-6-(1-methyl-1H-pyrazol-4-yl)pyrazolo[1,5-a]pyrazine-3-carbonitrile (Intermediate P7; 0.1014 g, 0.3176 mmol) in DMSO (6.4 mL) was treated with tert-butyl (azetidin-3-ylmethyl)carbamate (0.2366 g, 1.270 mmol) and $K_2CO_{3(s)}$ (0.1756 g, 1.270 mmol) and stirred 3 d at 110° C. After cooling to ambient temperature, the reaction mixture was diluted with water (10 mL), and extracted with DCM (2×20 mL). The combined organic extracts were dried over anhydrous $MgSO_{4(s)}$, filtered, and concentrated in vacuo. The residue was purified by silica chromatography (using 0-100% EtOAc/Hexanes as the gradient eluent). Fractions containing the desired product were concentrated in vacuo, then suspended in water (to remove residual DMSO), filtered and dried in vacuo to afford the title compound (97.1 mg, 63% yield). MS (apci) m/z=486.3 (M+H).

Step 2: Preparation of 4-(6-(3-(aminomethyl)azetidin-1-yl)pyridin-3-yl)-6-(1-methyl-1H-pyrazol-4-yl)pyrazolo[1,5-a]pyrazine-3-carbonitrile A solution of tert-butyl ((1-(5-(3-cyano-6-(1-methyl-1H-pyrazol-4-yl)pyrazolo[1,5-a]pyrazin-4-yl)pyridin-2-yl)azetidin-3-yl)methyl)carbamate (Step 1; 97 mg, 0.2 mmol) was dissolved in $CHCl_3$ (2.9 mL) and treated with 5 M HCl in iPrOH (0.21 mL, 1.1 mmol). The reaction mixture was stirred 4 h at ambient temperature and then concentrated in vacuo. The residue was dissolved in DCM and washed with saturated $Na_2CO_{3(aq)}$. The aqueous extracts were extracted with DCM (2×40 mL). The combined organic extracts were dried over anhydrous $MgSO_{4(s)}$, filtered, and concentrated in vacuo to afford the title compound (82.6 mg, 13% yield). MS (apci) m/z=386.2 (M+H).

Example 117

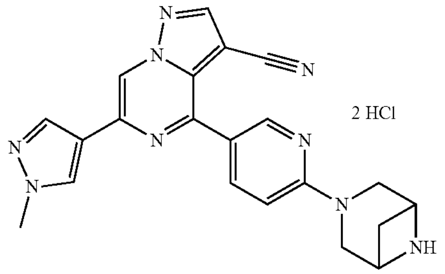 [SMILES: Cn1cc(-c2cn3ncc(C#N)c3c(-c3ccc(N4CC5CC(C4)N5)nc3)n2)cn1]

4-(6-(3,6-diazabicyclo[3.1.1]heptan-3-yl)pyridin-3-yl)-6-(1-methyl-1H-pyrazol-4-yl)pyrazolo[1,5-a]pyrazine-3-carbonitrile dihydrochloride Step 1: Preparation of tert-butyl 3-(5-(3-cyano-6-(1-methyl-1H-pyrazol-4-yl)pyrazolo[1,5-a]pyrazin-4-yl)pyridin-2-yl)-3,6-diazabicyclo[3.1.1]heptane-6-carboxylate In a pressure vessel, a mixture of 4-chloro-6-(1-methyl-1H-pyrazol-4-yl)pyrazolo[1,5-a]pyrazine-3-carbonitrile (Intermediate P2; 0.045 g, 0.17 mmol) and (6-(6-(tert-butoxycarbonyl)-3,6-diazabicyclo[3.1.1]heptan-3-yl)pyridin-3-yl)boronic acid (Intermediate R11; 0.06 g, 0.19 mmol) in 1,4-dioxane (2 mL) and 2 N $Na_2CO_{3(aq)}$ (0.75 mL, 1.0 mmol) was treated with $Pd(PPh_3)_4$ (6 mg, 0.005 mmol) and sparged with $N_{2(g)}$ for 15 min. The vessel was sealed and mixture was stirred overnight at 90° C. After cooling to ambient temperature, the mixture was diluted with water (3 mL) and DCM (8 mL), then stirred for 2 h at ambient temperature. The resulting biphasic mixture was extracted with additional DCM (3×) and the combined organic extracts were dried over anhydrous $MgSO_{4(s)}$, filtered, and concentrated in vacuo. The residue was suspended in $Et_2O$ (20 mL), and the suspension was stirred for 30 min at ambient temperature. The slurry was filtered, and the solids were dissolved in DCM for purification by silica chromatography (using 50-100% EtOAc/Hexanes as the gradient eluent) to cleanly afford the title compound (30 mg, 35% yield). MS (apci) m/z=498.2 (M+H).

Step 2: Preparation of 6-(1-methyl-1H-pyrazol-4-yl)-4-(6-(piperazin-1-yl)pyridin-3-yl)pyrazolo[1,5-a]pyrazine-3-carbonitrile A solution of tert-butyl 3-(5-(3-cyano-6-(1-methyl-1H-pyrazol-4-yl)pyrazolo[1,5-a]pyrazin-4-yl)pyridin-2-yl)-3,6-diazabicyclo[3.1.1]heptane-6-carboxylate (Step 1; 30 mg, 0.060 mmol) in DCM (5 mL) was treated with 5 M HCl in iPrOH (0.1 mL, 0.30 mmol) and stirred overnight at ambient temperature. The resulting mixture was concentrated in vacuo to cleanly afford the title compound (33 mg, quantitative yield). MS (apci) m/z=398.2 (M+H).

Example 118

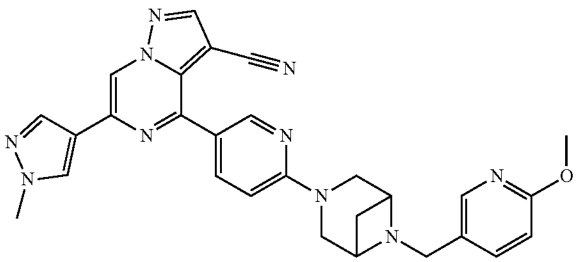 [SMILES: COc1ccc(CN2C3CC2CN(c2ccc(-c4nc(-c5cnn(C)c5)cn5ncc(C#N)c45)cn2)C3)cn1]

4-(6-(6-((6-methoxypyridin-3-yl)methyl)-3,6-diazabicyclo[3.1.1]heptan-3-yl)pyridin-3-yl)-6-(1-methyl-1H-pyrazol-4-yl)pyrazolo[1,5-a]pyrazine-3-carbonitrile A solution of 4-(6-(3,6-diazabicyclo[3.1.1]heptan-3-yl)pyridin-3-yl)-6-(1-methyl-1H-pyrazol-4-yl)pyrazolo[1,5-a]pyrazine-3-carbonitrile dihydrochloride (Example 117; 30 mg, 0.064 mmol) in DMA (1 mL) was treated sequentially with 6-methoxynicotinaldehyde (13 mg, 0.096 mmol) and $NaBH(AcO)_3$ (20 mg, 0.096 mmol). After stirring the mixture for 3 d at ambient temperature, additional 6-methoxynicotinaldehyde (8.7 mg, 0.064 mmol) and $NaBH(AcO)_3$ (13.3 mg, 0.064 mmol) were introduced along with TEA (30 μL, 0.41 mmol). The resulting mixture stirred until complete by LCMS at which point the reaction mixture was quenched with water and extracted with DCM (3×). The combined organic extracts were dried over anhydrous $Na_2SO_{4(s)}$, filtered, and concentrated in vacuo. The residue was purified first by C18 reverse phase chromatography (using 20-80% ACN/water as the gradient eluent) then by silica chromatography (using 0-25% MeOH/EtOAc as the gradient eluent) to cleanly afford the title compound (1.3 mg, 4% yield). MS (apci) m/z=519.0 (M+H).

Examples 119 and 120 tert-butyl ((1R,5S,6r)-3-(5-(3-cyano-6-(1-methyl-1H-pyrazol-4-yl)pyrazolo[1,5-a]pyrazin-4-yl)pyridin-2-yl)-3-azabicyclo[3.1.1]heptan-6-yl)carbamate (Ex. 119) and 4-(6-((1R,5S,6r)-6-amino-3-azabicyclo[3.1.1]heptan-3-yl)pyridin-3-yl)-6-(1-methyl-1H-pyrazol-4-yl)pyrazolo[1,5-a]pyrazine-3-carbonitrile (Ex. 120

Ex. 119

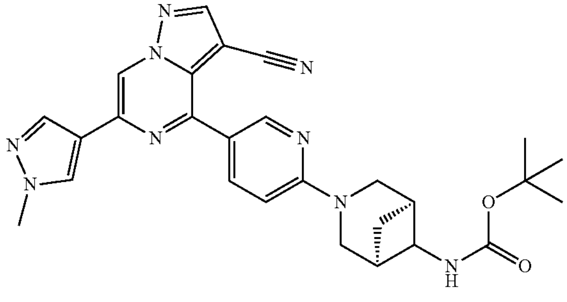

-continued

Ex. 120

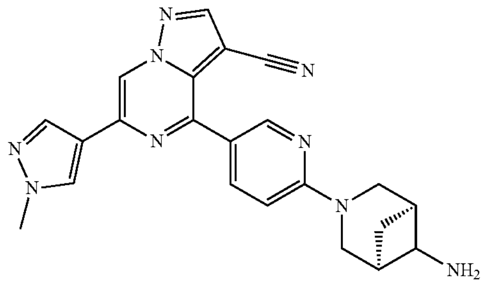

A suspension of 4-(6-fluoropyridin-3-yl)-6-(1-methyl-1H-pyrazol-4-yl)pyrazolo[1,5-a]pyrazine-3-carbonitrile (Intermediate P7; 30 mg, 0.094 mmol), tert-butyl ((1R,5S,6r)-3-azabicyclo[3.1.1]heptan-6-yl)carbamate (24 mg, 0.11 mmol) and $Cs_2CO_{3(s)}$ (153 mg, 0.47 mmol) in DMSO (0.5 mL) was stirred overnight at 90° C. in a sealed pressure vessel. After cooling to ambient temperature, the reaction mixture was poured into 2 N $NaOH_{(aq)}$ (2 mL), and extracted in a PS frit with 10% iPrOH in DCM (2×5 mL). The combined organic extracts were concentrated in vacuo and the residue was purified by C18 reverse phase chromatography (using 0-60% ACN/water as the gradient eluent) to afford the title compounds:

Peak 2: Example 119: tert-butyl ((1R,5S,6r)-3-(5-(3-cyano-6-(1-methyl-1H-pyrazol-4-yl)pyrazolo[1,5-a]pyrazin-4-yl)pyridin-2-yl)-3-azabicyclo[3.1.1]heptan-6-yl)carbamate (15 mg, 31% yield). MS (apci) m/z=512.2 (M+H).

Peak 1: Example 120: 4-(6-((1R,5S,6r)-6-amino-3-azabicyclo[3.1.1]heptan-3-yl)pyridin-3-yl)-6-(1-methyl-1H-pyrazol-4-yl)pyrazolo[1,5-a]pyrazine-3-carbonitrile (17 mg, 44% yield). MS (apci) m/z=412.2 (M+H).

Example 121

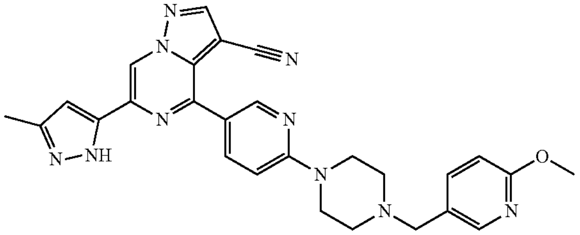

4-(6-(4-((6-methoxypyridin-3-yl)methyl)piperazin-1-yl)pyridin-3-yl)-6-(3-methyl-1H-pyrazol-5-yl)pyrazolo[1,5-a]pyrazine-3-carbonitrile A mixture of 6-bromo-4-(6-(4-((6-methoxypyridin-3-yl)methyl)piperazin-1-yl)pyridin-3-yl)pyrazolo[1,5-a]pyrazine-3-carbonitrile (Intermediate P9; 58 mg, 0.11 mmol), 3-methyl-5-(4,4,5,5-tetramethyl-1,3,2-dioxaborolan-2-yl)-1H-pyrazole (0.029 g, 0.14 mmol), 2 M $Na_2CO_{3(aq)}$ (0.13 mL, 0.25 mmol) and $Pd(PPh_3)_4$ (13 mg, 0.011 mmol) were suspended in 1,4-dioxane (1.1 mL). The resulting mixture was sparged with $Ar_{(g)}$ for 15 min, then sealed and stirred overnight at 90° C. After cooling to ambient temperature, the reaction mixture was partitioned between DCM and water, and the combined organic extracts were washed sequentially with water and brine. The combined organic extracts were dried over anhydrous $Na_2SO_{4(s)}$, filtered, and concentrated in vacuo. The crude residue was purified by C18 reverse phase chromatography (using 0-60% ACN/water as the gradient eluent) to afford the TFA salt of the title compound. The TFA salt was suspended in DCM and washed with saturated $Na_2CO_{3(s)}$. The resulting organic extracts were dried over anhydrous $Na_2SO_{4(s)}$, filtered, and concentrated in vacuo to cleanly afford the title compound (17 mg, 29% yield). MS (apci) m/z=507.3 (M+H).

ABBREVIATIONS

| | |
|---|---|
| ACN | Acetonitrile |
| Boc-anhydride | di-tert-butyl dicarbonate |
| $Cu(OAc)_2$ | Copper diacetate |
| d | day, days |
| DCE | 1,2-Dichloroethane |
| DCM | Dichloromethane |
| DIEA | N,N-Diisopropylethylamine |
| DI water | Deionized water |
| DMA | N,N-Dimethylacetamide |
| DMAP | 4-Dimethylaminopyridine |
| DME | 1,2-Dimethoxyethane |
| DMF | N,N-Dimethylformamide |
| DMSO | Dimethylsulfoxide |
| EDC-HCl | 1-Ethyl-3-(3-dimethylaminopropyl)carbodiimide hydrochloride |
| $Et_2O$ | Diethyl Ether |
| EtOAc | Ethyl Acetate |
| EtOH | Ethanol |
| eq | equivalent |
| h | hour, hours |
| HATU | 1-[Bis(dimethylamino)methylene]-1H-1,2,3-triazolo[4,5-b]pyridinium 3-oxide hexafluorophosphate or 2-(7-Aza-1H-benzotriazole-1-yl)-1,1,3,3-tetramethyluronium hexafluorophosphate |
| HBTU | 3-[Bis(dimethylamino)methyliumyl]-3H-benzotriazol-1-oxide hexafluorophosphate or 2-(1H-benzotriazole-1-yl)-1,1,3,3-tetramethyluronium hexafluorophosphate |
| HOAc | Acetic Acid |
| iPrOH | Isopropanol |
| i-PrMgCl | Isopropyl magnesium chloride |
| KOAc | Potassium Acetate |
| LCMS | Liquid chromatography-mass spectrometry |
| MeOH | Methanol |
| $Me_4N(AcO)_3BH$ | Tetramethylammonium Triacetoxyborohydride |
| min | minute, minutes |
| MSH | o-(mesitylsulfonyl)hydroxylamine |
| MTBE | Methyl tert-Butyl Ether |
| NCS | N-Chlorosuccinimide |
| NBS | N-Bromosuccinimide |
| NIS | N-Iodosuccinimide |
| $NaBH(AcO)_3$ | Sodium Triacetoxyborohydride |
| $NH_4OAc$ | Ammonium Acetate |
| $Pd(PPh_3)_4$ | Tetrakis(triphenylphosphine)palladium (0) |
| $Pd_2(dba)_3$ | tris(dibenzylideneacetone)dipalladium (0) |
| $PdCl_2(dppf){\bullet}CH_2Cl_2$ | 1,1'-Bis(diphenylphosphino)ferrocene-palladium(II)dichloride dichloromethane complex |
| PPTS | Pyridinium p-toluenesulfonate |
| PS frit | Biotage ® "Isolute Phase Separators" |
| PS paper | Whatman ® silicone treated Phase Separators filter paper |
| PVDF (0.45 μm) disc | polyvinylidene difluoride membrane with a 0.45-micron pore size |
| rt | Room temperature |
| TEA | Triethylamine |
| TFA | Trifluoroacetic acid |
| THF | tetrahydrofuran |
| Triphosgene | (bis(trichloromethyl) carbonate |
| X-phos | dicyclohexyl(2',4',6'-triisopropyl-[1,1'-biphenyl]-2-yl)phosphine |

What is claimed is:

1. A compound of the Formula I:

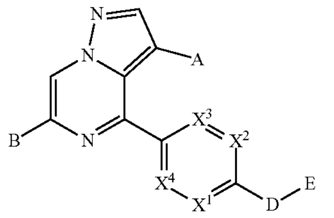

I or a pharmaceutically acceptable salt thereof, wherein:

$X^1$ is CH or N;

$X^2$ is CH;

$X^3$ is CH;

$X^4$ is CH;

A is H, Cl, or CN;

B is $hetAr^1$;

D is $hetCyc^1$ or $hetCyc^2$; and

E is selected from the group consisting of:

(i) C(O)—$C_1$-$C_6$ alkyl;

(r) C(O)-$hetCyc^4$;

(z) C(O)—$C_1$-$C_6$ alkylene-$Ar^2$; and (oo) $C_1$-$C_6$ alkylene-$hetAr^2$;

wherein $hetAr^1$ is pyrazolyl, optionally substituted with one or more substituents independently selected from the group consisting of $C_1$-$C_6$ alkyl, $C_1$-$C_6$ alkylene-O—$C_1$-$C_6$ alkyl, $C_1$-$C_6$ alkylene-$S(O)_2$—$C_1$-$C_6$ alkyl, $C_1$-$C_6$ alkylene-$HetCyc^a$, and $hetCyc^a$;

wherein each $C_1$-$C_6$ alkyl substituent of $hetAr^1$ is optionally and independently substituted with one, two, or three fluoro substituents;

wherein each $hetCyc^a$ substituent of $hetAr^1$ is independently a 4- to 6-membered heterocyclic ring comprising one ring heteroatom selected from the group consisting of nitrogen and oxygen;

wherein each $hetCyc^a$ substituent of $hetAr^1$ is optionally and independently substituted with one or more substituents independently selected from the group consisting of halogen, $C_1$-$C_6$ alkyl, $C_1$-$C_6$ alkylene-O—$C_1$-$C_6$ alkyl, C(O)—$CH_2N(C_1$-$C_3$ alkyl$)_2$, C(O)—$CH_2O$—$C_1$-$C_6$ alkyl, and C(O)—O—$C_1$-$C_6$ alkyl;

wherein $hetCyc^1$ is a 4- to 6-membered heterocyclic ring comprising one or two ring heteroatoms independently selected from the group consisting of nitrogen and oxygen;

wherein $hetCyc^2$ is optionally substituted with one oxo, one cycloalkylidene, or one or more independently selected $C_1$-$C_3$ alkyl substituents;

wherein each $C_1$-$C_3$ alkyl substituent of $hetCyc^1$ is optionally and independently substituted with one, two, or three fluoro substituents;

wherein $hetCyc^2$ is a 7- or 8-membered bridged heterocyclic ring comprising one, two, or three ring heteroatoms independently selected from the group consisting of nitrogen and oxygen;

wherein $hetCyc^2$ is optionally substituted with one or more independently selected $C_1$-$C_3$ alkyl substituents;

wherein $C_1$-$C_6$ alkyl of the C(O)—$C_1$-$C_6$ alkyl of E is optionally substituted with one NR'R", one —$CH_2$—NR'R", or one, two, or three fluoro substituents;

wherein R' of the NR'R" or —$CH_2$—NR'R" substituent of the $C_1$-$C_6$ alkyl of the C(O)—$C_1$-$C_6$ alkyl of E is H or $C_1$-$C_6$ alkyl;

wherein R" of the NR'R" or —$CH_2$—NR'R" substituent of the $C_1$-$C_6$ alkyl of the C(O)—$C_1$-$C_6$ alkyl of E is H or $C_1$-$C_6$ alkyl;

wherein $hetCyc^4$ of the C(O)-$hetCyc^4$ of E is selected from the group consisting of:

(a) a 4- to 6-membered heterocyclic ring comprising one or two ring heteroatoms or heteroatomic groups independently selected from the group consisting of nitrogen, oxygen, sulfur, and $S(O)_2$;

(b) a 7- or 8-membered bridged, heterocyclic ring comprising one or two ring heteroatoms independently selected from the group consisting of nitrogen and oxygen;

(c) a 6- to 12-membered fused, bicyclic, heterocyclic ring comprising one or two ring heteroatoms independently selected from the group consisting of nitrogen and oxygen; and (d) a 7- to 10-membered spirocyclic, heterocyclic ring comprising one or two ring heteroatoms independently selected from the group consisting of nitrogen and oxygen;

wherein $hetCyc^4$ of the C(O)-$hetCyc^4$ of E is optionally substituted with one or more substituents independently selected from the group consisting of halogen, CN, $C_1$-$C_6$ alkyl, $C_1$-$C_6$ alkylene-O—$C_1$-$C_6$ alkyl, C(O)—$C_1$-$C_6$ alkyl, OH, $OC_1$—$C_6$ alkyl, $C_3$-$C_6$ cycloalkyl, a 5- or 6-membered heterocyclic ring, and phenyl;

wherein each $C_1$-$C_6$ alkyl substituent of the $hetCyc^4$ of the C(O)-$hetCyc^4$ of E is optionally and independently substituted with one, two, or three fluoro substituents;

wherein each 5- or 6-membered heterocyclic ring substituent of the $hetCyc^4$ of the C(O)-$hetCyc^4$ of E comprises one or two ring heteroatoms independently selected from the group consisting of nitrogen and oxygen;

wherein each phenyl substituent of the $hetCyc^4$ of the C(O)-$hetCyc^4$ of E is optionally and independently substituted with one or more substituents independently selected from the group consisting of halogen, $C_1$-$C_6$ alkyl, and $OC_1$—$C_6$ alkyl;

wherein $C_1$-$C_6$ alkylene of the C(O)—$C_1$-$C_6$ alkylene-$Ar^2$ of E is optionally substituted with one 5- or 6-membered heterocyclic ring substituent or one or two substituents independently selected from the group consisting of $C_1$-$C_6$ alkyl, $C_1$-$C_3$ alkylene-$NR^eR^f$, $C_1$-$C_6$ alkylene-OH, $NR^eR^f$, OH, and $OC_1$—$C_6$ alkyl;

wherein the 5- or 6-membered heterocyclic ring substituent of the $C_1$-$C_6$ alkylene of the C(O)—$C_1$-$C_6$ alkylene-$Ar^2$ of E comprises one or two heteroatoms independently selected from the group consisting of nitrogen and oxygen;

wherein the 5- or 6-membered heterocyclic ring substituent of the $C_1$-$C_6$ alkylene of the C(O)—$C_1$-$C_6$ alkylene-$Ar^2$ of E is optionally substituted with one or more independently selected $C_1$-$C_6$ alkyl substituents;

wherein each $C_1$-$C_6$ alkyl substituent of the $C_1$-$C_6$ alkylene of the C(O)—$C_1$-$C_6$ alkylene-$Ar^2$ of E is optionally and independently substituted with one, two, or three fluoro substituents;

wherein each $R^e$ of each $C_1$-$C_3$ alkylene-$NR^eR^f$ or $NR^eR^f$ substituent of the $C_1$-$C_6$ alkylene of the C(O)—$C_1$-$C_6$ alkylene-$Ar^2$ of E is independently H or $C_1$-$C_6$ alkyl;

wherein each $R^f$ of each $C_1$-$C_3$ alkylene-$NR^eR^f$ or $NR^eR^f$ substituent of the $C_1$-$C_6$ alkylene of the C(O)—$C_1$-$C_6$ alkylene-$Ar^2$ of E is independently H or $C_1$-$C_6$ alkyl;

wherein $Ar^2$ of the C(O)—$C_1$-$C_6$ alkylene-$Ar^2$ of E is phenyl, optionally substituted with one or more substituents independently selected from the group consisting of halogen, CN, $C_1$-$C_6$ alkyl, $NR^iR^j$, $OC_1$—$C_6$ alkyl, and 5- or 6-membered heterocyclic ring;

wherein each $C_1$-$C_6$ alkyl and $OC_1$—$C_6$ alkyl substituent of the $Ar^2$ of the C(O)—$C_1$-$C_6$ alkylene-$Ar^2$ of E is optionally and independently substituted with one, two, or three fluoro substituents;

wherein each $R^i$ of each $NR^iR^j$ substituent of the $Ar^2$ of the C(O)—$C_1$-$C_6$ alkylene-$Ar^2$ of E is independently H or $C_1$-$C_6$ alkyl;

wherein each $R^j$ of each $NR^iR^j$ substituent of the $Ar^2$ of the C(O)—$C_1$-$C_6$ alkylene-$Ar^2$ of E is independently H or $C_1$-$C_6$ alkyl;

wherein the 5- or 6-membered heterocyclic ring substituent of the $Ar^2$ of the C(O)—$C_1$-$C_6$ alkylene-$Ar^2$ of E comprises one or two heteroatoms independently selected from the group consisting of nitrogen and oxygen;

wherein $hetAr^2$ of the $C_1$-$C_6$ alkylene-$hetAr^2$ of E is a 5- or 6-membered heteroaryl ring comprising one, two, or three heteroatoms independently selected from the group consisting of nitrogen, oxygen, and sulfur;

wherein $hetAr^2$ of the $C_1$-$C_6$ alkylene-$hetAr^2$ of E is optionally substituted with one or more substituents independently selected from the group consisting of halogen, CN, $C_1$-$C_6$ alkyl, $C_1$-$C_6$ alkyl-OH, $C_1$-$C_6$ alkylene-O—$C_1$-$C_6$ alkyl, NR'R", OH, $OC_1$—$C_6$ alkyl, and $C_3$-$C_6$ cycloalkyl;

wherein each $C_1$-$C_6$ alkyl and $OC_1$—$C_6$ alkyl substituent of the $hetAr^2$ of the $C_1$-$C_6$ alkylene-$hetAr^2$ of E is optionally and independently substituted with one, two, or three fluoro substituents;

wherein each R' of each NR'R" substituent of the $hetAr^2$ of the $C_1$-$C_6$ alkylene-$hetAr^2$ of E is independently H or $C_1$-$C_3$ alkyl; and wherein each R" of each NR'R" substituent of the $hetAr^2$ of the $C_1$-$C_6$ alkylene-$hetAr^2$ of E is independently H or $C_1$-$C_3$ alkyl.

2. The compound according to claim 1, or a pharmaceutically acceptable salt thereof, wherein A is H.

3. The compound according to claim 1, or a pharmaceutically acceptable salt thereof, wherein A is Cl.

4. The compound according to claim 1, or a pharmaceutically acceptable salt thereof, wherein A is CN.

5. The compound according to claim 1, or a pharmaceutically acceptable salt thereof, wherein $hetAr^1$ is pyrazolyl, optionally substituted with one or more independently selected C1-C6 alkyl substituents, wherein each $C_1$-$C_6$ alkyl substituent is optionally substituted with one, two, or three fluoro substituents.

6. The compound according to claim 1, or a pharmaceutically acceptable salt thereof, wherein D is $hetCyc^1$.

7. The compound according to claim 6, or a pharmaceutically acceptable salt thereof, wherein $hetCyc^2$ is selected from the group consisting of:

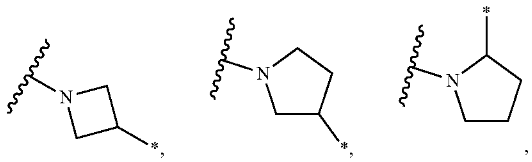

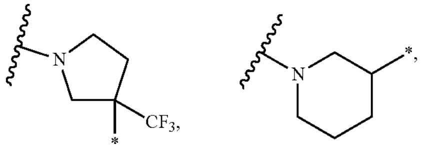

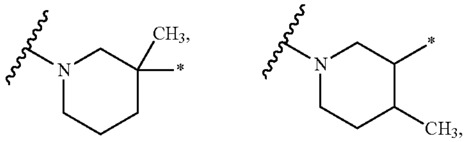

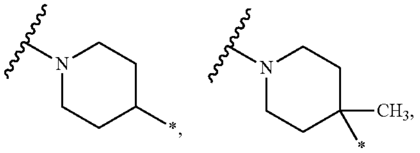

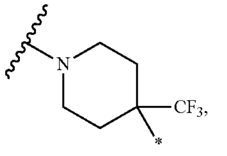

and

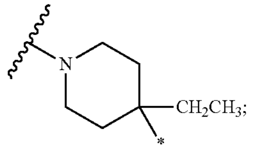

where the wavy line indicates the point of attachment to the ring comprising $X^1$, $X^2$, $X^3$, and $X^4$ and the asterisk indicates the point of attachment to E.

8. The compound according to claim 1, or a pharmaceutically acceptable salt thereof, wherein D is $hetCyc^2$.

9. The compound according to claim 8, or a pharmaceutically acceptable salt thereof, wherein $hetCyc^2$ is selected from the group consisting of:

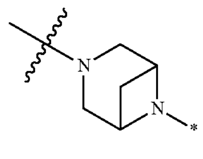

and

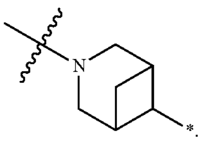

where the wavy line indicates the point of attachment to the ring comprising $X^1$, $X^2$, $X^3$, and $X^4$ and the asterisk indicates the point of attachment of E.

10. The compound according to claim 1, or a pharmaceutically acceptable salt thereof, wherein E is C(O)—$C_1$-$C_6$ alkyl;

wherein $C_1$-$C_6$ alkyl of the C(O)—$C_1$-$C_6$ alkyl of E is optionally substituted with one NR'R", one —$CH_2$—NR'R", or one, two, or three fluoro substituents;

wherein R' of the NR'R" substituent or the —$CH_2$—NR'R" substituent of the $C_1$-$C_6$ alkyl of the C(O)—$C_1$-$C_6$ alkyl of E is H or $C_1$-$C_6$ alkyl; and wherein R" of the NR'R" substituent or the —$CH_2$—NR'R" substituent of the $C_1$-$C_6$ alkyl of the C(O)—$C_1$-$C_6$ alkyl of E is H or $C_1$-$C_6$ alkyl.

11. The compound according to claim 1, or a pharmaceutically acceptable salt thereof, wherein E is C(O)—$C_1$-$C_6$ alkylene-$Ar^2$;

wherein $C_1$-$C_6$ alkylene of the C(O)—$C_1$-$C_6$ alkylene-$Ar^2$ of E is optionally substituted with one 5- or 6-membered heterocyclic ring substituent or one or two substituents independently selected from the group consisting of $C_1$-$C_6$ alkyl, $C_1$-$C_3$ alkylene-$NR^eR^f$, $C_1$-$C_6$ alkylene-OH, $NR^eR^f$, OH, and $OC_1$—$C_6$ alkyl;

wherein the 5- or 6-membered heterocyclic ring substituent of the $C_1$-$C_6$ alkylene of the C(O)—$C_1$-$C_6$ alkylene-$Ar^2$ of E comprises one or two heteroatoms independently selected from the group consisting of nitrogen and oxygen;

wherein the 5- or 6-membered heterocyclic ring substituent of the $C_1$-$C_6$ alkylene of the C(O)—$C_1$-$C_6$ alkylene-$Ar^2$ of E is optionally substituted with one or more independently selected $C_1$-$C_6$ alkyl substituents;

wherein each $C_1$-$C_6$ alkyl substituent of the $C_1$-$C_6$ alkylene of the C(O)—$C_1$-$C_6$ alkylene-$Ar^2$ of E is optionally and independently substituted with one, two, or three fluoro substituents;

wherein each $R^e$ of each $C_1$-$C_3$ alkylene-$NR^eR^f$ or $NR^eR^f$ substituent of the $C_1$-$C_6$ alkylene of the C(O)—$C_1$-$C_6$ alkylene-$Ar^2$ of E is independently H or $C_1$-$C_6$ alkyl; and wherein each $R^f$ of each $C_1$-$C_3$ alkylene-$NR^eR^f$ or $NR^eR^f$ substituent of the $C_1$-$C_6$ alkylene of the C(O)—$C_1$-$C_6$ alkylene-$Ar^2$ of E is independently H or $C_1$-$C_6$ alkyl.

12. A pharmaceutical composition comprising a pharmaceutically acceptable carrier or excipient and a compound according to claim 1, or a pharmaceutically acceptable salt thereof.

* * * * *

SEQUENCE LISTING

<160> NUMBER OF SEQ ID NOS: 1

<210> SEQ ID NO 1
<211> LENGTH: 1114
<212> TYPE: PRT
<213> ORGANISM: Homo sapiens

<400> SEQUENCE: 1

```
Met Ala Lys Ala Thr Ser Gly Ala Ala Gly Leu Arg Leu Leu Leu Leu
1               5                   10                  15

Leu Leu Leu Pro Leu Leu Gly Lys Val Ala Leu Gly Leu Tyr Phe Ser
            20                  25                  30

Arg Asp Ala Tyr Trp Glu Lys Leu Tyr Val Asp Gln Ala Ala Gly Thr
        35                  40                  45

Pro Leu Leu Tyr Val His Ala Leu Arg Asp Ala Pro Glu Glu Val Pro
    50                  55                  60

Ser Phe Arg Leu Gly Gln His Leu Tyr Gly Thr Tyr Arg Thr Arg Leu
65                  70                  75                  80

His Glu Asn Asn Trp Ile Cys Ile Gln Glu Asp Thr Gly Leu Leu Tyr
                85                  90                  95

Leu Asn Arg Ser Leu Asp His Ser Ser Trp Glu Lys Leu Ser Val Arg
            100                 105                 110

Asn Arg Gly Phe Pro Leu Leu Thr Val Tyr Leu Lys Val Phe Leu Ser
        115                 120                 125

Pro Thr Ser Leu Arg Glu Gly Glu Cys Gln Trp Pro Gly Cys Ala Arg
    130                 135                 140

Val Tyr Phe Ser Phe Phe Asn Thr Ser Phe Pro Ala Cys Ser Ser Leu
145                 150                 155                 160

Lys Pro Arg Glu Leu Cys Phe Pro Glu Thr Arg Pro Ser Phe Arg Ile
                165                 170                 175

Arg Glu Asn Arg Pro Pro Gly Thr Phe His Gln Phe Arg Leu Leu Pro
            180                 185                 190

Val Gln Phe Leu Cys Pro Asn Ile Ser Val Ala Tyr Arg Leu Leu Glu
        195                 200                 205

Gly Glu Gly Leu Pro Phe Arg Cys Ala Pro Asp Ser Leu Glu Val Ser
    210                 215                 220

Thr Arg Trp Ala Leu Asp Arg Glu Gln Arg Glu Lys Tyr Glu Leu Val
225                 230                 235                 240

Ala Val Cys Thr Val His Ala Gly Ala Arg Glu Glu Val Val Met Val
                245                 250                 255

Pro Phe Pro Val Thr Val Tyr Asp Glu Asp Asp Ser Ala Pro Thr Phe
            260                 265                 270

Pro Ala Gly Val Asp Thr Ala Ser Ala Val Val Glu Phe Lys Arg Lys
        275                 280                 285

Glu Asp Thr Val Val Ala Thr Leu Arg Val Phe Asp Ala Asp Val Val
    290                 295                 300

Pro Ala Ser Gly Glu Leu Val Arg Arg Tyr Thr Ser Thr Leu Leu Pro
305                 310                 315                 320

Gly Asp Thr Trp Ala Gln Gln Thr Phe Arg Val Glu His Trp Pro Asn
                325                 330                 335

Glu Thr Ser Val Gln Ala Asn Gly Ser Phe Val Arg Ala Thr Val His
            340                 345                 350

Asp Tyr Arg Leu Val Leu Asn Arg Asn Leu Ser Ile Ser Glu Asn Arg
        355                 360                 365
```

-continued

```
Thr Met Gln Leu Ala Val Leu Val Asn Asp Ser Asp Phe Gln Gly Pro
    370                 375                 380

Gly Ala Gly Val Leu Leu Leu His Phe Asn Val Ser Val Leu Pro Val
385                 390                 395                 400

Ser Leu His Leu Pro Ser Thr Tyr Ser Leu Ser Val Ser Arg Arg Ala
                405                 410                 415

Arg Arg Phe Ala Gln Ile Gly Lys Val Cys Val Glu Asn Cys Gln Ala
            420                 425                 430

Phe Ser Gly Ile Asn Val Gln Tyr Lys Leu His Ser Ser Gly Ala Asn
        435                 440                 445

Cys Ser Thr Leu Gly Val Val Thr Ser Ala Glu Asp Thr Ser Gly Ile
    450                 455                 460

Leu Phe Val Asn Asp Thr Lys Ala Leu Arg Arg Pro Lys Cys Ala Glu
465                 470                 475                 480

Leu His Tyr Met Val Val Ala Thr Asp Gln Gln Thr Ser Arg Gln Ala
                485                 490                 495

Gln Ala Gln Leu Leu Val Thr Val Glu Gly Ser Tyr Val Ala Glu Glu
            500                 505                 510

Ala Gly Cys Pro Leu Ser Cys Ala Val Ser Lys Arg Arg Leu Glu Cys
        515                 520                 525

Glu Glu Cys Gly Gly Leu Gly Ser Pro Thr Gly Arg Cys Glu Trp Arg
    530                 535                 540

Gln Gly Asp Gly Lys Gly Ile Thr Arg Asn Phe Ser Thr Cys Ser Pro
545                 550                 555                 560

Ser Thr Lys Thr Cys Pro Asp Gly His Cys Asp Val Val Glu Thr Gln
                565                 570                 575

Asp Ile Asn Ile Cys Pro Gln Asp Cys Leu Arg Gly Ser Ile Val Gly
            580                 585                 590

Gly His Glu Pro Gly Glu Pro Arg Gly Ile Lys Ala Gly Tyr Gly Thr
        595                 600                 605

Cys Asn Cys Phe Pro Glu Glu Glu Lys Cys Phe Cys Glu Pro Glu Asp
    610                 615                 620

Ile Gln Asp Pro Leu Cys Asp Glu Leu Cys Arg Thr Val Ile Ala Ala
625                 630                 635                 640

Ala Val Leu Phe Ser Phe Ile Val Ser Val Leu Leu Ser Ala Phe Cys
                645                 650                 655

Ile His Cys Tyr His Lys Phe Ala His Lys Pro Pro Ile Ser Ser Ala
            660                 665                 670

Glu Met Thr Phe Arg Arg Pro Ala Gln Ala Phe Pro Val Ser Tyr Ser
        675                 680                 685

Ser Ser Gly Ala Arg Arg Pro Ser Leu Asp Ser Met Glu Asn Gln Val
    690                 695                 700

Ser Val Asp Ala Phe Lys Ile Leu Glu Asp Pro Lys Trp Glu Phe Pro
705                 710                 715                 720

Arg Lys Asn Leu Val Leu Gly Lys Thr Leu Gly Glu Gly Glu Phe Gly
                725                 730                 735

Lys Val Val Lys Ala Thr Ala Phe His Leu Lys Gly Arg Ala Gly Tyr
            740                 745                 750

Thr Thr Val Ala Val Lys Met Leu Lys Glu Asn Ala Ser Pro Ser Glu
        755                 760                 765

Leu Arg Asp Leu Leu Ser Glu Phe Asn Val Leu Lys Gln Val Asn His
    770                 775                 780

Pro His Val Ile Lys Leu Tyr Gly Ala Cys Ser Gln Asp Gly Pro Leu
```

-continued

```
785                 790                 795                 800

Leu Leu Ile Val Glu Tyr Ala Lys Tyr Gly Ser Leu Arg Gly Phe Leu
                805                 810                 815

Arg Glu Ser Arg Lys Val Gly Pro Gly Tyr Leu Gly Ser Gly Gly Ser
            820                 825                 830

Arg Asn Ser Ser Ser Leu Asp His Pro Asp Glu Arg Ala Leu Thr Met
        835                 840                 845

Gly Asp Leu Ile Ser Phe Ala Trp Gln Ile Ser Gln Gly Met Gln Tyr
    850                 855                 860

Leu Ala Glu Met Lys Leu Val His Arg Asp Leu Ala Ala Arg Asn Ile
865                 870                 875                 880

Leu Val Ala Glu Gly Arg Lys Met Lys Ile Ser Asp Phe Gly Leu Ser
                885                 890                 895

Arg Asp Val Tyr Glu Glu Asp Ser Tyr Val Lys Arg Ser Gln Gly Arg
            900                 905                 910

Ile Pro Val Lys Trp Met Ala Ile Glu Ser Leu Phe Asp His Ile Tyr
        915                 920                 925

Thr Thr Gln Ser Asp Val Trp Ser Phe Gly Val Leu Leu Trp Glu Ile
    930                 935                 940

Val Thr Leu Gly Gly Asn Pro Tyr Pro Gly Ile Pro Pro Glu Arg Leu
945                 950                 955                 960

Phe Asn Leu Leu Lys Thr Gly His Arg Met Glu Arg Pro Asp Asn Cys
                965                 970                 975

Ser Glu Glu Met Tyr Arg Leu Met Leu Gln Cys Trp Lys Gln Glu Pro
            980                 985                 990

Asp Lys Arg Pro Val Phe Ala Asp  Ile Ser Lys Asp Leu  Glu Lys Met
        995                 1000                 1005

Met Val  Lys Arg Arg Asp Tyr  Leu Asp Leu Ala Ala  Ser Thr Pro
    1010                 1015                 1020

Ser Asp  Ser Leu Ile Tyr Asp  Asp Gly Leu Ser Glu  Glu Glu Thr
    1025                 1030                 1035

Pro Leu  Val Asp Cys Asn Asn  Ala Pro Leu Pro Arg  Ala Leu Pro
    1040                 1045                 1050

Ser Thr  Trp Ile Glu Asn Lys  Leu Tyr Gly Met Ser  Asp Pro Asn
    1055                 1060                 1065

Trp Pro  Gly Glu Ser Pro Val  Pro Leu Thr Arg Ala  Asp Gly Thr
    1070                 1075                 1080

Asn Thr  Gly Phe Pro Arg Tyr  Pro Asn Asp Ser Val  Tyr Ala Asn
    1085                 1090                 1095

Trp Met  Leu Ser Pro Ser Ala  Ala Lys Leu Met Asp  Thr Phe Asp
    1100                 1105                 1110

Ser
```

UNITED STATES PATENT AND TRADEMARK OFFICE
CERTIFICATE OF CORRECTION

PATENT NO. : 11,168,090 B2
APPLICATION NO. : 16/478071
DATED : November 9, 2021
INVENTOR(S) : Andrews et al.

Page 1 of 1

It is certified that error appears in the above-identified patent and that said Letters Patent is hereby corrected as shown below:

In the Claims

At Column 357, Line 66, delete "acceptable salt thereof, wherein $hetCyc^2$ is selected" and insert --acceptable salt thereof, wherein $hetCyc^1$ is selected--, therefor.

Signed and Sealed this
Eighth Day of February, 2022

Drew Hirshfeld
*Performing the Functions and Duties of the*
*Under Secretary of Commerce for Intellectual Property and*
*Director of the United States Patent and Trademark Office*